US012552771B2

(12) United States Patent
Schkeryantz et al.

(10) Patent No.: US 12,552,771 B2
(45) Date of Patent: *Feb. 17, 2026

(54) CARBOXYLIC ACID CONTAINING AZETIDINYL COMPOUNDS FOR THE TREATMENT OF NEURODEGENERATIVE DISEASES

(71) Applicant: Celgene Corporation, Princeton, NJ (US)

(72) Inventors: Jeffrey M. Schkeryantz, Summit, NJ (US); Karin Worm, Summit, NJ (US); Rulin Ma, Winchester, MA (US); Patrick W. Papa, Carlsbad, CA (US)

(73) Assignee: Celgene Corporation, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/422,500

(22) Filed: Jan. 25, 2024

(65) Prior Publication Data

US 2024/0270714 A1 Aug. 15, 2024

Related U.S. Application Data

(63) Continuation of application No. 17/840,876, filed on Jun. 15, 2022, now Pat. No. 11,919,879.

(60) Provisional application No. 63/211,313, filed on Jun. 16, 2021.

(51) Int. Cl.

| | |
|---|---|
| ***A61P 25/00*** | (2006.01) |
| ***A61K 31/397*** | (2006.01) |
| ***A61K 31/4523*** | (2006.01) |
| ***A61K 31/4545*** | (2006.01) |
| ***A61P 25/28*** | (2006.01) |
| ***A61P 37/00*** | (2006.01) |
| ***C07D 205/04*** | (2006.01) |
| ***C07D 401/10*** | (2006.01) |
| ***C07D 401/14*** | (2006.01) |
| ***C07D 403/10*** | (2006.01) |

(52) U.S. Cl.

CPC ......... *C07D 401/10* (2013.01); *C07D 401/14* (2013.01); *C07D 403/10* (2013.01)

(58) Field of Classification Search

None

See application file for complete search history.

(56) References Cited

U.S. PATENT DOCUMENTS

| | | | |
|---|---|---|---|
| 5,561,227 | A | 10/1996 | Thiruvengadam et al. |
| 6,093,731 | A | 7/2000 | Dickinson et al. |
| 10,392,366 | B2 | 8/2019 | Schwink et al. |
| 11,919,879 | B2 * | 3/2024 | Schkeryantz ........ C07D 205/04 |
| 2007/0021474 | A1 | 1/2007 | Schoenafinger et al. |
| 2017/0066717 | A1 | 3/2017 | Boubia et al. |
| 2017/0355685 | A1 | 12/2017 | Blomgren et al. |
| 2017/0355693 | A1 | 12/2017 | Blomgren et al. |
| 2018/0237419 | A1 | 8/2018 | Schwink et al. |
| 2022/0289675 | A1 | 9/2022 | Otani et al. |

FOREIGN PATENT DOCUMENTS

| | | | | |
|---|---|---|---|---|
| CN | 111484479 | A | 8/2020 | |
| CN | 111704613 | A | 9/2020 | |
| EP | 223440 | B1 | 3/1991 | |
| EP | 3409658 | A1 | 12/2018 | |
| EP | 3666770 | A1 | 6/2020 | |
| WO | 9414433 | A1 | 7/1994 | |
| WO | 9709328 | A1 | 3/1997 | |
| WO | 2003020029 | A1 | 3/2003 | |
| WO | 2004007455 | A1 | 1/2004 | |
| WO | 2004056800 | A1 | 7/2004 | |
| WO | 2004058149 | A2 | 7/2004 | |
| WO | 2006123121 | A1 | 11/2006 | |
| WO | 2008053131 | A1 | 5/2008 | |
| WO | 2008055959 | A1 | 5/2008 | |
| WO | 2010056788 | A1 | 5/2010 | |
| WO | 2010092371 | A1 | 8/2010 | |
| WO | 2011036889 | A1 | 3/2011 | |
| WO | 2011098776 | A1 | 8/2011 | |
| WO | 2011143129 | A1 | 11/2011 | |
| WO | 2011143365 | A1 | 11/2011 | |
| WO | 2012082947 | A1 | 6/2012 | |
| WO | 2013007387 | A1 | 1/2013 | |
| WO | 2013169622 | A1 | 11/2013 | |
| WO | WO-2014009447 | A1 * | 1/2014 | ............. A61P 37/02 |
| WO | 2014078609 | A1 | 5/2014 | |
| WO | 2015055771 | A1 | 4/2015 | |
| WO | 2015101957 | A2 | 7/2015 | |
| WO | 2015171722 | A1 | 11/2015 | |
| WO | 2016040225 | A1 | 3/2016 | |
| WO | 2017019540 | A2 | 2/2017 | |
| WO | 2017065473 | A1 | 4/2017 | |
| WO | 2017156165 | A1 | 9/2017 | |

(Continued)

OTHER PUBLICATIONS

Guerrero et al., "Sphingosine 1-phosphate receptor 1 agonists: a patent review (2013-2015)," Expert Opinion on Therapeutic Patents, 2016, 26(4):455-470.

Huang et al., "Stereoselective Synthesis of β-Lactam-triflones under Catalyst-Free Conditions," Org. Lett., 2015, 17 (22):5610-5613.

International Search Report and Written Opinion for PCT/US2022/033523, dated Oct. 4, 2022, Applicant: Celgene Corporation; 15 pages.

Machine Translation of CN111484479, dated Aug. 4, 2020, Li et al., 66 pages.

Machine Translation of CN111704613, dated Sep. 25, 2020, Zheng et al., 16 pages.

Machine Translation of WO 2020/071550, dated Apr. 9, 2020, Shirahase et al, 77 pages.

Machine Translation of WO2011/036889, dated Mar. 31, 2011, Aso et al., 88 pages.

(Continued)

*Primary Examiner* — Kortney L. Klinkel
*Assistant Examiner* — Alison Azar Salamatian
(74) *Attorney, Agent, or Firm* — McNeill PLLC

(57) ABSTRACT

Provided herein are compounds and compositions thereof for modulating S1P5. In some embodiments, the compounds and compositions are provided for treatment of neurological diseases.

18 Claims, No Drawings

(56) References Cited

FOREIGN PATENT DOCUMENTS

| | | | |
|---|---|---|---|
| WO | 2017205425 | A1 | 11/2017 |
| WO | 2018106818 | A1 | 6/2018 |
| WO | 2019031990 | A1 | 2/2019 |
| WO | 2019141803 | A1 | 7/2019 |
| WO | 2020035540 | A1 | 2/2020 |
| WO | 2020037203 | A2 | 2/2020 |
| WO | 2020071550 | A1 | 4/2020 |
| WO | 2020092401 | A1 | 5/2020 |
| WO | 2021001330 | A1 | 1/2021 |
| WO | 2021033729 | A1 | 2/2021 |
| WO | 2022140555 | A1 | 6/2022 |

OTHER PUBLICATIONS

Roberts et al., "Sphingosine 1-phosphate receptor agonists: a patent review (2010-2012)," Expert Opinion on Therapeutic Patents, 2013, 23(7):817-841.

Apodaca, "V3000 Molfile Enhanced Stereochemistry Representation," Feb. 9, 2022, 10 pages.

Lyapina et al., "Structural Basis for Receptor Selectivity and Inverse Agonism in S1P5 Receptors," Nature Communications, 2022, 13:4736 (14 pages).

* cited by examiner

CARBOXYLIC ACID CONTAINING AZETIDINYL COMPOUNDS FOR THE TREATMENT OF NEURODEGENERATIVE DISEASES

CROSS-REFERENCE TO RELATED APPLICATIONS

This application is a continuation of U.S. patent application Ser. No. 17/840,876, filed on Jun. 15, 2022, which claims priority to U.S. Provisional Application No. 63/211,313, filed on Jun. 16, 2021, the disclosure of each of which is incorporated herein by reference in its entirety for any purpose.

FIELD

The present disclosure relates generally to compounds, compositions, and methods for their preparation and use of the compounds and compositions for treating neurodegenerative diseases.

BACKGROUND

Sphingosine-1-phosphate (SIP; (2S,3R,4E)-2-amino-3-hydroxyoctadec-4-enyl-1-phosphate) is a bioactive sphingolipid that is synthesized by metabolic turnover of sphingolipids in cells and by the extracellular action of a secreted sphingosine kinase. S1P binds to and stimulates members of the endothelial cell differentiation gene family (EDG receptors), which are plasma membrane-localized G protein-coupled receptors. The five members of this family of receptors are S1P1 (EDG-1), S1P2 (EDG-5), S1P3 (EDG-3), S1P4 (EDG-6), and S1P5 (EDG-8). S1P mediates a wide variety of cellular responses including proliferation, cytoskeletal organization and migration, adherence- and tight junction assembly, and morphogenesis.

S1P5 is primarily expressed in the central nervous system. Specifically, S1P5 is highly expressed in oligodendrocytes (oligodendroglia) and oligodendrocyte progenitor cells (Jaillard, C. et al., *J. Neuroscience,* 2005, 25(6), 1459-1469; Novgorodov, A. S. et al., *FASEB J.,* 2007, 21, 1503-1514). Oligodendrocytes are glial cells that form myelin sheaths (myelin) by binding to the axons of nerve cells. Compounds that bind to S1P5 can modulate the function of S1P5 and may be useful for treating neurodegenerative diseases.

Accordingly, in one aspect, provided herein are compounds that modulate S1P5 for use in treating neurodegenerative diseases.

SUMMARY

Described herein, in certain embodiments, are compounds and compositions thereof for modulating S1P5. In various embodiments, the compounds and compositions thereof may be used for treatment of neurodegenerative diseases.

The present embodiments can be understood more fully by reference to the detailed description and examples, which are intended to exemplify non-limiting embodiments.

Embodiment 1 is a compound of Formula (I):

(I)

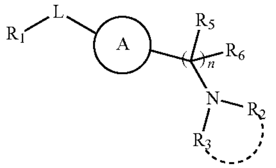

or a pharmaceutically acceptable salt thereof, wherein: Ring A is

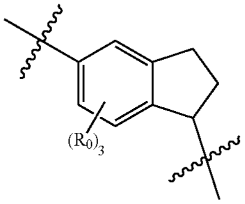

or

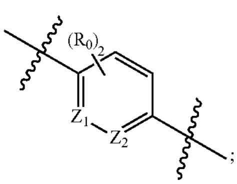

;

$Z_1$ and $Z_2$ are independently $CR_0$ or N;

L is azetidinyl optionally substituted with 1-5 substituents independently selected from halo and $C_1$-$C_6$ alkyl;

each $R_0$ is independently H, —CN, $C_1$-$C_6$ alkyl, $C_3$-$C_6$ cycloalkyl, halo, $C_1$-$C_6$ haloalkyl, or $C_1$-$C_6$ alkoxy, or two $R_0$ groups are taken together with the carbon atoms to which they are attached to form a fused phenylene;

$R_1$ is $C_6$-$C_{10}$ aryl or 5- to 6-membered heteroaryl, each of which is optionally substituted by 1-5

R' groups, wherein the heteroaryl contains 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl, or two R' groups are taken together with the carbon atoms to which they are attached to form a fused phenylene;

$R_2$ is H or $C_1$-$C_6$ alkyl;

$R_3$ is $—(CH_2)_x—CO_2H$;

or the dashed line between $R_2$ and $R_3$ represents a ring structure where $R_2$ and $R_3$ are taken together with the nitrogen atom to which they are attached to form a 4- to 6-membered heterocyclyl substituted by 1-5 $R_4$ groups, wherein at least one $R_4$ group is $—CO_2H$; x is 1-5;

each $R_4$ is independently $—CO_2H$, halo, $C_1$-$C_6$ alkyl, $C_1$-$C_6$ haloalkyl, or $C_1$-$C_6$ alkoxy;

$R_5$ and $R_6$ are independently H or $C_1$-$C_6$ alkyl; and n is 0 or 1.

Embodiment 2 is the compound of embodiment 1, or a pharmaceutically acceptable salt thereof, wherein:

Ring A is

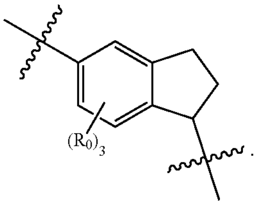

.

Embodiment 3 is the compound of embodiment 1, or a pharmaceutically acceptable salt thereof, wherein:

Ring A is

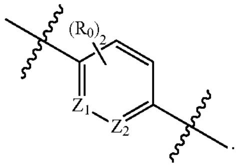

Embodiment 4 is the compound of embodiment 3, or a pharmaceutically acceptable salt thereof, wherein:

$Z_1$ and $Z_2$ are each independently $CR_0$.

Embodiment 5 is the compound of embodiment 3, or a pharmaceutically acceptable salt thereof, wherein:

$Z_1$ is N; and $Z_2$ is $CR_0$.

Embodiment 6 is the compound of embodiment 3, or a pharmaceutically acceptable salt thereof, wherein:

$Z_1$ is $CR_0$; and $Z_2$ is N.

Embodiment 7 is the compound of any one of embodiments 1-6, or a pharmaceutically acceptable salt thereof, wherein:

each $R_0$ is independently H, —CN, $C_1$-$C_3$ alkyl, $C_3$-$C_5$ cycloalkyl, halo, $C_1$-$C_3$ haloalkyl, or $C_1$-$C_3$ alkoxy, or two $R_0$ groups are taken together with the carbon atoms to which they are attached to form a fused phenylene.

Embodiment 8 is the compound of embodiment 7, or a pharmaceutically acceptable salt thereof, wherein:

each $R_0$ is independently H, —CN, methyl, ethyl, isopropyl, cyclopropyl, Cl, F, —$CF_3$, or —$OCH_3$, or two $R_0$ groups are taken together with the carbon atoms to which they are attached to form a fused phenylene.

Embodiment 9 is the compound of any one of embodiments 1, 2, 7, and 8, or a pharmaceutically acceptable salt thereof, wherein:

Ring A is

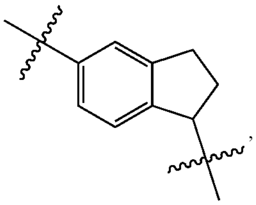,
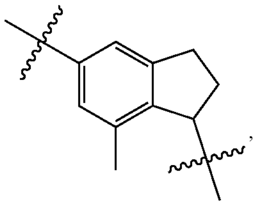, or
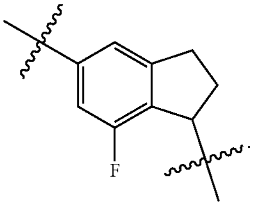.

Embodiment 10 is the compound of any one of embodiments 1 and 3-8, or a pharmaceutically acceptable salt thereof, wherein:

Ring A is

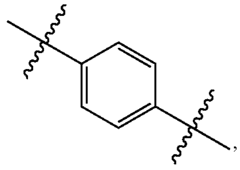,
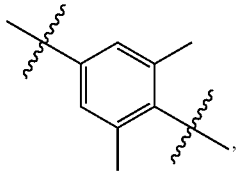,
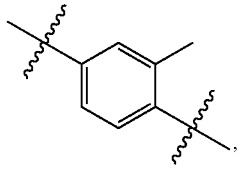,
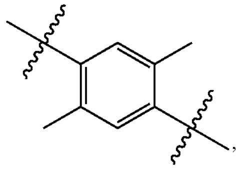,
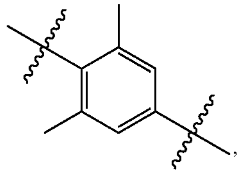,
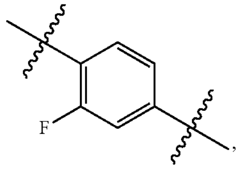,
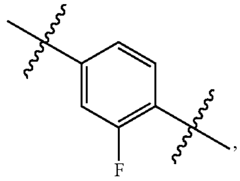,
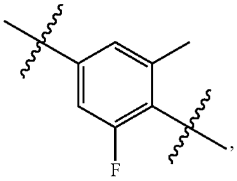,
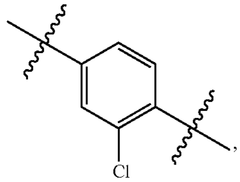,
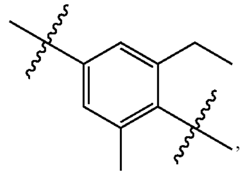,
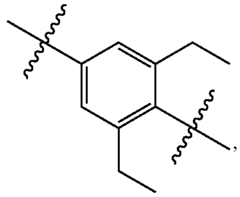,
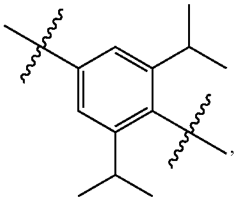,
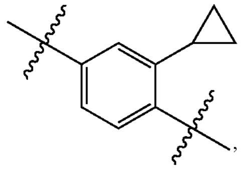,
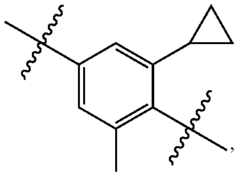,
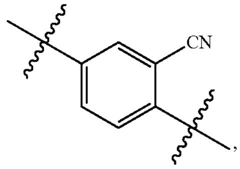,
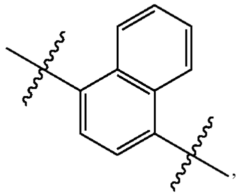,
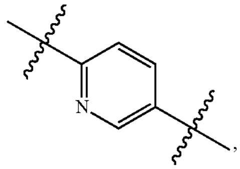,
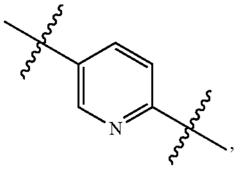, -continued

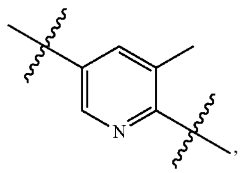,
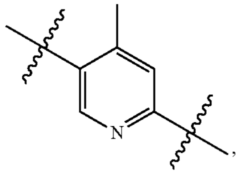,
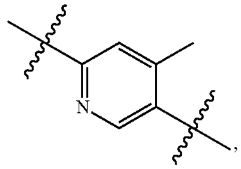,
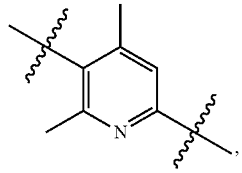,
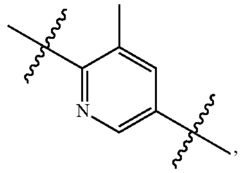,
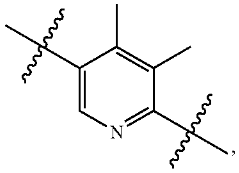,
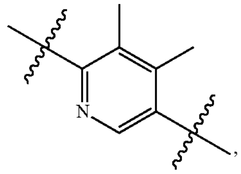,
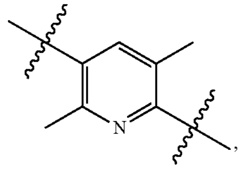,
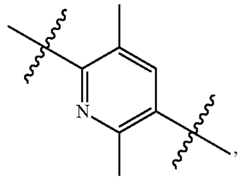, or
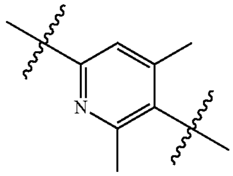.

Embodiment 11 is the compound of any one of embodiments 1-10, or a pharmaceutically acceptable salt thereof, wherein:

L is

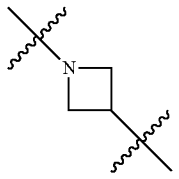 or 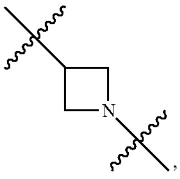, each of which is optionally substituted with 1-2 substituents independently selected from halo and $C_1$-$C_3$ alkyl.

Embodiment 12 is the compound of embodiment 11, or a pharmaceutically acceptable salt thereof, wherein:

L is

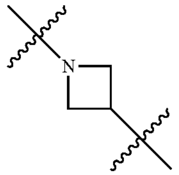 or 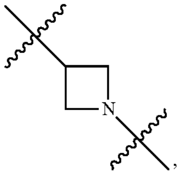, each of which is optionally substituted with one F, Cl, or methyl.

Embodiment 13 is the compound of embodiment 12, or a pharmaceutically acceptable salt thereof, wherein:

L is

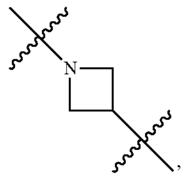, 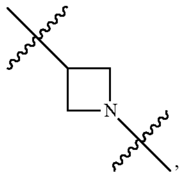, or
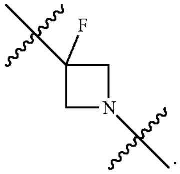.

Embodiment 14 is the compound of any one of embodiments 1-13, or a pharmaceutically acceptable salt thereof, wherein:

$R_1$ is phenyl or 5- to 6-membered heteroaryl, each of which is optionally substituted by 1-3 R' groups, wherein the heteroaryl contains 1-2 heteroatoms selected from nitrogen and oxygen.

Embodiment 15 is the compound of embodiment 14, or a pharmaceutically acceptable salt thereof, wherein:

$R_1$ is phenyl optionally substituted by 1-3 R' groups.

Embodiment 16 is the compound of any one of embodiments 1-15, or a pharmaceutically acceptable salt thereof, wherein:

each R' is independently halo, $C_1$-$C_3$ alkyl, $C_1$-$C_3$ haloalkyl, $C_1$-$C_3$ alkoxy, or $C_3$-$C_6$ cycloalkyl, or two R' groups are taken together with the carbon atoms to which they are attached to form a fused phenylene.

Embodiment 17 is the compound of embodiment 16, or a pharmaceutically acceptable salt thereof, wherein:

each R' is independently halo, $C_1$-$C_3$ alkyl, $C_1$-$C_3$ haloalkyl, or $C_3$-$C_6$ cycloalkyl, or two R' groups are taken together with the carbon atoms to which they are attached to form a fused phenylene.

Embodiment 18 is the compound of embodiment 17, or a pharmaceutically acceptable salt thereof, wherein:

each R' is independently F, Cl, methyl, ethyl, isopropyl, —$CHF_2$, or cyclopropyl, or two R' groups are taken together with the carbon atoms to which they are attached to form a fused phenylene.

Embodiment 19 is the compound of any one of embodiments 1-18, or a pharmaceutically acceptable salt thereof, wherein:

$R_1$ is

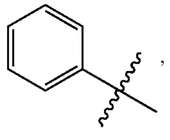, 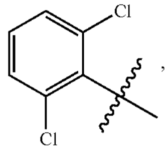,
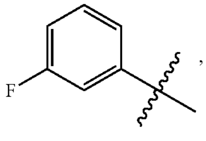, 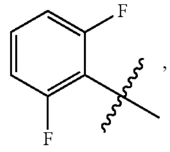,

-continued

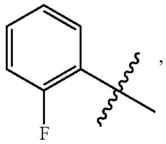, 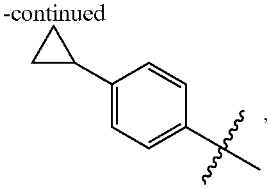, 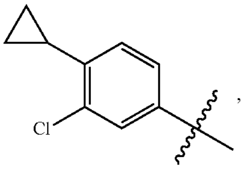, 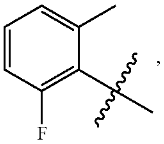, 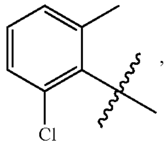, 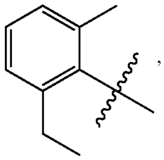, 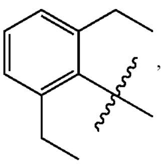, 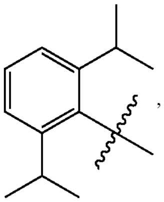, 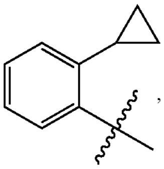, 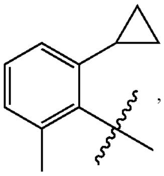, 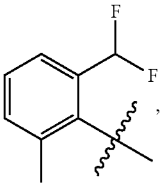, or 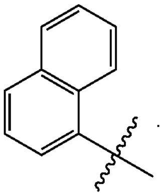.

Embodiment 20 is the compound of any one of embodiments 1-19, or a pharmaceutically acceptable salt thereof, wherein:

$R_2$ is H or $C_1$-$C_3$ alkyl;

$R_3$ is $-(CH_2)_x-CO_2H$; and x is 1-3.

Embodiment 21 is the compound of embodiment 20, or a pharmaceutically acceptable salt thereof, wherein:

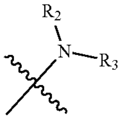 is 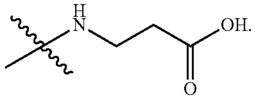

Embodiment 22 is the compound of any one of embodiments 1-19, or a pharmaceutically acceptable salt thereof, wherein:

$R_2$ and $R_3$ are taken together with the nitrogen atom to which they are attached to form a 4- to 6-membered heterocyclyl substituted by 1-3 $R_4$ groups, wherein at least one $R_4$ group is $-CO_2H$.

Embodiment 23 is the compound of embodiment 22, or a pharmaceutically acceptable salt thereof, wherein:

each $R_4$ is independently $-CO_2H$, halo, $C_1$-$C_3$ alkyl, $C_1$-$C_3$ haloalkyl, or $C_1$-$C_3$ alkoxy.

Embodiment 24 is the compound of embodiment 23, or a pharmaceutically acceptable salt thereof, wherein:

each $R_4$ is independently $-CO_2H$, methyl, F, Cl, $-CF_3$, or $-OCH_3$.

Embodiment 25 is the compound of any one of embodiments 1-19 and 22-24, or a pharmaceutically acceptable salt thereof, wherein:

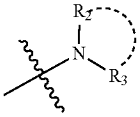 is 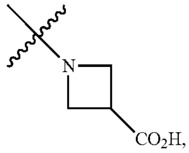, 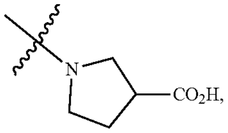, 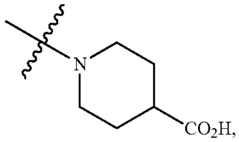, 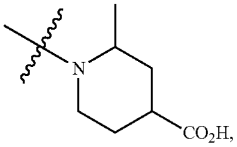, 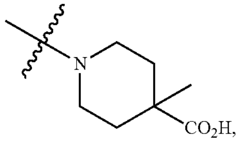, 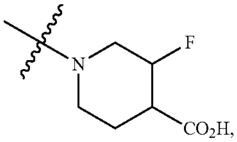, 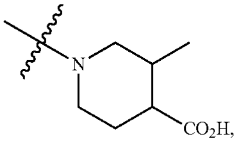, or 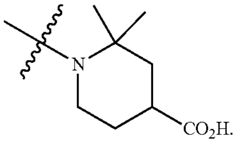.

Embodiment 26 is the compound of any one of embodiments 1-25, or a pharmaceutically acceptable salt thereof, wherein:

n is 0.

Embodiment 27 is the compound of any one of embodiments 1-25, or a pharmaceutically acceptable salt thereof, wherein:

n is 1.

Embodiment 28 is the compound of embodiment 27, or a pharmaceutically acceptable salt thereof, wherein:

$R_5$ and $R_6$ are independently H or $C_1$-$C_3$ alkyl.

Embodiment 29 is the compound of embodiment 28, or a pharmaceutically acceptable salt thereof, wherein:

$R_5$ and $R_6$ are independently H or methyl.

Embodiment 30 is the compound of embodiment 29, or a pharmaceutically acceptable salt thereof, wherein:

$-CR_5R_6-$ is $-CH_2-$, $-CH(CH_3)-$, or $-C(CH_3)_2-$.

Embodiment 31 is the compound of any one of embodiments 1, 2, and 7-9, and 11-26, or a pharmaceutically acceptable salt thereof, wherein the compound is of Formula (II):

(II)

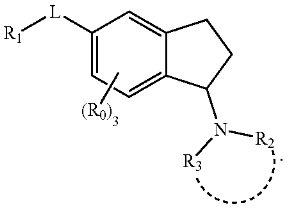

Embodiment 32 is the compound of any one of embodiments 1, 3-8, 10-19, 22-25, and 27-30, or a pharmaceutically acceptable salt thereof, wherein the compound is of Formula (III):

(III)

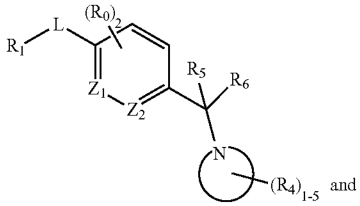

and

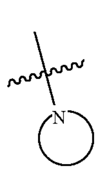

and is a 4- to 6-membered heterocyclyl, wherein at least one $R_4$ group is —$CO_2H$.

Embodiment 33 is a compound selected from the compounds of Table 1 and pharmaceutically acceptable salts thereof.

Embodiment 34 is a pharmaceutical composition comprising the compound of any one of embodiments 1-33, or a pharmaceutically acceptable salt thereof, and a pharmaceutically acceptable excipient.

Embodiment 35 is a method of modulating sphingosine 1-phosphate receptor 5 (S1P5) comprising contacting S1P5 with an effective amount of the compound of any one of embodiments 1-33, or a pharmaceutically acceptable salt thereof, or the pharmaceutical composition of embodiment 34.

Embodiment 36 is a method of treating a neurological disease in a subject in need thereof, comprising administering to the subject an effective amount of the compound of any one of embodiments 1-33, or a pharmaceutically acceptable salt thereof, or the pharmaceutical composition of embodiment 34.

Embodiment 37 is the method of embodiment 36, wherein the neurological disease is Alzheimer's disease or multiple sclerosis.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean±20%, ±10%, ±5%, or ±1% of the indicated range, value, or structure, unless otherwise indicated.

An "alkyl" group is a saturated, partially saturated, or unsaturated straight chain or branched non-cyclic hydrocarbon having from 1 to 10 carbon atoms ($C_1$-$C_{10}$ alkyl), typically from 1 to 8 carbons ($C_1$-$C_8$ alkyl) or, in some embodiments, from 1 to 6 ($C_1$-$C_6$ alkyl), 1 to 3 ($C_1$-$C_3$ alkyl), or 2 to 6 ($C_2$-$C_6$ alkyl) carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, an alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, —$CH{=}CH(CH_3)$, —$CH{=}C(CH_3)_2$, —$C(CH_3){=}CH_2$, —$C(CH_3){=}CH(CH_3)$, —$C(CH_2CH_3){=}CH_2$, —$C{\equiv}CH$, —$C{\equiv}C(CH_3)$, —$C{\equiv}C(CH_2CH_3)$, —$CH_2C{\equiv}CH$, —$CH_2C{\equiv}C(CH_3)$ and —$CH_2C{\equiv}C(CH_2CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido;

cyano; isocyanato; isothiocyanato; cyanato; thiocyanato; or —$B(OH)_2$. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

A "cycloalkyl" group is a saturated, or partially saturated cyclic alkyl group of from 3 to 10 carbon atoms ($C_3$-$C_{10}$ cycloalkyl) having a single cyclic ring or multiple condensed or bridged rings that can be optionally substituted. In some embodiments, the cycloalkyl group has 3 to 8 ring carbon atoms ($C_3$-$C_8$ cycloalkyl), whereas in other embodiments the number of ring carbon atoms ranges from 3 to 5 ($C_3$-$C_5$ cycloalkyl), 3 to 6 ($C_3$-$C_6$ cycloalkyl), or 3 to 7 ($C_3$-$C_7$ cycloalkyl). In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms ($C_6$-$C_{14}$ aryl) having a single ring (e.g., phenyl) or multiple condensed rings (e.g., naphthyl or anthryl). In some embodiments, aryl groups contain 6-14 carbons ($C_6$-$C_{14}$ aryl), and in others from 6 to 12 ($C_6$-$C_{12}$ aryl) or even 6 to 10 carbon atoms ($C_6$-$C_{10}$ aryl) in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "halogen" or "halo" is fluorine, chlorine, bromine or iodine.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl group has one to six carbon atoms and is substituted by one or more halo radicals ($C_1$-$C_6$ haloalkyl), or the haloalkyl group has one to three carbon atoms and is substituted by one or more halo radicals ($C_1$-$C_3$ haloalkyl). The halo radicals may be all the same or the halo radicals may be different. Unless specifically stated otherwise, a haloalkyl group is optionally substituted.

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "heterocyclyl" is a non-aromatic cycloalkyl in which one to four of the ring carbon atoms are independently replaced with a heteroatom selected from O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass saturated and partially saturated ring systems. Further, the term heterocyclyl is intended to encompass any non-aromatic ring containing at least one heteroatom, which ring may be fused to an aryl or heteroaryl ring, regardless of the attachment to the remainder of the molecule. The phrase also includes bridged polycyclic ring systems containing a heteroatom. Representative examples of a heterocyclyl group include, but are not limited to, aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "alkoxy" group is —O-(alkyl), wherein alkyl is defined above.

A "carboxy" group is a radical of the formula: —C(O)OH.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

Certain commonly used alternative chemical names may be used. For example, a divalent group such as a divalent "alkyl" group, a divalent "phenyl" group, a divalent "heteroaryl" group, a divalent "heterocyclyl" group etc., may also be referred to as an "alkylene" group, a "phenylene" group, a "heteroarylene" group, or a "heterocyclylene" group, respectively.

Embodiments of the disclosure are meant to encompass pharmaceutically acceptable salts, tautomers, isotopologues, and stereoisomers of the compounds provided herein, such as the compounds of Formula (I).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride, formic, and mesylate salts. Others are well-known in the art, see for example, *Remington's Pharmaceutical Sciences,* $18^{th}$ eds., Mack Publishing, Easton PA (1990) or *Remington: The Science and Practice of Pharmacy,* $19^{th}$ eds., Mack Publishing, Easton PA (1995).

As used herein and unless otherwise indicated, the term "stereoisomer" or "stereoisomerically pure" means one stereoisomer of a particular compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds disclosed herein can have chiral centers and can occur as racemates, individual enantiomers or diastereomers, and mixtures thereof. All such isomeric forms are included within the embodiments disclosed herein, including mixtures thereof.

The use of stereoisomerically pure forms of the compounds disclosed herein, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It should also be noted the compounds disclosed herein can include E and Z isomers, or a mixture thereof, and cis and trans isomers or a mixture thereof. In certain embodiments, the compounds are isolated as either the E or Z isomer. In other embodiments, the compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

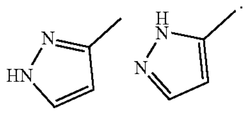

As readily understood by one skilled in the art, a wide variety of functional groups and other structures may exhibit tautomerism and all tautomers of compounds of Formula (I) are within the scope of the present disclosure.

It should also be noted the compounds disclosed herein can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium (H), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds disclosed herein, for example, the isotopologues are deuterium, carbon-13, and/or nitrogen-15 enriched compounds. As used herein, "deuterated", means a compound wherein at least one hydrogen (H) has been replaced by deuterium (indicated by D or $^2H$), that is, the compound is enriched in deuterium in at least one position.

It is understood that, independently of stereoisomerical or isotopic composition, each compound disclosed herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof disclosed herein, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a neurodegenerative disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a neurodegenerative disease, as described herein, or symptoms thereof.

The term "effective amount" in connection with a compound disclosed herein means an amount capable of treating or preventing a disorder, disease or condition, or symptoms thereof, disclosed herein.

The term "subject" or "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an S1P5 mediated disease, or a symptom thereof.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds

In one aspect, provided herein is a compound of Formula (I):

(I)

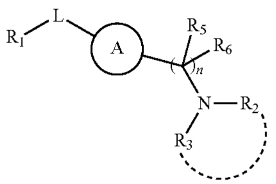

or a pharmaceutically acceptable salt thereof, wherein:

Ring A is

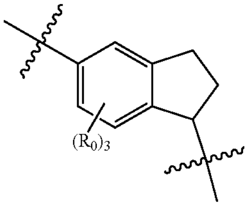

or

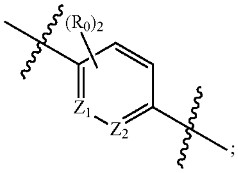

;

$Z_1$ and $Z_2$ are independently $CR_0$ or N;

L is azetidinyl optionally substituted with 1-5 substituents independently selected from halo and $C_1$-$C_6$ alkyl;

each $R_0$ is independently H, —CN, $C_1$-$C_6$ alkyl, $C_3$-$C_6$ cycloalkyl, halo, $C_1$-$C_6$ haloalkyl, or $C_1$-$C_6$ alkoxy, or two $R_0$ groups are taken together with the carbon atoms to which they are attached to form a fused phenylene;

$R_1$ is $C_6$-$C_{10}$ aryl or 5- to 6-membered heteroaryl, each of which is optionally substituted by 1-5 R' groups, wherein the heteroaryl contains 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl, or two R' groups are taken together with the carbon atoms to which they are attached to form a fused phenylene;

$R_2$ is H or $C_1$-$C_6$ alkyl;

$R_3$ is $—(CH_2)_x—CO_2H$;

or the dashed line between $R_2$ and $R_3$ represents a ring structure where $R_2$ and $R_3$ are taken together with the nitrogen atom to which they are attached to form a 4- to 6-membered heterocyclyl substituted by 1-5 $R_4$ groups, wherein at least one $R_4$ group is $—CO_2H$;

x is 1-5;

each $R_4$ is independently $—CO_2H$, halo, $C_1$-$C_6$ alkyl, $C_1$-$C_6$ haloalkyl, or $C_1$-$C_6$ alkoxy;

$R_5$ and $R_6$ are independently H or $C_1$-$C_6$ alkyl; and n is 0 or 1.

In some embodiments, Ring A is

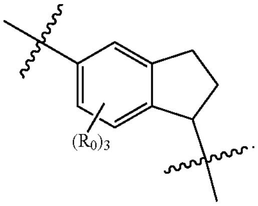

.

In some embodiments, Ring A is

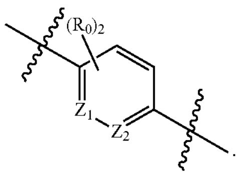

In some embodiments, $Z_1$ and $Z_2$ are independently $CR_0$ or N. In some embodiments, $Z_1$ and $Z_2$ are each independently $CR_0$. In some embodiments, one of $Z_1$ and $Z_2$ is N, and the other of $Z_1$ and $Z_2$ is $CR_0$. In some embodiments, $Z_1$ is N and $Z_2$ is $CR_0$. In some embodiments, $Z_1$ is $CR_0$ and $Z_2$ is N. In some embodiments, $Z_1$ and $Z_2$ are each N. In some embodiments, $Z_1$ and $Z_2$ are each CH. In some embodiments, $Z_1$ is CH and $Z_2$ is $CR_0$, wherein $R_0$ is $C_1$-$C_6$ alkyl. In some embodiments, $Z_1$ is $CR_0$, wherein $R_0$ is $C_1$-$C_6$ alkyl, and $Z_2$ is CH. In some embodiments, $Z_1$ is $CR_0$, wherein $R_0$ is halo, and $Z_2$ is CH. In some embodiments, $Z_1$ is CH and $Z_2$ is $CR_0$, wherein $R_0$ is halo. In some embodiments, $Z_1$ is N and $Z_2$ is CH. In some embodiments, $Z_1$ is CH and $Z_2$ is N. In some embodiments, $Z_1$ is N and $Z_2$ is $CR_0$, wherein $R_0$ is $C_1$-$C_6$ alkyl. In some embodiments, $Z_2$ is N and $Z_1$ is $CR_0$, wherein $R_0$ is $C_1$-$C_6$ alkyl.

In some embodiments, each $R_0$ is independently H, —CN, $C_1$-$C_6$ alkyl, $C_3$-$C_6$ cycloalkyl, halo, $C_1$-$C_6$ haloalkyl, or $C_1$-$C_6$ alkoxy. In some embodiments, each $R_0$ is independently H, —CN, $C_1$-$C_3$ alkyl, $C_3$-$C_5$ cycloalkyl, halo, $C_1$-$C_3$ haloalkyl, or $C_1$-$C_3$ alkoxy. In some embodiments, each $R_0$ is independently H, —CN, methyl, ethyl, isopropyl, cyclopropyl, Cl, F, —$CF_3$, or —$OCH_3$. In some embodiments, each $R_0$ is independently H, methyl, or F. In some embodiments, two $R_0$ groups are taken together with the carbon atoms to which they are attached to form a fused phenylene.

In some embodiments, $R_0$ is H.

In some embodiments, $R_0$ is —CN.

In some embodiments, $R_0$ is $C_1$-$C_6$ alkyl. In some embodiments, $R_0$ is $C_1$-$C_3$ alkyl. In some embodiments, $R_0$ is methyl, ethyl, n-propyl, or isopropyl. In some embodiments, $R_0$ is methyl. In some embodiments, $R_0$ is ethyl. In some embodiments, $R_0$ is n-propyl. In some embodiments, $R_0$ is isopropyl.

In some embodiments, $R_0$ is $C_3$-$C_6$ cycloalkyl. In some embodiments, $R_0$ is $C_3$-$C_5$ cycloalkyl. In some embodiments, $R_0$ is cyclopropyl, cyclobutyl, cyclopentyl, or cyclohexyl. In some embodiments, $R_0$ is cyclopropyl.

In some embodiments, $R_0$ is halo. In some embodiments, $R_0$ is Cl, F, or Br. In some embodiments, $R_0$ is Cl. In some embodiments, $R_0$ is F. In some embodiments, $R_0$ is Br.

In some embodiments, $R_0$ is $C_1$-$C_6$ haloalkyl. In some embodiments, $R_0$ is $C_1$-$C_6$ haloalkyl containing 1-13 halogen atoms. In some embodiments, $R_0$ is $C_1$-$C_3$ haloalkyl containing 1-7 halogen atoms. In some embodiments, $R_0$ is —$CF_3$, —$CHF_2$, —$CH_2F$, —$CCl_3$, —$CHCl_2$, —$CH_2Cl$, —$CF_2Cl$, —$CFCl_2$, —$CH_2CF_3$, —$CH_2CHF_2$, or —$CH_2CCl_3$. In some embodiments, $R_0$ is —$CF_3$.

In some embodiments, $R_0$ is $C_1$-$C_6$ alkoxy. In some embodiments, $R_0$ is $C_1$-$C_3$ alkoxy. In some embodiments, $R_0$ is —$OCH_3$, —$OCH_2CH_3$, —$OCH_2CH_2CH_3$, or —$OCH(CH_3)_2$. In some embodiments, $R_0$ is —$OCH_3$. In some embodiments, $R_0$ is —$OCH_2CH_3$.

In some embodiments, two $R_0$ groups are taken together with the carbon atoms to which they are attached to form a fused phenylene.

In some embodiments, Ring A is

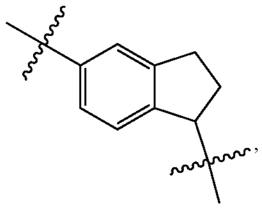,
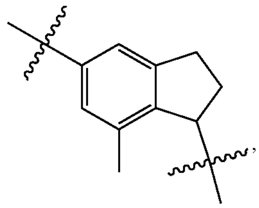, or
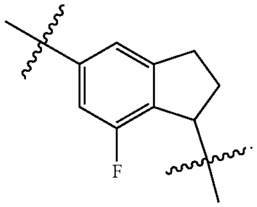.

In some embodiments, Ring A is:

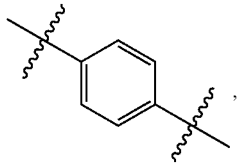,
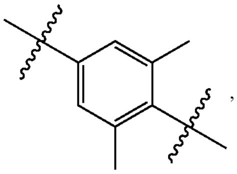,
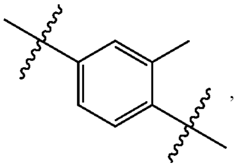,
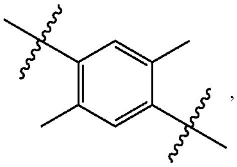,
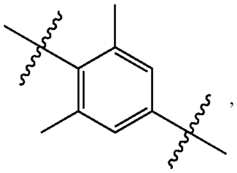,
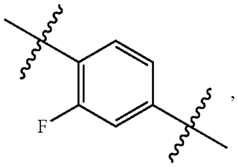,
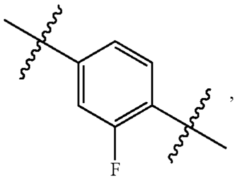,
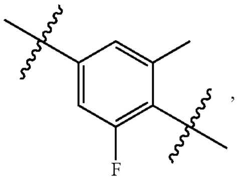,
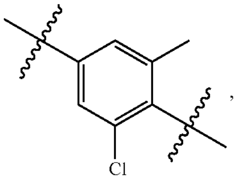,
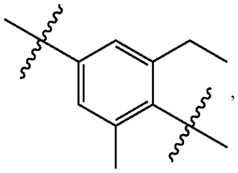,
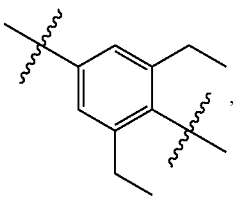,
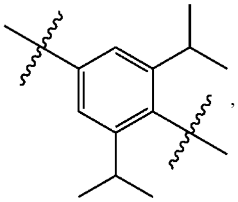, -continued

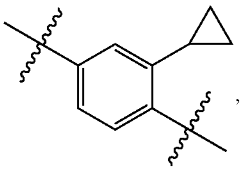,
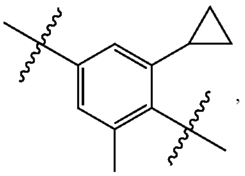,
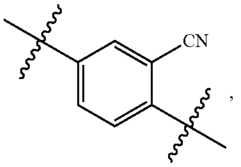,
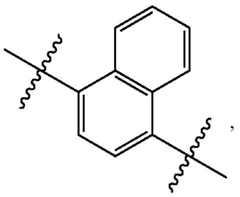,
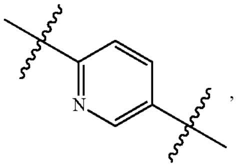,
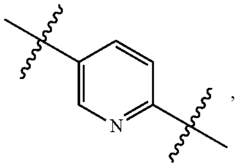,
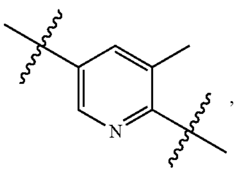,
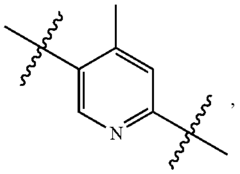,
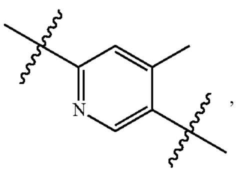,
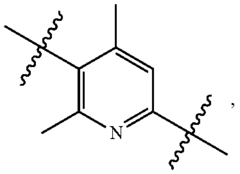,
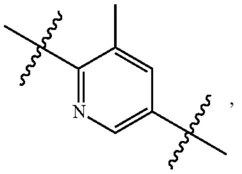,
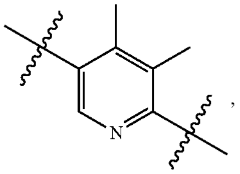,
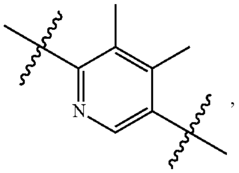,
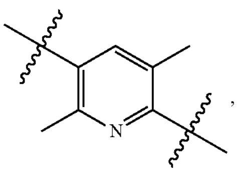,
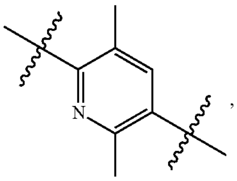, or
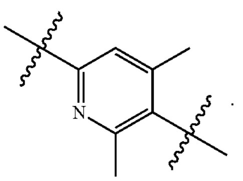.

In some embodiments, L is azetidinyl optionally substituted with 1-5 substituents independently selected from halo and $C_1$-$C_6$ alkyl. In some embodiments, L is

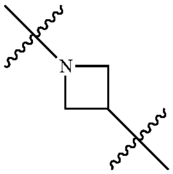 [SMILES: *C1CN(*)C1]

optionally substituted with 1-5 substituents independently selected from halo and $C_1$-$C_6$ alkyl.

In some embodiments, L is

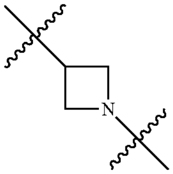 [SMILES: *C1CN(*)C1]

optionally substituted with 1-5 substituents independently selected from halo and $C_1$-$C_6$ alkyl. In some embodiments, L is azetidinyl optionally substituted with 1-3 substituents independently selected from halo and $C_1$-$C_6$ alkyl. In some embodiments, L is unsubstituted azetidinyl. In some embodiments, L is azetidinyl substituted with 1-5 substituents independently selected from halo and $C_1$-$C_6$ alkyl. In some embodiments, L is azetidinyl substituted with 1-3 substituents independently selected from halo and $C_1$-$C_6$ alkyl. In some embodiments, L is

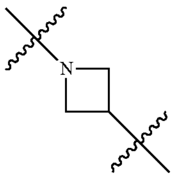 or 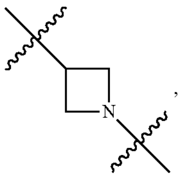, each of which is optionally substituted with 1-2 substituents independently selected from halo and $C_1$-$C_3$ alkyl. In some embodiments, L is

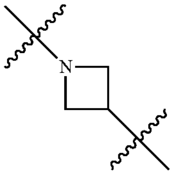 or 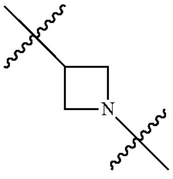, each of which is optionally substituted with one F, Cl, or methyl. In some embodiments, L is

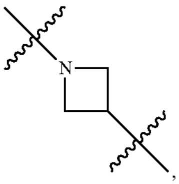, 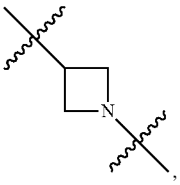, or

-continued

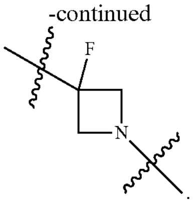.

In some embodiments, $R_1$ is $C_6$-$C_{10}$ aryl or 5- to 6-membered heteroaryl, each of which is optionally substituted by 1-5 R' groups, wherein the heteroaryl contains 1-3 heteroatoms selected from nitrogen and oxygen. In some embodiments, $R_1$ is phenyl or 5- to 6-membered heteroaryl, each of which is optionally substituted by 1-3 R' groups, wherein the heteroaryl contains 1-2 heteroatoms selected from nitrogen and oxygen. In some embodiments, $R_1$ is phenyl optionally substituted by 1-3 R' groups.

In some embodiments, $R_1$ is $C_6$-$C_{10}$ aryl optionally substituted by 1-5 R' groups. In some embodiments, $R_1$ is $C_6$-$C_{10}$ aryl optionally substituted by 1-3 R' groups. In some embodiments, $R_1$ is unsubstituted $C_6$-$C_{10}$ aryl. In some embodiments, $R_1$ is $C_6$-$C_{10}$ aryl substituted by 1-5 R' groups. In some embodiments, $R_1$ is $C_6$-$C_{10}$ aryl substituted by 1-5 R' groups. In some embodiments, $R_1$ is unsubstituted phenyl. In some embodiments, $R_1$ is phenyl substituted by 1-3 R' groups.

In some embodiments, $R_1$ is 5- to 6-membered heteroaryl optionally substituted by 1-5 R groups, wherein the heteroaryl contains 1-3 heteroatoms selected from nitrogen and oxygen. In some embodiments, $R_1$ is unsubstituted 5- to 6-membered heteroaryl, wherein the heteroaryl contains 1-3 heteroatoms selected from nitrogen and oxygen. In some embodiments, $R_1$ is 5- to 6-membered heteroaryl substituted by 1-5 R' groups, wherein the heteroaryl contains 1-3 heteroatoms selected from nitrogen and oxygen. In some embodiments, $R_1$ is 5- to 6-membered heteroaryl optionally substituted by 1-3 R' groups, wherein the heteroaryl contains 1-2 heteroatoms selected from nitrogen and oxygen. In some embodiments, $R_1$ is 5-membered heteroaryl optionally substituted by 1-5 R' groups, wherein the heteroaryl contains 1-3 heteroatoms selected from nitrogen and oxygen. In some embodiments, $R_1$ is pyrrolyl, pyrazolyl, imidazolyl, tetrazolyl, oxazolyl, or furanyl, each of which is optionally substituted by 1-5 R' groups. In some embodiments, $R_1$ is 6-membered heteroaryl optionally substituted by 1-5 R groups, wherein the heteroaryl contains 1-3 heteroatoms selected from nitrogen and oxygen. In some embodiments, $R_1$ is pyridinyl, pyrazinyl, pyrimidinyl, pyridazinyl, or triazinyl, each of which is optionally substituted by 1-5 R' groups.

In some embodiments, each R' is independently halo, $C_1$-$C_6$ alkyl, $C_1$-$C_6$ haloalkyl, $C_1$-$C_6$ alkoxy, or $C_3$-$C_6$ cycloalkyl. In some embodiments, each R' is independently halo, $C_1$-$C_3$ alkyl, $C_1$-$C_3$ haloalkyl, $C_1$-$C_3$ alkoxy, or $C_3$-$C_6$ cycloalkyl. In some embodiments, each R' is independently halo, $C_1$-$C_3$ alkyl, $C_1$-$C_3$ haloalkyl, or $C_3$-$C_6$ cycloalkyl. In some embodiments, each R' is independently F, Cl, methyl, ethyl, isopropyl, —$CHF_2$, or cyclopropyl. In some embodiments, two R' groups are taken together with the carbon atoms to which they are attached to form a fused phenylene.

In some embodiments, R' is halo. In some embodiments, R' is F, Cl, or Br. In some embodiments, R' is F. In some embodiments, R' is Cl. In some embodiments, R' is Br.

In some embodiments, R' is $C_1$-$C_6$ alkyl. In some embodiments, R' is $C_1$-$C_3$ alkyl. In some embodiments, R' is methyl, ethyl, n-propyl, or isopropyl. In some embodiments, R' is methyl. In some embodiments, R' is ethyl. In some embodiments, R' is n-propyl. In some embodiments, R' is isopropyl.

In some embodiments, R' is $C_1$-$C_6$ haloalkyl. In some embodiments, R' is $C_1$-$C_6$ haloalkyl containing 1-13 halogen atoms. In some embodiments, R' is $C_1$-$C_3$ haloalkyl. In some embodiments, R' is $C_1$-$C_3$ haloalkyl containing 1-7 halogen atoms. In some embodiments, R' is —$CF_3$, —$CHF_2$, —$CH_2F$, —$CCl_3$, —$CHCl_2$, —$CH_2Cl$, —$CF_2Cl$, —$CFCl_2$, —$CH_2CF_3$, —$CH_2CHF_2$, or —$CH_2CCl_3$. In some embodiments, R' is —$CF_3$. In some embodiments, R' is —$CHF_2$.

In some embodiments, R' is $C_1$-$C_6$ alkoxy. In some embodiments, R' is $C_1$-$C_3$ alkoxy. In some embodiments, R' is —$OCH_3$, —$OCH_2CH_3$, —$OCH_2CH_2CH_3$, or —$OCH(CH_3)_2$. In some embodiments, R' is —$OCH_3$.

In some embodiments, R' is $C_3$-$C_6$ cycloalkyl. In some embodiments, R' is $C_3$-$C_5$ cycloalkyl. In some embodiments, R' is cyclopropyl, cyclobutyl, cyclopentyl, or cyclohexyl. In some embodiments, R' is cyclopropyl. In some embodiments, R' is cyclobutyl.

In some embodiments, two R groups are taken together with the carbon atoms to which they are attached to form a fused phenylene.

In some embodiments, $R_1$ is:

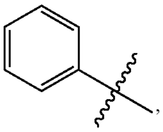, 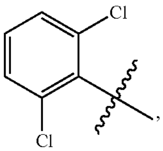, 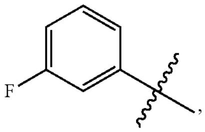,

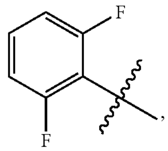, 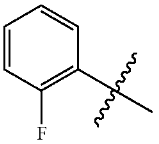,

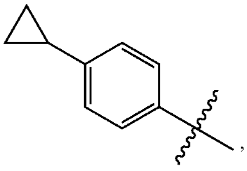, 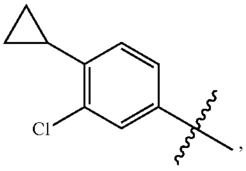,

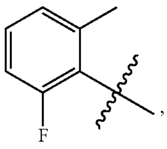, 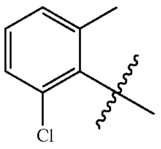, 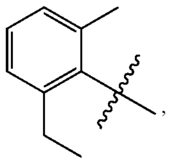,

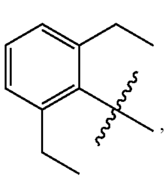, 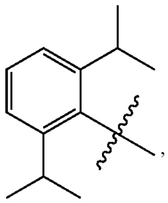, 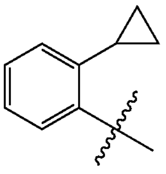,

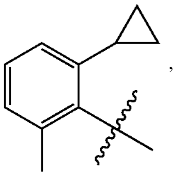, 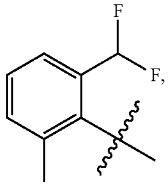 or 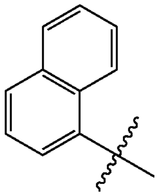.

In some embodiments, $R_2$ is H or $C_1$-$C_6$ alkyl. In some embodiments, $R_2$ is H. In some embodiments, $R_2$ is $C_1$-$C_6$ alkyl. In some embodiments, $R_2$ is $C_1$-$C_3$ alkyl. In some embodiments, $R_2$ is methyl, ethyl, n-propyl, or isopropyl. In some embodiments, $R_2$ is methyl. In some embodiments, $R_2$ is ethyl.

In some embodiments, $R_3$ is $-(CH_2)_x-CO_2H$, wherein x is 1-5. In some embodiments, $R_3$ is $-(CH_2)_x-CO_2H$, wherein x is 1-3. In some embodiments, $R_3$ is $-CH_2CO_2H$. In some embodiments, $R_3$ is $-(CH_2)_2CO_2H$. In some embodiments, $R_3$ is $-(CH_2)_3CO_2H$.

In some embodiments, x is 1-5. In some embodiments, x is 1-3. In some embodiments, x is 1. In some embodiments, x is 2. In some embodiments, x is 3. In some embodiments, x is 4. In some embodiments, x is 5.

In some embodiments, $R_2$ is H or $C_1$-$C_3$ alkyl; P3 is $-(CH_2)_x-CO_2H$; and x is 1-3. In some embodiments, $R_2$ is H; $R_3$ is $-(CH_2)_x-CO_2H$; and x is 1-3. In some embodiments, $R_2$ is $C_1$-$C_3$ alkyl; $R_3$ is $-(CH_2)_x-CO_2H$; and x is 1-3.

In some embodiments,

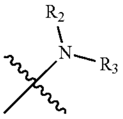 is 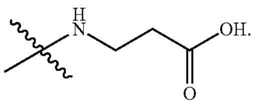

In some embodiments, $R_2$ and $R_3$ are taken together with the nitrogen atom to which they are attached to form a 4- to 6-membered heterocyclyl substituted by 1-5 $R_4$ groups, wherein at least one $R_4$ group is $-CO_2H$. In some variations, the heterocyclyl is saturated and has no additional heteroatoms. In some embodiments, $R_2$ and $R_3$ are taken together with the nitrogen atom to which they are attached to form a 4-membered heterocyclyl substituted by 1-5 $R_4$ groups, wherein at least one $R_4$ group is $-CO_2H$. In some embodiments, $R_2$ and $R_3$ are taken together with the nitrogen atom to which they are attached to form a 5-membered heterocyclyl substituted by 1-5 $R_4$ groups, wherein at least one $R_4$ group is $-CO_2H$. In some embodiments, $R_2$ and $R_3$ are taken together with the nitrogen atom to which they are attached to form a 6-membered heterocyclyl substituted by 1-5 $R_4$ groups, wherein at least one $R_4$ group is $-CO_2H$. In some embodiments, $R_2$ and $R_3$ are taken together with the nitrogen atom to which they are attached to form a 4- to 6-membered heterocyclyl substituted by 1-3 $R_4$ groups, wherein at least one $R_4$ group is $-CO_2H$. In some embodiments, the heterocyclyl is azetidinyl, pyrrolidinyl, or piperidinyl, each of which is substituted by 1-5 $R_4$ groups, wherein at least one $R_4$ group is $-CO_2H$.

In some embodiments, each $R_4$ is independently $-CO_2H$, halo, $C_1$-$C_6$ alkyl, $C_1$-$C_6$ haloalkyl, or $C_1$-$C_6$ alkoxy. In some embodiments, each $R_4$ is independently $-CO_2H$, halo, $C_1$-$C_3$ alkyl, $C_1$-$C_3$ haloalkyl, or $C_1$-$C_3$ alkoxy. In some embodiments, each $R_4$ is independently $-CO_2H$, methyl, F, Cl, $-CF_3$, or $-OCH_3$.

In some embodiments, $R_4$ is $-CO_2H$.

In some embodiments, $R_4$ is halo. In some embodiments, $R_4$ is F, Cl, or Br. In some embodiments, $R_4$ is F. In some embodiments, $R_4$ is Cl.

In some embodiments, $R_4$ is $C_1$-$C_6$ alkyl. In some embodiments, $R_4$ is $C_1$-$C_3$ alkyl. In some embodiments, $R_4$ is methyl, ethyl, n-propyl, or isopropyl. In some embodiments, $R_4$ is methyl. In some embodiments, $R_4$ is ethyl.

In some embodiments, $R_4$ is $C_1$-$C_6$ haloalkyl. In some embodiments, $R_4$ is $C_1$-$C_6$ haloalkyl containing 1-13 halogen atoms. In some embodiments, $R_4$ is $C_1$-$C_3$ haloalkyl. In some embodiments, $R_4$ is $C_1$-$C_3$ haloalkyl containing 1-7 halogen atoms. In some embodiments, $R_4$ is $-CF_3$, $-CHF_2$, $-CH_2F$, $-CCl_3$, $-CHCl_2$, $-CH_2Cl$, $-CF_2Cl$, $-CFCl_2$, $-CH_2CF_3$, $-CH_2CHF_2$, or $-CH_2CCl_3$. In some embodiments, $R_4$ is $-CF_3$.

In some embodiments, $R_4$ is $C_1$-$C_6$ alkoxy. In some embodiments, $R_4$ is $C_1$-$C_3$ alkoxy. In some embodiments, $R_4$ is $-OCH_3$, $-OCH_2CH_3$, $-OCH_2CH_2CH_3$, or $-OCH(CH_3)_2$. In some embodiments, $R_4$ is $-OCH_3$.

In some embodiments,

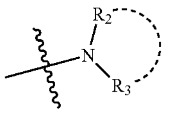 is 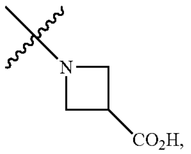

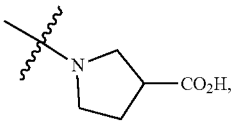 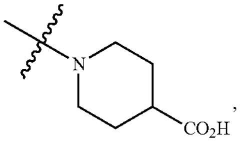,

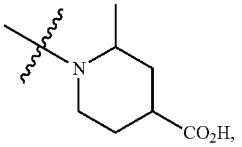 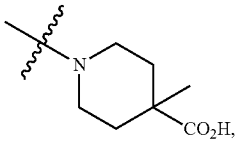

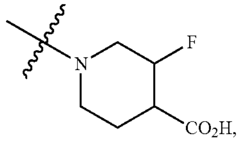 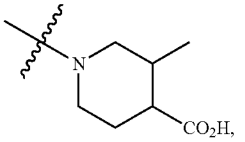 or

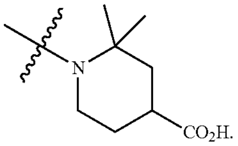

In some embodiments, n is 0. In some embodiments, n is 1.

In some embodiments, $R_5$ and $R_6$ are independently H or $C_1$-$C_6$ alkyl. In some embodiments, $R_5$ and $R_6$ are independently H or $C_1$-$C_3$ alkyl. In some embodiments, $R_5$ and $R_6$ are independently H or methyl.

In some embodiments, $R_5$ is H. In some embodiments, $R_5$ is $C_1$-$C_6$ alkyl. In some embodiments, $R_5$ is $C_1$-$C_3$ alkyl. In some embodiments, $R_5$ is methyl, ethyl, n-propyl, or isopropyl.

In some embodiments, $R_6$ is H. In some embodiments, $R_6$ is $C_1$-$C_6$ alkyl. In some embodiments, $R_6$ is $C_1$-$C_3$ alkyl. In some embodiments, $R_6$ is methyl, ethyl, n-propyl, or isopropyl.

In some embodiments, $R_5$ and $R_6$ are each H. In some embodiments, one of $R_5$ and $R_6$ is H and the other of $R_5$ and $R_6$ is $C_1$-$C_6$ alkyl. In some embodiments, one of $R_5$ and $R_6$ is H and the other of $R_5$ and $R_6$ is $C_1$-$C_3$ alkyl. In some embodiments, one of $R_5$ and $R_6$ is H and the other of $R_5$ and $R_6$ is methyl, ethyl, n-propyl, or isopropyl. In some embodiments, one of $R_5$ and $R_6$ is H and the other of $R_5$ and $R_6$ is methyl. In some embodiments, $-CR_5R_6-$ is $-CH_2-$, $-CH(CH_3)-$, or $-C(CH_3)_2-$.

In some embodiments, the compound of Formula (I) is a compound of Formula (II):

(II)

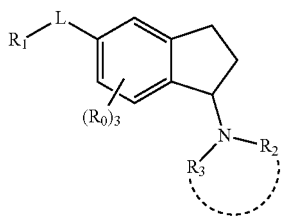

wherein L, $R_0$, $R_1$, $R_2$, and $R_3$ are as described for Formula (I).

In some embodiments, the compound of Formula (II) is a compound of Formula (IIA) or (IIB):

(IIA)

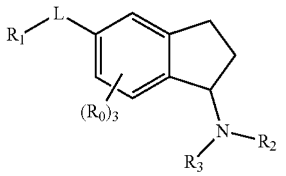

(IIB)

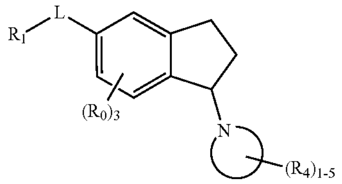

wherein L, $R_0$, $R_1$, $R_2$, $R_3$, and $R_4$ are as described for Formula (I), and

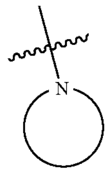

is a 4- to 6-membered heterocyclyl.

In some embodiments, the compound of Formula (II) is a compound of Formula (IIa), (IIb), (IIc), (IId), (IIe), or (IIf):

(IIa)

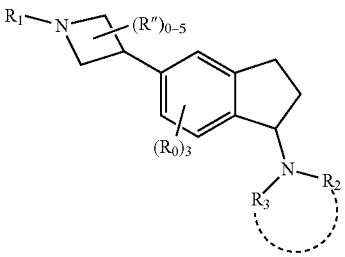

-continued (IIb)

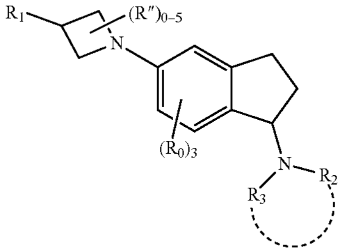

(IIc)

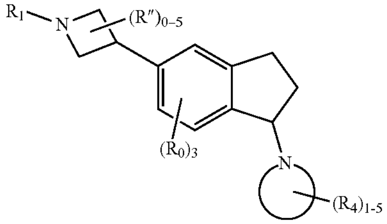

(IId)

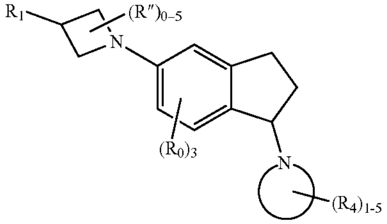

(IIe)

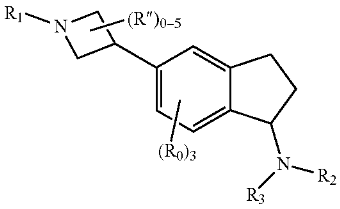

(IIf)

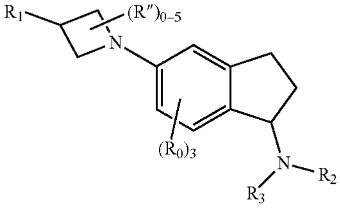

wherein $R_0$, $R_1$, $R_2$, $R_3$, and $R_4$ are as described for Formula (I);

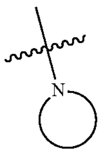 [SMILES: *N]

is a 4- to 6-membered heterocyclyl; and each R" is independently selected from halo and $C_1$-$C_6$ alkyl.

In some embodiments, the compound of Formula (II) is a compound of Formula (II-1), (11-2), or (II-3):

(II-1)

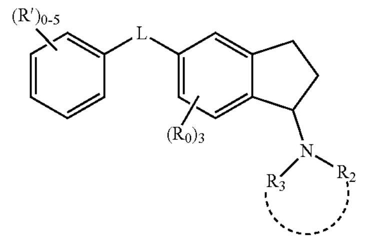

(II-2)

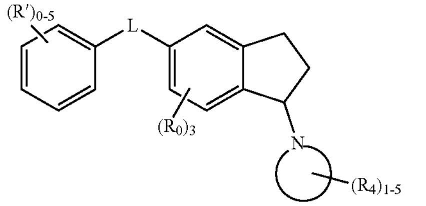

(II-3)

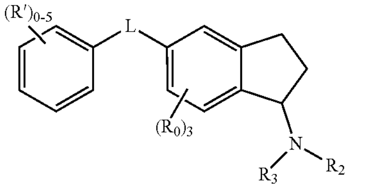

wherein L, $R_0$, $R_2$, $R_3$, $R_4$, and R' are as described for Formula (I), and

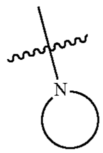 [SMILES: *N]

is a 4- to 6-membered heterocyclyl.

In some embodiments, the compound of Formula (II) is a compound of Formula (II-1a), (II-1b), (II-2a), (II-2b), (II-3a), or (II-3b):

(II-1a)

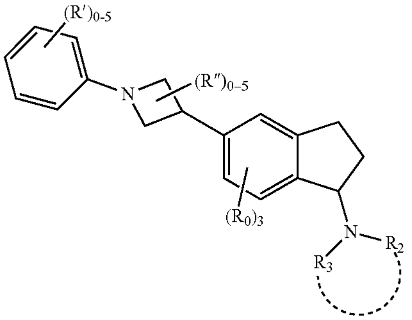

-continued (II-1b)

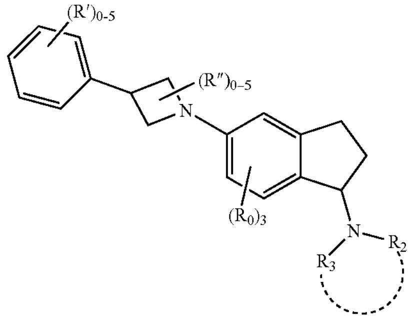

(II-2a)

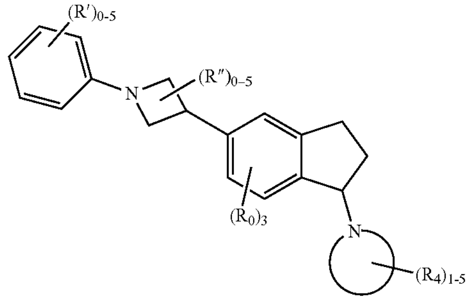

(II-2b)

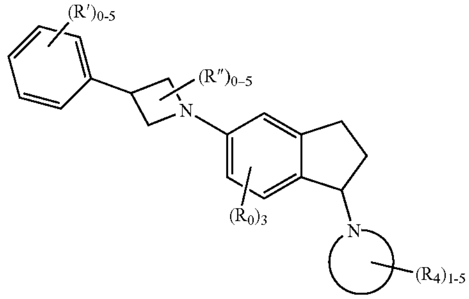

(II-3a)

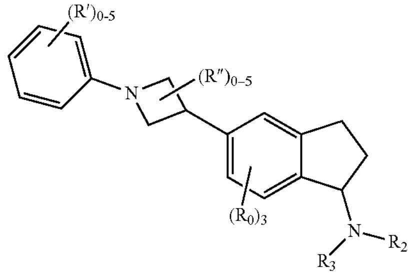

(II-3b)

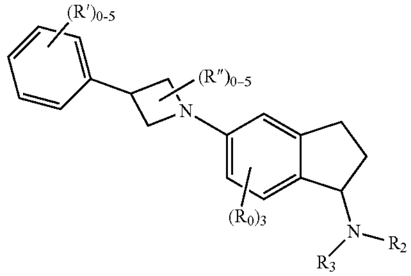

wherein $R_0$, $R_2$, $R_3$, $R_4$, and R' are as described for Formula (I);

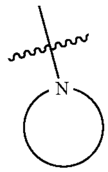 [SMILES: *N]

is a 4- to 6-membered heterocyclyl; and each R" is independently selected from halo and $C_1$-$C_6$ alkyl.

In some embodiments, the compound of Formula (I) is a compound of Formula (III):

(III)

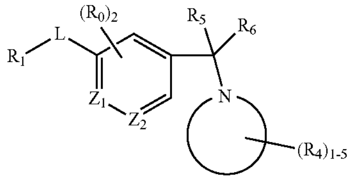

wherein L, $R_0$, $Z_1$, $Z_2$, $R_4$, $R_5$, and $R_6$ are as described for Formula (I), and

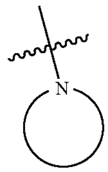

is a 4- to 6-membered heterocyclyl.

In some embodiments, the compound of Formula (III) is a compound of Formula (IIIA), (IIIB), (IIC), or (IIID):

(IIIA)

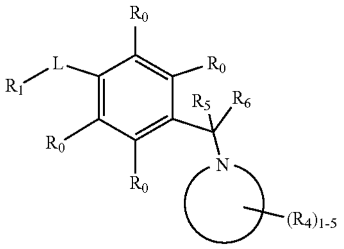

(IIIB)

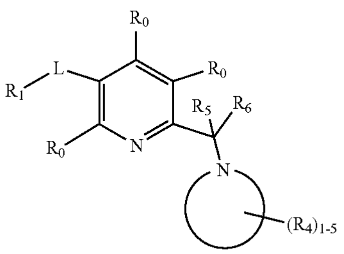

-continued (IIIC)

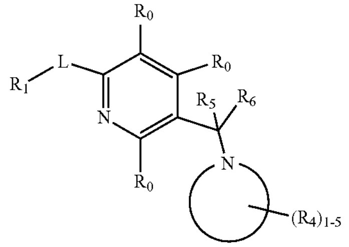

(IIID)

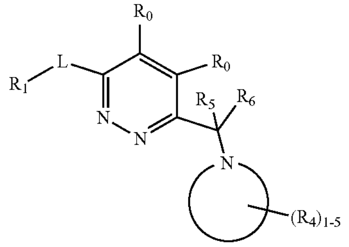

wherein L, $R_0$, $R_1$, $R_4$, $R_5$, and $R_6$ are as described for Formula (I), and

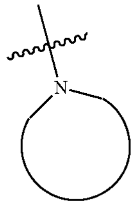

is a 4- to 6-membered heterocyclyl.

In some embodiments, the compound of Formula (III) is a compound of Formula (IIIa), (IIIb), (IIIc), (IIId), (IIIe), (IIIf), (IIIg), or (IIIh):

(IIIa)

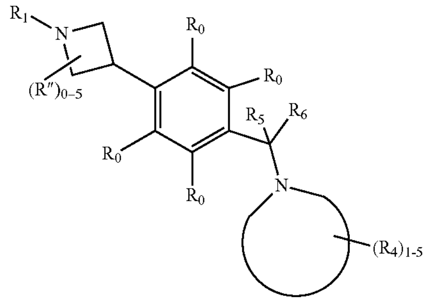

(IIIb)

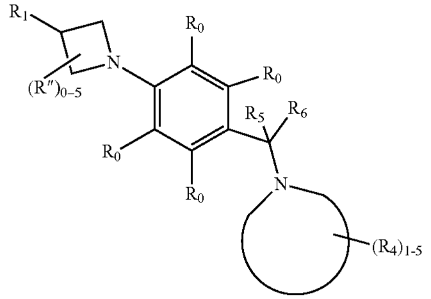

-continued
(IIIc)
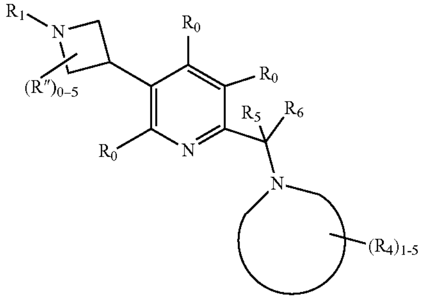
(IIId)
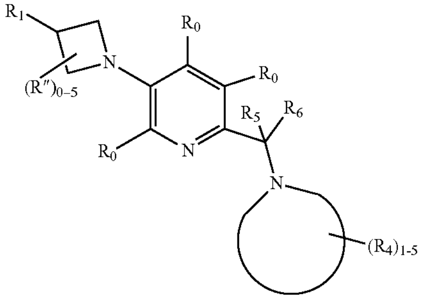
(IIIe)
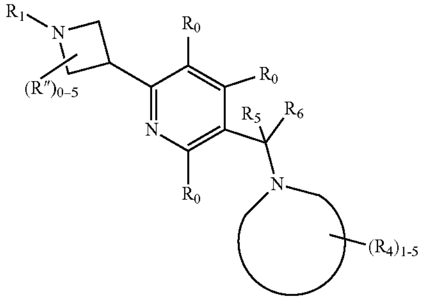
(IIIf)
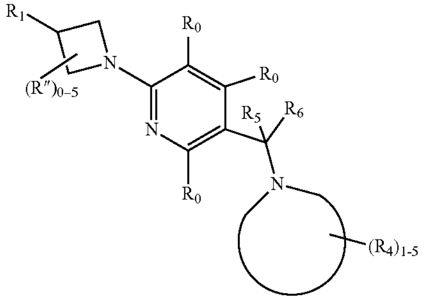
(IIIg)
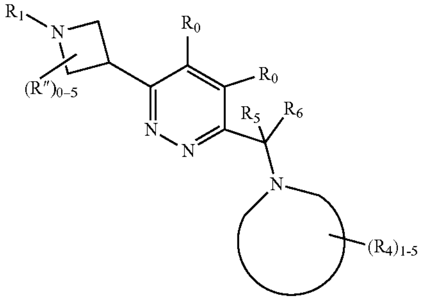
-continued
(IIIh)
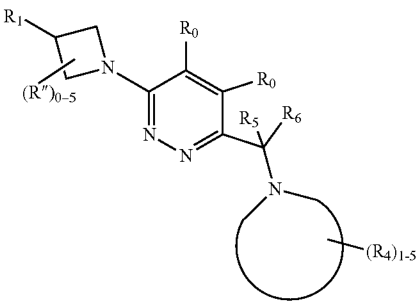
wherein $R_0$, $R_1$, $R_4$, $R_5$, and $R_6$ are as described for Formula (I);
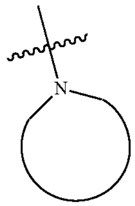
is a 4- to 6-membered heterocyclyl; and each R" is independently selected from halo and $C_1$-$C_6$ alkyl.
In some embodiments, the compound of Formula (III) is a compound of Formula (III-1), (III-2), (III-3), or (III-4):
(III-1)
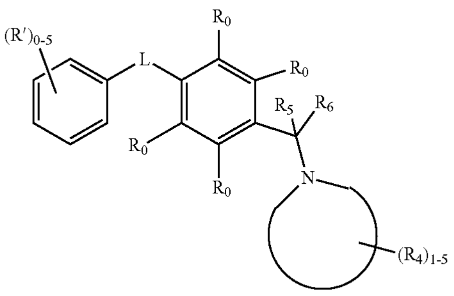
(III-2)
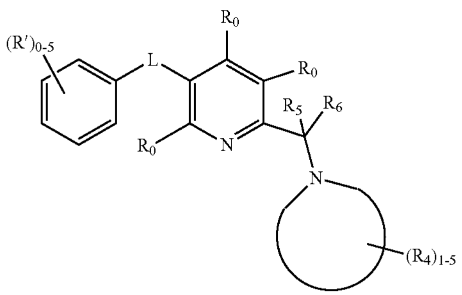

-continued
(III-3)
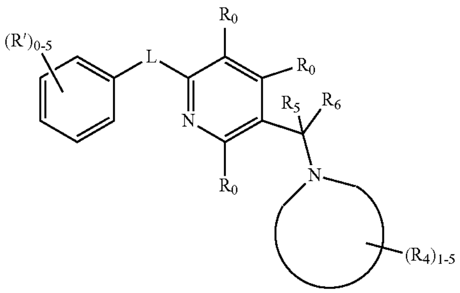
(III-4)
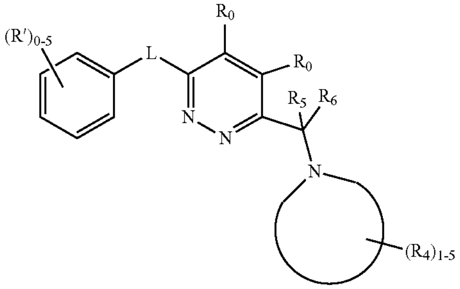
wherein L, $R_0$, $R_4$, $R_5$, $R_6$, and R' are as described for Formula (I), and
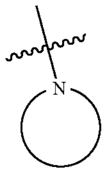 [SMILES: *N]
is a 4- to 6-membered heterocyclyl.
In some embodiments, the compound of Formula (III) is a compound of Formula (III-1a), (III-1b), (III-2a), (III-2b), (III-3a), (III-3b), (III-4a), or (III-4b):
(III-1a)
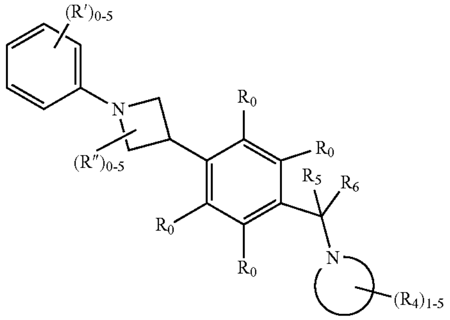
-continued
(III-1b)
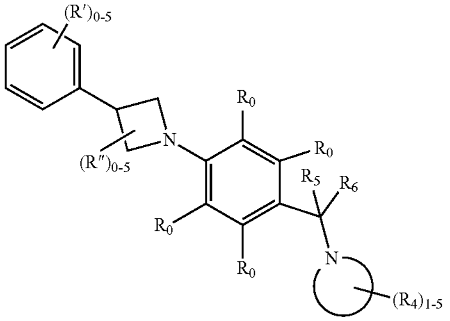
(III-2a)
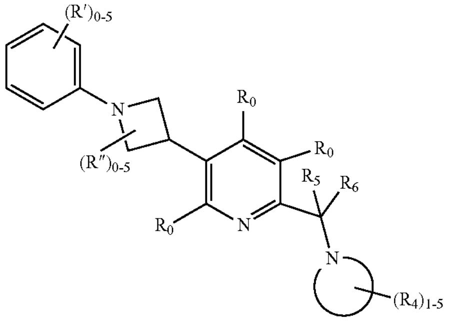
(III-2b)
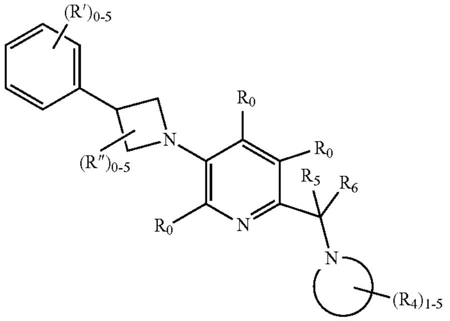
(III-3a)
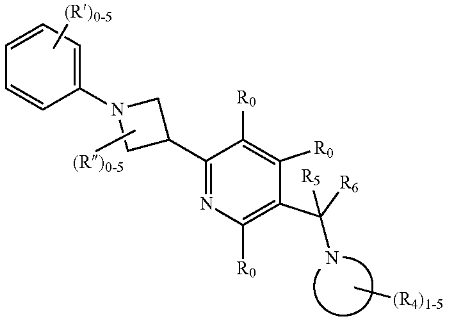
(III-3b)
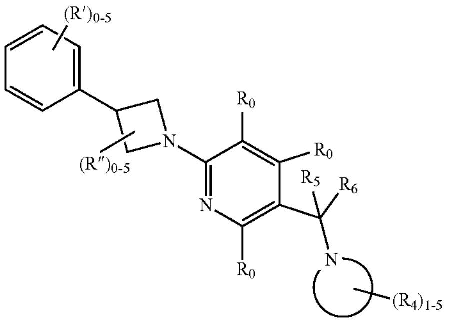

-continued
(III-4a)
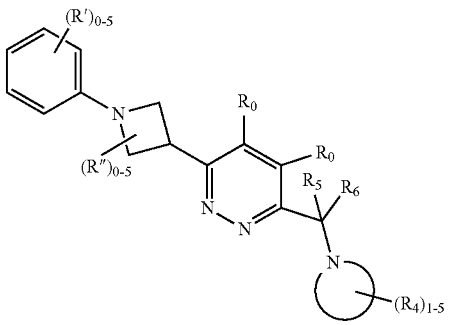
(III-4b)
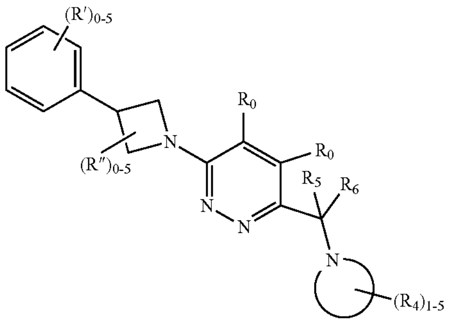
wherein $R_0$, $R_4$, $R_5$, $R_6$, and R' are as described for Formula (I);
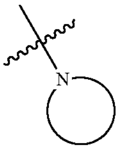 [SMILES: *N]
is a 4- to 6-membered heterocyclyl; and each R" is independently selected from halo and $C_1$-$C_6$ alkyl.
In some embodiments, the compound of Formula (III) is a compound of Formula (IV-a), (IV-b), (IV-c), (IV-d), (IV-e), or (IV-f):
(IV-a)
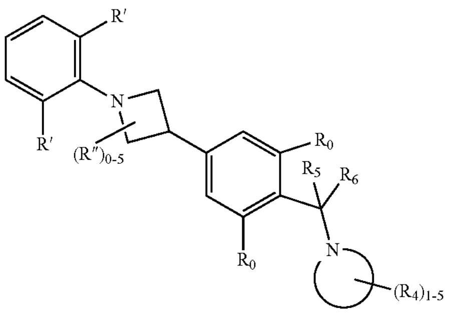
-continued
(IV-b)
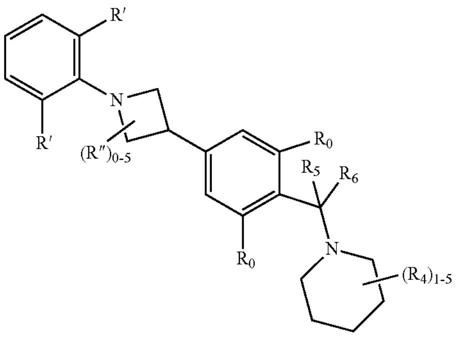
(IV-c)
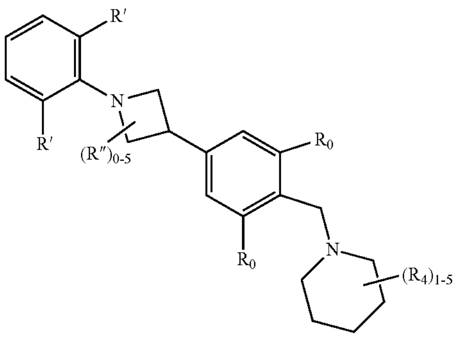
(IV-d)
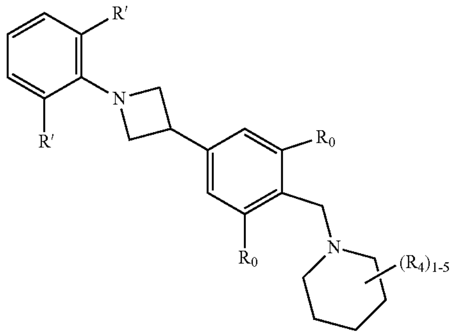
(IV-e)
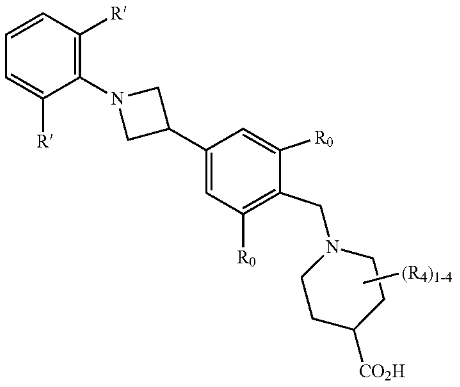

-continued (IV-f)

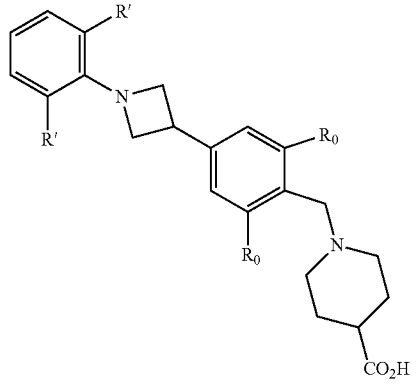

wherein $R_0$, $R_4$, $R_5$, $R_6$, and R' are as described for Formula (I);

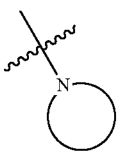 [SMILES: *N]

is a 4- to 6-membered heterocyclyl; and each R" is independently selected from halo and $C_1$-$C_6$ alkyl. In some variations, each R' is independently halo or $C_1$-$C_6$ alkyl; and each $R_0$ is independently halo or $C_1$-$C_6$ alkyl.

In the descriptions herein, it is understood that every description, variation, embodiment, or aspect of a moiety may be combined with every description, variation, embodiment, or aspect of other moieties the same as if each and every combination of descriptions is specifically and individually listed. For example, every description, variation, embodiment, or aspect provided herein with respect to Ring A of Formula (I) may be combined with every description, variation, embodiment, or aspect of L, $Z_1$, $Z_2$, $R_0$, R', $R_1$, $R_2$, $R_3$, $R_4$, $R_5$, $R_6$, x, and n the same as if each and every combination were specifically and individually listed. It is also understood that all descriptions, variations, embodiments, or aspects of Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (I), where applicable, apply equally to any of the formulae as detailed herein, such as Formulae (II), (IIA), (IIB), (IIa), (IIb), (IIc), (IId), (IIe), (IIf), (II-1), (II-2), (II-3), (II-1a), (II-1b), (II-2a), (II-2b), (II-3a), (II-3b), (III), (IIIA), (IIIB), (IIIC), (IIID), (IIIa), (IIIb), (IIIc), (IIId), (IIIe), (IIIf), (IIIg), (IIIh), (III-1), (III-2), (III-3), (III-4), (III-1a), (III-1b), (III-2a), (III-2b), (III-3a), (III-3b), (III-4a), (III-4b), (IV-a), (IV-b), (IV-c), (IV-d), (IV-e), and (IV-f) are equally described, the same as if each and every description, variation, embodiment, or aspect were separately and individually listed for all formulae.

In some embodiments, provided is a compound selected from the compounds in Table 1 or a pharmaceutically acceptable salt thereof. Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

TABLE 1

| Compound No. | Structure | Name |
| --- | --- | --- |
| 1a | 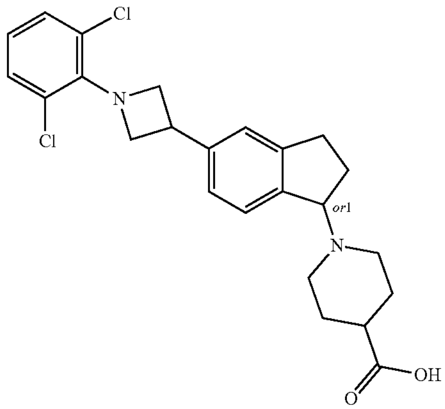 [SMILES: O=C(O)C1CCN(C2CCc3cc(C4CN(c5c(Cl)cccc5Cl)C4)ccc32)CC1] | 1-(5-(1-(2,6-dichlorophenyl)azetidin-3-yl)-2,3-dihydro-1H-inden-1-yl)piperidine-4-carboxylic acid Enantiomer 1 |

TABLE 1-continued
| Compound No. | Structure | Name |
|---|---|---|
| 1b | 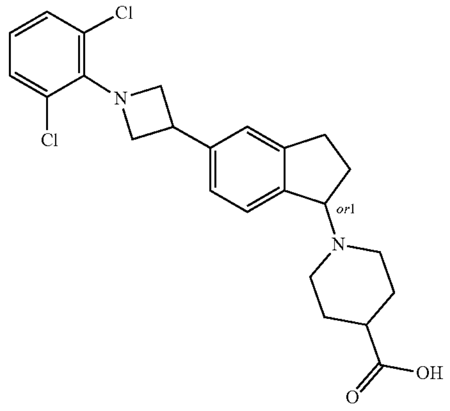 [SMILES: O=C(O)C1CCN(C2CCc3cc(C4CN(c5c(Cl)cccc5Cl)C4)ccc32)CC1] | 1-(5-(1-(2,6-dichlorophenyl)azetidin-3-yl)-2,3-dihydro-1H-inden-1-yl)piperidine-4-carboxylic acid Enantiomer 2 |
| 2a | 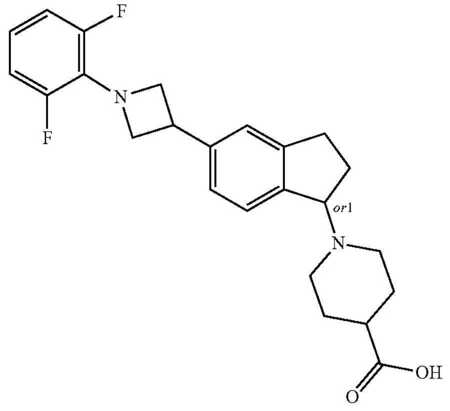 | 1-(5-(1-(2,6-difluorophenyl)azetidin-3-yl)-2,3-dihydro-1H-inden-1-yl)piperidine-4-carboxylic acid Enantiomer 1 |
| 2b | 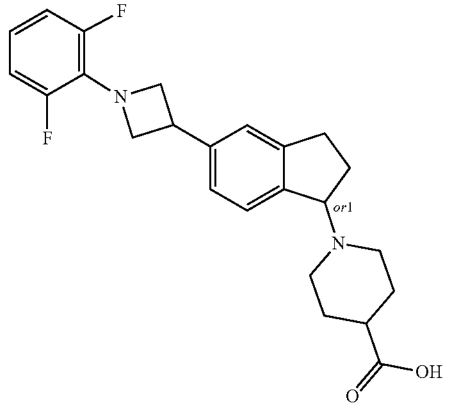 | 1-(5-(1-(2,6-difluorophenyl)azetidin-3-yl)-2,3-dihydro-1H-inden-1-yl)piperidine-4-carboxylic acid Enantiomer 2 |

TABLE 1-continued
| Compound No. | Structure | Name |
| --- | --- | --- |
| 3a | 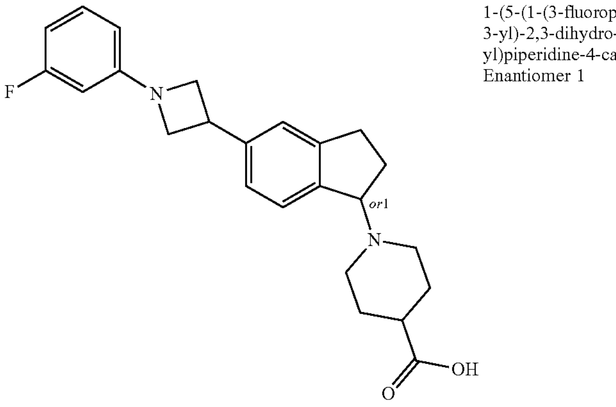 | 1-(5-(1-(3-fluorophenyl)azetidin-3-yl)-2,3-dihydro-1H-inden-1-yl)piperidine-4-carboxylic acid Enantiomer 1 |
| 3b | 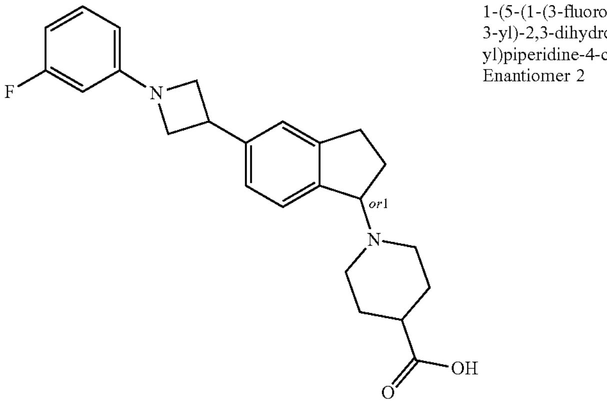 | 1-(5-(1-(3-fluorophenyl)azetidin-3-yl)-2,3-dihydro-1H-inden-1-yl)piperidine-4-carboxylic acid Enantiomer 2 |
| 4a | 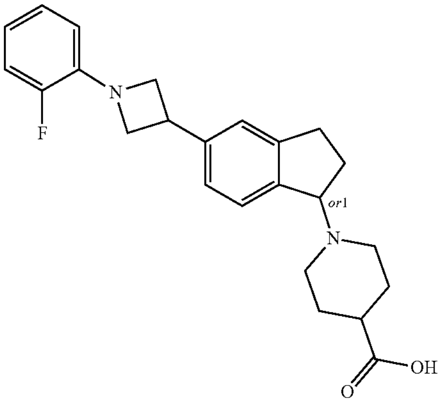 [SMILES: O=C(O)C1CCN(C2CCc3cc(C4CN(c5ccccc5F)C4)ccc32)CC1] | 1-(5-(1-(2-fluorophenyl)azetidin-3-yl)-2,3-dihydro-1H-inden-1-yl)piperidine-4-carboxylic acid Enantiomer 1 |

TABLE 1-continued

| Compound No. | Structure | Name |
| --- | --- | --- |
| 4b | 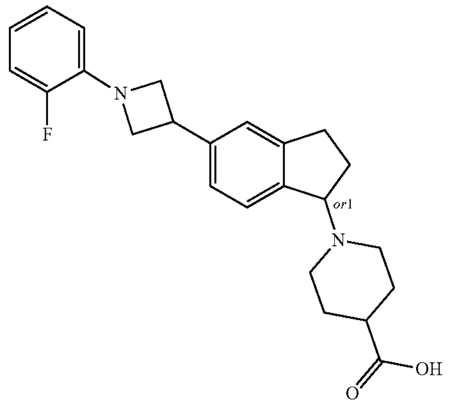 [SMILES: O=C(O)C1CCN(C2CCc3cc(C4CN(c5ccccc5F)C4)ccc32)CC1] | 1-(5-(1-(2-fluorophenyl)azetidin-3-yl)-2,3-dihydro-1H-inden-1-yl)piperidine-4-carboxylic acid Enantiomer 2 |
| 5 | 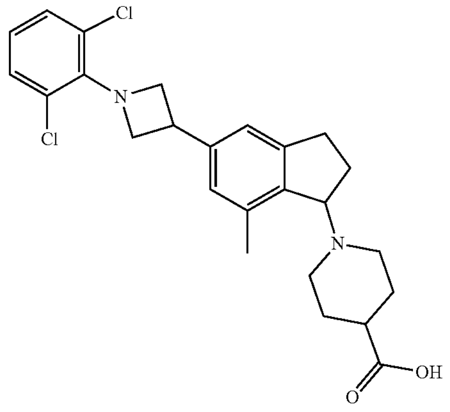 [SMILES: Cc1cc(C2CN(c3c(Cl)cccc3Cl)C2)cc2c1C(N1CCC(C(=O)O)CC1)CC2] | 1-(5-(1-(2,6-dichlorophenyl)azetidin-3-yl)-7-methyl-2,3-dihydro-1H-inden-1-yl)piperidine-4-carboxylic acid racemic |
| 6 | 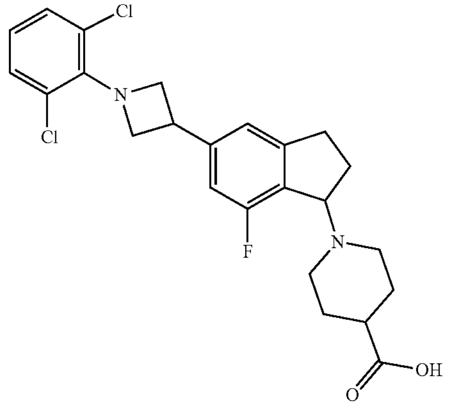 [SMILES: O=C(O)C1CCN(C2CCc3cc(C4CN(c5c(Cl)cccc5Cl)C4)cc(F)c32)CC1] | 1-(5-(1-(2,6-dichlorophenyl)azetidin-3-yl)-7-fluoro-2,3-dihydro-1H-inden-1-yl)piperidine-4-carboxylic acid racemic |
| 7 | 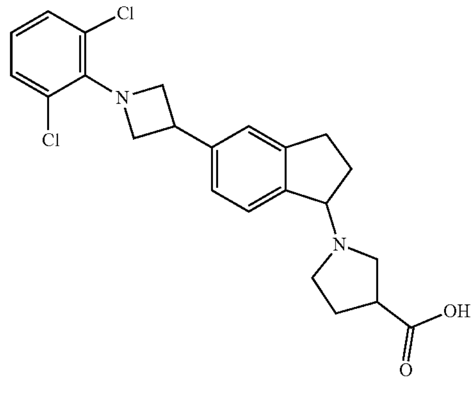 [SMILES: O=C(O)C1CCN(C2CCc3cc(C4CN(c5c(Cl)cccc5Cl)C4)ccc32)C1] | 1-(5-(1-(2,6-dichlorophenyl)azetidin-3-yl)-2,3-dihydro-1H-inden-1-yl)pyrrolidine-3-carboxylic acid |

TABLE 1-continued

| Compound No. | Structure | Name |
|---|---|---|
| 8a | 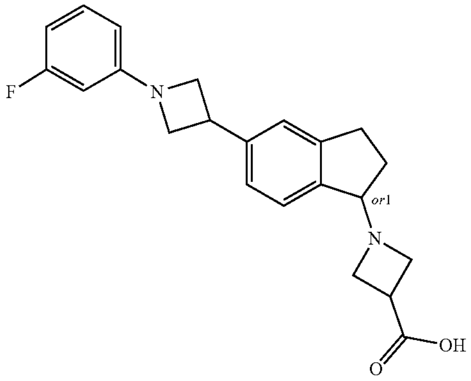 [SMILES: O=C(O)C1CN(C2CCc3cc(C4CN(c5cccc(F)c5)C4)ccc32)C1] | 1-(5-(1-(3-fluorophenyl)azetidin-3-yl)-2,3-dihydro-1H-inden-1-yl)azetidine-3-carboxylic acid Enantiomer 1 |
| 8b | 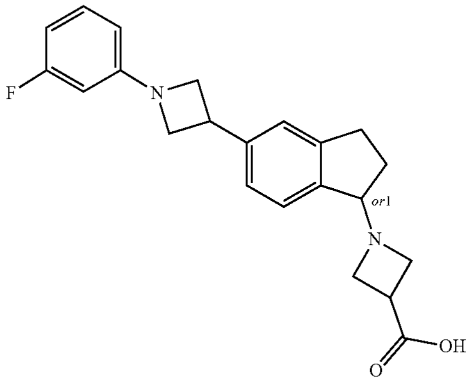 [SMILES: O=C(O)C1CN(C2CCc3cc(C4CN(c5cccc(F)c5)C4)ccc32)C1] | 1-(5-(1-(3-fluorophenyl)azetidin-3-yl)-2,3-dihydro-1H-inden-1-yl)azetidine-3-carboxylic acid Enantiomer 2 |
| 9a | 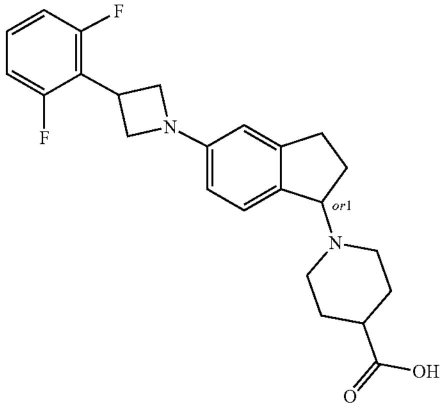 [SMILES: O=C(O)C1CCN(C2CCc3cc(N4CC(c5c(F)cccc5F)C4)ccc32)CC1] | 1-(5-(3-(2,6-difluorophenyl)azetidin-1-yl)-2,3-dihydro-1H-inden-1-yl)piperidine-4-carboxylic acid Enantiomer 1 |
| 9b | 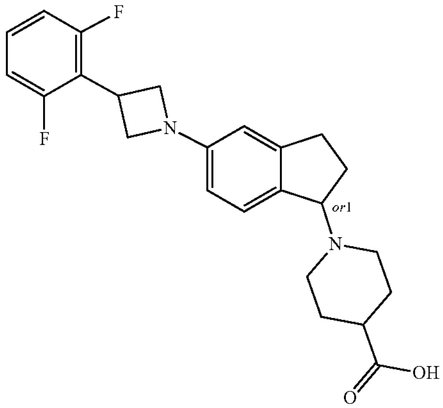 [SMILES: O=C(O)C1CCN(C2CCc3cc(N4CC(c5c(F)cccc5F)C4)ccc32)CC1] | 1-(5-(3-(2,6-difluorophenyl)azetidin-1-yl)-2,3-dihydro-1H-inden-1-yl)piperidine-4-carboxylic acid Enantiomer 2 |

TABLE 1-continued
| Compound No. | Structure | Name |
|---|---|---|
| 10a | 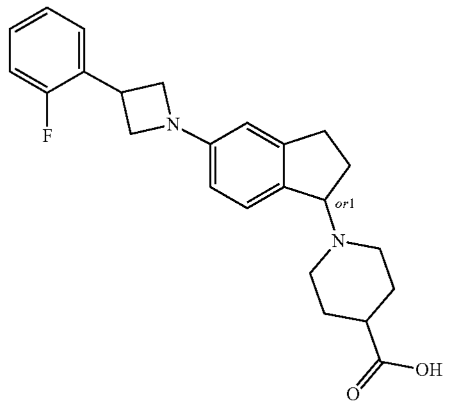 [SMILES: O=C(O)C1CCN(C2CCc3cc(N4CC(c5ccccc5F)C4)ccc32)CC1] | 1-(5-(3-(2-fluorophenyl)azetidin-1-yl)-2,3-dihydro-1H-inden-1-yl)piperidine-4-carboxylic acid Enantiomer 1 |
| 10b | 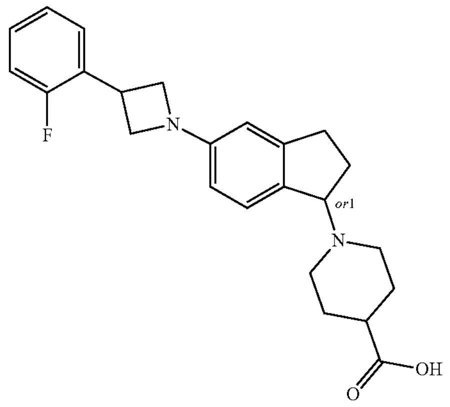 [SMILES: O=C(O)C1CCN(C2CCc3cc(N4CC(c5ccccc5F)C4)ccc32)CC1] | 1-(5-(3-(2-fluorophenyl)azetidin-1-yl)-2,3-dihydro-1H-inden-1-yl)piperidine-4-carboxylic acid Enantiomer 2 |
| 11 | 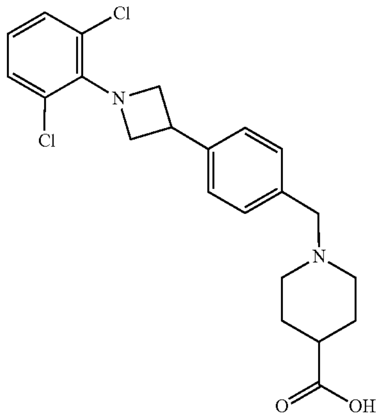 [SMILES: O=C(O)C1CCN(Cc2ccc(C3CN(c4c(Cl)cccc4Cl)C3)cc2)CC1] | 1-(4-(1-(2,6-dichlorophenyl)-azetidin-3-yl)benzyl)piperidine-4-carboxylic acid |

TABLE 1-continued
| Compound No. | Structure | Name |
| --- | --- | --- |
| 12a | 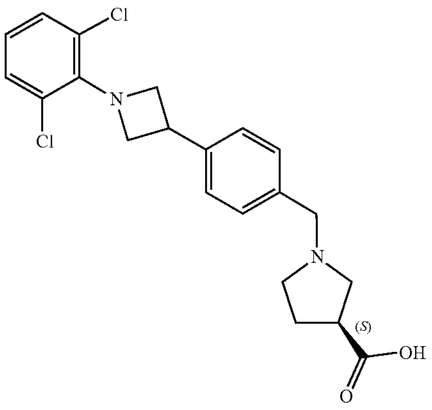 | (S)-1-(4-(1-(2,6-dichlorophenyl)azetidin-3-yl)benzyl)pyrrolidine-3-carboxylic acid |
| 12b | 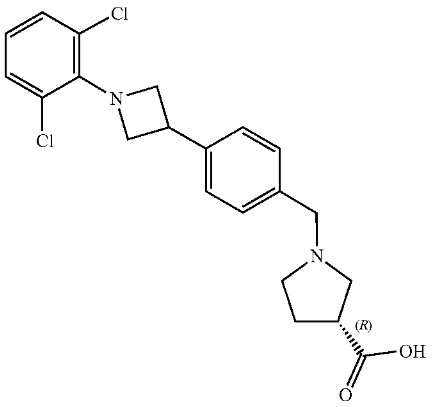 | (R)-1-(4-(1-(2,6-dichlorophenyl)azetidin-3 -yl)benzyl)pyrrolidine-3-carboxylic acid |
| 13 | 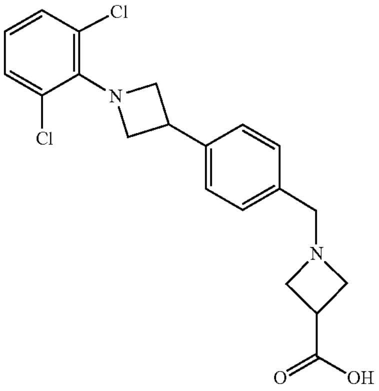 [SMILES: O=C(O)C1CN(Cc2ccc(C3CN(c4c(Cl)cccc4Cl)C3)cc2)C1] | 1-(4-(1-(2,6-dichlorophenyl)azetidin-3-yl)benzyl)azetidine-3-carboxylic acid |

TABLE 1-continued
| Compound No. | Structure | Name |
|---|---|---|
| 14 | 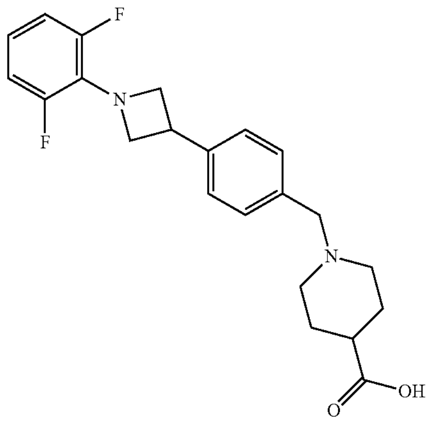 [SMILES: O=C(O)C1CCN(Cc2ccc(C3CN(c4c(F)cccc4F)C3)cc2)CC1] | 1-(4-(1-(2,6-difluorophenyl)azetidin-3-yl)benzyl)piperidine-4-carboxylic acid |
| 15 | 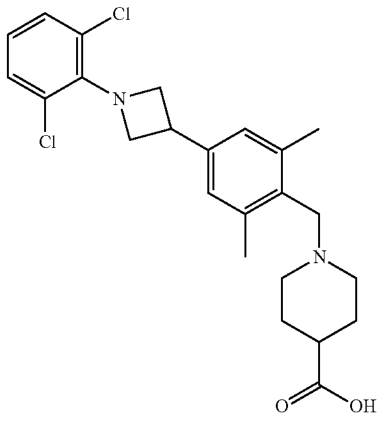 [SMILES: Cc1cc(C2CN(c3c(Cl)cccc3Cl)C2)cc(C)c1CN1CCC(C(=O)O)CC1] | 1-(4-(1-(2,6-dichlorophenyl)azetidin-3-yl)-2,6-dimethylbenzyl)piperidine-4-carboxylic acid |
| 16a | 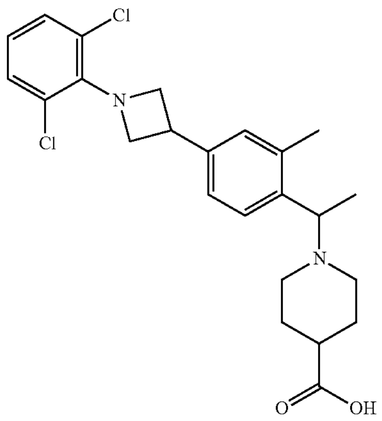 [SMILES: Cc1cc(C2CN(c3c(Cl)cccc3Cl)C2)ccc1C(C)N1CCC(C(=O)O)CC1] | 1-(1-(4-(1-(2,6-dichlorophenyl)azetidin-3-yl)-2-methylphenyl)ethyl)piperidine-4-carboxylic acid Enantiomer 1 |

TABLE 1-continued
| Compound No. | Structure | Name |
| --- | --- | --- |
| 16b | 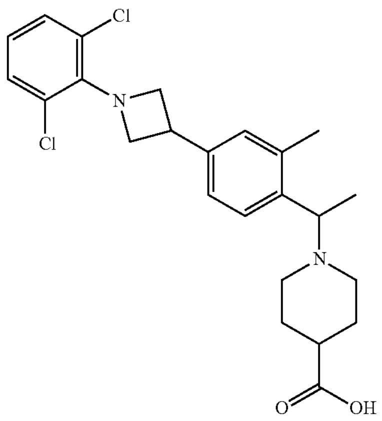 [SMILES: Cc1cc(C2CN(c3c(Cl)cccc3Cl)C2)ccc1C(C)N1CCC(C(=O)O)CC1] | 1-(1-(4-(1-(2,6-dichlorophenyl)azetidin-3-yl)-2-methylphenyl)ethyl)piperidine-4-carboxylic acid Enantiomer 2 |
| 17 | 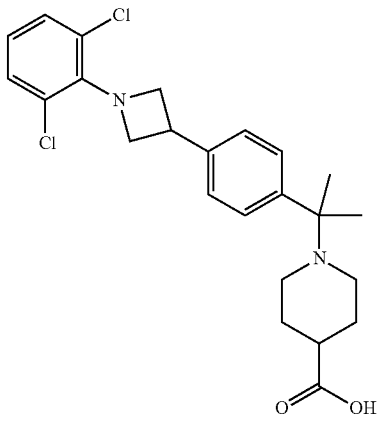 [SMILES: CC(C)(c1ccc(C2CN(c3c(Cl)cccc3Cl)C2)cc1)N1CCC(C(=O)O)CC1] | 1-(2-(4-(1-(2,6-dichlorophenyl)azetidin-3-yl)phenyl)propan-2-yl)piperidine-4-carboxylic acid |
| 18 | 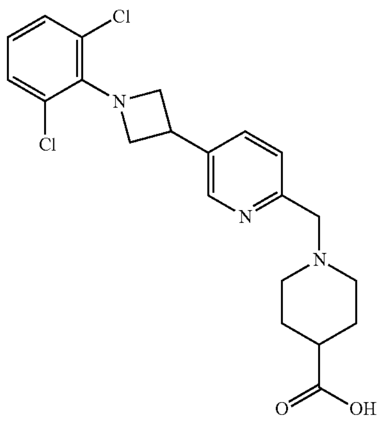 [SMILES: O=C(O)C1CCN(Cc2ccc(C3CN(c4c(Cl)cccc4Cl)C3)cn2)CC1] | 1-((5-(1-(2,6-dichlorophenyl)azetidin-3-yl)pyridin-2-yl)methyl)piperidine-4-carboxylic acid |

TABLE 1-continued
| Compound No. | Structure | Name |
| --- | --- | --- |
| 19 | 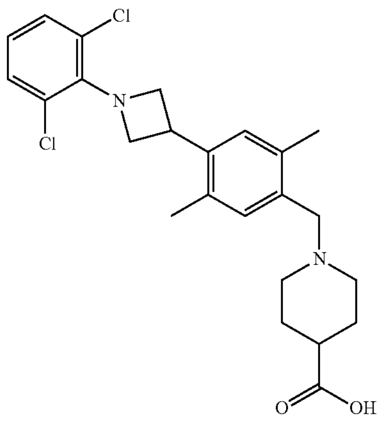 [SMILES: Cc1cc(C2CN(c3c(Cl)cccc3Cl)C2)c(C)cc1CN1CCC(C(=O)O)CC1] | 1-(4-(1-(2,6-dichlorophenyl)azetidin-3-yl)-2,5-dimethylbenzyl)piperidine-4-carboxylic acid |
| 20 | 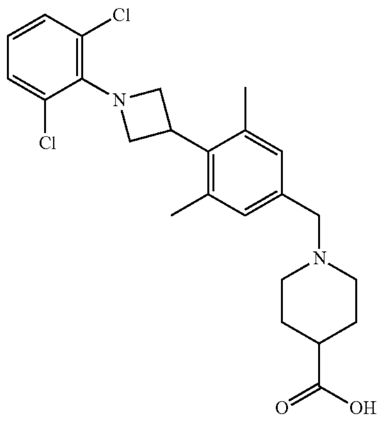 [SMILES: Cc1cc(CN2CCC(C(=O)O)CC2)cc(C)c1C1CN(c2c(Cl)cccc2Cl)C1] | 1-(4-(1-(2,6-dichlorophenyl)azetidin-3-yl)-3,5-dimethylbenzyl)piperidine-4-carboxylic acid |
| 21 | 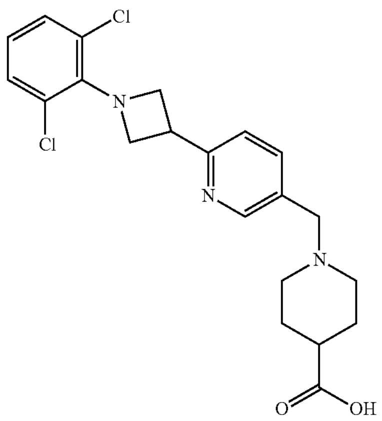 [SMILES: O=C(O)C1CCN(Cc2ccc(C3CN(c4c(Cl)cccc4Cl)C3)nc2)CC1] | 1-((6-(1-(2,6-dichlorophenyl)azetidin-3-yl)pyridin-3-yl)methyl)piperidine-4-carboxylic acid |

TABLE 1-continued
| Compound No. | Structure | Name |
|---|---|---|
| 22 | 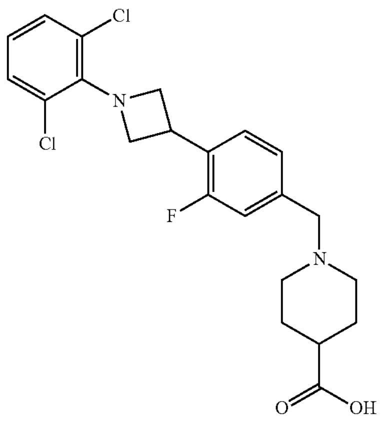 [SMILES: O=C(O)C1CCN(Cc2ccc(C3CN(c4c(Cl)cccc4Cl)C3)c(F)c2)CC1] | 1-(4-(1-(2,6-dichlorophenyl)azetidin-3-yl)-3-fluorobenzyl)piperidine-4-carboxylic acid |
| 23 | 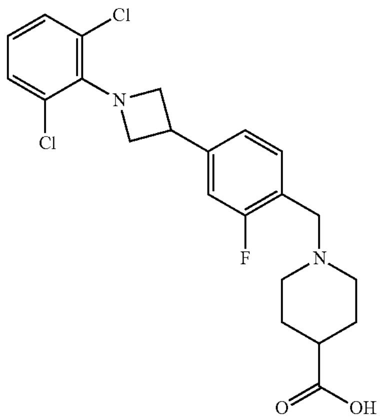 [SMILES: O=C(O)C1CCN(Cc2ccc(C3CN(c4c(Cl)cccc4Cl)C3)cc2F)CC1] | 1-(4-(1-(2,6-dichlorophenyl)azetidin-3-yl)-2-fluorobenzyl)piperidine-4-carboxylic acid |
| 24 | 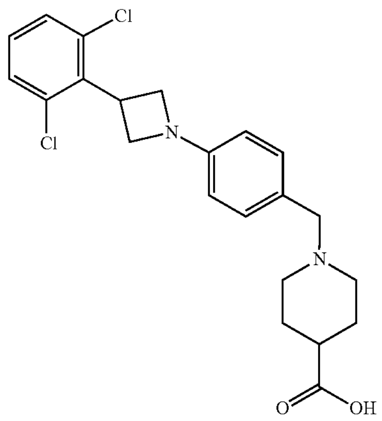 [SMILES: O=C(O)C1CCN(Cc2ccc(N3CC(c4c(Cl)cccc4Cl)C3)cc2)CC1] | 1-(4-(3-(2,6-dichlorophenyl)azetidin-1-yl)benzyl)piperidine-4-carboxylic acid |

TABLE 1-continued
| Compound No. | Structure | Name |
|---|---|---|
| 25 | 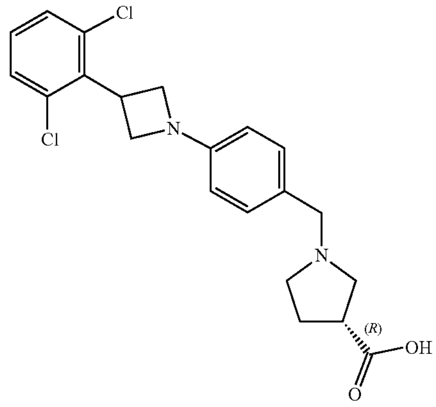 | (R)-1-(4-(3-(2,6-dichlorophenyl)azetidin-1-yl)benzyl)pyrrolidine-3-carboxylic acid |
| 26 | 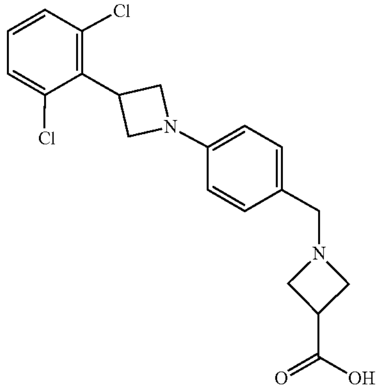 [SMILES: O=C(O)C1CN(Cc2ccc(N3CC(c4c(Cl)cccc4Cl)C3)cc2)C1] | 1-(4-(3-(2,6-dichlorophenyl)azetidin-1-yl)benzyl)azetidine-3-carboxylic acid |
| 27 | 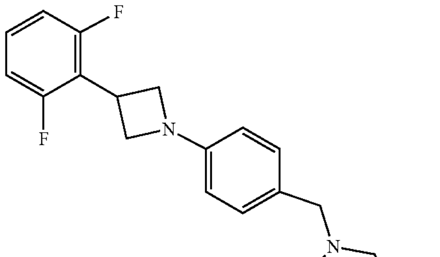 | 1-(4-(3-(2,6-difluorophenyl)azetidin-1-yl)benzyl)piperidine-4-carboxylic acid |

TABLE 1-continued
| Compound No. | Structure | Name |
|---|---|---|
| 28 | 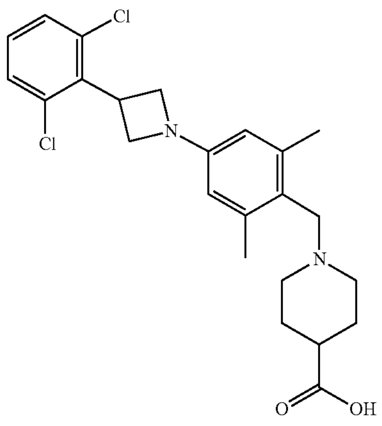 [SMILES: Cc1cc(N2CC(c3c(Cl)cccc3Cl)C2)cc(C)c1CN1CCC(C(=O)O)CC1] | 1-(4-(3-(2,6-dichlorophenyl)azetidin-1-yl)-2,6-dimethylbenzyl)piperidine-4-carboxylic acid |
| 29 | 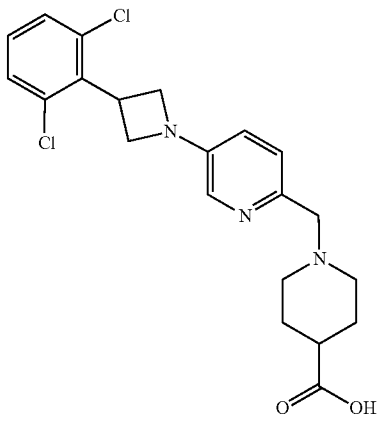 [SMILES: O=C(O)C1CCN(Cc2ccc(N3CC(c4c(Cl)cccc4Cl)C3)cn2)CC1] | 1-((5-(3-(2,6-dichlorophenyl)azetidin-1-yl)pyridin-2-yl)methyl)piperidine-4-carboxylic acid |
| 30 | 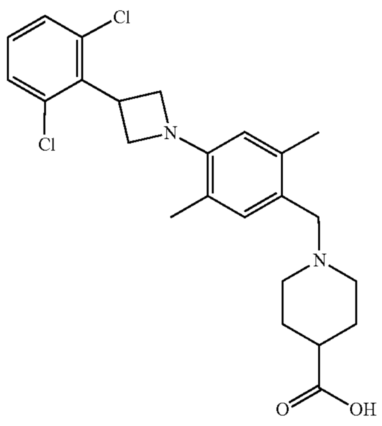 [SMILES: Cc1cc(N2CC(c3c(Cl)cccc3Cl)C2)c(C)cc1CN1CCC(C(=O)O)CC1] | 1-(4-(3-(2,6-dichlorophenyl)azetidin-1-yl)-2,5-dimethylbenzyl)piperidine-4-carboxylic acid |

TABLE 1-continued
| Compound No. | Structure | Name |
|---|---|---|
| 31 | 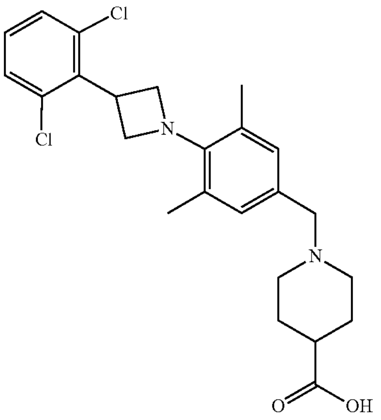 [SMILES: Cc1cc(CN2CCC(C(=O)O)CC2)cc(C)c1N1CC(c2c(Cl)cccc2Cl)C1] | 1-(4-(3-(2,6-dichlorophenyl)azetidin-1-yl)-3,5-dimethylbenzyl)piperidine-4-carboxylic acid |
| 32 | 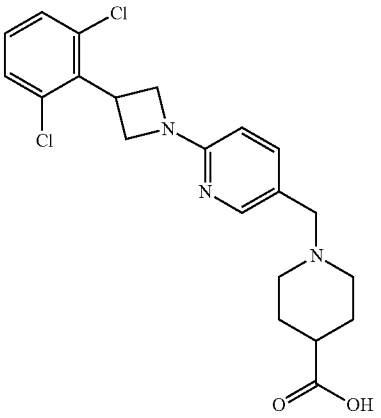 [SMILES: O=C(O)C1CCN(Cc2ccc(N3CC(c4c(Cl)cccc4Cl)C3)nc2)CC1] | 1-((6-(3-(2,6-dichlorophenyl)azetidin-1-yl)pyridin-3-yl)methyl)piperidine-4-carboxylic acid |
| 33 | 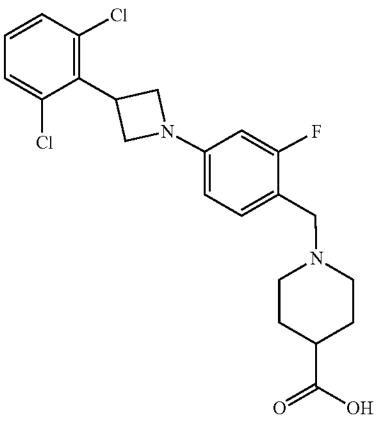 [SMILES: O=C(O)C1CCN(Cc2ccc(N3CC(c4c(Cl)cccc4Cl)C3)cc2F)CC1] | 1-(4-(3-(2,6-dichlorophenyl)azetidin-1-yl)-2-fluorobenzyl)piperidine-4-carboxylic acid |

TABLE 1-continued
| Compound No. | Structure | Name |
|---|---|---|
| 34 | 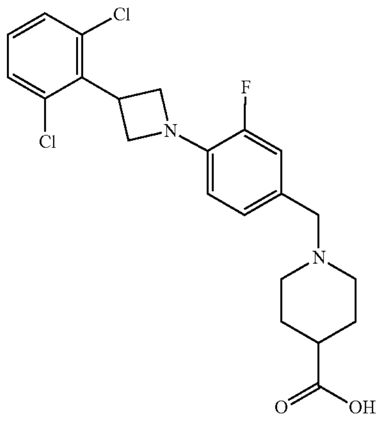 [SMILES: O=C(O)C1CCN(Cc2ccc(N3CC(c4c(Cl)cccc4Cl)C3)c(F)c2)CC1] | 1-(4-(3-(2,6-dichlorophenyl)azetidin-1-yl)-3-fluorobenzyl)piperidine-4-carboxylic acid |
| 35 | 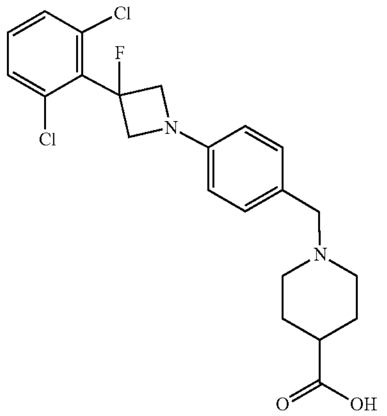 [SMILES: O=C(O)C1CCN(Cc2ccc(N3CC(F)(c4c(Cl)cccc4Cl)C3)cc2)CC1] | 1-(4-(3-(2,6-dichlorophenyl)-3-fluoroazetidin-1-yl)benzyl)-piperidine-4-carboxylic acid |
| 36 | 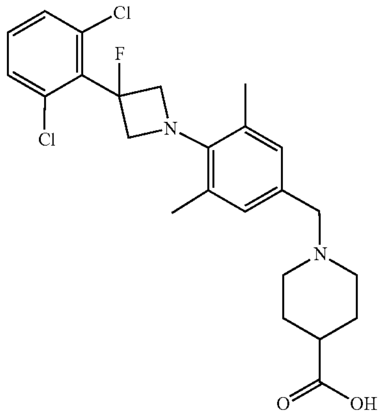 [SMILES: Cc1cc(CN2CCC(C(=O)O)CC2)cc(C)c1N1CC(F)(c2c(Cl)cccc2Cl)C1] | 1-(4-(3-(2,6-dichlorophenyl)-3-fluoroazetidin-1-yl)-3,5-dimethylbenzyl)piperidine-4-carboxylic acid |

TABLE 1-continued
| Compound No. | Structure | Name |
|---|---|---|
| 37 | 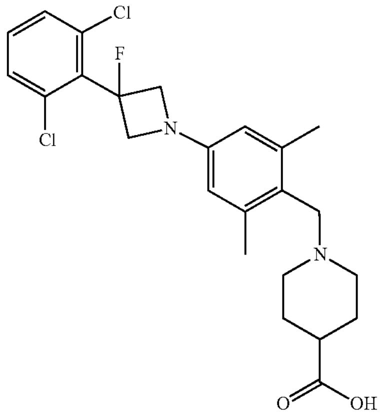 [SMILES: Cc1cc(N2CC(F)(c3c(Cl)cccc3Cl)C2)cc(C)c1CN1CCC(C(=O)O)CC1] | 1-(4-(3-(2,6-dichlorophenyl)-3-fluoroazetidin-1-yl)-2,6-dimethylbenzyl)piperidine-4-carboxylic acid |
| 38 | 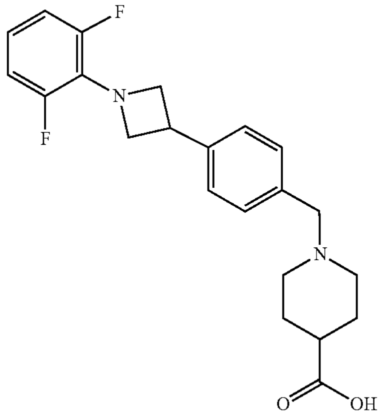 [SMILES: O=C(O)C1CCN(Cc2ccc(C3CN(c4c(F)cccc4F)C3)cc2)CC1] | 1-(4-(1-(2,6-difluorophenyl)azetidin-3-yl)benzyl)piperidine-4-carboxylic acid |
| 39 | 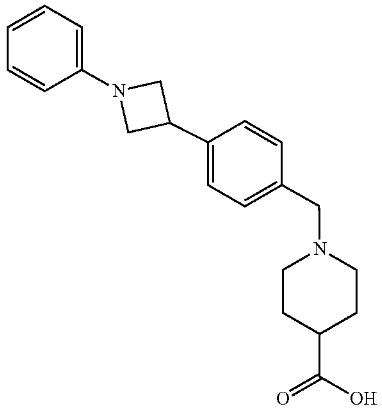 [SMILES: O=C(O)C1CCN(Cc2ccc(C3CN(c4ccccc4)C3)cc2)CC1] | 1-(4-(1-phenylazetidin-3-yl)benzyl)piperidine-4-carboxylic acid |

TABLE 1-continued
| Compound No. | Structure | Name |
| --- | --- | --- |
| 40 | 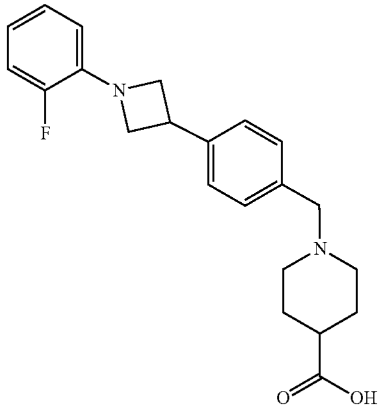 [SMILES: O=C(O)C1CCN(Cc2ccc(C3CN(c4ccccc4F)C3)cc2)CC1] | 1-(4-(1-(2-fluorophenyl)azetidin-3-yl)benzyl)piperidine-4-carboxylic acid |
| 41 | 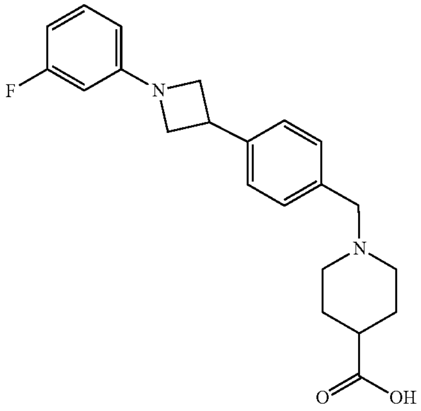 [SMILES: O=C(O)C1CCN(Cc2ccc(C3CN(c4cccc(F)c4)C3)cc2)CC1] | 1-(4-(1-(3-fluorophenyl)azetidin-3-yl)benzyl)piperidine-4-carboxylic acid |
| 42 | 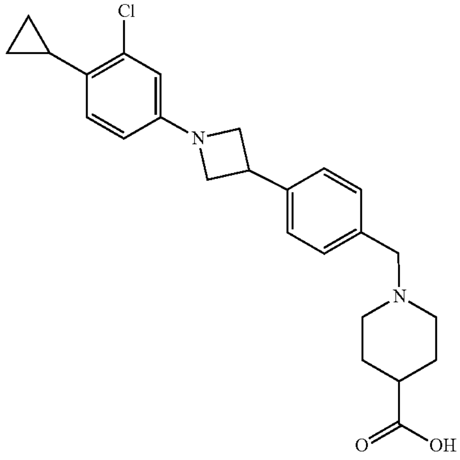 [SMILES: O=C(O)C1CCN(Cc2ccc(C3CN(c4ccc(C5CC5)c(Cl)c4)C3)cc2)CC1] | 1-(4-(1-(3-chloro-4-cyclopropylphenyl)azetidin-3-yl)benzyl)piperidine-4-carboxylic acid |

TABLE 1-continued
| Compound No. | Structure | Name |
| --- | --- | --- |
| 43 | 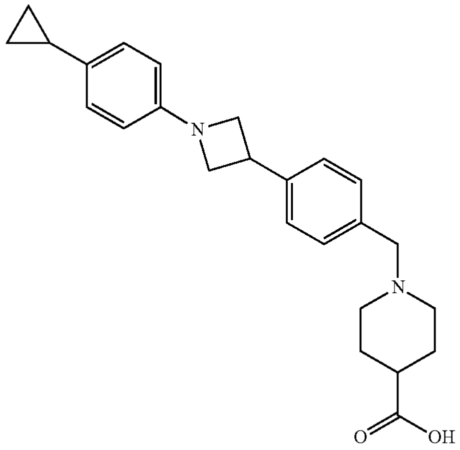 [SMILES: O=C(O)C1CCN(Cc2ccc(C3CN(c4ccc(C5CC5)cc4)C3)cc2)CC1] | 1-(4-(1-(4-cyclopropylphenyl)azetidin-3-yl)benzyl)piperidine-4-carboxylic acid |
| 44 | 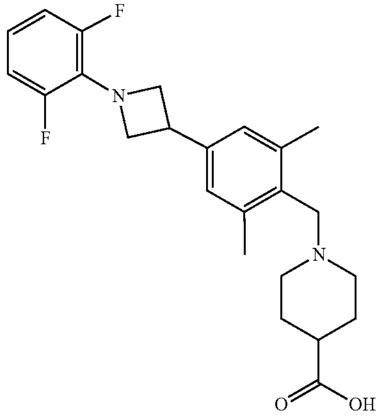 [SMILES: Cc1cc(C2CN(c3c(F)cccc3F)C2)cc(C)c1CN1CCC(C(=O)O)CC1] | 1-(4-(1-(2,6-difluorophenyl)azetidin-3-yl)-2,6-dimethylbenzyl)piperidine-4-carboxylic acid |
| 45 | 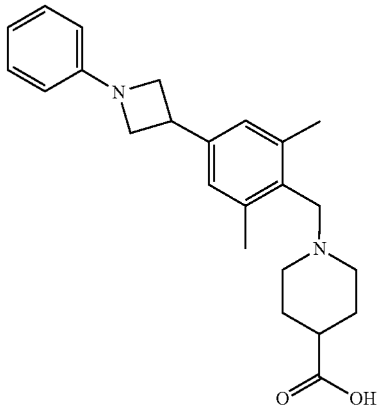 [SMILES: Cc1cc(C2CN(c3ccccc3)C2)cc(C)c1CN1CCC(C(=O)O)CC1] | 1-(2,6-dimethyl-4-(1-phenylazetidin-3-yl)benzyl)piperidine-4-carboxylic acid |

TABLE 1-continued
| Compound No. | Structure | Name |
| --- | --- | --- |
| 46 | 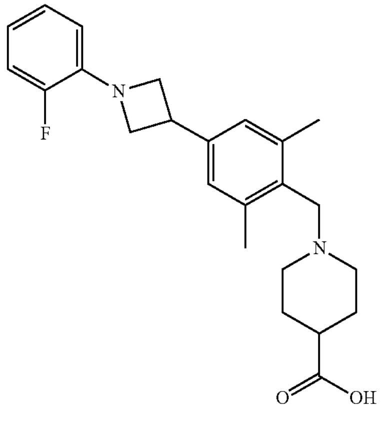 [SMILES: Cc1cc(C2CN(c3ccccc3F)C2)cc(C)c1CN1CCC(C(=O)O)CC1] | 1-(4-(1-(2-fluorophenyl)azetidin-3-yl)-2,6-dimethylbenzyl)piperidine-4-carboxylic acid |
| 47 | 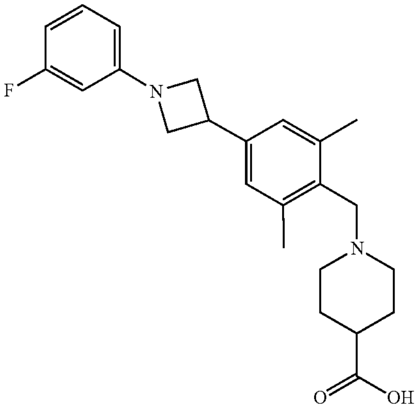 [SMILES: Cc1cc(C2CN(c3cccc(F)c3)C2)cc(C)c1CN1CCC(C(=O)O)CC1] | 1-(4-(1-(3-fluorophenyl)azetidin-3-yl)-2,6-dimethylbenzyl)piperidine-4-carboxylic acid |
| 48 | 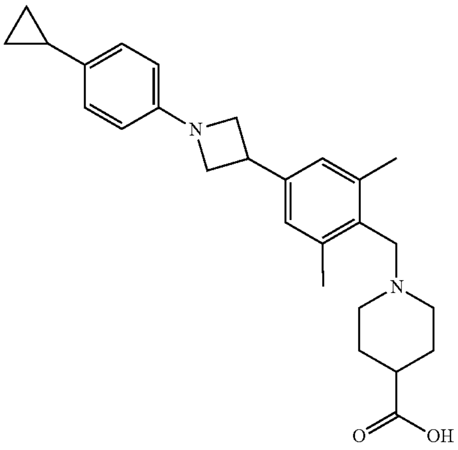 [SMILES: Cc1cc(C2CN(c3ccc(C4CC4)cc3)C2)cc(C)c1CN1CCC(C(=O)O)CC1] | 1-(4-(1-(4-cyclopropylphenyl)azetidin-3-yl)-2,6-dimethylbenzyl)piperidine-4-carboxylic acid |

TABLE 1-continued
| Compound No. | Structure | Name |
|---|---|---|
| 49 | 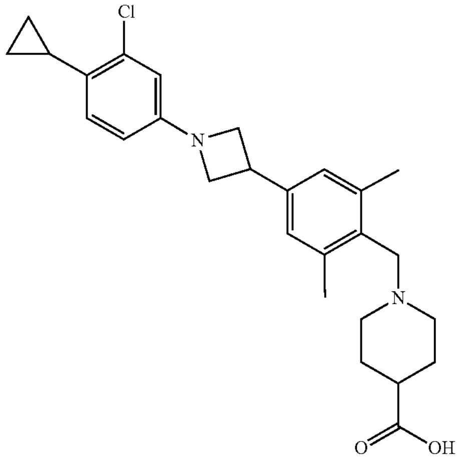 [SMILES: Cc1cc(C2CN(c3ccc(C4CC4)c(Cl)c3)C2)cc(C)c1CN1CCC(C(=O)O)CC1] | 1-(4-(1-(3-chloro-4-cyclopropylphenyl)azetidin-3-yl)-2,6-dimethylbenzyl)piperidine-4-carboxylic acid |
| 50 | 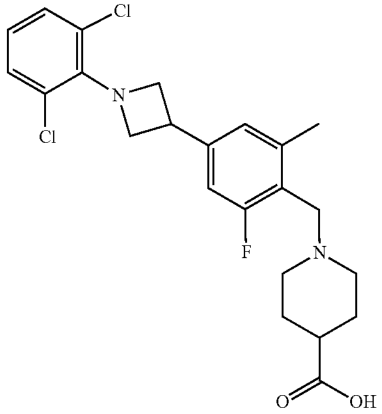 [SMILES: Cc1cc(C2CN(c3c(Cl)cccc3Cl)C2)cc(F)c1CN1CCC(C(=O)O)CC1] | 1-(4-(1-(2,6-dichlorophenyl)azetidin-3-yl)-2-fluoro-6-methylbenzyl)piperidine-4-carboxylic acid |
| 51 | 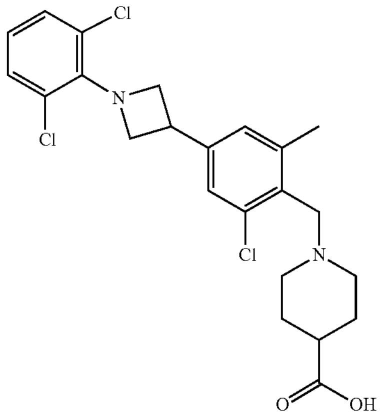 | 1-(2-chloro-4-(1-(2,6-dichlorophenyl)azetidin-3-yl)-6-methylbenzyl)piperidine-4-carboxylic acid |

TABLE 1-continued
| Compound No. | Structure | Name |
|---|---|---|
| 52 | 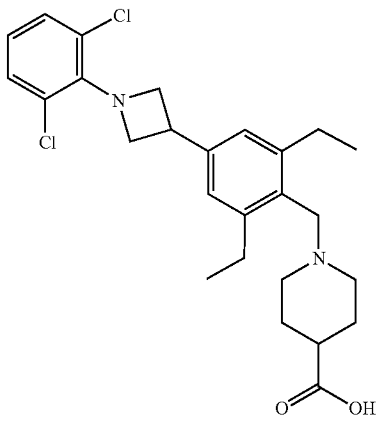 [SMILES: CCc1cc(C2CN(c3c(Cl)cccc3Cl)C2)cc(CC)c1CN1CCC(C(=O)O)CC1] | 1-(4-(1-(2,6-dichlorophenyl)azetidin-3-yl)-2,6-diethylbenzyl)piperidine-4-carboxylic acid |
| 53 | 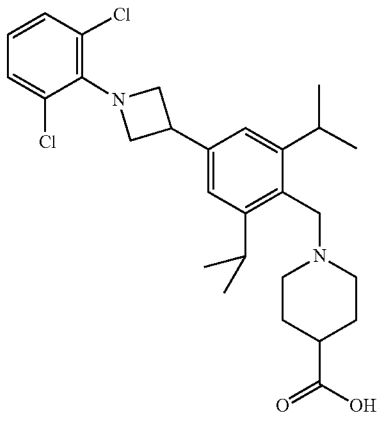 [SMILES: CC(C)c1cc(C2CN(c3c(Cl)cccc3Cl)C2)cc(C(C)C)c1CN1CCC(C(=O)O)CC1] | 1-(4-(1-(2,6-dichlorophenyl)azetidin-3-yl)-2,6-diisopropylbenzyl)piperidine-4-carboxylic acid |
| 54 | 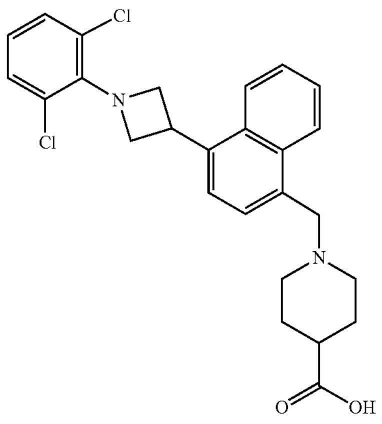 [SMILES: O=C(O)C1CCN(Cc2ccc(C3CN(c4c(Cl)cccc4Cl)C3)c3ccccc23)CC1] | 1-((4-(1-(2,6-dichlorophenyl)azetidin-3-yl)naphthalen-1-yl)methyl)piperidine-4-carboxylic acid |

TABLE 1-continued
| Compound No. | Structure | Name |
| --- | --- | --- |
| 55 | 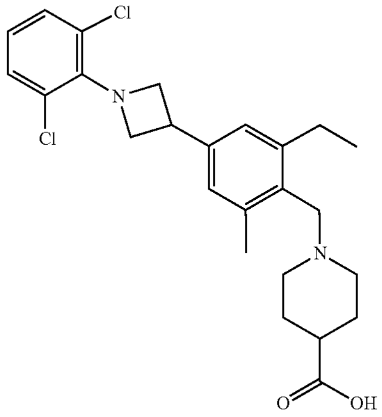 [SMILES: CCc1cc(C2CN(c3c(Cl)cccc3Cl)C2)cc(C)c1CN1CCC(C(=O)O)CC1] | 1-(4-(1-(2,6-dichlorophenyl)azetidin-3-yl)-2-ethyl-6-methylbenzyl)piperidine-4-carboxylic acid |
| 56 | 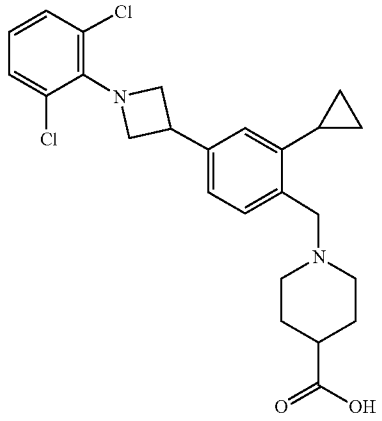 [SMILES: O=C(O)C1CCN(Cc2ccc(C3CN(c4c(Cl)cccc4Cl)C3)cc2C2CC2)CC1] | 1-(2-cyclopropyl-4-(1-(2,6-dichlorophenyl)azetidin-3-yl)benzyl)piperidine-4-carboxylic acid |
| 57 | 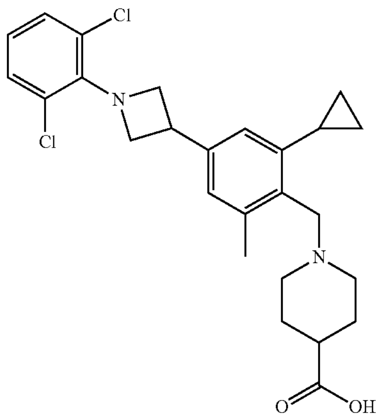 [SMILES: Cc1cc(C2CN(c3c(Cl)cccc3Cl)C2)cc(C2CC2)c1CN1CCC(C(=O)O)CC1] | 1-(2-cyclopropyl-4-(1-(2,6-dichlorophenyl)azetidin-3-yl)-6-methylbenzyl)piperidine-4-carboxylic acid |

TABLE 1-continued
| Compound No. | Structure | Name |
| --- | --- | --- |
| 58 | 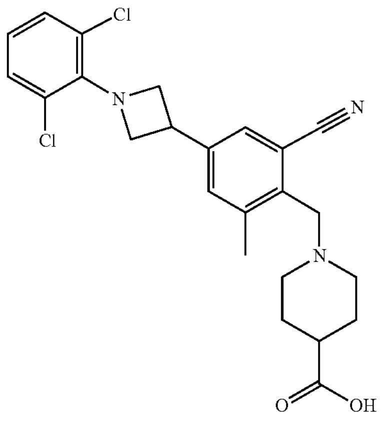 [SMILES: Cc1cc(C2CN(c3c(Cl)cccc3Cl)C2)cc(C#N)c1CN1CCC(C(=O)O)CC1] | 1-(2-cyano-4-(1-(2,6-dichlorophenyl)azetidin-3-yl)-6-methylbenzyl)piperidine-4-carboxylic acid |
| 59 | 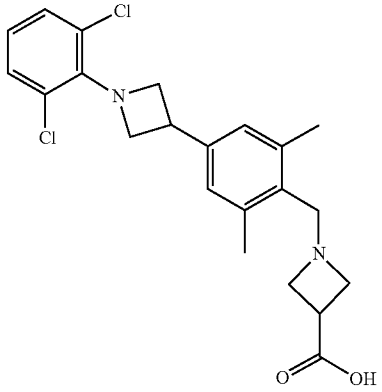 [SMILES: Cc1cc(C2CN(c3c(Cl)cccc3Cl)C2)cc(C)c1CN1CC(C(=O)O)C1] | 1-(4-(1-(2,6-dichlorophenyl)azetidin-3-yl)-2,6-dimethylbenzyl)azetidine-3-carboxylic acid |
| 60 | 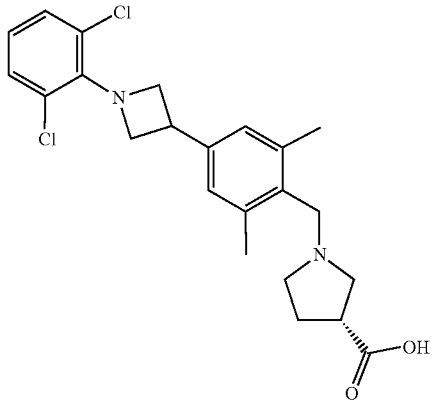 [SMILES: Cc1cc(C2CN(c3c(Cl)cccc3Cl)C2)cc(C)c1CN1CC[C@@H](C(=O)O)C1] | (R)-1-(4-(1-(2,6-dichlorophenyl)azetidin-3-yl)-2,6-dimethylbenzyl)pyrrolidine-3-carboxylic acid |

TABLE 1-continued
| Compound No. | Structure | Name |
|---|---|---|
| 61 | 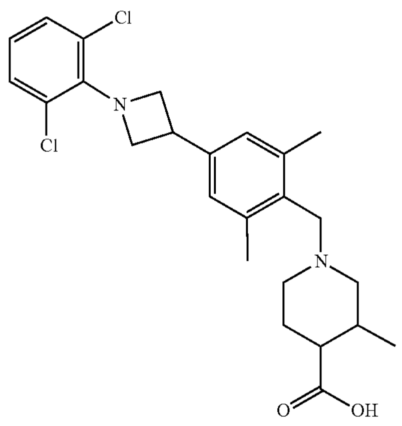 [SMILES: Cc1cc(C2CN(c3c(Cl)cccc3Cl)C2)cc(C)c1CN1CCC(C(=O)O)C(C)C1] | 1-(4-(1-(2,6-dichlorophenyl)azetidin-3-yl)-2,6-dimethylbenzyl)-3-methylpiperidine-4-carboxylic acid |
| 62 | 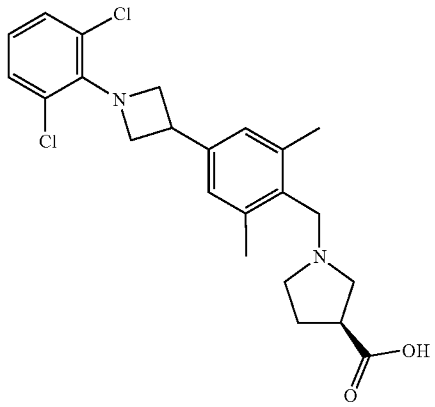 [SMILES: Cc1cc(C2CN(c3c(Cl)cccc3Cl)C2)cc(C)c1CN1CC[C@H](C(=O)O)C1] | (S)-1-(4-(1-(2,6-dichlorophenyl)azetidin-3-yl)-2,6-dimethylbenzyl)pyrrolidine-3-carboxylic acid |
| 63 | 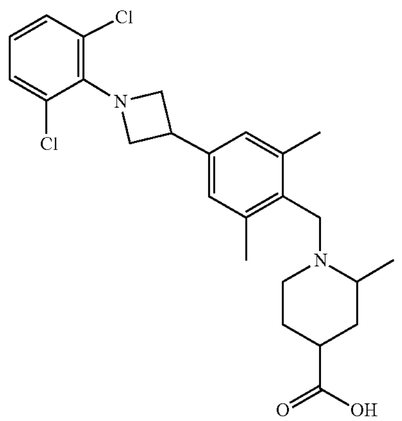 [SMILES: Cc1cc(C2CN(c3c(Cl)cccc3Cl)C2)cc(C)c1CN1CCC(C(=O)O)CC1C] | 1-(4-(1-(2,6-dichlorophenyl)azetidin-3-yl)-2,6-dimethylbenzyl)-2-methylpiperidine-4-carboxylic acid |

TABLE 1-continued
| Compound No. | Structure | Name |
| --- | --- | --- |
| 64 | 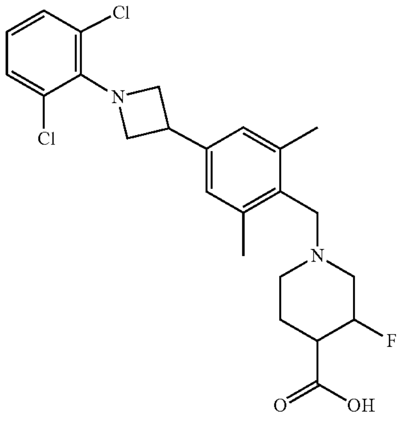 [SMILES: Cc1cc(C2CN(c3c(Cl)cccc3Cl)C2)cc(C)c1CN1CCC(C(=O)O)C(F)C1] | 1-(4-(1-(2,6-dichlorophenyl)azetidin-3-yl)-2,6-dimethylbenzyl)-3-fluoropiperidine-4-carboxylic acid |
| 65 | 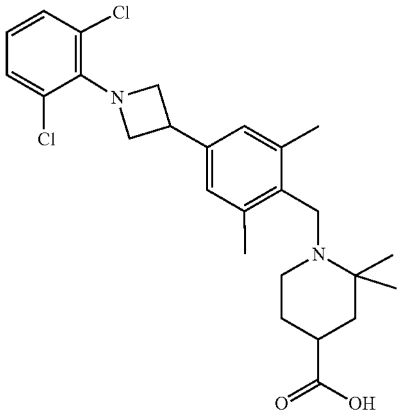 [SMILES: Cc1cc(C2CN(c3c(Cl)cccc3Cl)C2)cc(C)c1CN1CCC(C(=O)O)CC1(C)C] | 1-(4-(1-(2,6-dichlorophenyl)azetidin-3-yl)-2,6-dimethylbenzyl)-2,2-dimethylpiperidine-4-carboxylic acid |
| 66 | 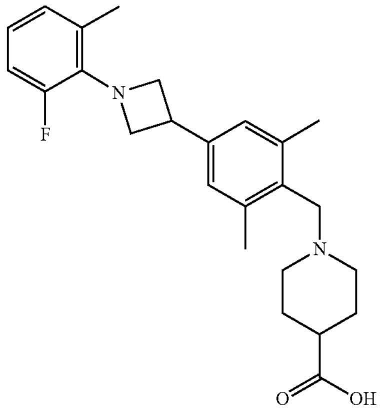 [SMILES: Cc1cc(C2CN(c3c(C)cccc3F)C2)cc(C)c1CN1CCC(C(=O)O)CC1] | 1-(4-(1-(2-fluoro-6-methylphenyl)azetidin-3-yl)-2,6-dimethylbenzyl)piperidine-4-carboxylic acid |

TABLE 1-continued
| Compound No. | Structure | Name |
| --- | --- | --- |
| 67 | 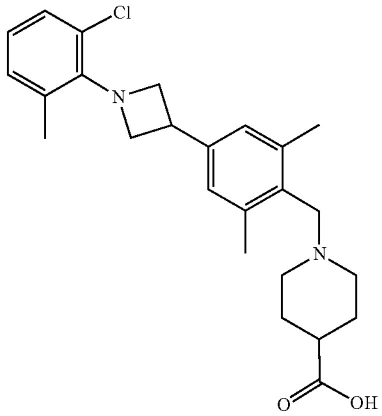 [SMILES: Cc1cc(C2CN(c3c(C)cccc3Cl)C2)cc(C)c1CN1CCC(C(=O)O)CC1] | 1-(4-(1-(2-chloro-6-methylphenyl)azetidin-3-yl)-2,6-dimethylbenzyl)piperidine-4-carboxylic acid |
| 68 | 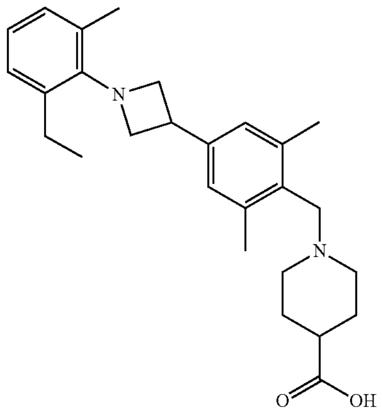 [SMILES: CCc1cccc(C)c1N1CC(c2cc(C)c(CN3CCC(C(=O)O)CC3)c(C)c2)C1] | 1-(4-(1-(2-ethyl-6-methylphenyl)azetidin-3-yl)-2,6-dimethylbenzyl)piperidine-4-carboxylic acid |
| 69 | 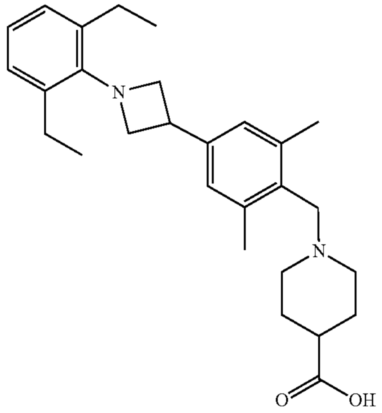 [SMILES: CCc1cccc(CC)c1N1CC(c2cc(C)c(CN3CCC(C(=O)O)CC3)c(C)c2)C1] | 1-(4-(1-(2,6-diethylphenyl)azetidin-3-yl)-2,6-dimethylbenzyl)piperidine-4-carboxylic acid |

TABLE 1-continued
| Compound No. | Structure | Name |
|---|---|---|
| 70 | 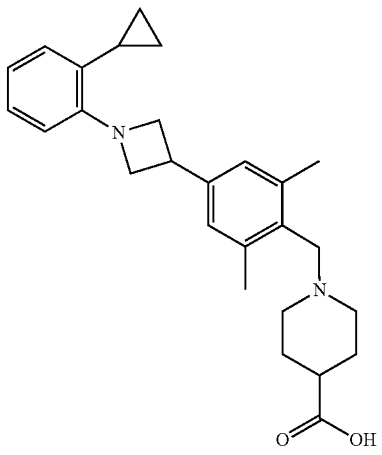 [SMILES: Cc1cc(C2CN(c3ccccc3C3CC3)C2)cc(C)c1CN1CCC(C(=O)O)CC1] | 1-(4-(1-(2-cyclopropylphenyl)azetidin-3-yl)-2,6-dimethylbenzyl)piperidine-4-carboxylic acid |
| 71 | 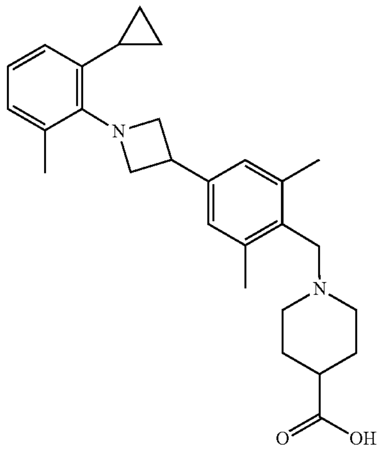 [SMILES: Cc1cc(C2CN(c3c(C)cccc3C3CC3)C2)cc(C)c1CN1CCC(C(=O)O)CC1] | 1-(4-(1-(2-cyclopropyl-6-methylphenyl)azetidin-3-yl)-2,6-dimethylbenzyl)piperidine-4-carboxylic acid |
| 72 | 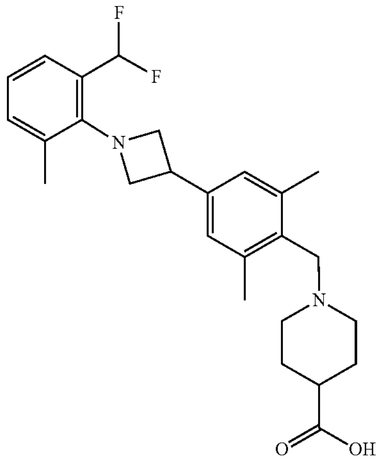 [SMILES: Cc1cc(C2CN(c3c(C)cccc3C(F)F)C2)cc(C)c1CN1CCC(C(=O)O)CC1] | 1-(4-(1-(2-(difluoromethyl)-6-methylphenyl)azetidin-3-yl)-2,6-dimethylbenzyl)piperidine-4-carboxylic acid |

TABLE 1-continued
| Compound No. | Structure | Name |
|---|---|---|
| 73 | 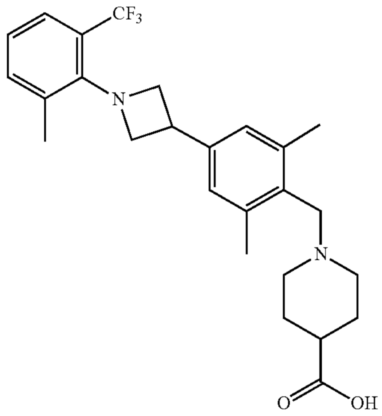 [SMILES: Cc1cc(C2CN(c3c(C)cccc3C(F)(F)F)C2)cc(C)c1CN1CCC(C(=O)O)CC1] | 1-(2,6-dimethyl-4-(1-(2-methyl-6-(trifluoromethyl)phenyl)azetidin-3-yl)benzyl)piperidine-4-carboxylic acid |
| 74 | 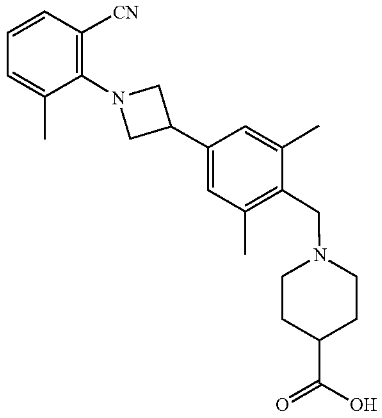 [SMILES: Cc1cc(C2CN(c3c(C)cccc3C#N)C2)cc(C)c1CN1CCC(C(=O)O)CC1] | 1-(4-(1-(2-cyano-6-methylphenyl)azetidin-3-yl)-2,6-dimethylbenzyl)piperidine-4-carboxylic acid |
| 75 | 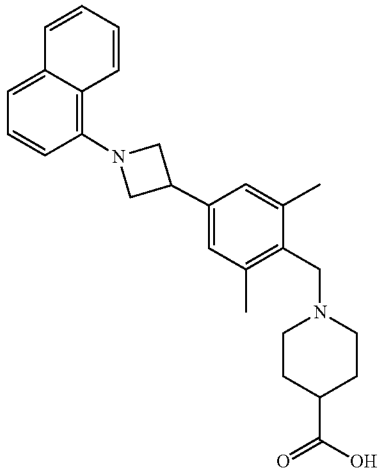 [SMILES: Cc1cc(C2CN(c3cccc4ccccc34)C2)cc(C)c1CN1CCC(C(=O)O)CC1] | 1-(2,6-dimethyl-4-(1-(naphthalen-1-yl)azetidin-3-yl)benzyl)piperidine-4-carboxylic acid |

TABLE 1-continued
| Compound No. | Structure | Name |
|---|---|---|
| 76 | 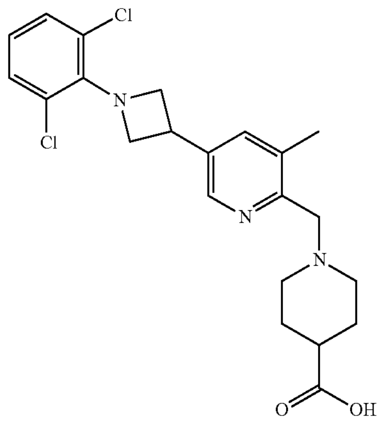 [SMILES: Cc1cc(C2CN(c3c(Cl)cccc3Cl)C2)cnc1CN1CCC(C(=O)O)CC1] | 1-((5-(1-(2,6-dichlorophenyl)azetidin-3-yl)-3-methylpyridin-2-yl)methyl)piperidine-4-carboxylic acid |
| 77 | 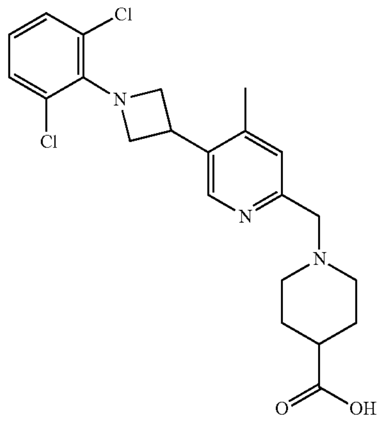 [SMILES: Cc1cc(CN2CCC(C(=O)O)CC2)ncc1C1CN(c2c(Cl)cccc2Cl)C1] | 1-((5-(1-(2,6-dichlorophenyl)azetidin-3-yl)-4-methylpyridin-2-yl)methyl)piperidine-4-carboxylic acid |
| 78 | 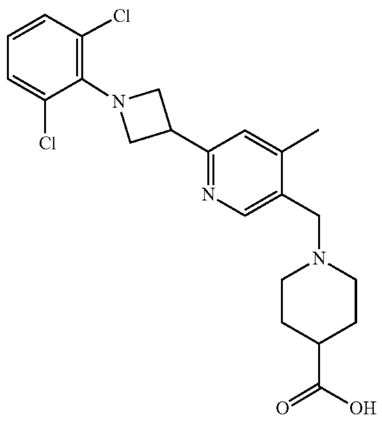 [SMILES: Cc1cc(C2CN(c3c(Cl)cccc3Cl)C2)ncc1CN1CCC(C(=O)O)CC1] | 1-((6-(1-(2,6-dichlorophenyl)azetidin-3-yl)-4-methylpyridin-3-yl)methyl)piperidine-4-carboxylic acid |

TABLE 1-continued
| Compound No. | Structure | Name |
| --- | --- | --- |
| 79 | 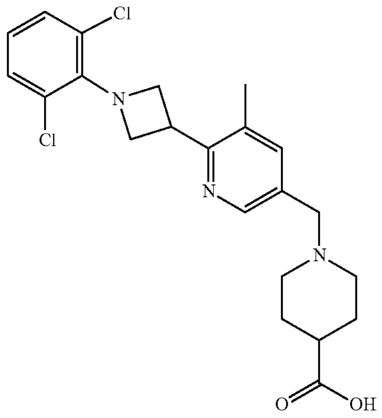 [SMILES: Cc1cc(CN2CCC(C(=O)O)CC2)cnc1C1CN(c2c(Cl)cccc2Cl)C1] | 1-((6-(1-(2,6-dichlorophenyl)azetidin-3-yl)-5-methylpyridin-3-yl)methyl)piperidine-4-carboxylic acid |
| 80 | 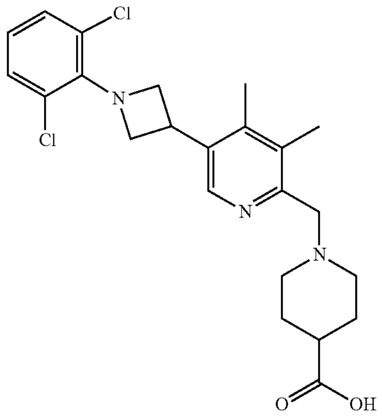 [SMILES: Cc1c(C2CN(c3c(Cl)cccc3Cl)C2)cnc(CN2CCC(C(=O)O)CC2)c1C] | 1-((5-(1-(2,6-dichlorophenyl)azetidin-3-yl)-3,4-dimethylpyridin-2-yl)methyl)piperidine-4-carboxylic acid |
| 81 | 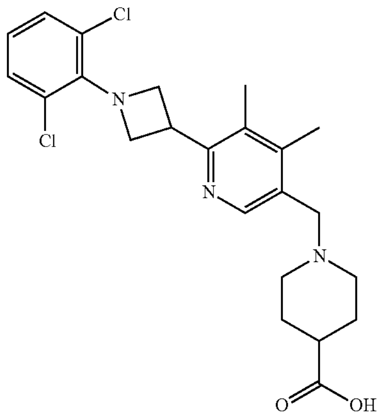 [SMILES: Cc1c(CN2CCC(C(=O)O)CC2)cnc(C2CN(c3c(Cl)cccc3Cl)C2)c1C] | 1-((6-(1-(2,6-dichlorophenyl)azetidin-3-yl)-4,5-dimethylpyridin-3-yl)methyl)piperidine-4-carboxylic acid |

TABLE 1-continued
| Compound No. | Structure | Name |
| --- | --- | --- |
| 82 | 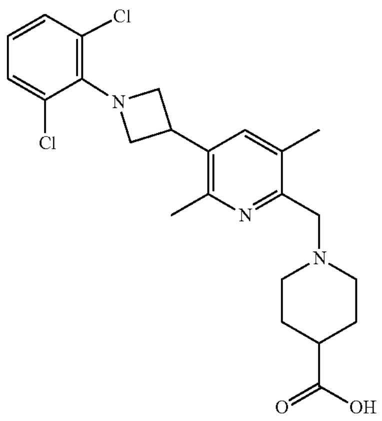 [SMILES: Cc1cc(C2CN(c3c(Cl)cccc3Cl)C2)c(C)nc1CN1CCC(C(=O)O)CC1] | 1-((5-(1-(2,6-dichlorophenyl)azetidin-3-yl)-3,6-dimethylpyridin-2-yl)methyl)piperidine-4-carboxylic acid |
| 83 | 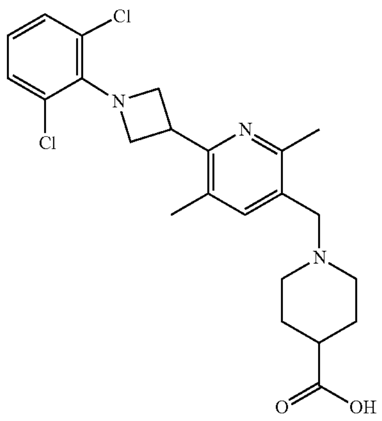 [SMILES: Cc1cc(CN2CCC(C(=O)O)CC2)c(C)nc1C1CN(c2c(Cl)cccc2Cl)C1] | 1-((6-(1-(2,6-dichlorophenyl)azetidin-3-yl)-2,5-dimethylpyridin-3-yl)methyl)piperidine-4-carboxylic acid |
| 84 | 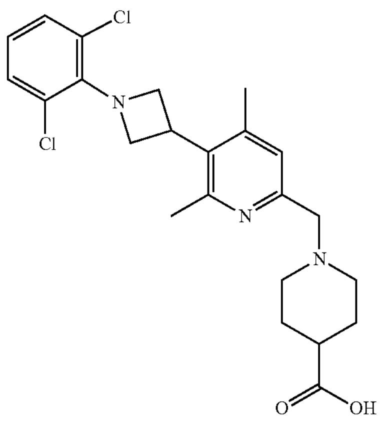 [SMILES: Cc1cc(CN2CCC(C(=O)O)CC2)nc(C)c1C1CN(c2c(Cl)cccc2Cl)C1] | 1-((5-(1-(2,6-dichlorophenyl)azetidin-3-yl)-4,6-dimethylpyridin-2-yl)methyl)piperidine-4-carboxylic acid |

TABLE 1-continued
| Compound No. | Structure | Name |
|---|---|---|
| 85 | 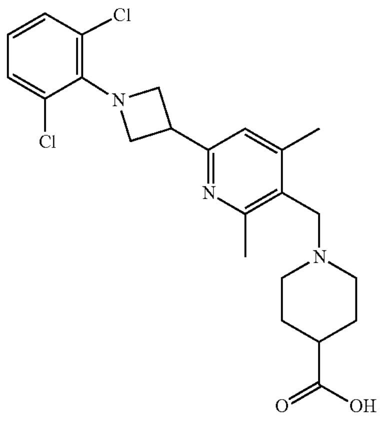 [SMILES: Cc1cc(C2CN(c3c(Cl)cccc3Cl)C2)nc(C)c1CN1CCC(C(=O)O)CC1] | 1-((6-(1-(2,6-dichlorophenyl)azetidin-3-yl)-2,4-dimethylpyridin-3-yl)methyl)piperidine-4-carboxylic acid |
| 86 | 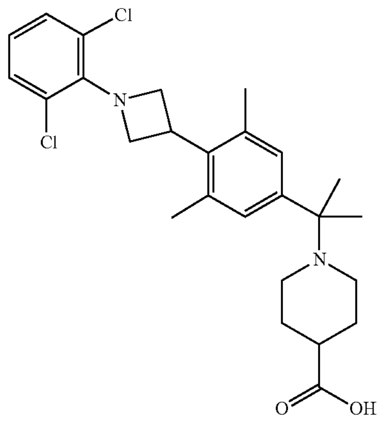 [SMILES: Cc1cc(C(C)(C)N2CCC(C(=O)O)CC2)cc(C)c1C1CN(c2c(Cl)cccc2Cl)C1] | 1-(2-(4-(1-(2,6-dichlorophenyl)azetidin-3-yl)-3,5-dimethylphenyl)propan-2-yl)piperidine-4-carboxylic acid |
| 87 | 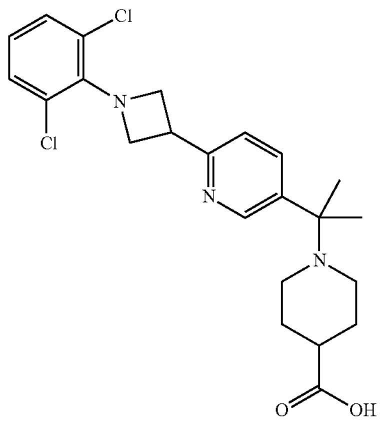 [SMILES: CC(C)(c1ccc(C2CN(c3c(Cl)cccc3Cl)C2)nc1)N1CCC(C(=O)O)CC1] | 1-(2-(6-(1-(2,6-dichlorophenyl)azetidin-3-yl)pyridin-3-yl)propan-2-yl)piperidine-4-carboxylic acid |

TABLE 1-continued

| Compound No. | Structure | Name |
| --- | --- | --- |
| 88 | 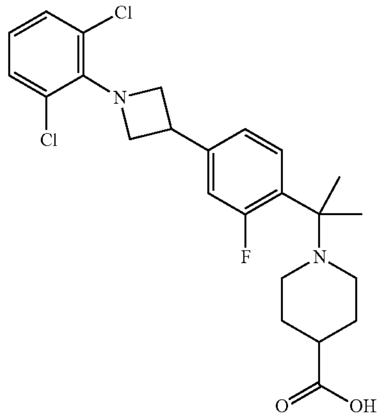 [SMILES: CC(C)(c1ccc(C2CN(c3c(Cl)cccc3Cl)C2)cc1F)N1CCC(C(=O)O)CC1] | 1-(2-(4-(1-(2,6-dichlorophenyl)azetidin-3-yl)-2-fluorophenyl)propan-2-yl)piperidine-4-carboxylic acid |
| 89 | 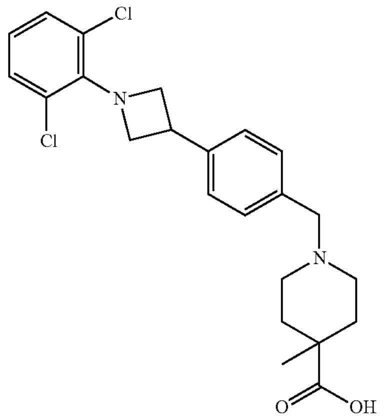 [SMILES: CC1(C(=O)O)CCN(Cc2ccc(C3CN(c4c(Cl)cccc4Cl)C3)cc2)CC1] | 1-(4-(1-(2,6-dichlorophenyl)azetidin-3-yl)benzyl)-4-methylpiperidine-4-carboxylic acid |
| 90 | 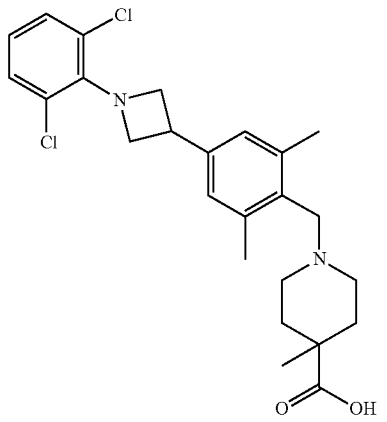 [SMILES: Cc1cc(C2CN(c3c(Cl)cccc3Cl)C2)cc(C)c1CN1CCC(C)(C(=O)O)CC1] | 1-(4-(1-(2,6-dichlorophenyl)azetidin-3-yl)-2,6-dimethylbenzyl)-4-methylpiperidine-4-carboxylic acid |

"or 1" indicates that the absolute stereochemistry was not determined.

or a pharmaceutically acceptable salt thereof.

It is understood that in the present description, combinations of substituents and/or variables of the depicted formulae are permissible only if such contributions result in stable compounds.

Furthermore, all compounds of Formula (I) that exist in free base or acid form can be converted to their pharmaceutically acceptable salts by treatment with the appropriate inorganic or organic base or acid by methods known to one skilled in the art. Salts of the compounds of Formula (I) can be converted to their free base or acid form by standard techniques.

Methods of Synthesis

The compounds described herein can be made using conventional organic syntheses and commercially available starting materials, or the methods provided herein. By way of example and not limitation, compounds of Formula (I) can be prepared as outlined in Scheme 1, as well as in the examples set forth herein. It should be noted that one skilled in the art would know how to modify the procedures set forth in the illustrative schemes and examples to arrive at the desired products.

Scheme 1.
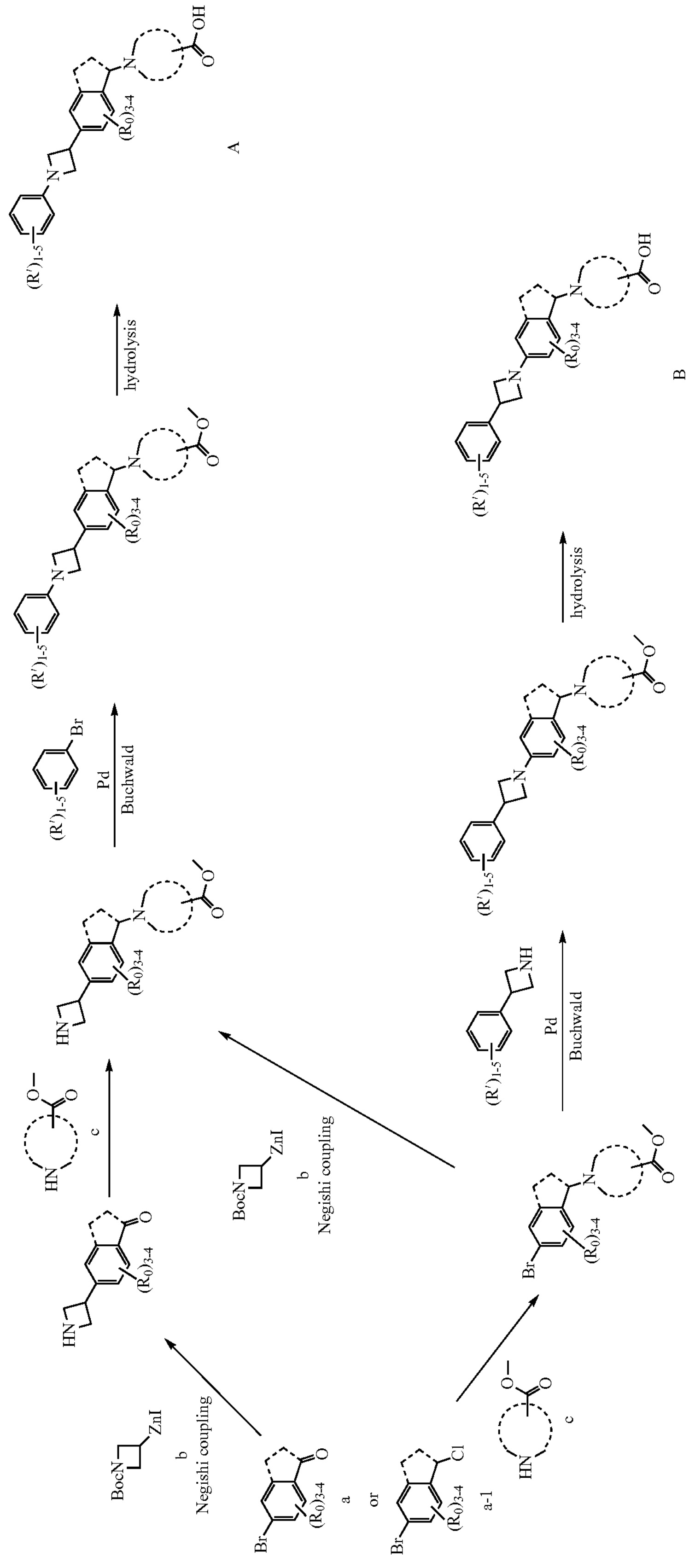

wherein R' and $R_0$ are as described for Formula (I), and each dashed line represents an optional bond.

As outlined in Scheme 1, compounds of general formula A can be synthesized from aryl bromide a or a-1 via Negishi coupling with azetidine b, followed by reductive amination with aminoacid ester c, Buchwald coupling with an aryl bromide, and subsequent hydrolysis. Alternatively, compounds of general formula A can be synthesized from aryl bromide a or a-1 by coupling with aminoacid ester c, following by Negishi coupling with azetidine b, Buchwald coupling with an aryl bromide, and subsequent hydrolysis.

Compounds of general formula B can be obtained from aryl bromide a or a-1 via coupling with aminoacid ester c, followed by Buchwald coupling with an aryl azetidine, and subsequent hydrolysis, as shown in Scheme 1.

Methods of Use

Embodiments of the present disclosure provide a method for modulating sphingosine 1-phosphate receptor 5 (S1P5) in a subject in need thereof, the method comprising administering to the subject an effective amount of a compound of Formula (I). Modulation (e.g., inhibition or activation) of S1P5 can be assessed and demonstrated by a wide variety of ways known in the art. Kits and commercially available assays can be utilized for determining whether and to what degree S1P5 has been modulated (e.g., inhibited or activated).

In one aspect, provided herein is a method of modulating S1P5 comprising contacting S1P5 with an effective amount of a compound of Formula (I) or any embodiment or variation thereof. In some embodiments, the compound of Formula (I) inhibits S1P5. In other embodiments, the compound of Formula (I) activates S1P5. In some embodiments, the compound of Formula (I) is an agonist of S1P5. In some embodiments, the compound of Formula (I) is an antagonist of S1P5.

In some embodiments, a compound of Formula (I) modulates the activity of S1P5 by about 1%, 5%, 0%, %15%, 20%, 25%, 30%, 35%, 40%, 45%, 50%, 55%, 60%, 65%, 70%, 75%, 80%, 85%, 90%, 95%, or 100%. In some embodiments, a compound of Formula (I) modulates the activity of S1P5 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

In another aspect, provided herein is a method for treating a neurological disease in a subject in need thereof, comprising administering to the subject an effective amount of a compound of Formula (I). In some embodiments, provided herein is a method for preventing a neurological disease in a subject in need thereof, comprising administering to the subject an effective amount of a compound of Formula (I). Non-limiting examples of a neurological disease include Alzheimer's disease, multiple sclerosis (MS), amyotrophic lateral sclerosis (ALS), Bell's Palsy, ataxia, cerebral aneurysm, epilepsy, seizures, acute spinal cord injury, Guillain-Barre syndrome, meningitis, Niemann Pick disease, and Parkinson's disease. In some embodiments, the neurological disease is Alzheimer's disease or multiple sclerosis. In some embodiments, the neurological disease is Alzheimer's disease. In some embodiments, the neurological disease is multiple sclerosis.

In some embodiments, administering a compound of Formula (I) to a subject that is predisposed to a neurological disease prevents the subject from developing any symptoms of the neurological disease. In some embodiments, administering a compound of Formula (I) to a subject that is does not yet display symptoms of a neurological disease prevents the subject from developing any symptoms of the neurological disease. In some embodiments, administering a compound of Formula (I) to a subject in need thereof diminishes the extent of the neurological disease in the subject. In some embodiments, administering a compound of Formula (I) to a subject in need thereof stabilizes the neurological disease (prevents or delays the worsening of the neurological disease). In some embodiments, administering a compound of Formula (I) to a subject in need thereof delays the occurrence or recurrence of the neurological disease. In some embodiments, administering a compound of Formula (I) to a subject in need thereof slows the progression of the neurological disease. In some embodiments, administering a compound of Formula (I) to a subject in need thereof provides a partial remission of the neurological disease. In some embodiments, administering a compound of Formula (I) to a subject in need thereof provides a total remission of the neurological disease. In some embodiments, administering a compound of Formula (I) to a subject in need thereof decreases the dose of one or more other medications required to treat the neurological disease. In some embodiments, administering a compound of Formula (I) to a subject in need thereof enhances the effect of another medication used to treat the neurological disease. In some embodiments, administering a compound of Formula (I) to a subject in need thereof delays the progression of the neurological disease. In some embodiments, administering a compound of Formula (I) to a subject in need thereof increases the quality of life of the subject having a neurological disease. In some embodiments, administering a compound of Formula (I) to a subject in need thereof prolongs survival of a subject having a neurological disease.

In one aspect, provided herein is method of preventing a subject that is predisposed to a neurological disease from developing any symptoms of the neurological disease, the method comprising administering a compound of Formula (I) to the subject. In some embodiments, provided herein is a method of preventing a subject that does not yet display symptoms of a neurological disease from developing any symptoms of the neurological disease, the method comprising administering a compound of Formula (I) to the subject.

In some aspects, provided herein is a method of diminishing the extent of a neurological disease in a subject, the method comprising administering a compound of Formula (I) to the subject. In some embodiments, provided herein is a method of stabilizing a neurological disease in a subject, the method comprising administering a compound of Formula (I) to the subject. In some embodiments, the method prevents the worsening of the neurological disease. In some embodiments, the method delays the worsening of the neurological disease.

In another aspect, provided herein is a method of delaying the occurrence or recurrence of a neurological disease in a subject, the method comprising administering a compound of Formula (I) to the subject.

In some embodiments, provided herein is a method of slowing the progression of a neurological disease in a subject, the method comprising administering a compound of Formula (I) to the subject. In some embodiments, the method provides a partial remission of the neurological disease. In some embodiments, the method provides a total remission of the neurological disease.

In further aspects, provided herein is a method of decreasing the dose of one or more other medications required to treat a neurological disease in a subject, the method comprising administering a compound of Formula (I) to the subject. In some embodiments, provided herein is a method of enhancing the effect of another medication used to treat a neurological disease in a subject, the method comprising administering a compound of Formula (I) to the subject.

Also provided here is a method of delaying the progression of a neurological disease in a subject, the method comprising administering a compound of Formula (I) to the subject. In some embodiments, the method increases the quality of life of the subject having a neurological disease. In some embodiments, the method prolongs survival of the subject having a neurological disease.

In another aspect, provided herein is a method for treating neurological symptoms caused by a disease in a subject in need thereof, comprising administering to the subject an effective amount of a compound of Formula (I). In some embodiments, provided herein is a method for preventing neurological symptoms caused by a disease in a subject in need thereof, comprising administering to the subject an effective amount of a compound of Formula (I). In some embodiments, administering a compound of Formula (I) to a subject that is predisposed to a disease which causes neurological symptoms prevents the subject from developing any neurological symptoms. In some embodiments, administering a compound of Formula (I) to a subject that is does not yet display neurological symptoms of a disease which causes neurological symptoms prevents the subject from developing any neurological symptoms. In some embodiments, administering a compound of Formula (I) to a subject in need thereof diminishes the extent of the neurological symptoms caused by the disease in the subject. In some embodiments, administering a compound of Formula (I) to a subject in need thereof stabilizes the neurological symptoms of the disease (prevents or delays the worsening of the neurological symptoms). In some embodiments, administering a compound of Formula (I) to a subject in need thereof delays the occurrence or recurrence of the neurological symptoms caused by the disease. In some embodiments, administering a compound of Formula (I) to a subject in need thereof slows the progression of the neurological symptoms caused by the disease. In some embodiments, administering a compound of Formula (I) to a subject in need thereof provides a partial remission of the disease which causes neurological symptoms. In some embodiments, administering a compound of Formula (I) to a subject in need thereof provides a total remission of the disease which causes neurological symptoms. In some embodiments, administering a compound of Formula (I) to a subject in need thereof decreases the dose of one or more other medications required to treat the disease which causes neurological symptoms. In some embodiments, administering a compound of Formula (I) to a subject in need thereof enhances the effect of another medication used to treat the neurological symptoms of the disease. In some embodiments, administering a compound of Formula (I) to a subject in need thereof delays the progression of the disease which causes neurological symptoms. In some embodiments, administering a compound of Formula (I) to a subject in need thereof increases the quality of life of the subject having a disease which causes neurological symptoms. In some embodiments, administering a compound of Formula (I) to a subject in need thereof prolongs survival of a subject having a disease which causes neurological symptoms. In some embodiments, the disease is Niemann-Pick disease.

In some embodiments, compounds of Formula (I) are useful for treating a disorder selected from Alzheimer's disease, arthritis, rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acute transverse myelitis, Huntington's chorea, Parkinson's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinemia), dilated cardiomyopathy, infertility, female infertility, ovarian failure, premature ovarian failure, fibrotic lung disease, chronic wound healing, cryptogenic fibrosing alveolitis, post-inflammatory interstitial lung disease, fibrosis, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polytnyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and ThI Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant Lymphoma, malignant histiocytosis, malignant melanoma, meningitis, meningococcemia, metabolic/idiopathic, migraine headache, mitochondrial multisystem disorder, mixed connective tissue disease, monoclonal gammopathy, multiple myeloma, multiple systems degenerations (Mencel Dejerine-Thomas Shi-Drager and Machado-Joseph), myasthenia gravis, *Mycobacterium avium* intracellulare, *Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, acute pain, age-associated memory impairment (AAMI), anxiety attention deficit disorder, attention deficit disorder in general, attention deficit hyperactivity disorder (ADHD), bipolar disorder, cancer pain, central neuropathic pain syndromes, central post-stroke pain, chemotherapy-induced neuropathy, cognitive deficits and dysfunction in psychiatric disorders, cognitive deficits associated with aging and neurodegeneration, cognitive deficits associated with diabetes, cognitive deficits of schizophrenia, complex regional pain syndrome, declines in cognitive function in Alzheimer's and associated dementias, deficits in attention, dementia, dementia associated with Down's syndrome, dementia associated with Lewy bodies, depression in Cushing's syndrome, diminished CNS function associated with traumatic brain injury, diseases with deficits of memory, dizziness, drug abuse, epilepsy, HIV sensory neuropathy, Huntingdon's disease, hyperalgesia including neuropathic pain, inflammation and inflammatory disorders, inflammatory hyperalgesia, inflammatory pain, insulin resistance syndrome, jet lag, lack of circulation, learning, major depressive disorder, medullary thyroid carcinoma, Meniere's disease, metabolic syndrome, mild cognitive impairment, mood alteration, motion sickness, multiple sclerosis pain, narcolepsy, need for new blood vessel growth associated with vascularization of skin grafts and lack of circulation, need for new blood vessel growth associated with wound healing, neuropathic pain, neuropathy, neuropathy secondary to tumor infiltration, non-inflammatory pain, obesity, obsessive compulsive disorder, painful diabetic neuropathy, panic disorder, Parkinson disease pain, pathological sleepiness, phantom limb pain, Pick's Disease, polycystic ovary syndrome, post traumatic stress disorder, post-herpetic neuralgia, post-mastectomy pain, post-surgical pain, psychotic depression, schizoaffective disorder, seizures, senile dementia, sepsis syndrome, sleep disorders, smoking cessation, spinal cord injury pain, steroid-induced acute psychosis, sub-categories of neuropathic pain including peripheral neuropathic pain syndromes, substance abuse including alcohol abuse, Syndrome X, Tourette's syndrome, treatment resistant depression, trigeminal neuralgia, type II diabetes, vertigo, and vestibular disorders.

Also provided herein is a compound of Formula (I), or a pharmaceutically acceptable salt thereof, for use in a method disclosed herein.

In a further aspect, provided herein is use of a compound of Formula (I), or a pharmaceutically acceptable salt thereof, for the manufacture of a medicament for a method disclosed herein.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds disclosed herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds of Formula (I) in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound of Formula (I) to be administered to a subject is rather widely variable and can be subject to the judgment of a health-care practitioner. In general, the compounds disclosed herein can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound of Formula (I) administered will depend on such factors as the solubility of the active component, the formulation used and the route of administration.

In some embodiments, a compound of Formula (I) is administered to a subject at a dose of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound of Formula (I).

In a particular embodiment, provided herein are unit dosage formulations comprising about 0.1 mg or 100 mg of a compound of Formula (I).

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a compound of Formula (I).

A compound of Formula (I) can be administered once, twice, three, four or more times daily. In a particular embodiment, doses of 100 mg or less are administered as a once daily dose and doses of more than 100 mg are administered twice daily in an amount equal to one half of the total daily dose.

A compound of Formula (I) can be administered orally for reasons of convenience. In one embodiment, when administered orally, a compound of Formula (I) is administered with a meal and water. In another embodiment, the compound of Formula (I) is dispersed in water or juice (e.g., apple juice or orange juice) or any other liquid and administered orally as a solution or a suspension.

The compounds disclosed herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound of Formula (I) without an additional carrier, excipient or vehicle.

In another embodiment, provided herein are compositions comprising an effective amount of a compound of Formula (I) and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound of Formula (I) with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound of Formula (I) as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound of Formula (I) can be delayed or prolonged by proper formulation. For example, a slowly soluble pellet of the compound of Formula (I) can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound of Formula (I) in oily or emulsified vehicles that allow it to disperse slowly in the serum.

EXEMPLARY EMBODIMENTS

The present disclosure is further described by the following embodiments. The features of each of the embodiments are combinable with any of the other embodiments where appropriate and practical.

Embodiment P1. A compound of Formula (I):

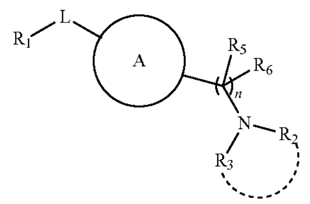

(I)

or a pharmaceutically acceptable salt thereof, wherein:

Ring A is

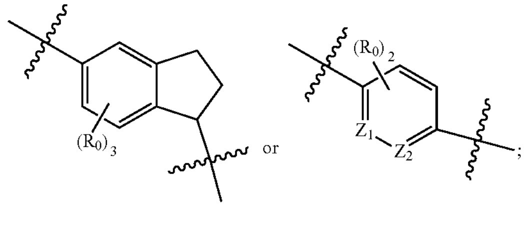

$Z_1$ and $Z_2$ are independently $CR_0$ or N;

L is azetidinyl optionally substituted with 1-5 substituents independently selected from halo and $C_1$-$C_6$ alkyl;

each $R_0$ is independently H, $C_1$-$C_6$ alkyl, halo, $C_1$-$C_6$ haloalkyl, or $C_1$-$C_6$ alkoxy;

$R_1$ is $C_6$-$C_{10}$ aryl or 5- to 6-membered heteroaryl, each of which is optionally substituted by 1-5 R' groups, wherein the heteroaryl contains 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl;

$R_2$ is H or $C_1$-$C_6$ alkyl;

$R_3$ is —$(CH_2)_x$—$CO_2H$;

or the dashed line between $R_2$ and $R_3$ represents a ring structure where $R_2$ and $R_3$ are taken together with the nitrogen atom to which they are attached to form a 4- to 6-membered heterocyclyl substituted by 1-5 $R_4$ groups, wherein at least one $R_4$ group is —$CO_2H$;

x is 1-5;

each $R_4$ is independently —$CO_2H$, halo, $C_1$-$C_6$ alkyl, $C_1$-$C_6$ haloalkyl, or $C_1$-$C_6$ alkoxy;

$R_5$ and $R_6$ are independently H or $C_1$-$C_6$ alkyl; and n is 0 or 1.

Embodiment P2. The compound of embodiment P1, or a pharmaceutically acceptable salt thereof, wherein:

Ring A is

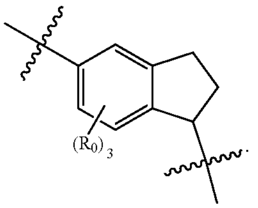

Embodiment P3. The compound of embodiment P1, or a pharmaceutically acceptable salt thereof, wherein:

Ring A is

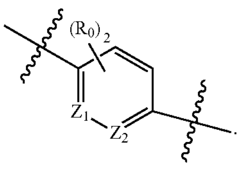

Embodiment P4. The compound of embodiment P3, or a pharmaceutically acceptable salt thereof, wherein:

$Z_1$ and $Z_2$ are each independently $CR_0$.

Embodiment P5. The compound of embodiment P3, or a pharmaceutically acceptable salt thereof, wherein:

$Z_1$ is N; and $Z_2$ is $CR_0$.

Embodiment P6. The compound of embodiment P3, or a pharmaceutically acceptable salt thereof, wherein:

$Z_1$ is $CR_0$; and $Z_2$ is N.

Embodiment P7. The compound of any one of embodiments P1-P6, or a pharmaceutically acceptable salt thereof, wherein:

each $R_0$ is independently H, $C_1$-$C_3$ alkyl, halo, $C_1$-$C_3$ haloalkyl, or $C_1$-$C_3$ alkoxy.

Embodiment P8. The compound of embodiment P7, or a pharmaceutically acceptable salt thereof, wherein:

each $R_0$ is independently H, methyl, Cl, F, —$CF_3$, or —$OCH_3$.

Embodiment P9. The compound of any one of embodiments P1, P2, P7, and P8, or a pharmaceutically acceptable salt thereof, wherein:

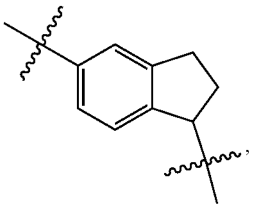

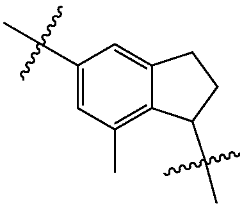

or

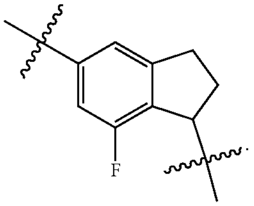

Ring A is

Embodiment P10. The compound of any one of embodiments P1 and P3-P8, or a pharmaceutically acceptable salt thereof, wherein:

Ring A is

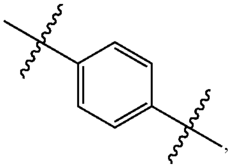

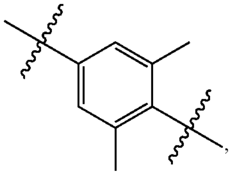

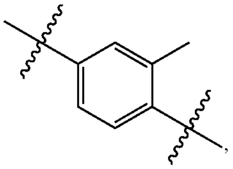

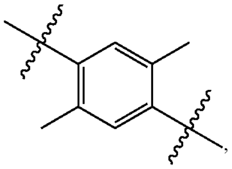

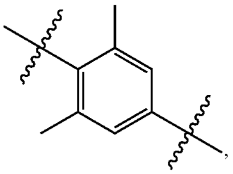

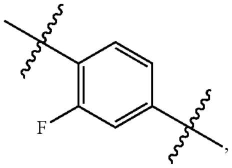

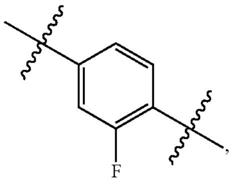

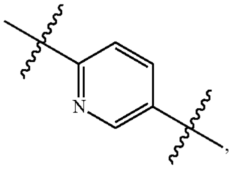

or

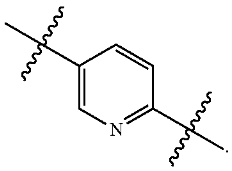

Embodiment P11. The compound of any one of embodiments P1-P10, or a pharmaceutically acceptable salt thereof, wherein:

L is

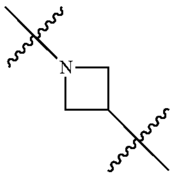 or 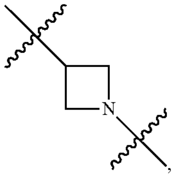, each of which is optionally substituted with 1-2 substituents independently selected from halo and $C_1$-$C_3$ alkyl.

Embodiment P12. The compound of embodiment P11, or a pharmaceutically acceptable salt thereof, wherein:

L is

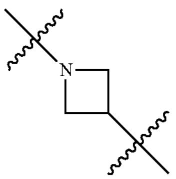 or 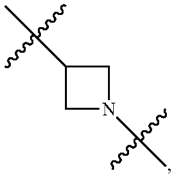, each of which is optionally substituted with one F, Cl, or methyl.

Embodiment P13. The compound of embodiment P12, or a pharmaceutically acceptable salt thereof, wherein:

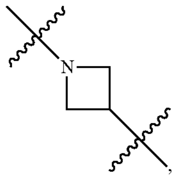, 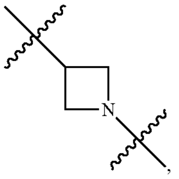, or

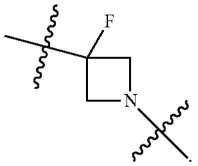.

L is

Embodiment P14. The compound of any one of embodiments P1-P13, or a pharmaceutically acceptable salt thereof, wherein:

$R_1$ is phenyl or 5- to 6-membered heteroaryl, each of which is optionally substituted by 1-3 R' groups, wherein the heteroaryl contains 1-2 heteroatoms selected from nitrogen and oxygen.

Embodiment P15. The compound of embodiment P14, or a pharmaceutically acceptable salt thereof, wherein:

$R_1$ is phenyl optionally substituted by 1-3 R' groups.

Embodiment P16. The compound of any one of embodiments P1-P15, or a pharmaceutically acceptable salt thereof, wherein:

each R' is independently halo, $C_1$-$C_3$ alkyl, $C_1$-$C_3$ haloalkyl, $C_1$-$C_3$ alkoxy, or $C_3$-$C_6$ cycloalkyl.

Embodiment P17. The compound of embodiment P16, or a pharmaceutically acceptable salt thereof, wherein:

each R' is independently halo or $C_3$-$C_6$ cycloalkyl.

Embodiment P18. The compound of embodiment P17, or a pharmaceutically acceptable salt thereof, wherein:

each R' is independently F, Cl, or cyclopropyl.

Embodiment P19. The compound of any one of embodiments P1-P18, or a pharmaceutically acceptable salt thereof, wherein:

$R_1$ is

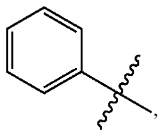, 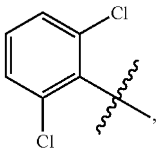,

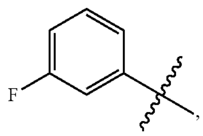, 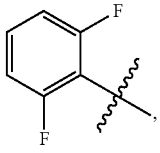,

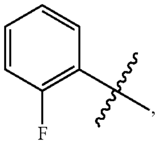, 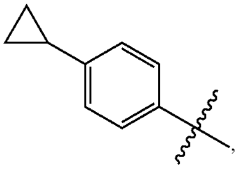, or

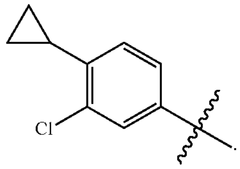.

Embodiment P20. The compound of any one of embodiments P1-P19, or a pharmaceutically acceptable salt thereof, wherein:

$R_2$ is H or $C_1$-$C_3$ alkyl;

$R_3$ is $-(CH_2)_x-CO_2H$; and x is 1-3.

Embodiment P21. The compound of embodiment P20, or a pharmaceutically acceptable salt thereof, wherein:

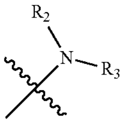 is 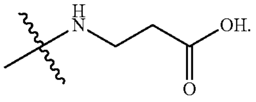

Embodiment P22. The compound of any one of embodiments P1-P19, or a pharmaceutically acceptable salt thereof, wherein:

$R_2$ and $R_3$ are taken together with the nitrogen atom to which they are attached to form a 4- to 6-membered heterocyclyl substituted by 1-3 $R_4$ groups, wherein at least one $R_4$ group is $-CO_2H$.

Embodiment P23. The compound of embodiment P22, or a pharmaceutically acceptable salt thereof, wherein:

each $R_4$ is independently $-CO_2H$, halo, $C_1$-$C_3$ alkyl, $C_1$-$C_3$ haloalkyl, or $C_1$-$C_3$ alkoxy.

Embodiment P24. The compound of embodiment P23, or a pharmaceutically acceptable salt thereof, wherein:

each $R_4$ is independently $-CO_2H$, methyl, Cl, $-CF_3$, or $-OCH_3$.

Embodiment P25. The compound of any one of embodiments P1-P19 and P22-P24, or a pharmaceutically acceptable salt thereof, wherein:

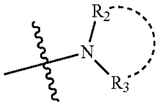 is 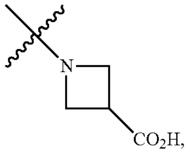

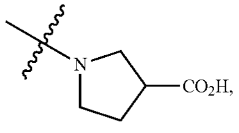 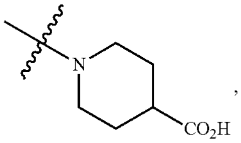, or

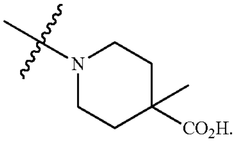

Embodiment P26. The compound of any one of embodiments P1-P25, or a pharmaceutically acceptable salt thereof, wherein:

n is 0.

Embodiment P27. The compound of any one of embodiments P1-P25, or a pharmaceutically acceptable salt thereof, wherein:

n is 1.

Embodiment P28. The compound of embodiment P27, or a pharmaceutically acceptable salt thereof, wherein:

$R_5$ and $R_6$ are independently H or $C_1$-$C_3$ alkyl.

Embodiment P29. The compound of embodiment P28, or a pharmaceutically acceptable salt thereof, wherein:

$R_5$ and $R_6$ are independently H or methyl.

Embodiment P30. The compound of embodiment P29, or a pharmaceutically acceptable salt thereof, wherein:

$—CR_5R_6—$ is $—CH_2—$ or $—CH(CH_3)—$.

Embodiment P31. The compound of any one of embodiments P1, P2, P7-P9, and P11-P26, or a pharmaceutically acceptable salt thereof, wherein the compound is of Formula (II):

(II)

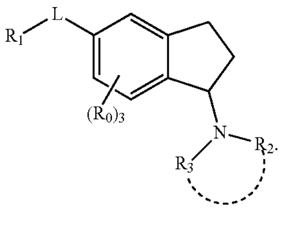

Embodiment P32. The compound of any one of embodiments P1, P3-P8, P10-P19, P22-P25, and P27-P30, or a pharmaceutically acceptable salt thereof, wherein the compound is of Formula (III):

(III)

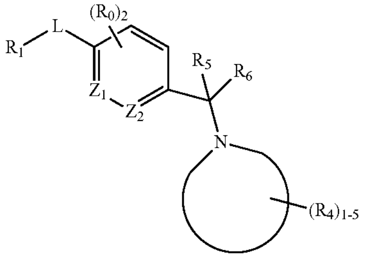 and 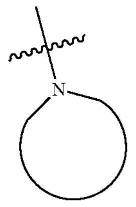

is a 4- to 6-membered heterocyclyl, wherein at least one $R_4$ group is $—CO_2H$.

Embodiment P33. A compound selected from the compounds of Table 1 or a pharmaceutically acceptable salt thereof.

Embodiment P34. A pharmaceutical composition comprising the compound of any one of embodiments P1-P33, or a pharmaceutically acceptable salt thereof, and a pharmaceutically acceptable excipient.

Embodiment P35. A method of modulating sphingosine 1-phosphate receptor 5 (S1P5) comprising contacting S1P5 with an effective amount of the compound of any one of embodiments P1-P33, or a pharmaceutically acceptable salt thereof, or the pharmaceutical composition of embodiment P34.

Embodiment P36. A method of treating a neurological disease in a subject in need thereof, comprising administering to the subject an effective amount of the compound of any one of embodiments P1-P33, or a pharmaceutically acceptable salt thereof, or the pharmaceutical composition of embodiment P34.

Embodiment P37. The method of embodiment P36, wherein the neurological disease is Alzheimer's disease or multiple sclerosis.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

As used in certain of the chemical structures provided in the following Examples, designation of a particular atom with "*" or "or 1" indicates that the absolute stereochemistry of the indicated atom was not determined.

The following abbreviations may be relevant for the application.

| Abbreviations | |
|---|---|
| ACN | acetonitrile |
| aq. | aqueous |

-continued

| Abbreviations | |
|---|---|
| Boc | tert-butyloxycarbonyl |
| $Cu(OAc)_2$ | copper(II) acetate |
| DCE | dichloroethane |
| DCM | dichloromethane |
| DIBAL-H | diisobutylaluminum hydride |
| DMF | dimethylformamide |
| DMSO | dimethyl sulfoxide |
| EA | ethyl acetate |
| ee | enantiomeric excess |
| equiv. | equivalents |
| ESI | electrospray ionization |
| EtOAc | ethyl acetate |
| EtOH | ethanol |
| FA | formic acid |
| h | hour(s) |
| Hex | hexane |
| HPLC | High Performance Liquid Chromatography |
| iPr | isopropanol |
| LCMS | liquid chromatography mass spectrometry |
| m-CPBA | meta-chloroperoxybenzoic acud |
| MeOH | methanol |
| mg | milligram(s) |
| min | minute(s) |
| $Pd_2(dba)_3$ | tris(dibenzylideneacetone)dipalladium |
| PE | petroleum ether |
| Prep. HPLC | Preparative High Performance Liquid Chromatography |
| RT | retention time |
| sat. | saturated |
| STAB | sodium triacetoxyborohydride |
| TBDMS | tert-butyldimethylsilyl |
| TBSOTf | tert-butyldimethylsilyl trifluoromethanesulfonate |
| tBuOH | tert-butanol |
| t-BuONa | sodium tert-butoxide |
| TEA | triethylamine |
| TFA | trifluoroacetic acid |
| THF | tetrahydrofuran |
| TLC | thin layer chromatography |
| UPLC | Ultra Performance Liquid Chromatography |

SYNTHETIC EXAMPLES

Example S1. 1-(5-(1-(2,6-dichlorophenyl)azetidin-3-yl)-2,3-dihydro-1H-inden-1-yl)-piperidine-4-carboxylic acid (1a and 1b)

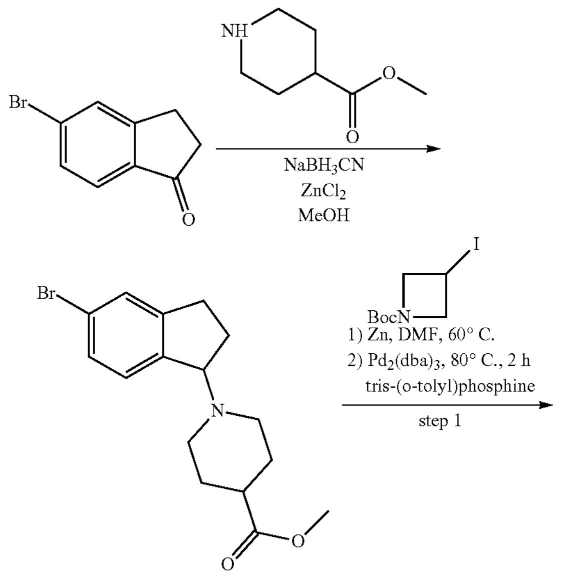

-continued

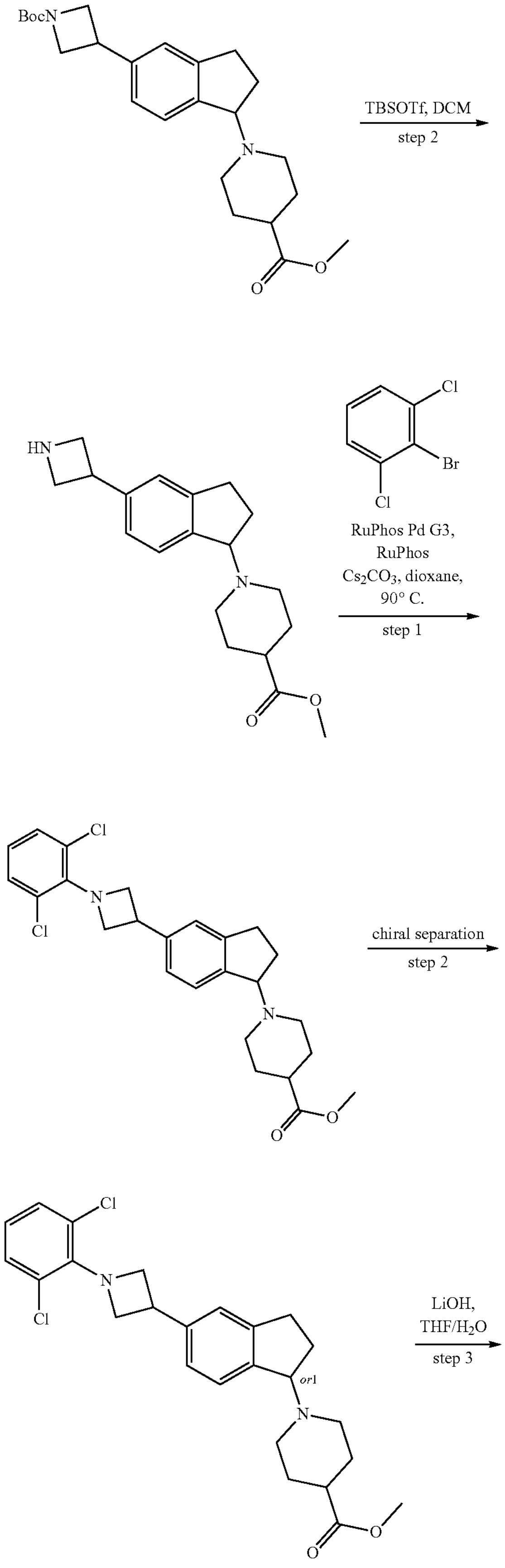

-continued

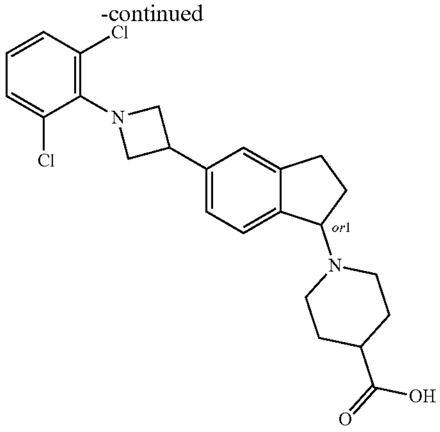

1a
chiral separation 1

Synthesis of methyl 1-(5-bromo-2,3-dihydro-1H-inden-1-yl)piperidine-4-carboxylate

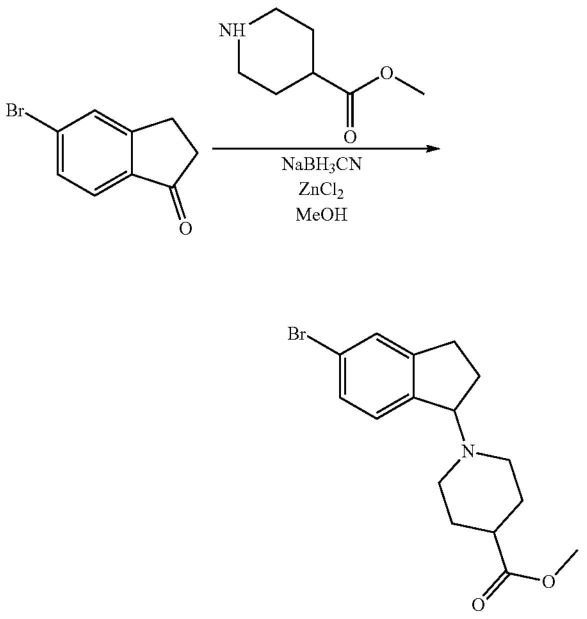

To a stirred solution of $NaBH_3CN$ (3.64 g, 56.9 mmol, 4.00 equiv.) in methanol (20 mL) was added $ZnCl_2$ (2 M in 2-Me-THF, 14.2 mL, 28.4 mmol, 2.00 equiv.). The resulting solution was stirred at room temperature for 15 min. Then methyl piperidine-4-carboxylate (4.07 g, 28.4 mmol, 2.00 equiv.) and 5-bromo-2,3-dihydro-1H-inden-1-one (3.00 g, 14.2 mmol, 1.00 equiv.) were added. The resulting mixture was stirred at 80° C. overnight. LCMS showed the reaction was complete. The reaction mixture was quenched with water (100 mL) and extracted with DCM (3*100 mL). The combined organic layers were dried over anhydrous $Na_2SO_4$ and concentrated under reduced pressure. The residue was purified by flash chromatography on silica gel with PE:EA=3:1 to afford methyl 1-(5-bromo-2,3-dihydro-1H-inden-1-yl)piperidine-4-carboxylate (2.84 g, 59%) as an oil. LCMS (ESI, m z): 338 $[M+H]^+$.

Synthesis of methyl 1-(5-(1-(tert-butoxycarbonyl)azetidin-3-yl)-2,3-dihydro-1H-inden-1-yl)piperidine-4-carboxylate

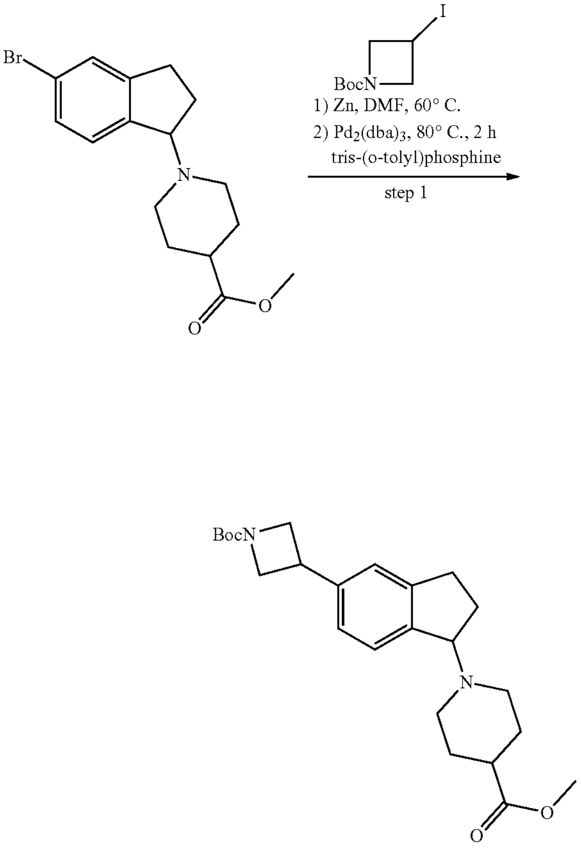

To a stirred solution of tert-butyl 3-iodoazetidine-1-carboxylate (2.0 g, 7.06 mmol, 1.00 equiv.) in DMF (15 mL) was added Zinc powder (693 mg, 10.6 mmol, 1.50 equiv.). The resulting mixture was stirred at 60° C. for 3h under $N_2$ atmosphere. Then $Pd_2(dba)_3$ (104 mg, 0.110 mmol, 0.016 equiv.), tris-(o-tolyl)phosphine (69 mg, 0.230 mmol, 0.032 equiv.) and methyl 1-(5-bromo-2,3-dihydro-1H-inden-1-yl)piperidine-4-carboxylate (383 mg, 1.130 mmol, 0.160 equiv.) were added. The resulting mixture was stirred at 80° C. overnight. LCMS showed the reaction was completed. The reaction mixture was diluted with saturated aq. $NH_4Cl$ (60 mL) and extracted with EtOAc (3*40 mL). The organic layers were combined and dried over $MgSO_4$ and concentrated. The crude was purified by flash chromatography on silica gel (eluted with PE/EtOAc, 1/1) to afford methyl 1-(5-(1-(tert-butoxycarbonyl)azetidin-3-yl)-2,3-dihydro-1H-inden-1-yl)piperidine-4-carboxylate (300 mg, 64%) as a yellow oil. LCMS (ESI, m z): 415 $[M+H]^+$.

Synthesis of methyl 1-(5-(azetidin-3-yl)-2,3-dihydro-1H-inden-1-yl)piperidine-4-carboxylate

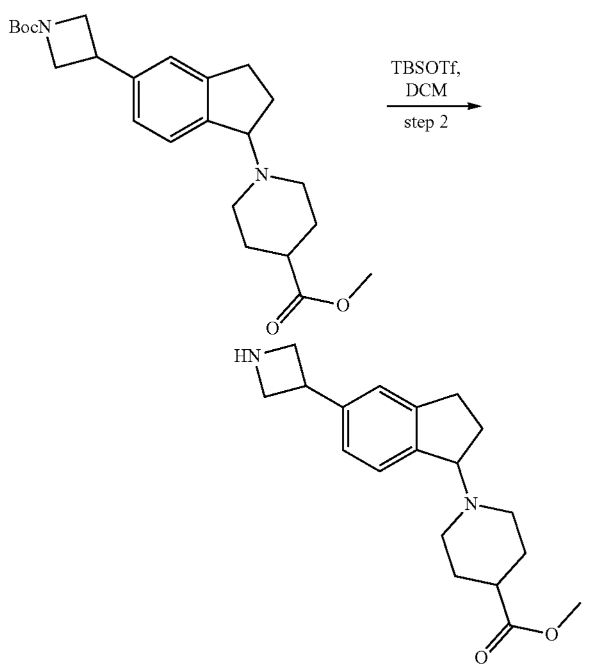

To a stirred solution of methyl 1-(5-(1-(tert-butoxycarbonyl)azetidin-3-yl)-2,3-dihydro-1H-inden-1-yl)piperidine-4-carboxylate (800 mg, 1.93 mmol, 1.00 equiv.) in DCM (10 mL) was added TBSOTf (1.33 mL, 5.79 mmol, 3.00 equiv.). The resulting mixture was stirred at room temperature for 2 h. LCMS showed the reaction was complete. The reaction mixture was concentrated under reduced pressure. The crude product was purified by flash column on C18 (eluted with water/ACN, 5/95) to afford methyl 1-(5-(azetidin-3-yl)-2,3-dihydro-1H-inden-1-yl)piperidine-4-carboxylate (500 mg, 82.4%) as a yellow oil. LCMS (ESI, m z): 315 $[M+H]^+$.

Synthesis of methyl 1-(5-(1-(2,6-dichlorophenyl)azetidin-3-yl)-2,3-dihydro-1H-inden-1-yl)piperidine-4-carboxylate

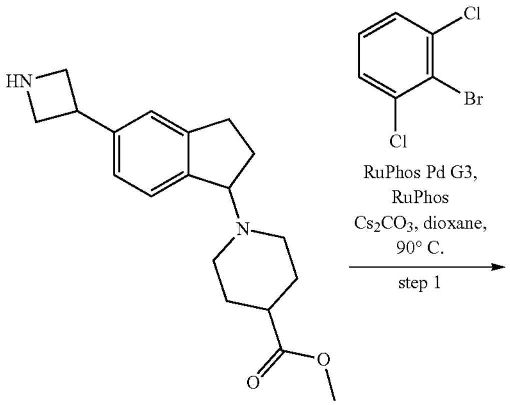

-continued

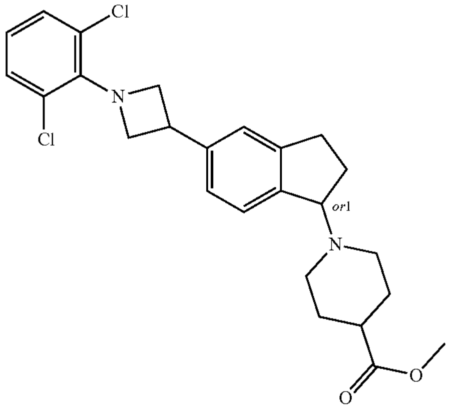

To a stirred solution of methyl 1-(5-(azetidin-3-yl)-2,3-dihydro-1H-inden-1-yl)piperidine-4-carboxylate (1.6 g, 5.09 mmol, 1.00 equiv.), 2-bromo-1,3-dichlorobenzene (1.7 g, 7.63 mmol, 1.50 equiv.), RuPhos Pd G3 (639 mg, 0.763 mmol, 0.15 equiv.) and RuPhos (357 mg, 0.763 mmol, 0.15 equiv.) in 1,4-dioxane (25 mL) was added $Cs_2CO_3$ (4.9 g, 15.3 mmol, 3.00 equiv.). The resulting mixture was stirred at 90° C. overnight. LCMS showed the reaction was completed. The reaction mixture was concentrated under reduced pressure. The residue was purified by column chromatography on silica gel (eluted with EtOAc/PE, 1/3) to afford crude product, which was then re-purified by prep-HPLC (Column: X-select CSH OBD Column, 30*150 mm, 5 μm; Mobile Phase A: water (0.05% TFA), Mobile Phase B: ACN; Flow rate: 60 mL/min; Gradient: 30% B to 52% B in 7 min; 210/254 nm; RT: 5.77 min) to afford methyl 1-(5-(1-(2,6-dichlorophenyl)azetidin-3-yl)-2,3-dihydro-1H-inden-1-yl)piperidine-4-carboxylate (160 mg, 6.8%) as a colorless oil. LCMS (ESI, m z): 459 $[M+H]^+$.

Chiral Separation of methyl 1-(5-(1-(2,6-dichlorophenyl)azetidin-3-yl)-2,3-dihydro-1H-inden-1-yl)piperidine-4-carboxylate

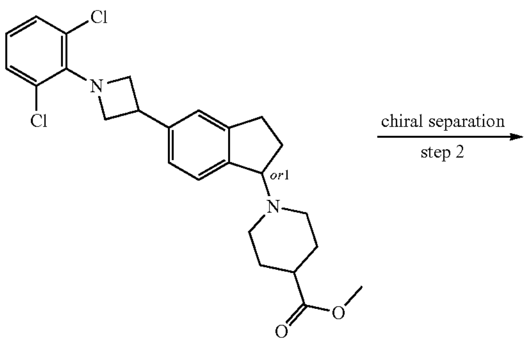

-continued

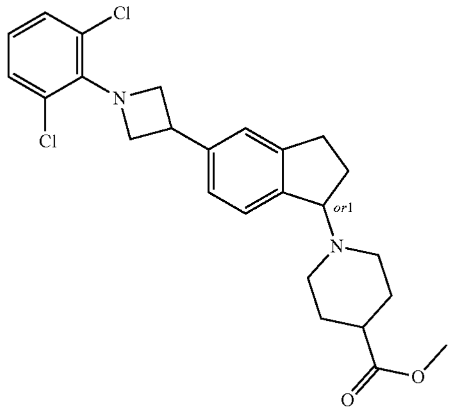

chiral separation 1

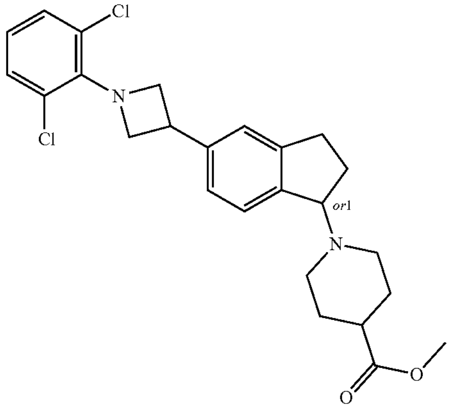

chiral separation 2

The racemic methyl 1-(5-(1-(2,6-dichlorophenyl)azetidin-3-yl)-2,3-dihydro-1H-inden-1-yl)piperidine-4-carboxylate was separated by Chiral HPLC (Column: CHIRALPAK IA, 2*25 cm, 5 μm; Mobile Phase A: Hex (0.5% 2M $NH_3$-MeOH), Mobile Phase B: EtOH; Flow rate: 20 mL/min; Gradient: 5% B to 5% B in 20 min; 220/254 nm; RT1: 10.089 min; RT2: 13.625 min; Injection Volume: 3 ml; Number Of Runs: 1) to afford the isomer 1 (60 mg, 100% ee) and the isomer 2 (60 mg, 99.9% ee), respectively.

Synthesis of 1-(5-(1-(2,6-dichlorophenyl)azetidin-3-yl)-2,3-dihydro-1H-inden-1-yl)piperidine-4-carboxylic acid (Enantiomer 1, 1a)

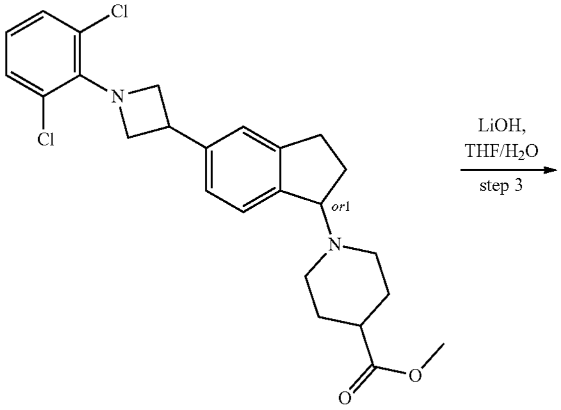

chiral separation 1

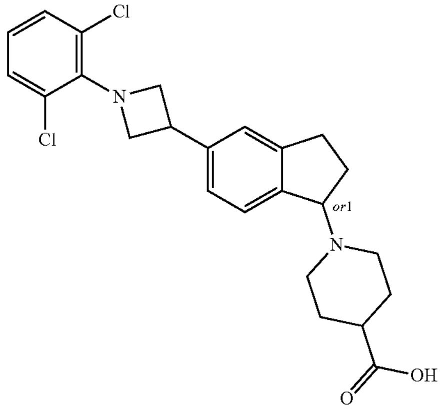

1a
chiral separation 1

To a stirred solution of methyl 1-(5-(1-(2,6-dichlorophenyl)azetidin-3-yl)-2,3-dihydro-1H-inden-1-yl)piperidine-4-carboxylate (60 mg, 0.130 mmol, 1.00 equiv.) in THE (1 mL) and water (1 mL) was added LiOH (10 mg, 0.390 mmol, 3.00 equiv.). The resulting mixture was stirred at room temperature for 3 h. LCMS showed the reaction was completed. The reaction mixture was acidified to pH 5-6 using acetic acid, and then was concentrated under reduced pressure. The residue was purified by prep-HPLC (Column: YMC-Actus Triart C18, 30*250 mm, 5 μm; Mobile Phase A: water (10 mM $NH_4HCO_3$+0.10% $NH_3 \cdot H_2O$), Mobile Phase B: ACN; Flow rate: 60 mL/min; Gradient: 30% B to 50% B in 8 min, hold at 50% B for 1 min; 254/210 nm; RT: 8.26 min) to afford 1-(5-(1-(2,6-dichlorophenyl)azetidin-3-yl)-2,3-dihydro-1H-inden-1-yl)piperidine-4-carboxylic acid (13.3 mg, 23%) as a white solid.

$^1H$ NMR (400 MHz, DMSO-$d_6$) δ 11.90 (br, 1H), 7.29-7.23 (m, 5H), 6.74 (t, J=8.0 Hz, 1H), 4.82 (t, J=8.0 Hz, 2H), 4.36-4.32 (m, 2H), 4.29-4.23 (m, 1H), 3.78-3.71 (m, 1H), 2.88-2.72 (m, 3H), 2.49-2.45 (m, 1H), 2.28-2.10 (m, 3H), 2.01-1.95 (m, 2H), 1.82-1.73 (m, 2H), 1.62-1.43 (m, 2H).

LCMS (ESI, m z): 445 $[M+H]^+$. Analytic Conditions: Shim-pack XR-ODS, 3.0*50 mm, 2.2 μm; Mobile Phase A: water (0.05% TFA), Mobile Phase B: Acetonitrile (0.05% TFA); Flow rate: 1.20 mL/min; Gradient: 5% B to 100% B in 2.0 min, hold at 100% B for 0.7 min, 100% B to 5% B in 0.05 min; 254 nm; RT: 1.720 min.

Synthesis of 1-(5-(1-(2,6-dichlorophenyl)azetidin-3-yl)-2,3-dihydro-1H-inden-1-yl)piperidine-4-carboxylic acid (Enantiomer 2, 1b)

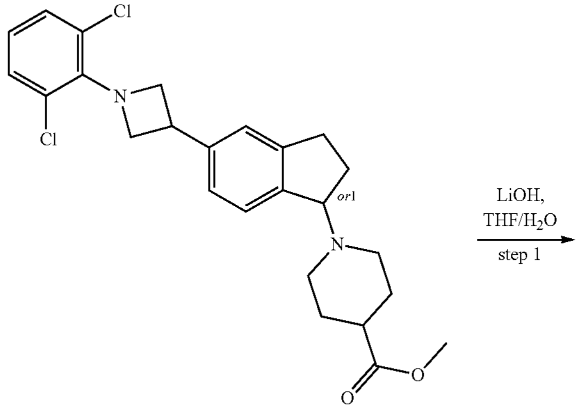

chiral separation 2

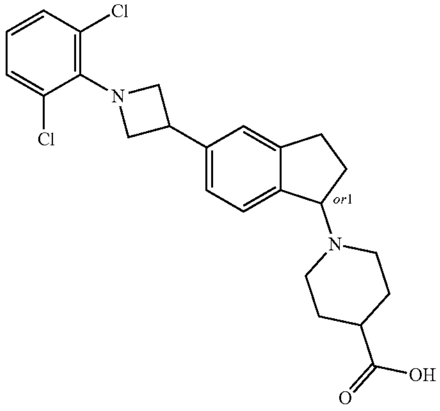

1b
chiral separation 2

To a stirred solution of the other enantiomer of methyl 1-(5-(1-(2,6-dichlorophenyl)azetidin-3-yl)-2,3-dihydro-1H-inden-1-yl)piperidine-4-carboxylate (60 mg, 0.130 mmol, 1.00 equiv.) in THE (1 mL) and water (1 mL) was added LiOH (10 mg, 0.390 mmol, 3.00 equiv.). The resulting mixture was stirred at room temperature for 3 h. LCMS showed the reaction was completed. The reaction mixture was acidified to pH 5-6 using acetic acid, and then was concentrated under reduced pressure. The residue was purified by prep-HPLC (Column: YMC-Actus Triart C18, 30*250 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 30% B to 50% B in 7 min; 254/210 nm; RT: 6.32 min) to afford 1-(5-(1-(2,6-dichlorophenyl)azetidin-3-yl)-2,3-dihydro-1H-inden-1-yl)piperidine-4-carboxylic acid (16.7 mg, 28.5%) as a white solid.

$^1$H NMR (400 MHz, DMSO-$d_6$) δ 12.07 (br, 1H), 7.29-7.22 (m, 5H), 6.75 (t, J=8.0 Hz, 1H), 4.82 (t, J=8.0 Hz, 2H), 4.36-4.32 (m, 2H), 4.26 (t, J=7.2 Hz, 1H), 3.78-3.71 (m, 1H), 2.88-2.70 (m, 3H), 2.49-2.45 (m, 1H), 2.28-2.10 (m, 3H), 2.01-1.95 (m, 2H), 1.82-1.73 (m, 2H), 1.62-1.40 (m, 2H).

LCMS (ESI, m z): 445 [M+H]$^+$. Analytic Conditions: Shim-pack XR-ODS, 3.0*50 mm, 2.2 μm; Mobile Phase A: water (0.05% TFA), Mobile Phase B: Acetonitrile (0.05% TFA); Flow rate: 1.20 mL/min; Gradient: 5% B to 100% B in 2.0 min, hold at 100% B for 0.7 min, 100% B to 5% B in 0.05 min; 254 nm; RT: 1.729 min.

Example S2. 1-(5-(1-(2,6-difluorophenyl)azetidin-3-yl)-2,3-dihydro-1H-inden-1-yl)piperidine-4-carboxylic acid (2a and 2b)

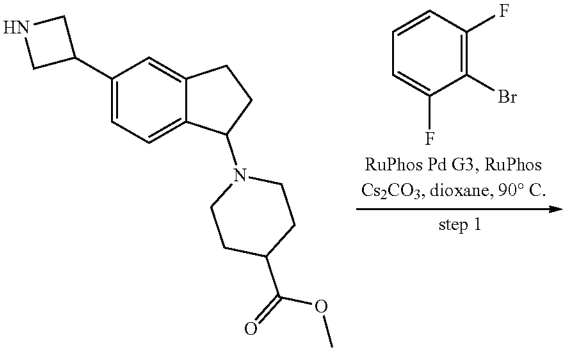

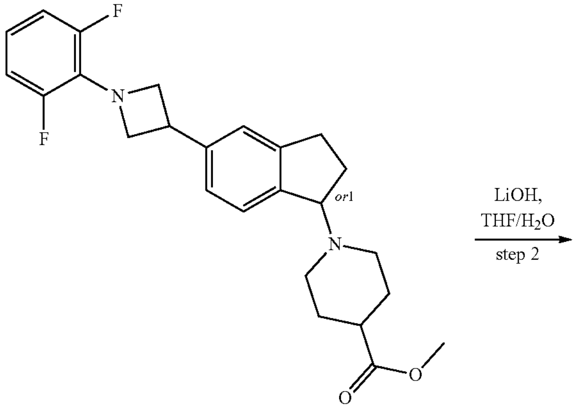

chiral separation 1

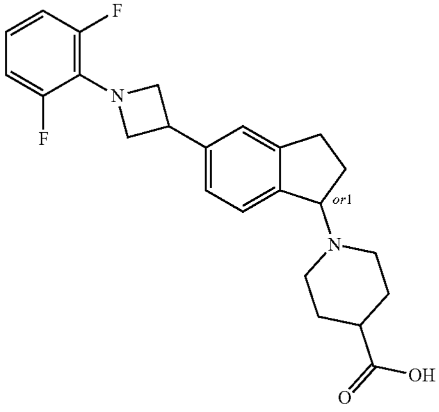

2a
chiral separation 1

Synthesis of methyl 1-(5-(1-(2,6-difluorophenyl) azetidin-3-yl)-2,3-dihydro-1H-inden-1-yl)piperidine-4-carboxylate

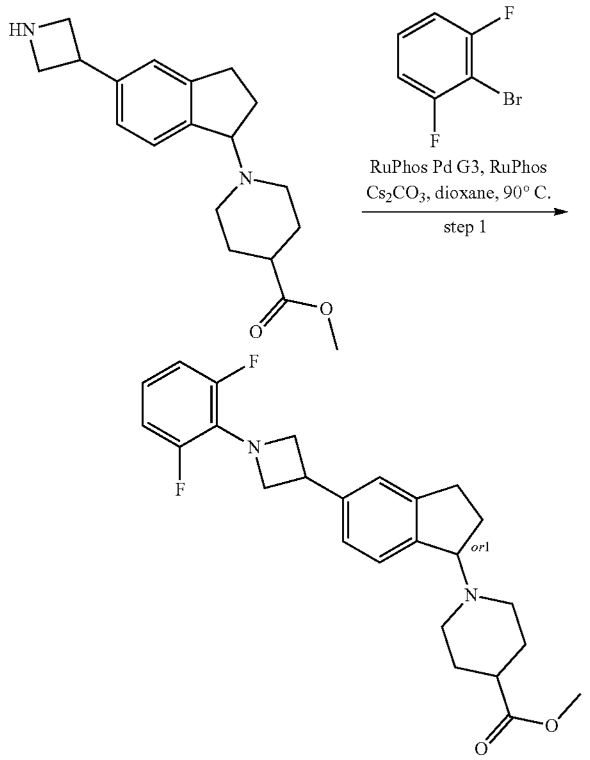

chiral separation 1

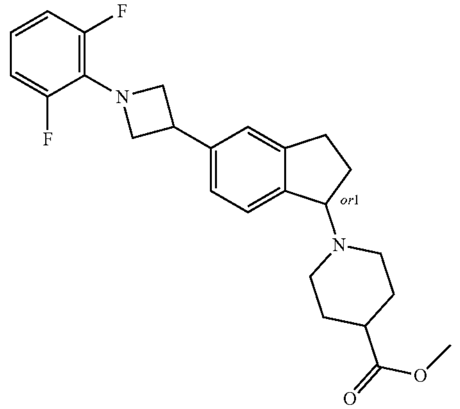

chiral separation 2

To a stirred solution of methyl 1-(5-(azetidin-3-yl)-2,3-dihydro-1H-inden-1-yl)piperidine-4-carboxylate (800 mg, 2.54 mmol, 1.00 equiv.), 2-bromo-1,3-difluoro-benzene (737 mg, 3.82 mmol, 1.50 equiv.), RuPhos Pd G3 (356 mg, 0.382 mmol, 0.150 equiv.) and RuPhos (178 mg, 0.382 mmol, 0.150 equiv.) in anhydrous 1,4-dioxane (20 mL) was added $Cs_2CO_3$ (2.48 g, 7.62 mmol, 3.00 equiv.). The resulting mixture was stirred at 90° C. under nitrogen atmosphere overnight. LCMS showed the reaction was complete. The reaction mixture was concentrated under reduced pressure. The crude product was purified by flash chromatography on silica gel (eluted with ethyl acetate/petroleum ether, 1/1) to afford methyl 1-(5-(1-(2,6-difluorophenyl)azetidin-3-yl)-2,3-dihydro-1H-inden-1-yl)piperidine-4-carboxylate (140 mg, 13%) as a yellow oil. LCMS (ESI, m z): 427 $[M+H]^+$. This racemic mixture was then resolved by Chiral-HPLC (Column: CHIRALPAK IA, 2*25 cm, 5 μm; Mobile Phase A: Hex (0.5% 2M $NH_3$-MeOH), Mobile Phase B: EtOH; Flow rate: 20 mL/min; Gradient: 10% B to 10% B in 11 min; 220/254 nm; RT1: 7.437 min, RT2: 8.632 min; Injection Volume: 0.7 mL; Number of Runs: 10) to afford the desired enantiomers (60 mg for each).

Synthesis of 1-(5-(1-(2,6-difluorophenyl)azetidin-3-yl)-2,3-dihydro-1H-inden-1-yl)-piperidine-4-carboxylic acid (Enantiomer 1, 2a)

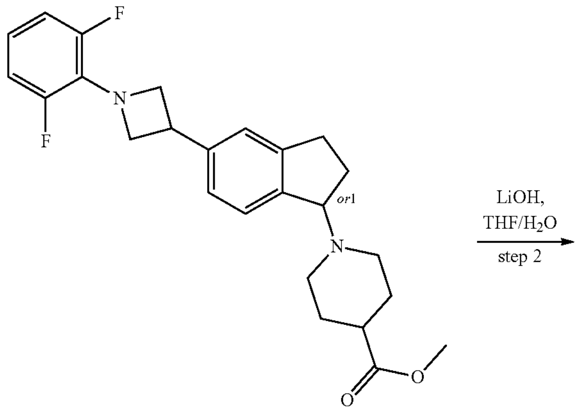

chiral separation 1

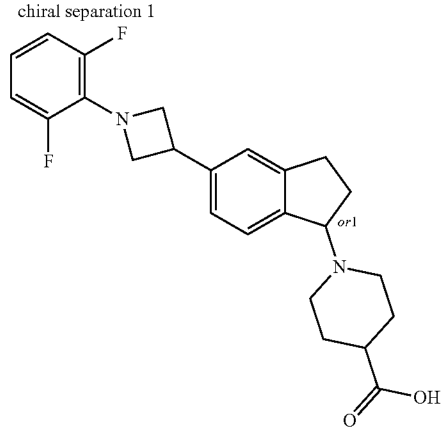

2a
chiral separation 1

To a stirred solution of methyl 1-(5-(1-(2,6-difluorophenyl)azetidin-3-yl)-2,3-dihydro-1H-inden-1-yl)piperidine-4-carboxylate (60 mg, 0.140 mmol, 1.00 equiv.) in THE (1 mL) and water (1 mL) was added LiOH (11 mg, 0.420 mmol, 3.00 equiv.). The resulting mixture was stirred at room temperature for 1 h. LCMS showed the reaction was complete. The reaction mixture was acidified to pH 4-5 using acetic acid and then was concentrated. The residue was purified by Prep-HPLC (Column: XBridge Shield RP18 OBD Column, 5 μm, 19*150 mm; Mobile Phase A: Water (10 mM $NH_4HCO_3$+0.1% $NH_3 \cdot H_2O$), Mobile Phase B: ACN; Flow rate: 60 mL/min; Gradient: 17% B to 47% B in 7 min; 210/254 nm; RT: 6.4 min) to afford 1-(5-(1-(2,6-difluorophenyl)azetidin-3-yl)-2,3-dihydro-1H-inden-1-yl) piperidine-4-carboxylic acid (26.6 mg, 45.7%) as a white solid.

LCMS (ESI, m/z): 413 $[M+H]^+$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.624 min.

$^1$H NMR (400 MHz, DMSO-$d_6$) δ 12.00 (br, 1H), 7.30-7.22 (m, 3H), 6.98-6.92 (m, 2H), 6.75-6.68 (m, 1H), 4.54-4.48 (m, 2H), 4.30-4.23 (m, 1H), 4.13-4.09 (m, 2H), 3.94-3.87 (m, 1H), 2.88-2.72 (m, 3H), 2.49-2.46 (m, 1H), 2.27-2.12 (m, 3H), 2.02-1.94 (m, 2H), 1.83-1.73 (m, 2H), 1.64-1.52 (m, 1H), 1.50-1.42 (m, 1H).

Synthesis of 1-(5-(1-(2,6-difluorophenyl)azetidin-3-yl)-2,3-dihydro-1H-inden-1-yl)-piperidine-4-carboxylic acid (Enantiomer 2, 2b)

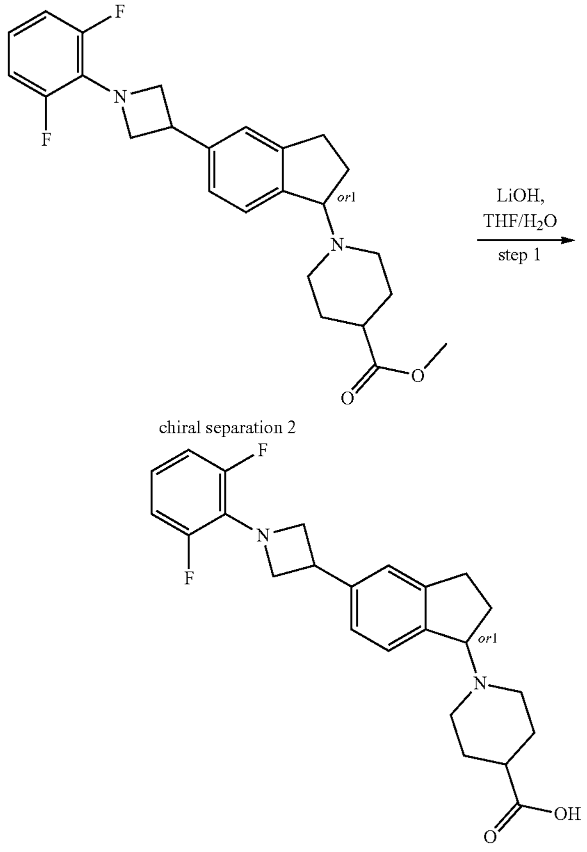

2b
chiral separation 2

To a stirred solution of methyl 1-(5-(1-(2,6-difluorophenyl)azetidin-3-yl)-2,3-dihydro-1H-inden-1-yl)piperidine-4-carboxylate (60 mg, 0.140 mmol, 1.00 equiv.) in THE (1 mL) and water (1 mL) was added LiOH (11 mg, 0.420 mmol, 3.00 equiv.). The resulting mixture was stirred at room temperature for 1 h. LCMS showed the reaction was complete. The reaction mixture was acidified to pH 4-5 using acetic acid and then was concentrated. The residue was purified by Prep-HPLC (Column: XBridge Shield RP18 OBD Column, 5 μm, 19*150 mm; Mobile Phase A: Water (10 mM $NH_4HCO_3$+0.1% $NH_3 \cdot H_2O$), Mobile Phase B: ACN; Flow rate: 60 mL/min; Gradient: 16% B to 46% B in 7 min; 210/254 nm; RT: 6.7 min) to afford 1-(5-(1-(2,6-difluorophenyl)azetidin-3-yl)-2,3-dihydro-1H-inden-1-yl) piperidine-4-carboxylic acid (27.5 mg, 47.2%) as a white solid.

LCMS (ESI, m/z): 413 $[M+H]^+$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.614 min.

$^1$H NMR (400 MHz, DMSO-$d_6$) δ 12.06 (br, 1H), 7.28 (s, 1H), 7.23-7.21 (m, 2H), 6.96-6.92 (m, 2H), 6.75-6.67 (m, 1H), 4.53-4.48 (m, 2H), 4.25 (t, J=6.8 Hz, 1H), 4.13-4.08 (m, 2H), 3.94-3.86 (m, 1H), 2.89-2.70 (m, 3H), 2.47-2.44 (m, 1H), 2.29-2.09 (m, 3H), 2.01-1.95 (m, 2H), 1.82-1.73 (m, 2H), 1.63-1.53 (m, 1H), 1.50-1.40 (m, 1H).

Example S3. 1-(5-(1-(3-fluorophenyl)azetidin-3-yl)-2,3-dihydro-1H-inden-1-yl)piperidine-4-carboxylic acid (3a and 3b)

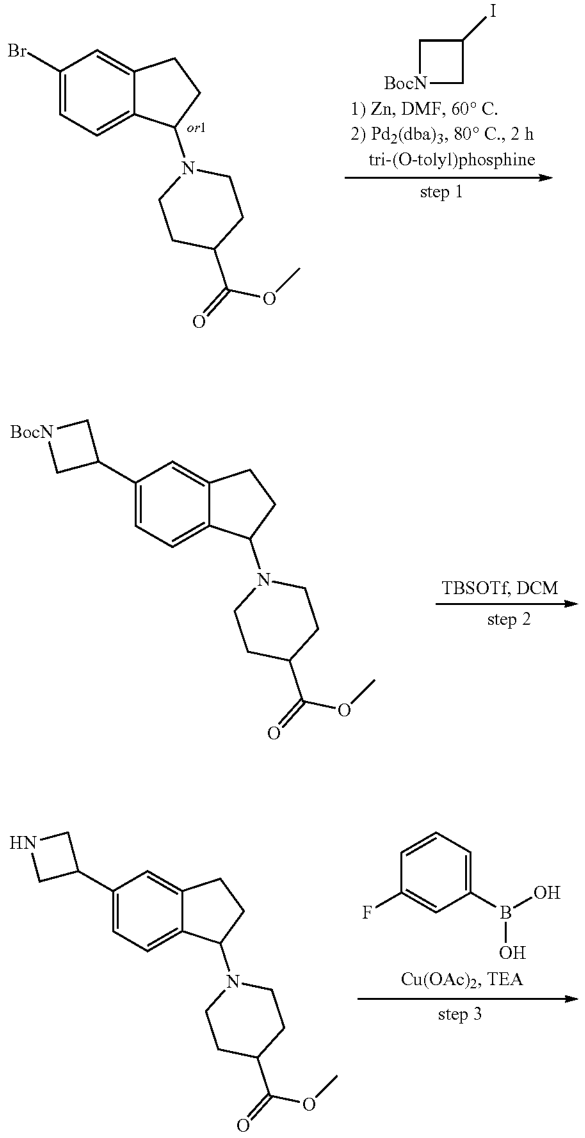

-continued

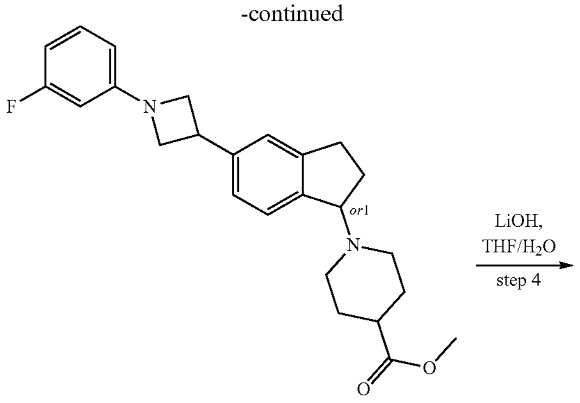

chiral separation 1

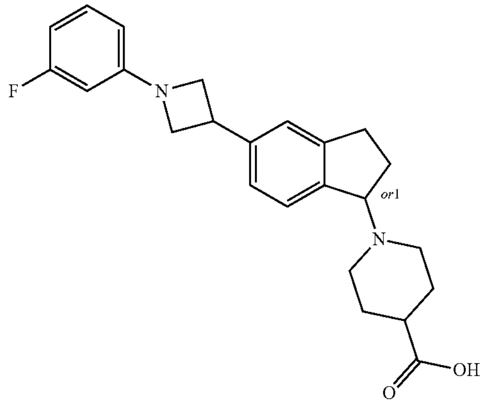

3a

Synthesis of methyl 1-(5-(1-(tert-butoxycarbonyl) azetidin-3-yl)-2,3-dihydro-1H-inden-1-yl)piperidine-4-carboxylate

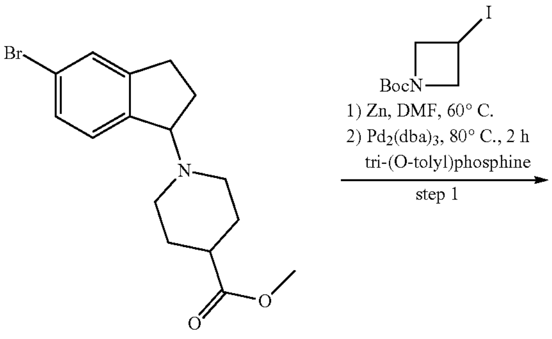

-continued

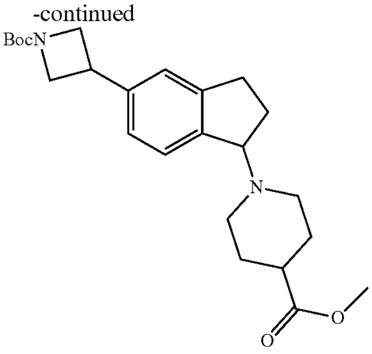

To a stirred solution of methyl 1-(5-bromo-2,3-dihydro-1H-inden-1-yl)piperidine-4-carboxylate (2.0 g, 7.06 mmol, 1.00 equiv.) in DMF (15 mL) was added Zinc powder (693 mg, 10.6 mmol, 1.50 equiv.). The resulting mixture was stirred at 60° C. for 3h under $N_2$ atmosphere. Then $Pd_2(dba)_3$ (104 mg, 0.110 mmol, 0.016 equiv.), tris-(o-tolyl)phosphine (69 mg, 0.230 mmol, 0.032 equiv.) and methyl 1-(5-bromoindan-1-yl)piperidine-4-carboxylate (383 mg, 1.130 mmol, 0.160 equiv.) were added. The resulting mixture was stirred at 80° C. overnight. LCMS showed the reaction was completed. The reaction mixture was diluted with saturated aq. $NH_4Cl$ (60 mL) and extracted with EtOAc (3*40 mL). The organic layers were combined and dried over $MgSO_4$ and concentrated. The crude was purified by flash chromatography on silica gel (eluted with PE/EtOAc, 1/1) to afford methyl 1-(5-(1-(tert-butoxycarbonyl)azetidin-3-yl)-2,3-dihydro-1H-inden-1-yl)piperidine-4-carboxylate (300 mg, 64%) as a yellow oil. LCMS (ESI, m z): 415 $[M+H]^+$.

Synthesis of methyl 1-(5-(azetidin-3-yl)-2,3-dihydro-1H-inden-1-yl)piperidine-4-carboxylate

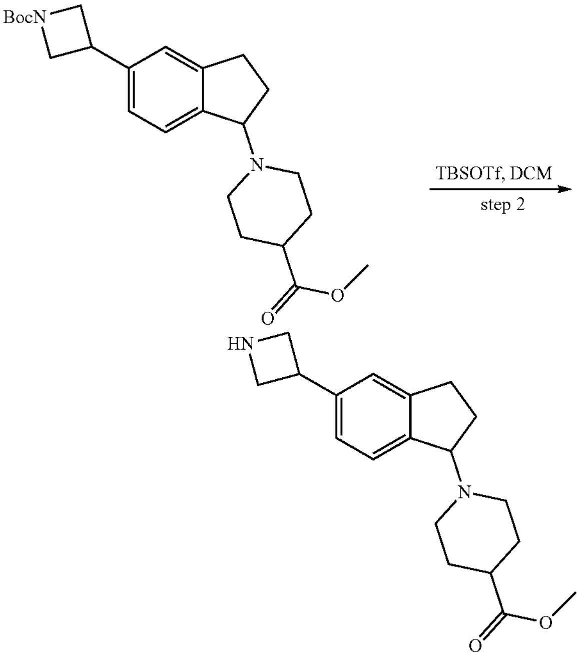

To a stirred solution of methyl 1-(5-(1-(tert-butoxycarbonyl)azetidin-3-yl)-2,3-dihydro-1H-inden-1-yl)piperidine-4-carboxylate (800 mg, 1.93 mmol, 1.00 equiv.) in DCM (10 mL) was added TBSOTf (1.33 mL, 5.79 mmol, 3.00 equiv.). The resulting mixture was stirred at room temperature for 2 h. LCMS showed the reaction was complete. The reaction mixture was concentrated under reduced pressure. The crude product was purified by flash column on C18 (eluted with water/ACN, 5/95) to afford methyl 1-(5-(azetidin-3-yl)-2,3-dihydro-1H-inden-1-yl)piperidine-4-carboxylate (500 mg, 82.4%) as a yellow oil. LCMS (ESI, m z): 315 $[M+H]^+$.

Synthesis of methyl 1-(5-(1-(3-fluorophenyl)azetidin-3-yl)-2,3-dihydro-1H-inden-1-yl)piperidine-4-carboxylate

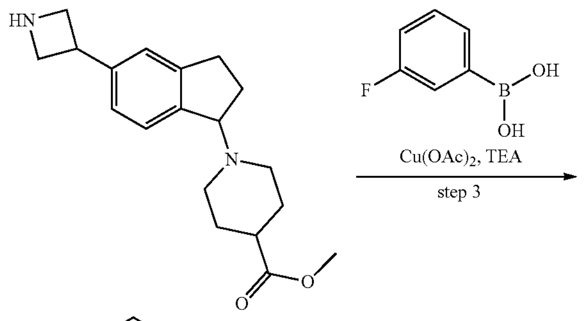

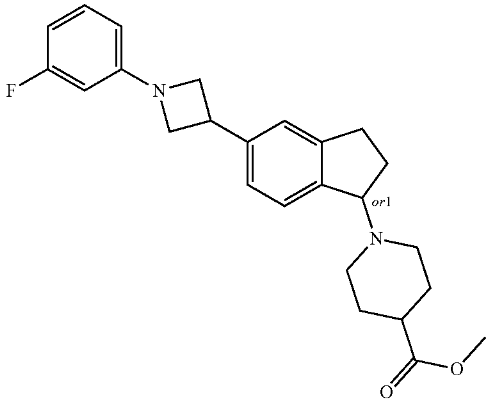

chiral separation 1

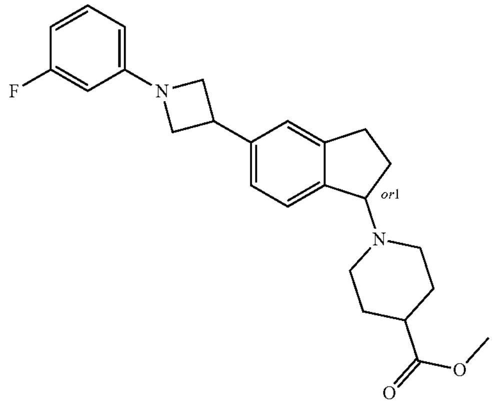

chiral separation 2

To a stirred solution of methyl 1-(5-(azetidin-3-yl)-2,3-dihydro-1H-inden-1-yl)piperidine-4-carboxylate (200 mg, 0.640 mmol, 1.00 equiv.) and (3-fluorophenyl)boronic acid (178 mg, 1.28 mmol, 2.00 equiv.) in ACN (8 mL) were added $Cu(OAc)_2$ (58 mg, 0.320 mmol, 0.500 equiv.) and TEA (193 mg, 1.92 mmol, 3.00 equiv.). The resulting mixture was stirred at 80° C. overnight. LCMS showed the reaction was complete. The reaction mixture was concentrated and purified by flash column on silica gel (eluted with PE/EA, 1/3) to afford methyl 1-(5-(1-(3-fluorophenyl)azetidin-3-yl)-2,3-dihydro-1H-inden-1-yl)piperidine-4-carboxylate (130 mg, 0.318 mmol) as a yellow oil. LCMS (ESI, m z): 409 $[M+H]^+$. That racemic mixture was then resolved by Chiral HPLC (Column: Chiralpak IA, 2*25 cm, 5 m; Mobile Phase A: Hex (8 mM $NH_3$·MeOH), Mobile Phase B: EtOH; Flow rate: 20 mL/min; Gradient: 10% B to 10% B in 20 min; 220/254 nm; RT1: 6.351 min; RT2: 9.977 min) to afford the desired enantiomers (40 mg for each).

Synthesis of 1-(5-(1-(3-fluorophenyl)azetidin-3-yl)-2,3-dihydro-1H-inden-1-yl)piperidine-4-carboxylic acid (Enantiomer 1, 3a)

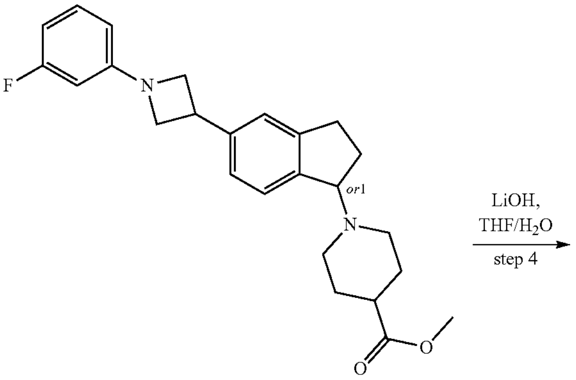

chiral separation 1

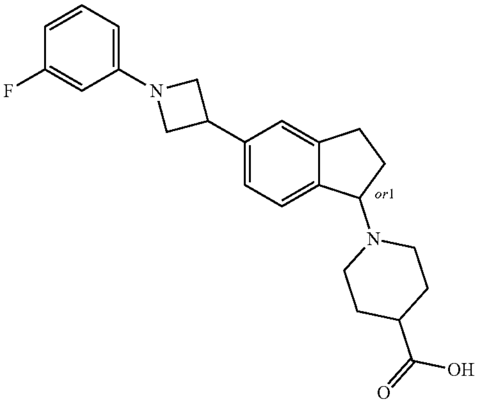

3a
chiral separation 1

To a stirred solution of methyl 1-(5-(1-(3-fluorophenyl)azetidin-3-yl)-2,3-dihydro-1H-inden-1-yl)piperidine-4-carboxylate (40 mg, 0.100 mmol, 1.00 equiv.) in THE (1 mL) and water (1 mL) was added LiOH (8 mg, 0.300 mmol, 3.00 equiv.). The resulting mixture was stirred at room temperature overnight. LCMS showed the reaction was complete. The reaction mixture was acidified to pH 4-5 using acetic acid and then was concentrated. The residue was purified by Prep-HPLC (Column: XBridge Shield RP18 OBD Column, 5 μm, 19*150 mm; Mobile Phase A: water (10 mM $NH_4HCO_3$+0.1% $NH_3$·$H_2O$), Mobile Phase B: ACN; Flow rate: 60 mL/min; Gradient: 20% B to 39% B in 10 min; 210/254 nm; RT: 9.10 min) to afford 1-(5-(1-(3-fluorophenyl)azetidin-3-yl)-2,3-dihydro-1H-inden-1-yl)piperidine-4-carboxylic acid (15.5 mg, 39.8%) as a white solid.

LCMS (ESI, m/z): 395 $[M+H]^+$. Analytic Conditions: column: EVO C18, 3.0*50 mm, 2.6 μm; mobile phase A: water (5 mM $NH_4HCO_3$), mobile phase B: acetonitrile, flow rate: 1.20 mL/min; gradient: 10% B to 95% B in 2.00 min, hold at 95% for 0.60 min, 95% B to 10% B in 0.15 min; 254 nm; RT: 1.112 min.

$^1$H NMR (400 MHz, DMSO-$d_6$) δ 12.07 (br, 1H), 7.25-7.17 (m, 4H), 6.49-6.44 (m, 1H), 6.32-6.26 (m, 2H), 4.28-4.22 (m, 3H), 3.96-3.89 (m, 1H), 3.81-3.78 (m, 2H), 2.89-2.70 (m, 3H), 2.49-2.46 (m, 1H), 2.26-2.14 (m, 3H), 2.02-1.91 (m, 2H), 1.82-1.73 (m, 2H), 1.63-1.50 (m, 1H), 1.47-1.41 (m, 1H).

Synthesis of 1-(5-(1-(3-fluorophenyl)azetidin-3-yl)-2,3-dihydro-1H-inden-1-yl)piperidine-4-carboxylic acid (Enantiomer 2, 3b)

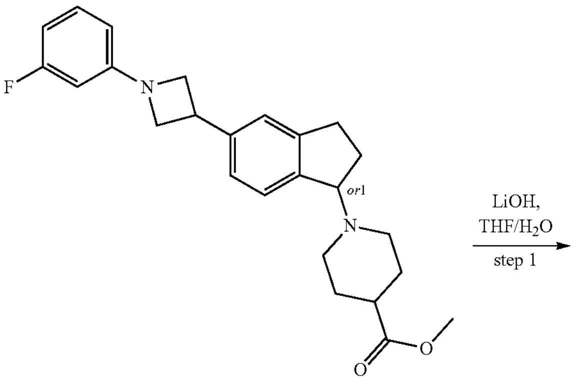

chiral separation 2

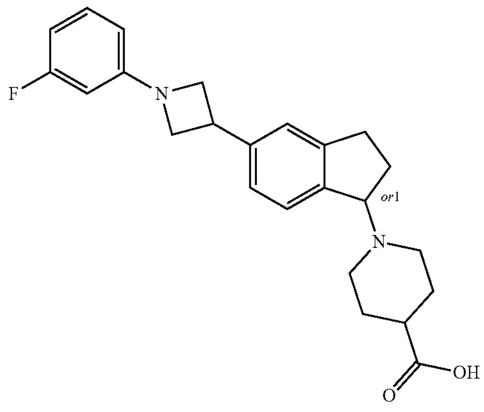

3b
chiral separation 2

To a stirred solution of methyl 1-(5-(1-(3-fluorophenyl)azetidin-3-yl)-2,3-dihydro-1H-inden-1-yl)piperidine-4-carboxylate (40 mg, 0.100 mmol, 1.00 equiv.) in THE (1 mL) and water (1 mL) was added LiOH (8 mg, 0.300 mmol, 3.00 equiv.). The resulting mixture was stirred at room temperature overnight. LCMS showed the reaction was complete. The reaction mixture was acidified to pH 4-5 using acetic acid and then was concentrated. The residue was purified by Prep-HPLC (Column: XBridge Shield RP18 OBD Column, 5 μm, 19*150 mm; Mobile Phase A: water (10 mM $NH_4HCO_3$+0.1% $NH_3 \cdot H_2O$), Mobile Phase B: ACN; Flow rate: 60 mL/min; Gradient: 20% B to 37% B in 10 min; 210/254 nm; RT: 9.58 min) to afford 1-(5-(1-(3-fluorophenyl)azetidin-3-yl)-2,3-dihydro-1H-inden-1-yl)piperidine-4-carboxylic acid (7.3 mg, 18.8%) as a white solid.

LCMS (ESI, m/z): 395 $[M+H]^+$. Analytic Conditions: column: EVO C18, 3.0*50 mm, 2.6 μm; mobile phase A: water (5 mM $NH_4HCO_3$), mobile phase B: acetonitrile, flow rate: 1.20 mL/min; gradient: 10% B to 95% B in 2.00 min, hold at 95% for 0.60 min, 95% B to 10% B in 0.15 min; 254 nm; RT: 1.115 min.

$^1$H NMR (400 MHz, DMSO-$d_6$) δ 12.07 (br, 1H), 7.26-7.17 (m, 4H), 6.49-6.44 (m, 1H), 6.32-6.26 (m, 2H), 4.28-4.22 (m, 3H), 3.97-3.90 (m, 1H), 3.81-3.78 (m, 2H), 2.89-2.71 (m, 3H), 2.49-2.46 (m, 1H), 2.29-2.14 (m, 3H), 2.02-1.91 (m, 2H), 1.84-1.75 (m, 2H), 1.63-1.50 (m, 1H), 1.47-1.41 (m, 1H).

Example S4. 1-(5-(1-(2-fluorophenyl)azetidin-3-yl)-2,3-dihydro-1H-inden-1-yl)piperidine-4-carboxylic acid (4a and 4b)

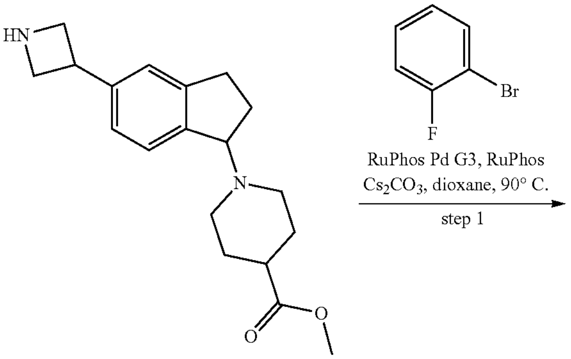

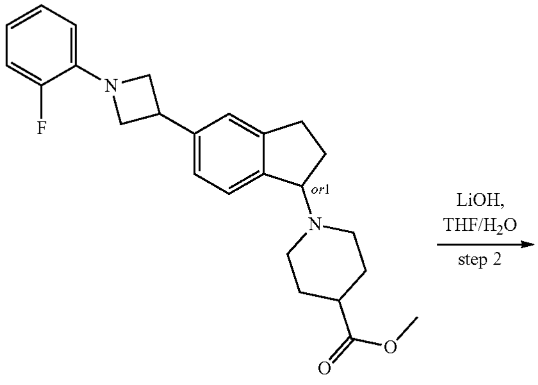

chiral separation 1

-continued

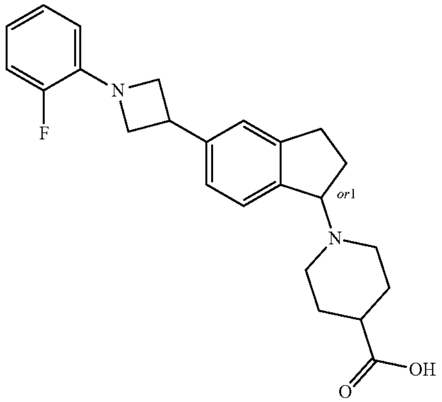

4a

Synthesis of methyl 1-(5-(1-(2-fluorophenyl)azetidin-3-yl)-2,3-dihydro-1H-inden-1-yl)piperidine-4-carboxylate

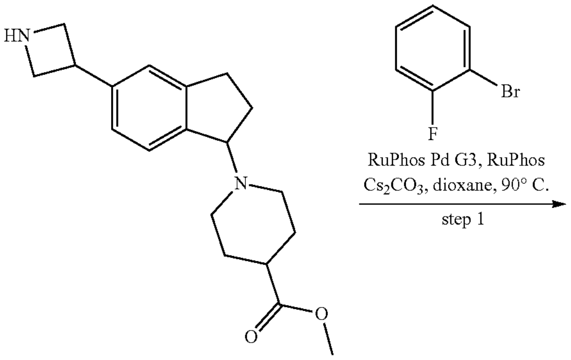

-continued

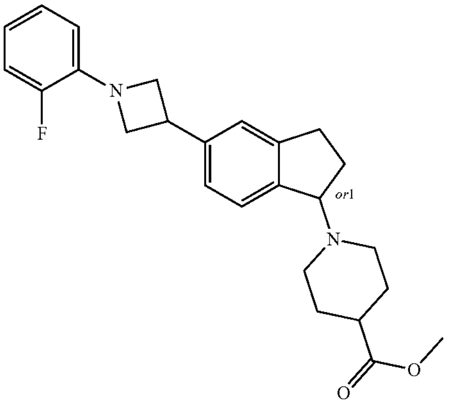

chiral separation 2

To a stirred solution of methyl 1-(5-(azetidin-3-yl)-2,3-dihydro-1H-inden-1-yl)piperidine-4-carboxylate (1.00 g, 3.18 mmol, 1.00 equiv.), 1-bromo-2-fluoro-benzene (668 mg, 3.82 mmol, 1.20 equiv.), RuPhos Pd G3 (445 mg, 0.480 mmol, 0.150 equiv.) and RuPhos (223 mg, 0.480 mmol, 0.150 equiv.) in 1,4-dioxane (8 mL) was added $Cs_2CO_3$ (3.1 g, 9.54 mmol, 3.00 equiv.). The resulting mixture was stirred at 90° C. for 6h under nitrogen atmosphere. LCMS showed the reaction was completed. The reaction mixture was concentrated under reduced pressure. The residue was purified by flash chromatography on silica gel (eluted with EtOAc/PE, 1/2) to afford methyl 1-(5-(1-(2-fluorophenyl)azetidin-3-yl)-2,3-dihydro-1H-inden-1-yl)piperidine-4-carboxylate (160 mg, 0.392 mmol, 12.3% yield) as a yellow oil. LCMS (ESI, m z): 409 $[M+H]^+$. This racemic product was then resolved by Chiral-HPLC (Column: CHIRALPAK IA, 2*25 cm, 5 μm; Mobile Phase A: Hex (0.5% 2M $NH_3$-MeOH), Mobile Phase B: EtOH; Flow rate: 20 mL/min; Gradient: 10% B to 10% B in 12 min; 220/254 nm; RT1: 6.377 min, RT2: 8.672 min) to afford the desired enantiomers (60 mg for each).

Synthesis of 1-(5-(1-(2-fluorophenyl)azetidin-3-yl)-2,3-dihydro-1H-inden-1-yl)piperidine-4-carboxylic acid (Enantiomer 1, 4a)

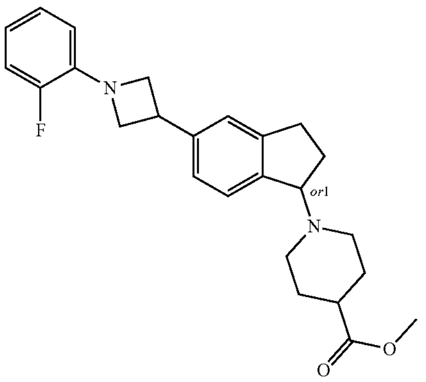

chiral separation 1

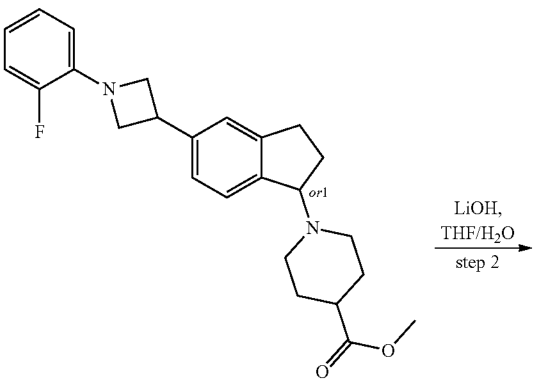

chiral separation 1

-continued

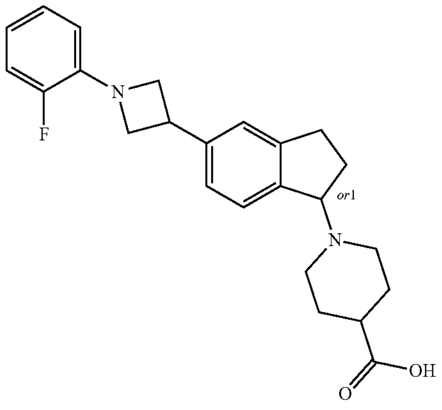

4a
chiral separation 1

To a stirred solution of methyl 1-(5-(1-(2-fluorophenyl)azetidin-3-yl)-2,3-dihydro-1H-inden-1-yl)piperidine-4-carboxylate (60 mg, 0.150 mmol, 1.00 equiv.) in THE (2 mL) and water (2 mL) was added LiOH (11 mg, 0.450 mmol, 3.00 equiv.). The resulting mixture was stirred at room temperature overnight. LCMS showed the reaction was complete. The reaction mixture was acidified to pH 4-5 using acetic acid and then was concentrated. The residue was purified by Prep-HPLC (Column: YMC-Actus Triart C18, 30*250, 5 μm; Mobile Phase A: water (10 mM $NH_4HCO_3$+0.1% $NH_3 \cdot H_2O$), Mobile Phase B: ACN; Flow rate: 60 mL/min; Gradient: 14% B to 44% B in 7 min; 254/210 nm; RT: 6.53 min) to afford 1-(5-(1-(2-fluorophenyl)azetidin-3-yl)-2,3-dihydro-1H-inden-1-yl)piperidine-4-carboxylic acid (24.4 mg, 42.7% yield) as a white solid.

LCMS (ESI, m/z): 395 $[M+H]^+$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.542 min.

$^1H$ NMR (400 MHz, DMSO-$d_6$) δ 12.02 (br, 1H), 7.26-7.19 (m, 3H), 7.09-7.01 (m, 2H), 6.77-6.71 (m, 1H), 6.64-6.59 (m, 1H), 4.34-4.29 (m, 2H), 4.25 (t, J=7.6 Hz, 1H), 3.97-3.85 (m, 3H), 2.89-2.70 (m, 3H), 2.49-2.45 (m, 1H), 2.28-2.22 (m, 1H), 2.19-2.09 (m, 2H), 2.01-1.96 (m, 2H), 1.82-1.73 (m, 2H), 1.63-1.53 (m, 1H), 1.50-1.40 (m, 1H).

Synthesis of 1-(5-(1-(2-fluorophenyl)azetidin-3-yl)-2,3-dihydro-1H-inden-1-yl)piperidine-4-carboxylic acid (Enantiomer 2, 4b)

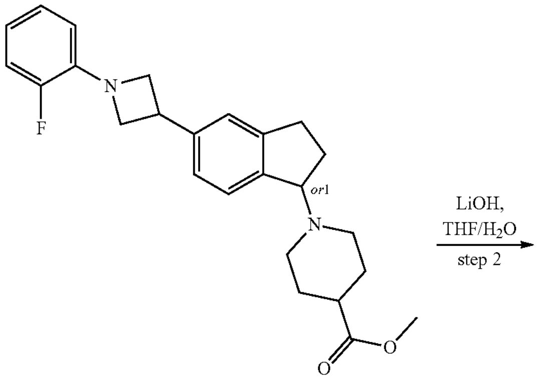

chiral separation 2

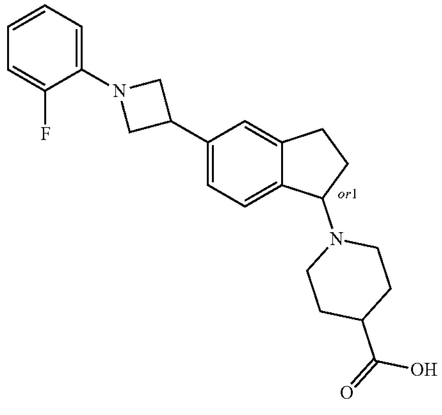

4b
chiral separation 2

To a stirred solution of methyl 1-(5-(1-(2-fluorophenyl)azetidin-3-yl)-2,3-dihydro-1H-inden-1-yl)piperidine-4-carboxylate (60 mg, 0.150 mmol, 1.00 equiv.) in THE (2 mL) and water (2 mL) was added LiOH (11 mg, 0.450 mmol, 3.00 equiv.). The resulting mixture was stirred at room temperature overnight. LCMS showed the reaction was complete. The reaction mixture was acidified to pH 4-5 using acetic acid and then was concentrated. The residue was purified by Prep-HPLC (Column: YMC-Actus Triart C18, 30*250, 5 μm; Mobile Phase A: water (10 mM $NH_4HCO_3$+0.1% $NH_3 \cdot H_2O$), Mobile Phase B: ACN; Flow rate: 60 mL/min; Gradient: 14% B to 44% B in 7 min; 254/210 nm; RT: 6.20 min) to afford 1-(5-(1-(2-fluorophenyl)azetidin-3-yl)-2,3-dihydro-1H-inden-1-yl)piperidine-4-carboxylic acid (30.9 mg, 53.3% yield) as a white solid.

LCMS (ESI, m/z): 395 $[M+H]^+$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.536 min.

$^1H$ NMR (400 MHz, DMSO-$d_6$) δ 7.25-7.18 (m, 3H), 7.09-7.02 (m, 2H), 6.77-6.71 (m, 1H), 6.64-6.59 (m, 1H), 4.33-4.29 (m, 2H), 4.25 (t, J=7.6 Hz, 1H), 3.96-3.85 (m, 3H), 2.88-2.70 (m, 3H), 2.49-2.45 (m, 1H), 2.28-2.21 (m,

1H), 2.17-2.08 (m, 2H), 2.01-1.95 (m, 2H), 1.81-1.71 (m, 2H), 1.62-1.52 (m, 1H), 1.49-1.40 (m, 1H).
Example S5. 1-(5-(1-(2,6-dichlorophenyl)azetidin-3-yl)-7-methyl-2,3-dihydro-1H-inden-1-yl)piperidine-4-carboxylic acid (5)
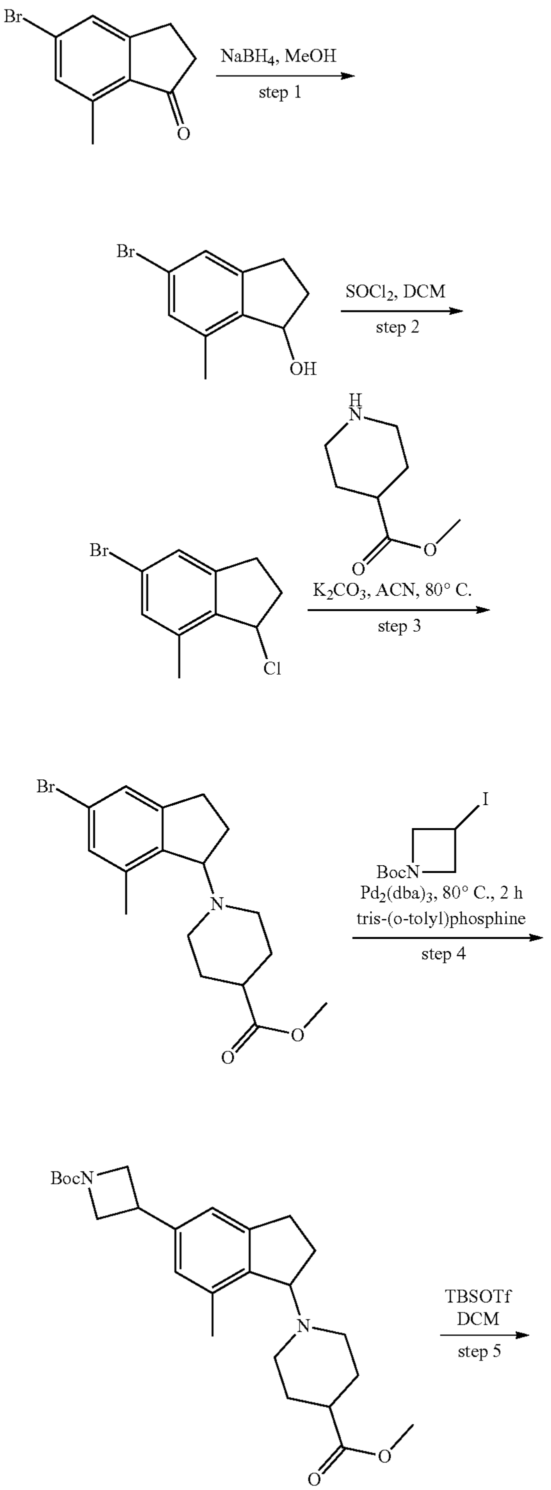
-continued
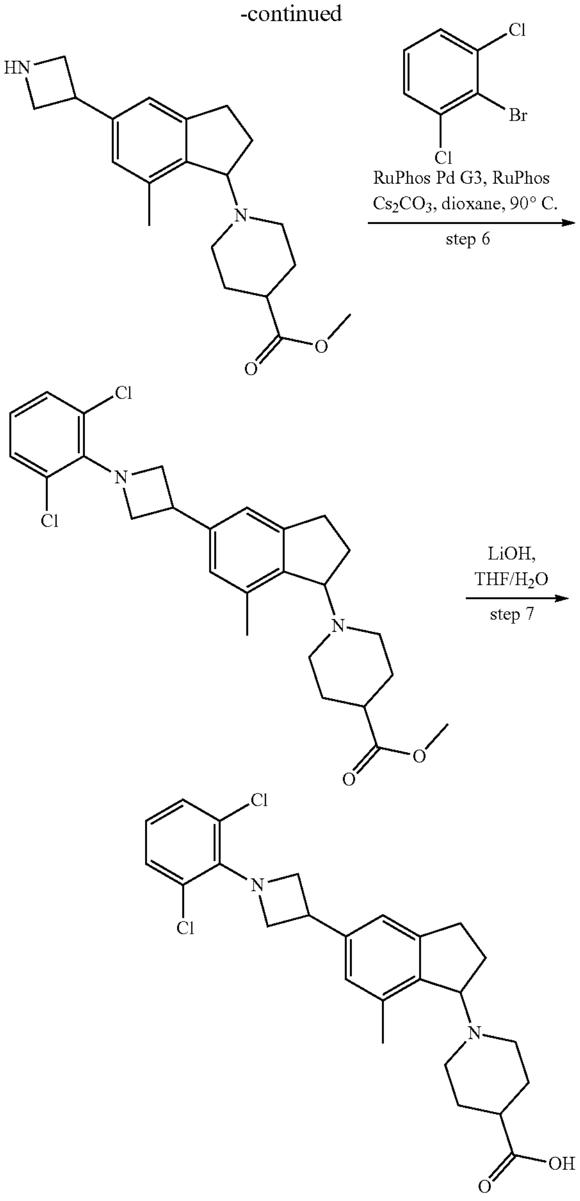
5
Synthesis of 5-bromo-7-methyl-2,3-dihydro-1-inden-1-ol
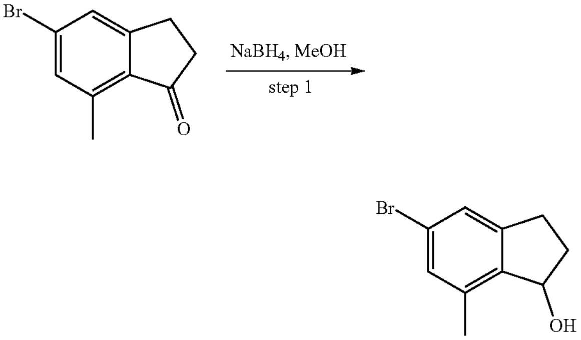

To a stirred solution of 5-bromo-7-methyl-2,3-dihydro-1H-inden-1-one (800 mg, 3.55 mmol, 1.00 equiv.) in methanol (10 mL) was added $NaBH_4$ (202 mg, 5.33 mmol, 1.50 equiv.). The resulting mixture was stirred at room temperature for 1 h. TLC showed the reaction was completed. The reaction was quenched with water (50 mL) and extracted with EtOAc (3*20 ml). The organic layers were concentrated under reduced pressure. The residue was purified by flash chromatography on silica gel (eluted with 100% EtOAc) to afford 5-bromo-7-methyl-2,3-dihydro-1H-inden-1-ol (800 mg, 99.1% yield) as a yellow oil. LCMS (ESI, m z): 227 $[M+H]^+$.

Synthesis of 5-bromo-1-chloro-7-methyl-2,3-dihydro-1H-indene

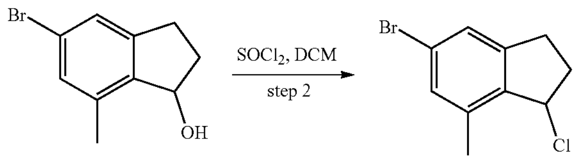

To a stirred solution of 5-bromo-7-methyl-2,3-dihydro-1H-inden-1-ol (800 mg, 3.52 mmol, 1.00 equiv.) in DCM (10 mL) was added $SOCl_2$ (4.19 g, 35.2 mmol, 10.0 equiv.) at 0° C. The resulting mixture was stirred at 0° C. for 2 h. TLC showed the reaction was completed. The reaction mixture was concentrated under reduced pressure. The residue was used directly for next step without further purification.

Synthesis of methyl 1-(5-bromo-7-methyl-2,3-dihydro-1H-inden-1-yl)piperidine-4-carboxylate

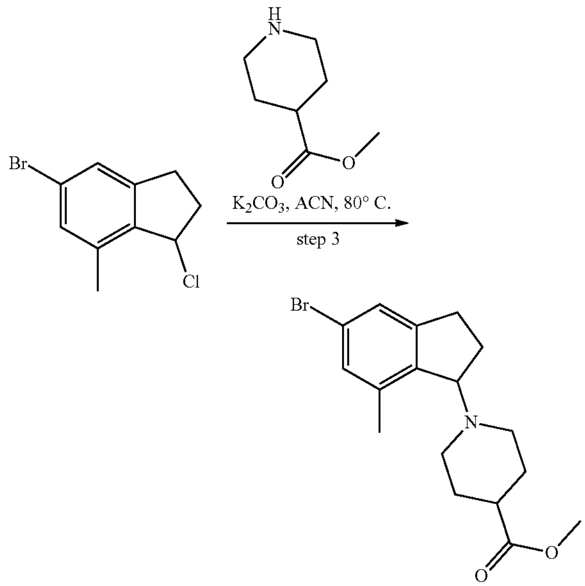

To a stirred solution of 5-bromo-1-chloro-7-methyl-2,3-dihydro-1H-indene (800 mg, 3.26 mmol, 1.00 equiv.) and methyl piperidine-4-carboxylate (700 mg, 4.89 mmol, 1.50 equiv.) in ACN (10 mL) was added $K_2CO_3$ (1.35 g, 9.77 mmol, 3.00 equiv.). The resulting mixture was stirred at 80° C. overnight. LCMS showed the reaction was completed. The reaction mixture was filtered through Celite and the filtrate was concentrated under reduced pressure. The residue was purified by flash chromatography on silica gel (eluted with PE/EtOAc, 4/1) to afford methyl 1-(5-bromo-7-methyl-2,3-dihydro-1H-inden-1-yl)piperidine-4-carboxylate (850 mg, 74.1% yield) as a yellow oil. LCMS (ESI, m z): 352 $[M+H]^+$.

Synthesis of methyl 1-(5-(1-(tert-butoxycarbonyl)azetidin-3-yl)-7-methyl-2,3-dihydro-1H-inden-1-yl)piperidine-4-carboxylate

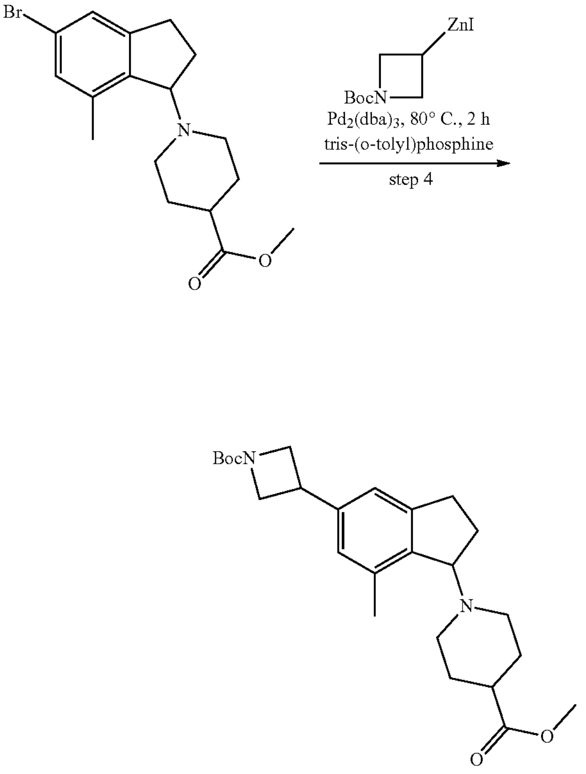

To a stirred solution of (1-tert-butoxycarbonylazetidin-3-yl)-iodo-zinc (791 mg, 2.27 mmol, 2.00 equiv.) in DMF (10 mL) were added $Pd_2(dba)_3$ (156 mg, 0.170 mmol, 0.150 equiv.), tris-(o-tolly)phosphine (104 mg, 0.340 mmol, 0.300 equiv.) and methyl methyl 1-(5-bromo-7-methyl-2,3-dihydro-1H-inden-1-yl)piperidine-4-carboxylate (400 mg, 1.14 mmol, 1.00 equiv.). The resulting mixture was stirred at 80° C. overnight under $N_2$ atmosphere. LCMS showed the reaction was completed. The reaction mixture was diluted with saturated aqueous $NH_4Cl$ (30 mL) and extracted with EtOAc (3*20 mL). The organic layers were concentrated under reduced pressure. The residue was purified by flash chromatography on silica gel (eluted with PE/EA, 4/1) to afford methyl 1-(5-(1-(tert-butoxycarbonyl)azetidin-3-yl)-7-methyl-2,3-dihydro-1H-inden-1-yl)piperidine-4-carboxylate (400 mg, 82.2% yield) as a yellow oil. LCMS (ESI, m z): 429 $[M+H]^+$.

Synthesis of methyl 1-(5-(azetidin-3-yl)-7-methyl-2,3-dihydro-1H-inden-1-yl)piperidine-4-carboxylate

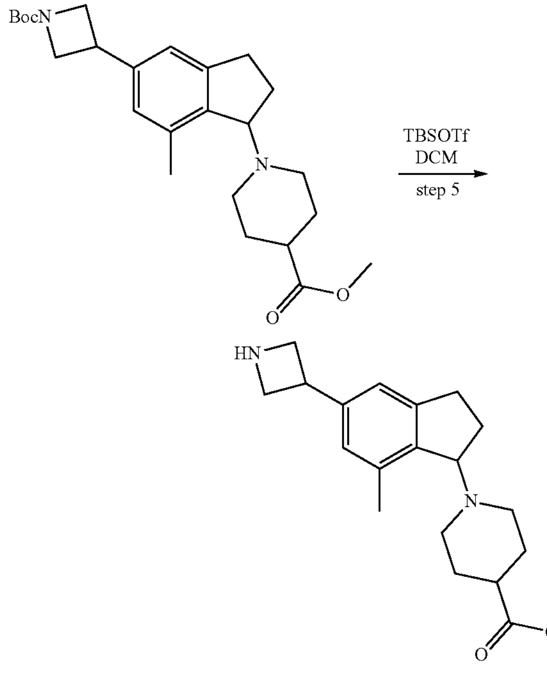

To a stirred solution of methyl 1-(5-(1-(tert-butoxycarbonyl)azetidin-3-yl)-7-methyl-2,3-dihydro-1H-inden-1-yl)piperidine-4-carboxylate (400 mg, 0.930 mmol, 1.00 equiv.) in DCM (8 mL) was added TBSOTf (0.5 mL, 2.80 mmol, 3.00 equiv.). The resulting mixture was stirred at room temperature for 1 h. LCMS showed the reaction was completed. The reaction mixture was concentrated under reduced pressure. The residue was purified by flash chromatography on C18 silica (eluted with ACN/water (0.05% TFA), 5/95) to afford methyl 1-(5-(azetidin-3-yl)-7-methyl-2,3-dihydro-1H-inden-1-yl)piperidine-4-carboxylate (300 mg, 98.0% yield) as a yellow oil. LCMS (ESI, m z): 329 [M+H]$^+$.

Synthesis of methyl 1-(5-(1-(2,6-dichlorophenyl)azetidin-3-yl)-7-methyl-2,3-dihydro-1H-inden-1-yl)piperidine-4-carboxylate

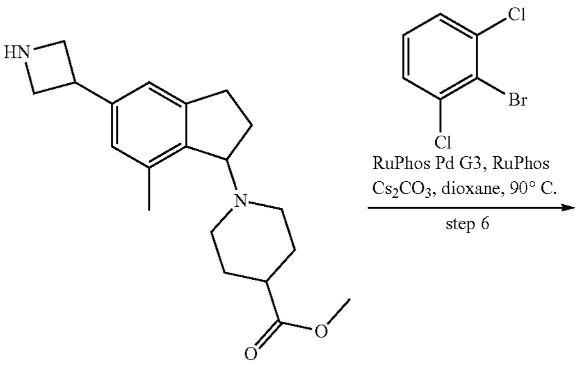

-continued

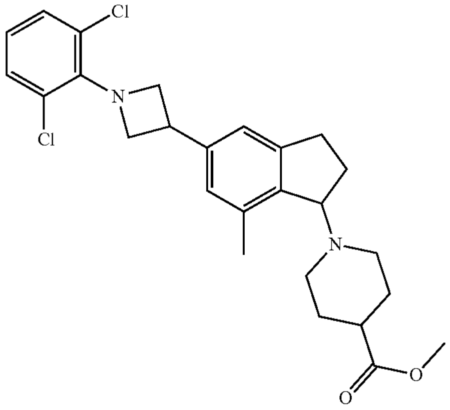

To a stirred solution of methyl 1-(5-(azetidin-3-yl)-7-methyl-2,3-dihydro-1H-inden-1-yl)piperidine-4-carboxylate (300 mg, 0.910 mmol, 1.00 equiv.), 2-bromo-1,3-dichloro-benzene (248 mg, 1.10 mmol, 1.20 equiv.) in 1,4-dioxane (8 mL) were added $Cs_2CO_3$ (891 mg, 2.73 mmol, 3.00 equiv.), RuPhos Pd G3 (115 mg, 0.140 mmol, 0.150 equiv.) and RuPhos (64 mg, 0.140 mmol, 0.150 equiv.). The resulting mixture was stirred at 90° C. overnight. LCMS showed the reaction was completed. The reaction mixture was filtered through Celite and the filtrate was concentrated under reduced pressure. The residue was purified by flash chromatography on silica gel (eluted with PE/EtOAc, 5/1) to afford methyl methyl 1-(5-(1-(2,6-dichlorophenyl)azetidin-3-yl)-7-methyl-2,3-dihydro-1H-inden-1-yl)piperidine-4-carboxylate (100 mg, 23.1% yield) as a yellow oil. LCMS (ESI, m z): 473 [M+H]$^+$.

Synthesis of 1-(5-(1-(2,6-dichlorophenyl)azetidin-3-yl)-7-methyl-2,3-dihydro-1H-inden-1-yl)piperidine-4-carboxylic acid (5)

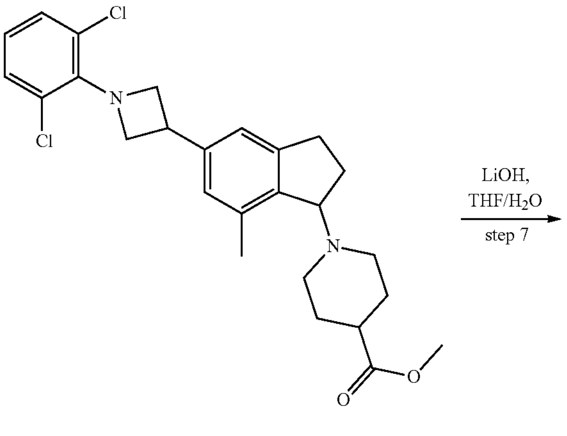

-continued

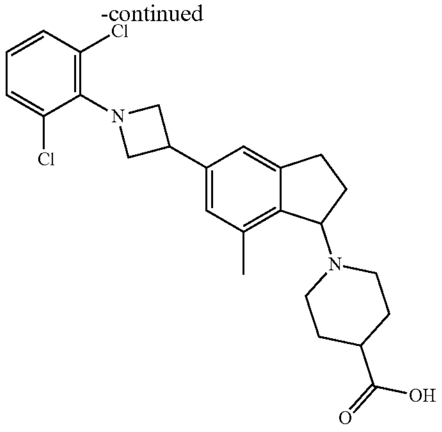

5

To a stirred solution of methyl 1-[5-[1-(2,6-dichlorophenyl)azetidin-3-yl]-7-methyl-indan-1-yl]piperidine-4-carboxylate (100 mg, 0.210 mmol, 1.00 equiv.) in THE (2 mL) and water (2 mL) was added LiOH (26 mg, 1.05 mmol, 5.00 equiv.). The resulting mixture was stirred at room temperature overnight. LCMS showed that the reaction was completed. The reaction was acidified to pH 4 by adding acetic acid and then concentrated under reduced pressure. The residue was purified by prep-HPLC (Column: YMC-Triart Diol Hilic, 20*150 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 30% B to 60% B in 7 min; 254/210 nm; RT: 6.32 min) to afford 1-(5-(1-(2,6-dichlorophenyl)azetidin-3-yl)-7-methyl-2,3-dihydro-1H-inden-1-yl)piperidine-4-carboxylic acid (23.3 mg, 23.8% yield) as a white solid.

LCMS (ESI, m/z): 459 $[M+H]^+$. Analytic Conditions: column: HALO C18, 3.0*30 mm, 2.7 μm; mobile phase A: water (0.05% TFA), mobile phase B: acetonitrile (0.05% TFA), flow rate: 1.20 mL/min; gradient: 5% B to 100% B in 1.30 min, hold at 100% for 0.50 min, 100% B to 5% B in 0.03 min; 254 nm; RT: 1.030 min.

$^1$H NMR (400 MHz, DMSO-$d_6$) δ 7.23 (d, J=8.0 Hz, 2H), 7.07 (s, 1H), 6.99 (s, 1H), 6.74 (t, J=8.0 Hz, 1H), 4.83-4.79 (m, 2H), 4.35-4.31 (m, 3H), 3.75-3.67 (m, 1H), 2.81-2.76 (m, 3H), 2.34 (s, 3H), 2.33-2.31 (m, 1H), 2.18-2.09 (m, 3H), 2.03-1.97 (m, 1H), 1.82-1.74 (m, 2H), 1.67-1.63 (m, 1H), 1.57-1.50 (m, 1H), 1.36-1.24 (m, 1H).

Example S6. 1-(5-(1-(2,6-dichlorophenyl)azetidin-3-yl)-7-fluoro-2,3-dihydro-1H-inden-1-yl)piperidine-4-carboxylic acid (6)

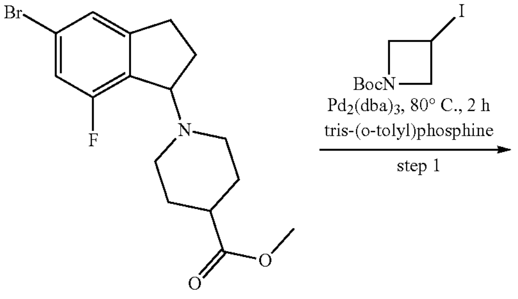

-continued

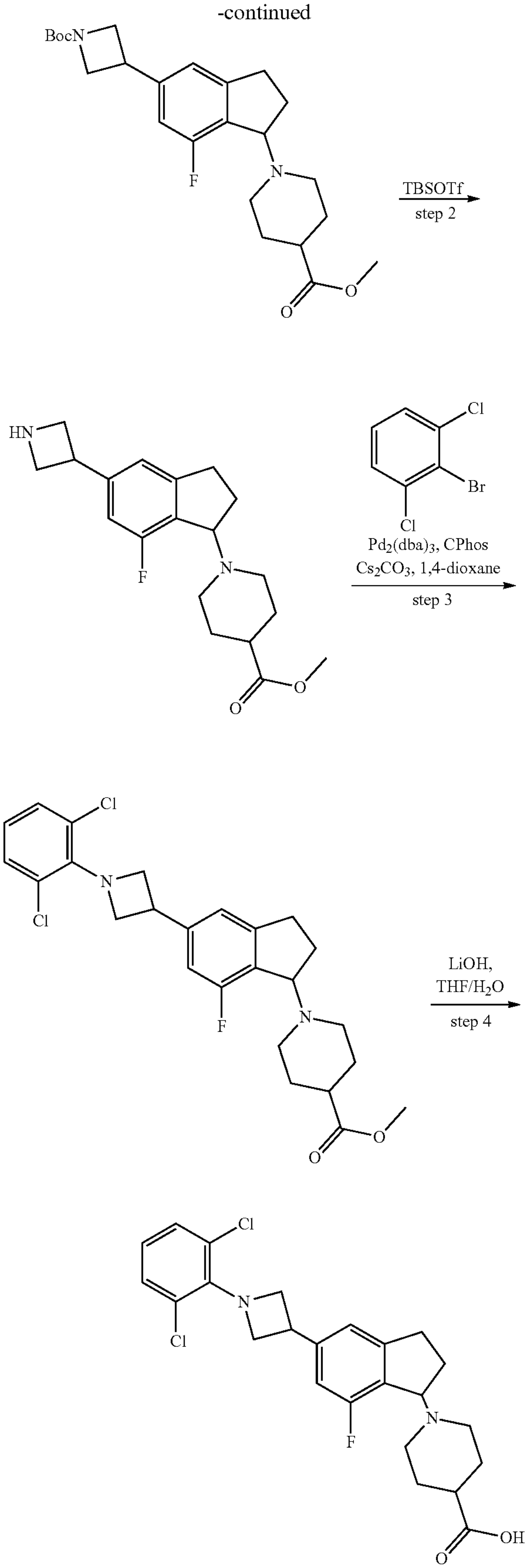

6

Synthesis of methyl 1-(5-(1-(tert-butoxycarbonyl)azetidin-3-yl)-7-fluoro-2,3-dihydro-1H-inden-1-yl)piperidine-4-carboxylate

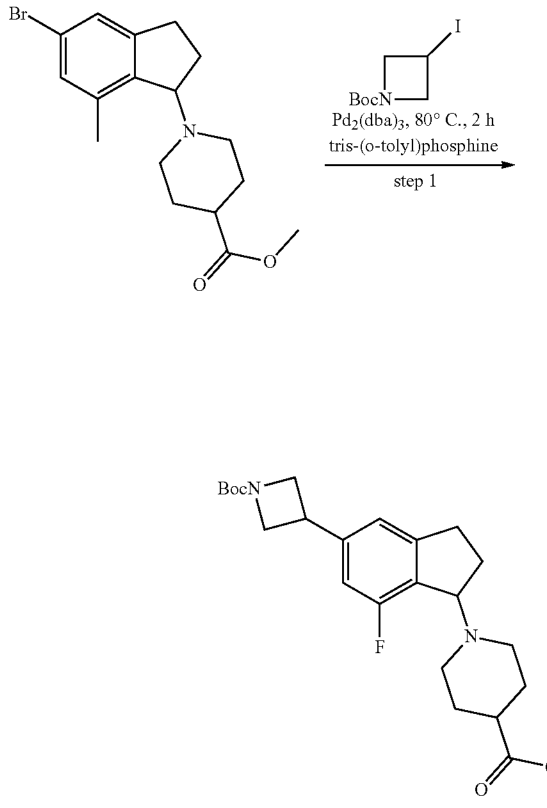

To a stirred solution of methyl 1-(5-bromo-7-fluoro-2,3-dihydro-1H-inden-1-yl)piperidine-4-carboxylate (4.70 g, 16.8 mmol, 10.0 equiv.) in DMF (15 mL) was added Zn (330 mg, 5.05 mmol, 3.00 equiv.). The mixture solution was stirred at 80° C. for 2 h. Then methyl 1-(5-bromo-7-fluoro-indan-1-yl)piperidine-4-carboxylate (600 mg, 1.68 mmol, 1.00 equiv.), $Pd_2(dba)_3$ (154 mg, 0.170 mmol, 0.10 equiv.) and tri-o-tolylphosphane (102 mg, 0.340 mmol, 0.20 equiv.) were added. The resulting mixture was stirred at 80° C. for 16 h. LCMS showed the reaction was completed. The reaction mixture was diluted with saturated aq. $NH_4Cl$ (60 mL) and extracted with EtOAc (3*30 mL). The organic layers were combined and dried over $MgSO_4$ and concentrated. The crude was purified by flash chromatography on silica gel (eluted with PE/EtOAc, 1/1) to afford methyl 1-(5-(1-(tert-butoxycarbonyl)azetidin-3-yl)-7-fluoro-2,3-dihydro-1H-inden-1-yl)piperidine-4-carboxylate (450 mg, 61% yield) as an off-white solid. LCMS (ESI, m/z): 433 $[M+H]^+$.

Synthesis of methyl 1-(5-(azetidin-3-yl)-7-fluoro-2,3-dihydro-1H-inden-1-yl)piperidine-4-carboxylate

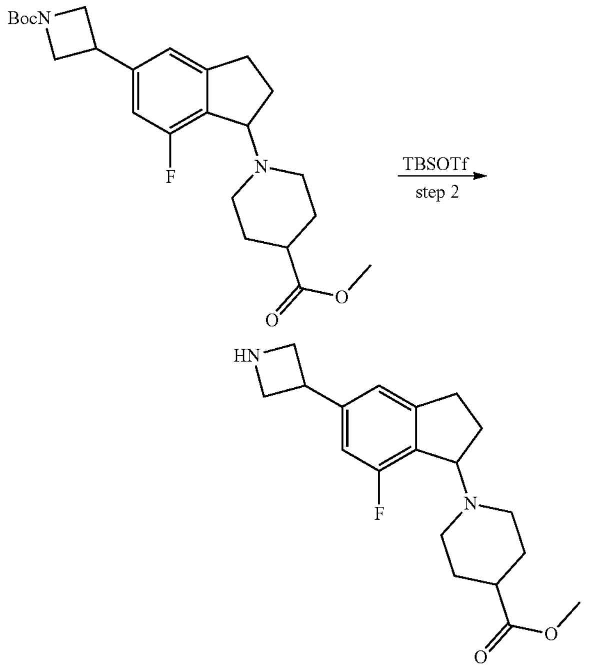

To a stirred solution of methyl 1-(5-(1-(tert-butoxycarbonyl)azetidin-3-yl)-7-fluoro-2,3-dihydro-1H-inden-1-yl)piperidine-4-carboxylate (450 mg, 1.04 mmol, 1.00 equiv.) in DCM (5 mL) was added TBSOTf (0.5 mL, 3.120 mmol, 3.00 equiv.). The mixture solution was stirred at 0° C. for 1 h. LCMS showed the reaction was completed. The reaction mixture was concentrated under reduced pressure. The crude product was purified by flash column on C18 (eluted with water/ACN, 5/95) to afford methyl 1-(5-(azetidin-3-yl)-7-fluoro-2,3-dihydro-1H-inden-1-yl)piperidine-4-carboxylate (450 mg, 96% yield) as an light-yellow oil. LCMS (ESI, m/z): 333 $[M+H]^+$.

Synthesis of methyl 1-(5-(1-(2,6-dichlorophenyl)azetidin-3-yl)-7-fluoro-2,3-dihydro-1H-inden-1-yl)piperidine-4-carboxylate

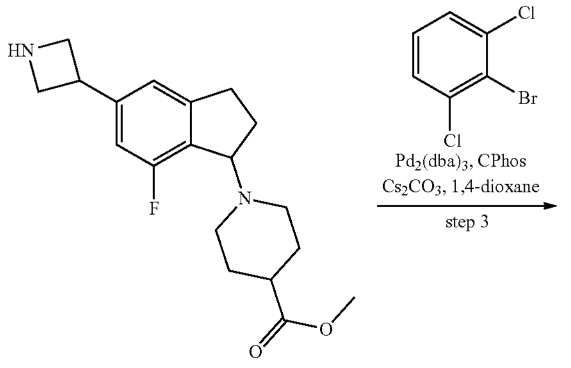

-continued

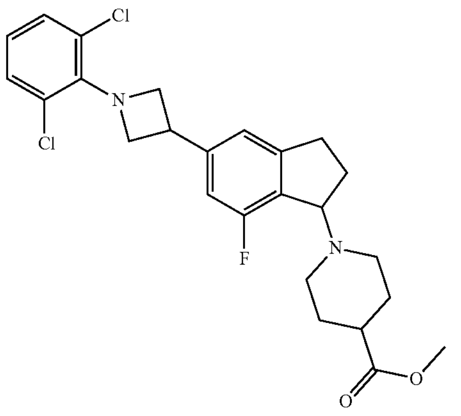

To a stirred solution of methyl 1-(5-(azetidin-3-yl)-7-fluoro-2,3-dihydro-1H-inden-1-yl)piperidine-4-carboxylate (200 mg, 0.600 mmol, 1.00 equiv.) and 2-bromo-1,3-dichloro-benzene (136 mg, 0.600 mmol, 1.00 equiv.) in 1,4-dioxane (5 mL) were added $Pd_2(dba)_3$ (55 mg, 0.060 mmol, 0.10 equiv.), CPhos (18 mg, 0.120 mmol, 0.20 equiv.) and $Cs_2CO_3$ (586 mg, 1.80 mmol, 3.00 equiv.). The resulting mixture was stirred at 80° C. for 16 h. LCMS showed the reaction was completed. The reaction mixture was concentrated and purified by flash column on silica gel (eluted with PE/EA, 1/3) to afford methyl methyl 1-(5-(1-(2,6-dichlorophenyl)azetidin-3-yl)-7-fluoro-2,3-dihydro-1H-inden-1-yl)piperidine-4-carboxylate (50 mg, 17% yield) as a light-yellow oil. LCMS (ESI, m/z): 477 $[M+H]^+$.

Synthesis of 1-(5-(1-(2,6-dichlorophenyl)azetidin-3-yl)-7-fluoro-2,3-dihydro-1H-inden-1-yl)piperidine-4-carboxylic acid (6)

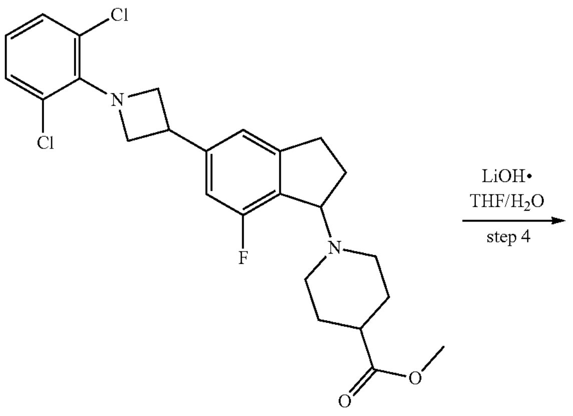

-continued

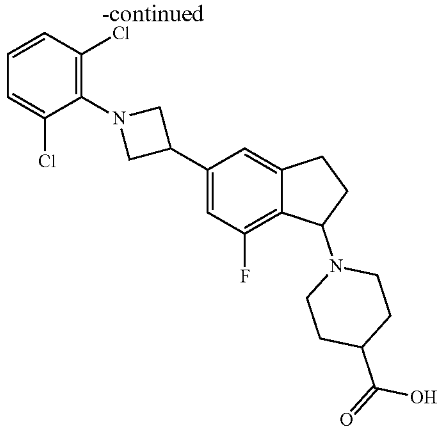

6

To a stirred solution of methyl 1-(5-(1-(2,6-dichlorophenyl)azetidin-3-yl)-7-fluoro-2,3-dihydro-1H-inden-1-yl)piperidine-4-carboxylate (50 mg, 0.100 mmol, 1.00 equiv.) in THE (2 mL) and Water (0.2 mL) was added $LiOH \cdot H_2O$ (13 mg, 0.310 mmol, 3.00 equiv.). The resulting mixture was stirred at room temperature overnight. LCMS showed the reaction was complete. The reaction mixture was acidified to pH 4-5 using acetic acid and then was concentrated. The residue was purified by Prep-HPLC (Column: XBridge Shield RP18 OBD Column, 5 μm, 19*150 mm; Mobile Phase A: water (10 mM $NH_4HCO_3$+0.1% $NH_3 \cdot H_2O$), Mobile Phase B: ACN; Flow rate: 60 mL/min; Gradient: 20% B to 39% B in 10 min; 210/254 nm; RT: 9.10 min) to afford 1-(5-(1-(2,6-dichlorophenyl)azetidin-3-yl)-7-fluoro-2,3-dihydro-1H-inden-1-yl)piperidine-4-carboxylic acid (25.9 mg, 52% yield) as an off-white solid.

LCMS (ESI, m/z): 463 $[M+H]^+$. Analytic Conditions: column: Poroshell HPH-C18, 3.0*50 mm, 2.7 μm; mobile phase A: water (5 mM $NH_4HCO_3$), mobile phase B: acetonitrile, flow rate: 1.20 mL/min; gradient: 10% B to 95% B in 2.00 min, hold at 95% for 0.60 min, 95% B to 10% B in 0.15 min; 254 nm; RT: 1.307 min.

$^1H$ NMR (300 MHz, DMSO-$d_6$) δ 12.06 (s, 1H), 7.25 (d, J=7.8 Hz, 2H), 7.16 (s, 1H), 7.06-7.03 (m, 1H), 6.76 (t, J=7.8 Hz, 1H), 4.82 (t, J=8.1 Hz, 2H), 4.39-4.34 (m, 3H), 3.82-3.72 (m, 1H), 3.01-2.90 (m, 1H), 2.84-2.71 (m, 2H), 2.60-2.55 (m, 1H), 2.24-2.05 (m, 5H), 1.78-1.74 (m, 2H), 1.58-1.40 (m, 2H).

Example S7. 1-(5-(1-(2,6-dichlorophenyl)azetidin-3-yl)-2,3-dihydro-1H-inden-1-yl)pyrrolidine-3-carboxylic acid (7)

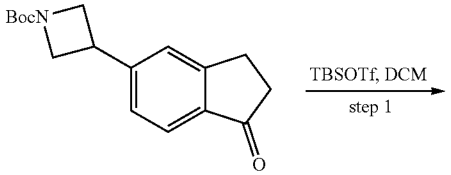

-continued

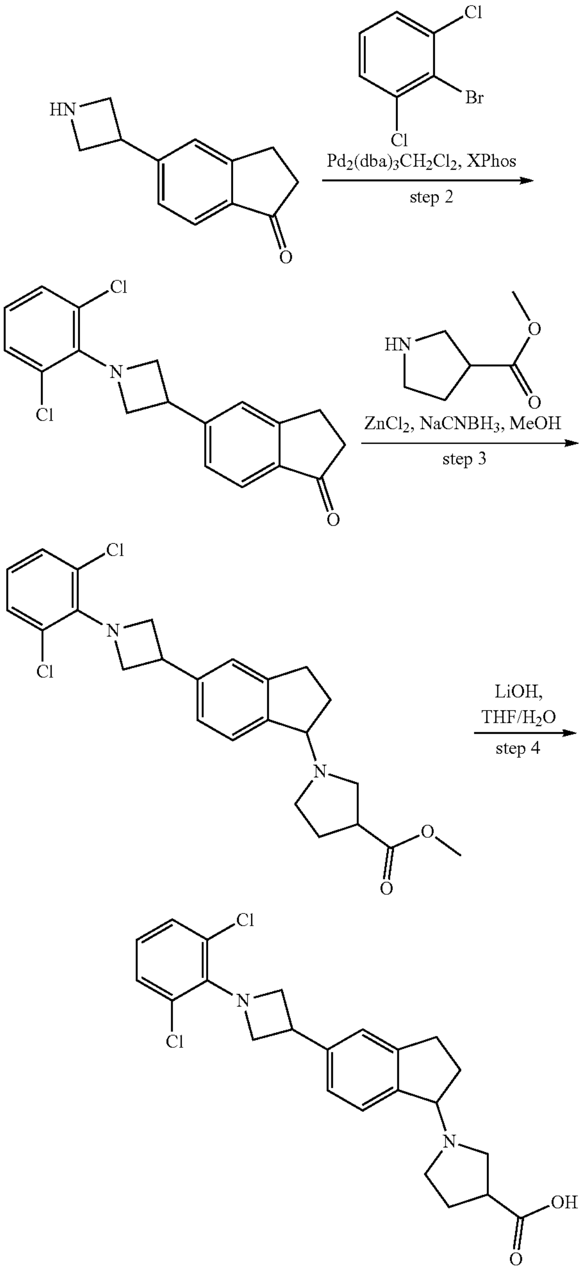

7

Synthesis of 5-(azetidin-3-yl)-2,3-dihydro-1H-inden-1-one

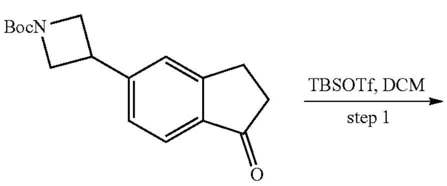

-continued

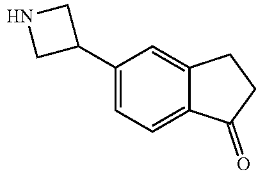

To a solution of tert-butyl 3-(1-oxo-2,3-dihydro-1H-inden-5-yl)azetidine-1-carboxylate (600 mg, 1.50 mmol, 1.00 equiv.) and in DCM (5 mL) was added TBSOTf (0.4 mL, 2.25 mmol, 1.50 equiv.). The resulting solution was stirred at room temperature for 1 h. TLC showed the reaction was completed. The reaction mixture was concentrated under reduced pressure. The crude product was purified by flash column on C18 (eluted with water/ACN, 5/95) to afford 5-(azetidin-3-yl)-2,3-dihydro-1H-inden-1-one (300 mg, 77%) as a white solid. LCMS (ESI, m z): 188 $[M+H]^+$.

Synthesis of 5-(1-(2,6-dichlorophenyl)azetidin-3-yl)-2,3-dihydro-1H-inden-1-one

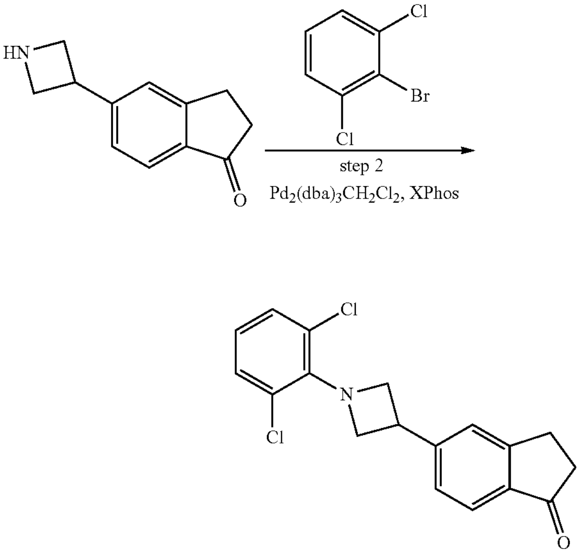

A solution of 5-(azetidin-3-yl)-2,3-dihydro-1H-inden-1-one (300 mg, 1.60 mmol, 1.00 equiv.), 2-bromo-1,3-dichlorobenzene (358 mg, 1.60 mmol, 1.00 equiv.), $Pd_2$(dba) 3·CH2Cl2 (166 mg, 0.160 mmol, 0.10 equiv.), t-BuONa (470 mg, 4.80 mmol, 3.00 equiv.) and XPhos (152 mg, 3.200 mmol, 0.20 equiv.) in toluene (10 mL) was stirred at 90° C. for 2h under $N_2$ atmosphere. LCMS showed the reaction was completed. The reaction mixture was concentrated and purified by flash column on silica gel (eluted with PE/EA, 1/1) to afford 5-(1-(2,6-dichlorophenyl)azetidin-3-yl)-2,3-dihydro-1H-inden-1-one (150 mg, 28%) as a yellow oil. LCMS (ESI, m z): 332 $[M+H]^+$.

Synthesis of methyl 1-(5-(1-(2,6-dichlorophenyl)azetidin-3-yl)-2,3-dihydro-1H-inden-1-yl)pyrrolidine-3-carboxylate

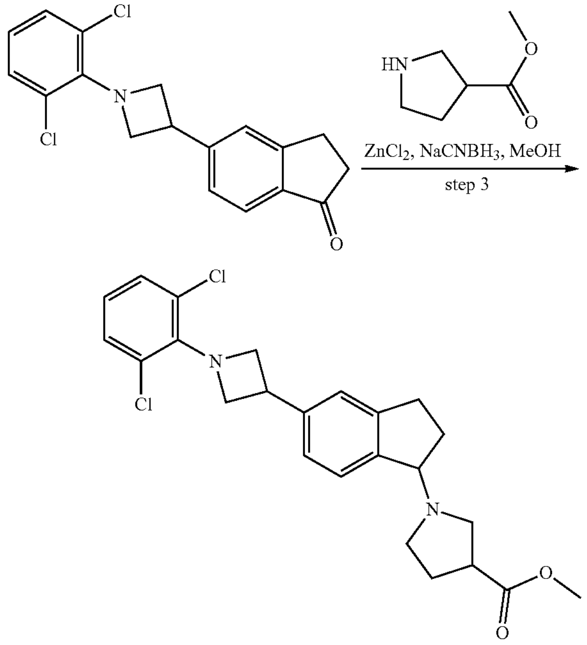

A solution of 5-(1-(2,6-dichlorophenyl)azetidin-3-yl)-2,3-dihydro-1H-inden-1-one (150 mg, 0.452 mmol, 1.00 equiv.), methyl piperidine-3-carboxylate (58 mg, 0.452 mmol, 1.00 equiv.), $ZnCl_2$ (120 mg, 0.904 mmol, 2.00 equiv.) and $NaBH_3CN$ (114 mg, 1.808 mmol, 4.00 equiv.) in methanol (10 mL) was stirred at 60° C. for 15 h. LCMS showed the reaction was completed. The reaction mixture was concentrated and purified by flash column on silica gel (eluted with PE/EA, 7/3) to afford methyl 1-(5-(1-(2,6-dichlorophenyl)azetidin-3-yl)-2,3-dihydro-1H-inden-1-yl)pyrrolidine-3-carboxylate (30 mg, 20%) as a yellow oil. LCMS (ESI, m z): 445 $[M+H]^+$.

Synthesis of 1-(5-(1-(2,6-dichlorophenyl)azetidin-3-yl)-2,3-dihydro-1H-inden-1-yl)pyrrolidine-3-carboxylic acid (7)

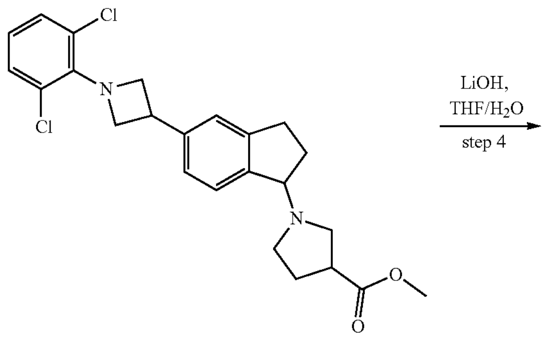

-continued

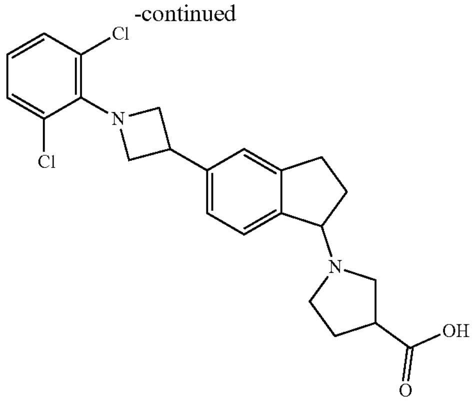

7

A solution of methyl 1-(5-(1-(2,6-dichlorophenyl)azetidin-3-yl)-2,3-dihydro-1H-inden-1-yl)pyrrolidine-3-carboxylate (30.0 mg, 0.070 mmol, 1.00 equiv.) and LiOH (5.00 mg, 0.210 mmol, 3.00 equiv.) in THF (1 mL) and water (1 mL) was stirred at room temperature for 1 h. LCMS showed the reaction was completed. The reaction mixture was acidified to pH 4-5 using acetic acid and then was concentrated. The residue was purified by Prep-HPLC (Column: YMC-Actus Triart C18 ExRS. 30*250, 5 μm; Mobile Phase A: water (10 mM $NH_4HCO_3$+0.1% $NH_3 \cdot H_2O$), Mobile Phase B: ACN; Flow rate: 60 mL/min; Gradient: 25% B to 50% B in 7 min; 254/210 nm; RT: 5.65 min) to afford 1-(5-(1-(2,6-dichlorophenyl)azetidin-3-yl)-2,3-dihydro-1H-inden-1-yl)pyrrolidine-3-carboxylic acid (1.9 mg, 6%) as a white solid.

LCMS (ESI, m/z): 431 $[M+H]^+$. Analytic Conditions: column: Poroshell HPH-C18, 3.0*50 mm, 2.7 μm; mobile phase A: water (5 mM $NH_4HCO_3$), mobile phase B: acetonitrile, flow rate: 1.20 mL/min; gradient: 10% B to 60% B in 1.85 min, 60% B to 95% B in 0.45 min, hold at 95% for 0.50 min, 95% B to 10% B in 0.03 min; 254 nm; RT: 1.566 min.

$^1H$ NMR (400 MHz, DMSO-$d_6$) δ 7.32-7.27 (m, 3H), 7.25-7.21 (m, 2H), 6.75 (t, J=8.0 Hz, 1H), 4.83 (t, J=8.0 Hz, 2H), 4.35 (t, J=8.0 Hz, 1H), 4.19-4.13 (m, 1H), 3.79-3.72 (m, 2H), 2.99-2.88 (m, 2H), 2.84-2.72 (m, 3H), 2.67-2.59 (m, 2H), 2.10-2.04 (m, 2H), 1.96-1.90 (m, 2H).

Example S8a. 1-(5-(1-(3-fluorophenyl)azetidin-3-yl)-2,3-dihydro-1H-inden-1-yl)azetidine-3-carboxylic acid (8a)

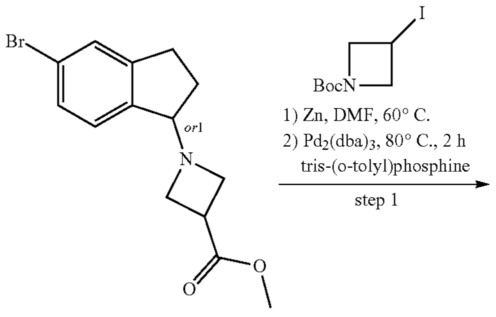

Chiral separation 1

-continued

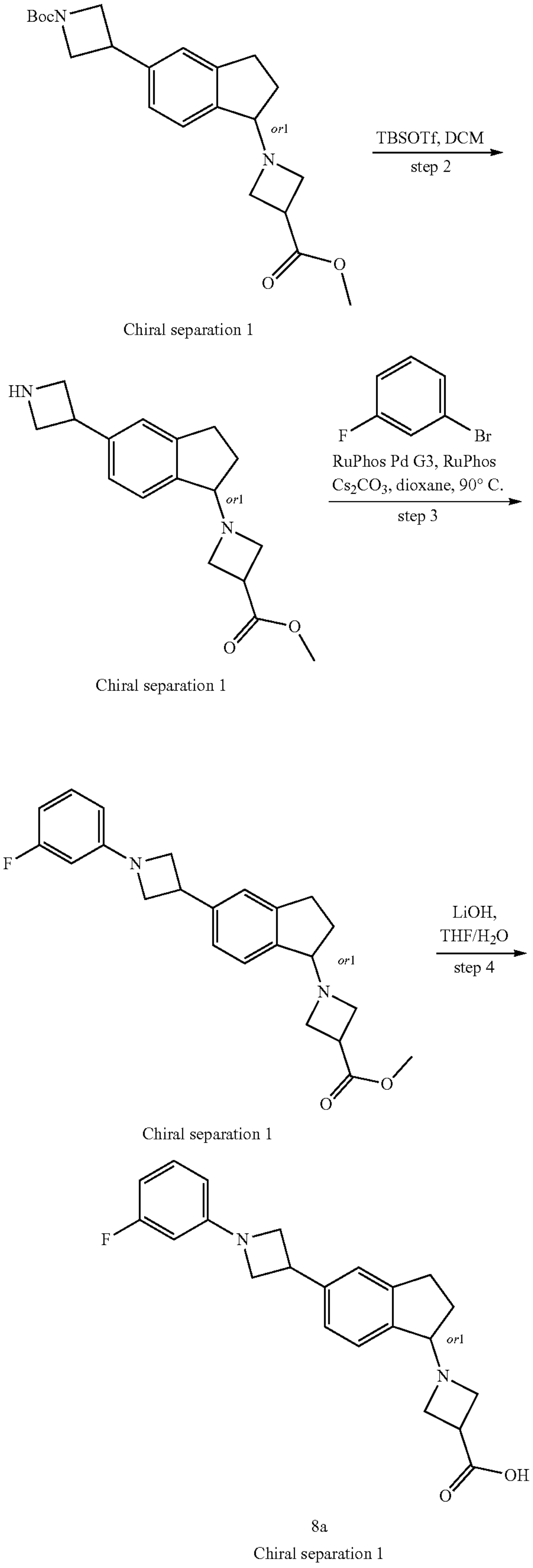

Synthesis of tert-butyl 3-(1-(3-(methoxycarbonyl)azetidin-1-yl)-2,3-dihydro-1H-inden-5-yl)azetidine-1-carboxylate

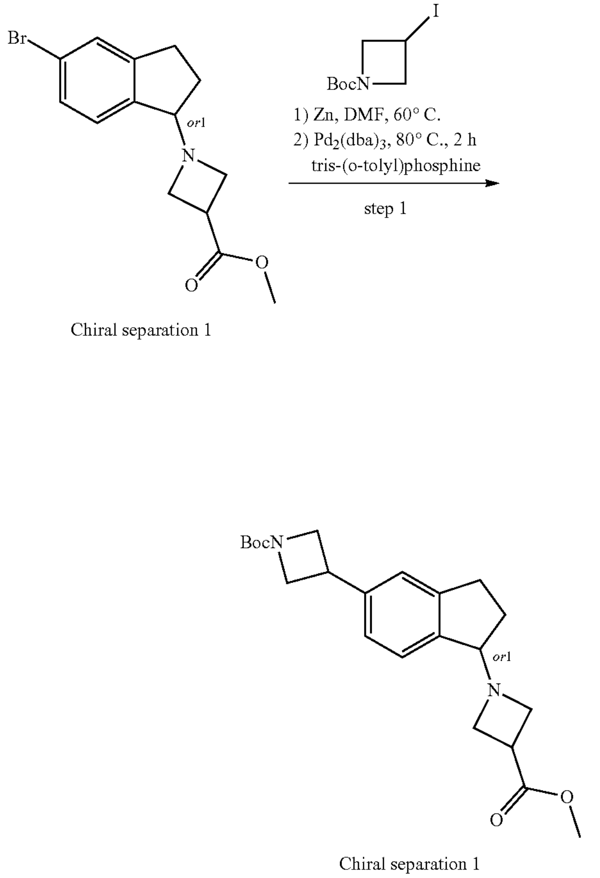

A solution of methyl 1-(5-bromo-2,3-dihydro-1H-inden-1-yl)azetidine-3-carboxylate (2.00 g, 7.06 mmol, 6.24 equiv.) and Zn (693 mg, 10.6 mmol, 9.36 equiv.) in DMF (15 mL) was stirred at 60° C. for 3 h under $N_2$ atmosphere. Then $Pd_2(dba)_3$ (104 mg, 0.110 mmol, 0.010 equiv.), tris-(o-tolyl)phosphine (69 mg, 0.230 mmol, 0.020 equiv.) and methyl 1-(5-bromoindan-1-yl)azetidine-3-carboxylate (350 mg, 1.13 mmol, 1.00 equiv.) were added. The resulting mixture was stirred at 80° C. overnight. LCMS showed the reaction was completed. The reaction mixture was quenched with saturated aqueous $NH_4Cl$ (50 mL) and extracted with EtOAc (3*20 mL). The organic layers were combined and concentrated. The residue was purified by flash chromatography on silica gel (eluted with PE/EtOAc, 1/1) to afford tert-butyl 3-(1-(3-(methoxycarbonyl)azetidin-1-yl)-2,3-dihydro-1H-inden-5-yl)azetidine-1-carboxylate (130 mg, 26.1%) as a yellow oil. LCMS (ESI, m z): 387 $[M+H]^+$.

Synthesis of methyl 1-(5-(azetidin-3-yl)-2,3-dihydro-1H-inden-1-yl)azetidine-3-carboxylate

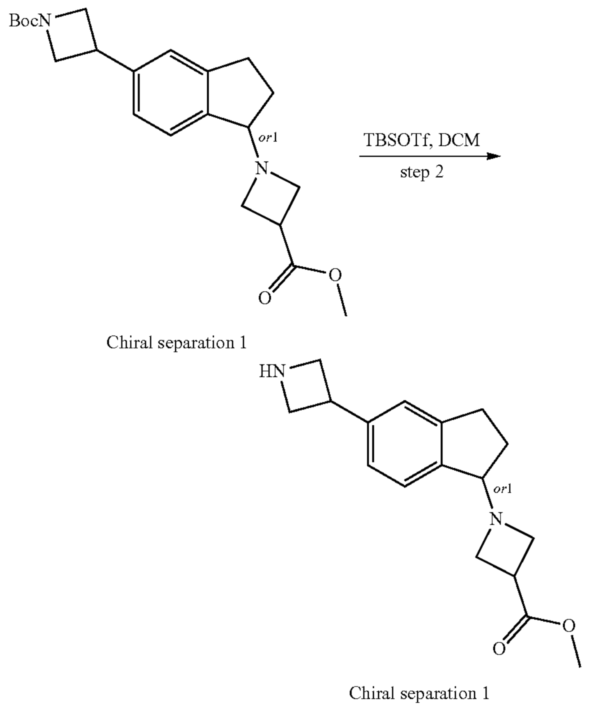

To a stirred solution of tert-butyl 3-(1-(3-(methoxycarbonyl)azetidin-1-yl)-2,3-dihydro-1H-inden-5-yl)azetidine-1-carboxylate (400 mg, 1.03 mmol, 1.00 equiv.) in DCM (6 mL) was added TBSOTf (820 mg, 3.09 mmol, 1.00 equiv.) dropwise. The resulting mixture was stirred at room temperature for 1 h. LCMS showed the reaction was completed. The reaction mixture was concentrated under reduced pressure. The crude product was purified by flash chromatography on C18 silica (eluted with ACN:$H_2O$, 1/10) to afford methyl 1-(5-(azetidin-3-yl)-2,3-dihydro-1H-inden-1-yl)azetidine-3-carboxylate (280 mg, 94.5% yield) as a yellow oil. LCMS (ESI, m z): 287 $[M+H]^+$.

Synthesis of methyl 1-(5-(1-(3-fluorophenyl)azetidin-3-yl)-2,3-dihydro-1H-inden-1-yl azetidine-3-carboxylate

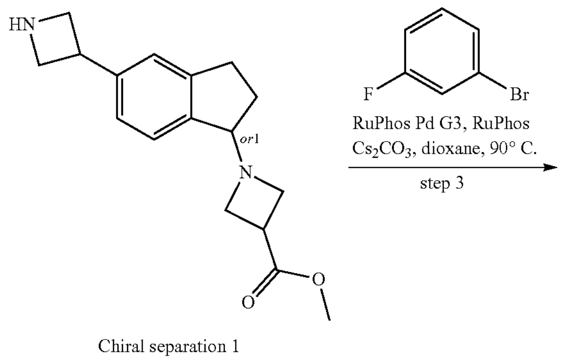

-continued

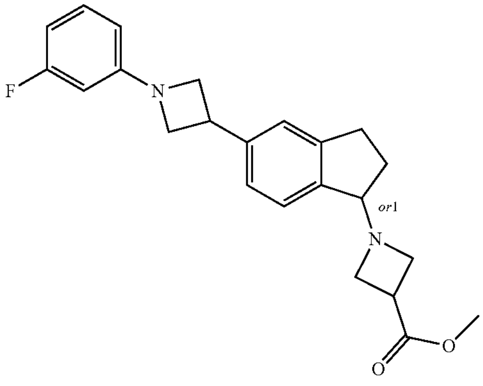

Chiral separation 1

To a stirred solution of methyl 1-(5-(azetidin-3-yl)-2,3-dihydro-1H-inden-1-yl)azetidine-3-carboxylate (280 mg, 0.980 mmol, 1.00 equiv.), 1-bromo-3-fluoro-benzene (171 mg, 0.980 mmol, 1.00 equiv.) in 1,4-Dioxane (5 mL) were added RuPhos (68 mg, 0.150 mmol, 0.150 equiv.), RuPhos Pd G3 (137 mg, 0.150 mmol, 0.150 equiv.) and $Cs_2CO_3$ (956 mg, 2.94 mmol, 3.00 equiv.). The resulting mixture was stirred at 90° C. overnight under nitrogen atmosphere. LCMS showed the reaction was completed. The reaction mixture was concentrated under reduced pressure. The crude product was purified by flash chromatography on silica gel (eluted with PE/EtOAc, 1/1) to afford methyl 1-(5-(1-(3-fluorophenyl)azetidin-3-yl)-2,3-dihydro-1H-inden-1-yl) azetidine-3-carboxylate (40 mg, 10.7% yield) as a yellow oil. LCMS (ESI, m z): 381 $[M+H]^+$.

Synthesis of 1-(5-(1-(3-fluorophenyl)azetidin-3-yl)-2,3-dihydro-1H-inden-1-yl)azetidine-3-carboxylic acid (Enantiomer 1, 8a)

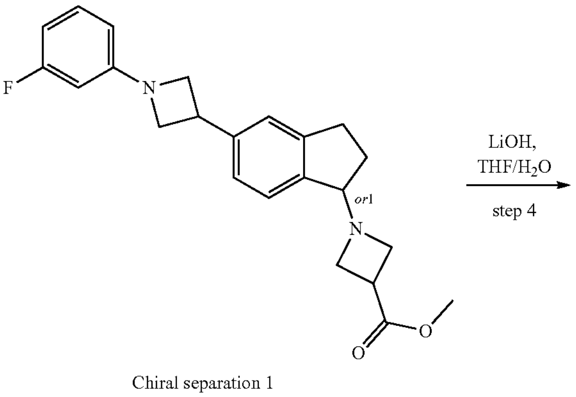

-continued

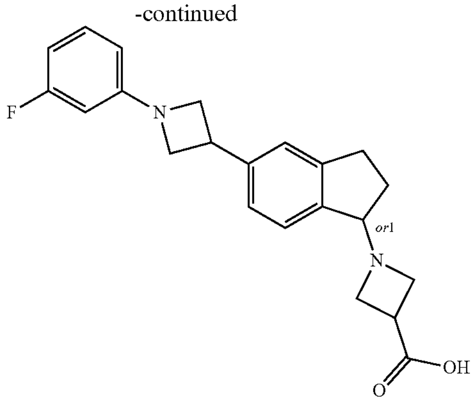

8a

Chiral separation 1

To a stirred solution of methyl methyl 1-(5-(1-(3-fluorophenyl)azetidin-3-yl)-2,3-dihydro-1H-inden-1-yl)azetidine-3-carboxylate (40 mg, 0.110 mmol, 1.00 equiv.) in THE (1 mL) and water (1 mL) was added LiOH (8 mg, 0.330 mmol, 3.00 equiv.). The resulting mixture was stirred at room temperature for 1 h. LCMS showed the reaction was complete. The reaction mixture was acidified to pH 4-5 using acetic acid and then was concentrated. The residue was purified by Prep-HPLC (Column: YMC-Actus Triart C18, 30*250, 5 μm; Mobile Phase A: water (10 mM $NH_4HCO_3$+0.1% $NH_3 \cdot H_2O$), Mobile Phase B: ACN; Flow rate: 60 mL/min; Gradient: 14% B to 44% B in 8 min; 254/210 nm; RT: 7.45 min) to afford 1-(5-(1-(3-fluorophenyl)azetidin-3-yl)-2,3-dihydro-1H-inden-1-yl)azetidine-3-carboxylic acid (19.8 mg, 51.3% yield) as a white solid.

LCMS (ESI, m/z): 413 $[M+H]^+$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.556 min.

$^1$H NMR (400 MHz, DMSO-$d_6$) δ 7.27-7.25 (m, 2H), 7.22-7.17 (m, 1H), 7.15-7.13 (m, 2H), 6.49-6.44 (m, 1H), 6.31-6.26 (m, 2H), 4.24 (t, J=7.6 Hz, 1H), 3.96-3.89 (m, 1H), 3.80-3.77 (m, 3H), 3.51-3.47 (m, 1H), 3.39-3.35 (m, 2H), 3.25-3.22 (m, 1H), 3.18-3.11 (m, 1H), 2.95-2.87 (m, 1H), 2.76-2.69 (m, 1H), 2.06-1.97 (m, 1H), 1.85-1.78 (m, 1H).

Example S8b. 1-(5-(1-(3-fluorophenyl)azetidin-3-yl)-2,3-dihydro-1H-inden-1-yl)azetidine-3-carboxylic acid (Enantiomer 2, 8b)

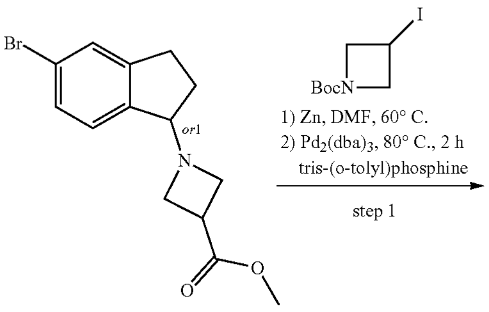

Chiral separation 2

-continued

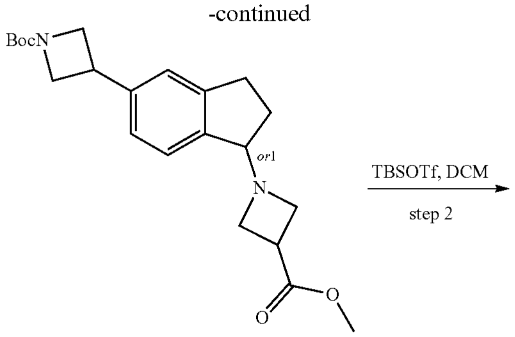

Chiral separation 2

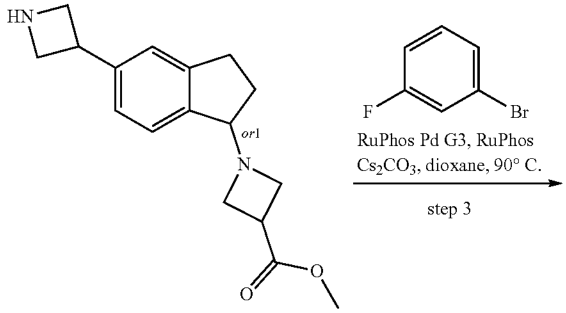

Chiral separation 2

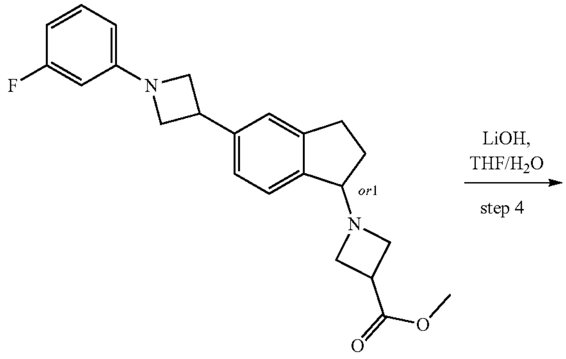

Chiral separation 2

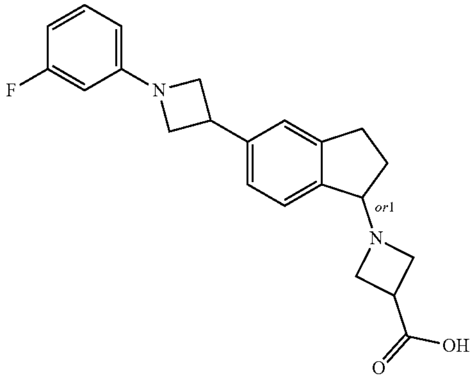

8b

Chiral separation 2

Synthesis of tert-butyl 3-(1-(3-(methoxycarbonyl) azetidin-1-yl)-2,3-dihydro-1H-inden-5-yl)azetidine-1-carboxylate

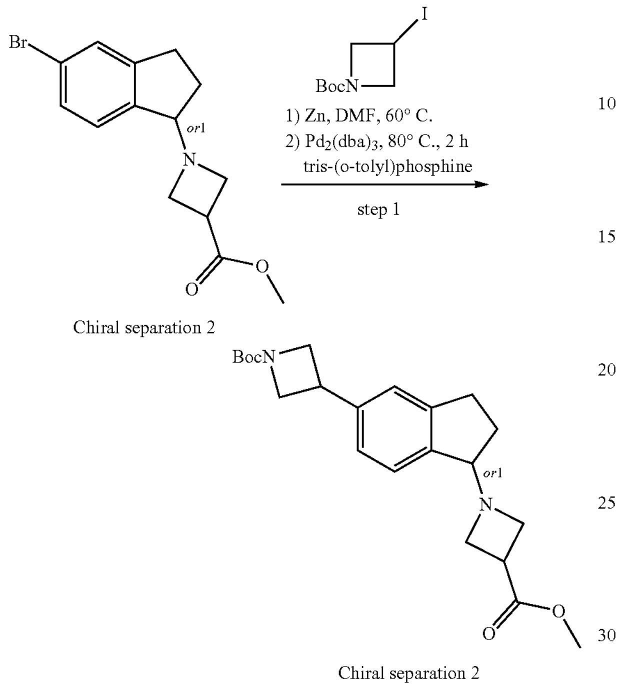

A solution of methyl 1-(5-bromo-2,3-dihydro-1H-inden-1-yl)azetidine-3-carboxylate (2.00 g, 7.06 mmol, 6.24 equiv.) and Zn (693 mg, 10.6 mmol, 9.36 equiv.) in DMF (15 mL) was stirred at 60° C. for 3h under $N_2$ atmosphere. Then $Pd_2(dba)_3$ (104 mg, 0.110 mmol, 0.010 equiv.), tris-(o-tolyl) phosphine (69 mg, 0.230 mmol, 0.020 equiv.) and methyl 1-(5-bromoindan-1-yl)azetidine-3-carboxylate (350 mg, 1.13 mmol, 1.00 equiv.) were added. The resulting mixture was stirred at 80° C. overnight. LCMS showed the reaction was completed. The reaction mixture was quenched with saturated aqueous $NH_4Cl$ (50 mL) and extracted with EtOAc (3*20 mL). The organic layers were combined and concentrated. The residue was purified by flash chromatography on silica gel (eluted with PE/EtOAc, 1/1) to afford tert-butyl 3-(1-(3-(methoxycarbonyl)azetidin-1-yl)-2,3-dihydro-1H-inden-5-yl)azetidine-1-carboxylate (130 mg, 26.1%) as a yellow oil. LCMS (ESI, m z): 387 $[M+H]^+$.

Synthesis of methyl 1-(5-(azetidin-3-yl)-2,3-dihydro-1H-inden-1-yl)azetidine-3-carboxylate

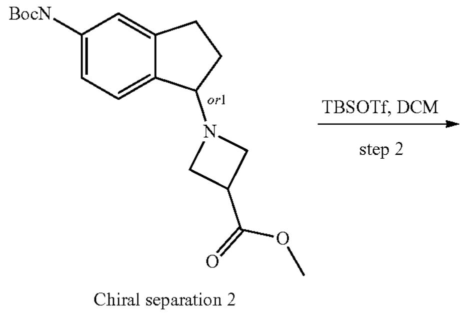

-continued

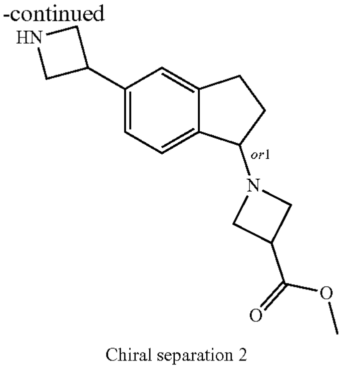

To a stirred solution of tert-butyl 3-(1-(3-(methoxycarbonyl)azetidin-1-yl)-2,3-dihydro-1H-inden-5-yl)azetidine-1-carboxylate (400 mg, 1.03 mmol, 1.00 equiv.) in DCM (6 mL) was added TBSOTf (820 mg, 3.09 mmol, 1.00 equiv.) dropwise. The resulting mixture was stirred at room temperature for 1 h. LCMS showed the reaction was completed. The reaction mixture was concentrated under reduced pressure. The crude product was purified by flash chromatography on C18 silica (eluted with ACN:$H_2O$, 1/10) to afford methyl 1-(5-(azetidin-3-yl)-2,3-dihydro-1H-inden-1-yl)azetidine-3-carboxylate (280 mg, 94.5% yield) as a yellow oil. LCMS (ESI, m z): 287 $[M+H]^+$.

Synthesis of methyl 1-(5-(1-(3-fluorophenyl)azetidin-3-yl)-2,3-dihydro-1H-inden-1-yl)azetidine-3-carboxylate

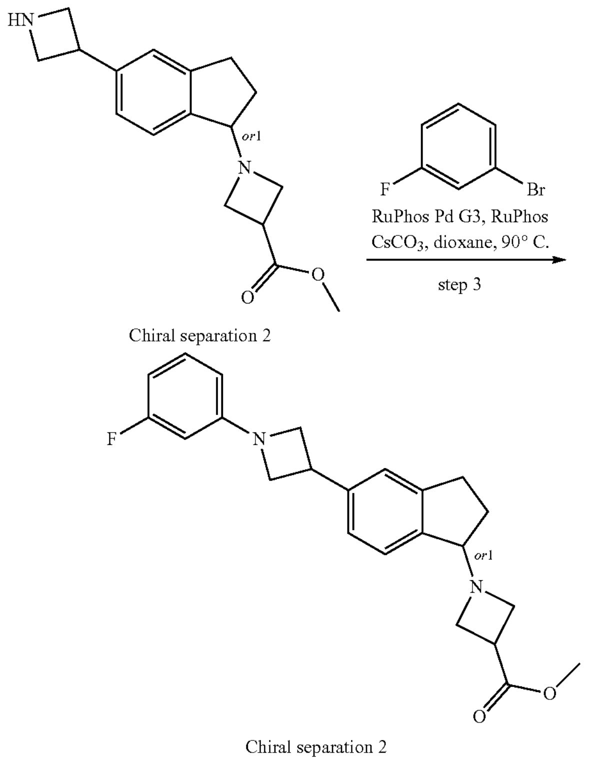 [SMILES: COC(=O)C1CN(C2CCc3cc(C4CNC4)ccc32)C1 ; Fc1cccc(Br)c1 ; COC(=O)C1CN(C2CCc3cc(C4CN(c5cccc(F)c5)C4)ccc32)C1]

To a stirred solution of methyl 1-(5-(azetidin-3-yl)-2,3-dihydro-1H-inden-1-yl)azetidine-3-carboxylate (280 mg, 0.980 mmol, 1.00 equiv.), 1-bromo-3-fluoro-benzene (171 mg, 0.980 mmol, 1.00 equiv.) in 1,4-dioxane (5 mL) were added RuPhos (68 mg, 0.150 mmol, 0.150 equiv.), RuPhos Pd G3 (137 mg, 0.150 mmol, 0.150 equiv.) and $Cs_2CO_3$ (956 mg, 2.94 mmol, 3.00 equiv.). The resulting mixture was stirred at 90° C. overnight under nitrogen atmosphere. LCMS showed the reaction was completed. The reaction mixture was concentrated under reduced pressure. The crude product was purified by flash chromatography on silica gel (eluted with PE/EtOAc, 1/1) to afford methyl 1-(5-(1-(3-fluorophenyl)azetidin-3-yl)-2,3-dihydro-1H-inden-1-yl) azetidine-3-carboxylate (40 mg, 10.7% yield) as a yellow oil. LCMS (ESI, m z): 381 $[M+H]^+$.

Synthesis of 1-(5-(1-(3-fluorophenyl)azetidin-3-yl)-2,3-dihydro-1H-inden-1-yl)azetidine-3-carboxylic acid

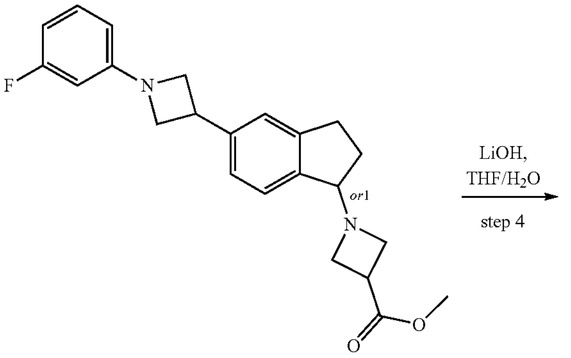

Chiral separation 2

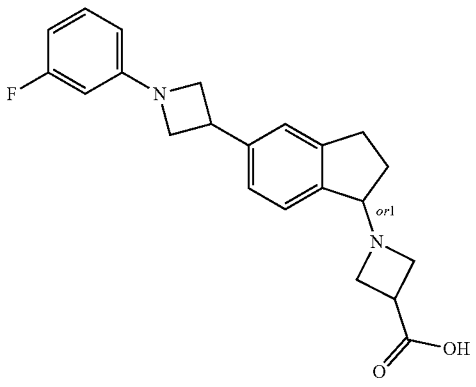

8b

Chiral separation 2

To a stirred solution of methyl 1-(5-(1-(3-fluorophenyl) azetidin-3-yl)-2,3-dihydro-1H-inden-1-yl)azetidine-3-carboxylate (40 mg, 0.110 mmol, 1.00 equiv.) in THE (1 mL) and water (1 mL) was added LiOH (8 mg, 0.330 mmol, 3.00 equiv.). The resulting mixture was stirred at room temperature for 1 h. LCMS showed the reaction was complete. The reaction mixture was acidified to pH 4-5 using acetic acid and then was concentrated. The residue was purified by Prep-HPLC (Column: YMC-Actus Triart C18, 30*250, 5 μm; Mobile Phase A: water (10 mM $NH_4HCO_3$+0.1% $NH_3 \cdot H_2O$), Mobile Phase B: ACN; Flow rate: 60 mL/min; Gradient: 20% B to 38% B in 10 min, hold at 38% B for 2 min; 254/210 nm; RT: 10.45 min) to afford 1-(5-(1-(3-fluorophenyl)azetidin-3-yl)-2,3-dihydro-1H-inden-1-yl) azetidine-3-carboxylic acid (28.5 mg, 73.0% yield) as a white solid.

LCMS (ESI, m/z): 413 $[M+H]^+$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.551 min.

$^1$H NMR (400 MHz, DMSO-$d_6$) δ 7.26-7.22 (m, 2H), 7.21-7.17 (m, 1H), 7.14-7.12 (m, 2H), 6.49-6.44 (m, 1H), 6.31-6.26 (m, 2H), 4.24 (t, J=7.6 Hz, 1H), 3.96-3.89 (m, 1H), 3.80-3.73 (m, 3H), 3.45 (t, J=7.2 Hz, 1H), 3.33-3.30 (m, 2H), 3.21-3.18 (m, 1H), 3.15-3.08 (m, 1H), 2.94-2.86 (m, 1H), 2.75-2.67 (m, 1H), 2.04-1.98 (m, 1H), 1.84-1.77 (m, 1H).

Example S9. 1-(5-(3-(2,6-difluorophenyl)azetidin-1-yl)-2,3-dihydro-1H-inden-1-yl)piperidine-4-carboxylic acid (9a and 9b)

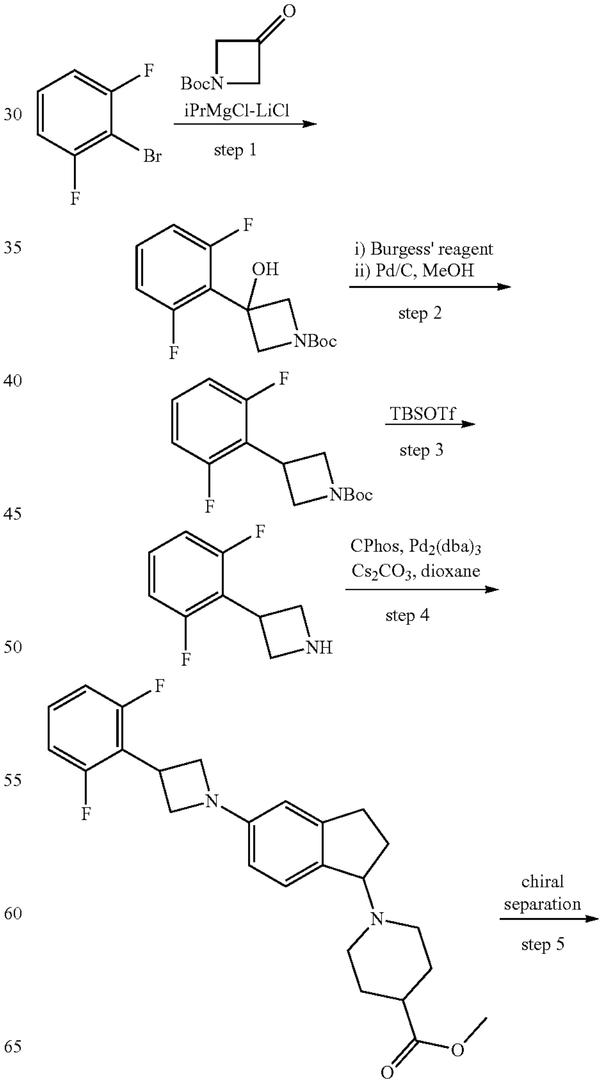

-continued

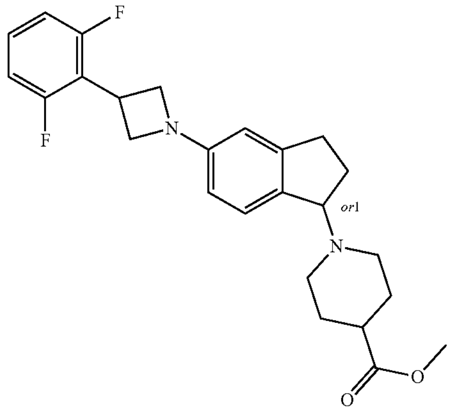

Chiral separation 1

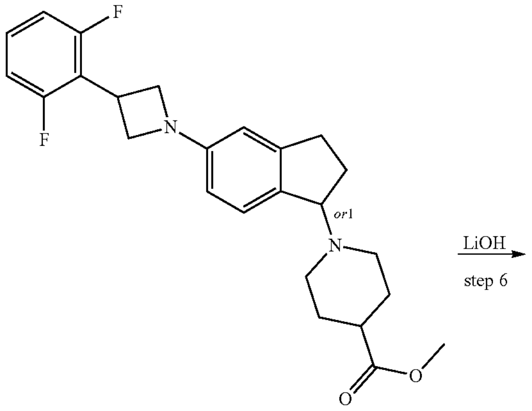

Chiral separation 2

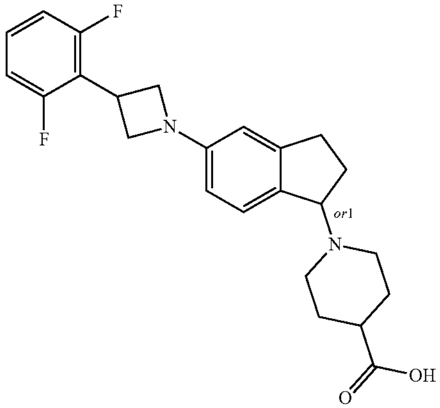

9a
Chiral separation 1

Synthesis of tert-butyl 3-(2,6-difluorophenyl)-3-hydroxyazetidine-1-carboxylate

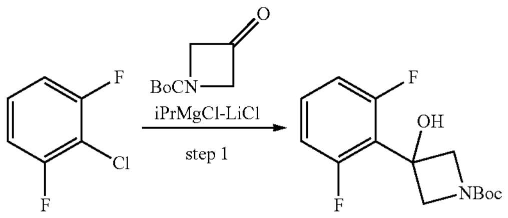

To a solution of 2-bromo-1,3-difluoro-benzene (3.0 g, 15.54 mmol, 1.00 equiv.) in dry THE (20 mL) was added iPrMgCl—LiCl (1.3 M in THF, 20.4 mL, 26.56 mmol, 2.00 equiv.) dropwise at −78° C. under nitrogen atmosphere. The resulting mixture was stirred at −78° C. for 3 h. Then a solution of tert-butyl 3-oxoazetidine-1-carboxylate (4.0 g, 23.32 mmol, 2.00 equiv.) in dry THE (5.0 mL) was added. The reaction was warmed to room temperature slowly and stirred at room temperature for further 12 h. The reaction was quenched with aq. $NH_4Cl$ (20 mL) and extracted with ether (2*25 mL). The combined organic layers were washed with water (10 mL) and brine (10 mL), and dried over anhydrous $Na_2SO_4$ and concentrated under vacuum. The residue was purified by flash column chromatography on C18 silica (eluted with water (5 mM $NH_4HCO_3$)/ACN, 4/1) to give tert-butyl 3-(2,6-difluorophenyl)-3-hydroxyazetidine-1-carboxylate (2.5 g, 56%) as a yellow solid. LCMS (ESI, m/z): 286 $[M+H]^+$.

Synthesis of tert-butyl 3-(2,6-difluorophenyl)azetidine-1-carboxylate

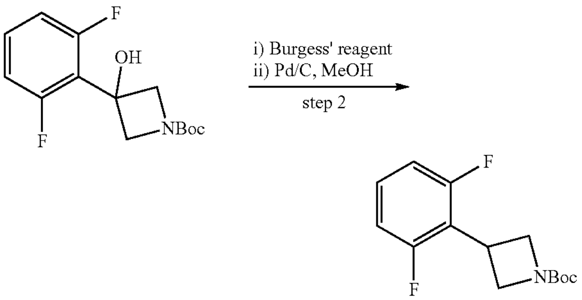

To a stirred solution of tert-butyl 3-(2,6-difluorophenyl)-3-hydroxy-azetidine-1-carboxylate (2.4 g, 8.41 mmol, 1.00 equiv.) in toluene (10 mL) was added Burgess' reagent (4.2 g, 17.67 mmol, 2.10 equiv.). The reaction was stirred at 110° C. for 12 h. LCMS showed the starting material was consumed completely. The reaction mixture was concentrated under reduced pressure. The residue was dissolved in methanol (20 mL), and Pd/C (200 mg, 1.880 mmol, 0.250 equiv.) was added. The resulting mixture was stirred at room temperature under hydrogen atmosphere for 2 h. LCMS showed the reaction was completed. The mixture was filtered and the filtration was concentrated under reduced pressure. The residue was purified by flash column chromatography on C18 silica (eluted with water (5 mM $NH_4HCO_3$)/ACN, 3/7) to afford tert-butyl 3-(2,6-difluorophenyl)azetidine-1-carboxylate (800 mg, 39%) as an off-white solid. LCMS (ESI, m/z): 270 [M+H]$^+$.

Synthesis of 3-(2,6-difluorophenyl)azetidine

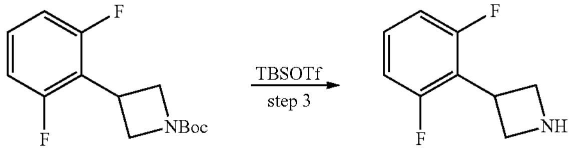 [SMILES: "TBSOTf" ; CC(C)(C)OC(=O)N1CC(c2c(F)cccc2F)C1 ; Fc1cccc(F)c1C1CNC1]

To a stirred solution of tert-butyl 3-(2,6-difluorophenyl) azetidine-1-carboxylate (200 mg, 0.740 mmol, 1.00 equiv.) in DCM (10.0 mL) was added TBSOTf (0.1 mL, 0.820 mmol, 1.10 equiv.). The resulting mixture was stirred at room temperature for 2 h. LCMS showed the reaction was completed. The reaction mixture was concentrated under reduced pressure. The crude 3-(2,6-difluorophenyl)azetidine was used in the next step directly without further purification. LCMS (ESI, m/z): 170 [M+H]$^+$.

Synthesis of methyl 1-(5-(3-(2,6-difluorophenyl) azetidin-1-yl)-2,3-dihydro-1H-inden-1-yl)piperidine-4-carboxylate

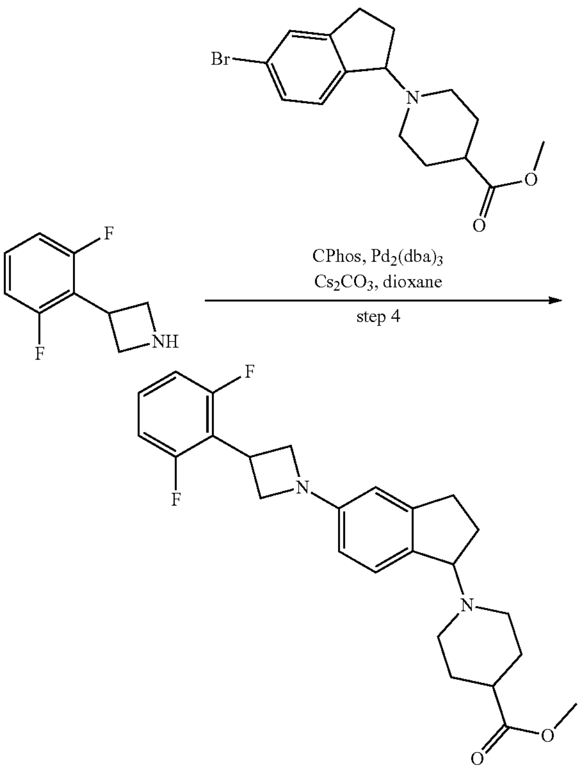

To a stirred solution of 3-(2,6-difluorophenyl)azetidine (240 mg, 1.42 mmol, 1.00 equiv.) and methyl 1-(5-bromo-2,3-dihydro-1H-inden-1-yl)piperidine-4-carboxylate (527 mg, 1.56 mmol, 1.10 equiv.) in 1,4-dioxane (10 mL) were added $Pd_2(dba)_3 \cdot CHCl_3$ (146 mg, 0.14 mmol, 0.10 equiv.), CPhos (43 mg, 0.28 mmol, 0.20 equiv.) and $Cs_2CO_3$ (1.4 g, 4.26 mmol, 3.00 equiv.). The resulting mixture was stirred at 100° C. under nitrogen atmosphere for 16 h. LCMS showed the reaction was completed. The reaction mixture was filtered and the filtration was concentrated under reduced pressure. The residue was purified by flash column chromatography on C18 silica (eluted with water (5 mM $NH_4HCO_3$/ACN, 1/9) to afford methyl 1-(5-(3-(2,6-difluorophenyl)azetidin-1-yl)-2,3-dihydro-1H-inden-1-yl)piperidine-4-carboxylate (240 mg, 39%) as an off-white solid. LCMS (ESI, m/z): 427 [M+H]$^+$.

Chiral Separation of methyl 1-(5-(3-(2,6-difluorophenyl)azetidin-1-yl)-2,3-dihydro-1H-inden-1-yl) piperidine-4-carboxylate

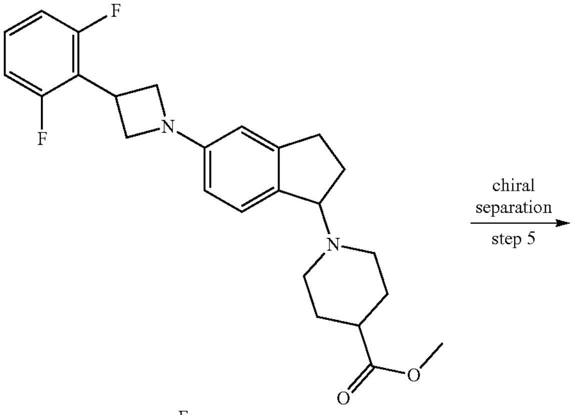

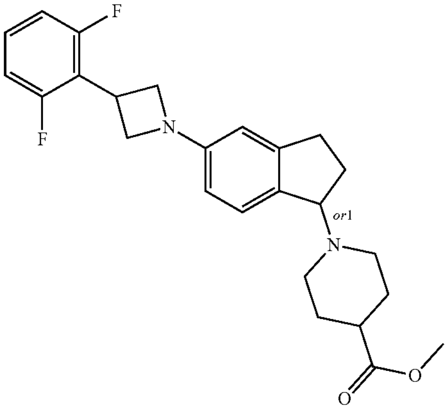

Chiral separation 1

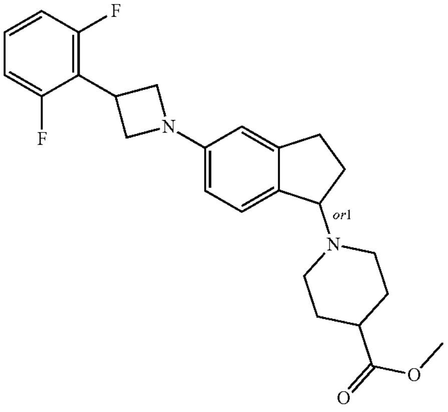

Chiral separation 2

The racemate (300 mg) was resolved by chiral HPLC (Column: CHIRALPAK IG, 3*25 cm, 5 μm; Mobile Phase A: Hex (0.1% IPA), Mobile Phase B: EtOH; Flow rate: 30 mL/min; Gradient: 50% B to 50% B in 32 min; 220/254 nm; RT1: 22.3 min; RT2: 27.6 min) to afford the isomer 1 (120 mg) and the isomer 2 (120 mg), respectively.

Synthesis of 1-(5-(3-(2,6-difluorophenyl)azetidin-1-yl)-2,3-dihydro-1H-inden-1-yl)piperidine-4-carboxylic acid (Enantiomer 1, 9a)

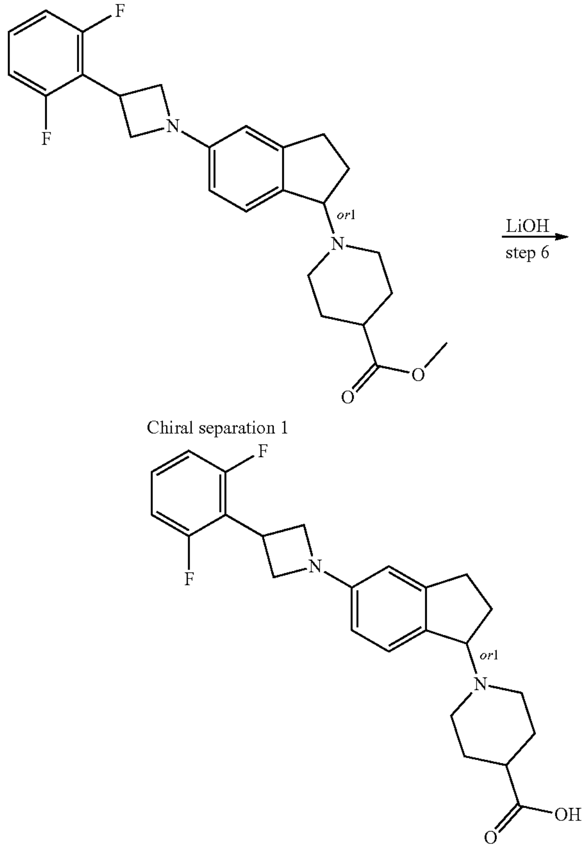

Chiral separation 1

9a
Chiral separation 1

To a stirred solution of methyl 1-(5-(3-(2,6-difluorophenyl)azetidin-1-yl)-2,3-dihydro-1H-inden-1-yl)piperidine-4-carboxylate (120 mg, 0.280 mmol, 1.00 equiv.) in THE (2.0 mL) and water (2.0 mL) was added LiOH·$H_2O$ (35 mg, 0.840 mmol, 3.00 equiv.). The resulting mixture was stirred at room temperature for 16 h. LCMS showed the reaction was completed. The reaction was acidified to pH 5-6 by adding acetic acid dropwise, and concentrated under reduced pressure. The residue was purified by flash column chromatography on C18 silica (eluted with water (10 mM $NH_4HCO_3$)/ACN, 1/1) to afford 1-(5-(3-(2,6-difluorophenyl)azetidin-1-yl)-2,3-dihydro-1H-inden-1-yl)piperidine-4-carboxylic acid (30 mg, 25%) as an off-white solid.

$^1$H NMR (300 MHz, DMSO-$d_6$) δ 7.37-7.32 (m, 1H), 7.11-7.04 (m, 3H), 6.34-6.32 (m, 2H), 4.34-4.25 (m, 3H), 4.16-4.13 (m, 1H), 3.88-3.82 (m, 2H), 2.78-2.66 (m, 3H), 2.24-2.07 (m, 4H), 1.97-1.90 (m, 2H), 1.80-1.71 (m, 2H), 1.60-1.40 (m, 2H).

LCMS (ESI, m/z): 413 $[M+H]^+$. Analytic Conditions: column: EVO C18 Column 3.0*50 mm, 2.6 mm; mobile Phase A: Water/5 mM $NH_4HCO_3$, mobile Phase B: acetonitrile; flow rate: 1.20 mL/min; gradient: 10% B to 95% B in 2.0 min, hold at 95% for 0.6 min, 95% B to 10% B in 0.15 min; 254 nm; RT: 1.097 min.

Synthesis of 1-(5-(3-(2,6-difluorophenyl)azetidin-1-yl)-2,3-dihydro-1H-inden-1-yl)piperidine-4-carboxylic acid (Enantiomer 2, 9b)

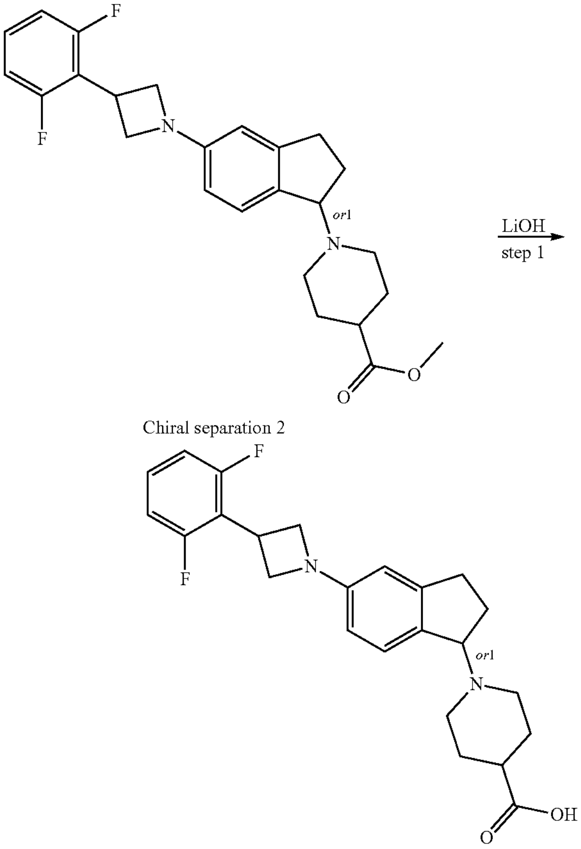

Chiral separation 2

9b
Chiral separation 2

To a stirred solution of methyl 1-(5-(3-(2,6-difluorophenyl)azetidin-1-yl)-2,3-dihydro-1H-inden-1-yl)piperidine-4-carboxylate (120 mg, 0.280 mmol, 1.00 equiv.) in THE (2.0 mL) and water (2.0 mL) was added LiOH·$H_2O$ (35 mg, 0.840 mmol, 3.00 equiv.). The resulting mixture was stirred at room temperature for 16 h. LCMS showed the reaction was completed. The reaction was acidified to pH 5-6 by adding acetic acid dropwise and concentrated under reduced pressure. The residue was purified by flash column chromatography on C18 silica (eluted with water (10 mM $NH_4HCO_3$)/ACN, 1/1) to afford 1-(5-(3-(2,6-difluorophenyl)azetidin-1-yl)-2,3-dihydro-1H-inden-1-yl)piperidine-4-carboxylic acid (28.4 mg, 24%) as an off-white solid.

$^1$H NMR (300 MHz, DMSO-$d_6$) δ 7.40-7.30 (m, 1H), 7.11-7.04 (m, 3H), 6.34-6.32 (m, 2H), 4.34-4.25 (m, 3H), 4.17-4.13 (m, 1H), 3.88-3.82 (m, 2H), 2.78-2.63 (m, 3H), 2.27-2.05 (m, 4H), 1.97-1.90 (m, 2H), 1.80-1.71 (m, 2H), 1.60-1.41 (m, 2H).

LCMS (ESI, m/z): 413 $[M+H]^+$. Analytic Conditions: column: EVO C18 Column 3.0*50 mm, 2.6 mm; mobile phase A: water/5 mM $NH_4HCO_3$, mobile phase B: acetonitrile; flow rate: 1.20 mL/min; gradient: 10% B to 95% B in 2.0 min, hold at 95% for 0.6 min, 95% B to 10% B in 0.15 min; 254 nm; RT: 1.101 min.

Example S10. 1-(5-(3-(2-fluorophenyl)azetidin-1-yl)-2,3-dihydro-1H-inden-1-yl)piperidine-4-carboxylic acid (10a and 10b)

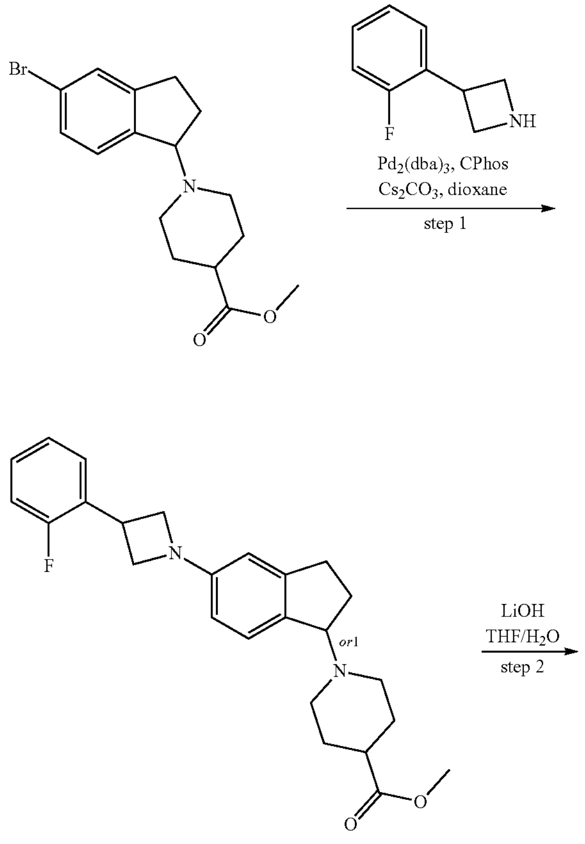

Chiral separation 1

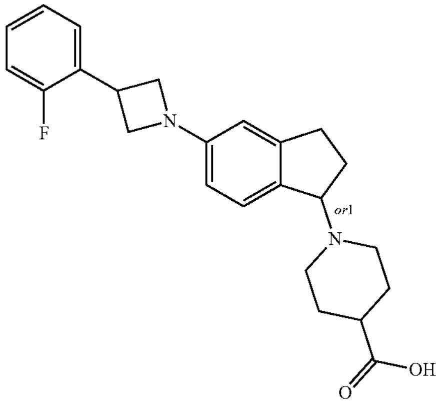

10a
Chiral separation 1

Synthesis of methyl 1-(5-(3-(2-fluorophenyl)azetidin-1-yl)-2,3-dihydro-1H-inden-1-yl)piperidine-4-carboxylate

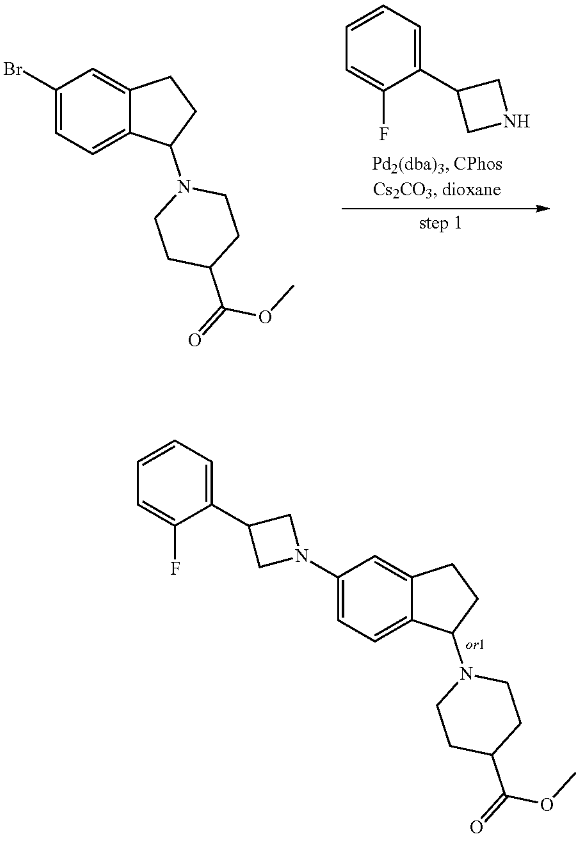

Chiral separation 1

A mixture of methyl 1-(5-bromo-2,3-dihydro-1H-inden-1-yl)piperidine-4-carboxylate (200 mg, 0.590 mmol, 1.00 equiv.), 3-(2-fluorophenyl)azetidine (89.4 mg, 0.590 mmol, 1.00 equiv.), CPhos (51.6 mg, 0.120 mmol, 0.200 equiv.), $Pd_2(dba)_3$ (108 mg, 0.120 mmol, 0.200 equiv.) and cesium carbonate (385 mg, 1.18 mmol, 2.00 equiv.) in anhydrous 1,4-dioxane (2 mL) was stirred at 90° C. under nitrogen atmosphere overnight. LCMS showed that the reaction was complete. The reaction mixture was concentrated. The residue was purified by prep-IPLC (Column: YMC-Actus Triart C18, 30*250, 5 mm; Mobile Phase A: water (10 mM $NH_4HCO_3$+0.1% $NH_3 \cdot H_2O$), Mobile Phase B: ACN; Flow rate: 60 mL/min; Gradient: 56% B to 72% B in 10 min, hold at 72% B for 5 min; 210/254 nm; RT: 12.68 min) to give methyl 1-(5-(3-(2-fluorophenyl)azetidin-1-yl)-2,3-dihydro-1H-inden-1-yl)piperidine-4-carboxylate (60 mg, 24.8%) as a light yellow solid. LCMS (ESI, m z): 409 $[M+H]^+$. The racemic product was then resolved by chiral-HPLC (Column: Chiralpak IA, 2*25 cm, 5 mm; Mobile Phase A: Hex (0.5% 2M $NH_3$-MeOH)-HPLC, Mobile Phase B: IPA-HPLC; Flow rate: 20 mL/min; Gradient: 30% B to 30% B in 20 min; 220/254 nm) to give chiral separation 1 enantiomer (22 mg) with retention time at 8.894 min and chiral separation 2 enantiomer (20 mg) with retention time at 10.086 min.

Synthesis of 1-(5-(3-(2-fluorophenyl)azetidin-1-yl)-2,3-dihydro-1H-inden-1-yl)piperidine-4-carboxylic acid (Enantiomer 1, 10a)

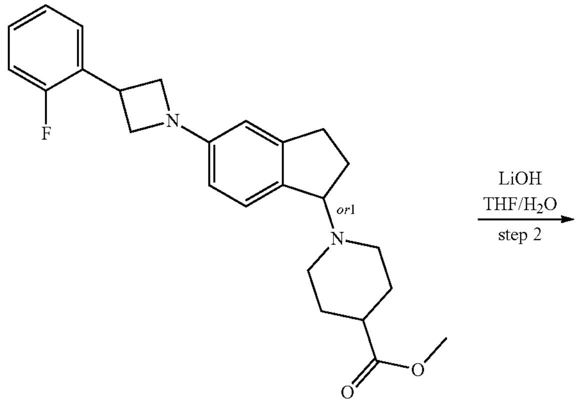

Chiral separation 1

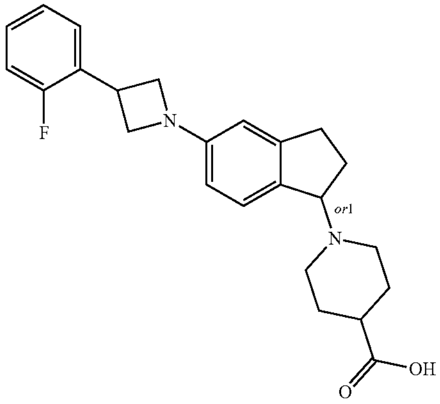

10a
Chiral separation 1

A mixture of chiral separation 1 enantiomer methyl 1-(5-(3-(2-fluorophenyl)azetidin-1-yl)-2,3-dihydro-1H-inden-1-yl)piperidine-4-carboxylate (22.0 mg, 0.050 mmol, 1.00 equiv.) and lithium hydroxide (2.58 mg, 0.110 mmol, 2.00 equiv.) in THE (1 mL) and water (1 mL) was stirred at room temperature overnight. LCMS showed that the reaction was completed. The reaction was acidified to pH 4 by adding acetic acid and then concentrated under reduced pressure. The residue was purified by prep-HPLC (Column: YMC-Actus Triart C18, 30*250, 5 mm; Mobile Phase A: water (10 mM $NH_4HCO_3$+0.1% $NH_3{\cdot}H_2O$), Mobile Phase B: ACN; Flow rate: 60 mL/min; Gradient: 20% B to 45% B in 8 min; 254/210 nm; RT: 7.52 min) to give 1-(5-(3-(2-fluorophenyl)azetidin-1-yl)-2,3-dihydro-1H-inden-1-yl)piperidine-4-carboxylic acid (11.2 mg, 51.5%) as a white solid.

LCMS (ESI, m/z): 393 $[M-H]^-$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.538 min.

$^1H$ NMR (400 MHz, DMSO-$d_6$) δ 11.9 (br, 1H), 7.53-7.49 (m, 1H), 7.34-7.28 (m, 1H), 7.24-7.16 (m, 2H), 7.07 (t, J=7.6 Hz, 1H), 6.35-6.33 (m, 2H), 4.26-4.23 (m, 2H), 4.18-4.11 (m, 2H), 3.82-3.78 (m, 2H), 2.83-2.75 (m, 2H), 2.71-2.63 (m, 1H), 2.49-2.43 (m, 1H), 2.25-2.06 (m, 3H), 1.98-1.91 (m, 2H), 1.81-1.72 (m, 2H), 1.61-1.51 (m, 1H), 1.48-1.38 (m, 1H).

Synthesis of 1-(5-(3-(2-fluorophenyl)azetidin-1-yl)-2,3-dihydro-1H-inden-1-yl)piperidine-4-carboxylic acid (Enantiomer 2, 10b)

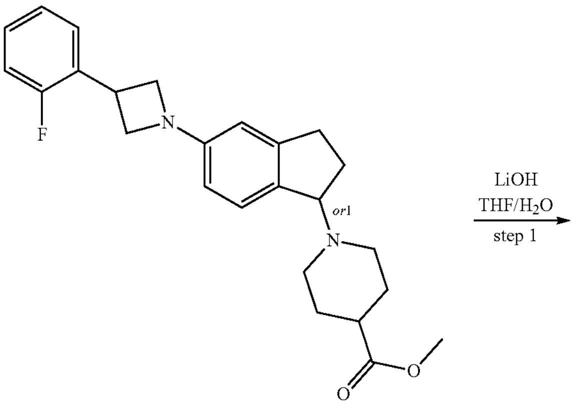

Chiral separation 2

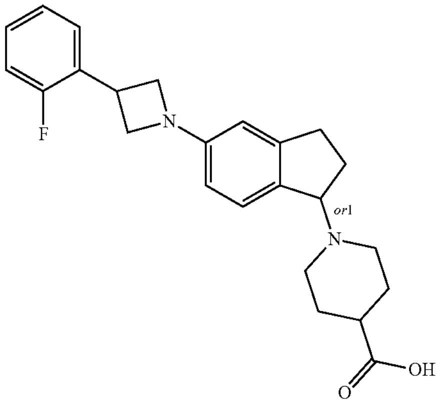

10b
Chiral separation 2

A mixture of chiral separation 2 enantiomer of methyl 1-(5-(3-(2-fluorophenyl)azetidin-1-yl)-2,3-dihydro-1H-inden-1-yl)piperidine-4-carboxylate (20.0 mg, 0.050 mmol, 1.00 equiv.) and lithium hydroxide (2.58 mg, 0.110 mmol, 2.00 equiv.) in THE (1 mL) and water (1 mL) was stirred at room temperature overnight. LCMS showed that the reaction was completed. The reaction was acidified to pH 4 by adding acetic acid and then concentrated under reduced pressure. The residue was purified by prep-HPLC (Column: YMC-Actus Triart C18, 30*250, 5 mm; Mobile Phase A: water (10 mmol/L $NH_4HCO_3$+0.1% $NH_3{\cdot}H_2O$), Mobile Phase B: ACN; Flow rate: 60 mL/min; Gradient: 20% B to 50% B in 8 min; 254/210 nm; RT: 6.16 min) to 1-(5-(3-(2-fluorophenyl)azetidin-1-yl)-2,3-dihydro-1H-inden-1-yl)piperidine-4-carboxylic acid (4.4 mg, 22.1%) as a white solid.

LCMS (ESI, m/z): 393 $[M-H]^-$. Analytic Conditions: column: Shim-pack XR-ODS, 3.0*50 mm, 2.2 μm; mobile phase A: water (0.05% TFA), mobile phase B: acetonitrile (0.05% TFA), flow rate: 1.20 mL/min; gradient: 5% B to 100% B in 2.00 min, hold at 100% for 0.70 min, 100% B to 5% B in 0.05 min; 254 nm; RT: 1.537 min.

$^1H$ NMR (400 MHz, DMSO-$d_6$) δ 12.00 (br, 1H), 7.53-7.49 (m, 1H), 7.34-7.28 (m, 1H), 7.24-7.16 (m, 2H), 7.07 (t, J=7.6 Hz, 1H), 6.35-6.33 (m, 2H), 4.26-4.23 (m, 2H), 4.18-4.11 (m, 2H), 3.82-3.78 (m, 2H), 2.83-2.75 (m, 2H), 2.71-2.63 (m, 1H), 2.49-2.43 (m, 1H), 2.24-2.08 (m, 3H), 1.98-1.91 (m, 2H), 1.80-1.71 (m, 2H), 1.61-1.51 (m, 1H), 1.48-1.38 (m, 1H).

Example S11. 1-(4-(1-(2,6-dichlorophenyl)azetidin-3-yl)benzyl)piperidine-4-carboxylic acid (11)

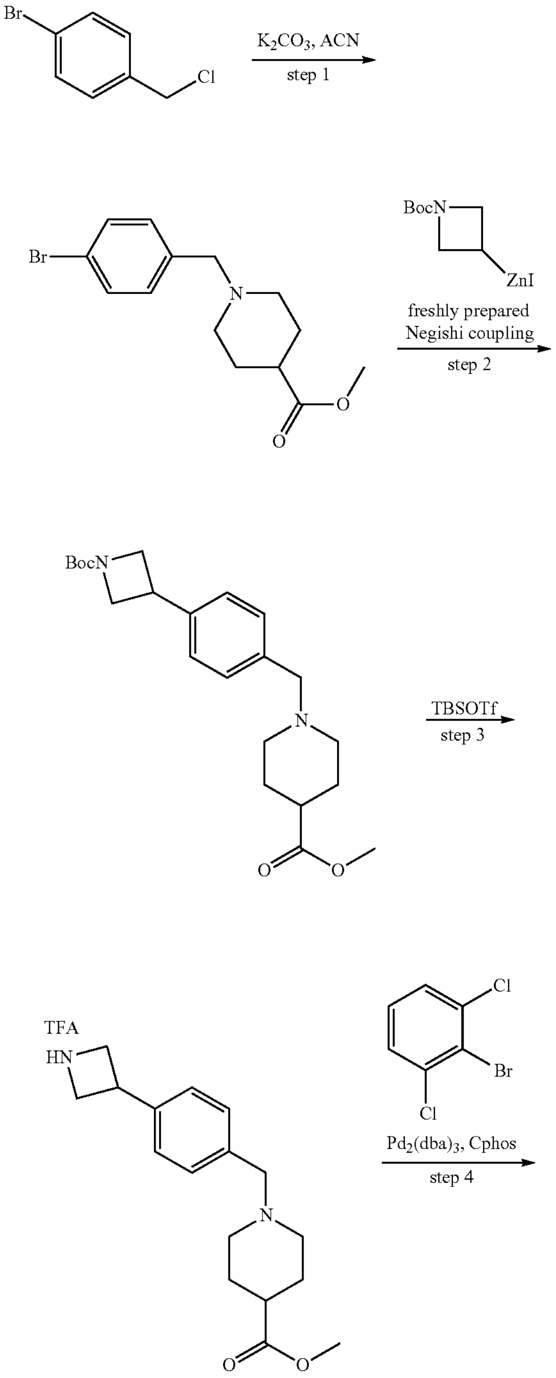

-continued

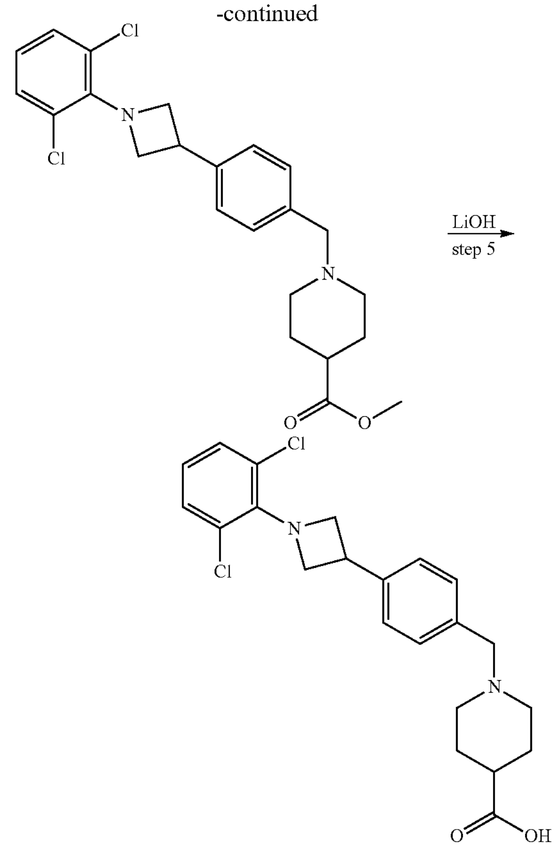

11

Synthesis of methyl 1-(4-bromobenzyl)piperidine-4-carboxylate

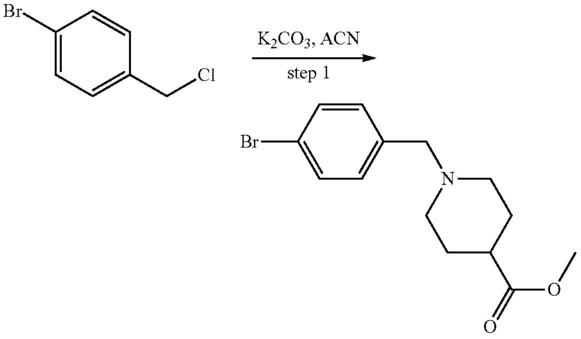

To a stirred solution of 1-bromo-4-(chloromethyl)benzene (10.0 g, 48.67 mmol, 1.00 equiv.) and methyl piperidine-4-carboxylate (13.9 g, 97.33 mmol, 2.00 equiv.) in ACN (100 mL) was added $K_2CO_3$ (20.1 g, 146 mmol, 3.00 equiv.). The resulting mixture was stirred at 60° C. for 2 h. LCMS showed the reaction was completed. The reaction was diluted with water (200 mL) and extracted with ethyl acetate (3*100 mL). The organic layers were combined and washed with brine, and then dried over anhydrous $Na_2SO_4$ and concentrated. The residue was purified by flash column chromatography on silica gel (eluted with EtOAc/PE, 1/3) to afford methyl 1-(4-bromobenzyl)piperidine-4-carboxylate (12.0 g, 78%) as a light-yellow oil. LCMS (ESI, m/z): 312 $[M+H]^+$.

Synthesis of methyl 1-(4-(1-(tert-butoxycarbonyl)azetidin-3-yl)benzyl)piperidine-4-carboxylate

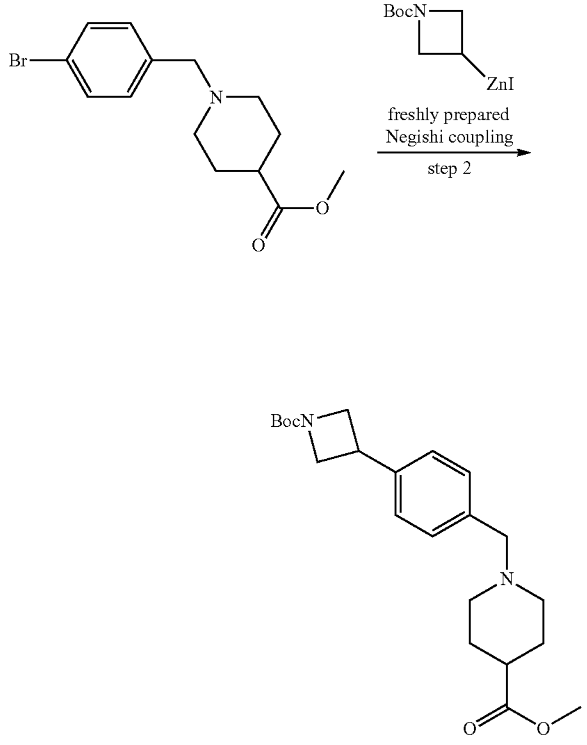

To a stirred solution of tert-butyl 3-iodoazetidine-1-carboxylate (40.8 g, 144.14 mmol, 10.00 equiv.) in DMF (100 mL) was added Zinc powder (2.8 g, 43.24 mmol, 3.00 equiv.). The resulting mixture was stirred at 60° C. under nitrogen atmosphere for 2 h. Then methyl 1-(4-bromobenzyl)piperidine-4-carboxylate (4.5 g, 14.41 mmol, 1.00 equiv.), $Pd_2(dba)_3$ (1.3 g, 1.44 mmol, 0.10 equiv.) and tri-m-tolylphosphane (876 mg, 2.88 mmol, 0.20 equiv.) were added. The resulting mixture was stirred at 80° C. under nitrogen for 16 h. LCMS showed the reaction was completed. The reaction was diluted with water (300 mL) and extracted with ethyl acetate (3*150 mL). The organic layers were combined and washed with brine, and then dried over anhydrous $Na_2SO_4$ and concentrated. The residue was purified by flash column chromatography on C18 silica (Mobile Phase A: water (10 mM $NH_4HCO_3$), Mobile Phase B: ACN; Flow rate: 120 mL/min; Gradient: 77% B to 85% B in 7 min; 254/210 nm) to afford methyl 1-(4-(1-(tert-butoxycarbonyl)azetidin-3-yl)benzyl)piperidine-4-carboxylate (5.2 g, 92%) as an off-white solid. LCMS (ESI, m/z): 389 $[M+H]^+$.

Synthesis of methyl 1-(4-(azetidin-3-yl)benzyl)piperidine-4-carboxylate

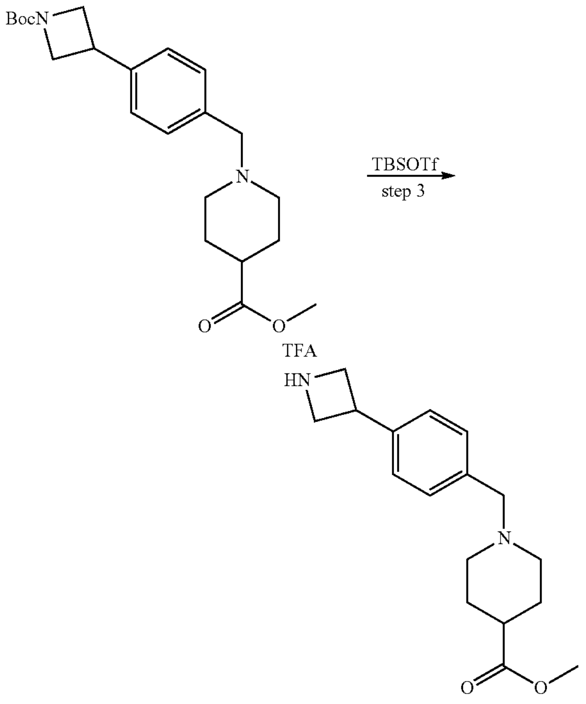

To a stirred solution of methyl 1-(4-(1-(tert-butoxycarbonyl)azetidin-3-yl)benzyl)piperidine-4-carboxylate (5.2 g, 13.38 mmol, 1.00 equiv.) in DCM (100 mL) was added TBSOTf (7.1 mL, 40.15 mmol, 3.00 equiv.). The resulting mixture was stirred at room temperature for 1 h. LCMS showed the reaction was completed. The reaction mixture was concentrated under vacuum. The residue was purified by flash column chromatography on C18 silica (Mobile Phase A: water (0.05% TFA), Mobile Phase B: ACN; Flow rate: 120 mL/min; Gradient: 10% B to 20% B in 5 min; 254/210 nm) to afford methyl 1-(4-(azetidin-3-yl)benzyl)piperidine-4-carboxylate (5.2 g, 96%) as a light-yellow oil. LCMS (ESI, m/z): 289 $[M+H]^+$.

Synthesis of methyl 1-(4-(1-(2,6-dichlorophenyl)azetidin-3-yl)benzyl)piperidine-4-carboxylate

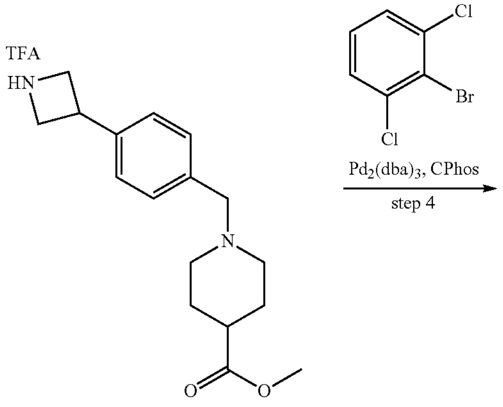

-continued

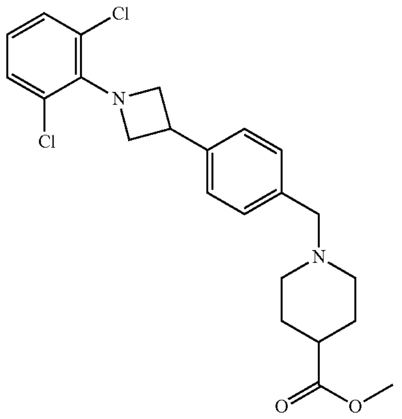

To a stirred solution of methyl 1-(4-(azetidin-3-yl)benzyl)piperidine-4-carboxylate (4.3 g, 14.91 mmol, 1.00 equiv.) and 2-bromo-1,3-dichloro-benzene (5.0 g, 22.37 mmol, 1.50 equiv.) in 1,4-dioxane (100 mL) were added $Pd_2(dba)_3$ (1.4 g, 1.49 mmol, 0.10 equiv.), CPhos (1.3 g, 2.98 mmol, 0.20 equiv.) and $Cs_2CO_3$ (14.5 g, 44.73 mmol, 3.00 equiv.). The resulting mixture was stirred at 80° C. for 16 h. LCMS showed the reaction was completed. The reaction was diluted with water (300 mL) and extracted with ethyl acetate (3*150 mL). The organic layers were combined and washed with brine, and then dried over anhydrous $Na_2SO_4$ and concentrated. The residue was purified by flash column chromatography on C18 silica (Mobile Phase A: water (10 mM $NH_4HCO_3$), Mobile Phase B: ACN; Flow rate: 120 mL/min; Gradient: 80% B to 90% B in 7 min; 254/210 nm) to afford methyl 1-(4-(1-(2,6-dichlorophenyl)azetidin-3-yl)benzyl)piperidine-4-carboxylate (750 mg, 11%) as an off-white solid. LCMS (ESI, m/z): 433 $[M+H]^+$.

Synthesis of 1-(4-(1-(2,6-dichlorophenyl)azetidin-3-yl)benzyl)piperidine-4-carboxylic acid (11)

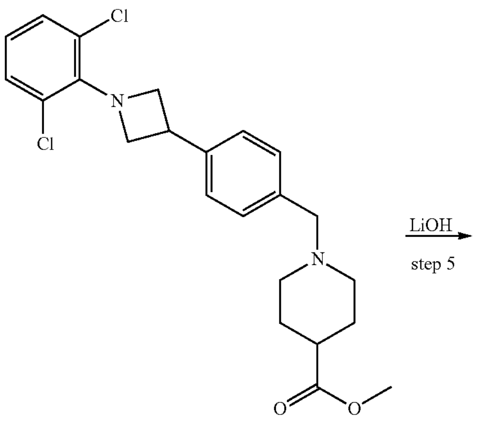

-continued

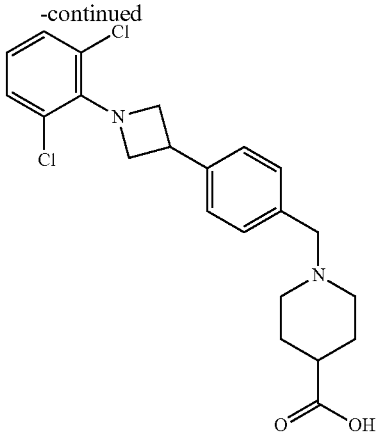

11

To a stirred solution of methyl 1-(4-(1-(2,6-dichlorophenyl)azetidin-3-yl)benzyl)piperidine-4-carboxylate (750 mg, 1.73 mmol, 1.00 equiv.) in THE (10 mL) and water (1 mL) was added $LiOH \cdot H_2O$ (217 mg, 5.19 mmol, 3.00 equiv.). The resulting mixture was stirred at room temperature for 16 h. LCMS showed the reaction was completed. The reaction was acidified to pH 5-6 by adding acetic acid dropwise, and then was concentrated under vacuum. The residue was purified by flash column chromatography on C18 silica (Mobile Phase A: water (10 mM $NH_4HCO_3$), Mobile Phase B: ACN; Flow rate: 100 mL/min; Gradient: 45% B to 50% B in 4 min; 254/210 nm) to afford 1-(4-(1-(2,6-dichlorophenyl)azetidin-3-yl)benzyl)piperidine-4-carboxylic acid (558.8 mg, 75%) as an off-white solid.

$^1H$ NMR (300 MHz, Chloroform-d) δ 7.41 (s, 4H), 7.15 (d, J=7.8 Hz, 2H), 6.65 (t, J=7.8 Hz, 1H), 4.92 (t, J=8.1 Hz, 2H), 4.49-4.44 (m, 2H), 3.93 (s, 2H), 3.79-3.69 (m, 1H), 3.26 (d, J=11.1 Hz, 2H), 2.45-2.25 (m, 3H), 2.10-2.06 (m, 2H), 1.99-1.91 (m, 2H).

LCMS (ESI, m/z): 419 $[M+H]^+$. Analytic Conditions: column: YMC Meteoric Core C18 BIO Column 2.1*30 mm, 2.7 μm; mobile phase A: water/5 mM $NH_4HCO_3$, mobile phase B: acetonitrile; flow rate: 1.20 mL/min; gradient: 10% B to 95% B in 1.19 min, hold at 95% for 0.58 min, 95% B to 10% B in 0.05 min; 254 nm; RT: 0.758 min.

Example S12a. (S)-1-(4-(1-(2,6-dichlorophenyl)azetidin-3-yl)benzyl)pyrrolidine-3-carboxylic acid (12a)

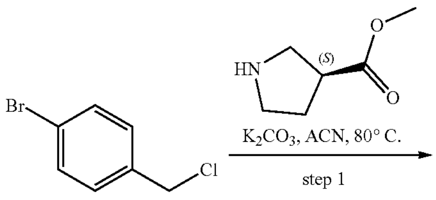

-continued

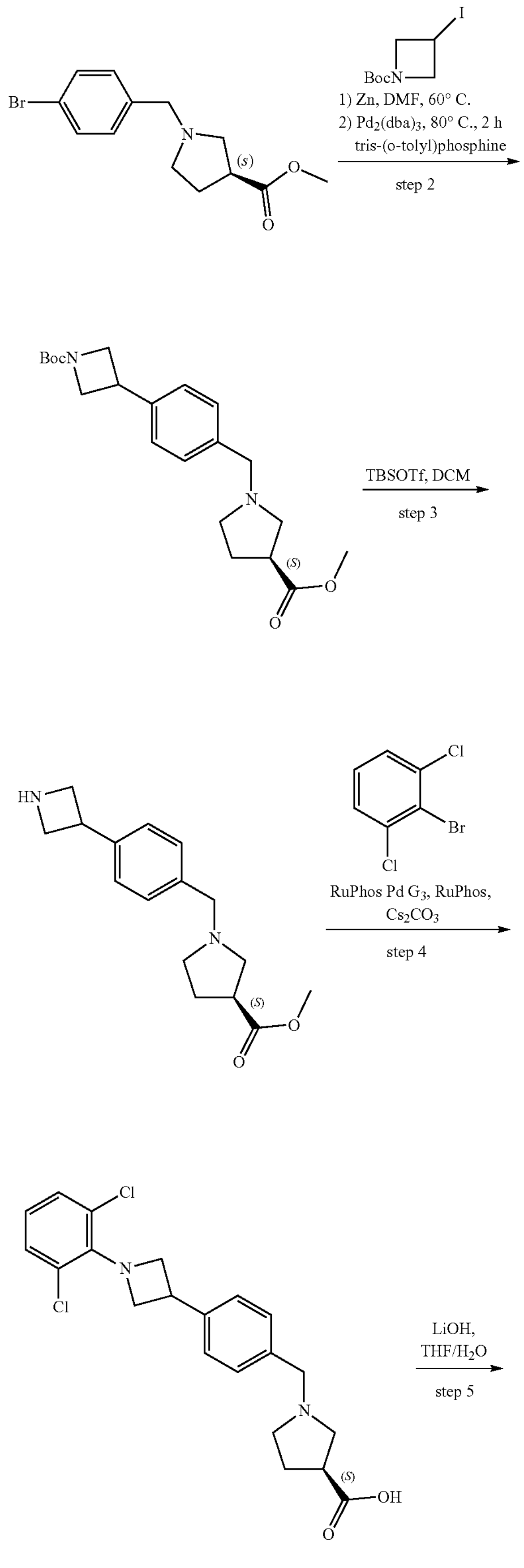

-continued

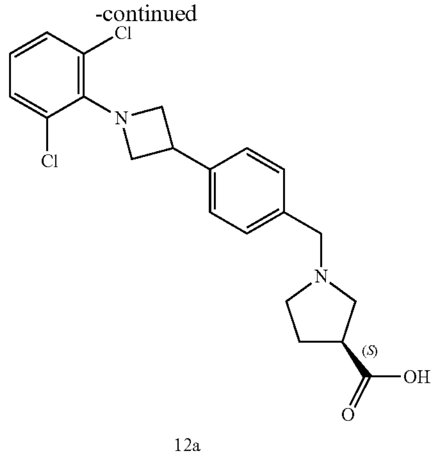

12a

Synthesis of methyl (S)-1-(4-bromobenzyl)pyrrolidine-3-carboxylate

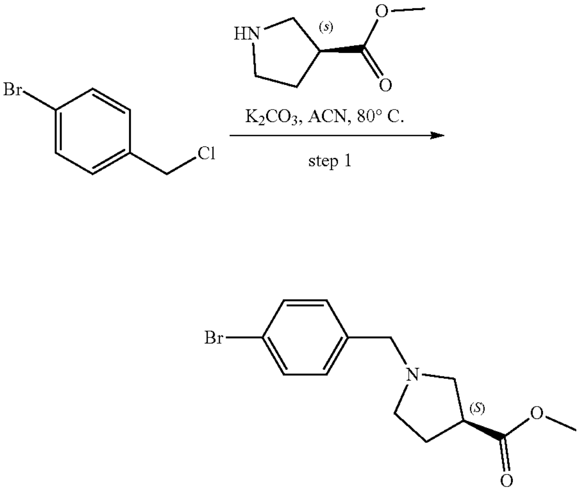

To a stirred solution of 1-bromo-4-(chloromethyl)benzene (3 g, 14.6 mmol, 1.00 equiv.) and methyl rac-(3S)-pyrrolidine-3-carboxylate (2.83 g, 21.9 mmol, 1.50 equiv.) in ACN (10 mL) was added $K_2CO_3$ (4.03 g, 29.2 mmol, 2.00 equiv.). The resulting mixture was stirred at 80° C. for 5 h. LCMS showed the reaction was completed. The solvent was removed by evaporation. The residue was diluted with water (20 mL), then extracted with ethyl acetate (3*20 mL). The combined organic layers were dried over anhydrous $Na_2SO_4$ and concentrated under reduce pressure. The crude product was purified by flash chromatography on C18 silica (eluted with water (0.05% TFA)/ACN, 3/7) to afford methyl (S)-1-(4-bromobenzyl)pyrrolidine-3-carboxylate (2.78 g, 63.9%) as a yellow oil. LCMS (ESI, m/z): 298 $[M+H]^+$.

Synthesis of methyl (S)-1-(4-(1-(tert-butoxycarbonyl)azetidin-3-yl)benzyl)-pyrrolidine-3-carboxylate

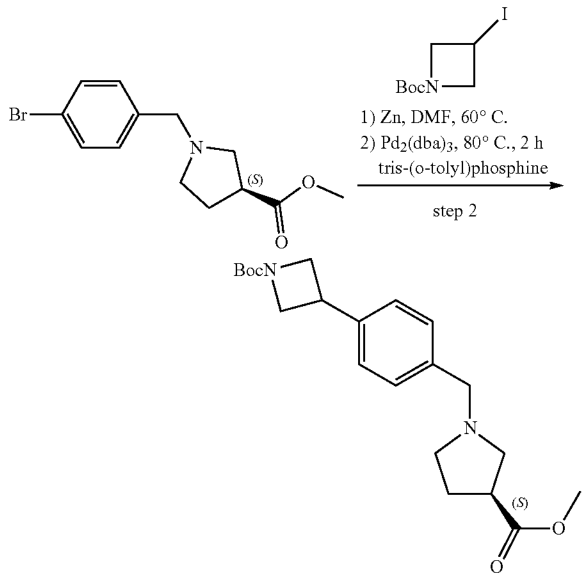

To a stirred solution of tert-butyl 3-iodoazetidine-1-carboxylate (11.3 g, 40.2 mmol, 6.00 equiv.) in DMF (30 mL) was added Zinc powder (2.6 g, 40.2 mmol, 6.00 equiv.). The resulting mixture was stirred at 60° C. for 3 h under $N_2$ atmosphere. Then $Pd_2(dba)_3$ (921 mg, 1.01 mmol, 0.15 equiv.), tris-(o-tolyl)phosphine (612 mg, 2.01 mmol, 0.30 equiv.) and methyl (S)-1-(4-bromobenzyl)pyrrolidine-3-carboxylate (2.00 g, 6.71 mmol, 1.00 equiv.) were added. The resulting mixture was stirred at 80° C. overnight. LCMS showed the reaction was completed. The reaction mixture was diluted with saturated aq. $NH_4Cl$ (100 mL) and extracted with EtOAc (3*40 mL). The organic layers were combined and dried over $MgSO_4$ and concentrated. The crude was purified by flash chromatography on silica gel (eluted with PE/EtOAc, 1/1) to afford methyl (S)-1-(4-(1-(tert-butoxycarbonyl)azetidin-3-yl)benzyl)pyrrolidine-3-carboxylate (2 g, 79.6%) as a yellow oil. LCMS (ESI, m z): 375 $[M+H]^+$.

Synthesis of methyl (S)-1-(4-(azetidin-3-yl)benzyl) pyrrolidine-3-carboxylate

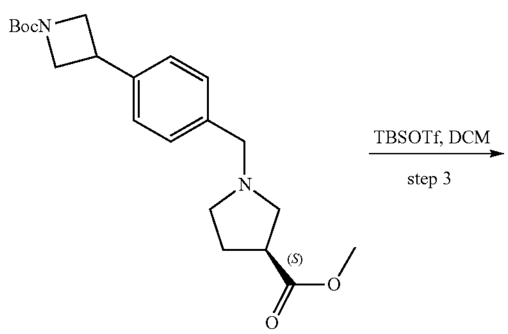

-continued

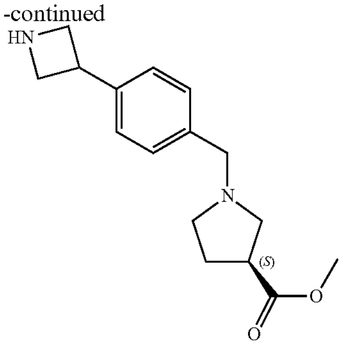

To a stirred solution of methyl (S)-1-(4-(1-(tert-butoxycarbonyl)azetidin-3-yl)benzyl)-pyrrolidine-3-carboxylate (2 g, 5.34 mmol, 1.00 equiv.) in DCM (3 mL) was added TBSOTf (2.5 mL, 14.1 mmol, 2.64 equiv.) dropwise. The resulting mixture was stirred at room temperature for 2 h. LCMS showed the reaction was complete. The reaction mixture was concentrated under reduced pressure. The crude product was purified by flash column on C18 (eluted with water/ACN, 5/95) to afford methyl (S)-1-(4-(azetidin-3-yl)benzyl)pyrrolidine-3-carboxylate (970 mg, 66.2%) as an orange oil. LCMS (ESI, m z): 275 $[M+H]^+$.

Synthesis of methyl (S)-1-(4-(1-(2,6-dichlorophenyl)azetidin-3-yl)benzyl)pyrrolidine-3-carboxylate

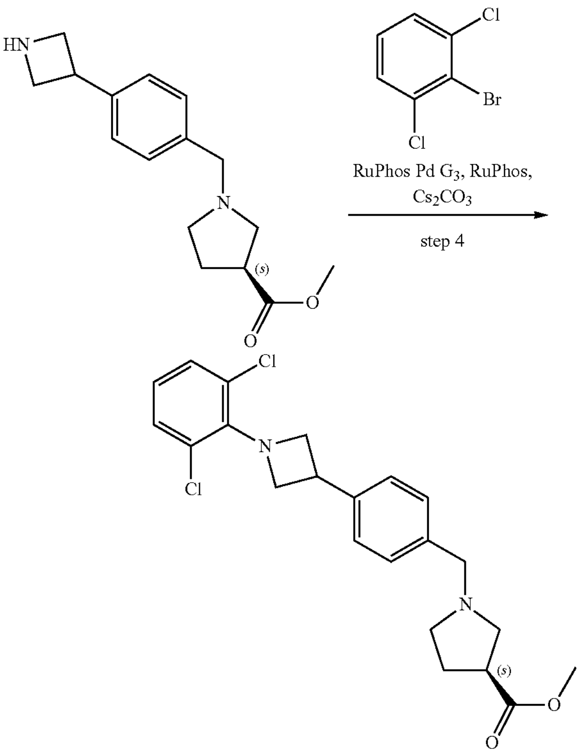

To a stirred solution of methyl (S)-1-(4-(azetidin-3-yl)benzyl)pyrrolidine-3-carboxylate (600 mg, 2.19 mmol, 1.00 equiv.) and 2-bromo-1,3-dichloro-benzene (988 mg, 4.37 mmol, 2.00 equiv.) in 1,4-dioxane (6 mL) were added RuPhos Pd G3 (183 mg, 0.220 mmol, 0.10 equiv.), $Cs_2CO_3$ (2.13 g, 6.56 mmol, 3.00 equiv.), and RuPhos (204 mg, 0.440 mmol, 0.20 equiv.). The resulting mixture was stirred at 90° C. overnight. LCMS showed the reaction was completed. The reaction mixture was concentrated and purified by flash column on silica gel (eluted with PE/EA, 1/3) to afford methyl (S)-1-(4-(1-(2,6-dichlorophenyl)azetidin-3-yl)-benzyl)pyrrolidine-3-carboxylate (120 mg, 13.1%) as a yellow oil. LCMS (ESI, m z): 419 [M+H]+.

Synthesis of (S)-1-(4-(1-(2,6-dichlorophenyl)azetidin-3-yl)benzyl)pyrrolidine-3-carboxylic acid (12a)

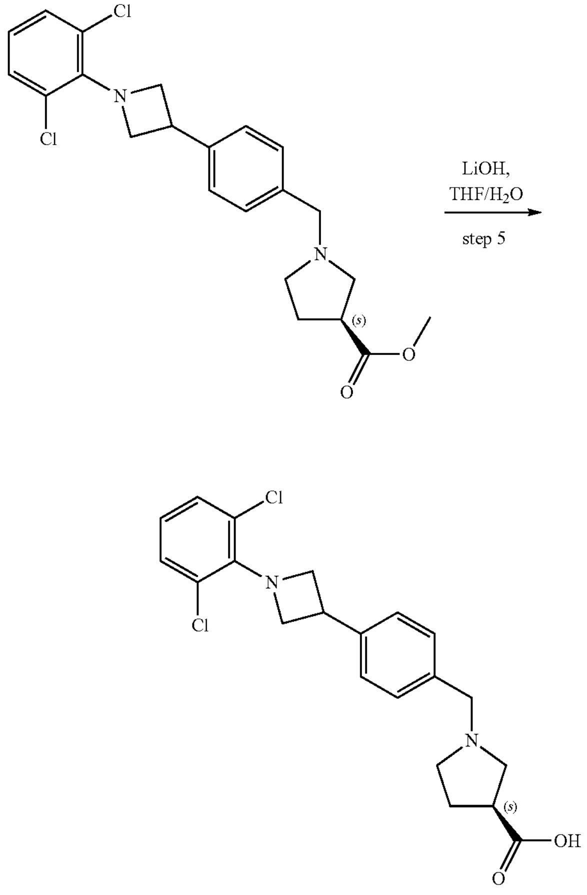

12a

To a stirred solution of methyl (S)-1-(4-(1-(2,6-dichlorophenyl)azetidin-3-yl)benzyl)-pyrrolidine-3-carboxylate (120 mg, 0.290 mmol, 1.00 equiv.) in THE (1.5 mL) and water (1.5 mL) was added LiOH (21 mg, 0.860 mmol, 3.00 equiv.). The resulting mixture was stirred at room temperature overnight. LCMS showed the reaction was completed. The reaction mixture was acidified to pH 4-5 using acetic acid and then was concentrated. The residue was purified by Prep-HPLC (Column: XBridge Prep C18 OBD Column, 30*100 mm, 5 mm; Mobile Phase A: water (10 mmol/L $NH_4HCO_3$), Mobile Phase B: ACN; Flow rate: 60 mL/min; Gradient: 30% B to 45% B in 9 min; Wavelength: 254/220 nm; RT: 8.85 min) to get (S)-1-(4-(1-(2,6-dichlorophenyl) azetidin-3-yl)benzyl)pyrrolidine-3-carboxylic acid (71.6 mg, 61.2%) as a white solid.

LCMS (ESI, m/z): 405 [M+H]+. Analytic Conditions: column: YMC Meteoric Core C18 BIO, 2.1*30 mm, 2.7 μm; mobile phase A: water (5 mM $NH_4HCO_3$), mobile phase B: acetonitrile, flow rate: 1.20 mL/min; gradient: 10% B to 95% B in 1.20 min, hold at 95% for 0.58 min, 95% B to 10% B in 0.05 min; 254 nm; RT: 0.749 min.

$^1H$ NMR (400 MHz, $CD_3OD$) δ 7.52 (d, J=8.4 Hz, 2H), 7.47 (d, J=8.4 Hz, 2H), 7.19 (d, J=8.0 Hz, 2H), 6.72 (t, J=8.0 Hz, 1H), 4.90 (t, J=8.0 Hz, 2H), 4.44-4.41 (m, 2H), 4.13 (q, J=8.8 Hz, 2H), 3.82-3.76 (m, 1H), 3.30-3.25 (m, 2H), 3.17-3.13 (m, 3H), 3.07-3.01 (m, 2H).

Example S12b. (R)-1-(4-(1-(2,6-dichlorophenyl) azetidin-3-yl)benzyl)pyrrolidine-3-carboxylic acid (12b)

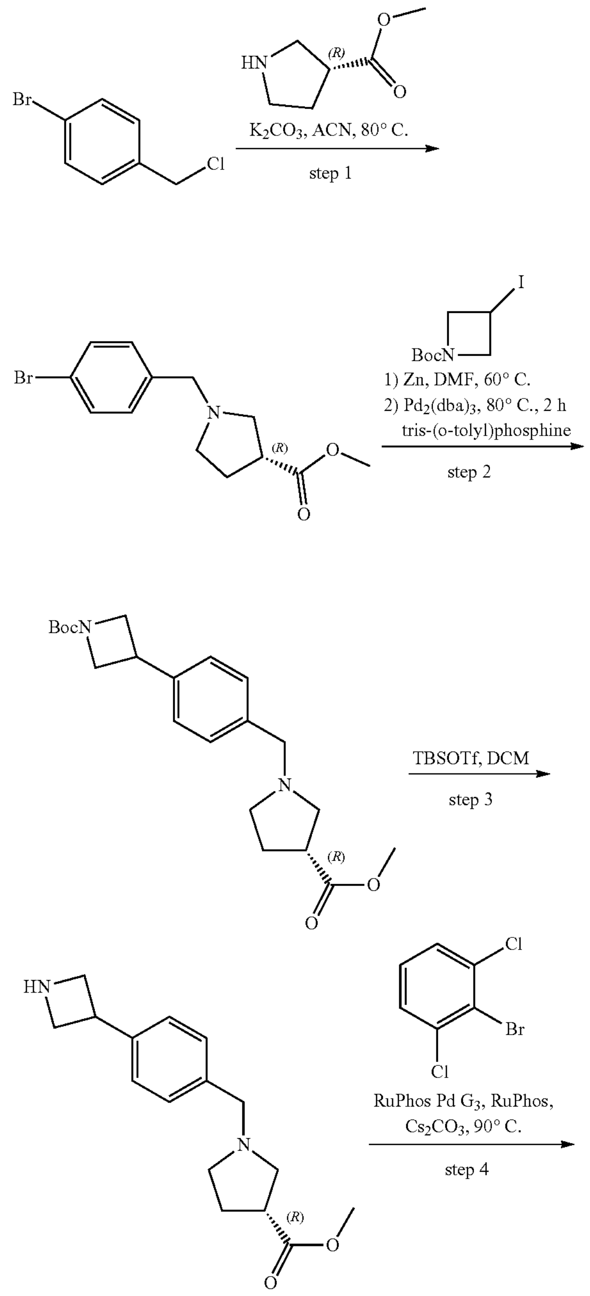

-continued

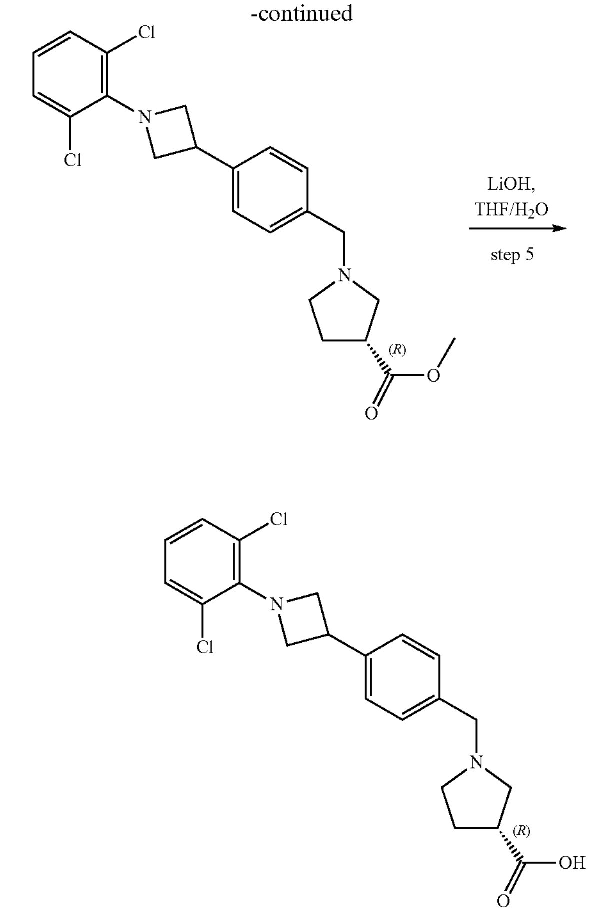

12a

Synthesis of methyl (R)-1-(4-bromobenzyl)pyrrolidine-3-carboxylate

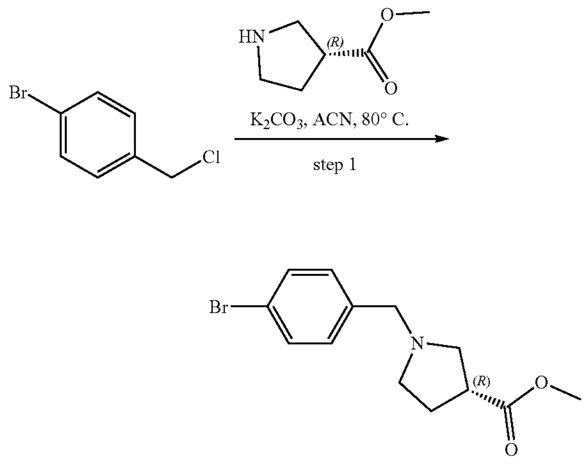

To a stirred solution of 1-bromo-4-(chloromethyl)benzene (3 g, 14.6 mmol, 1.00 equiv.) and methyl (R)-pyrrolidine-3-carboxylate (2.83 g, 21.9 mmol, 1.50 equiv.) in ACN (10 mL) was added $K_2CO_3$ (4.03 g, 29.2 mmol, 2.00 equiv.). The resulting mixture was stirred at 80° C. for 5 h. LCMS showed the reaction was completed. The solvent was removed by evaporation. The residue was diluted with water (20 mL), then extracted with ethyl acetate (3*20 mL). The combined organic layers were dried over anhydrous $Na_2SO_4$ and concentrated under reduce pressure. The crude product was purified by flash chromatography on C18 silica (eluted with water (0.05% TFA)/ACN, 3/7) to afford methyl (R)-1-(4-bromobenzyl)pyrrolidine-3-carboxylate (4.13 g, 94.9%) as a yellow oil. LCMS (ESI, m/z): 298 $[M+H]^+$.

Synthesis of methyl (R)-1-(4-(1-(tert-butoxycarbonyl)azetidin-3-yl)benzyl)pyrrolidine-3-carboxylate

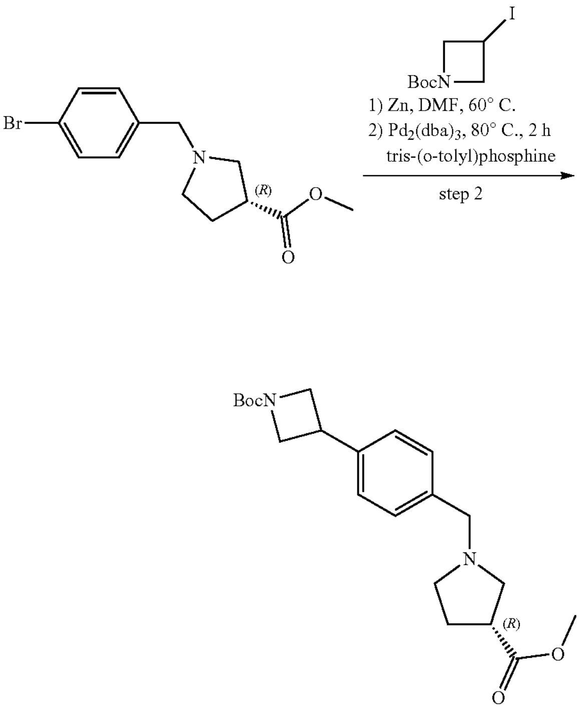

To a stirred solution of tert-butyl 3-iodoazetidine-1-carboxylate (11.3 g, 40.2 mmol, 6.00 equiv.) in DMF (30 mL) was added Zinc powder (2.6 g, 40.2 mmol, 6.00 equiv.). The resulting mixture was stirred at 60° C. for 3 h under $N_2$ atmosphere. Then $Pd_2(dba)_3$ (921 mg, 1.01 mmol, 0.15 equiv.), tris-(o-tolyl)phosphine (612 mg, 2.01 mmol, 0.30 equiv.) and methyl (R)-1-(4-bromobenzyl)pyrrolidine-3-carboxylate (2.00 g, 6.71 mmol, 1.00 equiv.) were added. The resulting mixture was stirred at 80° C. overnight. LCMS showed the reaction was completed. The reaction mixture was diluted with saturated aq. $NH_4Cl$ (100 mL) and extracted with EtOAc (3*40 mL). The organic layers were combined and dried over $MgSO_4$ and concentrated. The crude was purified by flash chromatography on silica gel (eluted with PE/EtOAc, 1/1) to afford methyl (R)-1-(4-(1-(tert-butoxycarbonyl)azetidin-3-yl)benzyl)pyrrolidine-3-carboxylate (1.9 g, 75.6%) as a yellow oil. LCMS (ESI, m/z): 375 $[M+H]^+$.

Synthesis of methyl (R)-1-(4-(azetidin-3-yl)benzyl) pyrrolidine-3-carboxylate

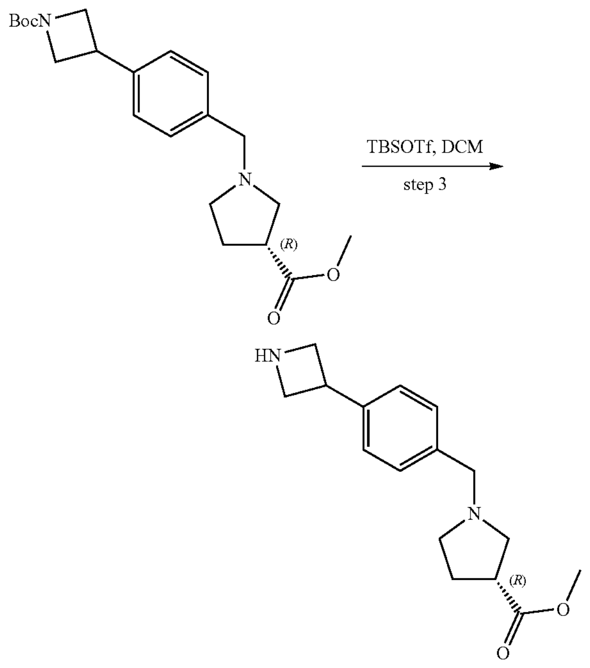

To a stirred solution of methyl (R)-1-(4-(1-(tert-butoxycarbonyl)azetidin-3-yl)benzyl)-pyrrolidine-3-carboxylate (2 g, 5.34 mmol, 1.00 equiv.) in DCM (3 mL) was added TBSOTf (2.5 mL, 14.1 mmol, 2.64 equiv.) dropwise. The resulting mixture was stirred at room temperature for 2 h. LCMS showed the reaction was complete. The reaction mixture was concentrated under reduced pressure. The crude product was purified by flash column on C18 (eluted with water/ACN, 5/95) to afford methyl (R)-1-(4-(azetidin-3-yl) benzyl)pyrrolidine-3-carboxylate (990 mg, 70.8%) as an orange oil. LCMS (ESI, m z): 275 [M+H]+.

Synthesis of methyl (R)-1-(4-(1-(2,6-dichlorophenyl)azetidin-3-yl)benzyl)pyrrolidine-3-carboxylate -continued

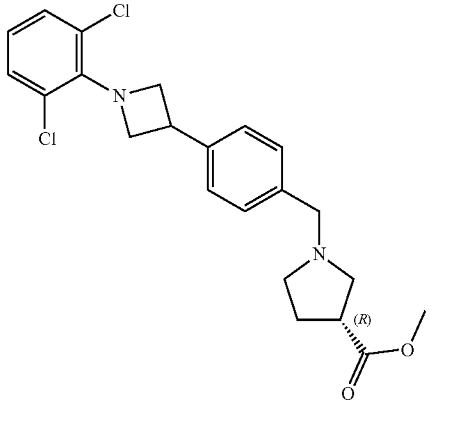

To a stirred solution of methyl (R)-1-(4-(azetidin-3-yl) benzyl)pyrrolidine-3-carboxylate (600 mg, 2.19 mmol, 1.00 equiv.) and 2-bromo-1,3-dichloro-benzene (988 mg, 4.37 mmol, 2.00 equiv.) in 1,4-dioxane (6 mL) were added $Pd_2(dba)_3$ (200 mg, 0.220 mmol, 0.10 equiv.), $Cs_2CO_3$ (2.13 g, 6.56 mmol, 3.00 equiv.), and CPhos (190 mg, 0.440 mmol, 0.20 equiv.). The resulting mixture was stirred at 90° C. overnight. LCMS showed the reaction was completed. The reaction mixture was concentrated and purified by flash column on silica gel (eluted with PE/EA, 1/3) to afford methyl (R)-1-(4-(1-(2,6-dichlorophenyl)azetidin-3-yl)benzyl)pyrrolidine-3-carboxylate (120 mg, 13.1%) as a yellow oil. LCMS (ESI, m z): 419 [M+H]+.

Synthesis of (R)-1-(4-(1-(2,6-dichlorophenyl)azetidin-3-yl)benzyl)pyrrolidine-3-carboxylic acid (12b)

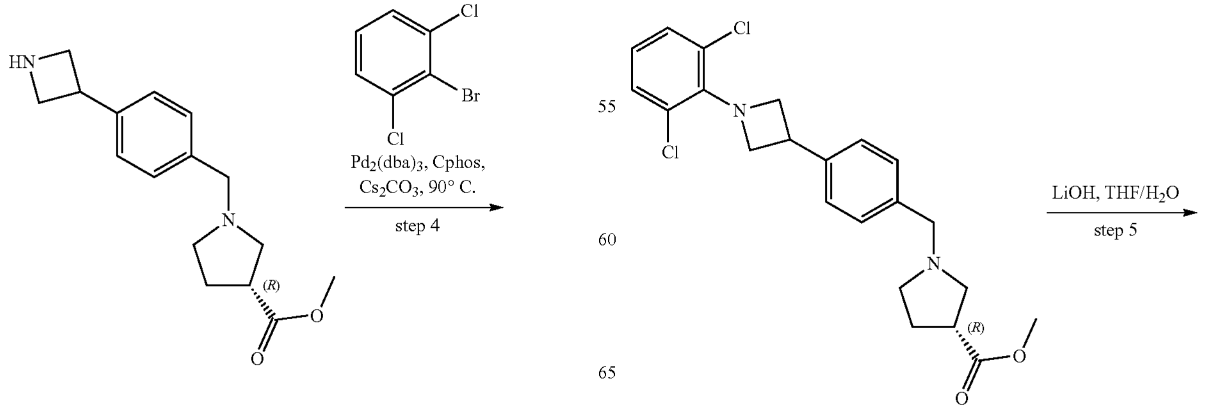

-continued

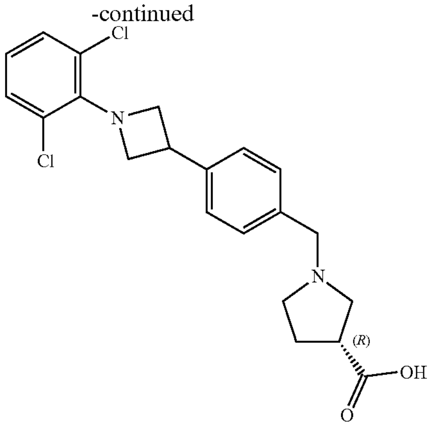

12b

To a stirred solution of methyl (R)-1-(4-(1-(2,6-dichlorophenyl)azetidin-3-yl)-benzyl)pyrrolidine-3-carboxylate (120 mg, 0.290 mmol, 1.00 equiv.) in THF (1.5 mL) and water (1.5 mL) was added LiOH (21 mg, 0.860 mmol, 3.00 equiv.). The resulting mixture was stirred at room temperature overnight. LCMS showed the reaction was completed. The reaction mixture was acidified to pH 4-5 using acetic acid and then was concentrated. The residue was purified by Prep-HPLC (Column: XBridge Prep C18 OBD Column, 30*100 mm, 5 mm; Mobile Phase A: water (10 mmol/L $NH_4HCO_3$), Mobile Phase B: ACN; Flow rate: 60 mL/min; Gradient: 20% B to 50% B in 7 min; Wavelength: 254/220 nm; RT: 6.32 min) to get (R)-1-(4-(1-(2,6-dichlorophenyl)azetidin-3-yl)benzyl)pyrrolidine-3-carboxylic acid (56.6 mg, 48.3%) as a white solid.

LCMS (ESI, m/z): 405 $[M+H]^+$. Analytic Conditions: column: YMC Meteoric Core C18 BIO, 2.1*30 mm, 2.7 μm; mobile phase A: water (5 mM $NH_4HCO_3$), mobile phase B: acetonitrile, flow rate: 1.20 mL/min; gradient: 10% B to 95% B in 1.20 min, hold at 95% for 0.58 min, 95% B to 10% B in 0.05 min; 254 nm; RT: 0.757 min.

$^1H$ NMR (400 MHz, $CD_3OD$) δ 7.51 (d, J=8.4 Hz, 2H), 7.46 (d, J=8.4 Hz, 2H), 7.19 (d, J=8.0 Hz, 2H), 6.72 (t, J=8.0 Hz, 1H), 4.90 (t, J=8.0 Hz, 2H), 4.44-4.41 (m, 2H), 4.13 (q, J=8.8 Hz, 2H), 3.82-3.75 (m, 1H), 3.28-3.18 (m, 2H), 3.16-3.00 (m, 3H), 2.25-2.17 (m, 2H).

Example S13. 1-(4-(1-(2,6-dichlorophenyl)azetidin-3-yl)benzyl)azetidine-3-carboxylic acid (13)

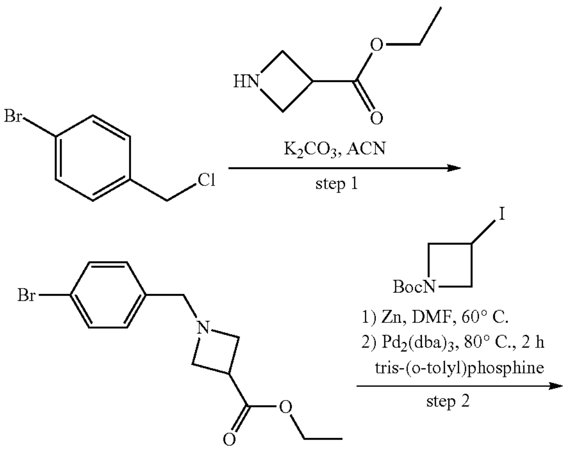

-continued

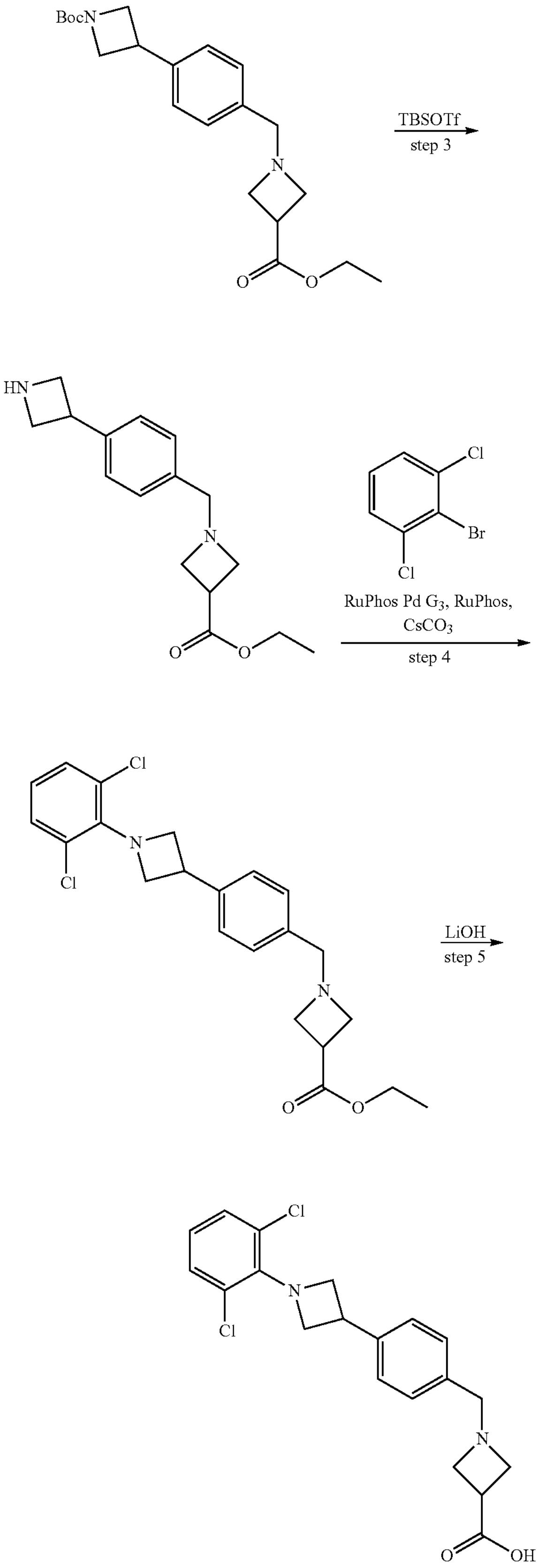

13

Synthesis of ethyl 1-(4-bromobenzyl)azetidine-3-carboxylate

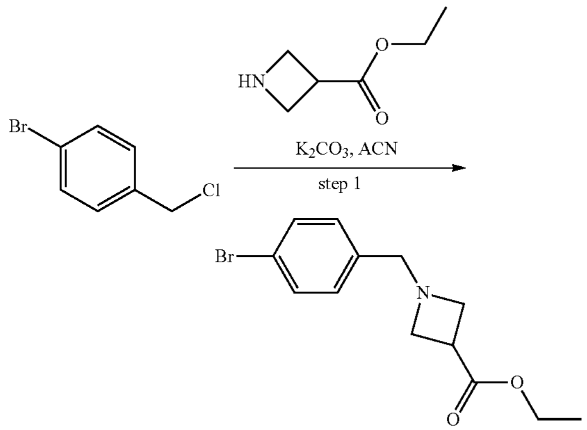

To a stirred solution of 1-bromo-4-(chloromethyl) benzene (2.12 g, 10.32 mmol, 1.00 equiv.) and ethyl azetidine-3-carboxylate (2.00 g, 15.48 mmol, 1.50 equiv.) in ACN (10 mL) was added $K_2CO_3$ (2.85 g, 20.63 mmol, 3.00 equiv.). This resulting mixture was stirred at 80° C. for 2 h. LCMS showed the reaction was completed. The solvent was removed by evaporation. The residue was diluted with water (20 mL), then extracted with ethyl acetate (3*20 mL). The combined organic layers were dried over anhydrous $Na_2SO_4$ and concentrated under reduce pressure. The crude product was purified by flash chromatography on C18 silica (eluted with water (0.05% TFA)/ACN, 3/7) to afford ethyl 1-(4-bromobenzyl)azetidine-3-carboxylate (2.50 g, 8.38 mmol, 81.3%) as a yellow oil. LCMS (ESI, m z): 298 $[M+H]^+$.

Synthesis of tert-butyl 3-(4-((3-(ethoxycarbonyl) azetidin-1-yl)methyl)phenyl)azetidine-1-carboxylate

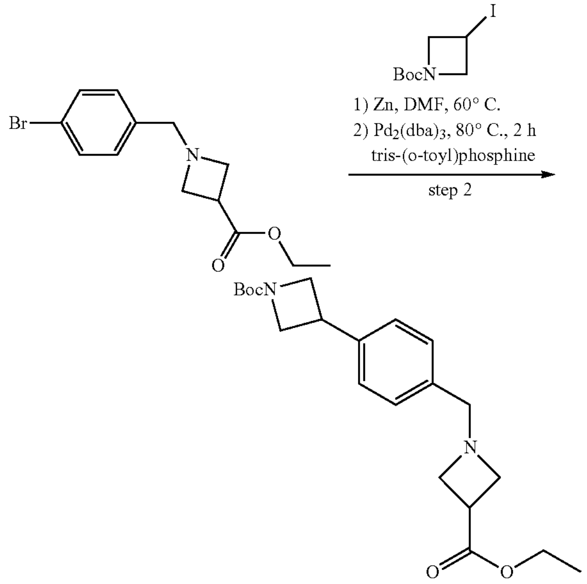

To a stirred solution of tert-butyl 3-iodoazetidine-1-carboxylate (22.8 g, 80.4 mmol, 10.0 equiv.) in DMF (100 mL) was added Zinc powder (5.22 g, 80.4 mmol, 10.0 equiv.). The resulting mixture was stirred at 60° C. for 3 h under $N_2$ atmosphere. Then $Pd_2(dba)_3$ (1.47 g, 1.62 mmol, 0.20 equiv.), tris-(o-tolyl)phosphine (1.72 g, 12.0 mmol, 0.70 equiv.) and ethyl 1-(4-bromobenzyl)azetidine-3-carboxylate (2.40 g, 8.04 mmol, 1.00 equiv.). The resulting mixture was stirred at 80° C. overnight under nitrogen atmosphere. LCMS showed the reaction was completed. The reaction mixture was diluted with saturated aq. $NH_4Cl$ (200 mL) and extracted with EtOAc (3*80 mL). The organic layers were combined and dried over $MgSO_4$ and concentrated. The crude was purified by flash chromatography on silica gel (eluted with PE/EtOAc, 1/1) to afford tert-butyl 3-(4-((3-(ethoxycarbonyl)azetidin-1-yl)methyl)-phenyl)azetidine-1-carboxylate (1.00 g, 33.2%) as a yellow oil. LCMS (ESI, m z): 375 $[M+H]^+$.

Synthesis of ethyl 1-(4-(azetidin-3-yl)benzyl)azetidine-3-carboxylate

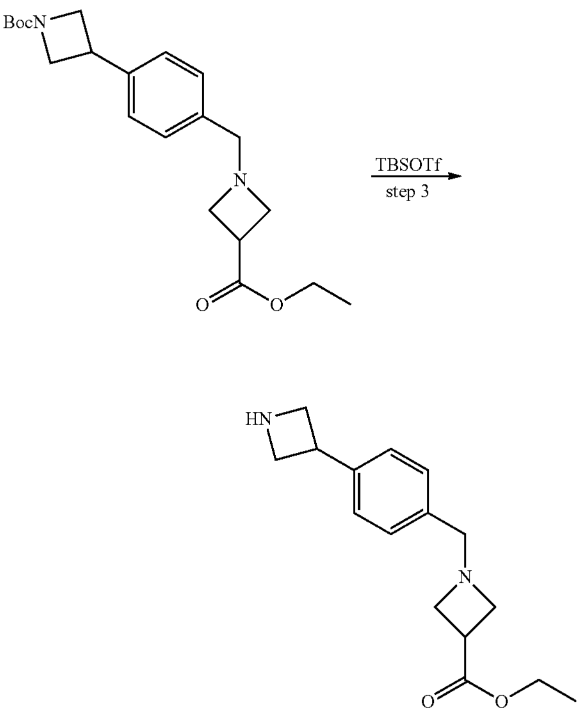

To a stirred solution of tert-butyl 3-(4-((3-(ethoxycarbonyl)azetidin-1-yl)methyl)-phenyl)azetidine-1-carboxylate (1.00 g, 2.67 mmol, 1.00 equiv.) in DCM (5 mL) was added TBSOTf (1.32 mL, 7.48 mmol, 2.80 equiv.). The resulting mixture was stirred at room temperature for 0.5 h. LCMS showed the reaction was completed. The reaction mixture was concentrated under reduced pressure. The crude product was purified by flash column on C18 (eluted with water/ACN, 5/95) to afford ethyl 1-(4-(azetidin-3-yl)benzyl)azetidine-3-carboxylate (600 mg, 2.19 mmol, 82%) as a yellow oil. LCMS (ESI, m z): 275 $[M+H]^+$.

Synthesis of ethyl 1-(4-(1-(2,6-dichlorophenyl)azetidin-3-yl)benzyl)azetidine-3-carboxylate

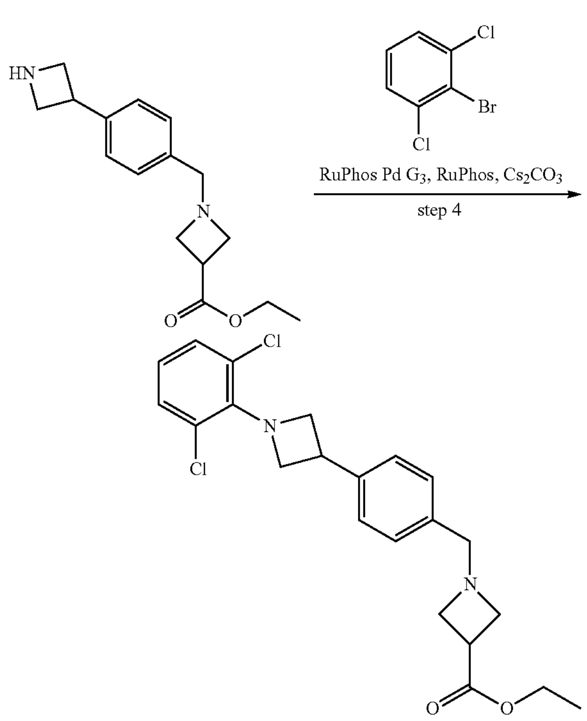

To a stirred solution of ethyl 1-(4-(azetidin-3-yl)benzyl) azetidine-3-carboxylate (600 mg, 2.19 mmol, 1.00 equiv.) and 2-bromo-1,3-dichloro-benzene (494 mg, 2.19 mmol, 1.00 equiv.) in 1,4-dioxane (2 mL) were added RuPhos (102 mg, 0.220 mmol, 0.100), RuPhos Pd G3 (183 mg, 0.220 mmol, 0.100 equiv.) and $Cs_2CO_3$ (2.13 g, 6.56 mmol, 3.00 equiv.). The resulting mixture was stirred at 90° C. overnight under nitrogen atmosphere. LCMS showed the reaction was completed. The reaction mixture was concentrated and purified by flash column on silica gel (eluted with PE/EA, 1/1) to afford ethyl 1-(4-(1-(2,6-dichlorophenyl)azetidin-3-yl)-benzyl)azetidine-3-carboxylate (120 mg, 13.1%) as a yellow oil. LCMS (ESI, m z): 420$[M+H]^+$.

Synthesis of 1-(4-(1-(2,6-dichlorophenyl)azetidin-3-yl)benzyl)azetidine-3-carboxylic acid (13)

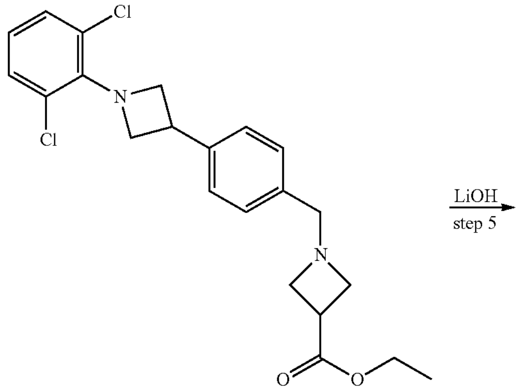

-continued

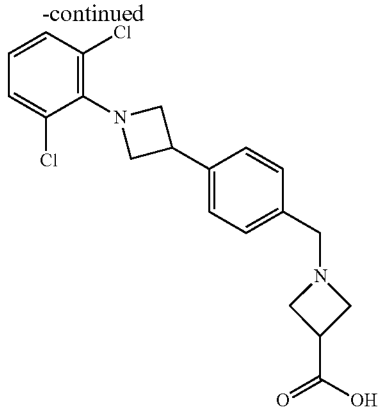

13

To a stirred solution of ethyl 1-(4-(1-(2,6-dichlorophenyl) azetidin-3-yl)benzyl)azetidine-3-carboxylate (120 mg, 0.290 mmol, 1.00 equiv.) in THE (1 mL) and water (1 mL) was added NaOH (34 mg, 0.860 mmol, 3.00 equiv.). The resulting mixture was stirred at room temperature overnight. LCMS showed the reaction was completed. The reaction mixture was acidified to pH 4-5 using acetic acid and then was concentrated. The residue was purified by Prep-HPLC (Column: XBridge Prep OBD C18 Column, 30*150 mm, 5 μm; Mobile Phase A: water (10 mM $NH_4HCO_3$), Mobile Phase B: ACN; Flow rate: 60 mL/min; Gradient: 20% B to 50% B in 10 min, 254/220 nm; RT: 9.67 min) to get 1-(4-(1-(2,6-dichlorophenyl)azetidin-3-yl)-benzyl)azetidine-3-carboxylic acid (36.3 mg, 31.9%) as a white solid.

LCMS (ESI, m/z): 391 $[M+H]^+$. Analytic Conditions: column: YMC Meteoric Core C18 BIO, 2.1*30 mm, 2.7 μm; mobile phase A: water (5 mM $NH_4HCO_3$), mobile phase B: acetonitrile, flow rate: 1.20 mL/min; gradient: 10% B to 55% B in 1.85 min, 55% B to 95% B in 0.45 min, hold at 95% for 0.50 min, 95% B to 10% B in 0.03 min; 254 nm; RT: 0.389 min.

$^1H$ NMR (400 MHz, $CD_3OD$) δ 7.55 (d, J=8.4 Hz, 2H), 7.44 (d, J=8.4 Hz, 2H), 7.20 (d, J=8.0 Hz, 2H), 6.73 (t, J=8.0 Hz, 1H), 4.91 (t, J=8.0 Hz, 2H), 4.44-4.41 (m, 2H), 4.24 (s, 2H), 4.11-4.03 (m, 4H), 3.83-3.76 (m, 1H), 3.41-3.35 (m, 1H).

Example S14. Synthesis of 1-(4-(1-(2,6-difluorophenyl)azetidin-3-yl)benzyl)piperidine-4-carboxylic acid (14)

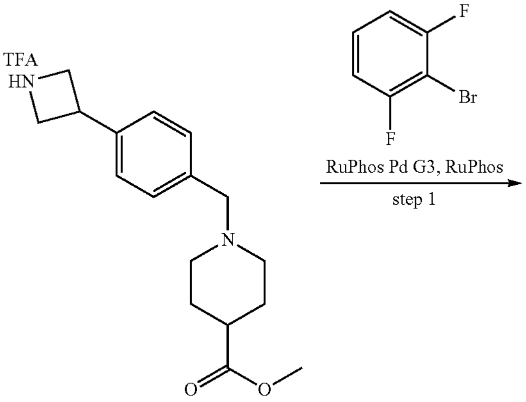

-continued

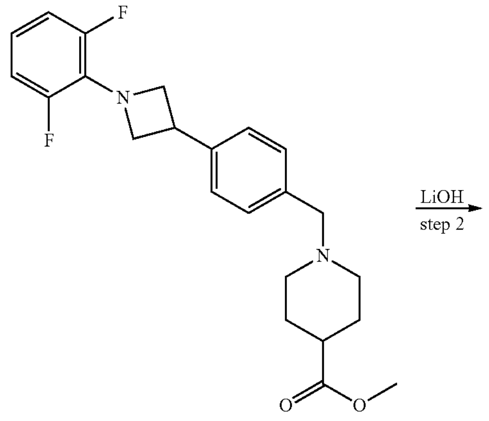

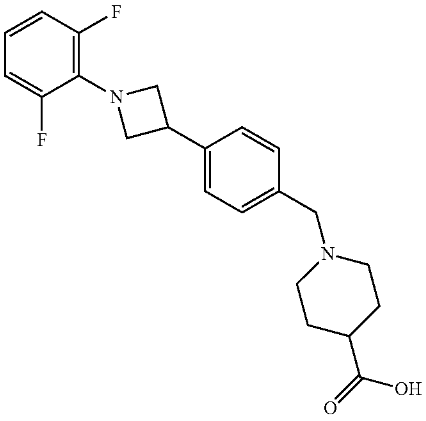

14

Synthesis of methyl 1-(4-(1-(2,6-difluorophenyl) azetidin-3-yl)benzyl)piperidine-4-carboxylate -continued

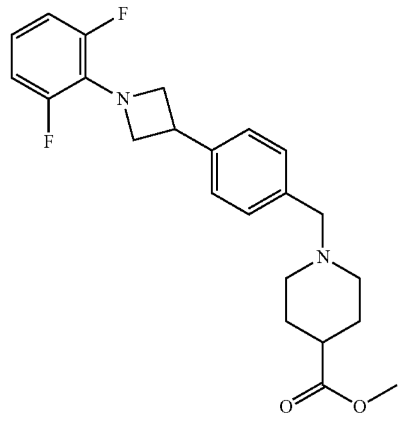

To a stirred solution of methyl 1-(4-(azetidin-3-yl)benzyl) piperidine-4-carboxylate (200 mg, 0.690 mmol, 1.00 equiv.) and 2-bromo-1,3-difluoro-benzene (133 mg, 0.690 mmol, 1.00 equiv.) in 1,4-dioxane (5 mL) were added RuPhos Pd G3 (64 mg, 0.070 mmol, 0.10 equiv.), RuPhos (64 mg, 0.140 mmol, 0.20 equiv.) and $Cs_2CO_3$ (676 mg, 2.080 mmol, 3.00 equiv.). The resulting mixture was stirred at 80° C. for 16 h. LCMS showed the reaction was completed. The reaction mixture was concentrated and purified by flash column on silica gel (eluted with PE/EA, 1/2) to afford methyl 1-(4-(1-(2,6-difluorophenyl)azetidin-3-yl)benzyl)piperidine-4-carboxylate (100 mg, 36% yield) as an off-white solid. LCMS (ESI, m/z): 401 $[M+H]^+$.

Synthesis of 1-(4-(1-(2,6-difluorophenyl)azetidin-3-yl)benzyl)piperidine-4-carboxylic acid

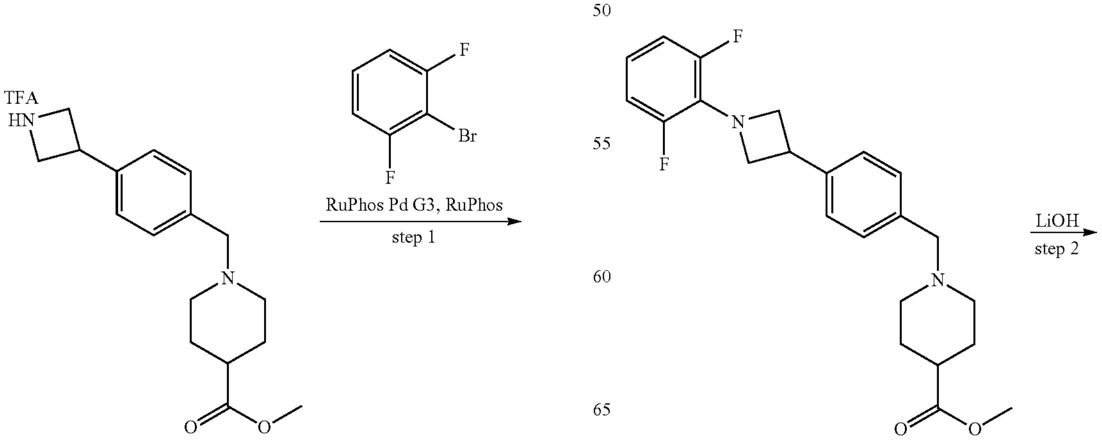

-continued

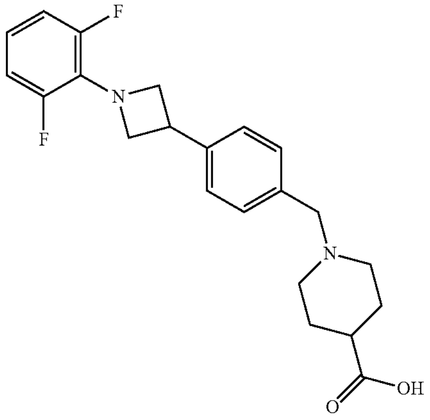

14

To a stirred solution of methyl 1-(4-(1-(2,6-difluorophenyl)azetidin-3-yl)benzyl)piperidine-4-carboxylate (80 mg, 0.200 mmol, 1.00 equiv.) in THE (2 mL) and water (0.2 mL) was added $LiOH \cdot H_2O$ (25 mg, 0.600 mmol, 3.00 equiv.). The mixture solution was stirred at room temperature for 16 h. LCMS showed the reaction was completed. The reaction mixture was acidified to pH 4-5 using acetic acid and then was concentrated. The residue was purified by Prep-HPLC (Column: XBridge Prep C18 OBD Column, 19×150 mm 5 um; Mobile Phase A: Water (10 mM $NH_4HCO_3$), Mobile Phase B: ACN; Flow rate: 25 mL/min; Gradient: 66% B to 80% B in 7 min; 254/210 nm; RT: 6.12 min) to afford 1-(4-(1-(2,6-difluorophenyl)azetidin-3-yl)benzyl)piperidine-4-carboxylic acid (33 mg, 42% yield) as an off-white solid.

LCMS (ESI, m/z): 387 $[M+H]^+$. Analytic Conditions: column: Poroshell HPH-C18, 3.0*50 mm, 2.7 μm; mobile phase A: water (5 mM $NH_4HCO_3$), mobile phase B: acetonitrile, flow rate: 1.20 mL/min; gradient: 10% B to 95% B in 2.00 min, hold at 95% for 0.60 min, 95% B to 10% B in 0.15 min; 254 nm; RT: 1.106 min.

$^1H$ NMR (300 MHz, DMSO-$d_6$) δ 12.00 (s, 1H), 7.36 (d, J=8.1 Hz, 2H), 7.27 (d, J=8.1 Hz, 2H), 6.98-6.92 (m, 2H), 6.76-6.7 (m, 1H), 4.56-4.49 (m, 2H), 4.15-4.09 (m, 2H), 3.97-3.87 (m, 1H), 3.42 (s, 2H), 2.77-2.71 (m, 2H), 2.24-2.14 (m, 1H), 2.01-1.92 (m, 2H), 1.81-1.75 (m, 2H), 1.60-1.47 (m, 2H).

Example S15. 1-(4-(1-(2,6-dichlorophenyl)azetidin-3-yl)-2,6-dimethylbenzyl)piperidine-4-carboxylic acid (15)

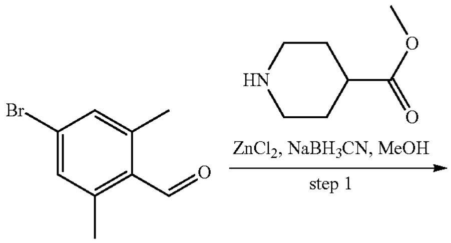

-continued

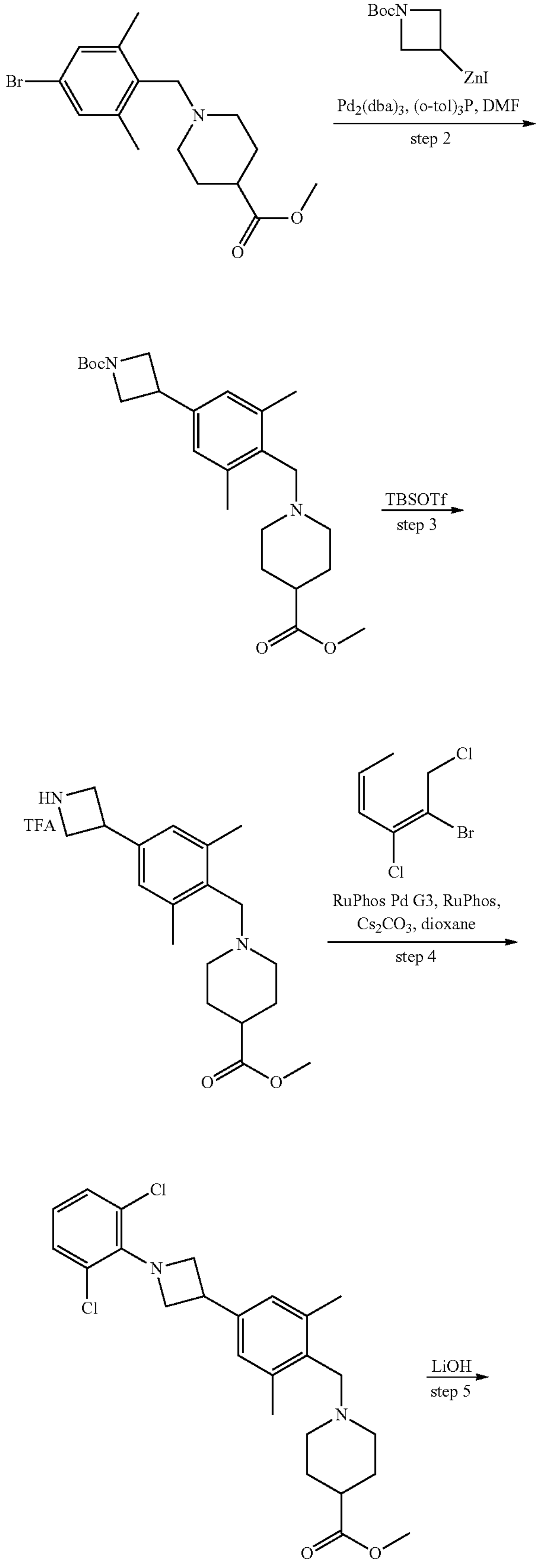

-continued

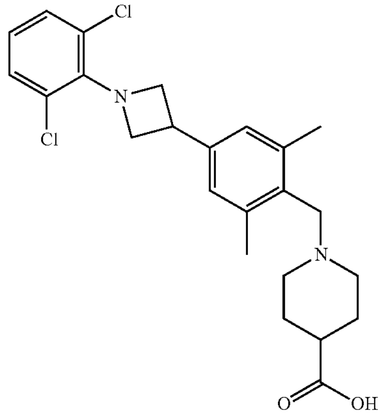

15

Synthesis of methyl 1-(4-bromo-2,6-dimethylbenzyl)piperidine-4-carboxylate

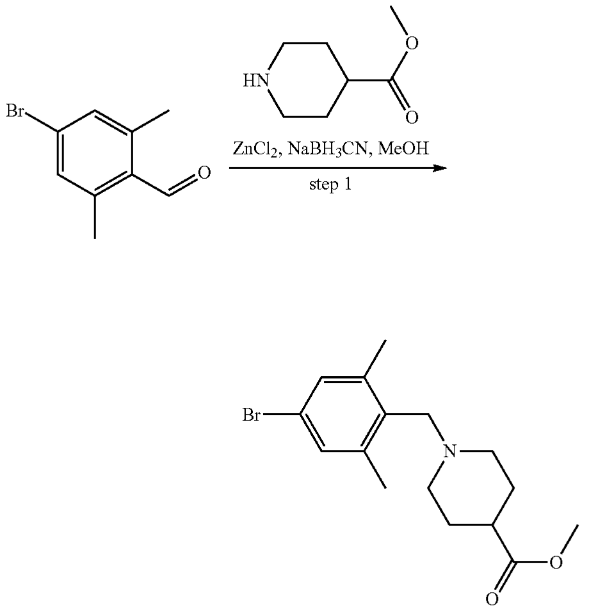

A solution of $ZnCl_2$ (1.9 M in Me-THF, 19.8 mL, 37.54 mmol, 2.00 equiv.) and $NaBH_3CN$ (4.72 g, 75.09 mmol, 4.00 equiv.) in methanol (8 mL) was stirred at room temperature for 10 min. Then 4-bromo-2,6-dimethyl-benzaldehyde (4 g, 18.77 mmol, 1.00 equiv.) and methyl piperidine-4-carboxylate (5.38 g, 37.55 mmol, 2.00 equiv.) were added. The resulting mixture was stirred at 80° C. overnight. LCMS showed that the reaction was complete. The reaction mixture was poured into DCM/$H_2O$ (1/1, 100 mL). The separated organic layer was washed with brine and dried over anhydrous $Na_2SO_4$ and concentrated under vacuum. The residue was purified by flash chromatography on silica gel (eluted with PE/EA, 3/1) to give methyl 1-(4-bromo-2,6-dimethylbenzyl)piperidine-4-carboxylate (3.5 g, 54.8%) as a yellow-light oil. LCMS (ESI, m/z): 340 [M+H]$^+$.

Synthesis of methyl 1-(4-(1-(tert-butoxycarbonyl)azetidin-3-yl)-2,6-dimethylbenzyl)-piperidine-4-carboxylate

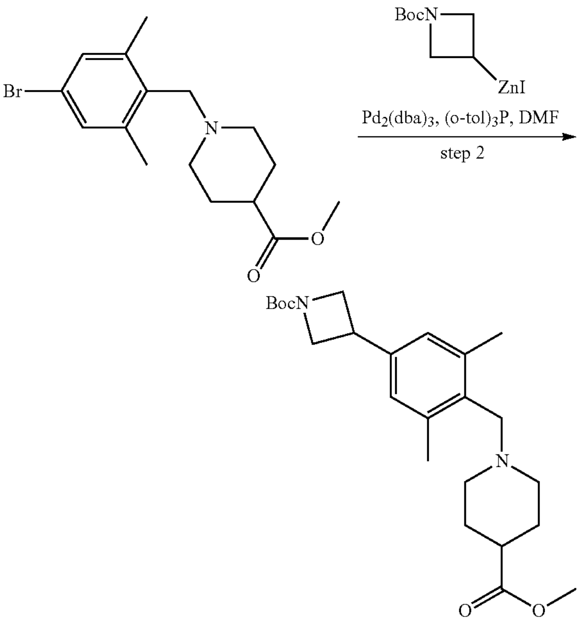

To a stirred solution of tert-butyl 3-iodoazetidine-1-carboxylate (13.24 g, 46.75 mmol, 10.0 equiv.) in DMF (75 mL) was added zinc powder (4.41 g, 67.48 mmol, 15.0 equiv.). The resulting mixture was stirred at 60° C. for 5 h. Then methyl 1-(4-bromo-2,6-dimethylbenzyl)piperidine-4-carboxylate (1.5 g, 4.41 mmol, 1.00 equiv.), $Pd_2(dba)_3$ (807 mg, 0.88 mmol, 0.20 equiv.) and tri(o-tolyl)phosphine (1.34 g, 4.41 mmol, 1.00 equiv.) were added. The resulting mixture was stirred at 80° C. overnight. LCMS showed that the reaction was complete. The reaction mixture was filtered through Celite, and the filtrate was concentrated under vacuum. The residue was purified by flash chromatography on C18 silica (eluted with 100% ACN) to give methyl 1-(4-(1-(tert-butoxycarbonyl)azetidin-3-yl)-2,6-dimethylbenzyl)piperidine-4-carboxylate (1.8 g, 98.0%) as a light-yellow oil. LCMS (ESI, m/z): 417 [M+H]$^+$.

Synthesis of methyl 1-(4-(azetidin-3-yl)-2,6-dimethylbenzyl)piperidine-4-carboxylate-2,2,2-trifluoroacetaldehyde

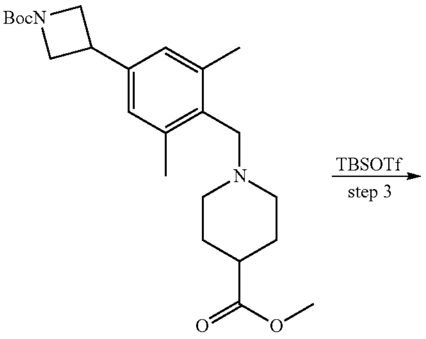

-continued

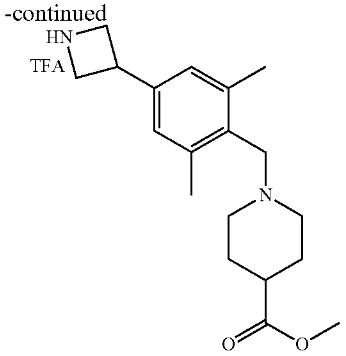

To a stirred solution of methyl 1-(4-(1-(tert-butoxycarbonyl)azetidin-3-yl)-2,6-dimethylbenzyl)piperidine-4-carboxylate (1.8 g, 4.32 mmol, 1.00 equiv.) in DCM (2 mL) was added TBSOTf (1.53 mL, 8.64 mmol, 2.00 equiv.) dropwise at room temperature. The resulting solution was stirred at room temperature for 1 h. LCMS showed the conversion was complete. The reaction mixture was concentrated under vacuum. The residue was purified by flash chromatography on C18 silica (eluted with 22% ACN in water (0.05% TFA)) to give methyl 1-(4-(azetidin-3-yl)-2,6-dimethylbenzyl)piperidine-4-carboxylate-2,2,2-trifluoroacetaldehyde (1.3 g, 95.1%) as a light-yellow oil. LCMS (ESI, m/z): 317 [M+H]+.

Synthesis of methyl 1-(4-(1-(2,6-dichlorophenyl)azetidin-3-yl)-2,6-dimethylbenzyl)-piperidine-4-carboxylate

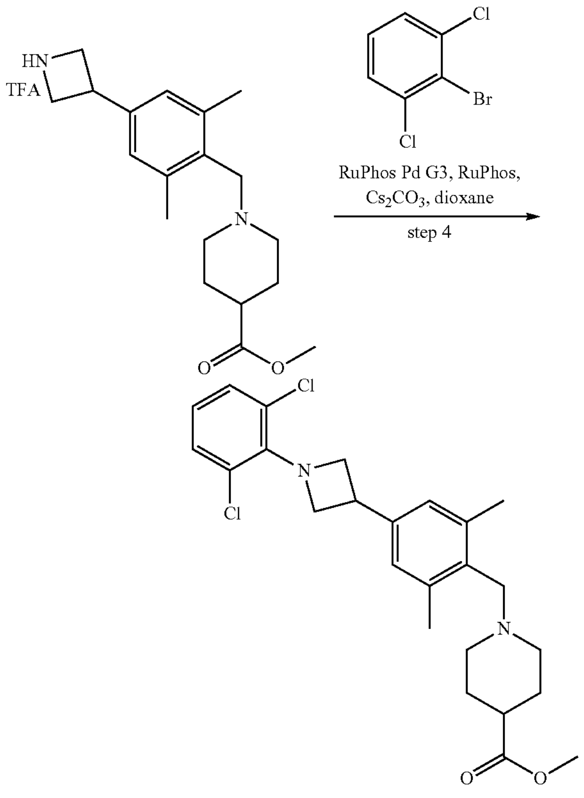

To a stirred solution of methyl 1-(4-(azetidin-3-yl)-2,6-dimethylbenzyl)piperidine-4-carboxylate-2,2,2-trifluoroacetaldehyde (2 g, 6.32 mmol, 1.00 equiv.), 2-bromo-1,3-dichloro-benzene (2.86 g, 12.64 mmol, 2.00 equiv.) in 1,4-dioxane (2 mL) were added RuPhos Pd G3 (884 mg, 0.95 mmol, 0.15 equiv.), RuPhos (442 mg, 0.95 mmol, 0.15 equiv.), $Cs_2CO_3$ (6.16 g, 18.96 mmol, 3.00 equiv.). The resulting mixture was stirred at 90° C. overnight under nitrogen atmosphere. LCMS showed that the reaction was complete. The reaction mixture was diluted with EtOAc (20 mL) and was filtered through Celite. The filtrate was concentrated under reduced pressure. The residue was purified by flash chromatography on C18 silica (eluted with 90% ACN in water (10 mM $NH_4HCO_3$)) to give methyl 1-(4-(1-(2,6-dichlorophenyl)azetidin-3-yl)-2,6-dimethylbenzyl)piperidine-4-carboxylate (500 mg, 17.1%) as a light-yellow oil. LCMS (ESI, m/z): 461 [M+H]+.

Synthesis of 1-(4-(1-(2,6-dichlorophenyl)azetidin-3-yl)-2,6-dimethylbenzyl)piperidine-4-carboxylic acid (15)

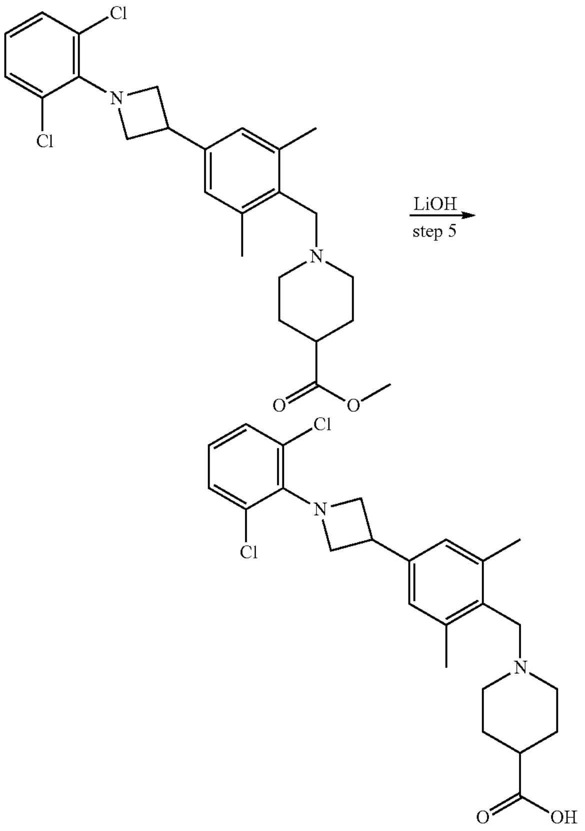

15

A mixture of methyl 1-(4-(1-(2,6-dichlorophenyl)azetidin-3-yl)-2,6-dimethylbenzyl)-piperidine-4-carboxylate (25 mg, 0.54 mmol, 1.00 equiv.) and LiOH (39 mg, 1.63 mmol, 1.00 equiv.) in THE (2.5 mL) and water (2.5 mL) was stirred at room temperature overnight. LCMS showed that the reaction was complete. The reaction mixture was acidified to pH 5-6 by adding acetic acid, and then was concentrated under reduced pressure. The residue was purified by prep-HPLC (Column: XBridge Prep C18 OBD Column, 30*100 mm, 5 μm; Mobile Phase A: water (10 mmol/L $NH_4HCO_3$), Mobile Phase B: ACN; Flow rate: 60 mL/min; Gradient: 30% B to 60% B in 7 min; Wavelength: 254/220 nm; RT: 5.92 min) to give 1-(4-(1-(2,6-dichlorophenyl)azetidin-3-yl)-2,6-dimethylbenzyl)piperidine-4-carboxylic acid (165.1 mg, 66.7%) as a white solid.

$^1H$ NMR (400 MHz, DMSO-$d_6$) δ 7.24 (d, J=7.6 Hz, 2H), 7.03 (s, 2H), 6.74 (t, J=7.6 Hz, 1H), 4.80 (t, J=8.0 Hz, 2H), 4.34 (t, J=8.0 Hz, 2H), 3.71-3.64 (m, 1H), 3.38 (s, 2H), 2.69-2.66 (m, 2H), 2.33 (s, 6H), 2.20-2.14 (m, 1H), 2.08-2.02 (m, 2H), 1.76-1.72 (m, 2H), 1.48-1.40 (m, 2H).

LCMS (ESI, m/z): 447 $[M+H]^+$. Analytic Conditions: column: YMCMeteoric C18 BIO, 2.1*30 mm, 2.7 μm; mobile phase A: water (5 mM $NH_4HCO_3$), mobile phase B: acetonitrile; flow rate: 1.20 mL/min; gradient: 10% B to 95% B in 1.20 min, hold at 95% for 0.58 min, 95% B to 10% B in 0.05 min; 254 nm; RT: 0.849 min.

Example S16. 1-(1-(4-(1-(2,6-dichlorophenyl)azetidin-3-yl)-2-methylphenyl)ethyl)-piperidine-4-carboxylic acid (16a and 16b)

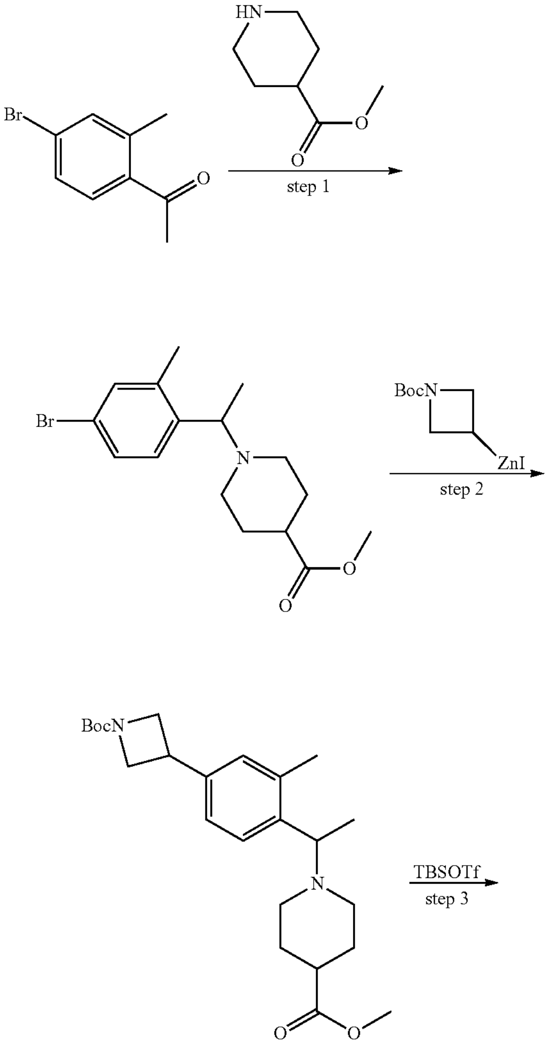

-continued

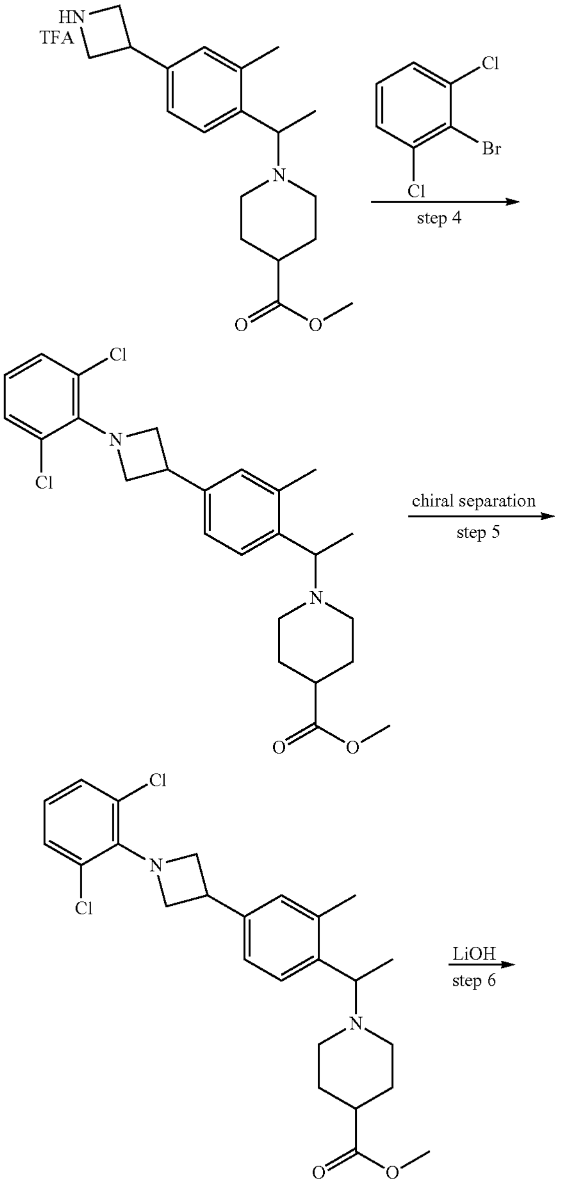

chiral separation 1

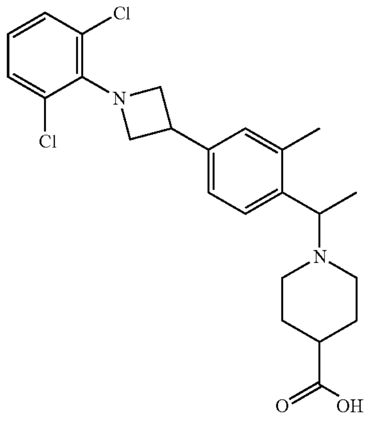

16a
chiral separation 1

Synthesis of methyl 1-(1-(4-bromo-2-methylphenyl) ethyl)piperidine-4-carboxylate

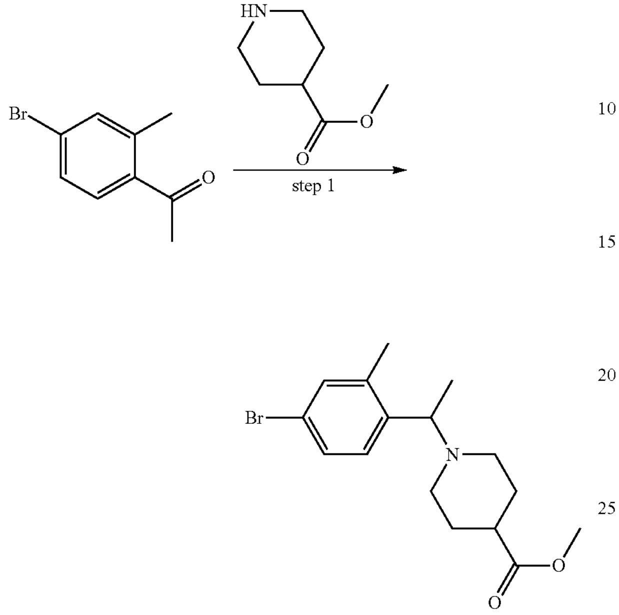

To a stirred solution of $NaCNBH_3$ (3.55 g, 93.87 mmol in methanol 25 mL) was added $ZnCl_2$ (1 M in THF, 23 mL, 23.47 mmol). The mixture was stirred at room temperature for 0.5 h. A solution of 1-(4-bromo-2-methyl-phenyl)ethanone (5.00 g, 23.47 mmol) and methyl piperidine-4-carboxylate (6.72 g, 46.93 mmol) in methanol (25 mL) was added dropwise. The resulting mixture was stirred at 60° C. for 12 h. LCMS showed the reaction was completed. The mixture was concentrated under reduced pressure. The crude product was purified by flash chromatography on silica gel (eluted with PE/EtOAc, 1/1) to afford methyl methyl 1-(1-(4-bromo-2-methylphenyl)ethyl)piperidine-4-carboxylate (5.5 g, 68.9% yield) as a yellow oil. LCMS (ESI, m z): 340[M+H]$^+$.

Synthesis of methyl 1-(1-(4-(1-(tert-butoxycarbonyl)azetidin-3-yl)-2-methylphenyl)ethyl)-piperidine-4-carboxylate

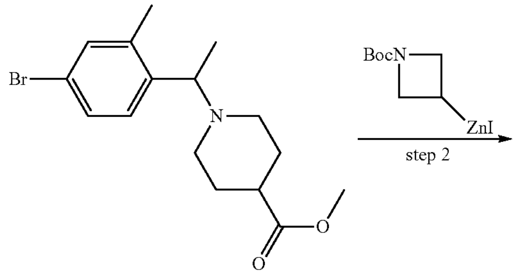

-continued

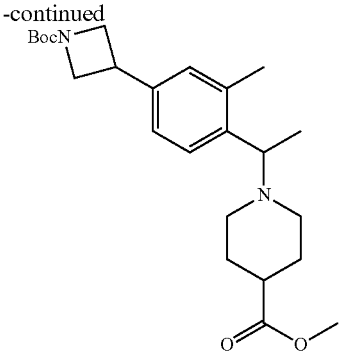

To a stirred solution of tert-butyl 3-iodoazetidine-1-carboxylate (24.6 g, 70.53 mmol, 4.00 equiv.) in DMF (30 mL) was added Zinc powder (5.76 g, 88.2 mmol, 5.00 equiv.). The resulting mixture was stirred at 60° C. for 3 h under $N_2$ atmosphere. Then $Pd_2(dba)_3$ (1.61 g, 1.76 mmol, 0.010 equiv.), tris-(o-tolyl)phosphine (1.07 g, 3.53 mmol 0.020 equiv.) and methyl 1-(1-(4-bromo-2-methylphenyl)ethyl)piperidine-4-carboxylate (6.00 g, 17.6 mmol, 1.00 equiv.) were added. The resulting mixture was stirred at 80° C. overnight. LCMS showed the reaction was completed. The reaction mixture was diluted with saturated aq. $NH_4Cl$ (200 mL) and extracted with EtOAc (3*80 mL). The organic layers were combined and dried over $MgSO_4$ and concentrated. The crude was purified by flash chromatography on silica gel (eluted with PE/EtOAc, 4/1) to afford methyl 1-(1-(4-(1-(tert-butoxycarbonyl)azetidin-3-yl)-2-methylphenyl)ethyl)piperidine-4-carboxylate (1.9 g, 25.9% yield) as a yellow solid. LCMS (ESI, m z): 417[M+H]$^+$.

Synthesis of methyl 1-(1-(4-(azetidin-3-yl)-2-methylphenyl)ethyl)piperidine-4-carboxylate-2,2,2-trifluoroacetaldehyde

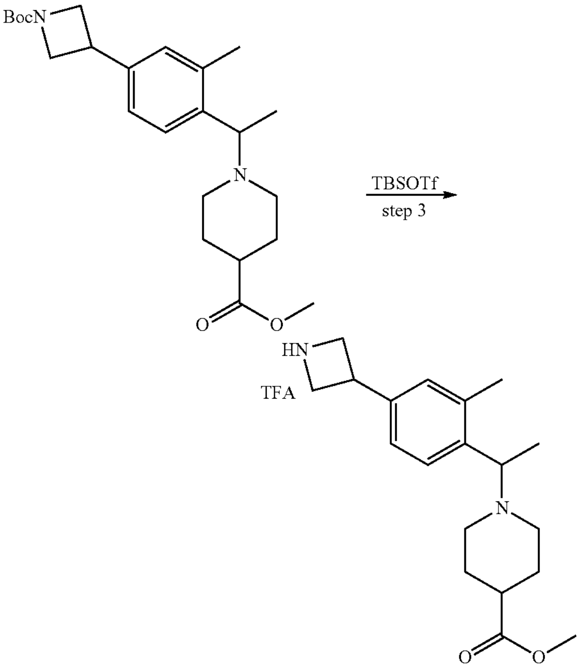

To a stirred solution of methyl 1-(1-(4-(1-(tert-butoxycarbonyl)azetidin-3-yl)-2-methylphenyl)ethyl)piperidine-4-carboxylate (1.9 g, 4.56 mmol) in DCM (10 mL) was added TBSOTF (5 mL, 56.44 mmol). The resulting solution was stirred at room temperature 0.5 h. LCMS showed the reaction was complete. The reaction mixture was concentrated under reduced pressure. The crude product was purified by flash column on C18 (eluted with water/ACN, 5/95) to afford methyl 1-(1-(4-(azetidin-3-yl)-2-methylphenyl)ethyl)piperidine-4-carboxylate-2,2,2-trifluoroacetaldehyde (900 mg, 62.4% yield) as a yellow oil. LCMS (ESI, m z): 317[M+H]$^+$.

Synthesis of methyl 1-(1-(4-(1-(2,6-dichlorophenyl)azetidin-3-yl)-2-methylphenyl)ethyl)-piperidine-4-carboxylate

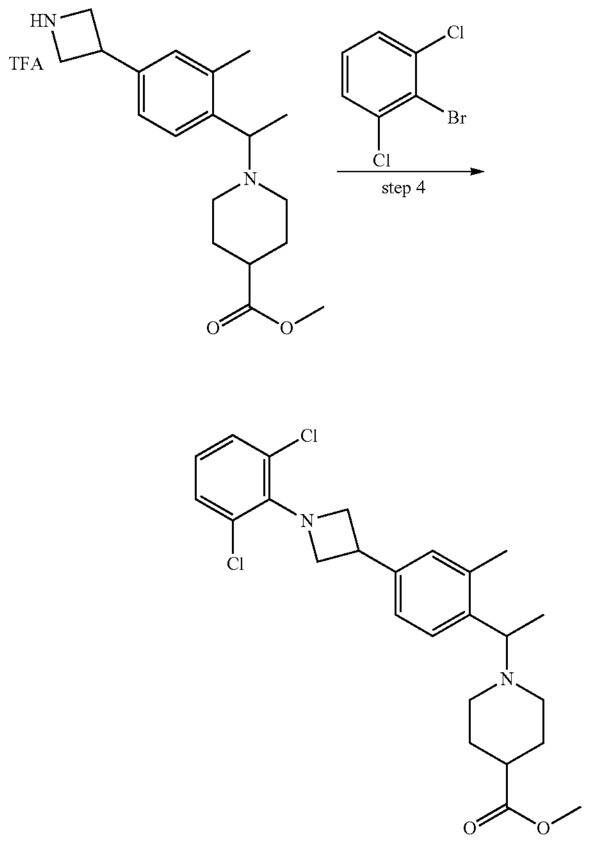

To a stirred solution of methyl 1-(1-(4-(azetidin-3-yl)-2-methylphenyl)ethyl)piperidine-4-carboxylate-2,2,2-trifluoroacetaldehyde (900 mg, 2.84 mmol) in 1,4-dioxane (10 mL) was added 2-bromo-1,3-dichloro-benzene (1.28 g, 5.69 mmol), RuPhos Pd G3 (530 mg, 0.570 mmol), RuPhos (133 mg, 0.280 mmol) and $Cs_2CO_3$ (2.78 g, 8.53 mmol). The resulting solution was stirred at 90° C. overnight. LCMS showed the reaction was completed. The reaction mixture was concentrated and purified by flash column on silica gel (eluted with PE/EA, 1/3) to afford methyl 1-(1-(4-(1-(2,6-dichlorophenyl)azetidin-3-yl)-2-methylphenyl)ethyl)piperidine-4-carboxylate (139 mg, 10.6% yield) as a yellow oil. LCMS (ESI, m z): 461 [M+H]$^+$.

Chiral Separation of methyl 1-(1-(4-(1-(2,6-dichlorophenyl)azetidin-3-yl)-2-methylphenyl)ethyl)-piperidine-4-carboxylate

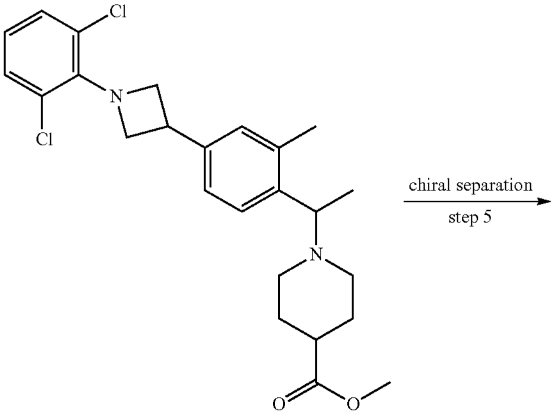

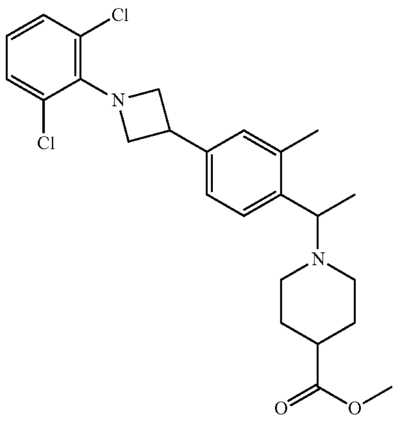

chiral separation 1

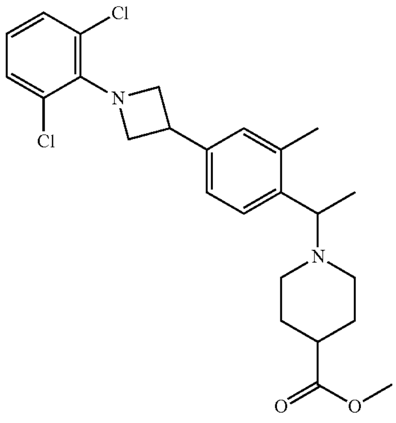

chiral separation 2

The racemate was resolved by chiral HPLC (Column: CHIRALPAK IG-3, 3.0*50 mm, 3 μm; Mobile Phase B: MeOH (1% 2M NH3-MeOH); Flow rate: 2 mL/min; Gradient: isocratic 20% B; Wavelength: 220 nm) to afford 65 mg of the first enantiomer and 50 mg of the second enantiomer.

Synthesis of 1-(1-(4-(1-(2,6-dichlorophenyl)azetidin-3-yl)-2-methylphenyl)ethyl)piperidine-4-carboxylic acid (Enantiomer 1, 16a)

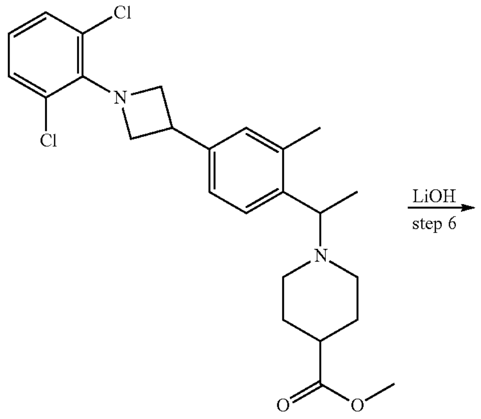

chiral separation 1

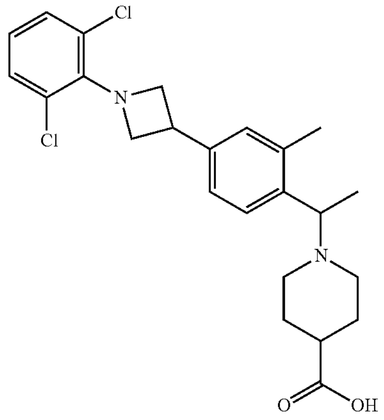

16a
chiral separation 1

A mixture of methyl 1-(1-(4-(1-(2,6-dichlorophenyl)azetidin-3-yl)-2-methylphenyl)ethyl)piperidine-4-carboxylate (enantiomer 1, 65 mg, 0.140 mmol) and LiOH (18 mg, 0.420 mmol) in THF (1 mL) and water (1 mL) was stirred at room temperature for 0.5 h. LCMS showed the reaction was complete. The reaction mixture was acidified to pH 4-5 using acetic acid and then was concentrated. The residue was purified by Prep-HPLC (Column: XBridge Prep OBD C18 Column, 30*150 mm, 5 μm; Mobile Phase A: water (10 mM $NH_4HCO_3$), Mobile Phase B: ACN; Flow rate: 60 mL/min; Gradient: 39% B to 64% B in 8 min; Wavelength: 254/220 nm; RT: 7.08 min) to give 1-(1-(4-(1-(2,6-dichlorophenyl)azetidin-3-yl)-2-methylphenyl)-ethyl)piperidine-4-carboxylic acid (22.8 mg, 35.9% yield) as a white solid.

LCMS (ESI, m/z): 447 $[M+H]^+$. Analytic Conditions: column: HALO C18, 3.0*30 mm, 2.7 μm; mobile phase A: water (0.05% TFA), mobile phase B: acetonitrile (0.05% TFA), flow rate: 1.20 mL/min; gradient: 5% B to 100% B in 1.20 min, hold at 100% for 0.60 min, 100% B to 5% B in 0.03 min; 254 nm; RT: 1.035 min.

$^1H$ NMR (300 MHz, $CD_3OD$) δ 7.52-7.37 (m, 3H), 7.26 (d, J=7.8 Hz, 2H), 6.73 (t, J=7.8 Hz, 1H), 4.89 (t, J=8.1 Hz, 2H), 4.51-4.40 (m, 3H), 3.80-3.73 (m, 1H), 3.65-3.55 (m, 1H), 3.21-3.16 (m, 1H), 2.92-2.84 (m, 2H), 2.45 (s, 3H), 2.39-2.32 (m, 1H), 2.12-1.81 (m, 4H), 1.64 (d, J=6.9 Hz, 3H).

Synthesis of 1-(1-(4-(1-(2,6-dichlorophenyl)azetidin-3-yl)-2-methylphenyl)-ethyl)piperidine-4-carboxylic acid (chiral separation 2, 16b)

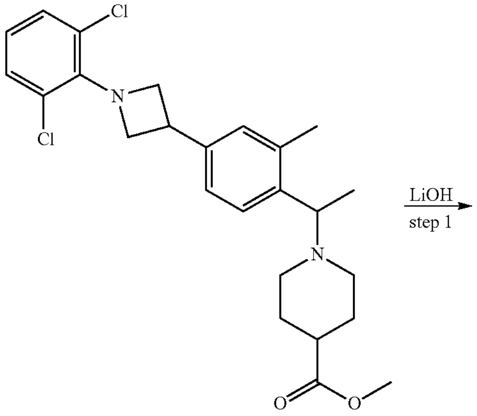

chiral separation 2

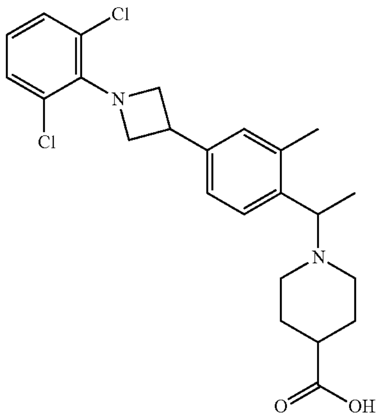

16b
chiral separation 2

A mixture of methyl 1-(1-(4-(1-(2,6-dichlorophenyl)azetidin-3-yl)-2-methylphenyl)ethyl)-piperidine-4-carboxylate (enantiomer 2, 50 mg, 0.110 mmol) and LiOH (14 mg, 0.330 mmol) in THF (1 mL) and water (1 mL) was stirred at room temperature for 0.5 h. LCMS showed the reaction was complete. The reaction mixture was acidified to pH 4-5 using acetic acid and then was concentrated. The residue was purified by Prep-HPLC (Column: XBridge Prep OBD C18 Column, 30*150 mm, 5 μm; Mobile Phase A: water (10 mM $NH_4HCO_3$), Mobile Phase B: ACN; Flow rate: 60 mL/min; Gradient: 39% B to 64% B in 8 min; Wavelength: 254/220 nm; RT: 7.10 min) to give 1-(1-(4-(1-(2,6-dichlorophenyl)azetidin-3-yl)-2-methylphenyl)-ethyl)-piperidine-4-carboxylic acid (25.4 mg, 51.9% yield) as a white solid.

LCMS (ESI, m/z): 447 $[M+H]^+$. Analytic Conditions: column: HALO C18, 3.0*30 mm, 2.7 μm; mobile phase A: water (0.05% TFA), mobile phase B: acetonitrile (0.05% TFA), flow rate: 1.20 mL/min; gradient: 5% B to 100% B in 1.20 min, hold at 100% for 0.60 min, 100% B to 5% B in 0.03 min; 254 nm; RT: 1.033 min.

$^1$H NMR (300 MHz, CD3OD) δ 7.52-7.38 (m, 3H), 7.19 (d, J=7.8 Hz, 2H), 6.72 (t, J=7.8 Hz, 1H), 4.90 (t, J=8.1 Hz, 2H), 4.53-4.41 (m, 3H), 3.80-3.71 (m, 1H), 3.65-3.55 (m, 1H), 3.21-3.16 (m, 1H), 2.94-2.85 (m, 2H), 2.45 (s, 3H), 2.39-2.32 (m, 1H), 2.12-1.85 (m, 4H), 1.64 (d, J=6.9 Hz, 3H).

Example S17. 1-(2-(4-(1-(2,6-dichlorophenyl)azetidin-3-yl)phenyl)propan-2-yl)piperidine-4-carboxylic acid (17)

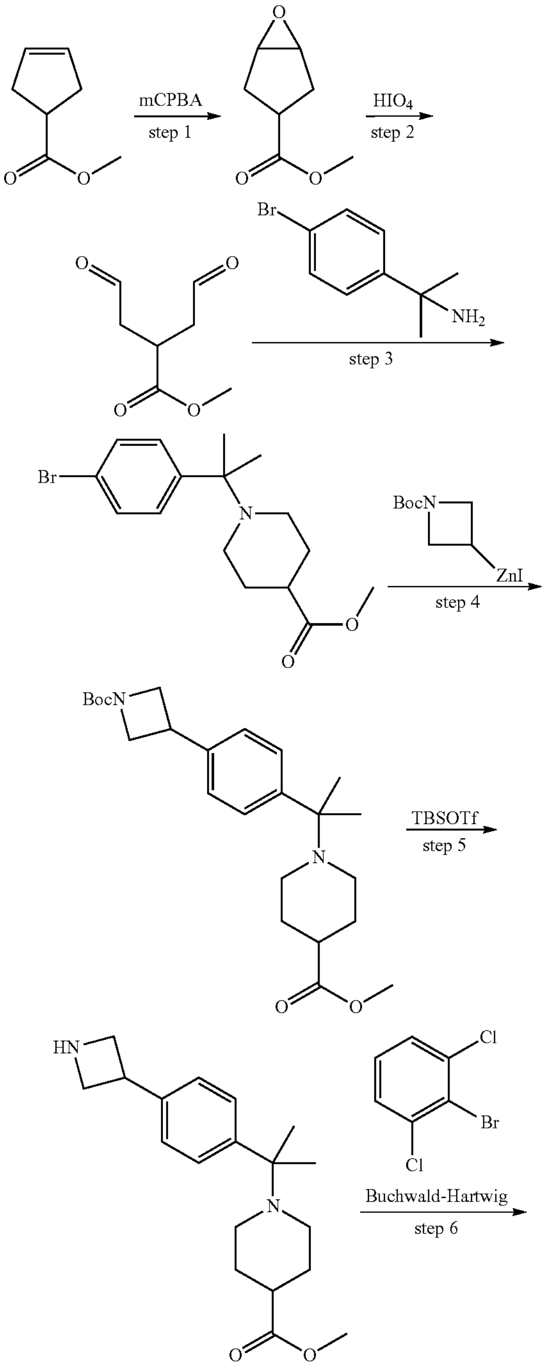

-continued

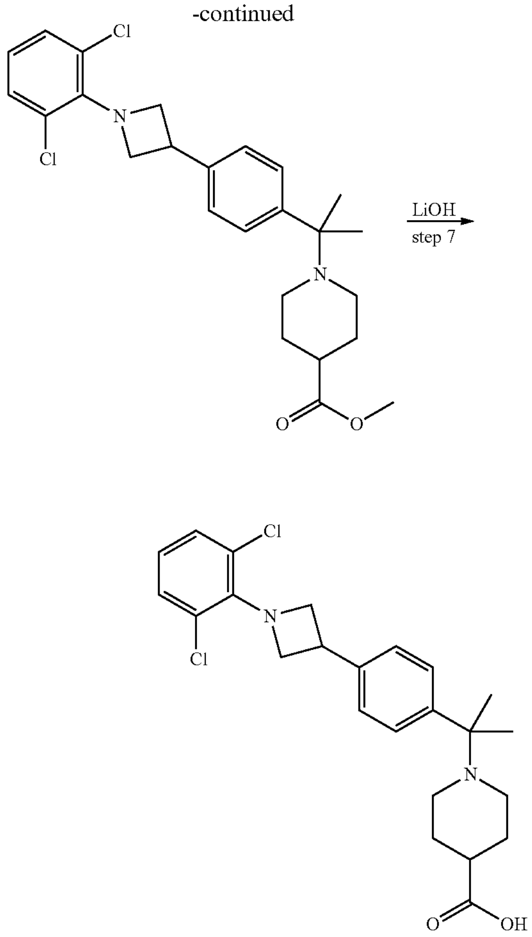

17

Synthesis of methyl 6-oxabicyclo[3.1.0]hexane-3-carboxylate

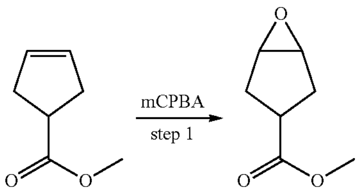

To a stirred solution of methyl cyclopent-3-ene-1-carboxylate (2.00 g, 15.9 mmol, 1.00 equiv.) in DCM (15 mL) was added m-CPBA (3.50 g, 20.3 mmol, 1.30 equiv.). The resulting mixture was stirred at 0° C. for 3 h. GCMS showed the reaction was complete. The resulting reaction was quenched by aqueous $Na_2S_2O_5$ and was filtered, and the filtrate was diluted with DCM (50 mL) and washed with brine, and dried over anhydrous $Na_2SO_4$ and concentrated under vacuum. This resulted in methyl 6-oxabicyclo[3.1.0]hexane-3-carboxylate (2 g, 88.7%) as a light-yellow oil crude, which was used directly in the next step.

Synthesis of methyl 4-oxo-2-(2-oxoethyl)butanoate

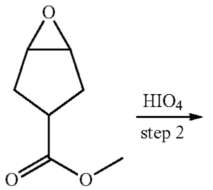

To a stirred solution of methyl 6-oxabicyclo[3.1.0]hexane-3-carboxylate (2 g, 14.07 mmol, 1.00 equiv.) in ethyl acetate (3 mL) was added $HIO_4$ (2.96 g, 15.48 mmol, 1.10 equiv.). The resulting mixture was stirred at 0° C. for 3.5 h. The reaction mixture was filtered. The reaction mixture was poured into EA/$H_2O$, and the organic layer was washed with brine and dried over anhydrous $Na_2SO_4$. This resulted in methyl 4-oxo-2-(2-oxoethyl)butanoate (2 g, 89.9%) as a light-yellow oil crude, which was used directly in the next step.

Synthesis of methyl 1-(2-(4-bromophenyl)propan-2-yl)piperidine-4-carboxylate

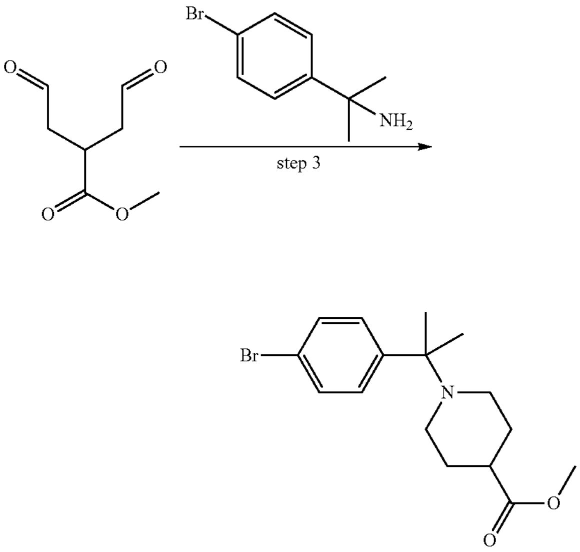

A solution of $ZnCl_2$ (2.0 M in THF, 8.5 mL, 19.0 mmol, 2.00 equiv.) and $NaBH_3CN$ (2.43 g, 37.9 mmol, 4.00 equiv.) in methanol (20 mL) was stirred at room temperature for 10 min. Then methyl 4-oxo-2-(2-oxoethyl)butanoate (1.50 g, 9.48 mmol, 1.00 equiv.) and 2-(4-bromophenyl)propan-2-amine (1.62 g, 7.59 mmol, 0.80 equiv.) were added. The resulting reaction was stirred at 80° C. overnight. LCMS showed that the reaction was complete. The solid was removed by filtration, and the filtrate was concentrated under reduced pressure. The crude product was purified by flash column on C18 (eluted with water/ACN, 20/80) to give methyl 1-(2-(4-bromophenyl)propan-2-yl)piperidine-4-carboxylate (600 mg, 18.6%) as a light-yellow oil. LCMS (ESI, m/z): 340 $[M+H]^+$.

Synthesis of methyl 1-(2-(4-(1-(tert-butoxycarbonyl)azetidin-3-yl)phenyl)propan-2-yl)piperidine-4-carboxylate

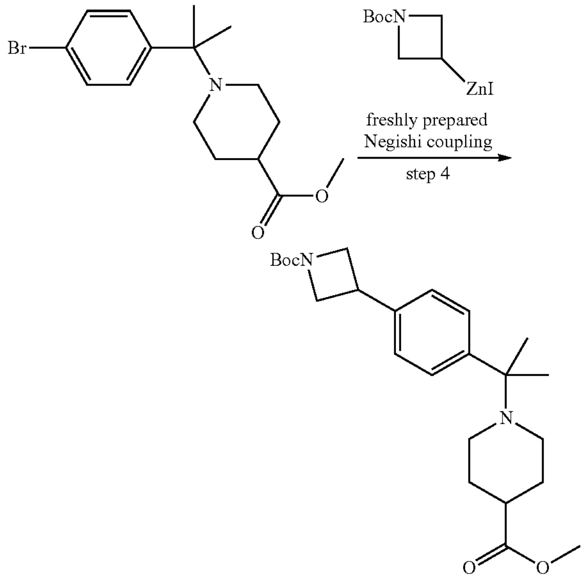

To a stirred solution of tert-butyl 3-iodoazetidine-1-carboxylate (5.29 g, 18.7 mmol, 10.0 equiv.) in DMF (30 mL) was added zinc (1.76 g, 26.99 mmol, 15.0 equiv.). The resulting mixture was stirred at 60° C. for 5 h. Then methyl 1-(2-(4-bromophenyl)propan-2-yl)piperidine-4-carboxylate (600 mg, 1.76 mmol, 1.00 equiv.), $Pd_2(bda)_3$ (323 mg, 0.35 mmol, 0.20 equiv.) and tri(o-tolyl)phosphine (536 mg, 1.76 mmol, 1.00 equiv.) were added. The resulting mixture was stirred at 80° C. overnight. LCMS showed that the reaction was complete. The reaction mixture was diluted with saturated aq. $NH_4Cl$ (60 mL) and extracted with EtOAc (3*40 mL). The organic layers were combined and dried over $MgSO_4$ and concentrated. The crude was purified by flash chromatography on silica gel (eluted with PE/EtOAc, 2/1) to afford methyl 1-(2-(4-(1-(tert-butoxycarbonyl)azetidin-3-yl)phenyl)propan-2-yl)piperidine-4-carboxylate (730 mg, 99.4%) as a light-yellow oil. LCMS (ESI, m/z): 417 $[M+H]^+$.

Synthesis of methyl 1-(2-(4-(azetidin-3-yl)phenyl)propan-2-yl)piperidine-4-carboxylate

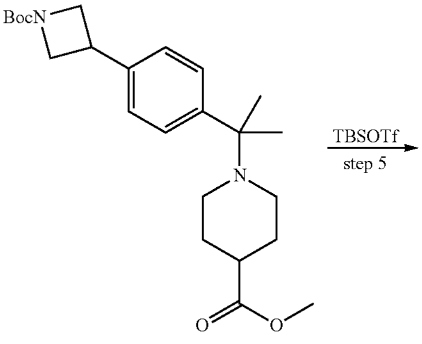

-continued

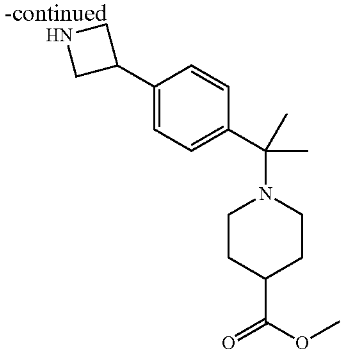

To a stirred solution of methyl 1-(2-(4-(1-(tert-butoxycarbonyl)azetidin-3-yl)phenyl)-propan-2-yl)piperidine-4-carboxylate (730 mg, 1.75 mmol, 1.00 equiv.) in DCM (2 mL) was added TBSOTf (0.62 mL, 3.5 mmol, 2.00 equiv.) dropwise. The resulting mixture was stirred at room temperature for 1 h. LCMS showed the conversion was complete. The reaction mixture was concentrated under reduced pressure. The crude product was purified by flash column on C18 (eluted with water/ACN, 5/95) to afford methyl 1-(2-(4-(azetidin-3-yl)phenyl)propan-2-yl)piperidine-4-carboxylate (550 mg, 99.2%) as a light-yellow oil. LCMS (ESI, m/z): 317 [M+H]+.

Synthesis of methyl 1-(2-(4-(1-(2,6-dichlorophenyl) azetidin-3-yl)phenyl)propan-2-yl)piperidine-4-carboxylate

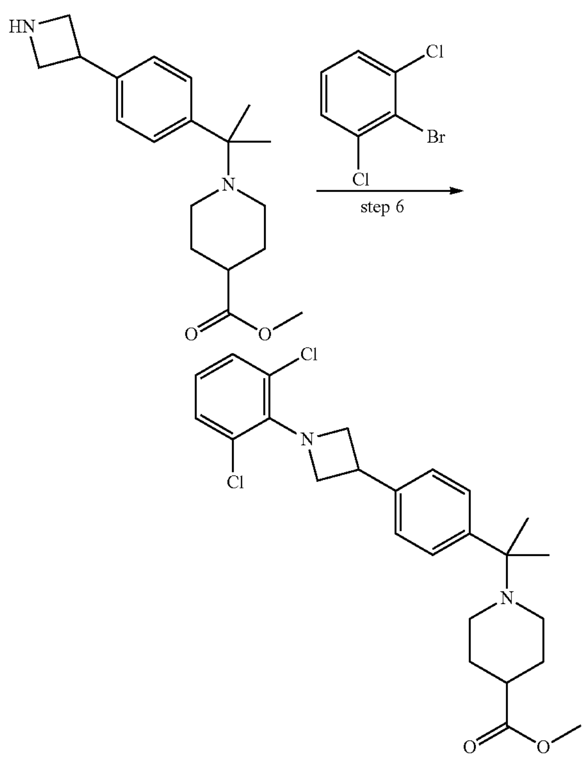

A solution of methyl 1-(2-(4-(azetidin-3-yl)phenyl)propan-2-yl)piperidine-4-carboxylate (550 mg, 1.74 mmol, 1.00 equiv.), 2-bromo-1,3-dichloro-benzene (785 mg, 3.48 mmol, 2.00 equiv.), RuPhos Pd G3 (243 mg, 0.26 mmol, 0.15 equiv.), RuPhos (122 mg, 0.26 mmol, 0.15 equiv.) and $Cs_2CO_3$ (1.69 g, 5.21 mmol, 3.00 equiv.) in 1,4-dioxane (2 mL) was stirred at 90° C. under nitrogen atmosphere overnight. LCMS showed that the reaction was complete. The reaction mixture was concentrated and purified by flash column on silica gel (eluted with PE/EA, 1/1) to afford methyl 1-(2-(4-(1-(2,6-dichlorophenyl)azetidin-3-yl)phenyl)propan-2-yl)piperidine-4-carboxylate (170 mg, 21.2%) as a light-yellow oil. LCMS (ESI, m/z): 461 [M+H]+.

Synthesis of 1-(2-(4-(1-(2,6-dichlorophenyl)azetidin-3-yl)phenyl)propan-2-yl)piperidine-4-carboxylic acid (17)

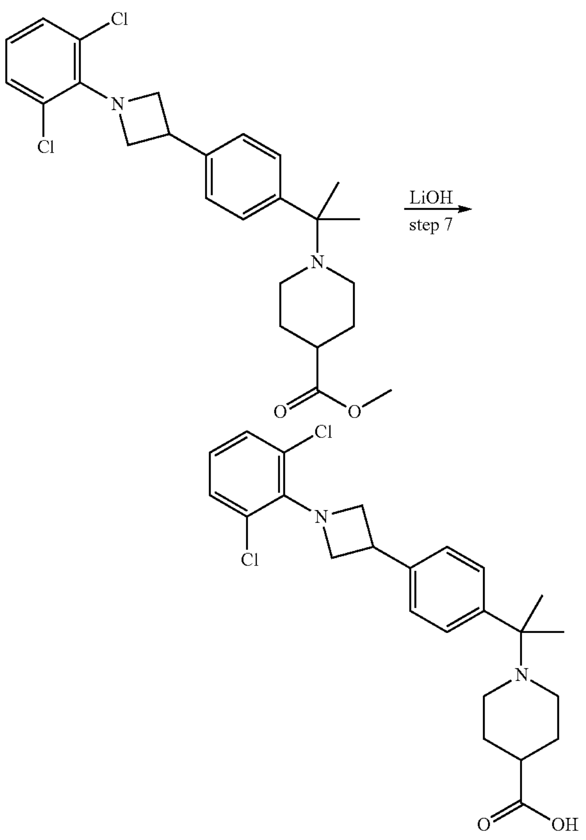

17

A mixture of methyl 1-(2-(4-(1-(2,6-dichlorophenyl)azetidin-3-yl)phenyl)propan-2-yl)piperidine-4-carboxylate (175 mg, 0.38 mmol, 1.00 equiv.) and LiOH (27 mg, 1.14 mmol, 3.00 equiv.) in THE (2 mL) and water (2 mL) was stirred at room temperature overnight. LCMS showed that the reaction was complete. The reaction mixture was acidified to pH 4-5 using acetic acid and then was concentrated. The residue was purified by Prep-HPLC (Column: XBridge Prep C18 OBD Column, 30*100 mm, 5 μm; Mobile Phase A: water (10 mM $NH_4HCO_3$), Mobile Phase B: ACN; Flow rate: 60 mL/min; Gradient: 25% B to 45% B in 10 min, hold at 45% B for 2 min; Wavelength: 254/220 nm; RT: 10.38 min) to give 1-(2-(4-(1-(2,6-dichlorophenyl)azetidin-3-yl) phenyl)propan-2-yl)piperidine-4-carboxylic acid (108.5 mg, 62.5%) as a white solid.

LCMS (ESI, m/z): 447 $[M+H]^+$. Analytic Conditions: column: YMC Meteoric Core C18 BIO, 2.1*30 mm, 2.7 μm; mobile phase A: water (5 mM $NH_4HCO_3$), mobile phase B: acetonitrile, flow rate: 1.20 mL/min; gradient: 10% B to 95% B in 1.20 min, hold at 95% for 0.58 min, 95% B to 10% B in 0.05 min; 254 nm; RT: 0.803 min.

$^1H$ NMR (400 MHz, DMSO-$d_6$) δ 12.0 (br, 1H), 7.47 (d, J=8.4 Hz, 2H), 7.35 (d, J=8.4 Hz, 2H), 7.24 (d, J=8.0 Hz, 2H), 6.75 (t, J=8.0 Hz, 1H), 4.83 (t, J=8.0 Hz, 2H), 4.37-4.34 (m, 2H), 3.79-3.71 (m, 1H), 2.72-2.69 (m, 2H), 2.18-2.04 (m, 3H), 1.77-1.73 (m, 2H), 1.55-1.45 (m, 2H), 1.27 (s, 6H).

Example S18. 1-((5-(1-(2,6-dichlorophenyl)azetidin-3-yl)pyridin-2-yl)methyl)piperidine-4-carboxylic acid (18)

General Route:

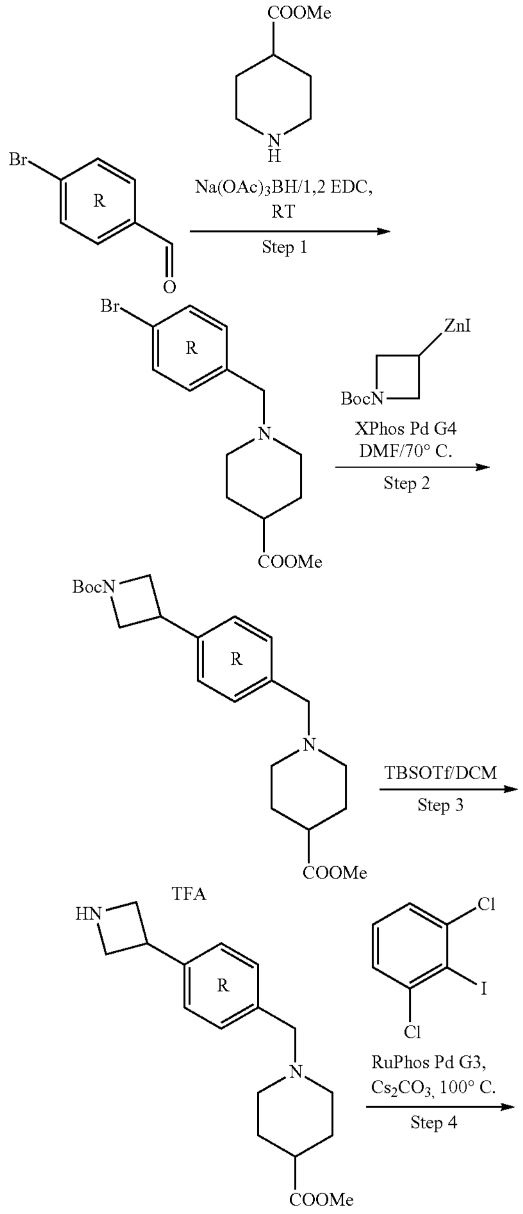

-continued

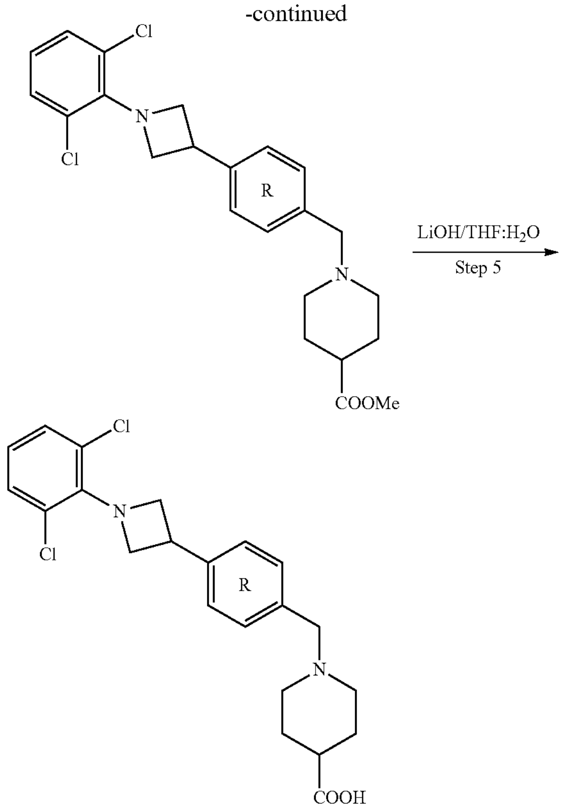

Synthesis of methyl 1-((5-bromopyridin-2-yl)methyl)piperidine-4-carboxylate (18-a)

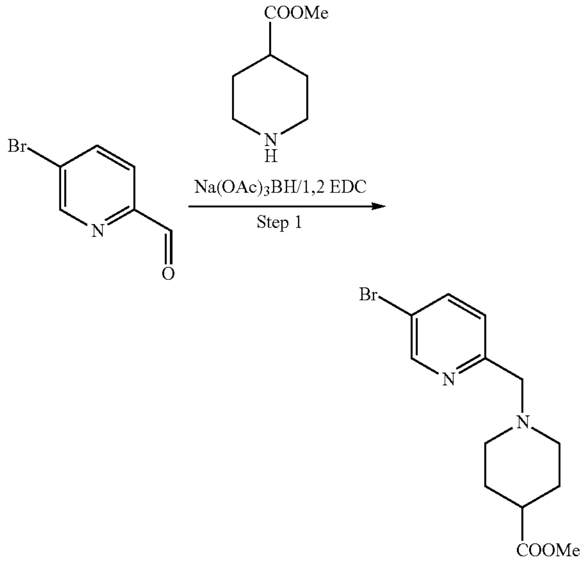

18-a

To a solution of 5-bromopicolinaldehyde (3 g, 16.13 mmol) in anhydrous 1,2 DCE (10 mL) was added methyl piperidine-4-carboxylate (2.309 g, 16.13 mmol) and the reaction mixture was allowed to stir at ambient temperature. After 10 min sodium triacetoxyborohydride (3.42 g, 16.13 mmol) was added and the reaction mixture was allowed to stir at room temperature. After 4 h, TLC analysis indicated complete conversion of the starting material. The reaction mixture was diluted with dichloromethane, washed with water, dried over sodium sulphate, and filtered. The filtrate was concentrated under reduced pressure and the resulting residue was purified by flash column chromatography on silica gel eluting with 0-100% ethyl acetate in petroleum ether to afford methyl 1-((5-bromopyridin-2-yl)methyl)piperidine-4-carboxylate (1.8 g, 35.6% yield) as colorless oil. LCMS (ESI, m/z): 313.0, 315.0 [M, M+2H]$^+$.

Synthesis of methyl 1-((5-(1-(tert-butoxycarbonyl) azetidin-3-yl)pyridin-2-yl)methyl)-piperidine-4-carboxylate (18-b)

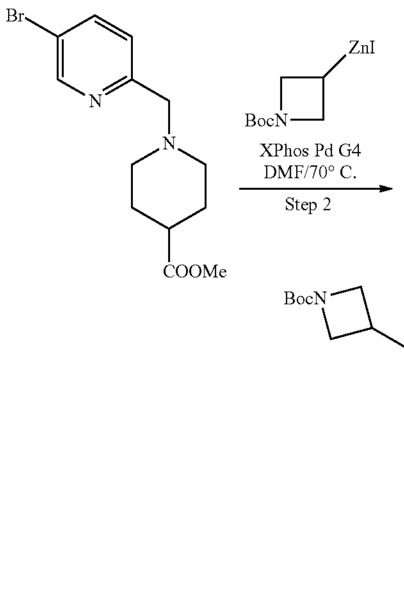

18-b

To a stirred solution of activated zinc (1.044 g, 15.96 mmol) in anhydrous DMF (20 mL) was added 1,2-dibromoethane (0.028 mL, 0.319 mmol) and heated to 60° C. After 30 min, the mixture was cooled to ambient temperature and added chlorotrimethylsilane (0.1 mL, 0.782 mmol). The reaction mixture was then allowed to stir at ambient temperature for another 30 min. Then a solution of tert-butyl 3-iodoazetidine-1-carboxylate (4.52 g, 15.96 mmol) in anhydrous DMF (15 mL) was added to the mixture and heated to 60° C. for 2 h to get (1-(tert-butoxycarbonyl) azetidin-3-yl)zinc(II) iodide.

In another two neck round bottom flask, to a solution of methyl 1-((5-bromopyridin-2-yl)methyl)piperidine-4-carboxylate (1.0 g, 3.19 mmol) in anhydrous DMF (20 mL) was added XPhos Pd G4 (0.549 g, 0.639 mmol). Freshly prepared (1-(tert-butoxycarbonyl)azetidin-3-yl)zinc(II) iodide was then added to the mixture via cannula under nitrogen atmosphere. The reaction mixture was then heated to 80° C. under nitrogen atmosphere and the progress of the reaction was monitored by LCMS. After 16 h, LCMS analysis indicated complete conversion of the starting material. The reaction mixture was cooled to ambient temperature and filtered through a pad of celite and washed with ethyl acetate. The filtrate was then transferred to a separating funnel and washed with cold water (300 mL) followed by brine solution (200 mL), dried over anhydrous sodium sulphate and concentrated under reduced pressure. The resulting residue was purified by flash column chromatography on silica gel (230-400 mesh) eluting with 0-5% methanol in dichloromethane to afford methyl 1-((5-(1-(tert-butoxycarbonyl)azetidin-3-yl)pyridin-2-yl)methyl)piperidine-4-carboxylate (1.4 g, 78% yield) as a yellow oil. LCMS (ESI, m/z): 390.2 [M+H]$^+$.

Synthesis of methyl 1-((5-(azetidin-3-yl)pyridin-2-yl)methyl)piperidine-4-carboxylate (18-c)

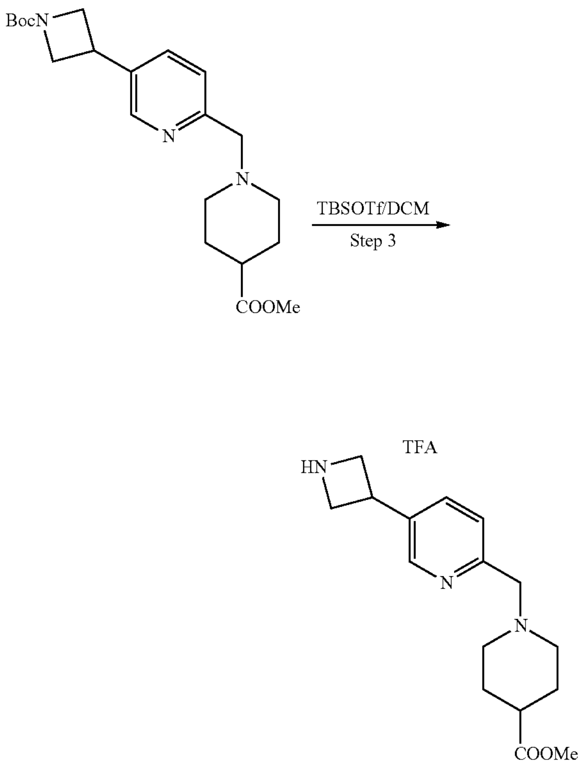

18-c

To a stirred solution of methyl 1-((5-(1-(tert-butoxycarbonyl)azetidin-3-yl)pyridin-2-yl)methyl)piperidine-4-carboxylate (1.3 g, 3.34 mmol) in anhydrous dichloromethane (40 mL) was added tert-butyldimethylsilyltrifluoromethanesulfonate (2.302 mL, 10.01 mmol) and the resulting mixture was stirred at room temperature. After 1 h, LCMS analysis indicated complete conversion of the starting material. The reaction mixture was concentrated under vacuum and the residue was purified by column chromatography on C18 silica (Mobile Phase A: water (0.05% TFA), Mobile Phase B: ACN; Flow rate: 120 mL/min; Gradient: 10% B to 20% B in 5 min; 254/210 nm). The required fractions were collected and concentrated under reduced pressure to afford methyl 1-((5-(azetidin-3-yl)pyridin-2-yl)methyl)piperidine-4-carboxylate. TFA (850 mg, 61.2% yield) as a brown gum. LCMS (ESI, m/z): 290.2 [M+H]$^+$.

Synthesis of methyl 1-((5-(1-(2,6-dichlorophenyl)azetidin-3-yl)pyridin-2-yl)methyl)-piperidine-4-carboxylate (18-d)

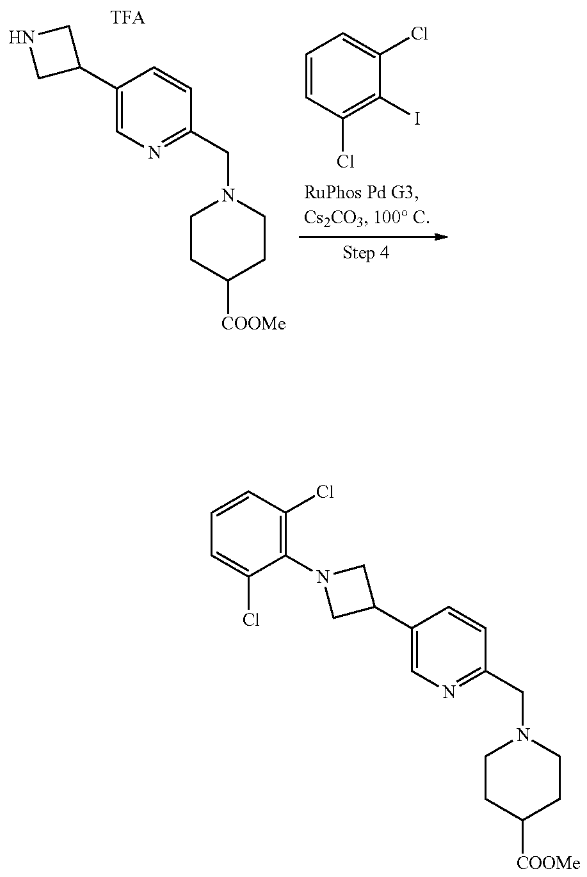

18-d

To a solution of methyl 1-((5-(azetidin-3-yl)pyridin-2-yl)methyl)piperidine-4-carboxylate (400 mg, 1.382 mmol), 1,3-dichloro-2-iodobenzene (453 mg, 1.659 mmol) in anhydrous 1,4 dioxane (20 mL) was added cesium carbonate (1.3 g, 4.15 mmol). The reaction mixture was then degassed with vacuum and back filled with nitrogen. RuPhos Pd G3 (116 mg, 0.138 mmol) was added to the mixture and heated to 100° C. After 16 h, TLC analysis indicated complete conversion of the starting material. The reaction mixture was cooled to ambient temperature and filtered through a pad of celite and washed with dichloromethane. The filtrate was then concentrated under reduced pressure and the resulting residue was purified by flash column chromatography on silica gel (230-400 mesh) eluting with 0-70% ethyl acetate in petroleum ether to afford methyl 1-((5-(1-(2,6-dichlorophenyl)azetidin-3-yl)pyridin-2-yl)methyl)piperidine-4-carboxylate (140 mg, 21.22% yield) as a yellow oil. LCMS (ESI, m/z): 434.0 $[M+H]^+$.

Synthesis of 1-((5-(1-(2,6-dichlorophenyl)azetidin-3-yl)pyridin-2-yl)methyl)piperidine-4-carboxylic acid (18)

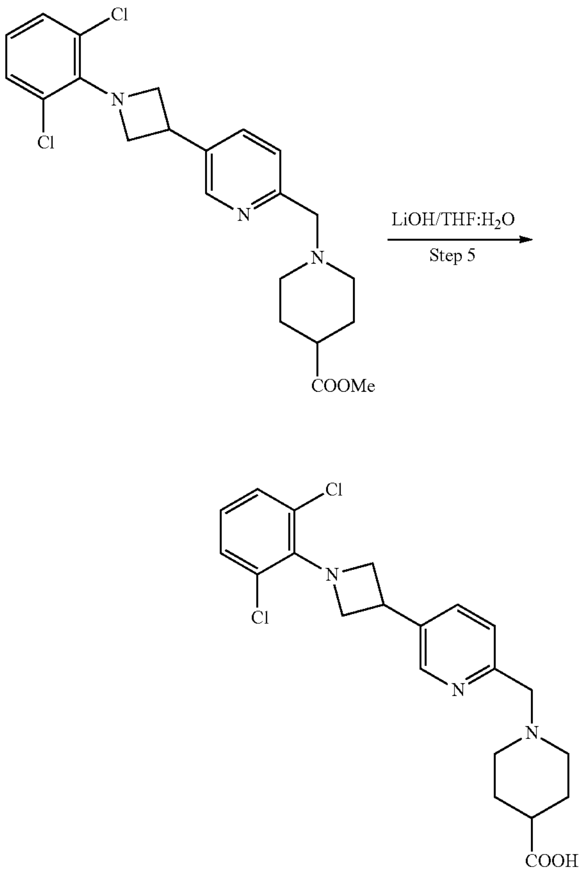

18

To a stirred solution of methyl 1-((5-(1-(2,6-dichlorophenyl)azetidin-3-yl)pyridin-2-yl)methyl)piperidine-4-carboxylate (140 mg, 0.322 mmol) in tetrahydrofuran (5 mL) and $H_2O$ (0.5 mL) was added lithium hydroxide (23.16 mg, 0.967 mmol) and the resulting mixture was allowed stirred at ambient temperature. After 2 h, TLC analysis indicated compete conversion of the starting material. The volatiles were removed under reduced pressure and the aqueous layer was the acidified using acetic acid by maintaining the pH=5. The resulting mixture was then purified by column chromatography on C18 silica (Mobile Phase A: water (10 mM ammonium formate), Mobile Phase B: ACN; Flow rate: 100 mL/min; Gradient: 45% B to 50% B in 4 min; 254/210 nm). The required fractions were collected and lyophilized to afford 1-((5-(1-(2,6-dichlorophenyl)azetidin-3-yl)pyridin-2-yl)methyl)piperidine-4-carboxylic acid, formic acid salt (45 mg, 28.1% yield) as a white solid. LCMS (ESI, m/z): 420.2 $[M+H]^+$; $^1H$ NMR (400 MHz, DMSO-$d_6$): δ 8.49-8.48 (m, 1H), 7.92-7.90 (m, 1H), 7.43 (d, J=8.00 Hz, 1H), 7.24 (d, J=8.00 Hz, 2H), 6.76 (t, J=8.00 Hz, 1H), 4.85 (t, J=8.00 Hz, 2H), 4.37 (t, J=6.80 Hz, 2H), 3.83-3.78 (m, 1H), 3.55 (s, 2H), 2.78-2.55 (m, 2H), 2.34-2.33 (m, 1H), 2.46-2.47 (m, 1H), 2.20-2.18 (m, 2H), 1.75 (m, 2H), 1.60-1.52 (m, 2H).

Example S19. 1-(4-(1-(2,6-dichlorophenyl)azetidin-3-yl)-2,5-dimethylbenzyl)piperidine-4-carboxylic acid (19)

Synthesis of methyl 1-(4-bromo-2,5-dimethylbenzyl)piperidine-4-carboxylate (19-a)

19-a

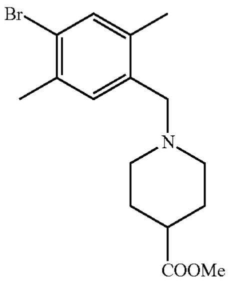

The title compound was synthesized by following the general procedure for the synthesis of 18-a. LCMS (ESI, m/z): 342.0 $[M+2H]^+$.

Synthesis of methyl 1-(4-(1-(tert-butoxycarbonyl)azetidin-3-yl)-2,5-dimethylbenzyl)piperidine-4-carboxylate (19-b)

19-b

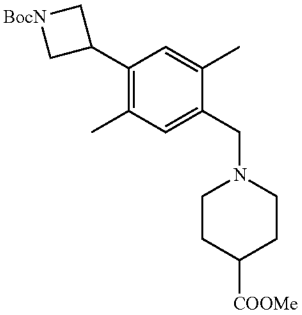

The title compound was synthesized by following the general procedure for the synthesis of 18-b. LCMS (ESI, m/z): 417.3 $[M+H]^+$.

Synthesis of methyl 1-(4-(azetidin-3-yl)-2,5-dimethylbenzyl)piperidine-4-carboxylate (19-c)

19-c

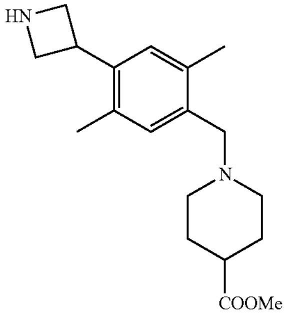

The title compound was synthesized by following the general procedure for the synthesis of 18-c. LCMS (ESI, m/z): 317.2 $[M+H]^+$.

Synthesis of methyl 1-(4-(1-(2,6-dichlorophenyl)azetidin-3-yl)-2,5-dimethylbenzyl)piperidine-4-carboxylate (19-d)

19-d

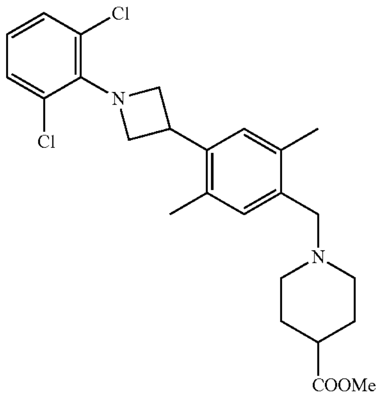

The title compound was synthesized by following the general procedure for the synthesis of 18-d. LCMS (ESI, m/z): 461.2 $[M+H]^+$.

Synthesis of 1-(4-(1-(2,6-dichlorophenyl)azetidin-3-yl)-2,5-dimethylbenzyl)piperidine-4-carboxylic acid (19)

19

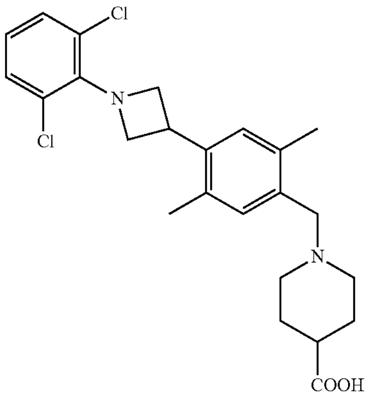

The title compound was synthesized by following the general procedure for the synthesis of 18. LCMS (ESI, m/z): 447.0 $[M+H]^+$; $^1H$ NMR (DMSO-$d_6$, 400 MHz): δ 7.23 (d, J=8.0 Hz, 2H), 7.18 (s, 1H), 6.98 (s, 1H), 6.74 (t, J=7.6 Hz, 1H), 4.84 (t, J=8.4 Hz, 2H), 4.33 (t, J=7.6 Hz, 2H), 3.92-3.88 (m, 1H), 3.31 (s, 3H), 2.72-2.69 (m, 2H), 2.28 (s, 3H), 2.18 (s, 3H), 2.16-2.14 (m, 1H), 1.98-1.93 (m, 2H), 1.76-1.73 (m, 2H), 1.49-1.47 (m, 2H).

Example S20. 1-(4-(1-(2,6-dichlorophenyl)azetidin-3-yl)-3,5-dimethylbenzyl)piperidine-4-carboxylic acid (20)

Synthesis of methyl 1-(4-bromo-3,5-dimethylbenzyl)piperidine-4-carboxylate (20-a)

20-a

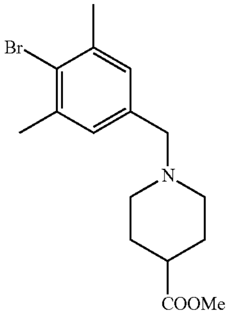

The title compound was synthesized by following the general procedure for the synthesis of 18-a. LCMS (ESI, m/z): 340.0, 342.0 $[M+2H]^+$.

Synthesis of methyl 1-(4-(1-(tert-butoxycarbonyl)azetidin-3-yl)-3,5-dimethylbenzyl)piperidine-4-carboxylate (20-b)

20-b

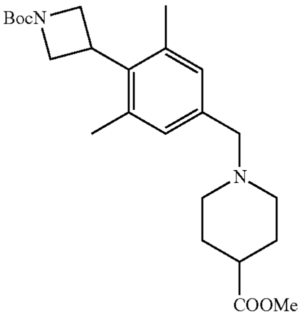

The title compound was synthesized by following the general procedure for the synthesis of 18-b. LCMS (ESI, m/z): 417.0 $[M+H]^+$.

Synthesis of methyl 1-(4-(azetidin-3-yl)-3,5-dimethylbenzyl)piperidine-4-carboxylate (20-c)

20-c

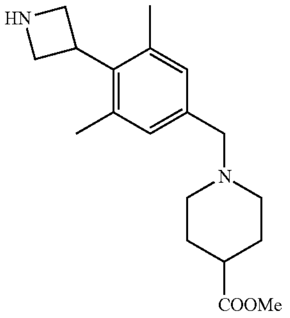

The title compound was synthesized by following the general procedure for the synthesis of 18-c. LCMS (ESI, m/z): 317.2 $[M+H]^+$.

Synthesis of methyl 1-(4-(1-(2,6-dichlorophenyl)azetidin-3-yl)-3,5-dimethylbenzyl)piperidine-4-carboxylate (20-d)

20-d

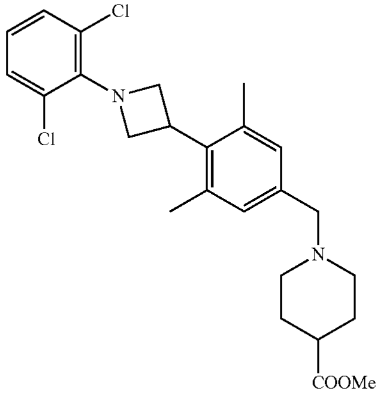

The title compound was synthesized by following the general procedure for the synthesis of 18-d. LCMS (ESI, m/z): 461.2 $[M+H]^+$.

Synthesis of 1-(4-(1-(2,6-dichlorophenyl)azetidin-3-yl)-3,5-dimethylbenzyl)piperidine-4-carboxylic acid (20)

20

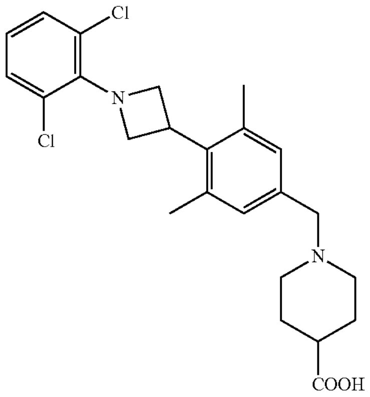

The title compound was synthesized by following the general procedure for the synthesis of 18. LCMS (ESI, m/z): 447.0 [M+H]; $^{1}$H NMR (DMSO-$d_6$, 400 MHz): δ 12.12 (bs, 1H), 7.22 (d, J=8.0 Hz, 2H), 6.87 (s, 2H), 6.73 (t, J=8.0 Hz, 1H), 4.96 (t, J=8.4 Hz, 2H), 4.44-4.40 (m, 2H), 4.19-4.15 (m, 1H), 3.33 (s, 2H), 2.72-2.67 (m, 2H), 2.26 (s, 6H), 2.19-2.13 (m, 1H), 1.95-1.90 (m, 2H), 1.76-1.74 (m, 2H), 1.56-1.50 (m, 2H).

Example S21. 1-((6-(1-(2,6-dichlorophenyl)azetidin-3-yl)pyridin-3-yl)methyl)piperidine-4-carboxylic acid (21)

Synthesis of methyl 1-((6-bromopyridin-3-yl)methyl)piperidine-4-carboxylate (21-a)

21-a

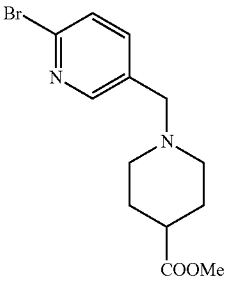

The title compound was synthesized by following the general procedure for the synthesis of 18-a. LCMS (ESI, m/z): 313.1, 315.0 [M, M+2H]$^+$.

Synthesis of methyl 1-((6-(1-(tert-butoxycarbonyl)azetidin-3-yl)pyridin-3-yl)methyl)piperidine-4-carboxylate (21-b)

21-b

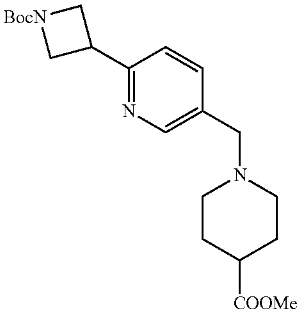

The title compound was synthesized by following the general procedure for the synthesis of 18-b. LCMS (ESI, m/z): 390.2 [M+H]$^+$.

Synthesis of methyl 1-((6-(azetidin-3-yl)pyridin-3-yl)methyl)piperidine-4-carboxylate (21-c)

21-c

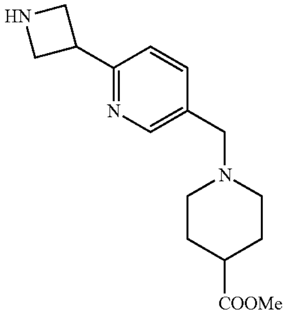

The title compound was synthesized by following the general procedure for the synthesis of 18-c. LCMS (ESI, m/z): 290.2 [M+H]$^+$.

Synthesis of methyl 1-((6-(1-(2,6-dichlorophenyl)azetidin-3-yl)pyridin-3-yl)methyl)piperidine-4-carboxylate (21-d)

21-d

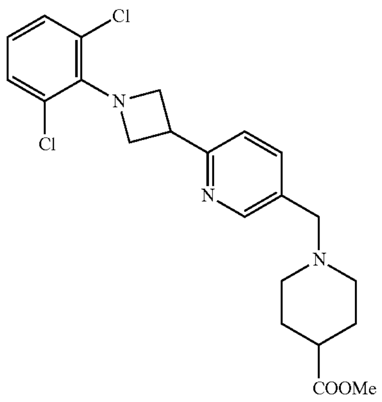

The title compound was synthesized by following the general procedure for the synthesis of 18-d. LCMS (ESI, m/z): 434.1 $[M+H]^+$.

Synthesis of 1-((6-(1-(2,6-dichlorophenyl)azetidin-3-yl)pyridin-3-yl)methyl)piperidine-4-carboxylic acid (21)

21

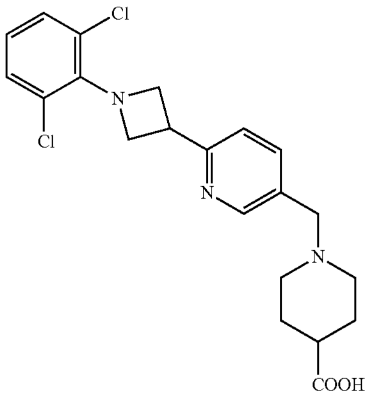

The title compound was synthesized by following the general procedure for the synthesis of 18. LCMS (ESI, m/z): 420.2 [M+H]; $^1H$ NMR (400 MHz, DMSO-$d_6$): δ 8.56 (m, 1H), 7.88-7.85 (m, 1H), 7.54 (d, J=8.00 Hz, 1H), 7.18 (d, J=8.00 Hz, 2H), 6.71 (t, J=8.00 Hz, 2H), 4.91 (m, 2H), 4.63-4.59 (m, 2H), 3.96 (m, 1H), 3.87 (s, 2H), 3.17-3.08 (m, 2H), 2.50 (m, 2H), 2.35 (m, 1H), 2.00-1.96 (m, 2H), 1.82-1.80 (m, 2H).

Example S22. 1-(4-(1-(2,6-dichlorophenyl)azetidin-3-yl)-3-fluorobenzyl)piperidine-4-carboxylic acid (22)

Synthesis of methyl 1-(4-bromo-3-fluorobenzyl)piperidine-4-carboxylate (22-a)

22-a

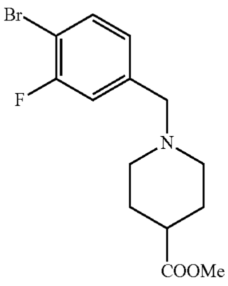

The title compound was synthesized by following the general procedure for the synthesis of 18-a. LCMS (ESI, m/z): 331.2 $[M+2H]^+$.

Synthesis of methyl 1-(4-(1-(tert-butoxycarbonyl)azetidin-3-yl)-3-fluorobenzyl)piperidine-4-carboxylate (22-b)

22-b

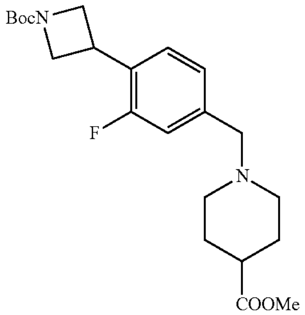

The title compound was synthesized by following the general procedure for the synthesis of 18-b. Pale yellow oil; LCMS (ESI, m/z): 407.1 $[M+H]^+$.

Synthesis of methyl 1-(4-(azetidin-3-yl)-3-fluorobenzyl)piperidine-4-carboxylate (22-c)

22-c

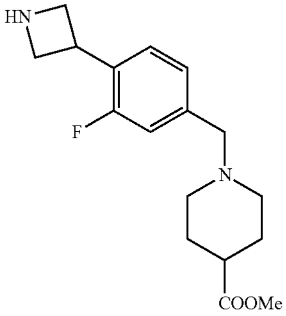

The title compound was synthesized by following the general procedure for the synthesis of 18-c. LCMS (ESI, m/z): 307.1 $[M+H]^+$.

Synthesis of methyl 1-(4-(1-(2,6-dichlorophenyl) azetidin-3-yl)-3-fluorobenzyl)piperidine-4-carboxylate (22-d)

22-d

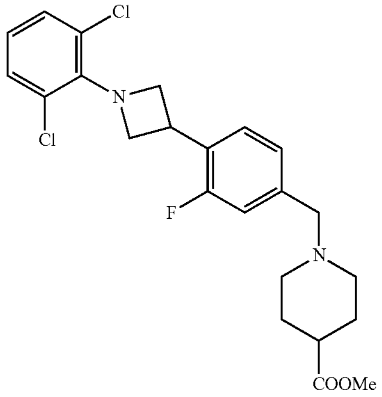

The title compound was synthesized by following the general procedure for the synthesis of 18-d. LCMS (ESI, m/z): 451.0 $[M+H]^+$.

Synthesis of 1-(4-(1-(2,6-dichlorophenyl)azetidin-3-yl)-3-fluorobenzyl)piperidine-4-carboxylic acid (22)

22

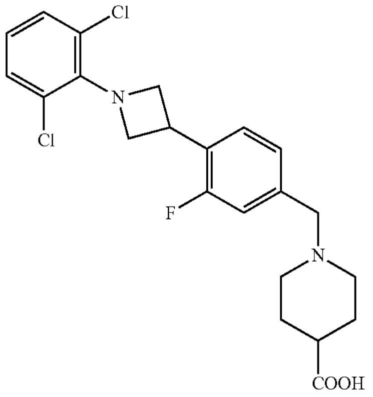

The title compound was synthesized by following the general procedure for the synthesis of 18. LCMS (ESI, m/z): 437.0 $[M+H]^+$; $^1$H NMR (400 MHz, DMSO-$d_6$): (400 MHz, DMSO-$d_6$) δ 7.49 (t, J=8 Hz, 1H), 7.23 (d, J=8 Hz, 2H), 7.15-7.07 (m, 2H), 6.75 (t, J=8 Hz, 1H), 4.85 (t, J=8 Hz, 2H), 4.40 (t, J=7.2 Hz, 2H), 3.98-3.94 (m, 1H), 3.44 (s, 2H), 2.74-2.71 (m, 2H), 2.21-2.15 (m, 1H), 2.01-1.98 (m, 2H), 1.80-1.70 (m, 2H), 1.59-1.49 (m, 2H).

Example S23. 1-(4-(1-(2,6-dichlorophenyl)azetidin-3-yl)-2-fluorobenzyl)piperidine-4-carboxylic acid (23)

Synthesis of methyl 1-(4-bromo-2-fluorobenzyl) piperidine-4-carboxylate (23-a)

23-a

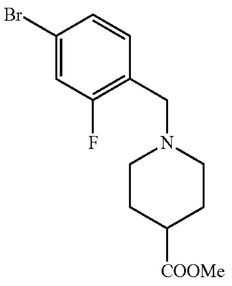

The title compound was synthesized by following the general procedure for the synthesis of 18-a. LCMS (ESI, m/z): 331.2 $[M+2H]^+$.

Synthesis of methyl 1-(4-(1-(tert-butoxycarbonyl) azetidin-3-yl)-2-fluorobenzyl)piperidine-4-carboxylate (23-b)

23-b

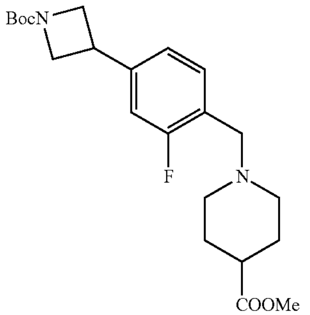

The title compound was synthesized by following the general procedure for the synthesis of 18-b. Pale yellow liquid; LCMS (ESI, m/z): 407.1 $[M+H]^+$.

Synthesis of methyl 1-(4-(azetidin-3-yl)-2-fluorobenzyl)piperidine-4-carboxylate (23-c)

23-c

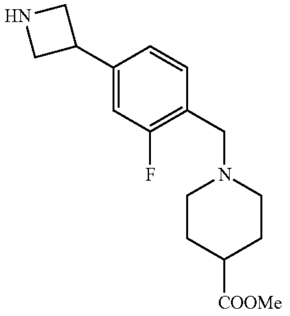

The title compound was synthesized by following the general procedure for the synthesis of 18-c. LCMS (ESI, m/z): 307.1 [M+H]+.

Synthesis of methyl 1-(4-(1-(2,6-dichlorophenyl) azetidin-3-yl)-2-fluorobenzyl)piperidine-4-carboxylate (23-d)

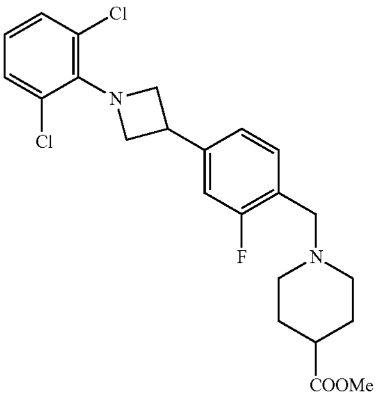

23-d

The title compound was synthesized by following the general procedure for the synthesis of 18-d. LCMS (ESI, m/z): 451.0 [M+H]+.

Synthesis of 1-(4-(1-(2,6-dichlorophenyl)azetidin-3-yl)-2-fluorobenzyl)piperidine-4-carboxylic acid (23)

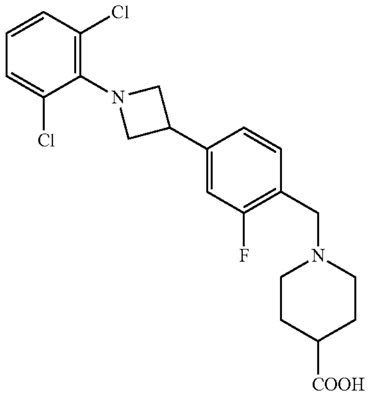

23

The title compound was synthesized by following the general procedure for the synthesis of 18. LCMS (ESI, m/z): 437.0 [M+H]+; $^1H$ NMR (400 MHz, DMSO-$d_6$): δ 7.53-7.49 (m, 1H), 7.40-7.48 (m, 2H), 7.21 (d, J=8.00 Hz, 2H), 6.75 (t, J=8.00 Hz, 1H), 4.93-4.91 (m, 2H), 4.45-4.41 (m, 2H), 4.15 (s, 2H), 3.79-3.83 (m, 2H), 2.86 (m, 2H), 2.45 (m, 2H), 2.05-2.09 (m, 2H), 1.87-1.90 (m, 2H).

Example S24. 1-(4-(3-(2,6-dichlorophenyl)azetidin-1-yl)benzyl)piperidine-4-carboxylic acid (24)

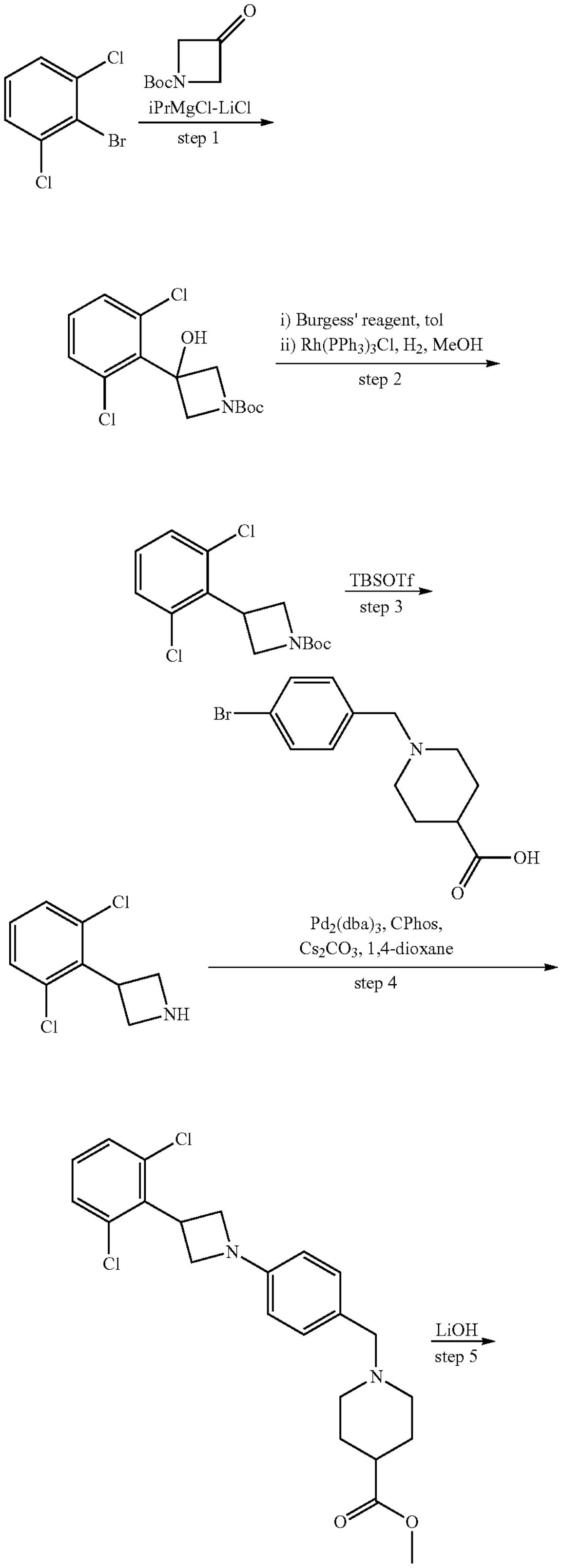

-continued

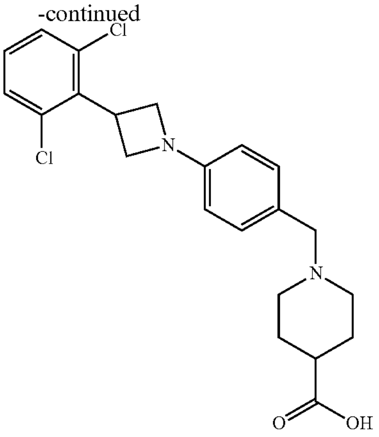

24

Synthesis of tert-butyl 3-(2,6-dichlorophenyl)-3-hydroxyazetidine-1-carboxylate

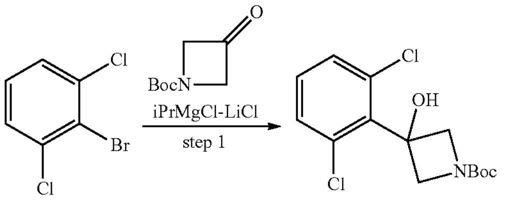 [SMILES: "iPrMgCl-LiCl" ; Clc1cccc(Cl)c1Br ; CC(C)(C)OC(=O)N1CC(=O)C1 ; CC(C)(C)OC(=O)N1CC(O)(c2c(Cl)cccc2Cl)C1]

To a solution of 2-bromo-1,3-dichloro-benzene (3.0 g, 13.28 mmol, 1.00 equiv.) in dry THE (20 mL) was added iPrMgCl—LiCl (1.3M in THF, 20.4 mL, 26.56 mmol, 2.00 equiv.) at −78° C. under nitrogen atmosphere. The resulting mixture was stirred at −78° C. for 3 h. Then a solution of tert-butyl 3-oxoazetidine-1-carboxylate (4.5 g, 26.56 mmol, 2.00 equiv.) in dry THE (5.0 mL) was added. The reaction was warmed to room temperature slowly and stirred at room temperature for further 12 h. The reaction was quenched with aq. $NH_4Cl$ (20 mL) and extracted with ether (2*25 mL). The combined organic layers were washed with water (10 mL) and brine (10 mL), and dried over anhydrous $Na_2SO_4$ and concentrated under vacuum. The residue was purified by flash column chromatography on C18 silica (eluted with water (5 mM $NH_4HCO_3$)/ACN, 80/20) to give tert-butyl 3-(2,6-dichlorophenyl)-3-hydroxyazetidine-1-carboxylate (2.0 g, 47%) as a yellow solid. LCMS (ESI, m/z): 318 $[M+H]^+$.

Synthesis of tert-butyl 3-(2,6-dichlorophenyl)azetidine-1-carboxylate

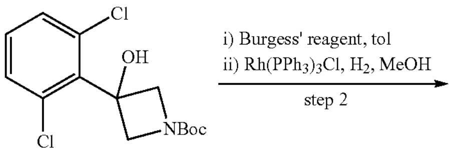

-continued

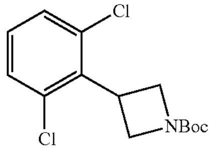

To a stirred solution of tert-butyl 3-(2,6-dichlorophenyl)-3-hydroxy-azetidine-1-carboxylate (2.0 g, 6.290 mmol, 1.00 equiv.) in toluene (10 mL) was added Burgess' reagent (2.2 g, 9.430 mmol, 1.50 equiv.). The reaction was stirred at 110° C. for 12 h. LCMS showed the starting material was consumed completely. The reaction mixture was concentrated under reduced pressure. The residue was dissolved in methanol (20 mL), and $Rh(PPh_3)_3Cl$ (1.1 g, 1.250 mmol, 2.00 equiv.) was added. The resulting mixture was stirred at 50° C. under hydrogen atmosphere for 12 h. LCMS showed the reaction was completed. The mixture was filtered and the filtration was concentrated under reduced pressure. The residue was purified by flash column chromatography on C18 silica (eluted with water (5 mM $NH_4HCO_3$/ACN, 30/70) to give tert-butyl 3-(2,6-dichlorophenyl) azetidine-1-carboxylate (560 mg, 30%) as a yellow solid. LCMS (ESI, m/z): 302 $[M+H]^+$.

Synthesis of 3-(2,6-dichlorophenyl)azetidine

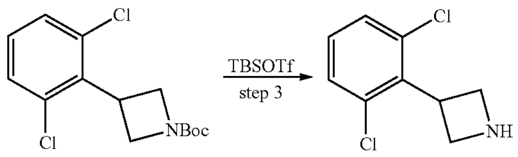 [SMILES: "TBSOTf" ; CC(C)(C)OC(=O)N1CC(c2c(Cl)cccc2Cl)C1 ; Clc1cccc(Cl)c1C1CNC1]

To a stirred solution of tert-butyl 3-(2,6-dichlorophenyl) azetidine-1-carboxylate (300 mg, 0.990 mmol, 1.00 equiv.) in DCM (5.0 mL) was added TBSOTf (0.3 mL, 1.99 mmol, 2.00 equiv.). The reaction was stirred at room temperature for 1 h. LCMS showed the reaction was completed. The reaction mixture was concentrated under reduced pressure. The crude 3-(2,6-dichlorophenyl)azetidine was used in the next step directly without further purification. LCMS (ESI, m/z): 202 $[M+H]^+$.

Synthesis of methyl 1-(4-(3-(2,6-dichlorophenyl) azetidin-1-yl)benzyl)piperidine-4-carboxylate

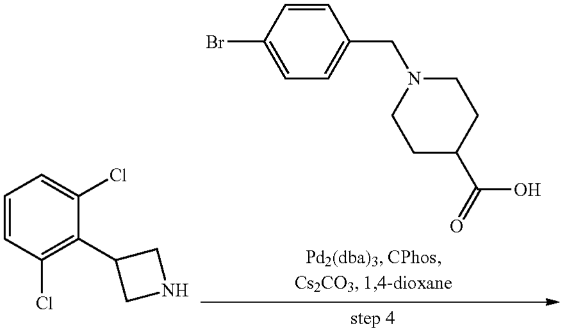

-continued

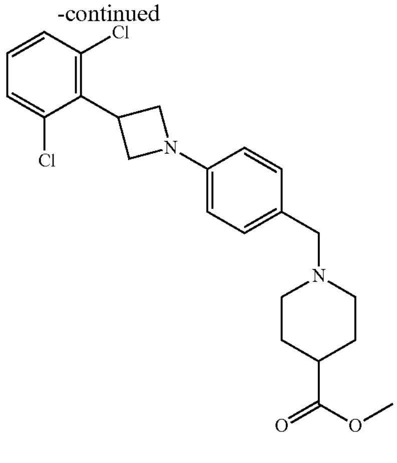

-continued

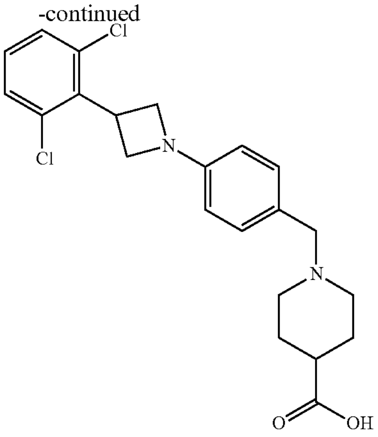

24

To a stirred solution of 3-(2,6-dichlorophenyl) azetidine (150 mg, 0.740 mmol, 1.00 equiv.) in 1,4-dioxane (5.0 mL) were added 1-(4-bromobenzyl)piperidine-4-carboxylic acid (278 mg, 0.890 mmol, 1.20 equiv.), CPhos (22 mg, 0.150 mmol, 0.20 equiv.), $Pd_2(dba)_3$ (67 mg, 0.070 mmol, 0.10 equiv.) and $Cs_2CO_3$ (725 mg, 2.230 mmol, 3.00 equiv.). The resulting mixture was stirred at 100° C. under nitrogen atmosphere for 12 h. LCMS showed the reaction was completed. The reaction mixture was filtered and the filtration was concentrated under reduced pressure. The residue was purified by flash column chromatography on C18 silica (eluted with water (5 mM $NH_4HCO_3$/ACN, 10/90) to give methyl 1-(4-(3-(2,6-dichlorophenyl)azetidin-1-yl)benzyl)-piperidine-4-carboxylate (230 mg, 71%) as a yellow solid. LCMS (ESI, m/z): 433 $[M+H]^+$.

Synthesis of 1-(4-(3-(2,6-dichlorophenyl)azetidin-1-yl)benzyl)piperidine-4-carboxylic acid (24)

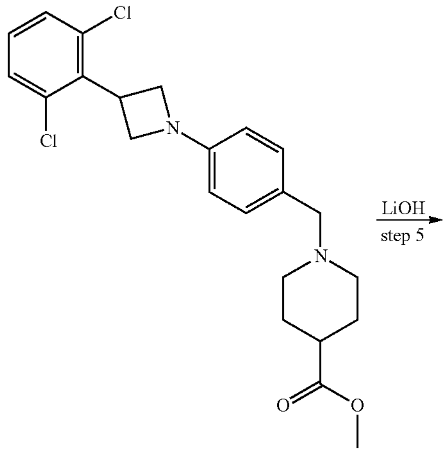

To a solution of methyl 1-(4-(3-(2,6-dichlorophenyl)azetidin-1-yl)benzyl)-piperidine-4-carboxylate (220 mg, 0.510 mmol, 1.00 equiv.) in THE (2.0 mL) and water (2.0 mL) was added $LiOH \cdot H_2O$ (42 mg, 1.02 mmol, 2.00 equiv.). The reaction was stirred at room temperature for 12 h. LCMS showed the reaction was completed. The reaction was acidified to pH 5-6 by adding acetic acid dropwise, and concentrated under reduced pressure. The residue was purified by prep-HPLC (Column: YMC-Actus Triart C18 ExRS, 30*150 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 15% B to 45% B in 8 min, 254/220 nm; RT: 7.82 min) to afford 1-(4-(3-(2,6-dichlorophenyl)azetidin-1-yl)benzyl)piperidine-4-carboxylic acid (54.6 mg, 25%) as an off-white solid.

$^1$H NMR (400 MHz, DMSO-$d_6$) δ 7.45 (d, J=8.0 Hz, 2H), 7.29 (t, J=8.0 Hz, 1H), 7.08 (d, J=8.4 Hz, 2H), 6.47 (d, J=8.4 Hz, 2H), 4.59-4.50 (m, 1H), 4.42 (t, J=7.6 Hz, 2H), 3.98 (t, J=7.6 Hz, 2H), 3.31 (s, 2H), 2.73-2.69 (m, 2H), 2.18-2.10 (m, 1H), 1.94-1.87 (m, 2H), 1.77-1.72 (m, 2H), 1.58-1.45 (m, 2H).

LCMS (ESI, m z): 419 $[M+H]^+$. Analytic Conditions: L-column3 C18, 3.0*30 mm, 2.0 μm; Mobile Phase A: water (5 mM $NH_4HCO_3$), Mobile Phase B: ACN; Flow rate: 1.50 mL/min; Gradient: 10% B to 60% B in 1.85 min, 60% B to 95% B in 0.45 min, hold at 95% B for 0.5 min, 95% B to 10% B in 0.03 min; 254 nm; RT: 1.587 min.

Example S25. (R)-1-(4-(3-(2,6-dichlorophenyl)azetidin-1-yl)benzyl)pyrrolidine-3-carboxylic acid

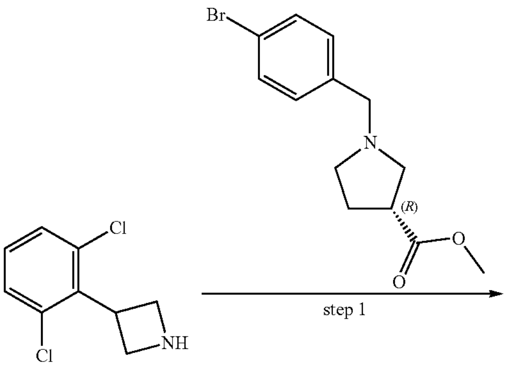

-continued

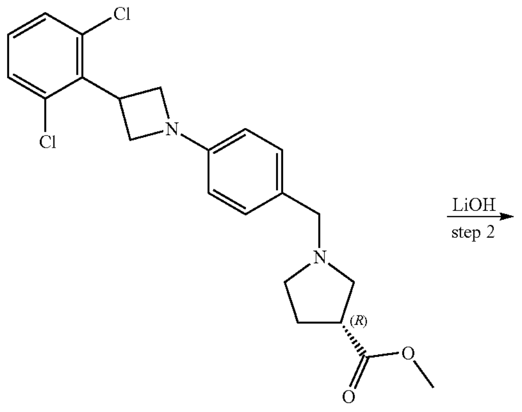

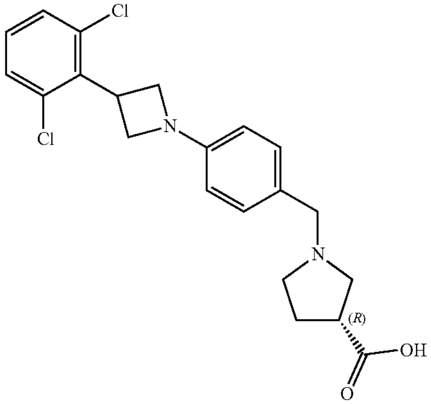

25

Synthesis of methyl (R)-1-(4-(3-(2,6-dichlorophenyl)azetidin-1-yl)benzyl)pyrrolidine-3-carboxylate

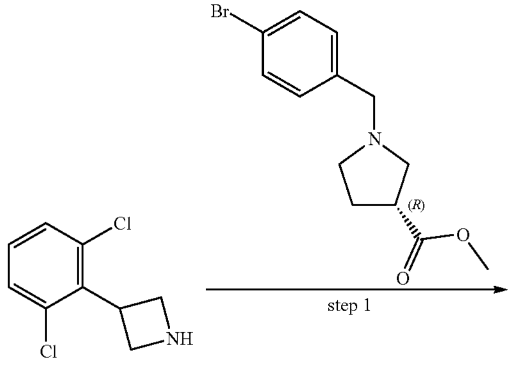

-continued

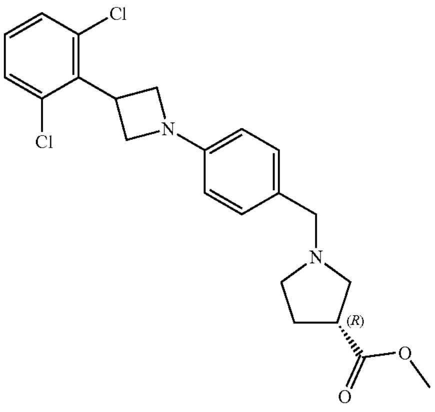

To a stirred solution of 3-(2,6-dichlorophenyl)azetidine (50 mg, 0.250 mmol, 1.00 equiv.) in tBuOH (5 mL) were added methyl (R)-1-(4-bromobenzyl)pyrrolidine-3-carboxylate (148 mg, 0.490 mmol, 2.00 equiv.), BrettPhos Pd G3 (23 mg, 0.020 mmol, 0.10 equiv.) and $K_2CO_3$ (171 mg, 1.24 mmol, 5.00 equiv.). The resulting mixture was stirred at 80° C. for 3 h. LCMS showed the reaction was completed. The reaction mixture was concentrated and purified by flash column on silica gel (eluted with PE/EA, 1/1) to afford methyl (R)-1-(4-(3-(2,6-dichlorophenyl)azetidin-1-yl)benzyl)pyrrolidine-3-carboxylate (31 mg, 29% yield) as an off white solid. LCMS (ESI, m z): 419 $[M+H]^+$.

Synthesis of (R)-1-(4-(3-(2,6-dichlorophenyl)azetidin-1-yl)benzyl)pyrrolidine-3-carboxylic acid (25)

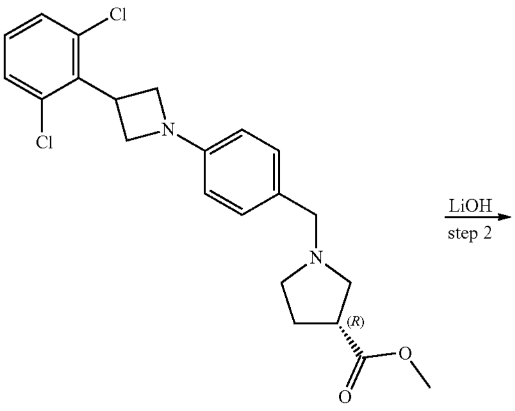

-continued

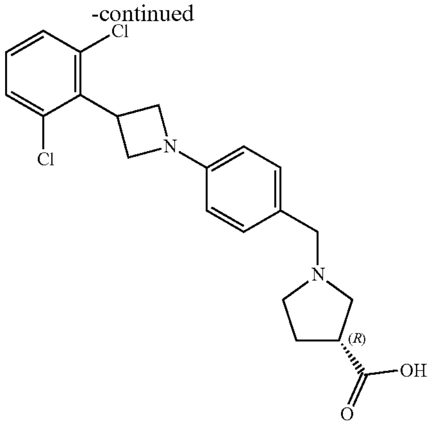

25

To a stirred solution of methyl (R)-1-(4-(3-(2,6-dichlorophenyl)azetidin-1-yl)benzyl)pyrrolidine-3-carboxylate (31 mg, 0.070 mmol, 1.00 equiv.) in THE (3 mL) and water (0.6 mL) were added LiOH·$H_2O$ (9 mg, 0.220 mmol, 3.00 equiv.). The resulting mixture was stirred at room temperature for 3 h. LCMS showed that the reaction was complete. The reaction mixture was acidified to pH 4-5 using acetic acid and then was concentrated. The residue was purified by Prep-HPLC (Column: XBridge Prep C18 OBD Column, 30*100 mm, 5 μm; Mobile Phase A: water (5 mM $NH_4HCO_3$), Mobile Phase B: ACN; Flow rate: 60 mL/min; Gradient: 47% B to 67% B in 7 min; Wavelength: 254/220 nm; RT: 6.53 min) to afford (R)-1-(4-(3-(2,6-dichlorophenyl)azetidin-1-yl)benzyl)pyrrolidine-3-carboxylic acid (7.6 mg, 25% yield) as an off white solid.

$^1$H NMR (400 MHz, DMSO-$d_6$) δ 7.46 (d, J=8.0 Hz, 2H), 7.30 (t, J=8.0 Hz, 1H), 7.10 (d, J=8.0 Hz, 2H), 6.47 (d, J=8.0 Hz, 2H), 4.60-4.52 (m, 1H), 4.42 (t, J=7.6 Hz, 2H), 3.99 (t, J=7.8 Hz, 2H), 3.43 (d, J=2.8 Hz, 2H), 2.92-2.84 (m, 1H), 2.70-2.63 (m, 2H), 2.50-2.35 (m, 2H), 1.94-1.89 (m, 2H).

LCMS (ESI, m/z): 405 $[M+H]^+$. Analytic Conditions: column: HALO C18 3.0*30 mm, 2.7 mm; Mobile Phase A: Water (0.05% TFA), Mobile Phase B: Acetonitrile (0.05% TFA); flow rate: 1.50 mL/min; gradient: 5% B to 60% B in 2.10 min, 60% B to 100% B in 0.30 min, hold at 100% for 0.40 min, 100% B to 5% B in 0.05 min; 254 nm; RT: 1.704 min.

Example S26. 1-(4-(3-(2,6-dichlorophenyl)azetidin-1-yl)benzyl)azetidine-3-carboxylic acid (26)

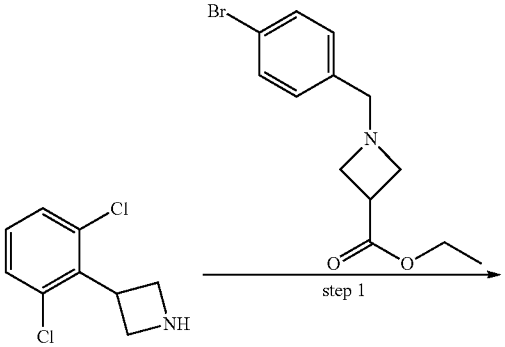

-continued

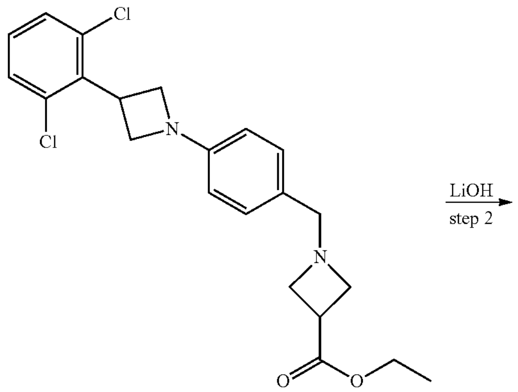

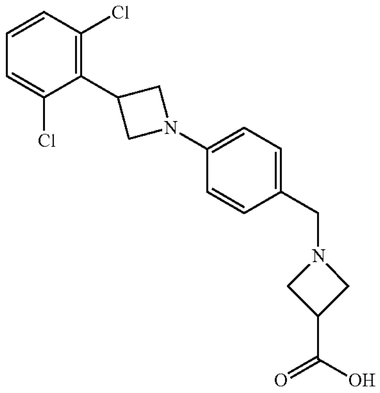

26

Synthesis of ethyl 1-(4-(3-(2,6-dichlorophenyl)azetidin-1-yl)benzyl)azetidine-3-carboxylate

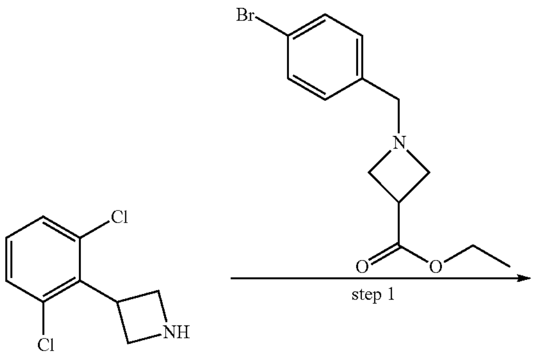

-continued

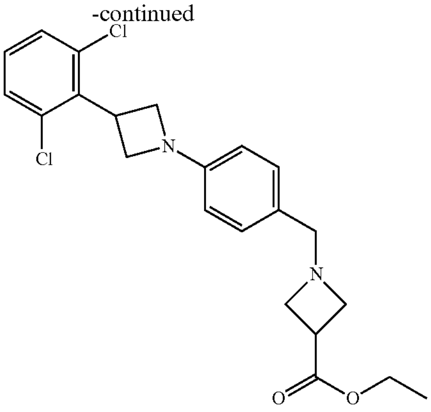

To a stirred solution of ethyl 1-(4-bromobenzyl)azetidine-3-carboxylate (120 mg, 0.400 mmol, 1.00 equiv.) and 3-(2,6-dichlorophenyl)azetidine (81 mg, 0.400 mmol, 1.00 equiv.) in tBuOH (4 mL) were added BrettPhos Pd G3 (36 mg, 0.040 mmol, 0.10 equiv.) and $K_2CO_3$ (166 mg, 1.210 mmol, 3.00 equiv.). The resulting mixture was stirred at 80° C. for 3 h. LCMS showed the reaction was completed. The reaction mixture was concentrated and purified by flash column on silica gel (eluted with PE/EA, 1/1) to afford ethyl 1-(4-(3-(2,6-dichlorophenyl)azetidin-1-yl)benzyl)azetidine-3-carboxylate (60 mg, 35% yield) as an off-white solid. LCMS (ESI, m/z): 405[M+H]$^+$.

Synthesis of 1-(4-(3-(2,6-dichlorophenyl)azetidin-1-yl)benzyl)azetidine-3-carboxylic acid (26)

To a stirred solution of ethyl 1-(4-(3-(2,6-dichlorophenyl)azetidin-1-yl)benzyl)azetidine-3-carboxylate (60 mg, 0.140 mmol, 1.00 equiv.) in THE (2 mL) and water (0.2 mL) was added $LiOH \cdot H_2O$ (18 mg, 0.430 mmol, 3.00 equiv.). The resulting mixture was stirred at room temperature for 2 h. LCMS showed that the reaction was complete. The reaction mixture was acidified to pH 4-5 using acetic acid and then was concentrated. The residue was purified by Prep-HPLC (Column: XBridge Prep C18 OBD Column, 30*100 mm, 5 μm; Mobile Phase A: water (5 mM $NH_4HCO_3$), Mobile Phase B: ACN; Flow rate: 60 mL/min; Gradient: 28% B to 45% B in 8 min; Wavelength: 254/220 nm; RT: 7.93 min) to give 1-(4-(3-(2,6-dichlorophenyl)azetidin-1-yl)benzyl)azetidine-3-carboxylic acid (20.5 mg, 36% yield) as an off-white solid.

$^1$H NMR (300 MHz, $CD_3OD$) δ 7.40 (d, J=8.1 Hz, 2H), 7.28 (d, J=8.1 Hz, 2H), 7.23 (t, J=7.8 Hz, 1H), 6.60 (d, J=7.8 Hz, 2H), 4.75-4.66 (m, 1H), 4.50 (t, J=8.1 Hz, 2H), 4.23-4.14 (m, 4H), 4.07-4.04 (m, 4H), 3.44-3.35 (m, 1H).

LCMS (ESI, m/z): 391 [M+H]$^+$. Analytic Conditions: column: HALO C18 Column 3.0*30 mm, 2.0 mm; Mobile Phase A: water (0.05% TFA), Mobile Phase B: acetonitrile (0.05% TFA); flow rate: 1.20 mL/min; gradient: 5% B to 60% B in 1.80 min, 60% B to 100% B in 0.15 min, hold at 100% for 0.70 min, 100% B to 5% B in 0.15 min; 254 nm; RT: 1.483 min.

Example S27. 1-(4-(3-(2,6-difluorophenyl)azetidin-1-yl)benzyl)piperidine-4-carboxylic acid (27)

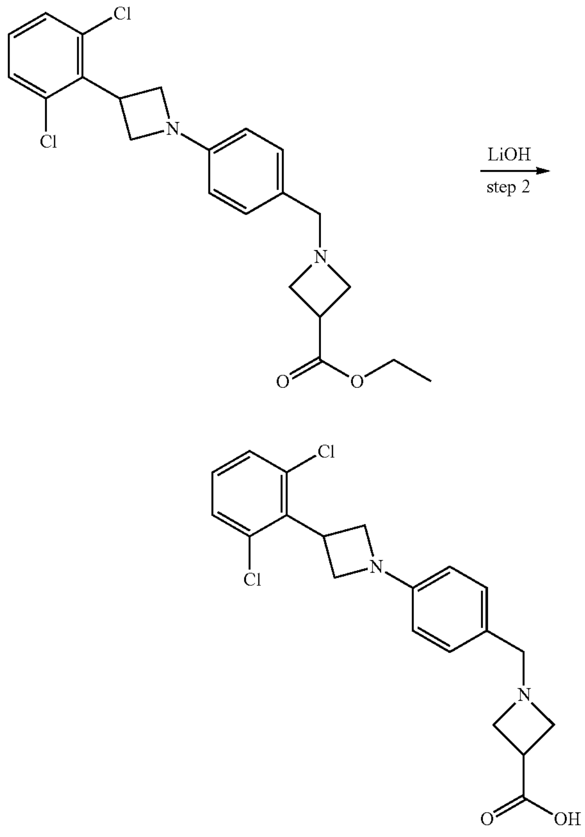

26

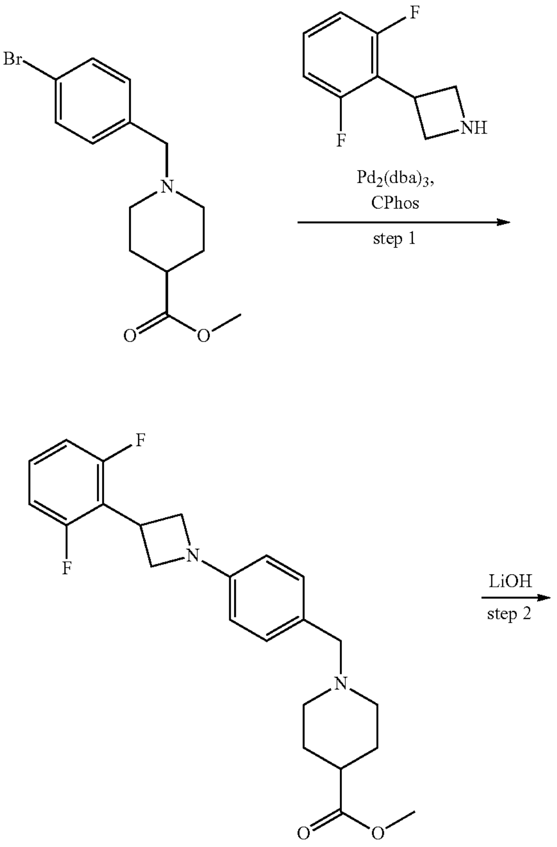

-continued

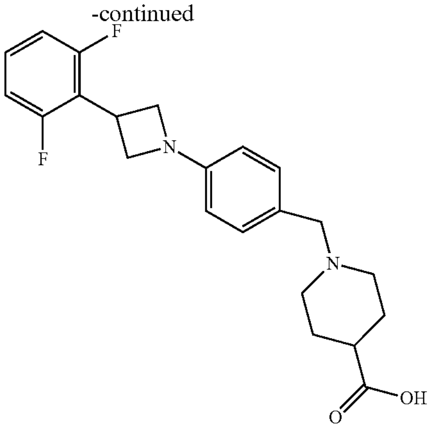

27

Synthesis of methyl 1-(4-(3-(2,6-difluorophenyl) azetidin-1-yl)benzyl)piperidine-4-carboxylate

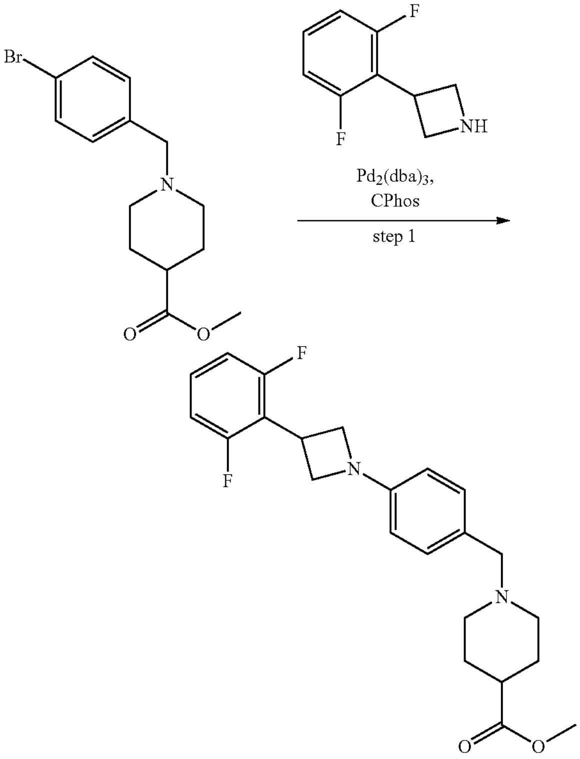

To a stirred solution of 3-(2,6-difluorophenyl)azetidine (80 mg, 0.470 mmol, 1.00 equiv.) and methyl methyl 1-(4-bromobenzyl)piperidine-4-carboxylate (162 mg, 0.520 mmol, 1.10 equiv.) in 1,4-dioxane (2 mL) were added $Pd_2(dba)_3$ (43 mg, 0.050 mmol, 0.10 equiv.), CPhos (41 mg, 0.090 mmol, 0.20 equiv.) and $Cs_2CO_3$ (153 mg, 0.470 mmol, 3.00 equiv.). The mixture solution was stirred at 80° C. for 16 h. LCMS showed the reaction was completed. The reaction mixture was concentrated and purified by flash column on silica gel (eluted with PE/EA, 1/1) to afford methyl 1-(4-(3-(2,6-difluorophenyl)azetidin-1-yl)benzyl)piperidine-4-carboxylate (150 mg, 79% yield) as an light-yellow oil. LCMS (ESI, m/z): 401 $[M+H]^+$.

Synthesis of 1-(4-(3-(2,6-difluorophenyl)azetidin-1-yl)benzyl)piperidine-4-carboxylic acid (27)

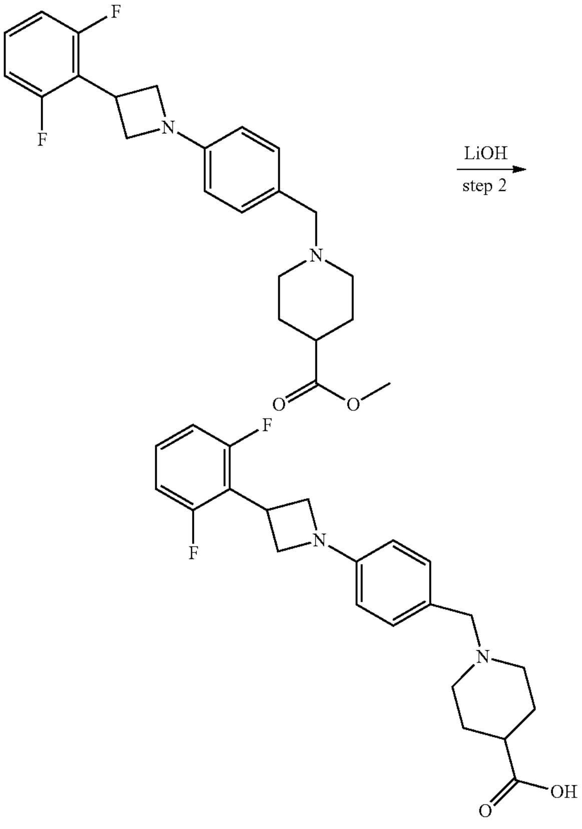

27

To a stirred solution of methyl 1-(4-(3-(2,6-difluorophenyl)azetidin-1-yl)benzyl)piperidine-4-carboxylate (150 mg, 0.370 mmol, 1.00 equiv.) in THE (2 mL) and water (0.2 mL) were added $LiOH \cdot H_2O$ (47 mg, 1.12 mmol, 3.00 equiv.). The mixture solution was stirred at room temperature for 16 h. LCMS showed the reaction was completed. The reaction mixture was acidified to pH 4-5 using acetic acid and then was concentrated. The residue was purified by Prep-HPLC (Column: XBridge Prep C18 OBD Column, 19*150 mm 5 μm; Mobile Phase A: water (10 mM $NH_4HCO_3$), Mobile Phase B: ACN; Flow rate: 25 mL/min; Gradient: 57% B to 66% B in 7 min; 254/210 nm; RT: 5.68 min) to afford 1-(4-(3-(2,6-difluorophenyl)azetidin-1-yl)benzyl)piperidine-4-carboxylic acid (55.9 mg, 38% yield) as an off-white solid.

LCMS (ESI, m/z): 387 $[M+H]^+$. Analytic Conditions: column: Poroshell HPH-C18, 3.0*50 mm, 2.7 μm; mobile phase A: water (5 mM $NH_4HCO_3$), mobile phase B: acetonitrile, flow rate: 1.20 mL/min; gradient: 10% B to 45% B in 1.70 min, 45% B to 95% B in 0.30 min, hold at 95% for 0.70 min, 95% B to 10% B in 0.10 min; 254 nm; RT: 1.607 min.

$^1H$ NMR (300 MHz, DMSO-$d_6$) δ 7.40-7.30 (m, 1H), 7.10-7.03 (m, 4H), 6.46-6.42 (m, 2H), 4.35-4.27 (m, 3H), 3.90-3.85 (m, 2H), 3.31 (s, 2H), 2.74-2.68 (m, 2H), 2.21-2.16 (m, 1H), 1.96-1.88 (m, 2H), 1.78-1.72 (m, 2H), 1.57-1.44 (m, 2H).

Example S28. 1-(4-(3-(2,6-dichlorophenyl)azetidin-1-yl)-2,6-dimethylbenzyl)piperidine-4-carboxylic acid (28)

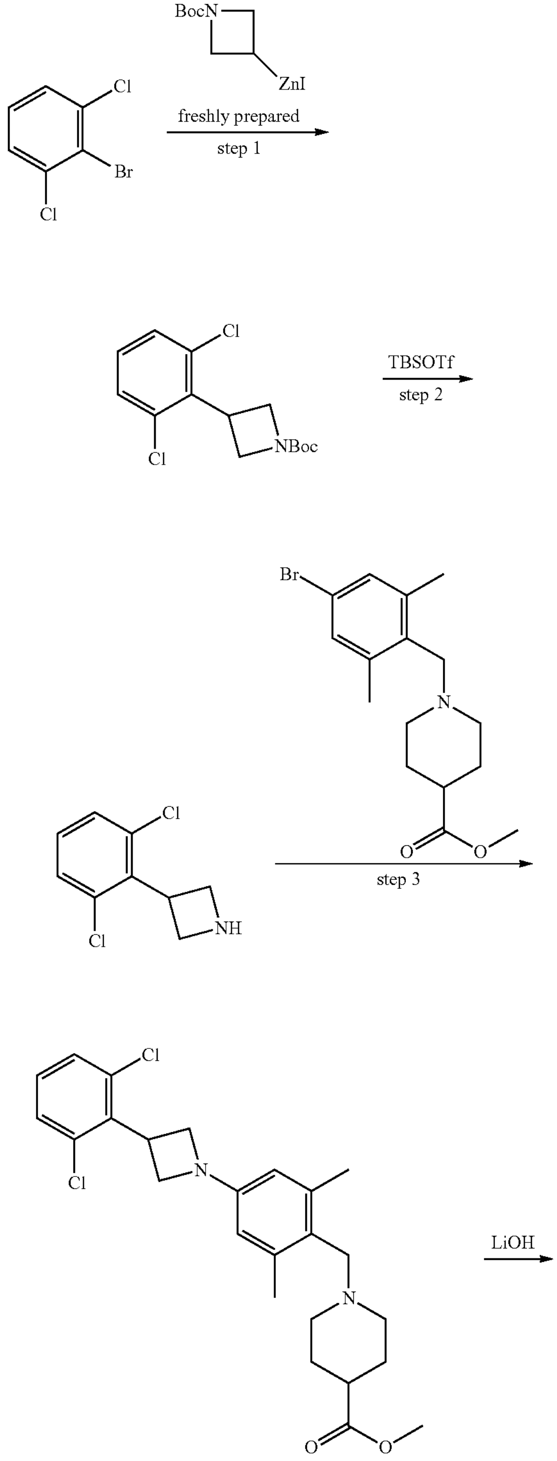

-continued

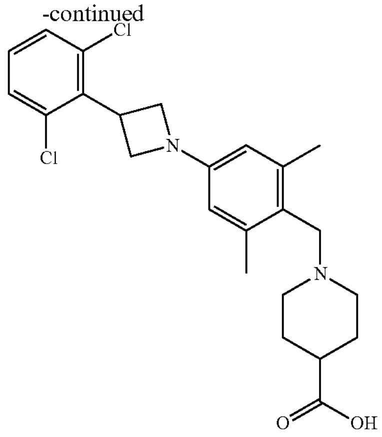

28

Synthesis of tert-butyl 3-(2,6-dichlorophenyl)azetidine-1-carboxylate

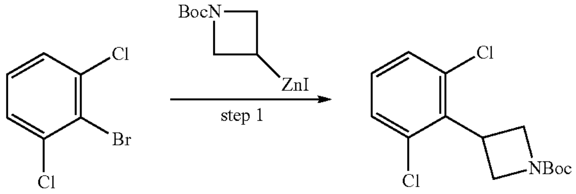

To a stirred solution of 2-bromo-1,3-dichloro-benzene (1.05 g, 4.65 mmol) in DMF (15 mL) were added (1-tert-butoxycarbonylazetidin-3-yl)-iodo-zinc (7.29 g, 20.9 mmol), $(o\text{-tol})_3P$ (245 mg, 0.930 mmol) and $Pd_2(dba)_3$ (267 mg, 0.460 mmol). The resulting mixture was stirred at 80° C. for 3 h. LCMS showed the reaction was completed. The reaction mixture was diluted with saturated aq. $NH_4Cl$ (60 mL) and extracted with EtOAc (3*40 mL). The organic layers were combined and dried over $MgSO_4$ and concentrated. The crude was purified by flash chromatography on silica gel (eluted with PE/EtOAc, 2/1) to afford tert-butyl 3-(2,6-dichlorophenyl)azetidine-1-carboxylate (320 mg, 22.8% yield) as an off-white solid. LCMS (ESI, m z): 302 $[M+H]^+$.

Synthesis of 3-(2,6-dichlorophenyl)azetidine

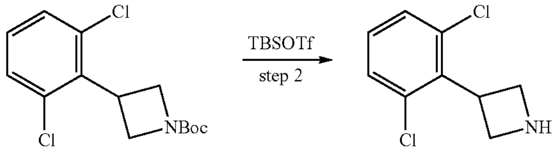 [SMILES: "TBSOTf" ; CC(C)(C)OC(=O)N1CC(c2c(Cl)cccc2Cl)C1 ; Clc1cccc(Cl)c1C1CNC1]

To a stirred solution of tert-butyl 3-(2,6-dichlorophenyl) azetidine-1-carboxylate (320 mg, 1.06 mmol, 1.00 equiv.) in DCM (3 mL) were added TBSOTf (0.2 mL). The reaction was stirred at room temperature for 0.5 h. LCMS showed the reaction was completed. The reaction mixture was concentrated under reduced pressure. The crude product was purified by flash column on C18 (eluted with water/ACN, 5/95)

to afford 3-(2,6-dichlorophenyl)azetidine (170 mg, 78.4%) as an yellow oil. LCMS (ESI, m z): 202 $[M+H]^+$.

Synthesis of methyl 1-(4-(3-(2,6-dichlorophenyl) azetidin-1-yl)-2,6-dimethylbenzyl)piperidine-4-carboxylate

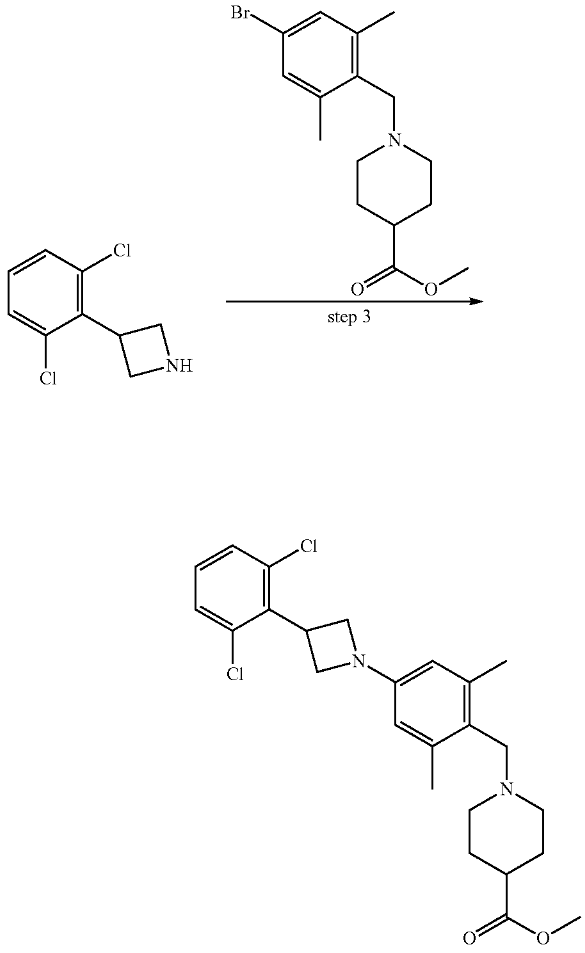

To a stirred solution of 3-(2,6-dichlorophenyl)azetidine (50 mg, 0.250 mmol, 1.00 equiv.) in tBuOH (3 mL) were added methyl 1-(4-bromo-2,6-dimethylbenzyl)piperidine-4-carboxylate (168 mg, 0.490 mmol, 2.00 equiv.), BrettPhos Pd G3 (23 mg, 0.020 mmol, 0.10 equiv.) and $K_2CO_3$ (171 mg, 1.24 mmol, 5.00 equiv.). The resulting mixture was stirred at 80° C. for 3 h. LCMS showed the reaction was completed. The reaction mixture was concentrated and purified by flash column on silica gel (eluted with PE/EA, 1/1) to afford methyl 1-(4-(3-(2,6-dichlorophenyl)azetidin-1-yl)-2,6-dimethylbenzyl)piperidine-4-carboxylate (33 mg, 28% yield) as an off white solid. LCMS (ESI, m z): 461$[M+H]^+$.

Synthesis of 1-(4-(3-(2,6-dichlorophenyl)azetidin-1-yl)-2,6-dimethylbenzyl)piperidine-4-carboxylic acid (28)

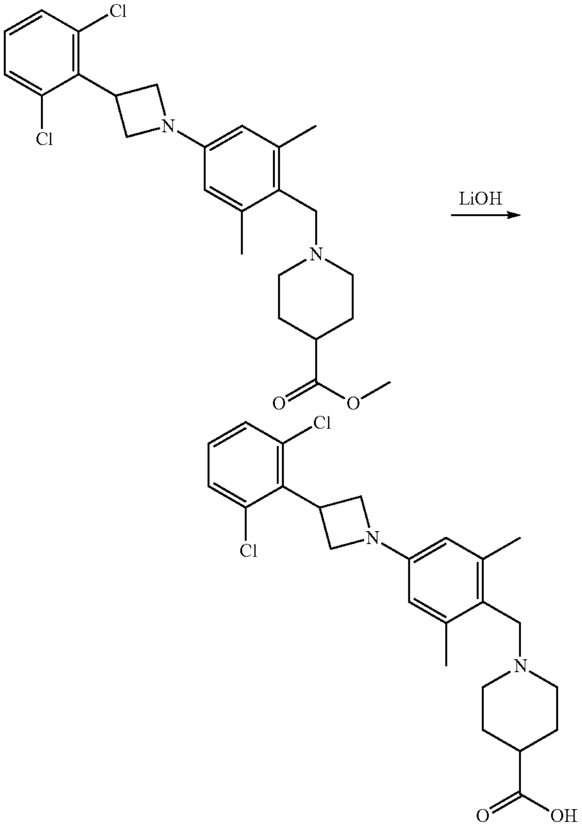

28

To a stirred solution of methyl 1-(4-(3-(2,6-dichlorophenyl)azetidin-1-yl)-2,6-dimethylbenzyl)piperidine-4-carboxylate (33 mg, 0.070 mmol, 1.00 equiv.) in THF (1 mL) and water (0.2 mL) was added $LiOH{\cdot}H_2O$ (9 mg, 0.210 mmol, 3.00 equiv.). The resulting mixture was stirred at room temperature overnight. LCMS showed that the reaction was complete. The reaction mixture was acidified to pH 4-5 using acetic acid and then was concentrated. The residue was purified by Prep-HPLC (Column: XBridge Prep C18 OBD Column, 30*100 mm, 5 μm; Mobile Phase A: water (5 mM $NH_4HCO_3$), Mobile Phase B: ACN; Flow rate: 60 mL/min; Gradient: 28% B to 45% B in 8 min; Wavelength: 254/220 nm; RT: 7.93 min) to give 1-(4-(3-(2,6-dichlorophenyl)azetidin-1-yl)-2,6-dimethylbenzyl)piperidine-4-carboxylic acid (10.9 mg, 34% yield) as an off white solid.

$^1H$ NMR (300 MHz, DMSO-$d_6$) δ 7.47 (d, J=8.1 Hz, 2H), 7.30 (t, J=8.1 Hz, 1H), 6.18 (s, 2H), 4.55-4.48 (m, 1H), 4.40 (t, J=7.5 Hz, 2H), 3.96 (t, J=7.5 Hz, 2H), 3.30 (s, 2H), 2.69-2.65 (m, 2H), 2.26 (s, 6H), 2.22-2.14 (m, 1H), 2.03-1.96 (m, 2H), 1.75-1.71 (m, 2H), 1.49-1.40 (m, 2H).

LCMS (ESI, m/z): 447 $[M+H]^+$. Analytic Conditions: column: HALO C18 3.0*30 mm, 2.7 mm; mobile Phase A: water (0.05% TFA), mobile Phase B: acetonitrile (0.05% TFA); flow rate: 1.50 mL/min; gradient: 5% B to 100% B in 2.00 min, hold at 100% for 0.70 min, 100% B to 5% B in 0.05 min; 254 nm; RT: 1.273 min.

Example S29. 1-((5-(3-(2,6-dichlorophenyl)azetidin-1-yl)pyridin-2-yl)methyl)piperidine-4-carboxylic acid (29)

General Scheme:

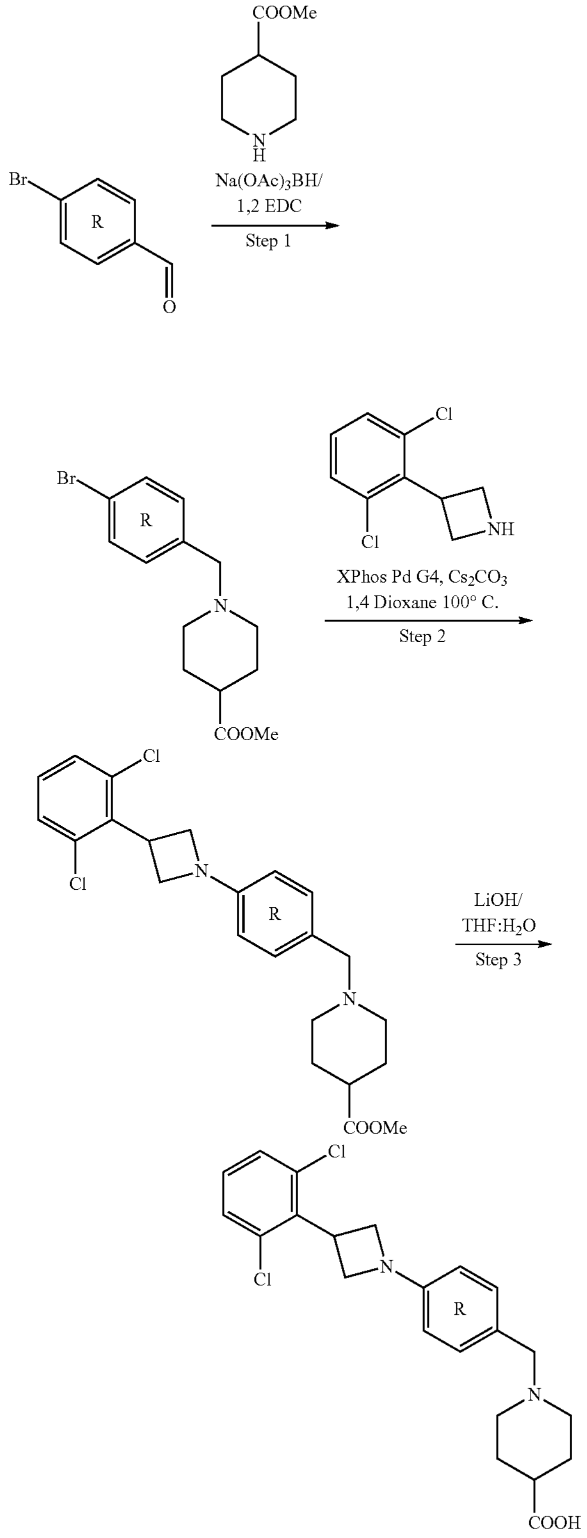

Synthesis of methyl 1-((5-bromopyridin-2-yl)methyl)piperidine-4-carboxylate (29-a)

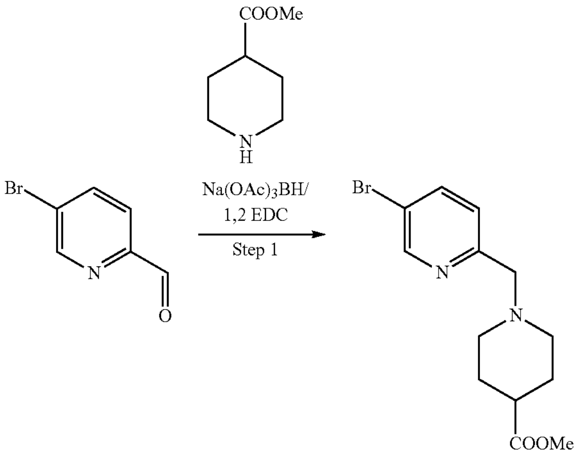

29-a

To a solution of 5-bromopicolinaldehyde (3 g, 16.13 mmol) in anhydrous 1,2 DCE (10 mL) was added methyl piperidine-4-carboxylate (2.309 g, 16.13 mmol) and the reaction mixture was allowed to stir at ambient temperature. After 10 min, sodium triacetoxyborohydride (3.42 g, 16.13 mmol) was added and the reaction mixture was allowed to stir at room temperature. After 4 h, TLC analysis indicated complete conversion of the starting material. The reaction mixture was diluted with dichloromethane, washed with water, dried over sodium sulphate and filtered. The filtrate was concentrated under reduced pressure and the resulting residue was purified by flash column chromatography on silica gel eluting with 0-100% ethyl acetate in petroleum ether to afford methyl 1-((5-bromopyridin-2-yl)methyl)piperidine-4-carboxylate (1.8 g, 35.6% yield) as colorless oil. LCMS (ESI, m/z): 313.0, 315.0 [M, M+2H]$^+$.

Synthesis of methyl 1-((5-(3-(2,6-dichlorophenyl)azetidin-1-yl)pyridin-2-yl)methyl)piperidine-4-carboxylate (29-b)

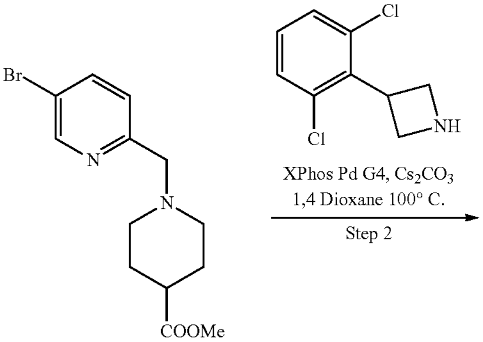

-continued

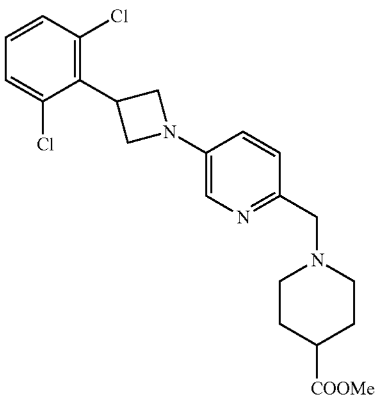

29-b

To a solution of methyl 1-((5-bromopyridin-2-yl)methyl) piperidine-4-carboxylate (250 mg, 0.798 mmol) and 3-(2,6-dichlorophenyl)azetidine (194 mg, 0.958 mmol) in anhydrous 1,4 dioxane (5 mL) was added cesium carbonate (2.395 mmol). The reaction mixture was then degassed with nitrogen for 10 min followed by the addition of added XPhos Pd G4 (68.7 mg, 0.080 mmol) and heated 100° C. After 16 h, TLC analysis indicated complete conversion of the starting material. The reaction mixture was then cooled to room temperature and filtered through a celite pad washed with DCM:MeOH (1:1) mixture. The filtrate was concentrated under reduced pressure and the resulting residue was purified by flash column chromatography on silica gel (230-400 mesh) eluting with 0-100% ethyl acetate in petroleum ether to afford methyl 1-((5-(3-(2,6-dichlorophenyl)azetidin-1-yl) pyridin-2-yl)methyl)piperidine-4-carboxylate (180 mg, 41.5% yield) as a yellow liquid. LCMS (ESI, m/z): 434.0 $[M+H]^+$.

Synthesis of 1-((5-(3-(2,6-dichlorophenyl)azetidin-1-yl)pyridin-2-yl)methyl)piperidine-4-carboxylic acid (29)

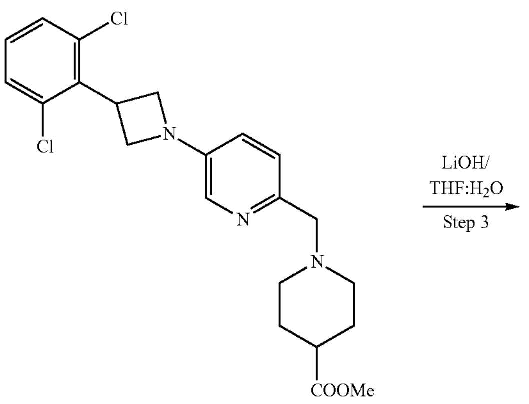

-continued

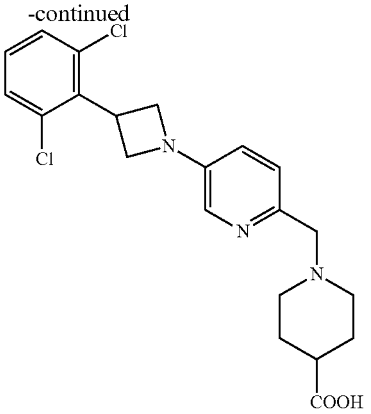

29

To a stirred solution of methyl 1-((5-(3-(2,6-dichlorophenyl)azetidin-1-yl)pyridin-2-yl)methyl)piperidine-4-carboxylate (180 mg, 0.414 mmol) in tetrahydrofuran (5 mL) and $H_2O$ (0.5 mL) was added LiOH (29.8 mg, 1.243 mmol). The resulting mixture was stirred at room temperature and the progress of the reaction was monitored by TLC analysis. After 16 h. TLC analysis indicated complete conversion of the starting material. The reaction mixture was then acidified using acetic acid by maintaining the pH=4 and concentrated under reduced pressure. The resulting residue was purified by reverse phase preparative HPLC on C18 silica (Mobile Phase A: water (10 mM ammonium formate), Mobile Phase B: ACN; Flow rate: 100 mL/min; Gradient: 45% B to 50% B in 4 min; 254/210 nm). The required fractions were collected and lyophilized to afford 1-((5-(3-(2,6-dichlorophenyl)azetidin-1-yl)pyridin-2-yl)methyl)piperidine-4-carboxylic acid (63 mg, 31.8% yield) as an off-white solid. LCMS (ESI, m/z): 420.0 [M+H]+; $^1$H-NMR (400 MHz, $CD_3OD$): δ 8.55 (s, 1H), 7.95 (m, 1H), 7.41-7.33 (m, 3H), 7.26-7.22 (m, 1H), 7.01-6.98 (m, 1H), 4.86-4.78 (m, 2H), 4.58-4.54 (m, 2H), 4.13 (s, 2H), 3.45-3.30 (m, 1H), 2.94-2.88 (m, 2H), 2.41-2.36 (m, 1H), 2.08-2.03 (m, 2H), 1.95-1.90 (m, 2H).

Example S30. 1-(4-(3-(2,6-dichlorophenyl)azetidin-1-yl)-2,5-dimethylbenzyl)piperidine-4-carboxylic acid (30)

Synthesis of methyl 1-(4-bromo-2,5-dimethylbenzyl)piperidine-4-carboxylate (30-a)

30-a

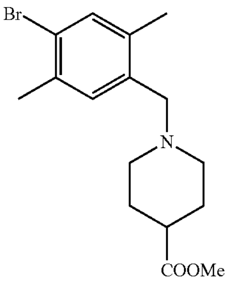

The title compound was synthesized by following the general procedure for the synthesis of 29-a. LCMS (ESI, m/z): 342.0 $[M+2H]^+$.

Synthesis of methyl 1-(4-(3-(2,6-dichlorophenyl)azetidin-1-yl)-2,5-dimethylbenzyl)piperidine-4-carboxylate (30-b)

30-b

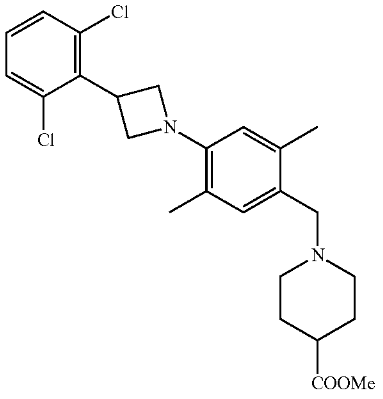

The title compound was synthesized by following the general procedure for the synthesis of 29-b. LCMS (ESI, m/z): 462.1 [M+H]+.

Synthesis of 1-(4-(3-(2,6-dichlorophenyl)azetidin-1-yl)-2,5-dimethylbenzyl)piperidine-4-carboxylic acid (30)

30

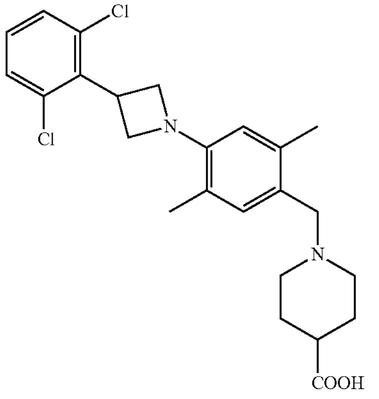

The title compound was synthesized by following the general procedure for the synthesis of 29. LCMS (ESI, m/z): 445.0 [M−H]−. $^1$H NMR (400 MHz, $CD_3OD$): δ 7.38 (d, J=8 Hz, 2H), 7.24-7.20 (m, 1H), 7.09 (s, 1H), 6.49 (s, 1H), 4.59-4.56 (m, 3H), 4.22-4.16 (m, 4H), 3.50-3.43 (m, 2H), 3.04 (m, 2H), 2.45-2.42 (m, 1H), 2.37 (s, 3H), 2.29 (s, 3H), 2.09-2.06 (m, 2H), 1.91 (m, 2H).

Example S31. 1-(4-(3-(2,6-dichlorophenyl)azetidin-1-yl)-3,5-dimethylbenzyl)piperidine-4-carboxylic acid (31)

Synthesis of methyl 1-(4-bromo-3,5-dimethylbenzyl)piperidine-4-carboxylate (31-a)

31-a

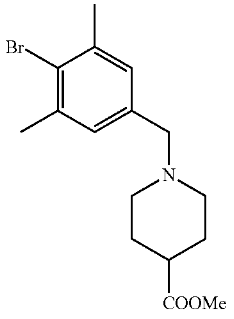

The title compound was synthesized by following the general procedure for the synthesis of 29-a. LCMS (ESI, m/z): 342.0 [M+2H]+.

Synthesis of methyl 1-(4-(3-(2,6-dichlorophenyl)azetidin-1-yl)-3,5-dimethylbenzyl)piperidine-4-carboxylate (31-b)

31-b

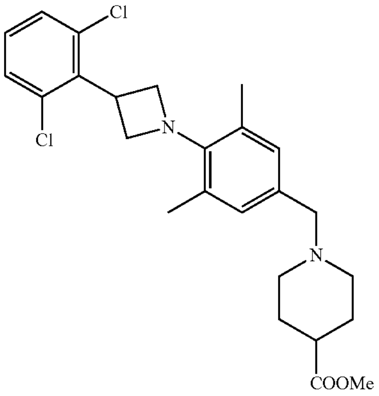

The title compound was synthesized by following the general procedure for the synthesis of 29-b. LCMS (ESI, m/z): 462.1 [M+H]+.

Synthesis of 1-(4-(3-(2,6-dichlorophenyl)azetidin-1-yl)-3,5-dimethylbenzyl)piperidine-4-carboxylic acid (31)

31

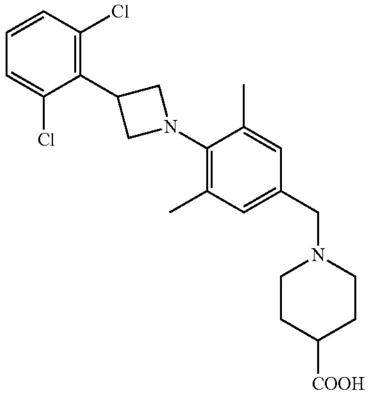

The title compound was synthesized by following the general procedure for the synthesis of 29. LCMS (ESI, m/z): 445.1 [M−H]⁻; $^1$H-NMR (400 MHz, DMSO-$d_6$): δ 7.43 (d, J=8 Hz, 2H), 7.30-7.26 (m, 1H), 6.72 (s, 2H), 4.68 (s, 2H), 4.31-4.28 (m, 3H), 3.34 (s, 2H), 2.71-2.67 (m, 2H), 2.26 (s, 6H), 2.15-2.14 (m, 1H), 1.91-1.86 (m, 2H), 1.75-1.72 (m, 2H), 1.54-1.44 (m, 2H).

Example S32. 1-((6-(3-(2,6-dichlorophenyl)azetidin-1-yl)pyridin-3-yl)methyl)piperidine-4-carboxylic acid (32)

Synthesis of methyl 1-((6-bromopyridin-3-yl)methyl)piperidine-4-carboxylate (32-a)

32-a

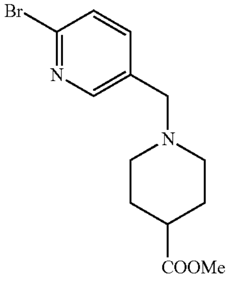

The title compound was synthesized by following the general procedure for the synthesis of 29-a. LCMS (ESI, m/z): 313.1, 315.0 [M, M+2H]$^+$.

Synthesis of methyl 1-((6-(3-(2,6-dichlorophenyl)azetidin-1-yl)pyridin-3-yl)methyl)piperidine-4-carboxylate (32-b)

32-b

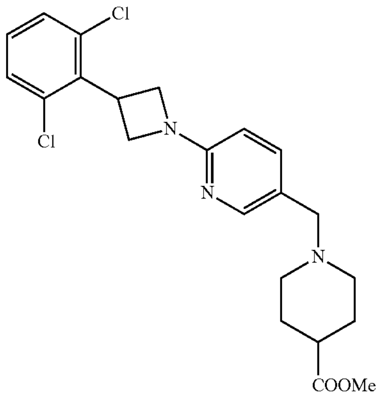

To a solution of 3-(2,6-dichlorophenyl)azetidine, TFA (120 mg, 0.380 mmol) in anhydrous 1,4-dioxane (5 mL) was added methyl 1-((6-bromopyridin-3-yl)methyl)piperidine-4-carboxylate (119 mg, 0.380 mmol), and cesium carbonate (371 mg, 1.139 mmol) The reaction mixture was then heated to 100° C. and the progress of the reaction was monitored by TLC and LCMS analysis. After 16 h the reaction mixture was cooled to ambient temperature and concentrated under reduced pressure. The resulting residue was purified by flash column chromatography on silica gel eluting with 0-100% ethyl acetate in petroleum ether to afford methyl 1-((6-(3-(2,6-dichlorophenyl)azetidin-1-yl)pyridin-3-yl)methyl)piperidine-4-carboxylate (60 mg, 21.1% yield). LCMS (ESI, m/z): 434.0 [M+H]$^+$.

Synthesis of 1-((6-(3-(2,6-dichlorophenyl)azetidin-1-yl)pyridin-3-yl)methyl)piperidine-4-carboxylic acid (32)

32

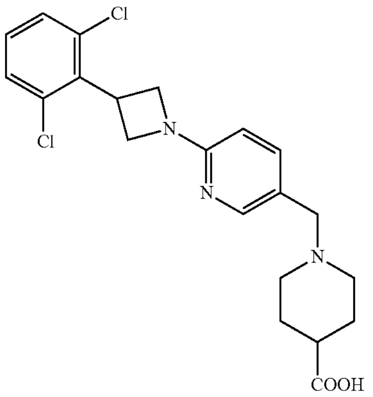

The title compound was synthesized by following the general procedure for the synthesis of 29. LCMS (ESI, m/z): 418.0 [M−H]⁻; $^1$H NMR: (400 MHz, $CD_3OD$) δ 8.10 (s, 1H), 7.65 (d, J=8.4 Hz, 1H), 7.42 (m, 2H), 7.27-7.23 (m, 1H), 6.55 (d, J=8.8 Hz, 1H), 4.88 (m, 2H), 4.57-4.49 (m, 4H), 4.01 (s, 2H), 2.81 (m, 2H), 2.36 (m, 1H), 2.05-2.04 (m, 2H), 1.88-1.85 (m, 2H).

Example S33. 1-(4-(3-(2,6-dichlorophenyl)azetidin-1-yl)-2-fluorobenzyl)piperidine-4-carboxylic acid (33)

Synthesis of methyl 1-(4-bromo-2-fluorobenzyl) piperidine-4-carboxylate (33-a)

33-a

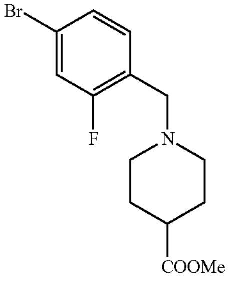

The title compound was synthesized by following the general procedure for the synthesis of 29-a. LCMS (ESI, m/z): 331.2 $[M+2H]^+$.

Synthesis of methyl 1-(4-(3-(2,6-dichlorophenyl) azetidin-1-yl)-2-fluorobenzyl)piperidine-4-carboxylate (33-b)

33-b

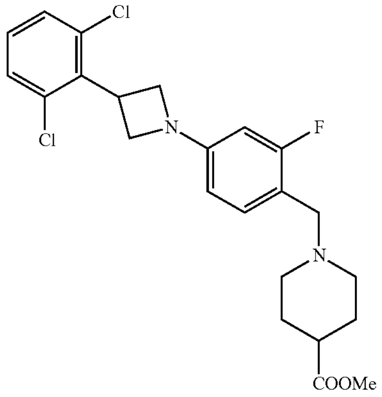

The title compound was synthesized by following the general procedure for the synthesis of 29-b. LCMS (ESI, m/z): 452.0 $[M+H]^+$.

Synthesis of 1-(4-(3-(2,6-dichlorophenyl)azetidin-1-yl)-2-fluorobenzyl)piperidine-4-carboxylic acid (33)

33

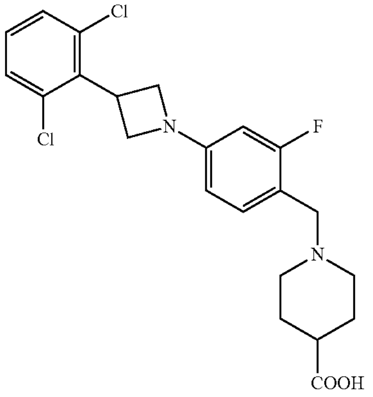

The title compound was synthesized by following the general procedure for the synthesis of 29. LCMS (ESI, m/z): 436.0 $[M-H]^-$; $^1H$ NMR: (400 MHz, $CD_3OD$): δ 7.41 (d, J=8 Hz, 2H), 7.33-7.22 (m, 2H), 6.43-6.34 (m, 2H), 4.81-4.77 (m, 1H), 4.50-4.46 (m, 2H), 4.32-4.28 (m, 2H), 4.19 (s, 2H), 3.42 (m, 2H), 3.02 (m, 2H), 2.44 (m, 1H), 2.17-2.12 (m, 2H), 1.91 (m, 2H).

Example S34. 1-(4-(3-(2,6-dichlorophenyl)azetidin-1-yl)-3-fluorobenzyl)piperidine-4-carboxylic acid (34)

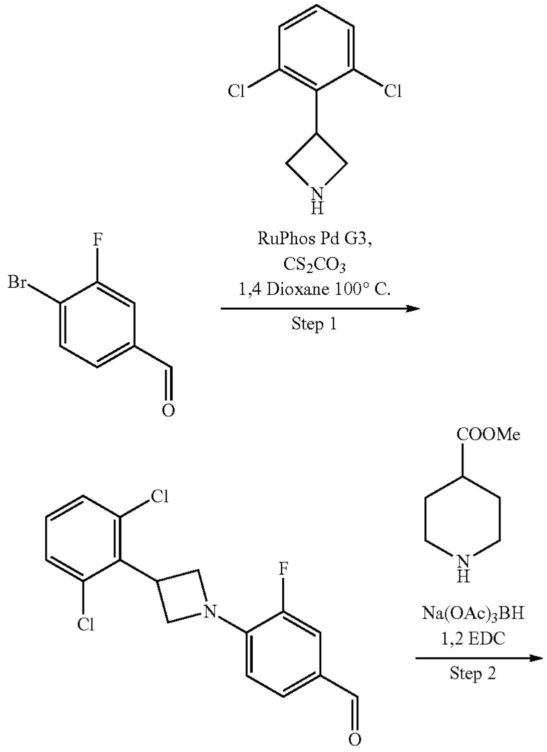

-continued

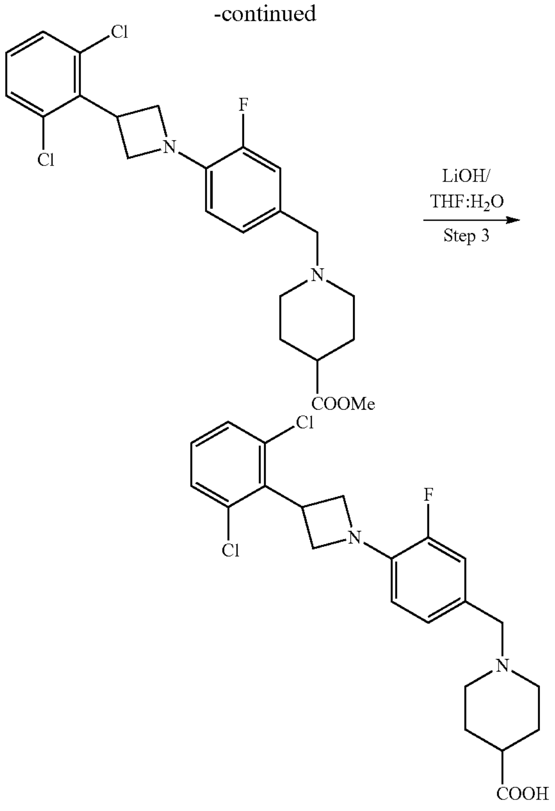

34

Synthesis of 4-(3-(2,6-dichlorophenyl)azetidin-1-yl)-3-fluorobenzaldehyde

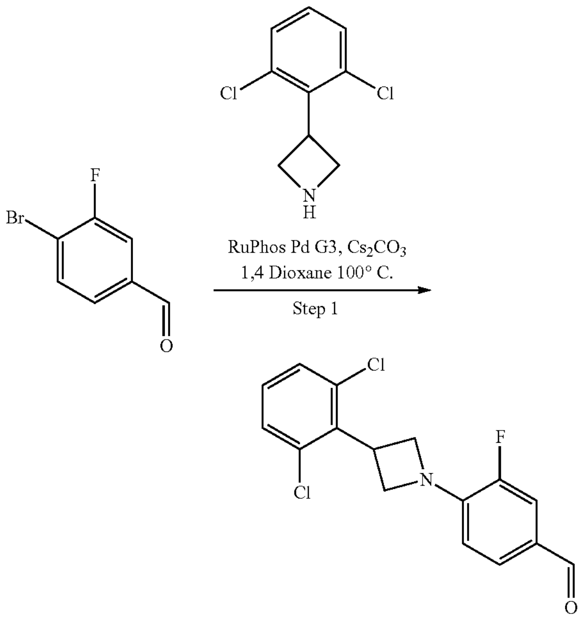

In a microwave vial, to a solution of 4-bromo-3-fluorobenzaldehyde (100 mg, 0.493 mmol), and 3-(2,6-dichlorophenyl)azetidine (119 mg, 0.591 mmol) in anhydrous 1,4-dioxane was added cesium carbonate (1.478 mmol) followed by the addition of Ruphos Pd G3 (41.2 mg, 0.049 mmol) under nitrogen atmosphere. The vial was sealed and irradiated to 110° C. in a microwave reactor. After 4 h, the reaction mixture was cooled to room temperature and filtered through a celite pad and washed with dichloromethane. The filtrate was then concentrated under vacuum and the resulting residue was purified by flash column chromatography on silica gel (230-400 mesh) eluting with 0-10% ethyl acetate in petroleum ether to afford 4-(3-(2,6-dichlorophenyl)azetidin-1-yl)-3-fluorobenzaldehyde (80 mg, 19.04% yield) as a yellow oil. LCMS (ESI, m/z): 324.0 $[M+H]^+$.

Synthesis of methyl 1-(4-(3-(2,6-dichlorophenyl)azetidin-1-yl)-3-fluorobenzyl)piperidine-4-carboxylate

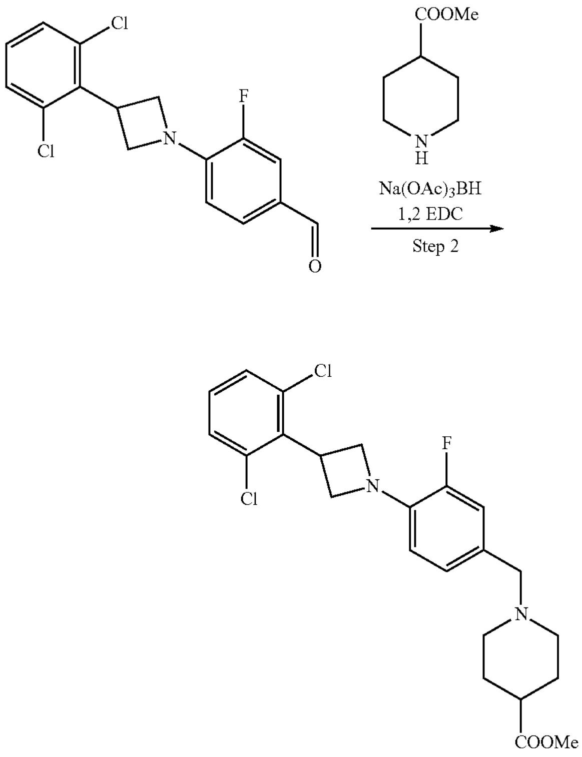

To a stirred solution of 4-(3-(2,6-dichlorophenyl)azetidin-1-yl)-3-fluorobenzaldehyde (80 mg, 0.247 mmol) and methyl piperidine-4-carboxylate (35.3 mg, 0.247 mmol) in anhydrous methanol (10 mL) was added acetic acid (0.014 mL, 0.247 mmol) and the mixture was allowed to stir at ambient temperature. After 1 h, MP-cyano borohydride resin (78 mg, 0.370 mmol) was added to the reaction mixture and allowed to stir at the same temperature. After 16 h, TLC analysis indicated complete conversion of the starting material. The reaction mixture was then filtered and washed with dichloromethane. The filtrate was then washed with water (20 mL), dried over sodium sulphate and concentrated. The resulting residue was purified by flash column chromatography on silica gel (230-400 mesh) eluting with 0-30% ethyl acetate in petroleum ether to afford methyl 1-(4-(3-(2,6-dichlorophenyl)azetidin-1-yl)-3-fluorobenzyl)piperidine-4-carboxylate (60 mg, 37.5% yield) as a yellow oil. LCMS (ESI, m/z): 452.0 $[M+H]^+$.

Synthesis of 1-(4-(3-(2,6-dichlorophenyl)azetidin-1-yl)-3-fluorobenzyl)piperidine-4-carboxylic acid (34)

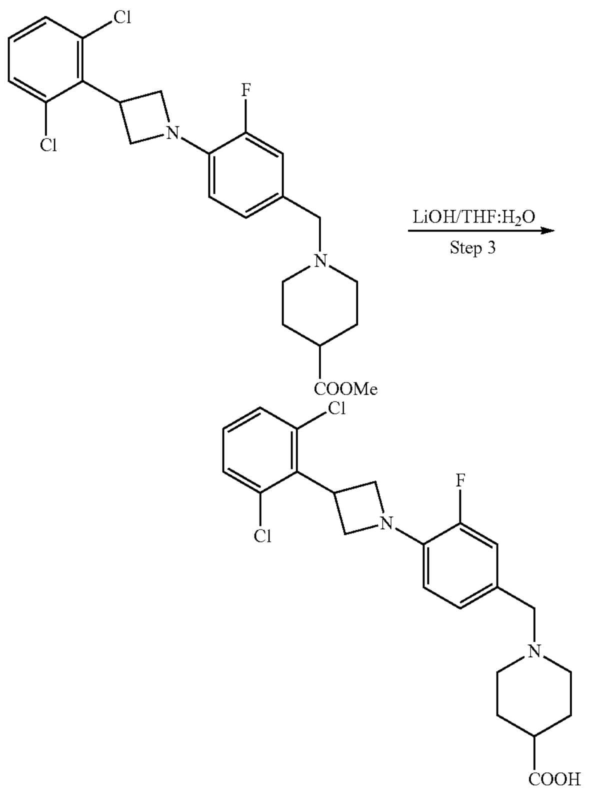

34

To a stirred solution of methyl 1-(4-(3-(2,6-dichlorophenyl) azetidin-1-yl)-3-fluorobenzyl)piperidine-4-carboxylate (80 mg, 0.177 mmol) in tetrahydrofuran (5 mL) and $H_2O$ (0.5 mL) was added lithium hydroxide (12.73 mg, 0.532 mmol) and the resulting mixture was allowed to stir at room temperature. After 16 h, LCMS analysis indicated complete conversion of the starting material. The reaction was acidified using acetic acid by maintaining the pH=4-5 and then concentrated under reduced pressure. The resulting residue was purified by preparative HPLC (Method: Column: Xselect C18 (250×19) mm, 5 micron Mobile phase A: 0.1% Formic acid in water Mobile phase B: Acetonitrile). The required fractions were collected and lyophilized to afford 1-(4-(3-(2,6-dichlorophenyl)azetidin-1-yl)-3-fluorobenzyl) piperidine-4-carboxylic acid, formic acid salt (22.8 mg, 26.5% yield)) as a white solid. LCMS (ESI, m/z): 435.2 $[M-H]^-$; $^1H$ NMR: (400 MHz, $CD_3OD$): δ 7.39 (d, J=8 Hz, 2H), 7.25-7.21 (m, 1H), 7.16-7.12 (m, 2H), 6.68 (t, J=8.8 Hz, 1H), 4.63-4.59 (m, 4H), 4.33-4.29 (m, 2H), 4.05 (s, 2H), 2.86 (m, 2H), 2.37 (m, 1H), 2.07-2.04 (m, 2H), 1.89 (m, 2H).

LCMS Condition: Column: Kinetex XB—C18 (75×3.0) mm, 2.6 μm, Mobile Phase: A: 5 mM Ammonium formate pH 3.3:ACN (98:02), Mobile Phase: B: 5 mM Ammonium formate pH 3.3:ACN (98:02), Flow Rate: 1.0 mL/min.

LCMS Methods for Following Examples

Method 1: Column: Kinetex XB—C18 (75×3.0) mm, 2.6 μm; Mobile Phase A: 5 mM Ammonium formate pH 3.3: ACN (98:02); Mobile Phase B: ACN: Buffer (98:02); Flow Rate: 1.0 ml/min.

Method 2: Column: XBridge C8 (50×4.6 mm) 5 μm; Mobile phase A: 0.1% TFA in $H_2O$; Mobile phase B: 0.1% TFA in ACN; Flow Rate: 1.5 ml/min.

Method 3: Column: Aquity Uplc BEH C18 (50×3.0) mm, 1.7 μm; Mobile Phase: A: 0.1% FA in Water; Mobile Phase: B: 0.1% TFA in CAN; Flow Rate: 1.0 ml/min.

Method 4: Column: Aquity BEH C18 (50×3.0) mm, 1.7 μm; Mobile Phase A: 5 mM Ammonium formate pH 3.3: ACN (98:02); Mobile Phase B: ACN: Buffer (98:02); Flow Rate: 0.7 ml/min.

Method 5: Column: XSELECT CSH C18(50×4.6 mm) 5 μm, Mobile phase A: 0.1% FA in $H_2O$, Mobile phase B: ACN, Flow Rate: 1.5 ml/min.

Method 6: Column: XBridge C8 (50×4.6 mm) 3.5 μm, Mobile phase A: 0.1% FA in $H_2O$, Mobile phase B: ACN, Flow Rate: 1.5 ml/min.

General Route to Compounds 35-37

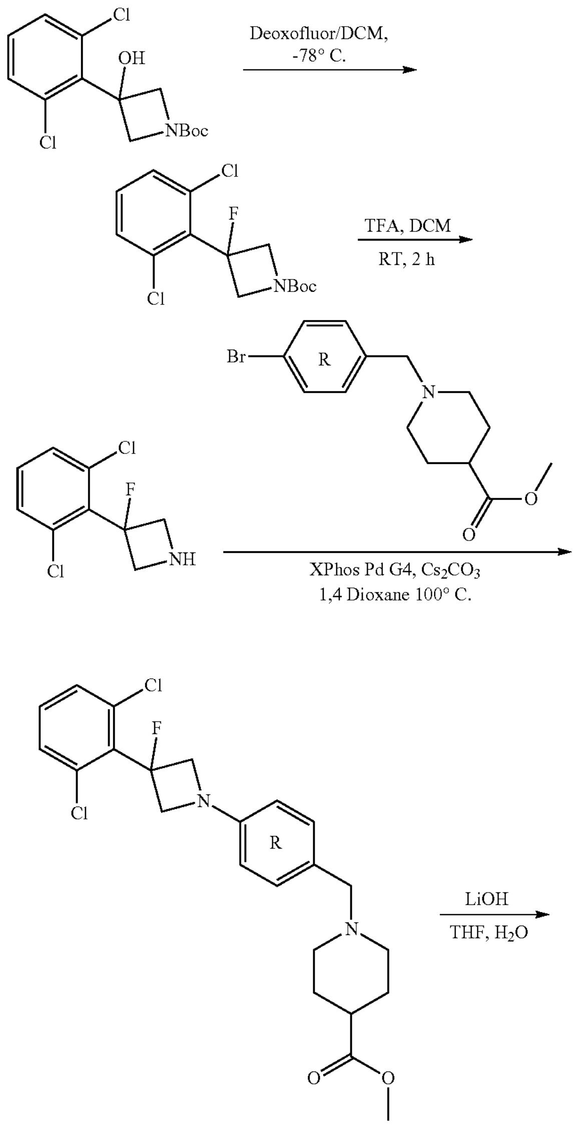

-continued

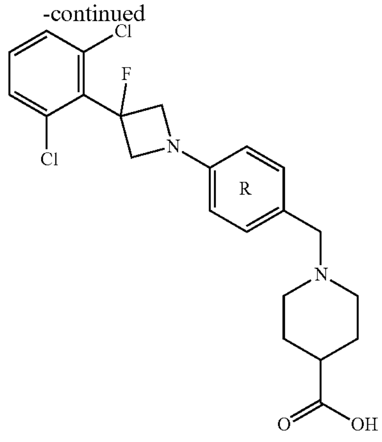

35-37

Synthesis of tert-butyl 3-(2,6-dichlorophenyl)-3-fluoroazetidine-1-carboxylate

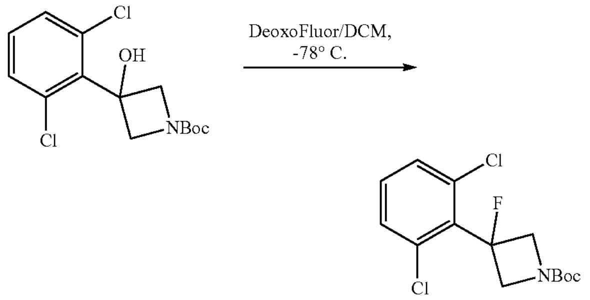

To a solution of tert-butyl 3-(2,6-dichlorophenyl)-3-hydroxyazetidine-1-carboxylate (1.8 g, 5.66 mmol) in anhydrous DCM (20 mL) at −75° C. was added Deoxo-Fluor (4.99 mL, 8.49 mmol) and the mixture was stirred at room temperature for 1 hour. Then the reaction was quenched with saturated sodium bicarbonate solution and extracted with ethyl acetate, washed with water (3×50 mL), dried over sodium sulphate and concentrated under reduced pressure. The resulting residue was purified by flash column chromatography on silica gel (230-400 mesh), eluted with 0-50% ethyl acetate in petroleum ether to afford tert-butyl 3-(2,6-dichlorophenyl)-3-fluoroazetidine-1-carboxylate (1.1 g, 3.44 mmol, 60.7% yield). LCMS method 1; LCMS (ESI, m/z): 220.0 [M−100]$^+$.

Synthesis of 3-(2,6-dichlorophenyl)-3-fluoroazetidine

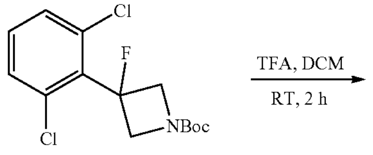

-continued

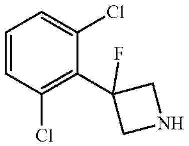

To a stirred solution of tert-butyl 3-(2,6-dichlorophenyl)-3-fluoroazetidine-1-carboxylate (1 g, 3.12 mmol) in anhydrous DCM (10 mL) at 0° C. was added TFA (2.390 mL, 31.2 mmol). The mixture was allowed to warm up, stirred at ambient temperature and the progress of the reaction was monitored by TLC. After 1 h, the reaction mixture was concentrated under reduced pressure and the resulting residue was triturated with diethyl ether to afford 3-(2,6-dichlorophenyl)-3-fluoroazetidine as a TFA salt (690 mg, 70% yield) as a white solid. LCMS method 1; LCMS (ESI, m/z): 220.0 [M+H]$^+$.

Synthesis of methyl 1-(4-(3-(2,6-dichlorophenyl)-3-fluoroazetidin-1-yl)benzyl)piperidine-4-carboxylate

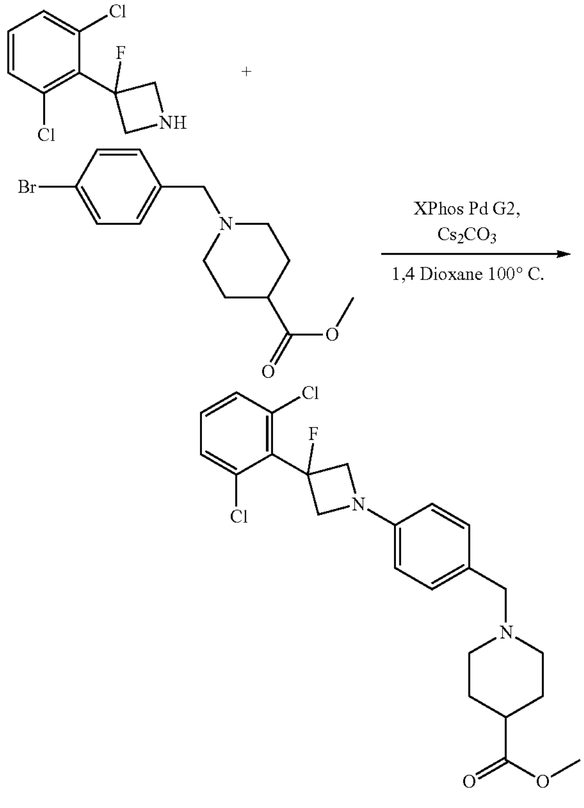

To a solution of methyl 1-(4-bromobenzyl)piperidine-4-carboxylate (148 mg, 0.475 mmol) and 3-(2,6-dichlorophenyl)-3-fluoroazetidine (150 mg, 0.475 mmol) in anhydrous 1,4 dioxane (5 mL) was added cesium carbonate (387 mg, 1.186 mmol). The reaction mixture was degassed with nitrogen for 10 min followed by the addition of XPhos Pd G2 (37.3 mg, 0.47 mmol) and heating to 100° C. After 16 h, TLC analysis indicated complete conversion of the starting material. The reaction mixture was cooled to room temperature and filtered through a celite pad, which was washed with EtOAc. The combined filtrate was concentrated under reduced pressure and the resulting residue was purified by flash column chromatography on silica gel (230-400 mesh) eluting with 0-100% ethyl acetate in petroleum ether to afford methyl 1-(4-(3-(2,6-dichlorophenyl)-3-fluoroazetidin-1-yl)benzyl)piperidine-4-carboxylate (90 mg, 42% yield) as a yellow solid. LCMS method 1; LCMS (ESI, m/z): 309.0 $[M-142]^+$.

Synthesis of Methyl 1-(4-(3-(2,6-dichlorophenyl)-3-fluoroazetidin-1-yl)-3,5-dimethyl-benzyl)-piperidine-4-carboxylate

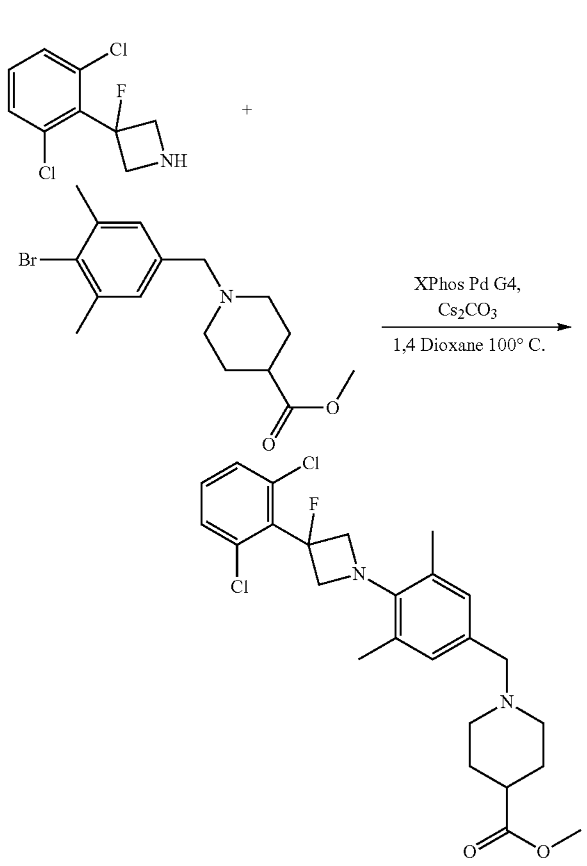

To a solution of methyl 1-(4-bromo-3,5-dimethylbenzyl) piperidine-4-carboxylate (250 mg, 0.735 mmol) and 1-(3-(2,6-dichlorophenyl)-3-fluoroazetidin-1-yl)-2,2,2-trifluoro-ethan-1-one (232 mg, 0.735 mmol) in anhydrous 1,4 dioxane (4 mL) was added cesium carbonate (718 mg, 2.204 mmol). The reaction mixture was degassed with nitrogen for 10 min, followed by the addition of XPhos Pd G4 (63.2 mg, 0.073 mmol) and heating to 100° C. After 16 h, TLC analysis indicated complete conversion of the starting material. The reaction mixture was cooled to room temperature and filtered through a celite pad, which was washed with EtOAc. The filtrate was concentrated under reduced pressure and the resulting residue was purified by flash column chromatography on silica gel (100-200 mesh) eluting with 0-100% ethyl acetate in petroleum ether to afford methyl 1-(4-(3-(2,6-dichlorophenyl)-3-fluoroazetidin-1-yl)-3,5-dimethylbenzyl)piperidine-4-carboxylate (150 mg, 42.6% yield) as a yellow semi-solid. LCMS method 1, LCMS (ESI, m/z): 336.0 $[M-142]^+$.

Synthesis of methyl 1-(4-(3-(2,6-dichlorophenyl)-3-fluoroazetidin-1-yl)-2,6-dimethylbenzyl)-piperidine-4-carboxylate

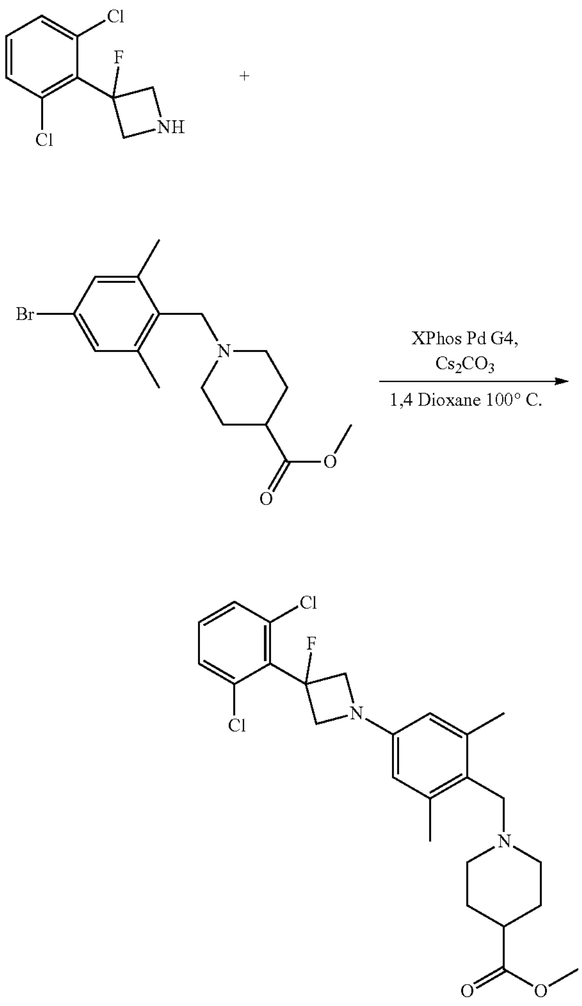

To a solution of methyl 1-(4-bromo-2,6-dimethylbenzyl) piperidine-4-carboxylate (200 mg, 0.588 mmol) and 1-(3-(2,6-dichlorophenyl)-3-fluoroazetidin-1-yl)-2,2,2-trifluoro-ethan-1-one (186 mg, 0.588 mmol) in anhydrous 1,4 dioxane (4 mL) was added cesium carbonate (575 mg, 1.763 mmol). The reaction mixture was degassed with nitrogen for 10 min followed by the addition of XPhos Pd G4 (25.3 mg, 0.029 mmol) and heating to 100° C. After 16 h, TLC analysis indicated complete conversion of the starting material. The reaction mixture was cooled to room temperature and filtered through a celite pad, which was washed with EtOAc. The filtrate was concentrated under reduced pressure and the resulting residue was purified by flash column chromatography on silica gel (100-200 mesh) eluting with 0-100% ethyl acetate in petroleum ether to afford methyl 1-(4-(3-(2,6-dichlorophenyl)-3-fluoroazetidin-1-yl)-2,6-dimethylbenzyl)piperidine-4-carboxylate (170 mg, 60.3% yield) as a yellow solid. LCMS method 1, LCMS (ESI, m/z): 336.0 $[M-142]^+$.

Example S35. 1-(4-(3-(2,6-dichlorophenyl)-3-fluoroazetidin-1-yl)benzyl)piperidine-4-carboxylic acid (35)

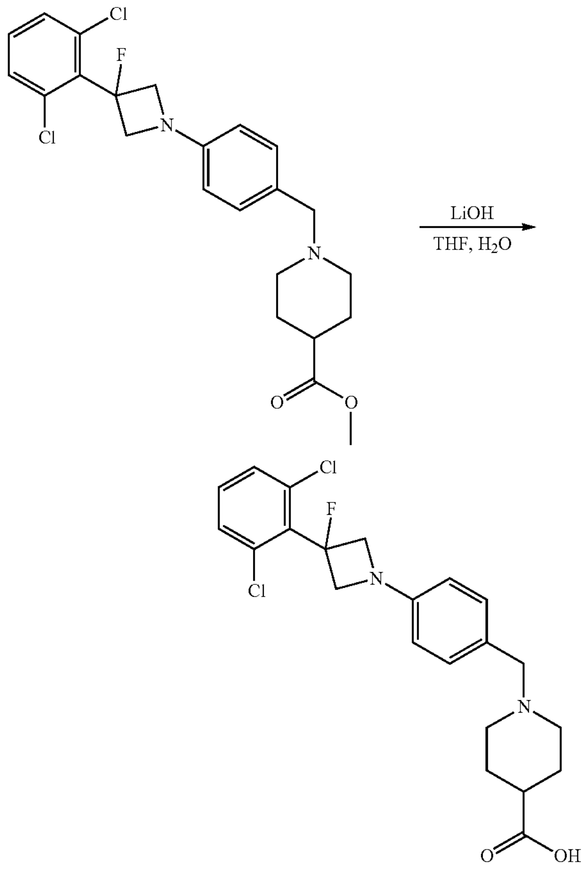

35

To a stirred solution of methyl 1-(4-(3-(2,6-dichlorophenyl)-3-fluoroazetidin-1-yl)benzyl)piperidine-4-carboxylate (80 mg, 0.177 mmol) in THF (2 mL) and $H_2O$ (0.5 mL) was added LiOH (22.31 mg, 0.532 mmol). The resulting mixture was stirred at room temperature and the progress of the reaction was monitored by TLC. After 1 h, TLC analysis indicated complete conversion of the starting material. The reaction mixture was then acidified with acetic acid and concentrated under reduced pressure. The resulting residue was purified by reverse phase preparative HPLC. Prep. HPLC method: Diluent: THF:Acetonitrile (30:70), Column: Symmetry C8 (300×19) mm, 7 micron, Mobile phase A: 0.1% Formic acid in water, Mobile phase B: Acetonitrile. The required fractions were collected and lyophilized to afford 1-(4-(3-(2,6-dichlorophenyl)-3-fluoroazetidin-1-yl)-benzyl)piperidine-4-carboxylic acid (11 mg, 12.67% yield, 99.2% pure) as a white solid. $^1H$ NMR: (400 MHz, MeOD) δ 7.50 (d, J=7.50 Hz, 2H), 7.40 (t, J=7.40 Hz, 1H), 7.32 (d, J=7.34 Hz, 2H), 6.69 (d, J=6.72 Hz, 2H), 4.82-4.69 (m, 2H), 4.51-4.42 (m, 2H), 4.08 (s, 2H), 2.88 (s, 2H), 2.34 (s, 1H), 2.03 (d, J=2.06 Hz, 2H), 1.87 (s, 2H). 2H are merged with MeOD solvent signal peak. LCMS method 1, LCMS (ESI, m/z): 435.3 $[M]^-$.

Example S36. 1-(4-(3-(2,6-dichlorophenyl)-3-fluoroazetidin-1-yl)-3,5-dimethylbenzyl)-piperidine-4-carboxylic acid (36)

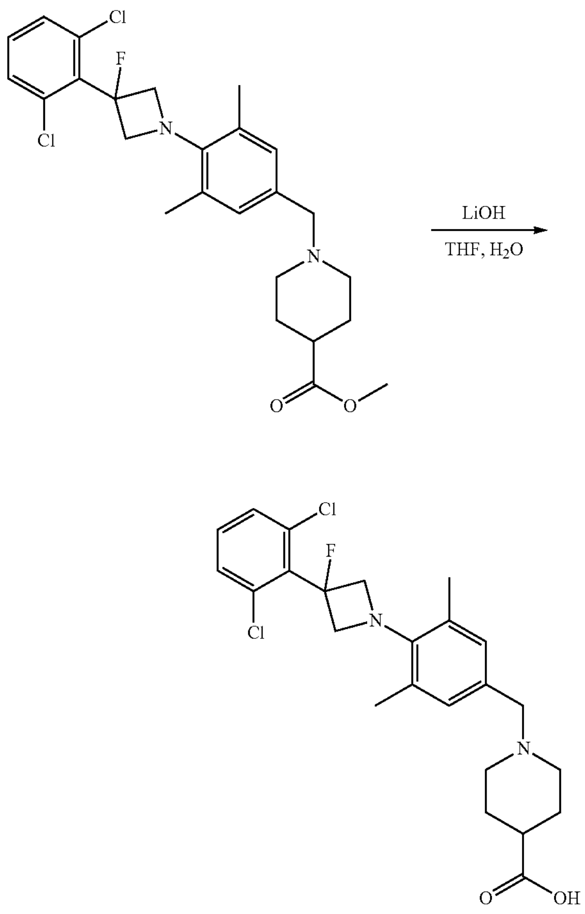

36

To a stirred solution of methyl 1-(4-(3-(2,6-dichlorophenyl)-3-fluoroazetidin-1-yl)-3,5-dimethylbenzyl)piperidine-4-carboxylate (150 mg, 0.313 mmol) in THF (4 mL) and $H_2O$ (1 mL) was added LiOH (39.4 mg, 0.939 mmol). The resulting mixture was stirred at room temperature and the progress of the reaction was monitored by TLC. After 1 h, TLC analysis indicated complete conversion of the starting material. The reaction mixture was acidified with acetic acid and concentrated under reduced pressure. The resulting residue was purified by reverse phase preparative HPLC. Prep. HPLC method: Diluent: THF:Acetonitrile (50:50), Column: Xselect C18 (250×19) mm, 5 micron, Mobile phase A: 10 mM Ammonium formate in water, Mobile phase B: Acetonitrile. The required fractions were collected and lyophilized to afford 1-(4-(3-(2,6-dichlorophenyl)-3-fluoroazetidin-1-yl)benzyl)piperidine-4-carboxylic acid (11 mg, 12.67% yield, 99.5% pure) as a white solid. $^1H$ NMR (400 MHz, MeOD): δ 7.49-7.47 (m, 2H), 7.41-7.37 (m, 1H), 6.99 (s, 2H), 5.03-4.94 (m, 2H), 4.78-4.75 (m, 1H), 4.71-4.68 (m, 1H), 4.07 (s, 2H), 2.96 (m, 2H), 2.40 (s, 7H), 2.05 (s, 2H), 1.84 (s, 1H). 2H are merged with MeOD solvent signal peak. LCMS method 1, LCMS (ESI, m/z): 465.2 $[M]^-$.

Example S37. 1-(4-(3-(2,6-dichlorophenyl)-3-fluoroazetidin-1-yl)-2,6-dimethylbenzyl)-piperidine-4-carboxylic acid (37)

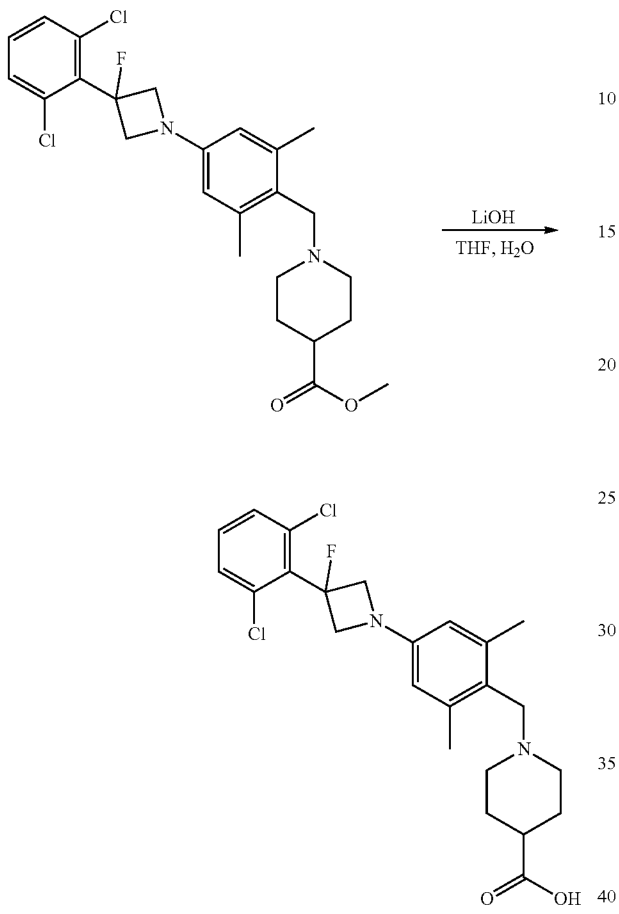

37

To a stirred solution of methyl 1-(4-(3-(2,6-dichlorophenyl)-3-fluoroazetidin-1-yl)-2,6-dimethylbenzyl)piperidine-4-carboxylate (150 mg, 0.313 mmol) in THF (4 mL) and $H_2O$ (1 mL) was added LiOH (39.4 mg, 0.939 mmol). The resulting mixture was stirred at room temperature and the progress of the reaction was monitored by TLC. After 1 h, TLC analysis indicated complete conversion of the starting material. The reaction mixture was then acidified using acetic acid and concentrated under reduced pressure. The resulting residue was purified by reverse phase preparative HPLC. Prep. HPLC method: Diluent: THF:Acetonitrile (50:50), Column: Xselect C18 (250×19) mm, 5 micron, Mobile phase A: 10 mM Ammonium formate in water, Mobile phase B: Acetonitrile. The required fractions were collected and lyophilized to afford 1-(4-(3-(2,6-dichlorophenyl)-3-fluoroazetidin-1-yl)-2,6-dimethylbenzyl)piperidine-4-carboxylic acid, formic acid salt (32 mg, 0.062 mmol, 19.77% yield, 98.4% pure) as a white solid. $^1H$ NMR: (400 MHz, MeOD) δ 7.48 (d, J=7.50 Hz, 2H), 7.40 (m, 1H), 6.43 (s, 2H), 4.69 (m, 2H), 4.44 (d, J=4.47 Hz, 1H), 4.38 (d, J=4.40 Hz, 1H), 4.24 (s, 2H), 3.44 (m, 2H), 3.08 (s, 2H), 2.42 (s, 7H), 2.05 (d, J=2.08 Hz, 2H), 1.89 (m, 2H). LCMS method 1; LCMS (ESI, m/z): 465.0 $[M]^-$.

General Route to Compounds 38-43

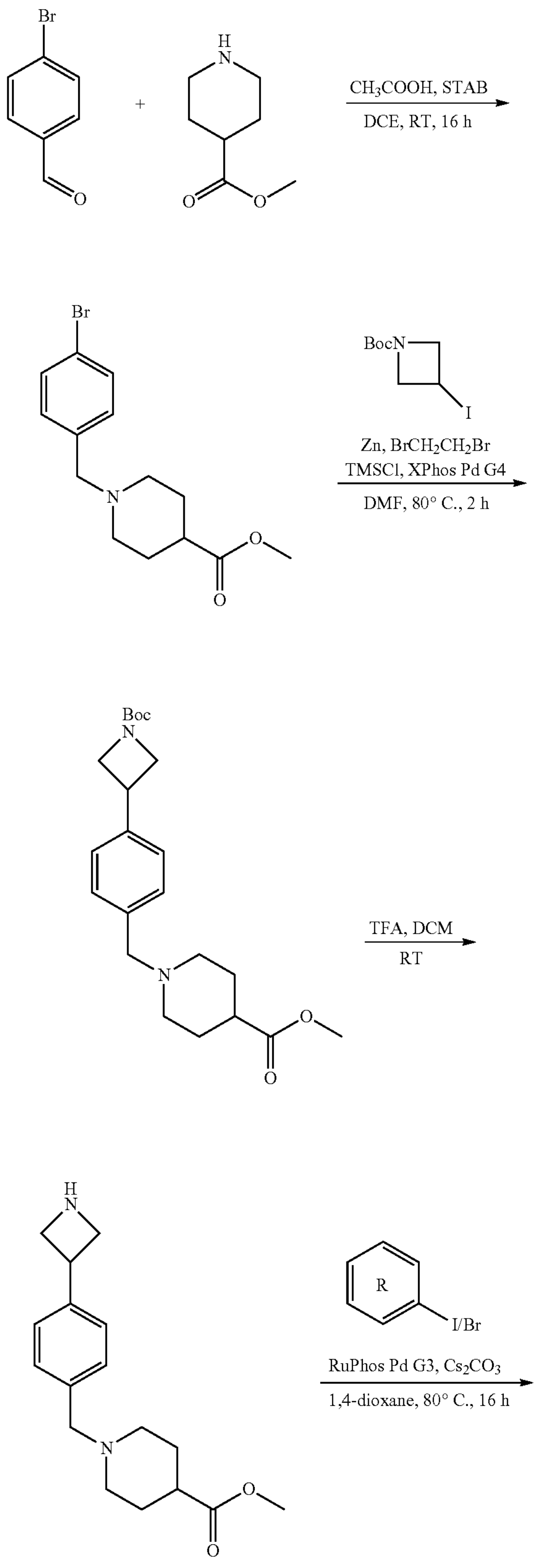

-continued

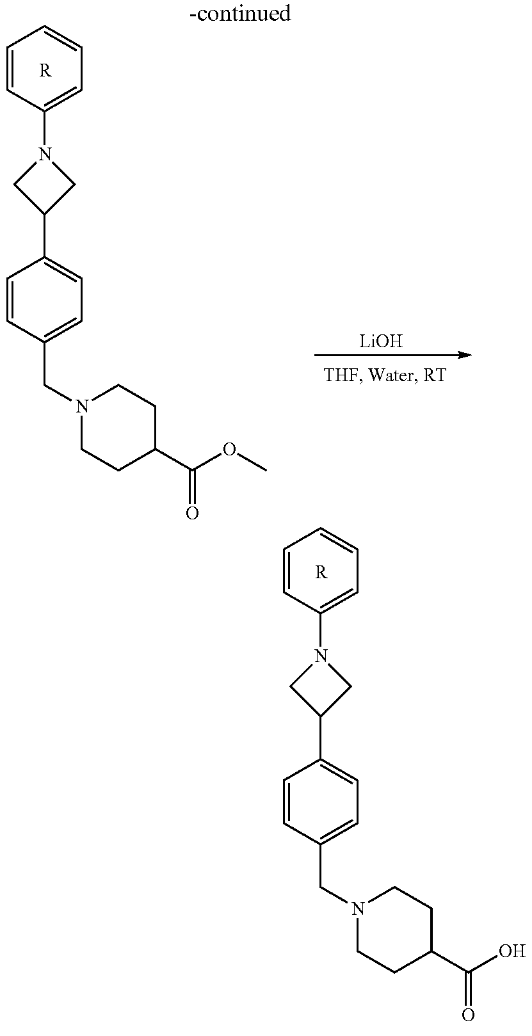

38-43

Synthesis of methyl 1-(4-(1-(2,6-difluorophenyl) azetidin-3-yl)benzyl)piperidine-4-carboxylate

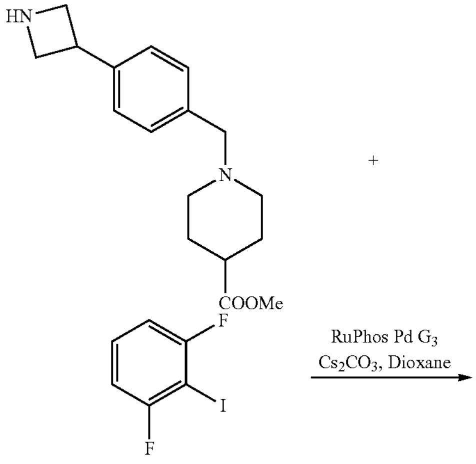

-continued

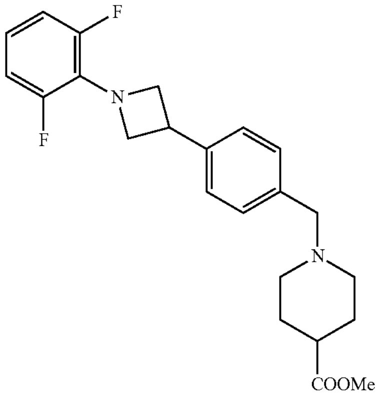

To a solution of methyl 1-(4-(azetidin-3-yl)benzyl)piperidine-4-carboxylate (300 mg, 1.040 mmol) and 1,3-difluoro-2-iodobenzene (225 mg, 0.936 mmol) in anhydrous 1,4 dioxane (5 mL) was added $Cs_2CO_3$ (847 mg, 2.60 mmol). The reaction mixture was degassed with nitrogen for 10 min followed by addition of RuPhos Pd G3 (87 mg, 0.104 mmol) and heated to 95° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 20-50% ethyl acetate in petroleum ether to afford methyl 1-(4-(1-(2,6-difluorophenyl)azetidin-3-yl)benzyl)piperidine-4-carboxylate (100 mg, 23% yield) as a yellow semi-solid; LCMS method 5, LCMS (ESI, m/z): 400.6 $[M+H]^+$.

Synthesis of methyl 1-(4-(1-phenylazetidin-3-yl) benzyl)piperidine-4-carboxylate

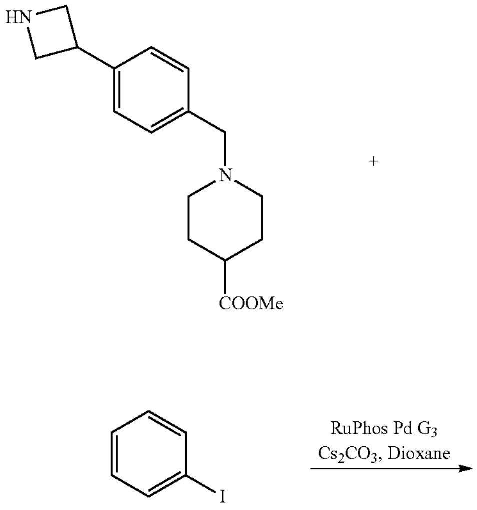

-continued

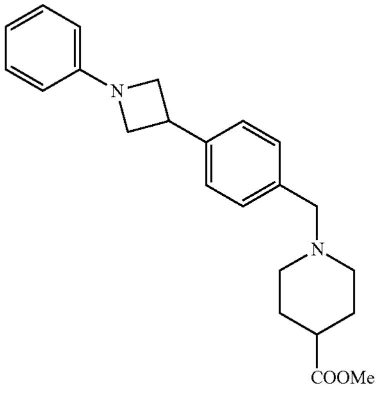

Under nitrogen, to a solution of methyl 1-(4-(azetidin-3-yl)benzyl)piperidine-4-carboxylate, TFA (300 mg, 0.746 mmol) and iodobenzene (152 mg, 0.746 mmol) in anhydrous 1,4-dioxane (5 mL) was added cesium carbonate (607 mg, 1.864 mmol) followed by the addition of iodobenzene (152 mg, 0.746 mmol). The reaction mixture was then heated to 95° C. After 16 h, TLC analysis indicated complete conversion of the starting material. The reaction mixture was cooled to ambient temperature and filtered through a pad of celite which was washed with ethyl acetate. The filtrate was then concentrated under reduced pressure and the resulting residue was purified by flash column chromatography on silica gel (230-400 mesh) eluting with 0-50% ethyl acetate in petroleum ether to afford methyl 1-(4-(1-phenylazetidin-3-yl)benzyl)piperidine-4-carboxylate (110 mg, 37.2%) as a pale brown gum. LCMS method 1, LCMS (ESI, m/z): 365.2 $[M+H]^+$.

Synthesis of methyl 1-(4-(1-(2-fluorophenyl)azetidin-3-yl)benzyl)piperidine-4-carboxylate

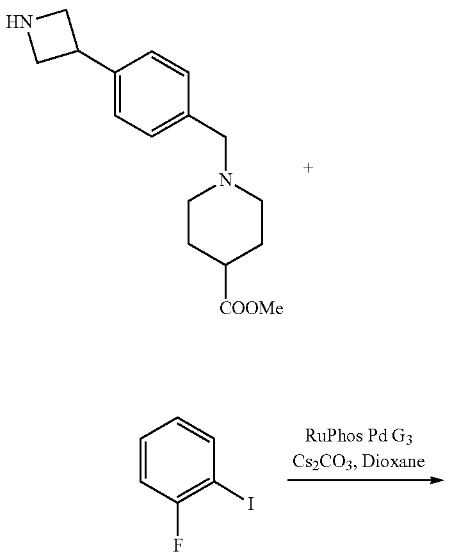

-continued

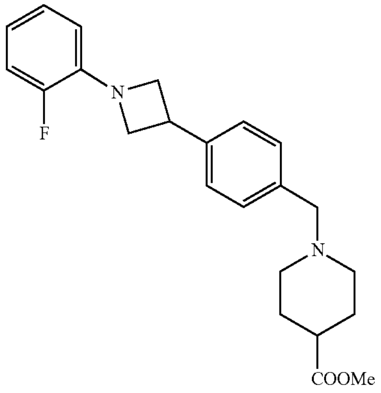

To a solution of methyl 1-(4-(azetidin-3-yl)benzyl)piperidine-4-carboxylate (200 mg, 0.694 mmol) and 1-fluoro-2-iodobenzene (139 mg, 0.624 mmol) in anhydrous 1,4 dioxane (10 mL) was added $Cs_2CO_3$ (565 mg, 1.734 mmol). The reaction mixture was degassed with nitrogen for 10 min followed by addition of RuPhos Pd G3 (58.1 mg, 0.069 mmol) and heated to 95° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (60-120 mesh) eluting with 0-50% ethyl acetate in petroleum ether to afford methyl 1-(4-(1-(2-fluorophenyl)azetidin-3-yl)benzyl)piperidine-4-carboxylate (50 mg, 18% yield) as a yellow semi-solid. LCMS method 1, LCMS (ESI, m/z): 382.8.0 $[M+2H]^+$.

Synthesis of methyl 1-(4-(1-(3-fluorophenyl)azetidin-3-yl)benzyl)piperidine-4-carboxylate

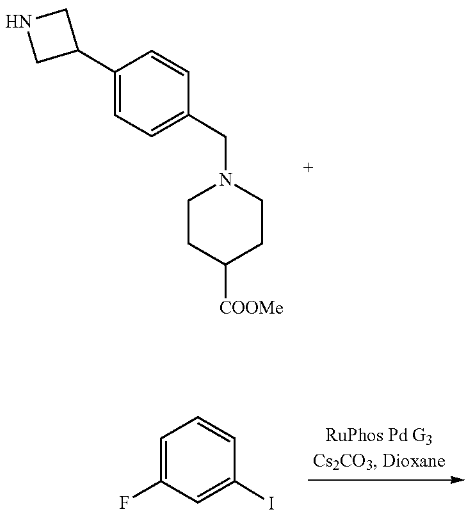

-continued

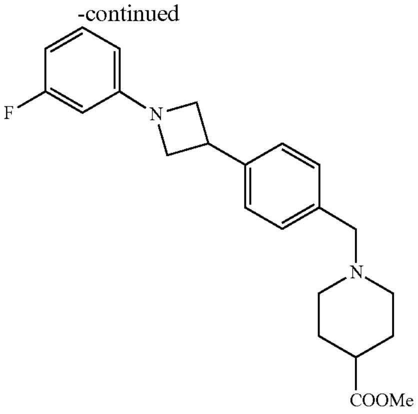

To a solution of methyl 1-(4-(azetidin-3-yl)benzyl)piperidine-4-carboxylate (300 mg, 1.040 mmol) and 1-fluoro-3-iodobenzene (208 mg, 0.936 mmol) in anhydrous 1,4 dioxane (5 mL) was added $Cs_2CO_3$ (847 mg, 2.60 mmol). The reaction mixture was degassed with nitrogen for 10 min followed by addition of RuPhos Pd G3 (87 mg, 0.104 mmol) and heated to 95° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 20-50% ethyl acetate in petroleum ether to afford methyl 1-(4-(1-(3-fluorophenyl)azetidin-3-yl)benzyl)piperidine-4-carboxylate (142 mg, 35% yield) as a white solid. LCMS method 2, LCMS (ESI, m/z): 383.2 $[M+H]^+$.

Synthesis of methyl 1-(4-(1-(3-chloro-4-cyclopropylphenyl)azetidin-3-yl)-benzyl)piperidine-4-carboxylate

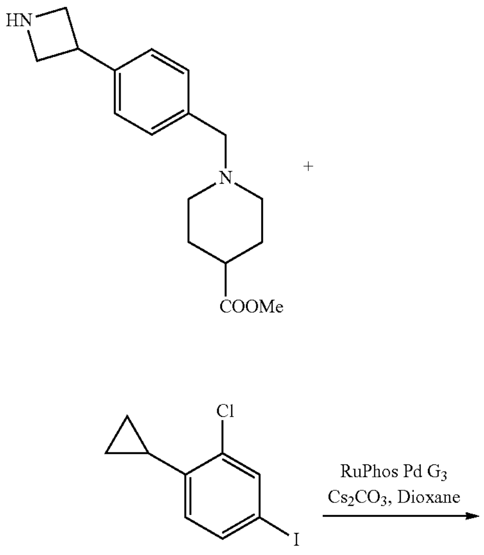

-continued

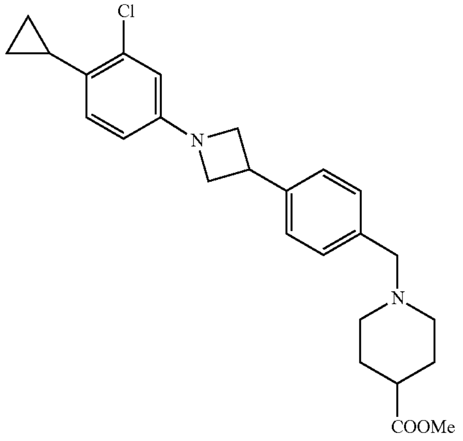

To a stirred solution of methyl 1-(4-(azetidin-3-yl)benzyl)piperidine-4-carboxylate (207 mg, 0.718 mmol) in 1,4-dioxane (5 mL) was added 2-chloro-1-cyclopropyl-4-iodobenzene (200 mg, 0.718 mmol) and cesium carbonate (468 mg, 1.436 mmol). The reaction mixture was degassed under vacuum and back filled with nitrogen. After 10 min, Ruphos Pd G3 (60.1 mg, 0.072 mmol) was added and the mixture heated to 100° C. After 16 h, TLC analysis indicated complete conversion of the starting material. The reaction mixture was then cooled to ambient temperature and filtered through a pad of celite and washed with ethyl acetate. The filtrate was then concentrated under reduced pressure and the resulting residue was dissolved in ethyl acetate (10 mL) and washed with ice cold water. The organic layer was dried over sodium sulphate and concentrated. The crude material was then purified by flash column chromatography on silica gel (230-400 mesh) eluting with 30-70% ethyl acetate in petroleum ether to afford methyl 1-(4-(1-(3-chloro-4-cyclopropylphenyl)azetidin-3-yl)benzyl)piperidine-4-carboxylate (90 mg, 28% yield) as a yellow-semi solid. LCMS method 1, LCMS (ESI, m/z): 439.3 $[M+H]^+$.

Synthesis of methyl 1-(4-(1-(4-cyclopropylphenyl)azetidin-3-yl)benzyl)piperidine-4-carboxylate

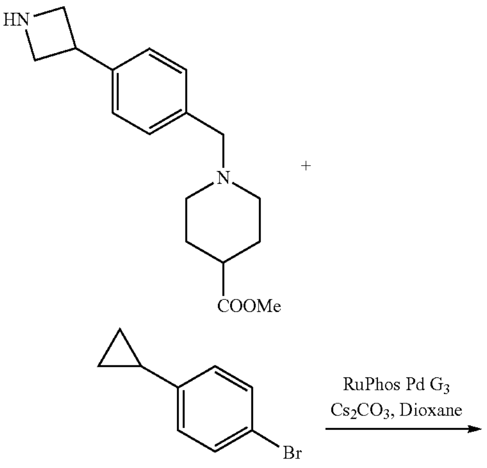

-continued

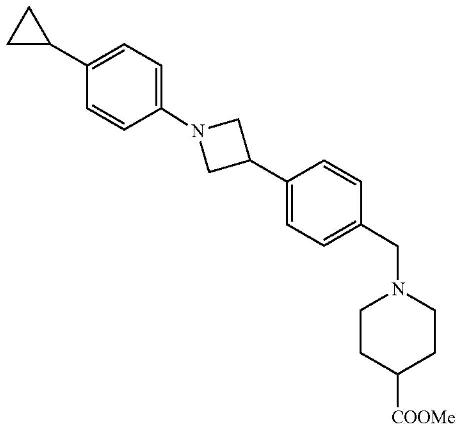

To a solution of methyl 1-(4-(azetidin-3-yl)benzyl)piperidine-4-carboxylate, TFA (150 mg, 0.373 mmol) and 1-bromo-4-cyclopropylbenzene (66.1 mg, 0.335 mmol) in anhydrous 1,4-dioxane (5 mL) was added cesium carbonate (304 mg, 0.932 mmol) followed by the addition of Ruphos Pd G3 (31.2 mg, 0.037 mmol). The reaction mixture was degassed under vacuum and back-filled with nitrogen, then heated to 90° C. under nitrogen atmosphere. After 16 h, TLC analysis indicated complete conversion of the starting material. The reaction mixture was cooled to room temperature and filtered through a pad of celite, washed with ethyl acetate. The filtrate was then concentrated under reduced pressure and the resulting residue was purified by flash column chromatography on silica gel eluting with 0-100% ethyl acetate in petroleum ether to afford methyl 1-(4-(1-(4-cyclopropylphenyl)azetidin-3-yl)benzyl)piperidine-4-carboxylate (53 mg, 34.1%) as colorless oil. LCMS method 1, LCMS (ESI, m/z): 405.3 $[M+H]^+$.

Example S38. 1-(4-(1-(2,6-difluorophenyl)azetidin-3-yl)benzyl)piperidine-4-carboxylic acid (38)

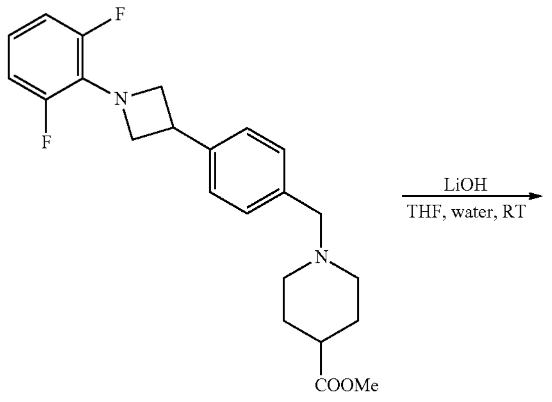

-continued

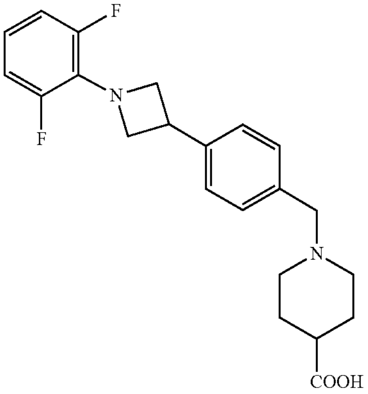

38

To a solution of methyl 1-(4-(1-(2,6-difluorophenyl)azetidin-3-yl)benzyl)piperidine-4-carboxylate (40 mg, 0.100 mmol) in THF (3 mL) and water (1 mL) was added LiOH (12.57 mg, 0.300 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid to a pH of 5-6. The resulting solid was filtered and washed with diethyl ether to yield 1-(4-(1-(2,6-difluorophenyl)azetidin-3-yl)benzyl)piperidine-4-carboxylic acid (15 mg, 38.2% yield, 98.3% pure) as a white solid. $^1H$ NMR (400 MHz, MeOD): δ 7.54-7.52 (m, 2H), 7.47-7.45 (m, 2H), 6.86-6.79 (m, 2H), 6.73-6.66 (m, 1H), 4.63-4.57 (m, 2H), 4.20-4.15 (m, 2H), 4.11 (s, 1H), 4.00-3.94 (m, 1H), 3.33-3.32 (m, 1H), 2.84 (s, 2H), 2.37-2.35 (m, 1H), 2.06-2.03 (m, 2H), 1.89-1.86 (m, 2H). LCMS method 2; LCMS (ESI, m/z): 386.8 $[M+H]^+$.

Example S39. 1-(4-(1-phenylazetidin-3-yl)benzyl)piperidine-4-carboxylic acid (39)

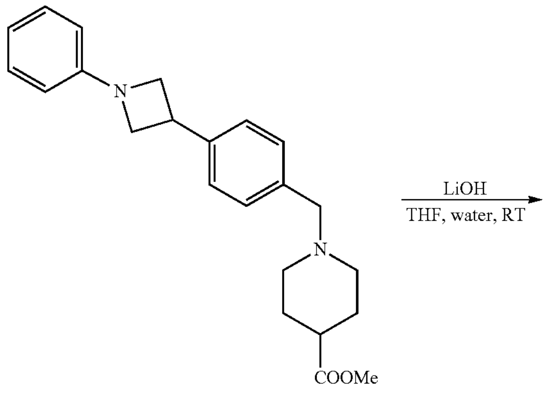

-continued

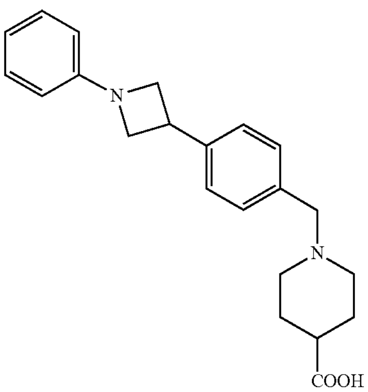

39

-continued

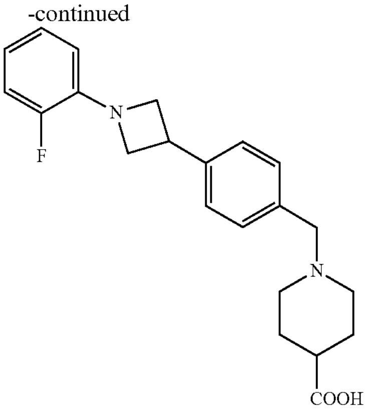

40

To a solution of methyl 1-(4-(1-phenylazetidin-3-yl)benzyl)piperidine-4-carboxylate (110 mg, 0.278 mmol) in THF (5 mL) and water (1 mL) was added LiOH (26.6 mg, 1.111 mmol). The reaction mixture was allowed to stir at ambient temperature and the progress of the reaction was monitored by TLC analysis. After 16 h, TLC analysis indicated complete conversion of the starting material. The reaction mixture was concentrated under reduced pressure and the aqueous layer was then acidified with acetic acid to pH=4. The precipitate was filtered, rinsed with diethyl ether and dried under vacuum to afford 1-(4-(1-phenylazetidin-3-yl)benzyl) piperidine-4-carboxylic acid (40 mg, 40.2%) as a beige solid. $^1$H NMR (400 MHz, $CD_3OD$) δ 7.33 (d, J=8 Hz, 2H), 7.26 (d, J=8.4 Hz, 2H), 7.21-7.17 (m, 2H), 6.72-6.68 (m, 1H), 6.49 (d, J=7.6 Hz), 4.25-4.21 (m, 2H), 3.95-3.92 (m, 1H), 3.78-3.75 (m, 2H), 3.42 (s, 2H), 2.74-2.67 (m, 2H), 2.21-2.17 (m, 1H), 1.99-1.93 (m, 2H), 1.78-1.75 (m, 2H), 1.57-1.51 (m, 2H). LCMS method 1; LCMS (ESI, m/z): 351.2 [M+H]$^+$.

Example S40. 1-(4-(1-(2-fluorophenyl)azetidin-3-yl) benzyl)piperidine-4-carboxylic acid (40)

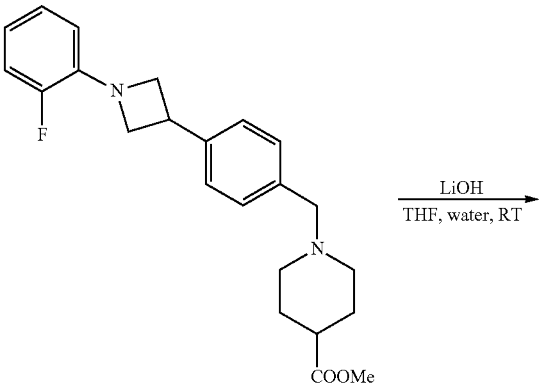

To a solution of methyl 1-(4-(1-(2-fluorophenyl)azetidin-3-yl)benzyl)piperidine-4-carboxylate (45 mg, 0.118 mmol) in THF (4 mL) and water (1 mL) was added LiOH (14.81 mg, 0.353 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Symmetry C8 (300×19) mm, 7 micron. Mobile phase A: 5 mM Ammonium formate in water Mobile phase B: Acetonitrile. The required fractions were collected and lyophilized to afford 1-(4-(1-(2-fluorophenyl)azetidin-3-yl)benzyl)piperidine-4-carboxylic acid, formic acid salt (14 mg, 0.034 mmol, 28.5% yield, 99.1% pure) as an off white solid. $^1$H NMR (400 MHz, DMSO-d6): δ 7.35-7.33 (m, 2H), 7.27-7.25 (m, 2H), 7.08-7.02 (m, 2H), 6.76-6.71 (m, 1H), 6.64-6.59 (m, 1H), 4.33-4.30 (m, 2H), 3.95-3.85 (m, 3H), 3.49-3.48 (m, 2H), 2.74-2.67 (m, 2H), 2.17-2.11 (m, 1H), 1.97-1.92 (t, J=11.2 Hz, 2H), 1.77-1.74 (m, 2H), 1.56-1.48 (m, 2H). LCMS method 1; LCMS (ESI, m/z): 367.2 [M+H]$^+$.

Example S41. 1-(4-(1-(3-fluorophenyl)azetidin-3-yl)-2,6-dimethylbenzyl)piperidine-4-carboxylic acid (41)

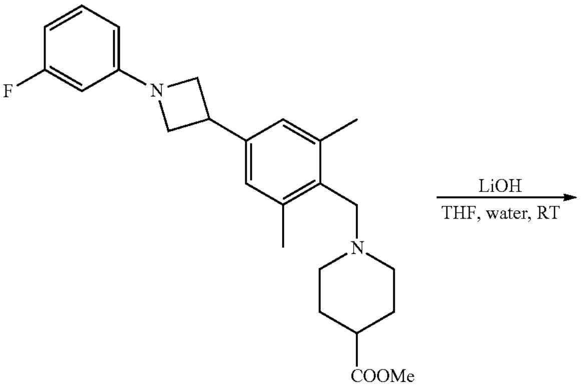

-continued

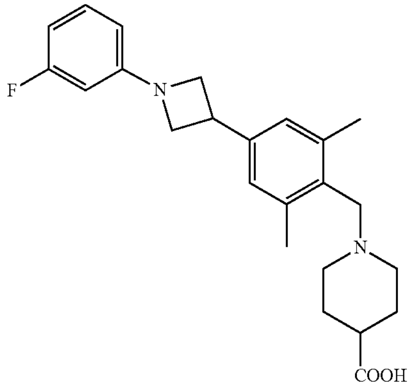

41

To a solution of methyl 1-(4-(1-(3-fluorophenyl)azetidin-3-yl)benzyl)piperidine-4-carboxylate (140 mg, 0.366 mmol) in THF (3 mL) and water (1 mL) was added LiOH (46.1 mg, 1.098 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid to pH 5-6. The solid thus obtained was filtered off and washed with diethyl ether to yield 1-(4-(1-(3-fluorophenyl)azetidin-3-yl)benzyl)piperidine-4-carboxylic acid (38 mg, 0.102 mmol, 27.9% yield, 99.18% pure) as an off-white solid. $^1$H NMR (400 MHz, DMSO-$d_6$): δ 7.33-7.31 (m, 2H), 7.27-7.25 (m, 2H), 7.22-7.16 (m, 1H), 6.49-6.44 (m, 1H), 6.31-6.26 (m, 2H), 4.26-4.22 (m, 2H), 3.96-3.92 (m, 1H), 3.81-3.78 (m, 2H), 3.41 (s, 2H), 2.74-2.67 (m, 2H), 2.20-2.14 (m, 1H), 1.98-1.90 (m, 2H), 1.77-1.75 (m, 2H), 1.53-1.51 (m, 2H). LCMS method 1; LCMS (ESI, m/z): 369.2 $[M+H]^+$.

Example S42. 1-(4-(1-(3-chloro-4-cyclopropylphenyl)azetidin-3-yl)benzyl)piperidine-4-carboxylic acid (42)

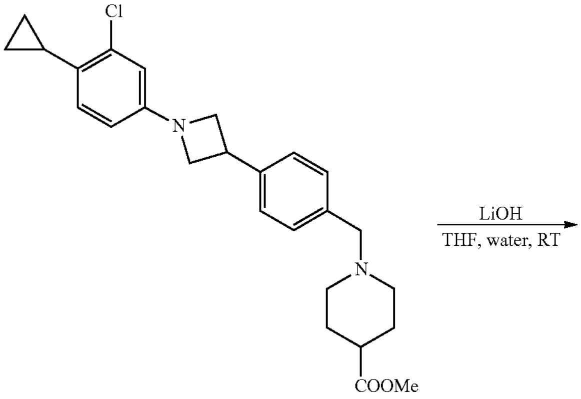

-continued

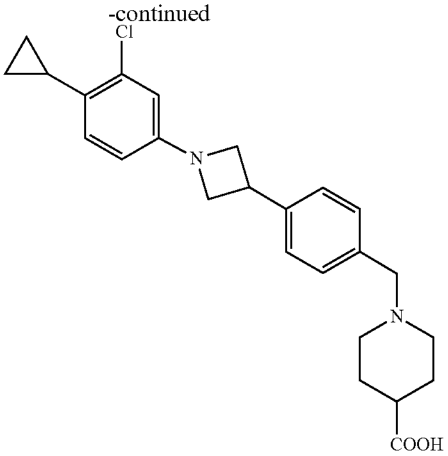

42

To a solution of methyl 1-(4-(1-(3-chloro-4-cyclopropylphenyl)azetidin-3-yl)benzyl)piperidine-4-carboxylate (90 mg, 0.205 mmol) in THF (4 mL) and water (1 mL) was added LiOH (14.73 mg, 0.615 mmol). The resulting mixture was stirred at ambient temperature and the progress of the reaction was monitored by TLC analysis. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30) Column: Xselect C18 (150×19) mm, 5 micron. Mobile phase A: 0.1% Formic acid in water, Mobile phase B: Acetonitrile. The required fractions were collected and lyophilized to afford 1-(4-(1-(3-chloro-4-cyclopropyl-phenyl)azetidin-3-yl)benzyl)piperidine-4-carboxylic acid, formic acid salt (17.8 mg, 0.037 mmol, 18.00% yield, 97.7% pure) as a white solid. $^1$H NMR: (400 MHz, MeOD): δ 12.05 (s, 1H), 7.25-7.33 (m, 4H), 6.88 (d, J=8.40 Hz, 1H), 6.53 (d, J=2.40 Hz, 1H), 6.37-6.39 (m, 1H), 4.20-4.24 (m, 2H), 3.78-3.94 (m, 1H), 2.68-3.76 (m, 2H), 2.53-2.68 (m, 2H), 2.50-2.51 (m, 2H), 1.99-2.00 (m, 1H), 1.95-1.98 (m, 3H), 1.77 (d, J=10.40 Hz, 2H), 1.53 (d, J=9.60 Hz, 2H), 0.87-0.91 (m, 2H), 0.55-0.58 (m, 2H). LCMS method 1; LCMS (ESI, m/z): 425.2 $[M+H]^+$.

Example S43. 1-(4-(1-(4-cyclopropylphenyl)azetidin-3-yl)benzyl)piperidine-4-carboxylic acid (43)

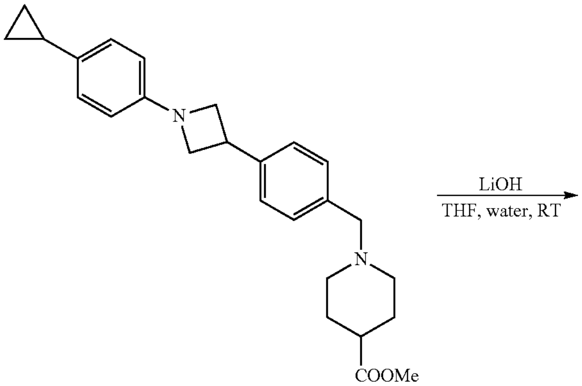

-continued

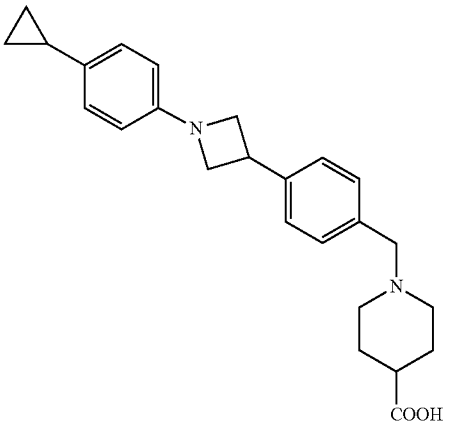

43

To a solution of methyl 1-(4-(1-(4-cyclopropylphenyl)azetidin-3-yl)benzyl)piperidine-4-carboxylate (50 mg, 0.124 mmol) in THF (5 mL) and water (1 mL) was added LiOH (8.88 mg, 0.371 mmol) and the reaction mixture was stirred at room temperature. After 16 h, TLC analysis indicated complete conversion of the starting material. The reaction mixture was then concentrated under reduced pressure and the aqueous layer was extracted with diethyl ether (15 mL). The aqueous layer was then acidified with acetic acid to pH 4 and the precipitate was collected by filtration, rinsed with diethyl ether and dried under vacuum to afford 1-(4-(1-(4-cyclopropylphenyl)azetidin-3-yl)benzyl)piperidine-4-carboxylic acid (24 mg, 47.9%) as beige solid. $^1$H NMR (400 MHz, $CD_3OD$); δ 7.50 (d, J=8.0 Hz, 2H), 7.45 (d, J=8.4 Hz, 2H), 6.98-6.95 (m, 2H), 6.50-6.48 (m, 2H), 4.29-4.25 (m, 2H), 4.12 (s, 2H), 4.09-3.97 (m, 1H), 3.83-3.80 (m, 2H), 2.86 (m, 2H), 2.38 (m, 1H), 2.06-2.03 (m, 2H), 1.89-1.79 m, 3H), 0.89-0.85 (m, 2H), 0.59-0.56 (m, 2H). LCMS method 1; LCMS (ESI, m/z): 391.2 [M+H]$^+$.

General Route to Compounds 44-49

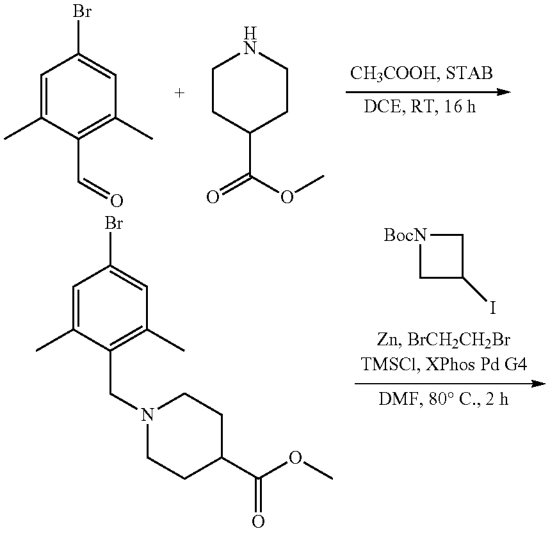

-continued

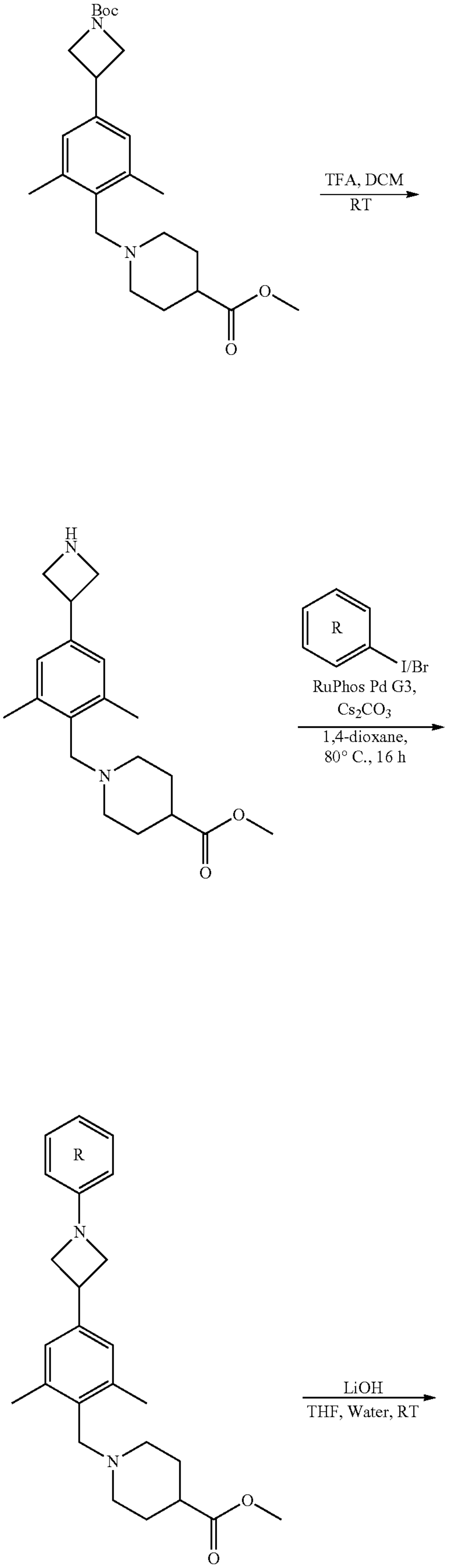

-continued

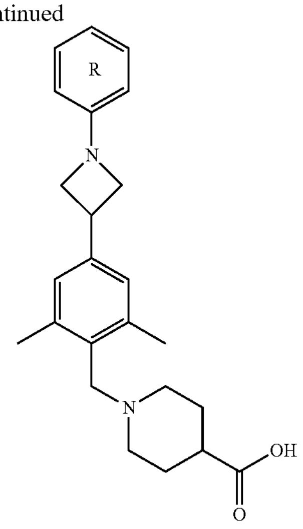

44-49

Synthesis of methyl 1-(4-(1-(2,6-difluorophenyl) azetidin-3-yl)-2,6-dimethyl-benzyl)piperidine-4-carboxylate

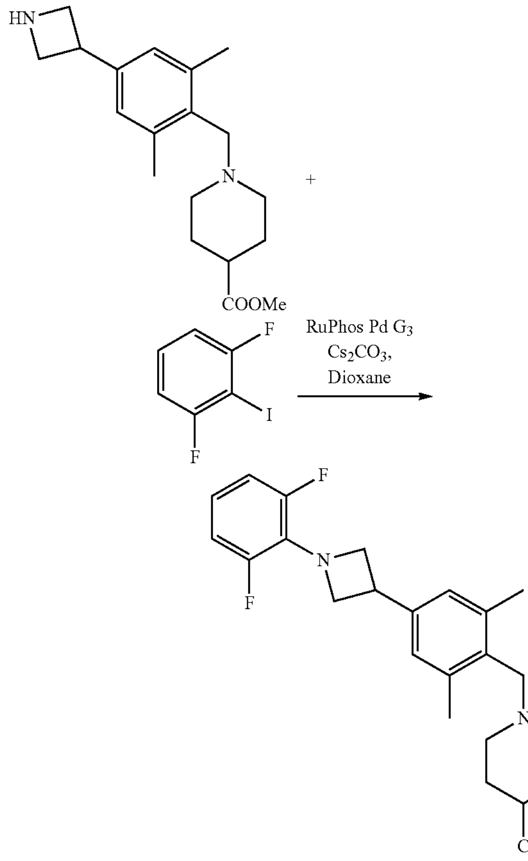

To a solution of methyl 1-(4-(azetidin-3-yl)-2,6-dimethylbenzyl)piperidine-4-carboxylate, TFA (300 mg, 0.697 mmol) and 1,3-difluoro-2-iodobenzene (201 mg, 0.836 mmol) in anhydrous 1,4 dioxane (10 mL) was added cesium carbonate (1135 mg, 3.48 mmol). The reaction mixture was degassed with nitrogen for 10 min followed by addition of RuPhos Pd G3 (58.3 mg, 0.070 mmol) and heating to 100° C. After 16 h, TLC analysis indicated complete conversion of the starting material. The reaction mixture was cooled to room temperature and filtered through a pad of celite which was washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2,6-difluorophenyl)azetidin-3-yl)-2,6-dimethylbenzyl)piperidine-4-carboxylate (190 mg, 41.7% yield) as a light brown semi-solid. LCMS method 1, LCMS (ESI, m/z): 429.2 $[M+H]^+$.

Synthesis of methyl 1-(2,6-dimethyl-4-(1-phenylazetidin-3-yl)benzyl)piperidine-4-carboxylate

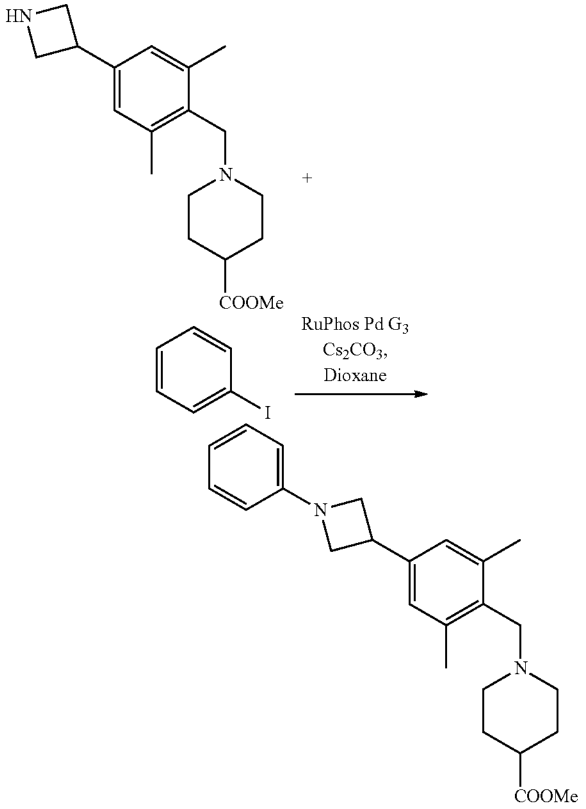

To a solution of methyl 1-(4-(azetidin-3-yl)-2,6-dimethylbenzyl)piperidine-4-carboxylate, TFA (300 mg, 0.697 mmol) and iodobenzene (171 mg, 0.836 mmol) in anhydrous 1,4 dioxane (10 mL) was added cesium carbonate (1135 mg, 3.48 mmol). The reaction mixture was degassed with nitrogen for 10 min followed by addition of RuPhos-Pd-G3 (58.3 mg, 0.070 mmol) and heating to 100° C. After 16 h, TLC analysis indicated complete conversion of the starting material. The reaction mixture was cooled to room temperature and filtered through a pad of celite which was washed with EtOAc. The filtrate was concentrated under reduced pressure and the resulting residue was purified by flash column chromatography on silica gel (230-400 mesh) eluting with 0-35% ethyl acetate in petroleum ether to afford methyl 1-(2,6-dimethyl-4-(1-phenylazetidin-3-yl)benzyl)piperidine-4-carboxylate (170 mg, 59.0% yield) as a light brown semi-solid. LCMS method 1, LCMS (ESI, m/z): 393.3 $[M+H]^+$.

Synthesis of methyl 1-(4-(1-(2-fluorophenyl)azetidin-3-yl)-2,6-dimethyl-benzyl)piperidine-4-carboxylate

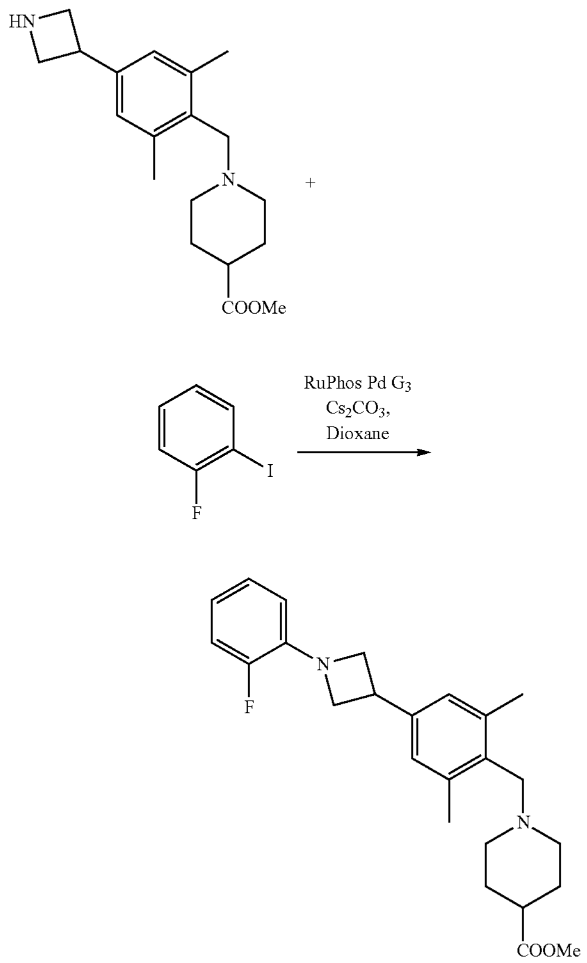

To a solution of methyl 1-(4-(azetidin-3-yl)-2,6-dimethylbenzyl)piperidine-4-carboxylate (300 mg, 0.948 mmol) and 1-ethyl-2-iodo-3-methylbenzene (467 mg, 1.896 mmol) in anhydrous 1,4 dioxane (10 mL) was added cesium carbonate (2.84 mmol). The reaction mixture was then degassed with nitrogen for 10 min followed by addition of RuPhos Pd G3 (79 mg, 0.095 mmol) and heating to 80° C. After 12 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (60-120 mesh) eluting with 0-50% ethyl acetate in petroleum ether to afford methyl 1-(4-(1-(2-ethyl-6-methylphenyl)azetidin-3-yl)-2,6-dimethylbenzyl)piperidine-4-carboxylate (170 mg, 41.0% yield) as a brown liquid. LCMS method 1, LCMS (ESI, m/z): 435.2 $[M+H]^+$.

Synthesis of methyl 1-(4-(1-(3-fluorophenyl)azetidin-3-yl)-2,6-dimethyl-benzyl)piperidine-4-carboxylate

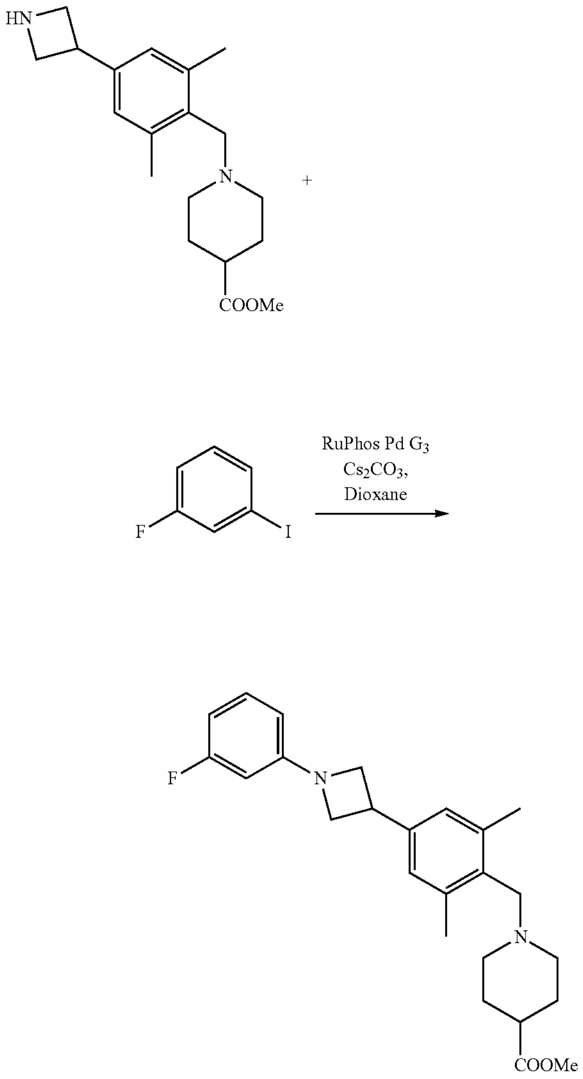

To a solution of methyl 1-(4-(azetidin-3-yl)-2,6-dimethylbenzyl)piperidine-4-carboxylate (500 mg, 1.580 mmol) and 1,3-diethyl-2-iodobenzene (493 mg, 1.896 mmol) in anhydrous 1,4 dioxane (10 mL) was added cesium carbonate (4.74 mmol). The reaction mixture was degassed with nitrogen for 10 min followed by addition of RuPhos Pd G3 (132 mg, 0.158 mmol) and heating to 80° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (60-120 mesh) eluting with 0-50% ethyl acetate in petroleum ether to afford methyl 1-(4-(1-(2,6-diethylphenyl)azetidin-3-yl)-2,6-dimethylbenzyl)piperidine-4-carboxylate (300 mg, 42% yield) as a yellow solid. LCMS method 3, LCMS (ESI, m/z): 449.2 $[M+H]^+$.

Synthesis of methyl 1-(4-(1-(4-cyclopropylphenyl) azetidin-3-yl)-2,6-dimethyl-benzyl)piperidine-4-carboxylate

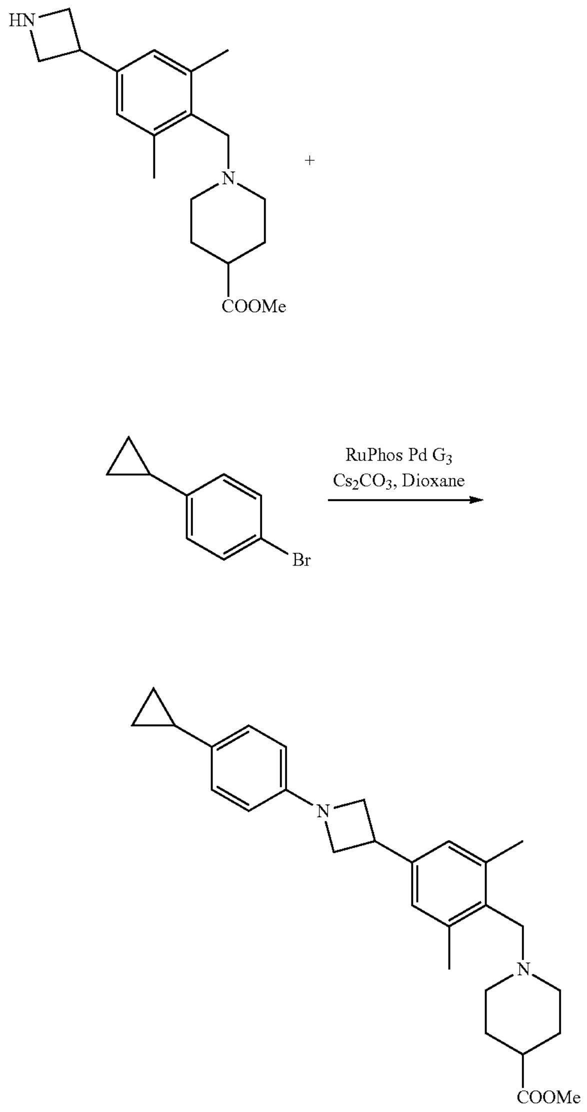

To a solution of methyl 1-(4-(azetidin-3-yl)-2,6-dimethylbenzyl)piperidine-4-carboxylate, TFA (500 mg, 1.162 mmol) and 1-cyclopropyl-2-iodobenzene (354 mg, 1.452 mmol) in anhydrous 1,4 dioxane (8 mL) was added cesium carbonate (1135 mg, 3.48 mmol). The reaction mixture was degassed with nitrogen for 10 min followed by addition of RuPhos Pd G3 (97 mg, 0.116 mmol) and heating to 80° C. After 16 h, TLC analysis indicated complete conversion of the starting material. The reaction mixture was cooled to room temperature and filtered through a pad of celite which was washed with EtOAc. The filtrate was concentrated under reduced pressure and the resulting residue was purified by flash column chromatography on silica gel (100-200 mesh) eluting with 5-30% ethyl acetate in petroleum ether to afford methyl 1-((5-(1-(2,6-dichlorophenyl)azetidin-3-yl)-3-methylpyridin-2-yl)methyl)piperidine-4-carboxylate (210 mg, 31.6% yield) as a light brown semi-solid. LCMS method 1, LCMS (ESI, m/z): 433.2 $[M+H]^+$.

Synthesis of methyl 1-(4-(1-(3-chloro-4-cyclopropylphenyl)azetidin-3-yl)-2,6-dimethyl-benzyl)piperidine-4-carboxylate

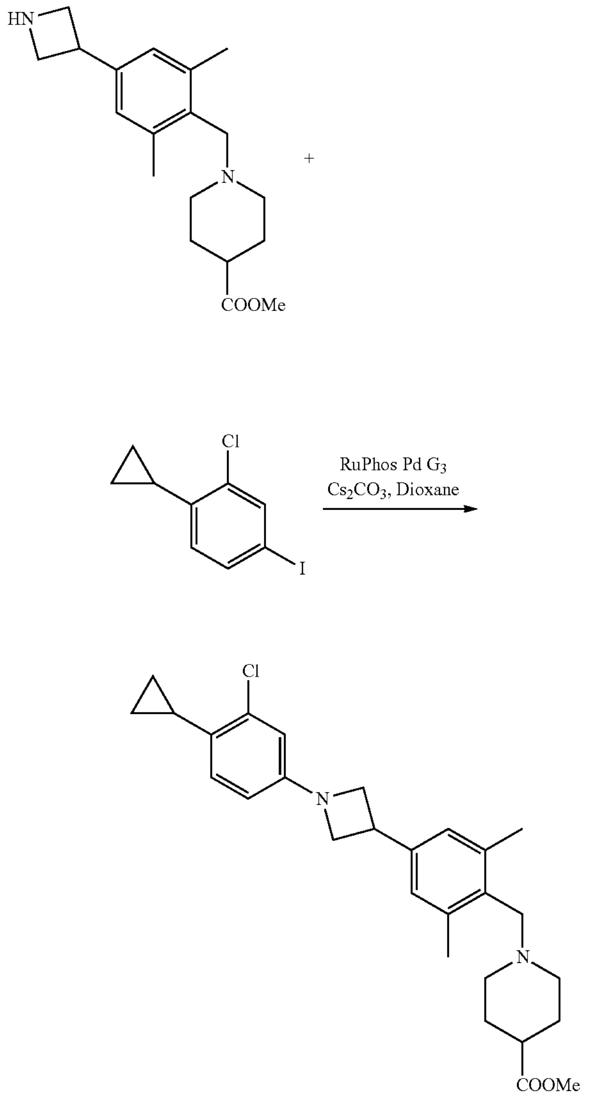

To a solution of methyl 1-(4-(azetidin-3-yl)-2,6-dimethylbenzyl)piperidine-4-carboxylate, TFA (300 mg, 0.697 mmol) and 1-cyclopropyl-2-iodo-3-methylbenzene (198 mg, 0.767 mmol) in anhydrous 1,4 dioxane (10 mL) was added cesium carbonate (681 mg, 2.091 mmol). The reaction mixture was degassed with nitrogen for 10 min followed by addition of RuPhos Pd G3 (58.4 mg, 0.070 mmol) and heating to 100° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2-cyclopropyl-6-methylphenyl)azetidin-3-yl)-2,6-dimethylbenzyl)piperidine-4-carboxylate (50 mg, 16% yield) as a colorless semi-solid. LCMS method 1, LCMS (ESI, m/z): 447.2 $[M+H]^+$.

Example S44. 1-(4-(1-(2,6-difluorophenyl)azetidin-3-yl)-2,6-dimethylbenzyl)piperidine-4-carboxylic acid (44)

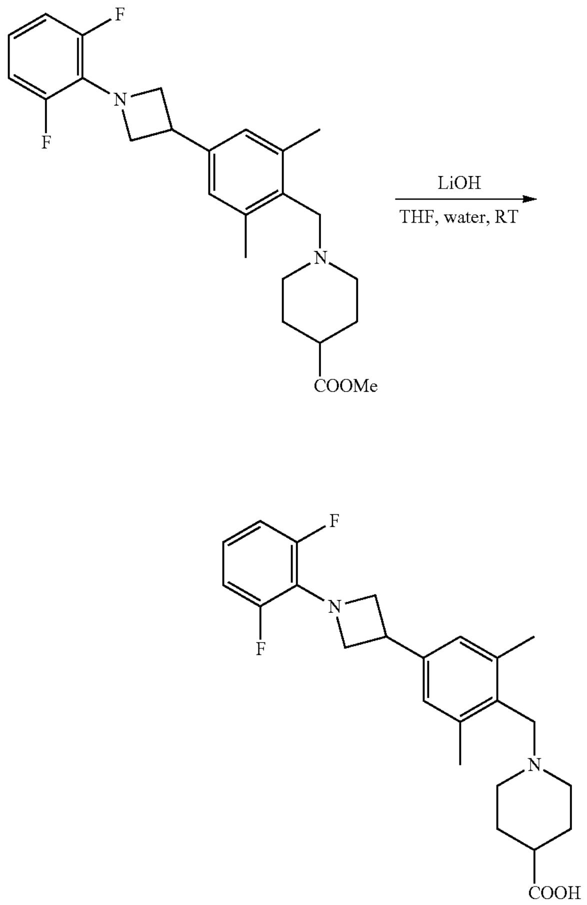

44

To a solution of methyl 1-(4-(1-(2,6-difluorophenyl)azetidin-3-yl)-2,6-dimethylbenzyl)piperidine-4-carboxylate (190 mg, 0.291 mmol) in THF (4 mL) and water (1 mL) was added LiOH (34.8 mg, 1.454 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water: ACN (50:20:30), Column-1: Xselect C18 (150×19) mm, 5 micron, Mobile phase A: 0.1% Formic acid in water, Mobile phase B: Acetonitrile. The required fractions were collected and lyophilized to afford 1-(4-(1-(2-fluoro-6-methylphenyl)azetidin-3-yl)-2,6-dimethylbenzyl)piperidine-4-carboxylic acid (55 mg, 0.130 mmol, 26.4% yield, 97.3% pure) as a white solid. $^1$H NMR (MeOD, 400 MHz): δ 6.86 (s, 2H), 6.89-6.78 (m, 2H), 6.73-6.66 (m, 1H), 4.58-4.53 (m, 2H), 4.17-4.12 (m, 4H), 3.86-3.84 (m, 1H), 2.96-2.91 (m, 2H), 2.46 (s, 6H), 2.43-2.39 (m, 2H), 2.06-2.01 (m, 2H), 1.91-1.86 (m, 2H). LCMS method 1; LCMS (ESI, m/z): 415.2 $[M+H]^+$.

Example S45. 1-(2,6-dimethyl-4-(1-phenylazetidin-3-yl)benzyl)piperidine-4-carboxylic acid (45)

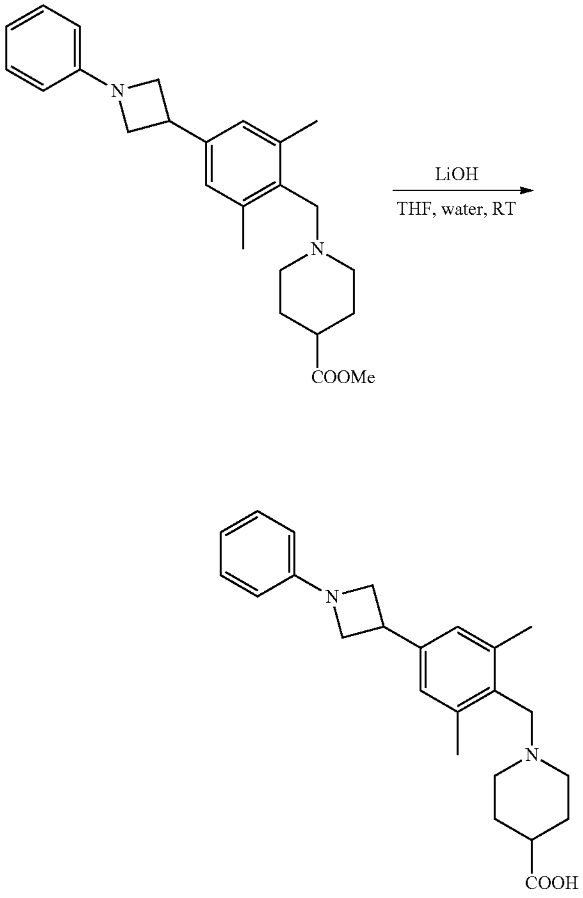

45

To a solution of methyl 1-(2,6-dimethyl-4-(1-phenylazetidin-3-yl)benzyl)piperidine-4-carboxylate (170 mg, 0.411 mmol) in THF (4 mL) and water (1 mL) was added LiOH (49.3 mg, 2.057 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water: ACN (50:20:30), Column-1: Xselect C18 (150×19) mm, 5 micron, Mobile phase A: 0.1% Formic acid in water, Mobile phase B: Acetonitrile. The required fractions were collected and lyophilized to afford 1-(2,6-dimethyl-4-(1-phenylazetidin-3-yl)-benzyl)piperidine-4-carboxylic acid, formic acid salt (82 mg, 0.193 mmol, 46.9% yield, 99.9% pure) as an off-white solid. $^1$H NMR (MeOD, 400 MHz): δ 7.24-7.17 (m, 4H), 6.77 (t, J=8 Hz, 1H), 6.56 (dd, J=8.4, 8.8 Hz, 2H), 4.28-4.25 (m, 2H), 4.14 (s, 2H), 3.92-3.81 (m, 3H), 2.94-2.89 (m, 2H), 2.45 (s, 6H), 2.43-2.38 (m, 2H), 2.05-2.00 (m, 2H), 1.90-1.85 (m, 2H). LCMS method 1; LCMS (ESI, m/z): 427.2 $[M+H]^+$.

Example S46. 1-(4-(1-(2-fluorophenyl)azetidin-3-yl)-2,6-dimethylbenzyl)piperidine-4-carboxylic acid (46)

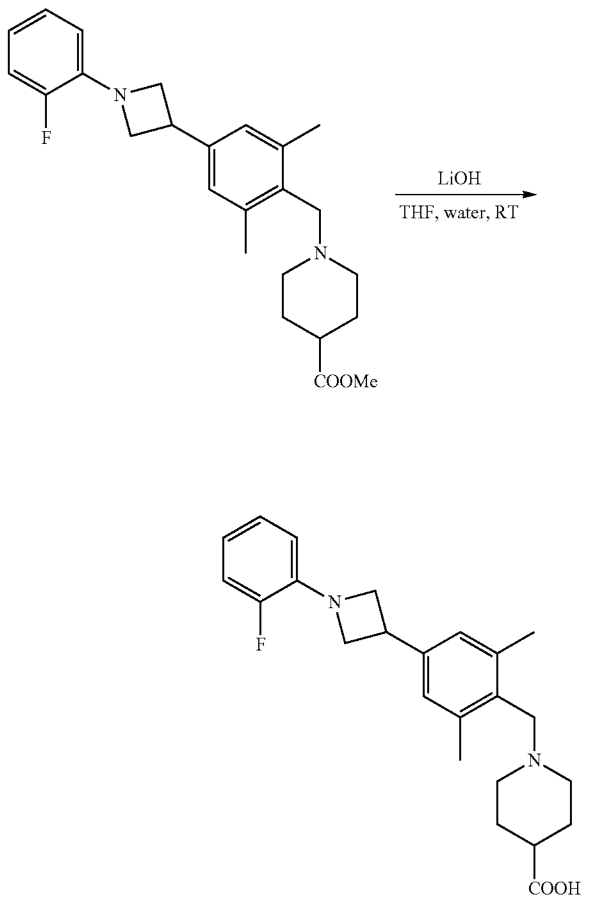

46

To a solution of methyl 1-(4-(1-(2-ethyl-6-methylphenyl) azetidin-3-yl)-2,6-dimethylbenzyl)piperidine-4-carboxylate (160 mg, 0.368 mmol) in THF (4 mL) and water (1 mL) was added LiOH (26.4 mg, 1.104 mmol). The resulting mixture was stirred at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water: ACN (50:20:30), Column-1: Xselect C18 (150×19) mm, 5 micron, Mobile phase A: 0.1% Formic acid in water, Mobile phase B: Acetonitrile. The required fractions were collected and lyophilized to afford 1-(4-(1-(2-ethyl-6-methylphenyl) azetidin-3-yl)-2,6-dimethylbenzyl)piperidine-4-carboxylic acid, formic acid salt (90.2 mg, 0.180 mmol, 49.0% yield, 93.3% pure) as a white solid. $^1$H NMR: (400 MHz, MeOD): δ 7.26 (m, 2H), 6.90-6.95 (m, 2H), 6.76-6.80 (m, 1H), 4.45-4.75 (m, 2H), 4.04-4.20 (m, 4H), 3.76-3.80 (m, 1H), 2.71-2.99 (m, 4H), 2.48 (m, 8H), 2.38 (m, 4H), 2.04-2.07 (m, 2H), 1.91 (s, 2H), 1.20-1.24 (m, 3H). LCMS method 1; LCMS (ESI, m/z): 421.2 [M+H]$^+$.

Example S47. 1-(4-(1-(3-fluorophenyl)azetidin-3-yl)-2,6-dimethylbenzyl)piperidine-4-carboxylic acid (47)

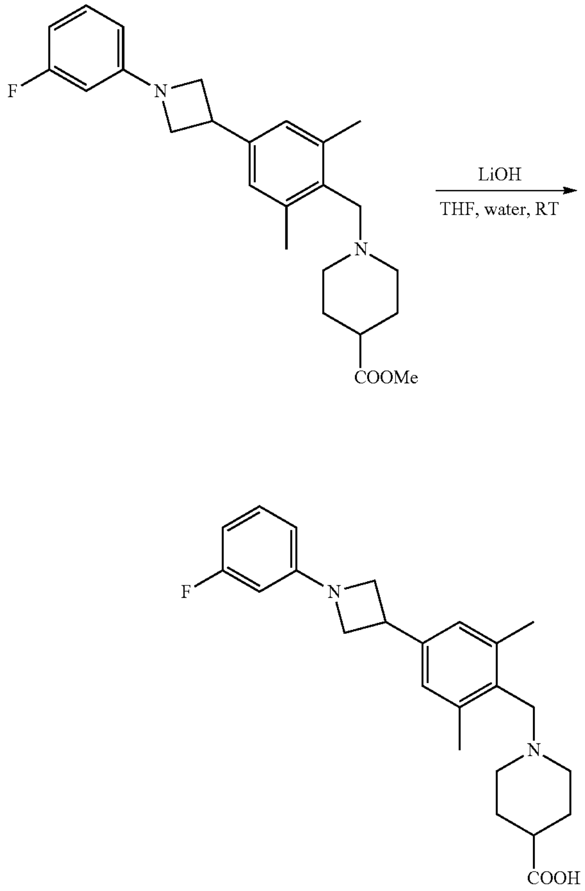

47

To a solution of methyl 1-(4-(1-(2,6-diethylphenyl)azetidin-3-yl)-2,6-dimethylbenzyl)piperidine-4-carboxylate (300 mg, 0.669 mmol) in THF (4 mL) and water (1 mL) was added LiOH (48.0 mg, 2.006 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water: ACN (50:10:40), Column-1: Xbridge C8 (150×19) mm, 5 micron, Mobile phase A: 0.1% Formic acid in water, Mobile phase B: Acetonitrile. The required fractions were collected and lyophilized to afford 1-(4-(1-(2,6-diethylphenyl)azetidin-3-yl)-2,6-dimethylbenzyl)piperidine-4-carboxylic acid, formic acid salt (106.6 mg, 0.213 mmol, 31.9% yield, 96.2% pure) as a white solid. $^1$H-NMR (400 MHz, MeOD): δ 7.30 (bs, 2H), 6.97-6.99 (m, 2H), 6.87-6.91 (m, 1H), 4.50-4.53 (m, 2H), 4.20 (s, 2H), 4.01-4.04 (m, 2H), 3.79-3.83 (m, 1H), 3.33-3.38 (m, 2H), 2.98 (bs, 2H), 2.76-2.82 (m, 4H), 2.40-2.49 (m, 8H), 2.04-2.07 (m, 2H), 1.87-2.03 (m, 2H), 1.23-1.27 (m, 6H). LCMS method 1; LCMS (ESI, m/z): 435.2 [M+H]$^+$.

Example S48. 1-(4-(1-(4-cyclopropylphenyl)azetidin-3-yl)-2,6-dimethylbenzyl)piperidine-4-carboxylic acid (48)

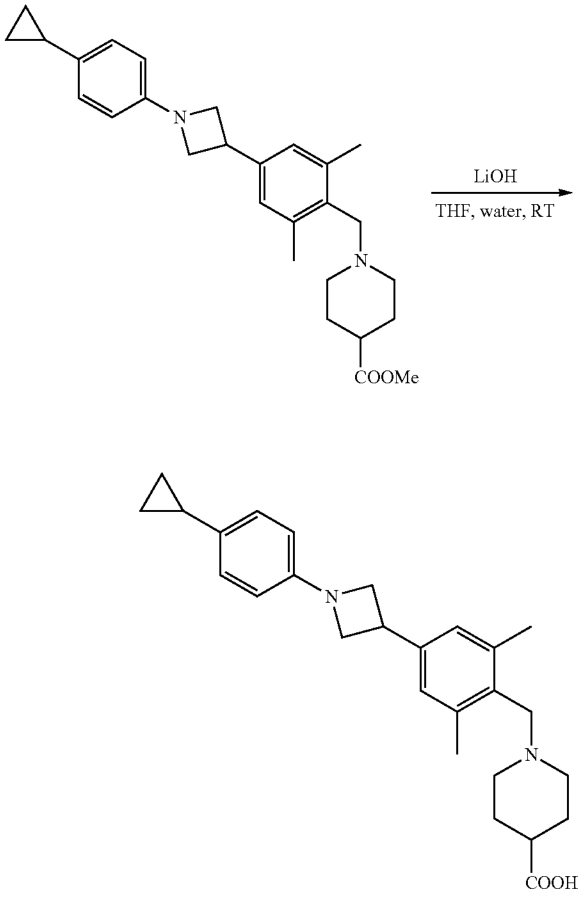

48

To a solution of methyl 1-(4-(1-(2-cyclopropylphenyl)azetidin-3-yl)-2,6-dimethylbenzyl)piperidine-4-carboxylate (160 mg, 0.370 mmol) in THF (4 mL) and water (1 mL) was added LiOH (46.6 mg, 1.110 mmol). The resulting mixture was stirred at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water: ACN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-(4-(1-(2-cyclopropylphenyl)azetidin-3-yl)-2,6-dimethylbenzyl)piperidine-4-carboxylic acid, formic acid salt (62 mg, 0.133 mmol, 35.8% yield, 99.3% pure) as a white solid. $^1$H NMR (400 MHz, MeOD); δ 7.21 (s, 2H), 7.09-7.21 (m, 1H), 6.99 (d, J=7.60 Hz, 1H), 6.77 (dt, J=1.20, 10.27 Hz, 1H), 6.59 (dd, J=0.80, 8.00 Hz, 1H), 4.41-4.45 (m, 2H), 4.13 (s, 2H), 3.95-3.99 (m, 2H), 3.84-3.86 (m, 1H), 3.29 (m, 1H), 2.90 (m, 2H), 2.46 (s, 6H), 2.04 (m, 1H), 2.00-2.04 (m, 2H). LCMS method 1; LCMS (ESI, m/z): 419.2 $[M+H]^+$.

Example S49. 1-(4-(1-(3-chloro-4-cyclopropylphenyl)azetidin-3-yl)-2,6-dimethylbenzyl)-piperidine-4-carboxylic acid (49)

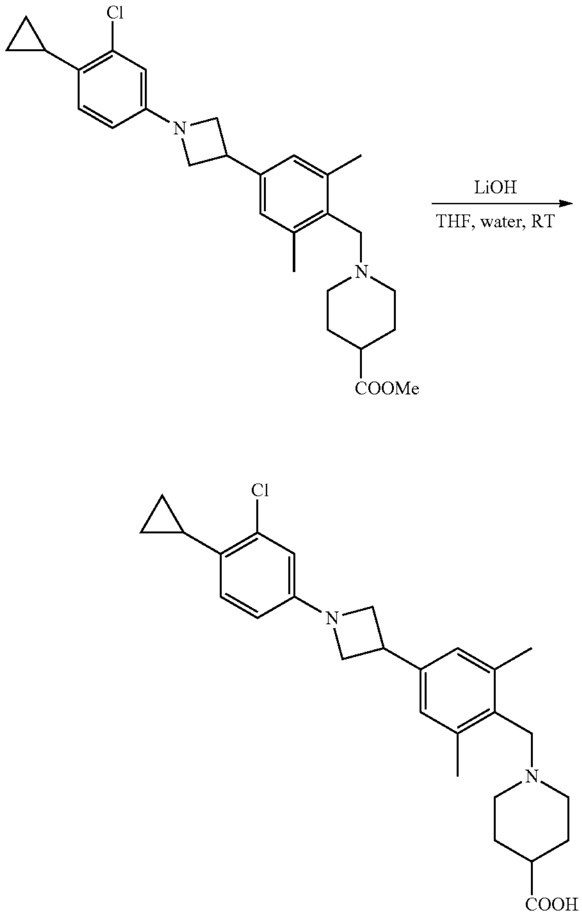

49

To a solution of methyl 1-(4-(1-(2-cyclopropyl-6-methylphenyl)azetidin-3-yl)-2,6-dimethylbenzyl)piperidine-4-carboxylate (50 mg, 0.112 mmol) in THF (2 mL) and water (0.5 mL) was added LiOH (14.09 mg, 0.336 mmol). The resulting mixture was stirred at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30) Column: Xselect C18 (150×19) mm, 5 micron, Mobile phase A: 0.1% Formic acid in water, Mobile phase B: Acetonitrile. The required fractions were collected and lyophilized to afford 1-(4-(1-(2-cyclopropyl-6-methylphenyl)azetidin-3-yl)-2,6-dimethylbenzyl)piperidine-4-carboxylic acid, formic acid salt (4.50 mg, 9.06 μmol, 8.09% yield, 96.3% pure) as an off-white solid. $^1$H NMR (400 MHz, MeOD): δ 7.22 (s, 2H), 6.90-6.86 (m, 2H), 6.70-6.66 (m, 1H), 4.71-4.67 (m, 2H), 4.21-4.17 (m, 4H), 2.95 (bs, 2H), 2.46 (s, 8H), 2.31 (s, 3H), 2.09-2.01 (m, 4H), 1.88 (bs, 2H), 0.91-0.88 (m, 2H), 0.39-0.11 (m, 2H). LCMS method 2; LCMS (ESI, m/z): 453.2 $[M+H]^+$.

General Route to Compounds 50-54
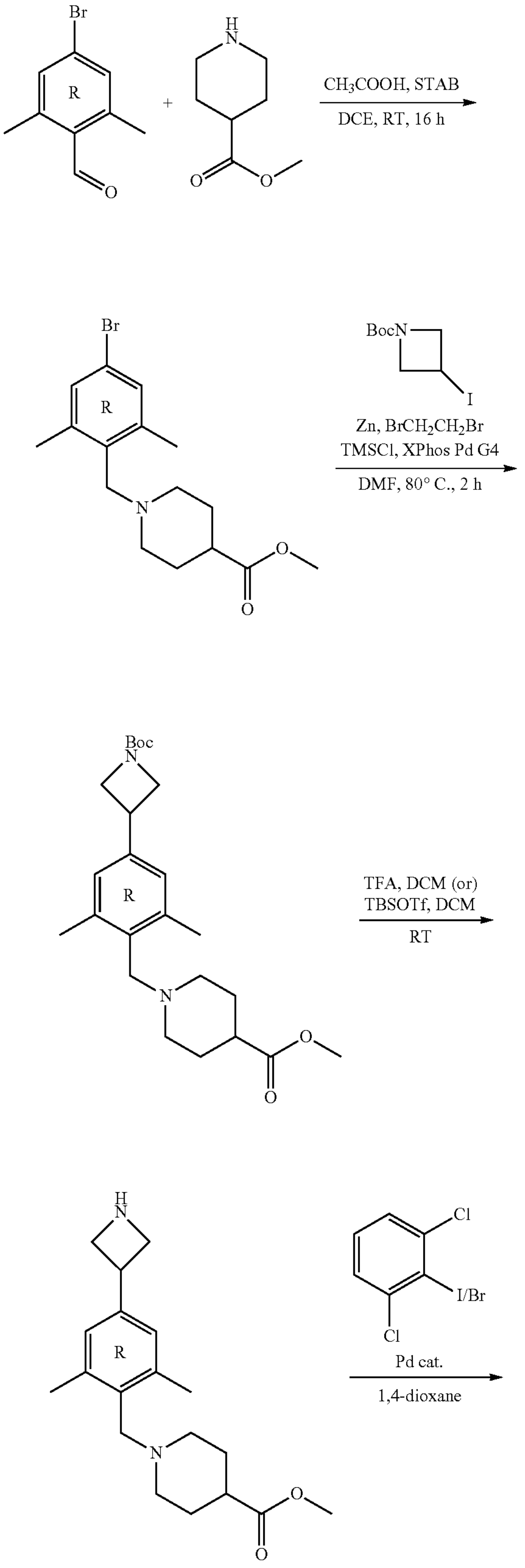
-continued
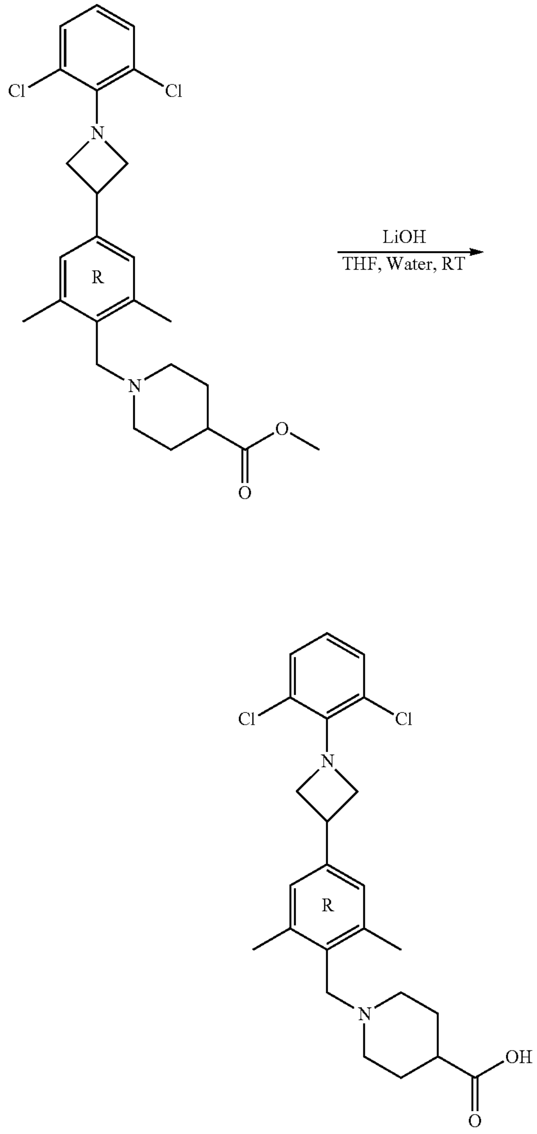
50-54
Synthesis of methyl 1-(4-bromo-2-fluoro-6-methylbenzyl)piperidine-4-carboxylate
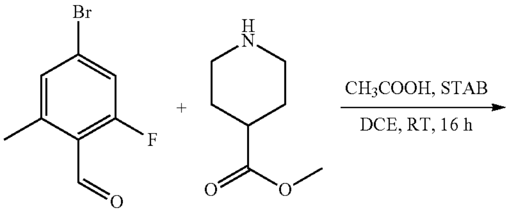

-continued

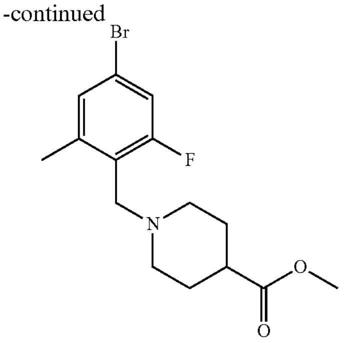

To a stirred solution of 4-bromo-2-fluoro-6-methylbenzaldehyde (750 mg, 3.46 mmol) and methyl piperidine-4-carboxylate (495 mg, 3.46 mmol) in DCE (15 mL) was added AcOH (0.1 mL) and stirred for 30 min at room temperature. Sodium triacetoxyborohydride (1099 mg, 5.18 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (30 mL) and dried over $Na_2SO_4$, filtered and the solvent evaporated under reduced pressure. The resulting residue was purified by flash column chromatography on silica gel (100-200 mesh) eluting with 30-50% ethyl acetate in petroleum ether to afford the methyl 1-(4-bromo-2-fluoro-6-methylbenzyl)piperidine-4-carboxylate (660 mg, 55% yield) as a yellow semi-solid. LCMS method 1, LCMS (ESI, m/z): 344.0 $[M+H]^+$.

Synthesis of methyl 1-(4-bromo-2-chloro-6-methylbenzyl)piperidine-4-carboxylate

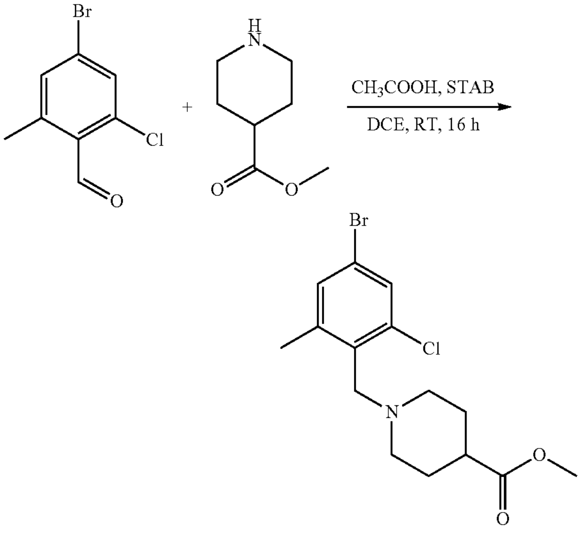

To a stirred solution of 4-bromo-2-chloro-6-methylbenzaldehyde (500 mg, 2.141 mmol) and methyl piperidine-4-carboxylate (307 mg, 2.141 mmol) in DCE (15 mL) was added acetic acid (0.123 mL, 2.141 mmol) and stirred for 30 min at room temperature. Sodium triacetoxyborohydride (681 mg, 3.21 mmol) was added at ice cold temperature and allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (30 mL) and dried over $Na_2SO_4$, filtered and the solvent evaporated under reduced pressure. The resulting residue was purified by flash column chromatography on silica gel (100-200 mesh) eluting with 30-50% ethyl acetate in petroleum ether to afford the methyl 1-(4-bromo-2-chloro-6-methylbenzyl)piperidine-4-carboxylate (200 mg, 27% yield) as a yellow liquid. LCMS method 1, LCMS (ESI, m/z): 360.0 $[M+H]^+$.

Synthesis of methyl 1-(4-bromo-2,6-diethylbenzyl)piperidine-4-carboxylate

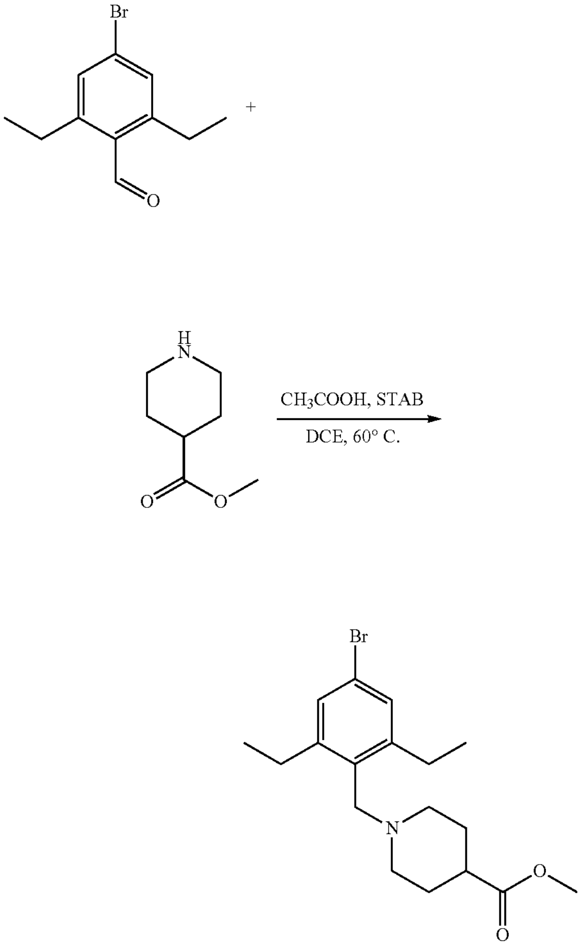

To a solution of 4-bromo-2,6-diethylbenzaldehyde (1.405 g, 5.83 mmol) and methyl piperidine-4-carboxylate (1.001 g, 6.99 mmol) in anhydrous 1,2-dichloroethane (10 ml) was added sodium triacetoxyborohydride (1.605 g, 7.57 mmol) and the reaction mixture was then heated to 60° C. for 1 h. The reaction mixture was cooled to room temperature and concentrated under reduced pressure. The resulting residue was purified by flash column chromatography on silica gel eluting with 0-50% ethyl acetate in petroleum ether to afford methyl 1-(4-bromo-2,6-diethylbenzyl)piperidine-4-carboxylate (905 mg, 40.9%) as yellow gum. LCMS method 1, LCMS (ESI, m/z): 369.9 $[M+H]^+$.

Synthesis of methyl 1-(4-bromo-2,6-diisopropylbenzyl)piperidine-4-carboxylate

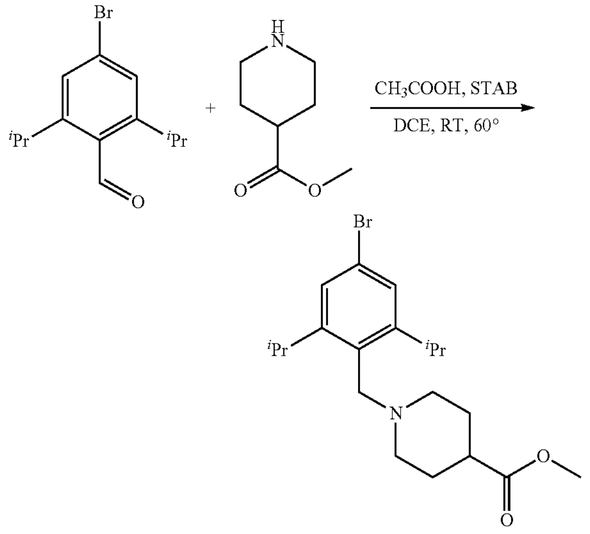

To a solution of 4-bromo-2,6-diisopropylbenzaldehyde (0.7 g, 2.60 mmol) and methyl piperidine-4-carboxylate (0.372 g, 2.60 mmol) in anhydrous 1,2-dichloroethane (10 ml) was added sodium triacetoxyborohydride (0.661 g, 3.12 mmol) and the reaction mixture was then heated to 60° C. for 1 h. The reaction mixture was cooled to room temperature and concentrated under reduced pressure. The resulting residue was purified by flash column chromatography on silica gel eluting with 0-40% ethyl acetate in petroleum ether to afford methyl 1-(4-bromo-2,6-diisopropylbenzyl)piperidine-4-carboxylate (400 mg, 36.9%). LCMS method 1, LCMS (ESI, m/z): 396.2 $[M+H]^+$.

Synthesis of methyl 1-((4-bromonaphthalen-1-yl)methyl)piperidine-4-carboxylate

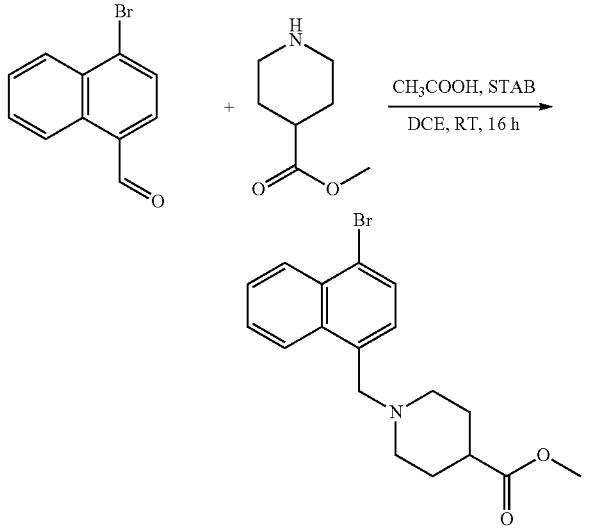

To a stirred solution of 4-bromo-1-naphthaldehyde (2 g, 8.51 mmol) and methyl piperidine-4-carboxylate (1.218 g, 8.51 mmol) in DCE (30 mL) was added acetic acid (0.0487 mL, 0.851 mmol) and stirred for 30 min at room temperature. Sodium triacetoxyborohydride (2.70 g, 12.76 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×30 mL), the combined organic phase was washed with water (50 mL) and dried over $Na_2SO_4$, filtered and the solvent evaporated under reduced pressure. The resulting residue was purified by flash column chromatography on silica gel (100-200 mesh) eluting with 0-50% ethyl acetate in petroleum ether to afford the methyl 1-((4-bromonaphthalen-1-yl)methyl)piperidine-4-carboxylate (2.255 g, 73.2% yield) as a yellow liquid. LCMS method 1, LCMS (ESI, m/z): 362.0 $[M+H]^+$.

Synthesis of methyl 1-(4-(1-(tert-butoxycarbonyl)azetidin-3-yl)-2-fluoro-6-methyl-benzyl)piperidine-4-carboxylate

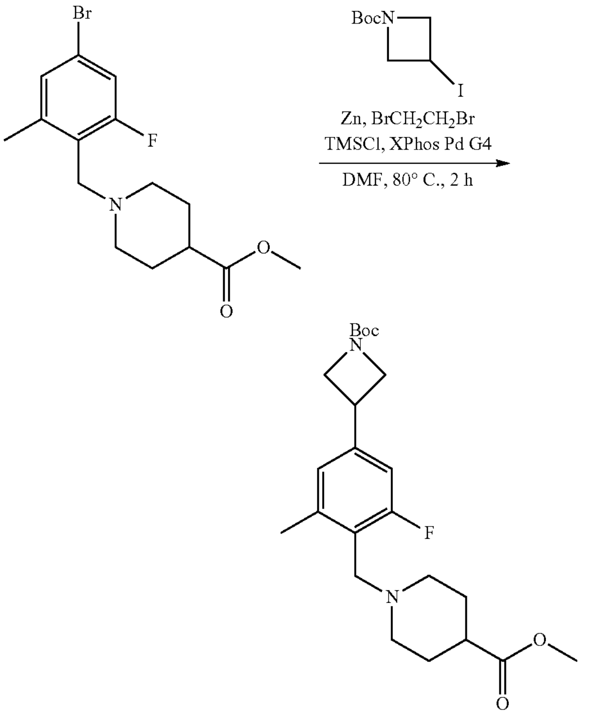

To a suspension of activated zinc (1852 mg, 28.3 mmol) in anhydrous DMF (10 mL) was added 1,2-dibromoethane (0.016 mL, 0.189 mmol) and the mixture was heated to 75° C. After 15 min, the reaction mixture was cooled to room temperature, trimethylchlorosilane (0.024 mL, 0.189 mmol) was added and allowed to stir at ambient temperature for additional 30 min. Then a solution of tert-butyl 3-iodoazetidine-1-carboxylate (1336 mg, 4.72 mmol) in 2 mL of anhydrous DMF was added to the reaction mixture and stirred at room temperature for another 30 min., followed by methyl 1-(4-bromo-2-fluoro-6-methylbenzyl)piperidine-4-carboxylate (650 mg, 1.888 mmol) and XPhos Pd G4 (162 mg, 0.189 mmol) in 3 mL of DMF. The reaction mixture was stirred at 80° C. for 2 h. After completion of the reaction, the mixture was cooled to room temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-(4-(1-(tert-butoxycarbonyl)azetidin-3-yl)-2-fluoro-6-methylbenzyl)piperidine-4-carboxylate (570 mg, 71% yield) as a colorless semi-solid. LCMS method 1, LCMS (ESI, m/z): 421.2 $[M+H]^+$.

Synthesis of methyl 1-(4-(1-(tert-butoxycarbonyl) azetidin-3-yl)-2-chloro-6-methyl-benzyl)piperidine-4-carboxylate

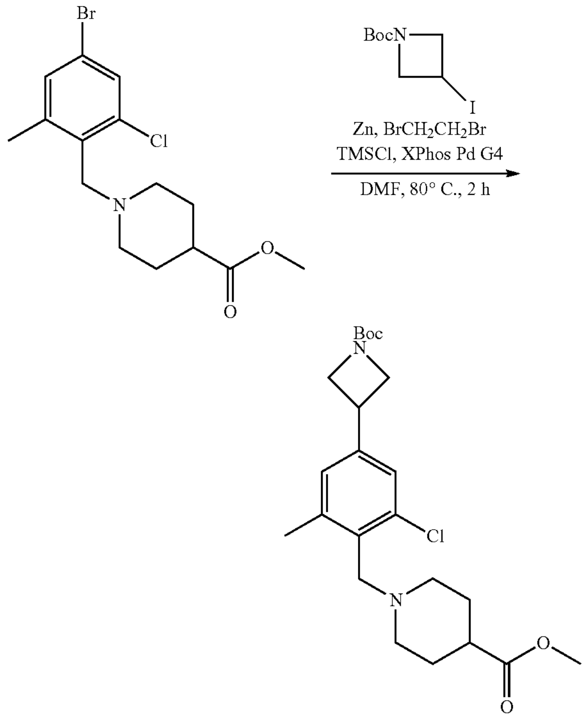

To a suspension of activated zinc (544 mg, 8.32 mmol) in anhydrous DMF (10 mL) was added 1,2-dibromoethane (4.78 µL, 0.055 mmol) and the mixture heated to 75° C. After 15 min, the reaction mixture was cooled to room temperature, trimethylchlorosilane (7.09 µL, 0.055 mmol) was added and allowed to stir at ambient temperature for additional 30 min. Then a solution of tert-butyl 3-iodoazetidine-1-carboxylate (785 mg, 2.77 mmol) in 2 mL of anhydrous DMF was added and the mixture was stirred at room temperature for another 30 min, followed by addition of methyl 1-(4-bromo-2-chloro-6-methylbenzyl)piperidine-4-carboxylate (200 mg, 0.555 mmol) and SPhos Pd G4 (44.0 mg, 0.055 mmol) in 3 mL of DMF. The reaction mixture was stirred at 80° C. for 2 h. After completion of the reaction, the reaction mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-(4-(1-(tert-butoxycarbonyl)azetidin-3-yl)-2-chloro-6-methylbenzyl)piperidine-4-carboxylate (150 mg, 61% yield) as a yellow semi-solid. LCMS method 1, LCMS (ESI, m/z): 437.4 $[M+H]^+$.

Synthesis of methyl 1-(4-(1-(tert-butoxycarbonyl) azetidin-3-yl)-2,6-diethylbenzyl)-piperidine-4-carboxylate

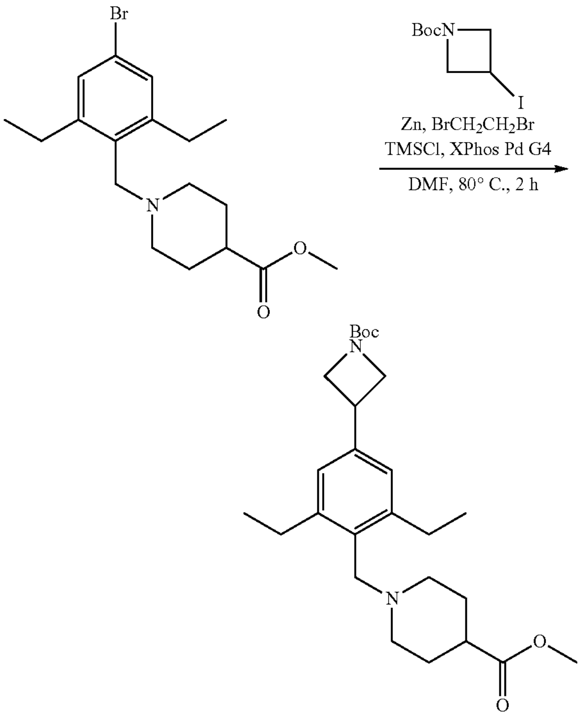

To a suspension of activated zinc (2.4 g, 36.7 mmol) in anhydrous DMF (10 mL) was added 1,2-dibromoethane (0.098 ml, 1.137 mmol) and the mixture was heated to 75° C. After 15 min, the reaction mixture was cooled to room temperature, trimethylsilyl chloride (0.031 ml, 0.244 mmol) was added and allowed to stir at ambient temperature for additional 30 min. Then a solution of tert-butyl 3-iodoazetidine-1-carboxylate (2.4 g, 8.55 mmol) in 10 mL of anhydrous DMF was added to the reaction mixture and stirred at room temperature for another 30 min., followed by methyl 1-(4-bromo-2,6-diethylbenzyl)piperidine-4-carboxylate (900 mg, 2.444 mmol) as DMF solution and XPhos Pd G4 (235 mg, 0.244 mmol). The reaction mixture was stirred at 80° C. for 16 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-(4-(1-(tert-butoxycarbonyl)azetidin-3-yl)-2,6-diethylbenzyl)-piperidine-4-carboxylate (447 mg, 29.3%) as a colorless oil. LCMS method 1, LCMS (ESI, m/z): 445.4 [M+H]$^+$.

Synthesis of methyl 1-(4-(1-(tert-butoxycarbonyl) azetidin-3-yl)-2,6-diisopropylbenzyl)-piperidine-4-carboxylate

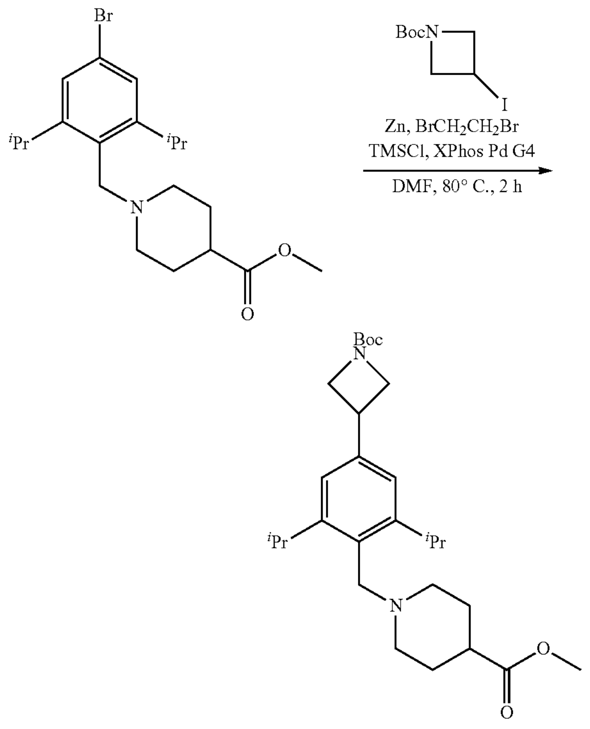

To a suspension of activated zinc (990 mg, 15.14 mmol) in anhydrous DMF (5 mL) was added 1,2-dibromoethane (18.96 mg, 0.101 mmol) and the mixture was heated to 60° C. After 30 min, the reaction mixture was cooled to room temperature and added chlorotrimethylsilane (10.96 mg, 0.101 mmol). The mixture was then allowed to stir at room temperature for another 30 min. A solution of tert-butyl 3-iodoazetidine-1-carboxylate (857 mg, 3.03 mmol) in DMF (5 mL) was added and the mixture was stirred at room temperature. After 2 h, a solution of methyl 1-(4-bromo-2,6-diisopropylbenzyl)piperidine-4-carboxylate (400 mg, 1.009 mmol) in anhydrous DMF (5 mL) was added followed by the addition of X Phos Pd G4 (87 mg, 0.101 mmol) under nitrogen atmosphere. The reaction mixture was then heated to 80° C. and the progress of the reaction was monitored by TLC. After 16 h, TLC analysis indicated complete conversion of the starting material. The reaction mixture was then cooled to room temperature and filtered through a pad of celite and washed with ethyl acetate. The filtrate was then washed with cold water, dried over sodium sulphate and concentrated under reduced pressure. The resulting residue was purified by flash column chromatography on silica gel eluting with 0-40% ethyl acetate in petroleum ether to afford methyl 1-(4-(1-(tert-butoxycarbonyl)azetidin-3-yl)-2,6-diisopropylbenzyl)piperidine-4-carboxylate (370 mg, 73.1%). LCMS method 1, LCMS (ESI, m/z): 473.3 [M+H]$^+$.

Synthesis of methyl 1-((4-(1-(tert-butoxycarbonyl) azetidin-3-yl)naphthalen-1-yl)-methyl)piperidine-4-carboxylate

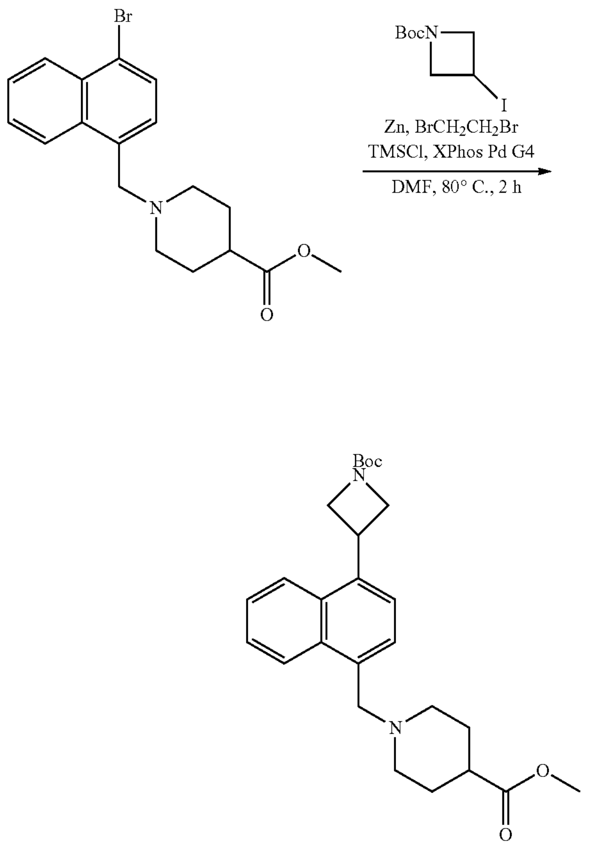

To a suspension of activated zinc (2.166 g, 33.1 mmol) in anhydrous DMF (20 mL) was added 1,2-dibromoethane (0.143 mL, 1.656 mmol) and heated to 75° C. After 15 min, the reaction mixture was cooled to room temperature, trimethylchlorosilane (0.212 mL, 1.656 mmol) was added and allowed to stir at ambient temperature for additional 30 min. Then a solution of tert-butyl 3-iodoazetidine-1-carboxylate (2.81 g, 9.94 mmol) in 5 mL of anhydrous DMF was added and stirred at room temperature for another 30 min, followed by addition of methyl 1-((4-bromonaphthalen-1-yl)methyl) piperidine-4-carboxylate (1.2 g, 3.31 mmol) and XPhos Pd G4 (0.570 g, 0.662 mmol) in 5 mL of DMF. The reaction mixture was allowed to stir at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((4-(1-(tert-butoxycarbonyl)azetidin-3-yl) naphthalen-1-yl)methyl)piperidine-4-carboxylate (1.2 g, 83% yield) as a off white-solid. LCMS method 1, LCMS (ESI, m/z): 439.4 [M+H]$^+$.

Synthesis of methyl 1-(4-(azetidin-3-yl)-2-fluoro-6-methylbenzyl)piperidine-4-carboxylate

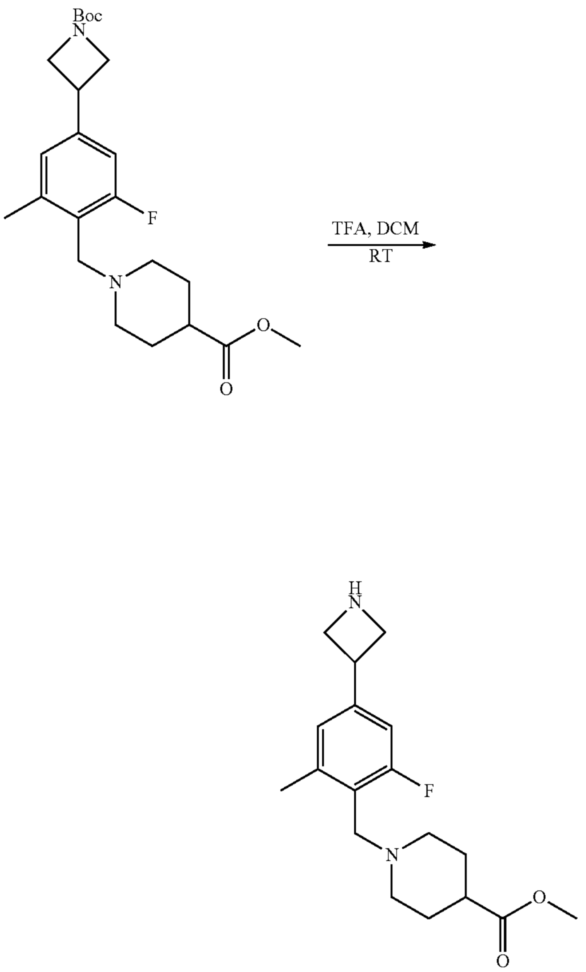

To a stirred solution of methyl 1-(4-(1-(tert-butoxycarbonyl)azetidin-3-yl)-2-fluoro-6-methylbenzyl)piperidine-4-carboxylate (550 mg, 1.308 mmol) in anhydrous DCM (20 mL) was added TBDMS triflate (0.752 mL, 3.27 mmol) at 0° C. The reaction mixture was stirred at room temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(4-(azetidin-3-yl)-2-fluoro-6-methylbenzyl)piperidine-4-carboxylate (400 mg, 95% yield) as a light pink solid. LCMS method 1, LCMS (ESI, m/z): 321.0 $[M+H]^+$.

Synthesis of methyl 1-(4-(azetidin-3-yl)-2-chloro-6-methylbenzyl)piperidine-4-carboxylate, TFA salt

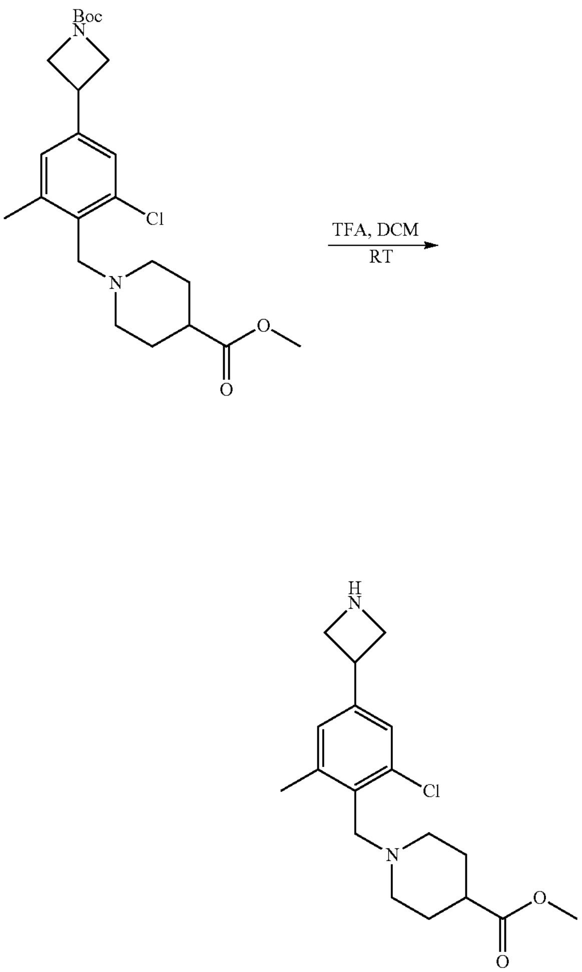

To a stirred solution of methyl 1-(4-(1-(tert-butoxycarbonyl)azetidin-3-yl)-2-chloro-6-methylbenzyl)piperidine-4-carboxylate (150 mg, 0.343 mmol) in anhydrous DCM (20 mL) was added tert-butyldimethylsilyl trifluoromethanesulfonate (0.237 mL, 1.030 mmol) at 0° C. Then reaction mixture was stirred at room temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(4-(azetidin-3-yl)-2-chloro-6-methylbenzyl)piperidine-4-carboxylate, TFA (150 mg, 96% yield) as a brown liquid. LCMS method 1, LCMS (ESI, m/z): 337.2 $[M+H]^+$.

Synthesis of methyl 1-(4-(azetidin-3-yl)-2,6-diethylbenzyl)piperidine-4-carboxylate

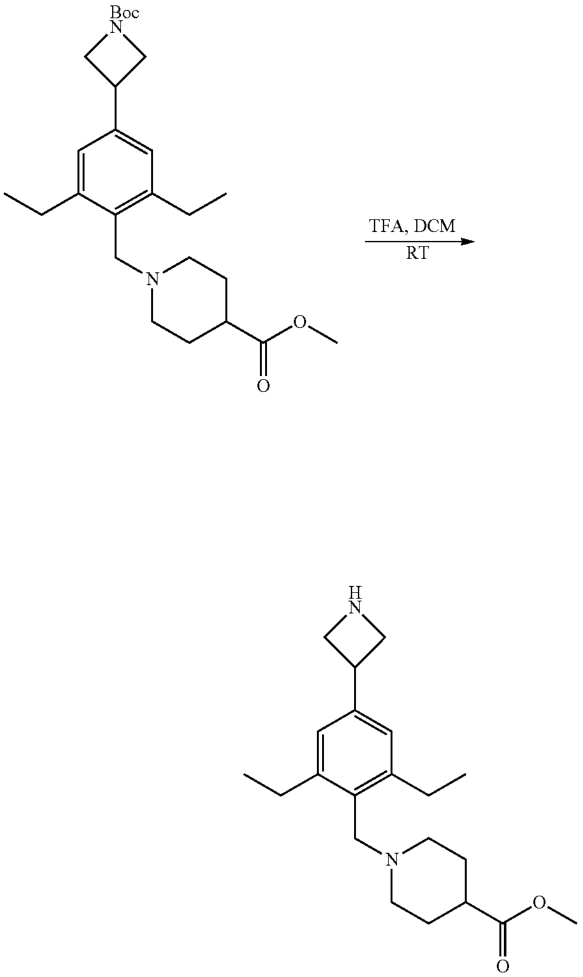

To a stirred solution of methyl 1-(4-(1-(tert-butoxycarbonyl)azetidin-3-yl)-2,6-diethylbenzyl)piperidine-4-carboxylate (440 mg, 0.990 mmol) in DCM (5 mL) at 0° C. was added tert-butyldimethylsilyl trifluoromethanesulfonate (0.682 mL, 2.97 mmol) and the reaction mixture was allowed to stir at ambient temperature for 2 h. The progress of the reaction was monitored by TLC analysis. After completion of the reaction, the mixture was concentrated under reduced pressure. The residue obtained was washed with diethyl ether (10 mL), and filtered to afford methyl 1-(4-(azetidin-3-yl)-2,6-diethylbenzyl)piperidine-4-carboxylate, TFA (675 mg, crude) as an off-white solid. LCMS method 1, LCMS (ESI, m/z): 345.3 $[M+H]^+$.

Synthesis of methyl 1-(4-(azetidin-3-yl)-2,6-diisopropylbenzyl)piperidine-4-carboxylate, TFA salt

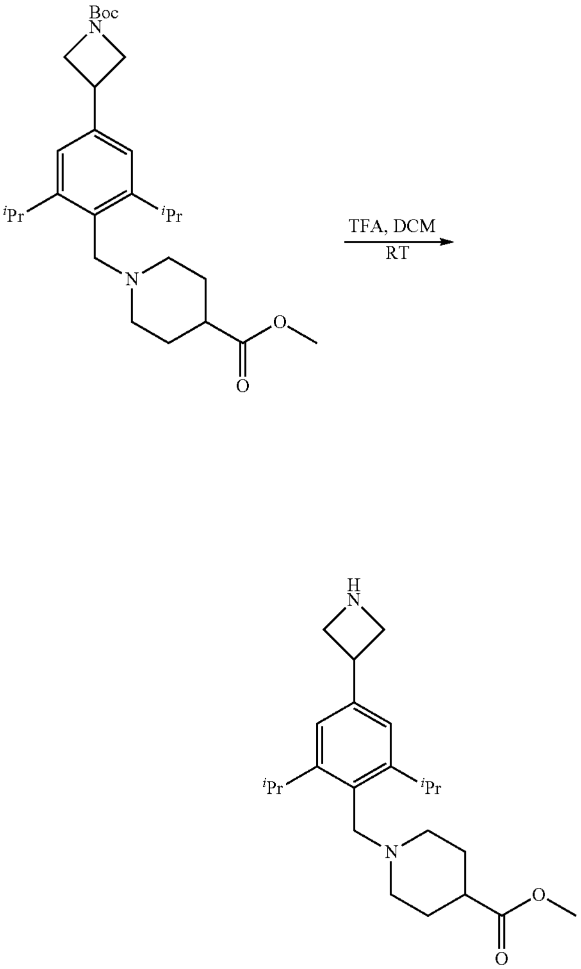

To a solution of methyl 1-(4-(1-(tert-butoxycarbonyl)azetidin-3-yl)-2,6-diisopropylbenzyl)piperidine-4-carboxylate (370 mg, 0.783 mmol) in anhydrous DCM (10 mL) was added tert-butyldimethylsilyl trifluoromethanesulfonate (0.450 mL, 1.957 mmol) and the reaction mixture was allowed to stir at room temperature. After 1 h, TLC analysis indicated complete conversion of the starting material. The reaction mixture was concentrated under reduced pressure and the residue was triturated with diethyl ether and concentrated to afford methyl 1-(4-(azetidin-3-yl)-2,6-diisopropylbenzyl)piperidine-4-carboxylate, trifluoromethanesulfonate salt (350 mg, 0.671 mmol, 86% yield) as an off-white solid and used further without purification. LCMS method 1, LCMS (ESI, m/z): 373.4 $[M+H]^+$.

Synthesis of methyl 1-((4-(azetidin-3-yl)naphthalen-1-yl)methyl)piperidine-4-carboxylate

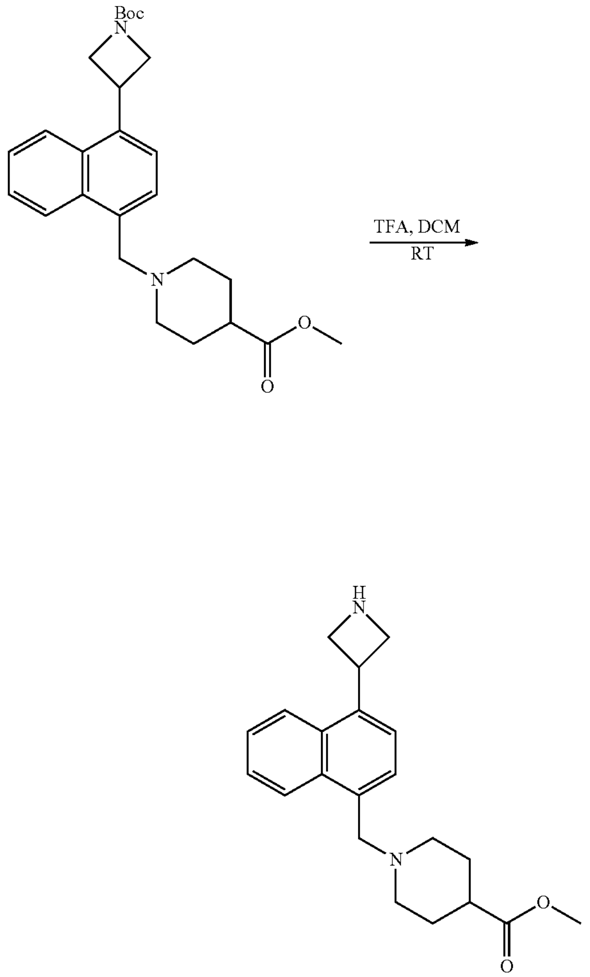

To a stirred solution of methyl 1-((4-(1-(tert-butoxycarbonyl)azetidin-3-yl)naphthalen-1-yl)methyl)piperidine-4-carboxylate (800 mg, 1.824 mmol) in anhydrous DCM (20 mL) was added TFA (1.405 mL, 18.24 mmol) at 0° C. The reaction mixture was stirred at ambient temperature and the progress of the reaction monitored by TLC analysis. After 1 h, TLC analysis indicated complete conversion of the starting material. The reaction mixture was concentrated under reduced pressure and the resulting residue was triturated with diethyl ether to afford methyl 1-((4-(azetidin-3-yl)naphthalen-1-yl)methyl)piperidine-4-carboxylate, TFA (825 mg, 1.824 mmol, 100% yield) as a light pink solid. LCMS method 1, LCMS (ESI, m/z): 339.2 [M+H]$^+$.

Synthesis of methyl 1-(4-(1-(2,6-dichlorophenyl)azetidin-3-yl)-2-fluoro-6-methylbenzyl)-piperidine-4-carboxylate

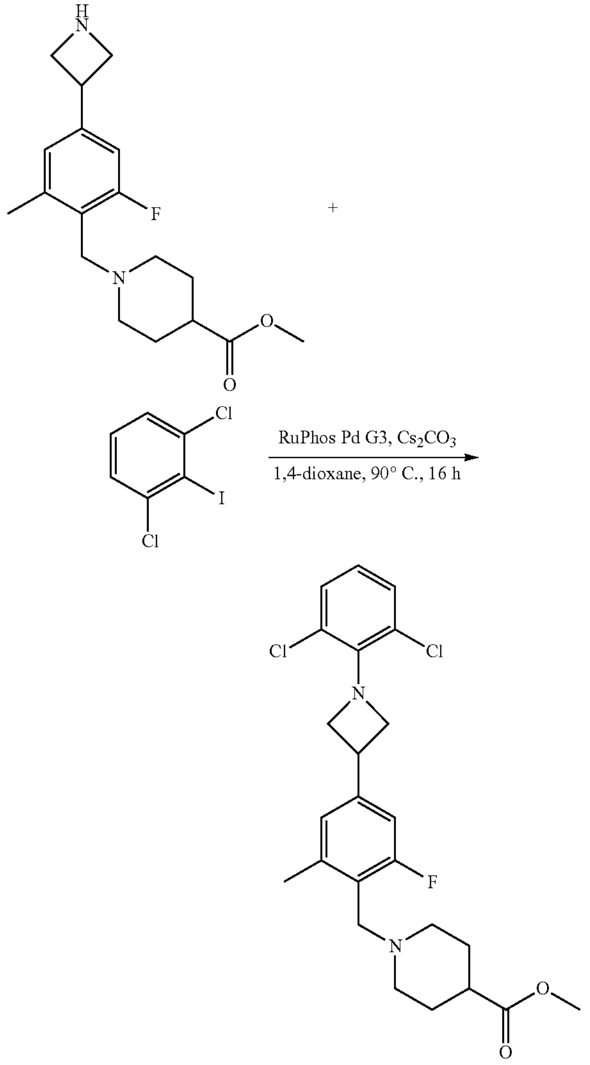

To a solution of methyl 1-(4-(azetidin-3-yl)-2-fluoro-6-methylbenzyl)piperidine-4-carboxylate (400 mg, 1.248 mmol) and 1,3-dichloro-2-iodobenzene (341 mg, 1.248 mmol) in anhydrous 1,4 dioxane (5 mL) was added $Cs_2CO_3$ (1017 mg, 3.12 mmol). The reaction mixture was degassed with nitrogen for 10 min followed by addition of RuPhos Pd G3 (105 mg, 0.125 mmol) and heated to 90° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-100% ethyl acetate in petroleum ether to afford methyl 1-(4-(1-(2,6-dichlorophenyl)azetidin-3-yl)-2-fluoro-6-methylbenzyl)piperidine-4-carboxylate (285 mg, 50% yield) as a yellow solid. LCMS method 1, LCMS (ESI, m/z): 465.0 [M+H]$^+$.

Synthesis of methyl 1-(2-chloro-4-(1-(2,6-dichlorophenyl)azetidin-3-yl)-6-methylbenzyl)-piperidine-4-carboxylate

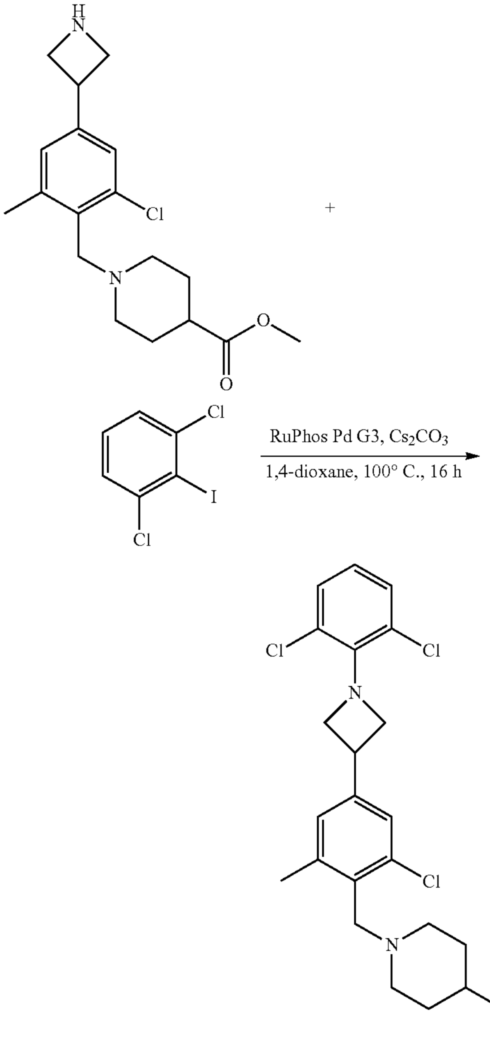

To a solution of methyl 1-(4-(azetidin-3-yl)-2-chloro-6-methylbenzyl)piperidine-4-carboxylate, TFA (150 mg, 0.346 mmol) and 1,3-dichloro-2-iodobenzene (146 mg, 0.534 mmol) in anhydrous 1,4 dioxane (5 mL) was added $Cs_2CO_3$ (434 mg, 1.336 mmol). The reaction mixture was degassed with nitrogen for 10 min followed by addition of RuPhos Pd G3 (37.2 mg, 0.045 mmol) and heated to 100° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-100% ethyl acetate in petroleum ether to afford methyl 1-(2-chloro-4-(1-(2,6-dichlorophenyl)azetidin-3-yl)-6-methylbenzyl)piperidine-4-carboxylate (82 mg, 50% yield) as a yellow liquid. LCMS method 1, LCMS (ESI, m/z): 481.0 $[M+H]^+$.

Synthesis of methyl 1-(4-(1-(2,6-dichlorophenyl)azetidin-3-yl)-2,6-diethylbenzyl)-piperidine-4-carboxylate

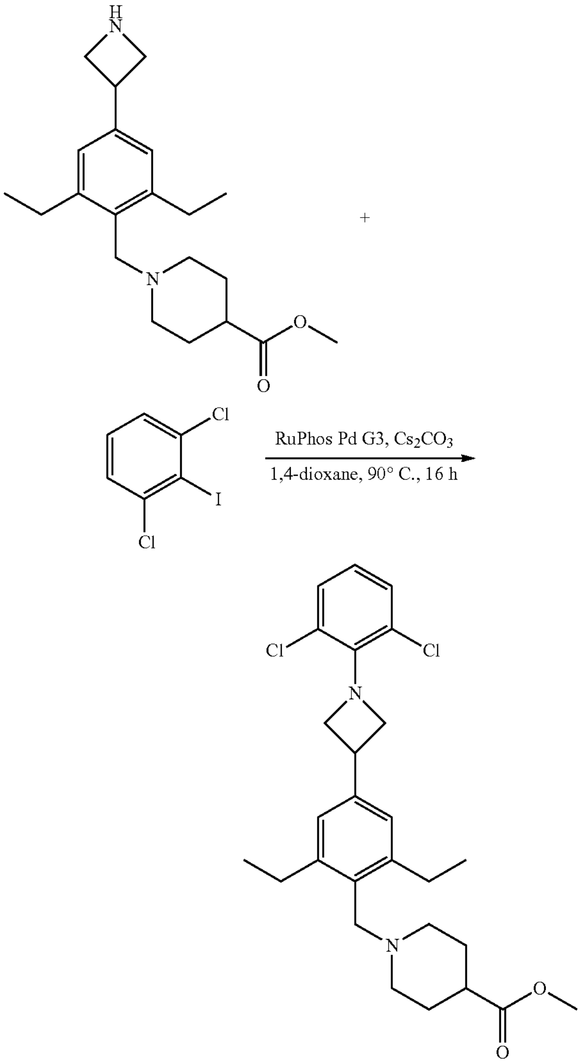

To a stirred solution of methyl 1-(4-(azetidin-3-yl)-2,6-diethylbenzyl)piperidine-4-carboxylate, TFA (675 mg, 1.472 mmol) and 1,3-dichloro-2-iodobenzene (402 mg, 1.472 mmol) in 1,4-dioxane (10 mL), was added cesium carbonate (1199 mg, 3.68 mmol). The reaction mixture was degassed with nitrogen. After 10 min, RuPhos-Pd-G3 (123 mg, 0.147 mmol) was added and the reaction mixture was stirred at 90° C. The progress of the reaction was monitored by TLC analysis. After 16 h, the reaction mixture was cooled to room temperature, diluted with ethyl acetate (30 mL) and the organic layer was washed with water, dried over sodium sulphate and concentrated under reduced pressure. The resulting residue was purified by flash column chromatography on silica gel eluting with 0-60% ethyl acetate in petroleum ether to afford methyl 1-(4-(1-(2,6-dichlorophenyl)azetidin-3-yl)-2,6-diethylbenzyl)piperidine-4-carboxylate (395 mg, 34.1%) as a yellow oil. LCMS method 1, LCMS (ESI, m/z): 489.2 $[M+H]^+$.

Synthesis of methyl 1-(4-(1-(2,6-dichlorophenyl) azetidin-3-yl)-2,6-diisopropylbenzyl)piperidine-4-carboxylate

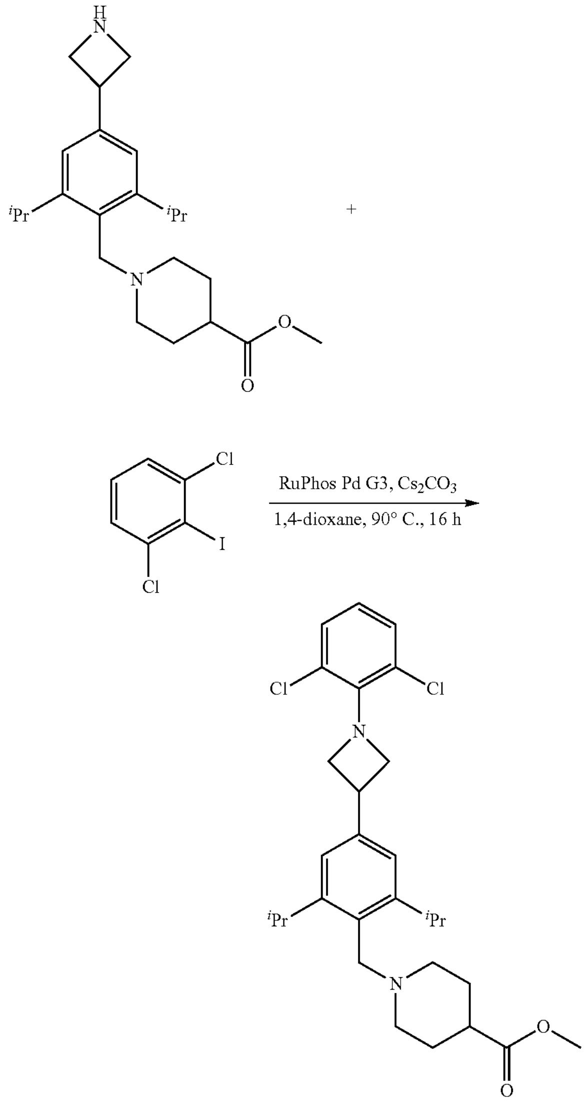

To a solution of methyl 1-(4-(azetidin-3-yl)-2,6-diisopropylbenzyl)piperidine-4-carboxylate, TFA (350 mg, 0.671 mmol) and 1,3-dichloro-2-iodobenzene (183 mg, 0.671 mmol) in anhydrous 1,4-dioxane (10 mL) was added cesium carbonate (547 mg, 1.677 mmol) followed by the addition of Ruphos Pd G3 (56.1 mg, 0.067 mmol). The reaction mixture was then heated to 90° C. and the progress of the reaction was monitored by TLC analysis. After completion, the mixture was cooled to room temperature and filtered through a pad of celite and washed with ethyl acetate. The filtrate was then concentrated under reduced pressure and the resulting residue was purified by flash column chromatography on silica gel (230-400 mesh) eluting with 0-40% ethyl acetate in petroleum ether to afford methyl 1-(4-(1-(2,6-dichlorophenyl)azetidin-3-yl)-2,6-diisopropylbenzyl)piperidine-4-carboxylate (140 mg, 28.2%) as a colorless oil. LCMS method 1, LCMS (ESI, m/z): 517.2 $[M+H]^+$.

Synthesis of methyl 1-((4-(1-(2,6-dichlorophenyl) azetidin-3-yl)naphthalen-1-yl)-methyl)piperidine-4-carboxylate

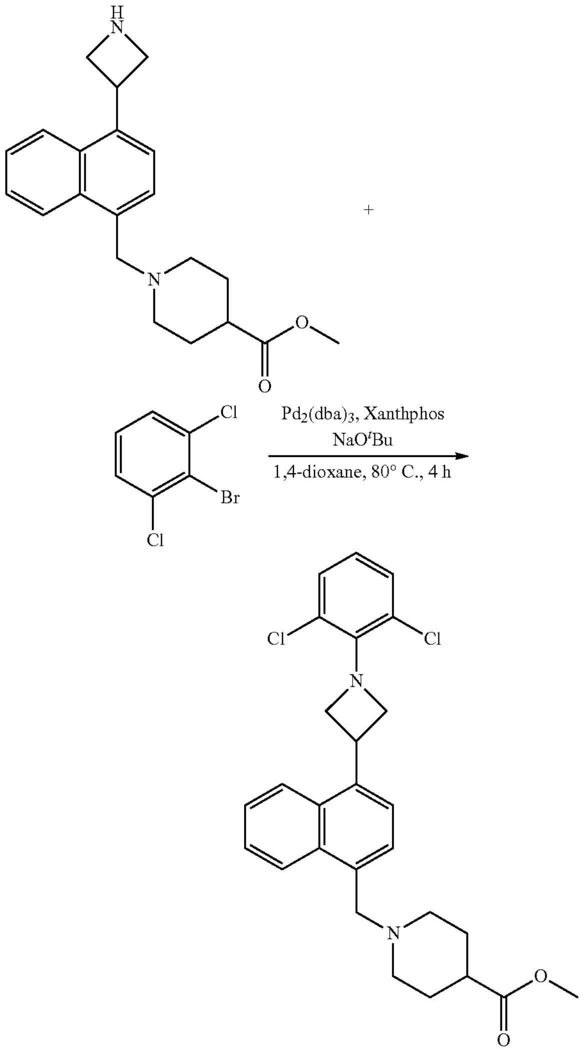

To a solution of methyl 1-((4-(azetidin-3-yl)naphthalen-1-yl)methyl)piperidine-4-carboxylate, TFA (200 mg, 0.442 mmol) and 2-bromo-1,3-dichlorobenzene (125 mg, 0.553 mmol) in anhydrous 1,4 dioxane (5 mL) was added sodium tert-butoxide (63.7 mg, 0.663 mmol). The reaction mixture was degassed with nitrogen for 10 min followed by addition of $Pd_2(dba)_3$ (20.24 mg, 0.022 mmol) and xantphos (25.6 mg, 0.044 mmol) and heated to 80° C. After 4 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-100% ethyl acetate in petroleum ether to afford methyl 1-((4-(1-(2,6-dichlorophenyl)azetidin-3-yl)naphthalen-1-yl)methyl)piperidine-4-carboxylate (50 mg, 23.40% yield) as an off-white solid. LCMS method 1, LCMS (ESI, m/z): 483.1 $[M+H]^+$.

Example S50. 1-(4-(1-(2,6-dichlorophenyl)azetidin-3-yl)-2-fluoro-6-methylbenzyl)-piperidine-4-carboxylic acid (50)

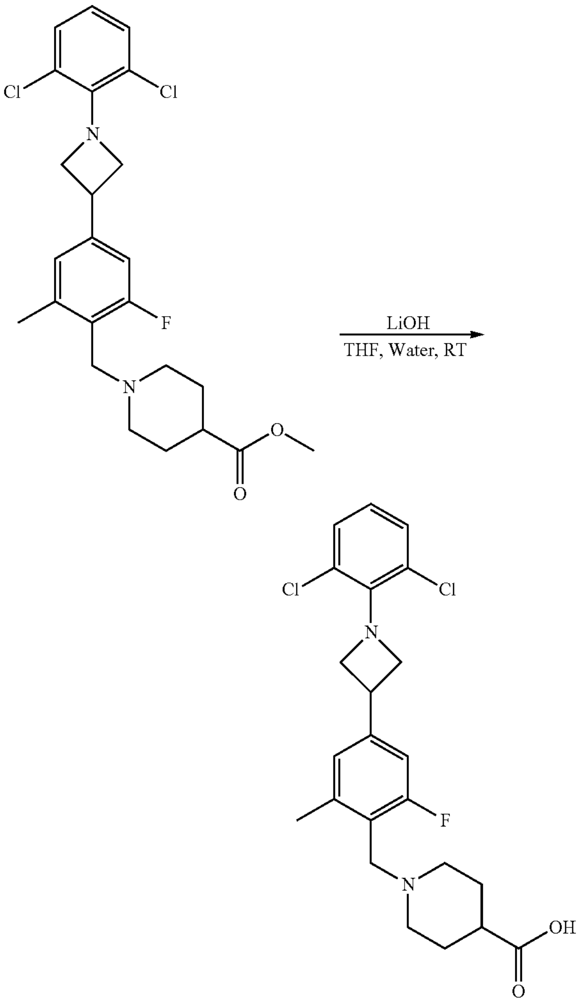

50

To a solution of methyl 1-(4-(1-(2,6-dichlorophenyl)azetidin-3-yl)-2-fluoro-6-methylbenzyl)piperidine-4-carboxylate (280 mg, 0.602 mmol) in THF (6 mL) and water (2 mL) was added LiOH (76 mg, 1.805 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Symmetry C8 (300×19) mm, 7 micron. Mobile phase A: 5 mM Ammonium formate in water, Mobile phase B: Acetonitrile. The required fractions were collected and lyophilized to afford 1-(4-(1-(2,6-dichlorophenyl)azetidin-3-yl)-2-fluoro-6-methylbenzyl)piperidine-4-carboxylic acid, formate salt (105 mg, 0.206 mmol, 34.2% yield, 97.1% pure) as a white solid. $^{1}$H NMR (400 MHz, MeOD): δ 7.25 (s, 1H), 7.21-7.18 (m, 3H), 6.76-6.72 (m, 1H), 4.91-4.86 (m, 2H), 4.43-4.39 (m, 2H), 4.15 (m, 2H), 3.78-3.71 (m, 1H), 3.36-3.32 (m, 1H), 2.95-2.89 (m, 2H), 2.50-2.46 (m, 3H), 2.45-2.41 (m, 1H), 2.08-2.04 (m, 2H), 1.95-1.87 (m, 2H). LCMS method 1; LCMS (ESI, m/z): 451.0 $[M+H]^+$.

Example S51. 1-(2-chloro-4-(1-(2,6-dichlorophenyl)azetidin-3-yl)-6-methylbenzyl)-piperidine-4-carboxylic acid (51)

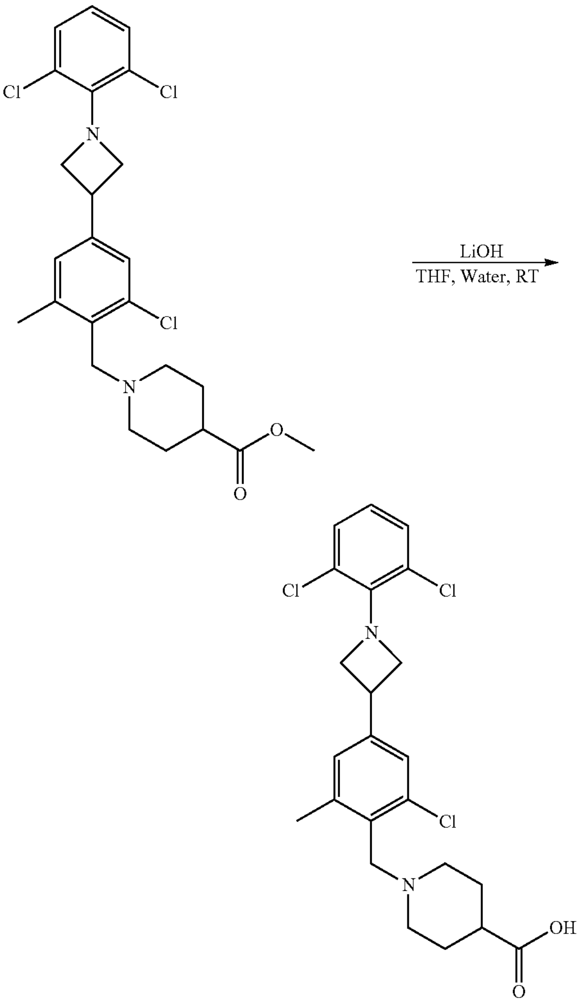

51

To a solution of methyl 1-(2-chloro-4-(1-(2,6-dichlorophenyl)azetidin-3-yl)-6-methylbenzyl)piperidine-4-carboxylate (80 mg, 0.166 mmol) in THF (2 mL) and water (0.5 mL) was added LiOH (11.93 mg, 0.498 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Xselect C18 (150×19) mm, 5 micron. Mobile phase A: 0.1% Formic acid in water, Mobile phase B: Acetonitrile. The required fractions were collected and lyophilized to afford 1-(2-chloro- 4-(1-(2,6-dichlorophenyl)azetidin-3-yl)-6-methylbenzyl)piperidine-4-carboxylic acid, formic acid salt (24.5 mg, 0.047 mmol, 28.6% yield, 99.51% pure) as a white solid. $^1$H NMR: (400 MHz, MeOD): δ 7.41 (s, 1H), 7.32 (s, 1H), 7.20 (d, J=8.00 Hz, 2H), 6.74 (t, J=8.00 Hz, 1H), 4.86-4.90 (m, 2H), 4.39-4.42 (m, 2H), 4.02 (s, 2H), 3.68-3.75 (m, 1H), 3.14-3.17 (m, 2H), 2.65-2.71 (m, 2H), 2.52 (s, 3H), 2.31-2.38 (m, 1H), 1.96-1.99 (m, 2H), 1.75-1.95 (m, 2H). LCMS method 1; LCMS (ESI, m/z): 469.0 [M+2H]$^+$.

Example S52. 1-(4-(1-(2,6-dichlorophenyl)azetidin-3-yl)-2,6-diethylbenzyl)piperidine-4-carboxylic acid (52)

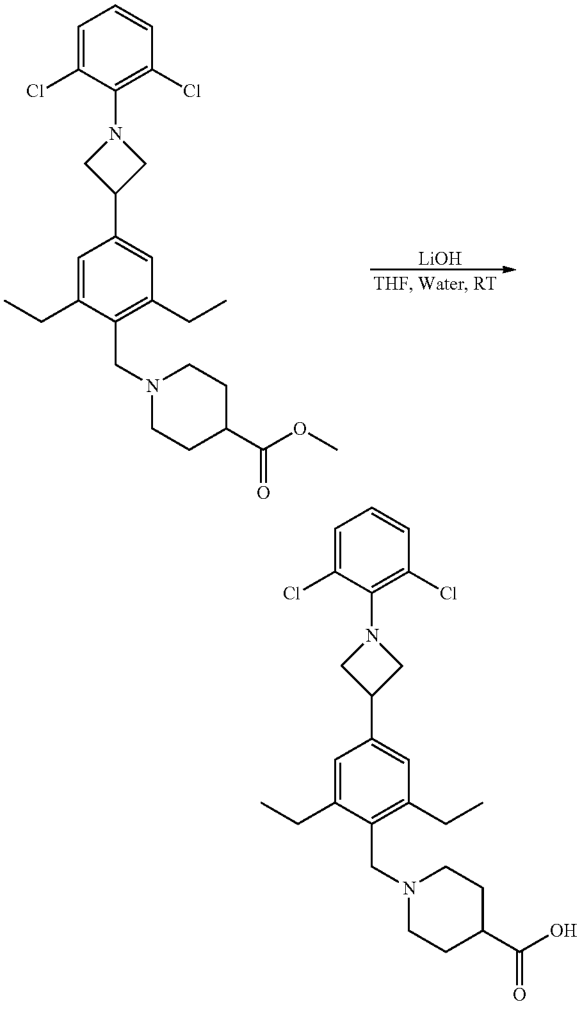

52

To a stirred solution of methyl 1-(4-(1-(2,6-dichlorophenyl)azetidin-3-yl)-2,6-diethylbenzyl)piperidine-4-carboxylate (390 mg, 0.797 mmol) in THF (10 mL) and water (3 mL) was added LiOH (100 mg, 2.390 mmol). The reaction mixture was stirred at ambient temperature. After 16 h, the reaction mixture was concentrated under reduced pressure. The aqueous layer was extracted with diethyl ether (10 mL). The aqueous layer was then separated and acidified with acetic acid to pH 4. The mixture was concentrated under reduced pressure and the residue obtained was purified by preparative HPLC. Prep. HPLC method: Diluent: THF:Water:ACN (50:20:30), Column: Symmetry C8 (300×19) mm, 7 micron, Mobile phase A: 0.1% Formic acid in water (80%-40%), Mobile phase B: Acetonitrile (20%-60%), Flow rate: 15 mL/min. The required fractions were collected and lyopholized to afford 1-(4-(1-(2,6-dichlorophenyl)azetidin-3-yl)-2,6-diethylbenzyl)piperidine-4-carboxylic acid, formic acid salt (70 mg, 12.42%) as white solid. $^1$H-NMR (400 MHz, MeOD): δ 7.26 (s, 2H), 7.20 (d, J=−8.00 Hz, 2H), 6.74 (t, J=8.00 Hz, 1H), 4.39-4.43 (m, 2H), 4.12-4.23 (m, 2H), 3.73-3.76 (m, 1H), 2.79-2.89 (m, 6H), 2.41 (s, 1H), 2.00-2.03 (m, 2H), 1.83-1.85 (m, 2H), 1.23-1.31 (m, 6H) (4H are merged with MeOD solvent signals). LCMS method 1; LCMS (ESI, m/z): 475.0 [M+H]$^+$.

Example S53. 1-(4-(1-(2,6-dichlorophenyl)azetidin-3-yl)-2,6-diisopropylbenzyl)piperidine-4-carboxylic acid (53)

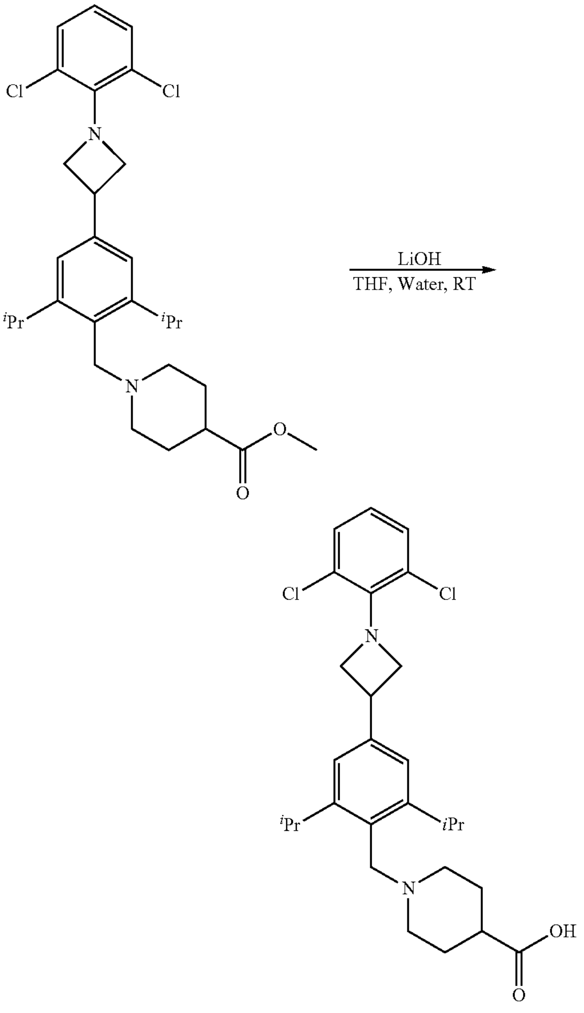

53

To a solution of methyl 1-(4-(1-(2,6-dichlorophenyl)azetidin-3-yl)-2,6-diisopropylbenzyl)piperidine-4-carboxylate (140 mg, 0.189 mmol) in anhydrous THF (5 mL) and water (2 mL) was added LiOH (13.60 mg, 0.568 mmol) and the reaction mixture was allowed to stir at ambient temperature.

After 4 h, TLC analysis indicated complete conversion of the starting material. The reaction mixture was concentrated under reduced pressure and the aqueous layer was acidified using 1.5 N HCl to pH 4-5. The precipitated was collected by filtration and rinsed with ethyl acetate to afford 1-(4-(1-(2,6-dichlorophenyl)azetidin-3-yl)-2,6-diisopropylbenzyl) piperidine-4-carboxylic acid (75 mg, 0.144 mmol, 76% yield, 96.8% pure) as a white solid. $^1$H NMR (400 MHz, $CD_3OD$) δ 7.25 (s, 2H), 7.22 (d, J=8 Hz, 2H), 6.76 (t, J=8 Hz, 1H), 4.91-4.85 (m, 2H), 4.50 (s, 2H), 4.40-4.38 (m, 2H), 3.81-3.74 (m, 1H), 3.53-3.49 (m, 2H), 3.33-3.72 (m, 3H), 2.72 (m, 1H), 2.23-2.17 (m, 2H), 2.03 (m, 2H), 1.32-1.23 (m, 12H). LCMS method 1; LCMS (ESI, m/z): 503.2 $[M+H]^+$.

Example S54. 1-((4-(1-(2,6-dichlorophenyl)azetidin-3-yl)naphthalen-1-yl)methyl)-piperidine-4-carboxylic acid (54)

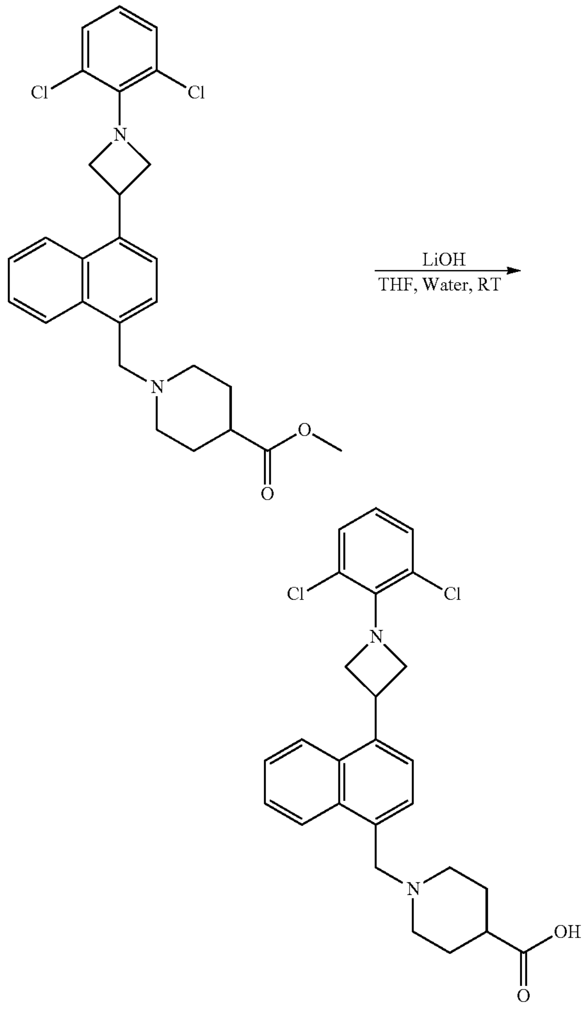

54

To a solution of methyl 1-((4-(1-(2,6-dichlorophenyl) azetidin-3-yl)naphthalen-1-yl)methyl)piperidine-4-carboxylate (45 mg, 0.093 mmol) in THF (2 mL) and water (0.5 mL) was added LiOH (11.15 mg, 0.465 mmol). The mixture was stirred at room temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Xbridge C8 (250×19) mm, 5 micron; Column temp: Ambient; Mobile phase A: 0.1% Formic acid in water. Mobile phase B: Acetonitrile. The required fractions were collected and lyophilized to afford 1-((4-(1-(2,6-dichlorophenyl)azetidin-3-yl)naphthalen-1-yl)methyl)-piperidine-4-carboxylic acid, formic acid salt (16 mg, 0.031 mmol, 33.1% yield, 99.4% pure) as a white solid. $^1$H NMR (400 MHz, MeOD): δ 8.32 (dd, J=−1.60, −7.40 Hz, 1H), 8.06 (dd, J=−2.40, −7.00 Hz, 1H), 7.723-7.662 (m, 4H), 7.20 (d, J=−8.00 Hz, 2H), 6.73 (t, J=−8.00 Hz, 1H), 5.158-5.121 (m, 2H), 4.605-4.542 (m, 5H), 2.966 (bs, 2H), 2.431 (bs, 1H) 2.052-2.018 (m, 2H), 1.893 (bs, 2H). (2H are merged with solvent signal). LCMS method 1; LCMS (ESI, m/z): 469.0 $[M+2H]^+$.

General Route to Compounds 55-57

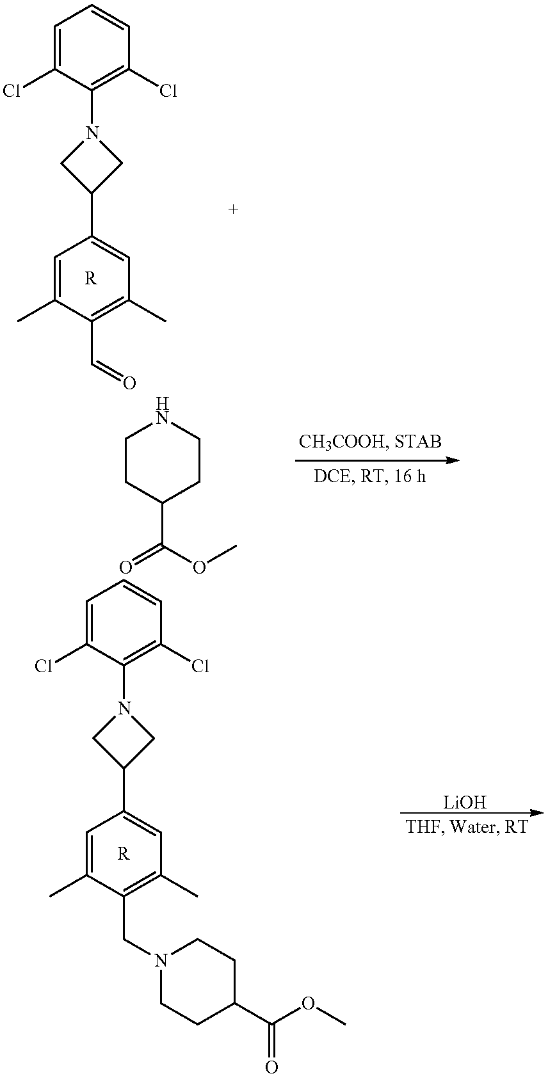

-continued

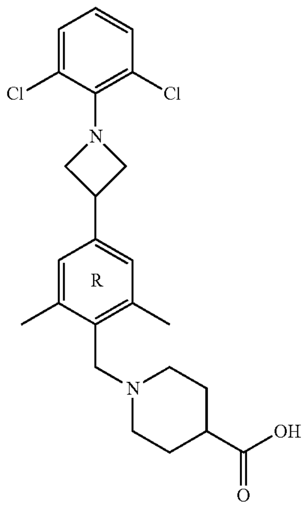

55-57

Synthesis of methyl 1-(4-(1-(2,6-dichlorophenyl) azetidin-3-yl)-2-ethyl-6-methylbenzyl)piperidine-4-carboxylate

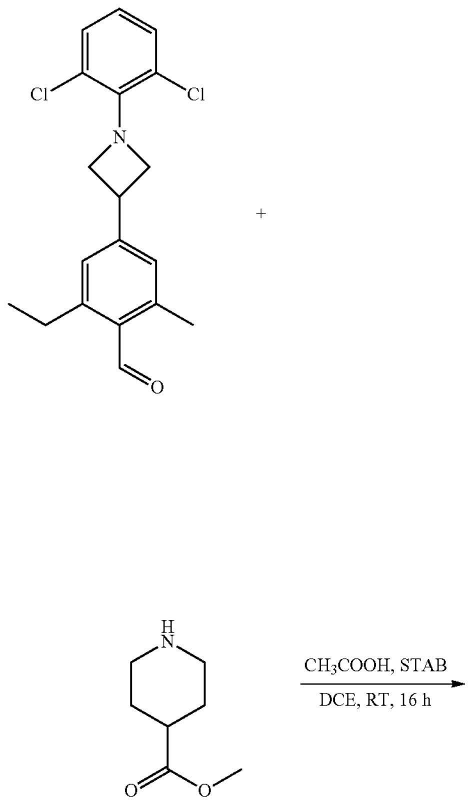

-continued

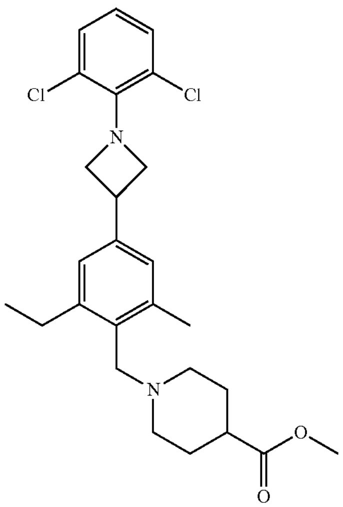

To a stirred solution of 4-(1-(2,6-dichlorophenyl)azetidin-3-yl)-2-ethyl-6-methylbenzaldehyde (300 mg, 0.861 mmol) and methyl piperidine-4-carboxylate (123 mg, 0.861 mmol) in DCE (15 mL) was added acetic acid (0.1 mL) and the mixture was stirred for 30 min at room temperature. Sodium triacetoxyborohydride (274 mg, 1.292 mmol) was added at ice cold temperature and allowed to reach room temperature and stirred for 16 h. The reaction mixture was diluted with DCM (10 mL) and quenched with sat. ammonium chloride solution. The aqueous layer was extracted with DCM (2×10 mL), the combined organic phase was washed with water (20 mL) and dried over $Na_2SO_4$, filtered and the solvent evaporated under reduced pressure. The resulting residue was purified by flash column chromatography on silica gel (100-200 mesh) eluting with 20-50% ethyl acetate in petroleum ether to afford the methyl 1-(4-(1-(2,6-dichlorophenyl) azetidin-3-yl)-2-ethyl-6-methylbenzyl)piperidine-4-carboxylate (270 mg, 66% yield) as a brown semi-solid. LCMS method 1, LCMS (ESI, m/z): 475.2 $[M+H]^+$.

Synthesis of methyl 1-(2-cyclopropyl-4-(1-(2,6-dichlorophenyl)azetidin-3-yl)benzyl)piperidine-4-carboxylate

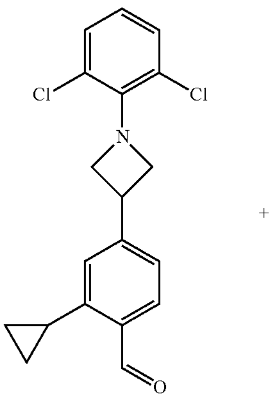

-continued

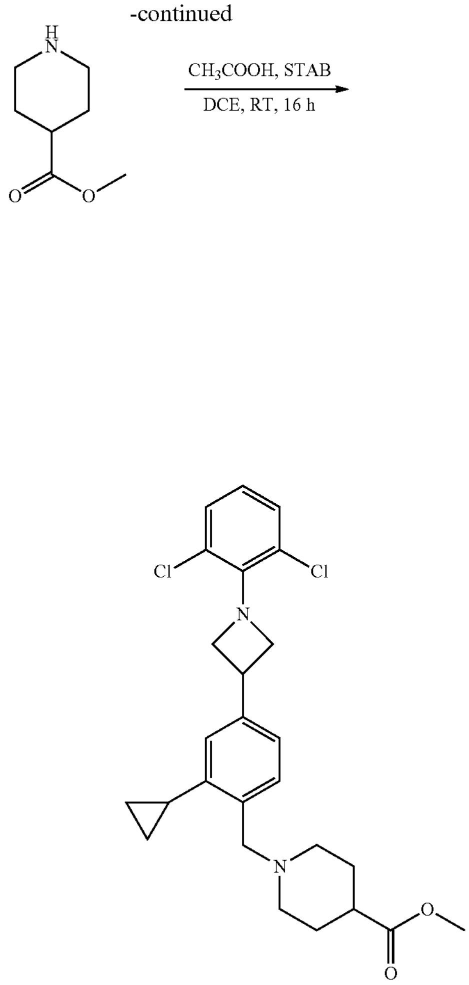

Synthesis of methyl 1-(2-cyclopropyl-4-(1-(2,6-dichlorophenyl)azetidin-3-yl)-6-methylbenzyl)piperidine-4-carboxylate

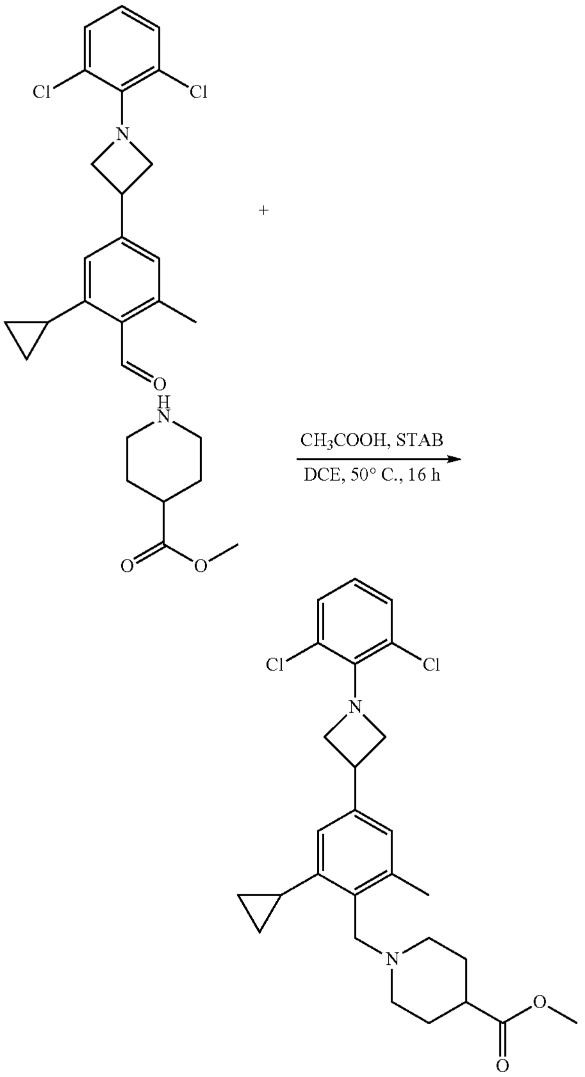

To a stirred solution of 2-cyclopropyl-4-(1-(2,6-dichlorophenyl)azetidin-3-yl)benzaldehyde (200 mg, 0.578 mmol) and methyl piperidine-4-carboxylate (83 mg, 0.578 mmol) in DCE (5 mL) was added acetic acid (0.033 mL, 0.578 mmol) and stirred for 30 min at room temperature. Sodium triacetoxyborohydride (184 mg, 0.866 mmol) was added at ice cold temperature and allowed to reach room temperature and stirred for 16 h. The reaction mixture was diluted with DCM (10 mL) and quenched with sat. ammonium chloride solution. The aqueous layer was extracted with DCM (2×10 mL), the combined organic phase was washed with water (20 mL) and dried over $Na_2SO_4$, filtered and the solvent evaporated under reduced pressure. The resulting residue was purified by flash column chromatography on silica gel (100-200 mesh) eluting with 20-50% ethyl acetate in petroleum ether to afford the methyl 1-(2-cyclopropyl-4-(1-(2,6-dichlorophenyl)azetidin-3-yl)benzyl)piperidine-4-carboxylate (110 mg, 40% yield) as a pale yellow semi-solid. LCMS method 1, LCMS (ESI, m/z): 474.9 $[M+H]^+$.

To a stirred solution of 4-bromo-2-chloro-6-methylbenzaldehyde (500 mg, 2.141 mmol) and methyl piperidine-4-carboxylate (59.6 mg, 0.416 mmol) in DCE (15 mL) was added acetic acid (12.50 mg, 0.208 mmol) and stirred for 30 min at room temperature. Sodium triacetoxyborohydride (203 mg, 0.625 mmol) was added at ice cold temperature and allowed to reach room temperature and stirred for 16 h at 50° C. The reaction mixture was diluted with DCM (20 mL) and quenched with sat. ammonium chloride solution. The aqueous layer was extracted with DCM (2×20 mL), the combined organic phase was washed with water (30 mL) and dried over $Na_2SO_4$, filtered and the solvents were evaporated under reduced pressure. The resulting residue was purified by flash column chromatography on silica gel (100-200 mesh) eluting with 30-50% ethyl acetate in petroleum ether to afford the methyl 1-(2-cyclopropyl-4-(1-(2,6-dichlorophenyl)azetidin-3-yl)-6-methylbenzyl)piperidine-4-carboxylate (100 mg, 49% yield) as a yellow semi-solid. LCMS method 1, LCMS (ESI, m/z): 487.2 $[M+H]^+$.

Example S55. 1-(4-(1-(2,6-dichlorophenyl)azetidin-3-yl)-2-ethyl-6-methylbenzyl)-piperidine-4-carboxylic acid (55)

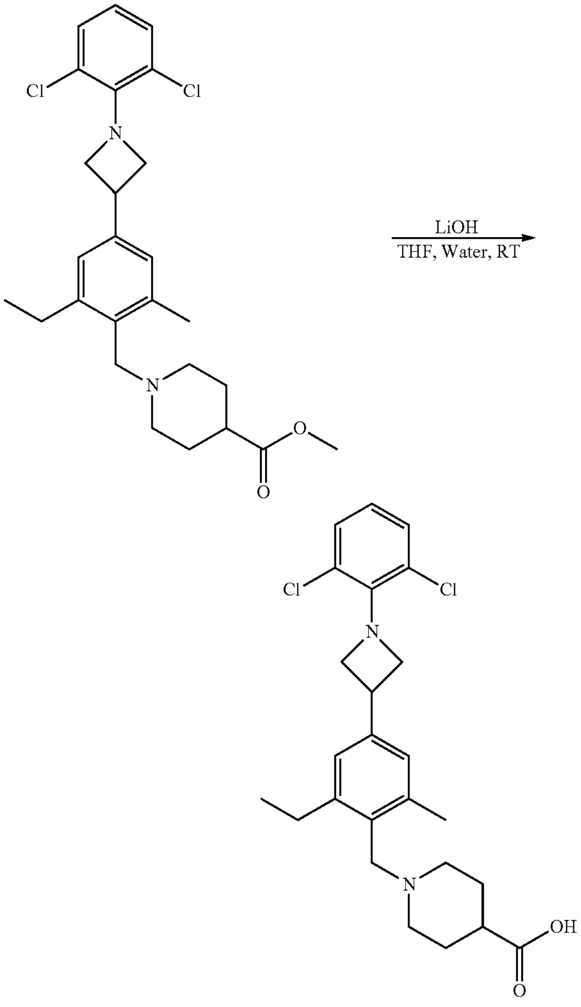

55

To a solution of methyl 1-(4-(1-(2,6-dichlorophenyl)azetidin-3-yl)-2-ethyl-6-methylbenzyl)piperidine-4-carboxylate (250 mg, 0.526 mmol) in THF (4 mL) and water (1 mL) was added LiOH (66.2 mg, 1.577 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30) Column: Sunfire C18 (150×19) mm, 5 micron, Mobile phase A: 5 mM Ammonium formate in water Mobile phase B: Acetonitrile. The required fractions were collected and lyophilized to afford 1-(4-(1-(2,6-dichlorophenyl)azetidin-3-yl)-2-ethyl-6-methylbenzyl) piperidine-4-carboxylic acid, formic acid salt (45 mg, 0.089 mmol, 16.86% yield, 99.9% pure) as a brown solid. $^1$H NMR (400 MHz, MeOD): δ 7.24 (s, 2H), 7.20-7.18 (d, J=8 Hz, 2H), 6.75-6.71 (t, J=8 Hz, 1H), 4.42-4.39 (m, 2H), 4.14 (s, 2H), 3.74-3.72 (m, 1H), 2.92 (bs, 2H), 2.84-2.78 (q, J=7.6 Hz, 2H), 2.48 (s, 3H), 2.42-2.41 (m, 1H), 2.06-2.05 (m, 2H), 2.04 (bs, 1H), 2.01-1.85 (m, 2H), 1.26-1.22 (t, J=7.6 Hz, 3H). LCMS method 1; LCMS (ESI, m/z): 461.2 [M+H]$^+$.

Example S56. 1-(2-cyclopropyl-4-(1-(2,6-dichlorophenyl)azetidin-3-yl)benzyl)piperidine-4-carboxylic acid (56)

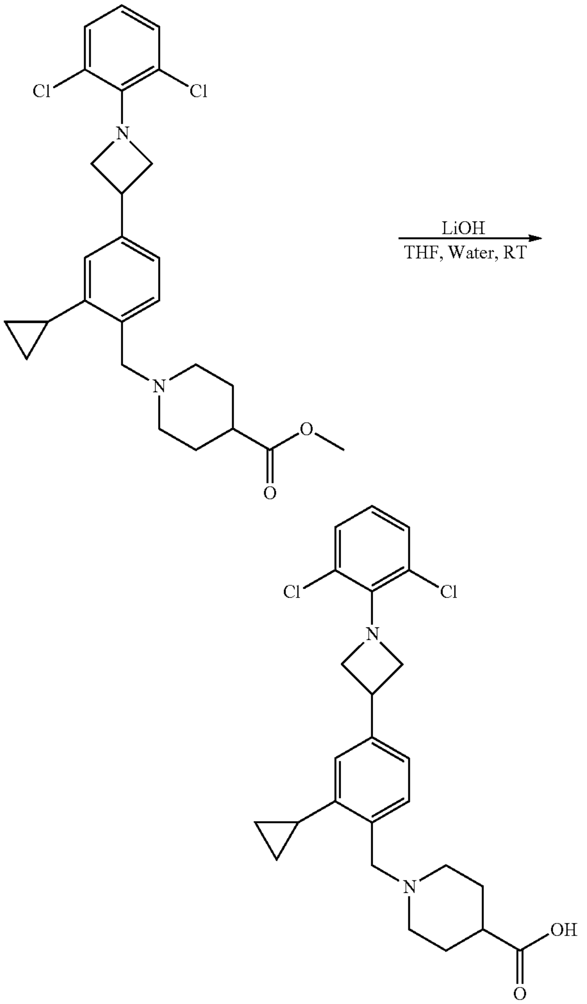

56

To a solution of methyl 1-(2-cyclopropyl-4-(1-(2,6-dichlorophenyl)azetidin-3-yl)benzyl)piperidine-4-carboxylate (110 mg, 0.232 mmol) in THF (4 mL) and water (1 mL) was added LiOH (55.6 mg, 2.323 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid to pH 5-6. The solid thus obtained was filtered and washed with diethyl ether to yield 1-(2-cyclopropyl-4-(1-(2,6-dichlorophenyl)azetidin-3-yl)benzyl)piperidine-4-carboxylic acid, formic acid salt (70.4 mg, 0.137 mmol, 59.0% yield, 98.4% pure) as a white solid. $^1$H-NMR (400 MHz, MeOD): 7.41-7.48 (m, 2H), 7.19-7.21 (m, 3H), 6.74 (t, J=8.00 Hz, 1H), 4.41-4.60 (m, 5H), 3.73-4.37 (m, 1H), 3.34-3.50 (m, 2H), 3.05-3.08 (m, 2H), 2.45 (s, 1H), 2.05-2.16 (m, 4H), 1.93 (s, 2H), 1.08-1.13 (m, 2H), 0.76-0.80 (m, 2H). LCMS method 3; LCMS (ESI, m/z): 459.1 $[M+H]^+$.

Example S57. 1-(2-cyclopropyl-4-(1-(2,6-dichlorophenyl)azetidin-3-yl)-6-methylbenzyl)-piperidine-4-carboxylic acid (57)

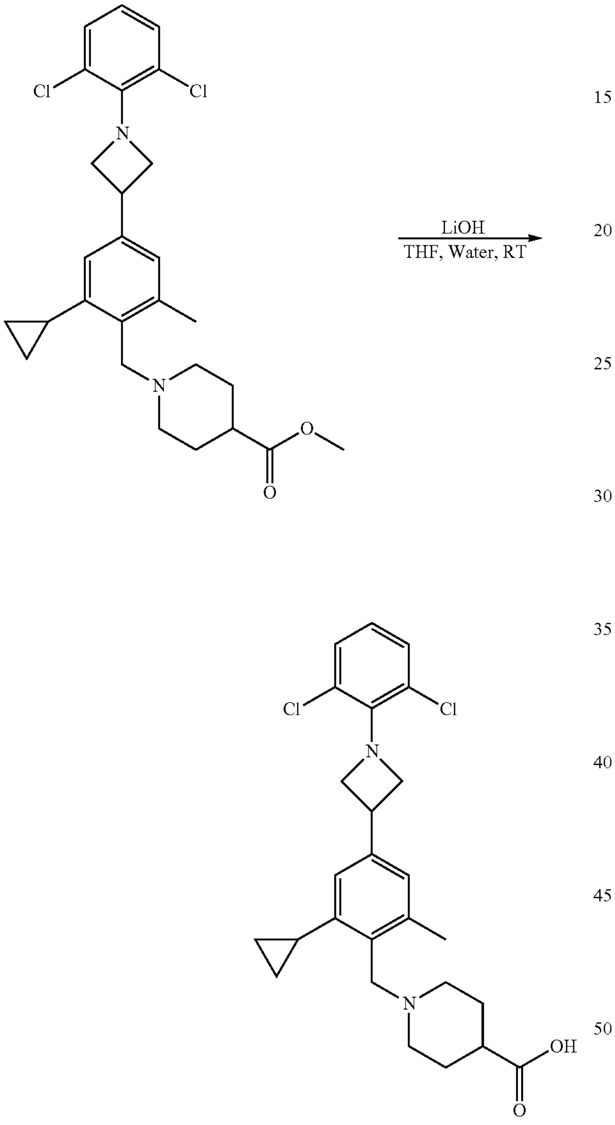

57

To a solution of methyl 1-(2-cyclopropyl-4-(1-(2,6-dichlorophenyl)azetidin-3-yl)-6-methylbenzyl)piperidine-4-carboxylate (60 mg, 0.123 mmol) in THF (2 mL) and water (0.5 mL) was added LiOH (15.49 mg, 0.369 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30), Column: Zorbax C18 (50×21.5) mm, 5 micron. Mobile phase A: 0.1% Formic acid in water. Mobile phase B: Acetonitrile. The required fractions were collected and lyophilized to afford 1-(2-cyclopropyl-4-(1-(2,6-dichlorophenyl)azetidin-3-yl)-6-methylbenzyl)piperidine-4-carboxylic acid, formic acid salt (30 mg, 0.058 mmol, 46.8% yield, 99.7% pure) as a white solid. $^1H$ NMR (400 MHz, MeOD): δ 7.23 (d, J=8.00 Hz, 2H), 7.06 (s, 1H), 6.81 (s, 1H), 6.75 (t, J=8.00 Hz, 1H), 4.79 (t, J=8.40 Hz, 2H), 4.31-4.49 (m, 2H), 3.66-3.70 (m, 1H), 3.61 (s, 2H), 2.73-2.68 (m, 2H), 2.36 (s, 3H), 2.36-2.22 (m, 2H), 2.10 (s, 2H), 1.75-1.77 (m, 2H), 1.45-1.48 (m, 2H), 0.90 (d, J=8.00 Hz, 2H), 0.61 (d, J=4.40 Hz, 2H). LCMS method 2; LCMS (ESI, m/z): 473.2 $[M+H]^+$.

General Route to Compound 58

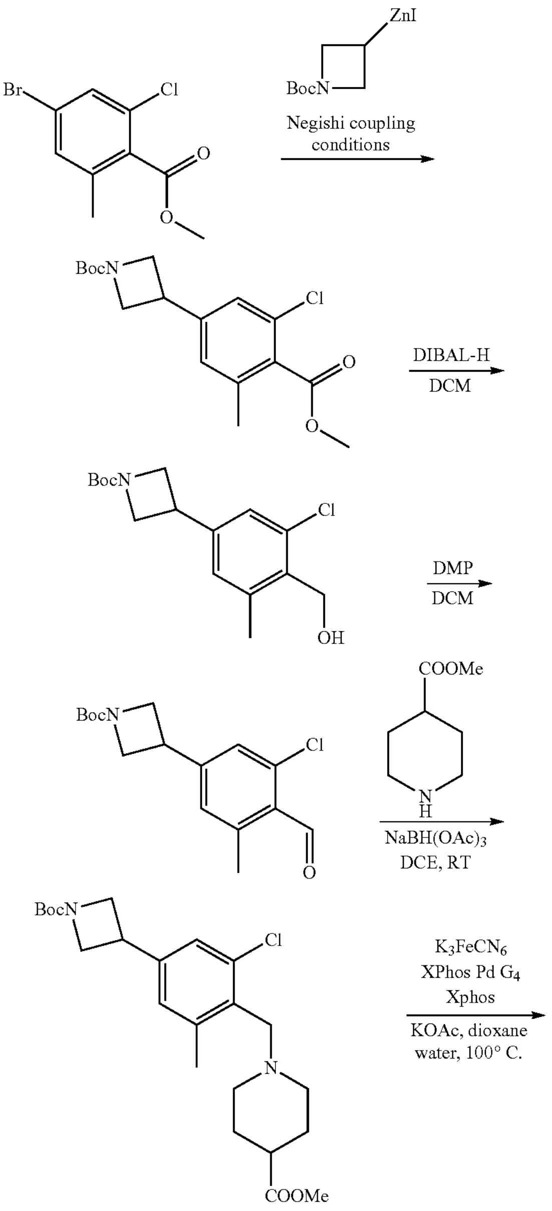

-continued

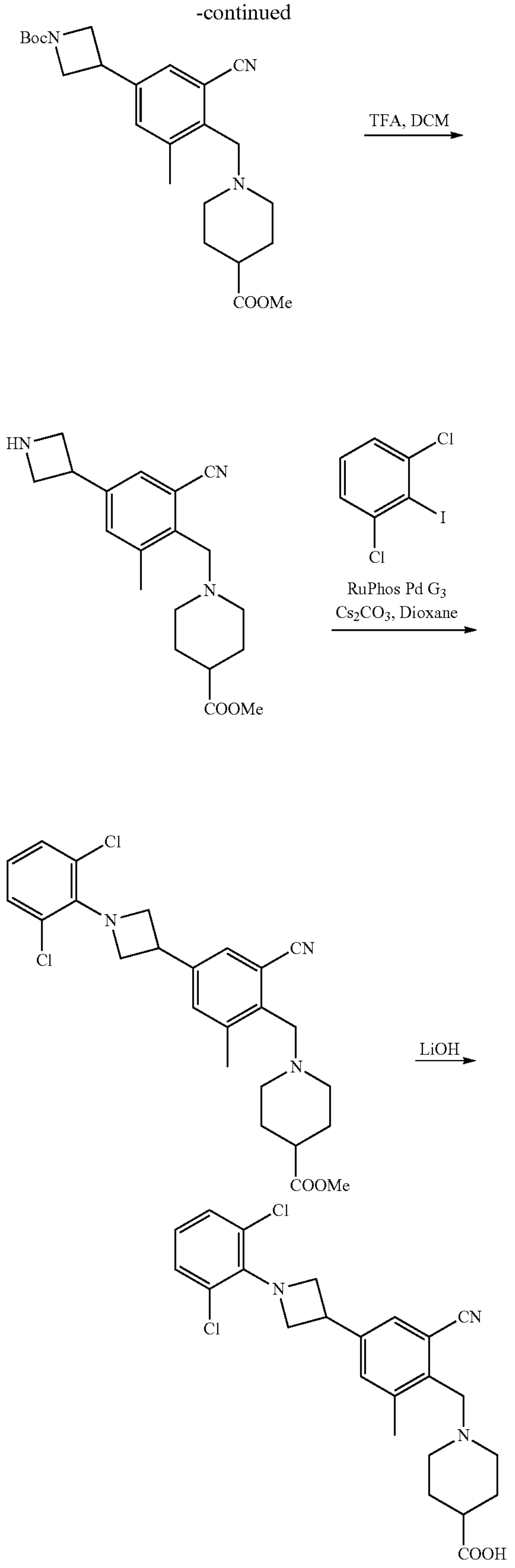

58

Synthesis of tert-butyl 3-(3-chloro-4-(methoxycarbonyl)-5-methylphenyl)azetidine-1-carboxylate

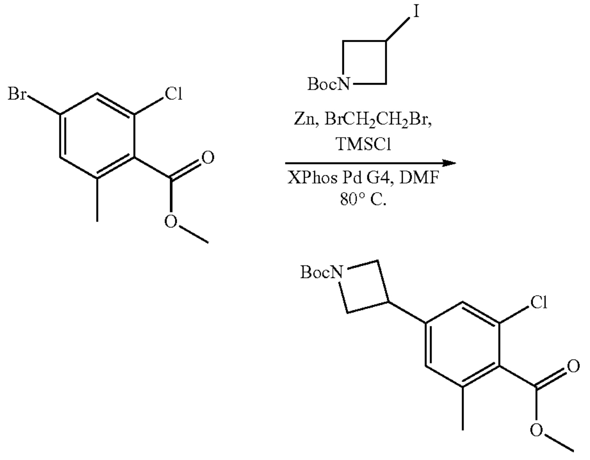

To a suspension of activated zinc (12.41 g, 190 mmol) in anhydrous DMF (100 mL) was added 1,2-dibromoethane (0.164 mL, 1.897 mmol) and heated to 75° C. After 15 min, the reaction mixture was cooled to room temperature, trimethylchlorosilane (0.243 mL, 1.897 mmol) was added and allowed to stir at ambient temperature for additional 30 min. Then a solution of tert-butyl 3-iodoazetidine-1-carboxylate (21.49 g, 76 mmol) in 10 mL of anhydrous DMF was added and stirred at room temperature for another 30 min, followed by methyl 4-bromo-2-chloro-6-methylbenzoate (5.0 g, 18.97 mmol) and XPhos Pd G4 (1.633 g, 1.897 mmol) in 10 mL of DMF. The reaction mixture was allowed to stir at 80° C. for 2 h. After completion of the reaction, the reaction mixture was cooled to room temperature and quenched with sat. ammonium chloride solution. The crude was filtered through a pad of celite and washed with ethyl acetate. The filtrate was then transferred to a separating funnel and washed with cold water, dried over anhydrous sodium sulphate and concentrated under reduced pressure. The resulting residue was purified by flash column chromatography on silica gel (100-200 mesh) eluting with 0-50% ethyl acetate in petroleum ether to afford tert-butyl 3-(3-chloro-4-(methoxycarbonyl)-5-methylphenyl)azetidine-1-carboxylate (4.8 g, 74% yield) as a colorless semi-solid. LCMS method 3, LCMS (ESI, m/z): 239.8 [M−100]+.

Synthesis of tert-butyl 3-(3-chloro-4-(hydroxymethyl)-5-methylphenyl)azetidine-1-carboxylate

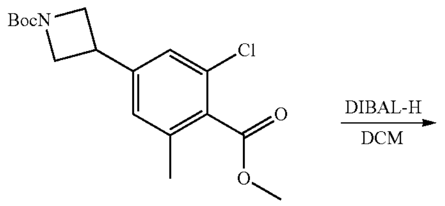

-continued

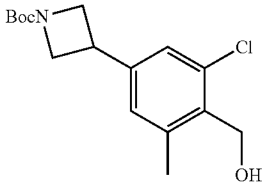

To a stirred solution of tert-butyl 3-(3-chloro-4-(methoxycarbonyl)-5-methylphenyl)azetidine-1-carboxylate (2.0 g, 5.89 mmol) in DCM (20 mL) was added DIBAL-H (11.7 mL, 11.70 mmol) at −78° C. and stirred for 4 h at −78° C. The reaction mixture was quenched with saturated ammonium chloride solution (10 ml), extracted with DCM (60 mL) and washed with brine. The combined organic layer was dried over $Na_2SO_4$, filtered and the solvents were evaporated under reduced pressure to afford the title compound tert-butyl 3-(3-chloro-4-(hydroxymethyl)-5-methylphenyl)azetidine-1-carboxylate (1.1 g, 59% yield) as an off-white solid. LCMS method 4, LCMS (ESI, m/z): 212.0 $[M-100]^+$.

Synthesis of tert-butyl 3-(3-chloro-4-formyl-5-methylphenyl)azetidine-1-carboxylate

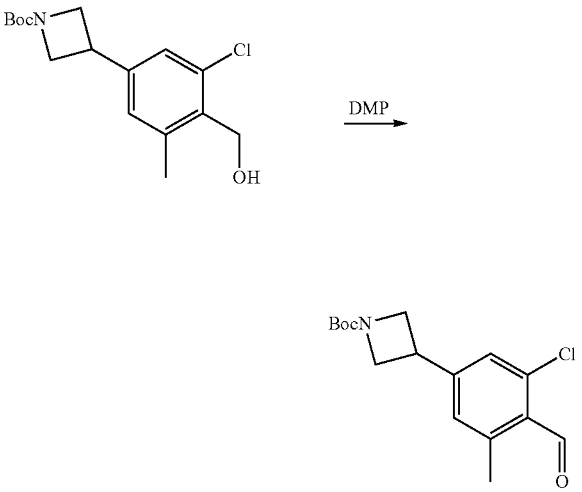 [SMILES: Cc1cc(C2CN(C(=O)OC(C)(C)C)C2)cc(Cl)c1CO ; Cc1cc(C2CN(C(=O)OC(C)(C)C)C2)cc(Cl)c1C=O]

To a stirred solution of tert-butyl 3-(3-chloro-4-(hydroxymethyl)-5-methylphenyl)azetidine-1-carboxylate (1.2 g, 3.85 mmol) in DCM (10 mL) was added Dess-Martin periodinane (1.959 g, 4.62 mmol) at 0° C. under nitrogen atmosphere. After 1 h, TLC analysis indicated complete conversion of the starting material. The reaction mixture was filtered through a celite pad washed with EtOAc. The filtrate was concentrated under reduced pressure to yield tert-butyl 3-(3-chloro-4-formyl-5-methylphenyl)azetidine-1-carboxylate (0.9 g, 75%) as a light brown semi-solid. LCMS method 3, LCMS (ESI, m/z): 210.0 [M−100]+.

Synthesis of methyl 1-(4-(1-(tert-butoxycarbonyl)azetidin-3-yl)-2-chloro-6-methylbenzyl)piperidine-4-carboxylate

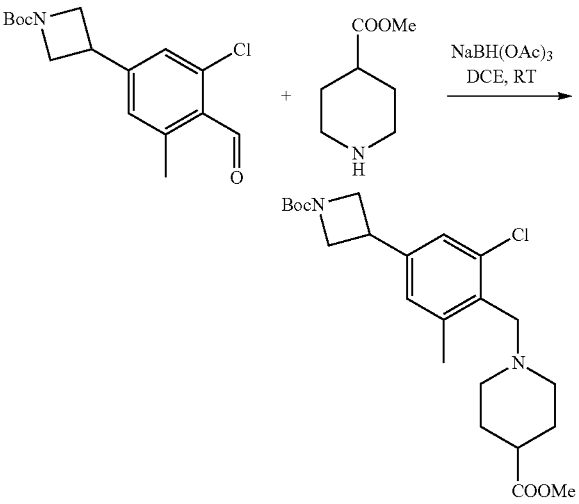

To a stirred solution of tert-butyl 3-(3-chloro-4-formyl-5-methylphenyl)azetidine-1-carboxylate (500 mg, 1.614 mmol) and methyl piperidine-4-carboxylate (277 mg, 1.937 mmol) in DCE (10 mL) was added acetic acid (9.24 μl, 0.161 mmol) and stirred for 30 min at room temperature. Sodium triacetoxyborohydride (342 mg, 1.614 mmol) was added at ice cold temperature and allowed to reach room temperature and stirred for 16 h. The reaction mixture was diluted with DCM (10 mL) and quenched with sat. ammonium chloride solution. The aqueous layer was extracted with DCM (2×10 mL), the combined organic phase was washed with water (20 mL) and dried over $Na_2SO_4$, filtered and the solvent evaporated under reduced pressure. The resulting residue was purified by flash column chromatography on silica gel (100-200 mesh) eluting with 0-50% ethyl acetate in petroleum ether to afford methyl 1-(4-(1-(tert-butoxycarbonyl)azetidin-3-yl)-2-chloro-6-methylbenzyl)piperidine-4-carboxylate (700 mg, 99% yield) as a yellow liquid. LCMS method 1, LCMS (ESI, m/z): 437.2 $[M+H]^+$.

Synthesis of methyl 1-(4-(1-(tert-butoxycarbonyl)azetidin-3-yl)-2-cyano-6-methylbenzyl)piperidine-4-carboxylate

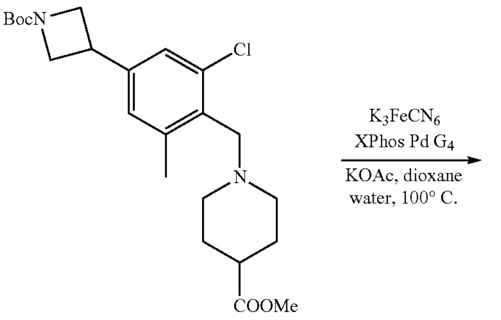

-continued

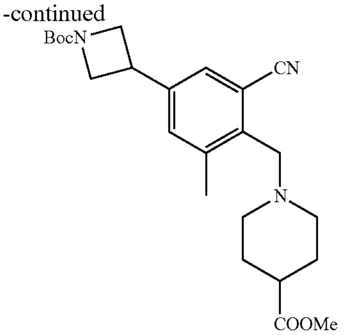

To a stirred solution of methyl 1-(4-(1-(tert-butoxycarbonyl)azetidin-3-yl)-2-chloro-6-methylbenzyl)piperidine-4-carboxylate (700 mg, 1.602 mmol) in 1,4-dioxane (3 mL) a solution of potassium ferrocyanide (1180 mg, 3.20 mmol) and potassium acetate (18.87 mg, 0.192 mmol) in water 1 mL was added at room temperature under nitrogen atmosphere. The reaction mixture was stirred at room temperature for 15 min and followed by addition of XPhos Pd G4 (138 mg, 0.160 mmol) and XPhos (76 mg, 0.160 mmol). The resulting reaction mixture was stirred for 16 h at 100° C. The reaction mixture was diluted with water (10 mL) and extracted with EtOAc (3x10 mL), the combined organic phase was washed with water (30 mL) and dried over $Na_2SO_4$, filtered and the solvent evaporated under reduced pressure. The resulting residue was purified by flash column chromatography on silica gel (100-200 mesh) eluting with 0-40% ethyl acetate in petroleum ether to afford methyl 1-(4-(1-(tert-butoxycarbonyl)azetidin-3-yl)-2-cyano-6-methylbenzyl)piperidine-4-carboxylate (400 mg, 58% yield) as a yellow liquid. LCMS method 3, LCMS (ESI, m/z): 428.0 $[M+H]^+$.

Synthesis of methyl 1-(4-(azetidin-3-yl)-2-cyano-6-methylbenzyl)piperidine-4-carboxylate

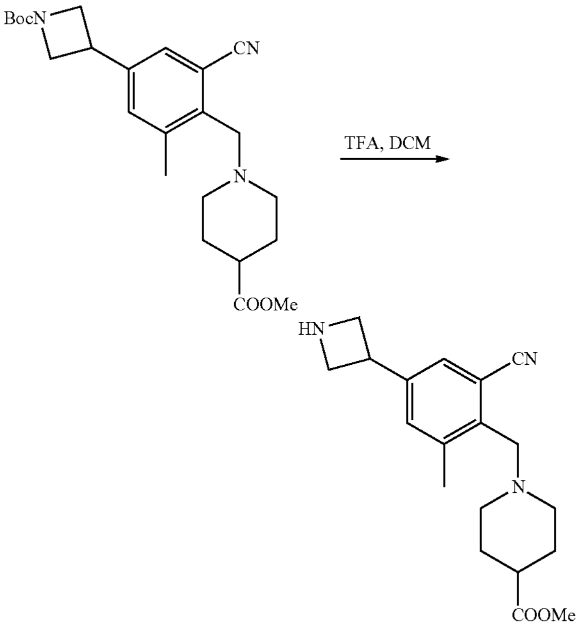

To a stirred solution of methyl 1-(4-(1-(tert-butoxycarbonyl)azetidin-3-yl)-2-cyano-6-methylbenzyl)piperidine-4-carboxylate (400 mg, 0936 mmol) in anhydrous DCM (10 mL) was added TFA (0.72 mL, 9.36 mmol) at 0° C. The reaction mixture was stirred at room temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(4-(azetidin-3-yl)-2-cyano-6-methylbenzyl)piperidine-4-carboxylate, TFA (400 mg, 97% yield) as a yellow semi-solid. LCMS method 31, LCMS (ESI, m/z): 328.0 $[M+H]^+$.

Synthesis of methyl 1-(2-cyano-4-(1-(2,6-dichlorophenyl)azetidin-3-yl)-6-methylbenzyl)piperidine-4-carboxylate

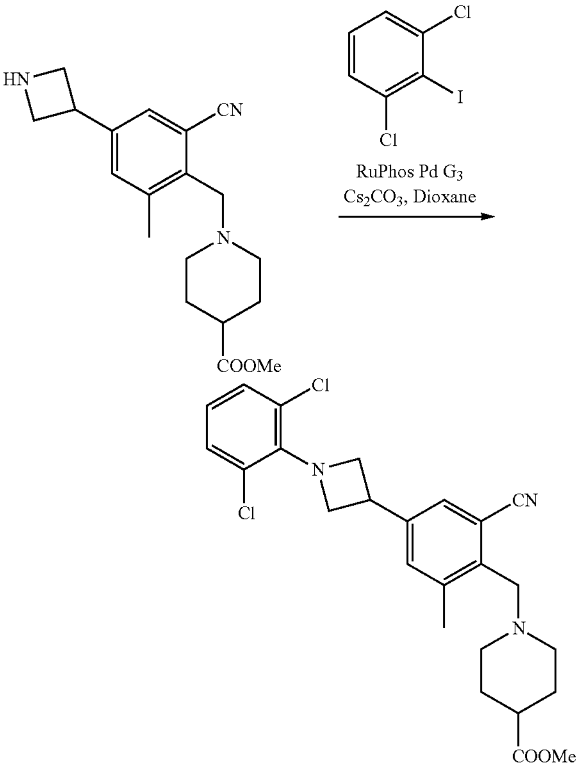

To a stirred solution of methyl 1-(4-(azetidin-3-yl)-2-cyano-6-methylbenzyl)piperidine-4-carboxylate, TFA (300 mg, 0.680 mmol) and 1,3-dichloro-2-iodobenzene (232 mg, 0.849 mmol) in 1,4-dioxane (8 mL), was added cesium carbonate (664 mg, 2.039 mmol). The reaction mixture was degassed with nitrogen. After 10 min, RuPhos Pd G3 (56.8 mg, 0.068 mmol) was added and the reaction mixture was stirred at 80° C. The progress of the reaction was monitored by TLC. After 16 h, the reaction mixture was cooled to room temperature, diluted with ethyl acetate (30 mL) and the organic layer was washed with water, dried over sodium sulphate, and concentrated under reduced pressure. The resulting residue was purified by flash column chromatography on silica gel eluting with 5-30% ethyl acetate in petroleum ether to afford methyl 1-(2-cyano-4-(1-(2,6-dichlorophenyl)azetidin-3-yl)-6-methylbenzyl)piperidine-4-carboxylate (120 mg, 37.4% yield) as a brown semi-solid. LCMS method 3, LCMS (ESI, m/z): 472.2 [M+H]$^+$.

Example S58. 1-(2-cyano-4-(1-(2,6-dichlorophenyl)azetidin-3-yl)-6-methylbenzyl)-piperidine-4-carboxylic acid (58)

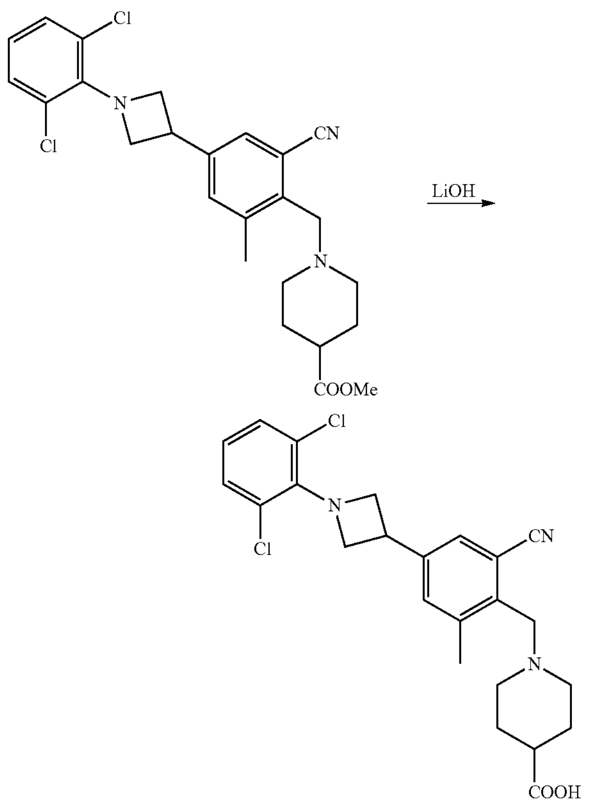

58

To a solution of methyl 1-(2-cyano-4-(1-(2,6-dichlorophenyl)azetidin-3-yl)-6-methylbenzyl)piperidine-4-carboxylate (120 mg, 0.254 mmol) in THE (6 mL) and water (2 mL) was added LiOH (30.4 mg, 1.270 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Symmetry C8 (300×19) mm, 7 micron. Mobile phase A: 5 mM Ammonium formate in water Mobile phase B: Acetonitrile. The required fractions were collected and lyophilized to afford 1-(2-cyano-4-(1-(2,6-dichlorophenyl)azetidin-3-yl)-6-methylbenzyl)piperidine-4-carboxylic acid, formic acid salt (101 mg, 0.198 mmol, 78% yield, 99% pure) as a white solid. $^1$H NMR (400 MHz, DMSO-$d_6$): δ 7.63 (s, 2H), 7.20 (d, J=8.00 Hz, 2H), 6.75 (t, J=8.00 Hz, 1H), 4.88 (m, 2H), 4.40-4.44 (m, 2H), 3.74-3.78 (m, 3H), 2.08-2.91 (m, 2H), 2.51 (s, 3H), 2.28-2.36 (m, 3H), 1.89-1.91 (m, 2H), 1.64-1.73 (m, 2H). LCMS method 1; LCMS (ESI, m/z): 458.2 [M+H]$^+$.

General Route to Compounds 59-61

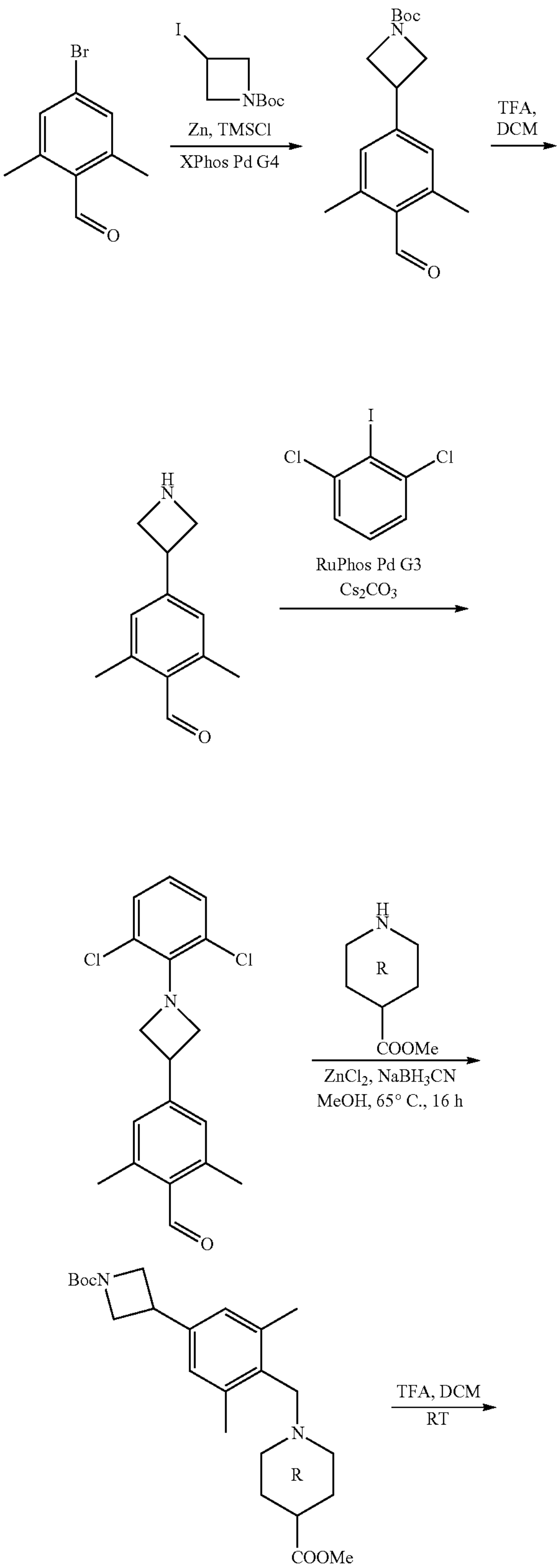

-continued

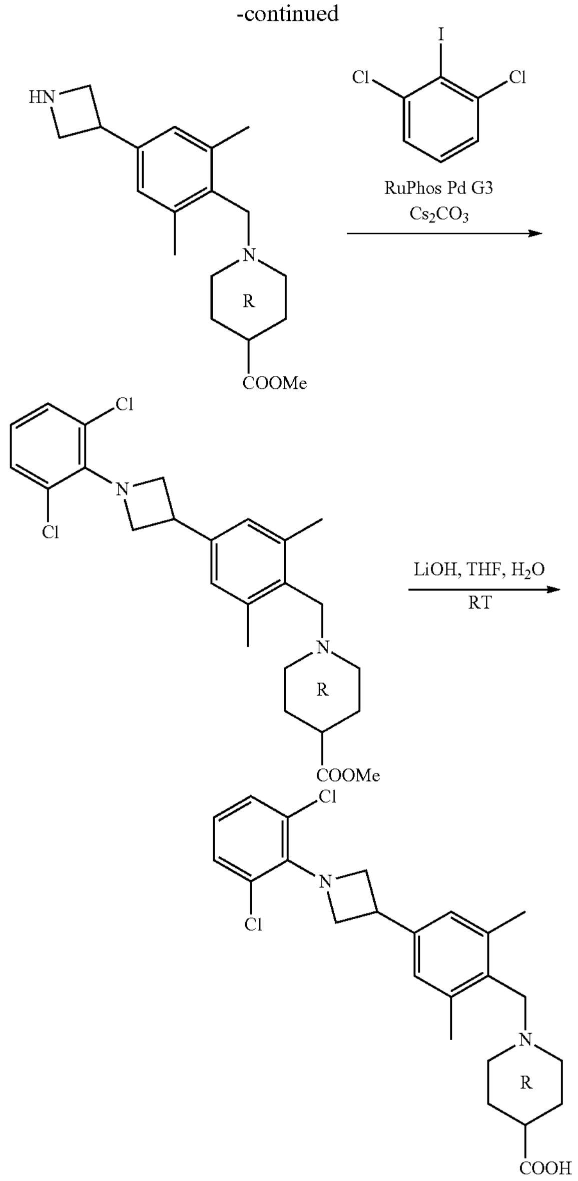

59-61

Synthesis of tert-butyl 3-(4-formyl-3,5-dimethylphenyl)azetidine-1-carboxylate

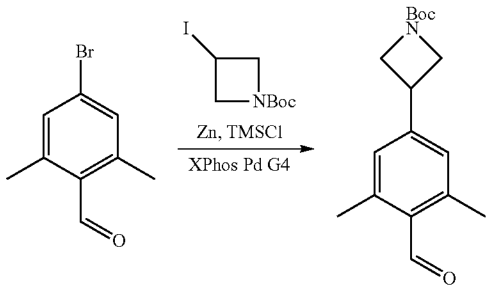

To a suspension of activated zinc (15.34 g, 235 mmol) in anhydrous DMF (200 mL) was added 1,2-dibromoethane (1.01 mL, 11.73 mmol) and the mixture heated to 75° C. After 15 min, the reaction mixture was cooled to room temperature, chloro trimethylsilane (1.5 mL, 11.73 mmol) was added and allowed to stir at ambient temperature for additional 30 min. Then a solution of tert-butyl 3-iodoazetidine-1-carboxylate (19.93 g, 70.4 mmol) in 50 mL of anhydrous DMF was added to the reaction mixture and stirred at room temperature for another 30 min, followed by addition of 4-bromo-2,6-dimethylbenzaldehyde (5 g, 23.47 mmol) and XPhos Pd G4 (4.04 g, 4.69 mmol) in 50 mL of DMF. The reaction mixture was stirred at 80° C. for 2 h. After completion of the reaction, the mixture was cooled to ambient temperature and quenched with sat. ammonium chloride solution. The crude was filtered through a pad of celite which was washed with ethyl acetate. The filtrate was then transferred to a separating funnel and washed with cold water (250 mL), dried over anhydrous sodium sulphate and concentrated under reduced pressure. The resulting residue was purified by flash column chromatography on silica gel (100-200 mesh) eluting with 0-20% ethyl acetate in petroleum ether to afford tert-butyl 3-(4-formyl-3,5-dimethylphenyl)azetidine-1-carboxylate (4.3 g, 63% yield). LCMS Method 1; LCMS (ESI, m/z): 190.2 $[M-100]^+$.

Synthesis of 4-(azetidin-3-yl)-2,6-dimethylbenzaldehyde

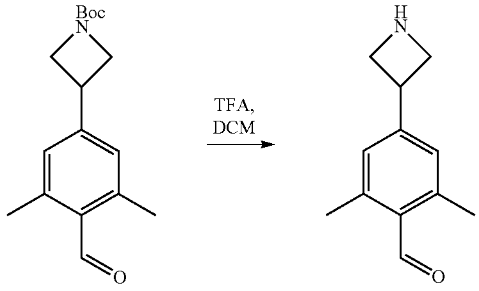

To a stirred solution of tert-butyl 3-(4-formyl-3,5-dimethylphenyl)azetidine-1-carboxylate (2 g, 6.91 mmol) in anhydrous DCM (40 mL) was added trifluoroacetic acid (5.32 mL, 69.1 mmol) at 0° C. The mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford 4-(azetidin-3-yl)-2,6-dimethylbenzaldehyde as a brown semi-solid (1.96 g, 98% yield). LCMS Method 1; LCMS (ESI, m/z): 190.0 $[M+H]^+$.

Synthesis of 4-(1-(2,6-dichlorophenyl)azetidin-3-yl)-2,6-dimethylbenzaldehyde

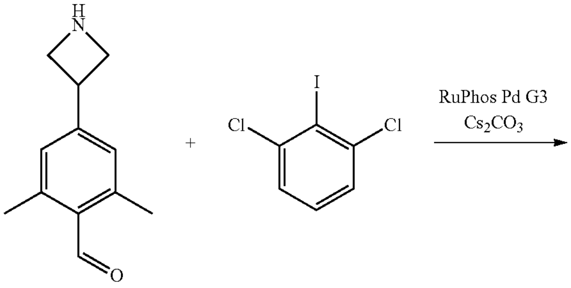

-continued

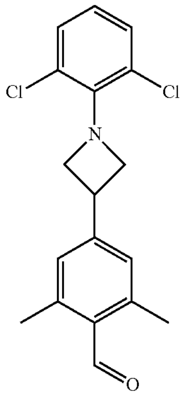

To a solution of 4-(azetidin-3-yl)-2,6-dimethylbenzaldehyde, TFA salt (1.8 g, 5.94 mmol) and 1,3-dichloro-2-iodobenzene (2.02 g, 7.42 mmol) in anhydrous 1,4 dioxane (30 mL) was added cesium carbonate (5.8 g, 17.8 mmol). The reaction mixture was degassed with nitrogen for 10 min and RuPhos Pd G3 (248 mg, 0.297 mmol) was added. The reaction mixture was allowed to stir at 80° C. for 16 h. Upon completion of the reaction, the reaction mixture was cooled to room temperature and filtered through a celite pad which was washed with EtOAc. The filtrate was concentrated under reduced pressure and the resulting residue was purified by flash column chromatography on silica gel (230-400 mesh) eluting with 0-20% ethyl acetate in petroleum ether to afford 4-(1-(2,6-dichlorophenyl)azetidin-3-yl)-2,6-dimethylbenzaldehyde (600 mg, 30% yield) as a white solid. LCMS Method 1; LCMS (ESI, m/z): 334.0 $[M+H]^+$.

Synthesis of tert-butyl 3-(4-((3-(methoxycarbonyl)azetidin-1-yl)methyl)-3,5-dimethyl-phenyl)azetidine-1-carboxylate

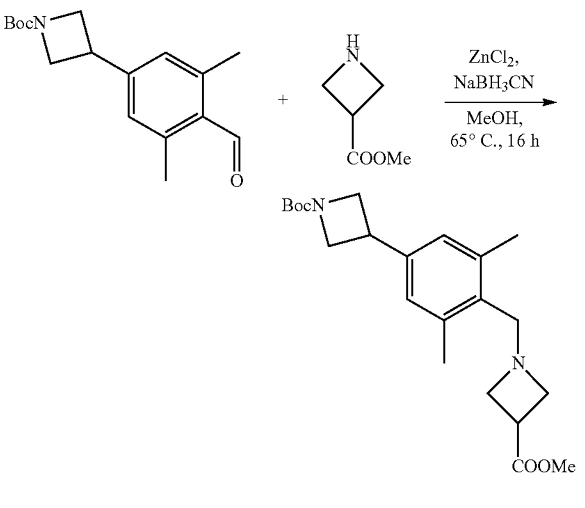

To a stirred solution of methyl azetidine-3-carboxylate HCl (143 mg, 1.244 mmol) in MeOH (20 mL) was added sodium bicarbonate (400 mg, 4.7 mmol.) and the mixture stirred for 1 h at room temperature. The mixture was filtered through celite and concentrated to yield free amine. To the free methyl azetidine-3-carboxylate was added tert-butyl 3-(4-formyl-3,5-dimethylphenyl)azetidine-1-carboxylate (300 mg, 1.037 mmol) in MeOH (8 mL) and zinc chloride (141 mg, 1.037 mmol). The mixture was stirred for 1 h at 25° C. After 1 h, sodium cyanoborohydride (98 mg, 1.555 mmol) was added and the mixture was heated to 65° C. for 12 h. Upon completion of the reaction, the reaction mixture was diluted with DCM (20 mL) and washed with sat. ammonium chloride solution and water (20 mL). The organic phase was dried over $Na_2SO_4$, filtered and the solvent evaporated under reduced pressure. The crude residue was purified by flash column chromatography on silica gel (100-200 mesh) eluting with 0-50% ethyl acetate in petroleum ether to afford tert-butyl 3-(4-((3-(methoxycarbonyl)azetidin-1-yl)methyl)-3,5-dimethylphenyl)azetidine-1-carboxylate (300 mg, 77% yield) as a yellow liquid. LCMS Method 2; LCMS (ESI, m/z): 389.2 $[M+H]^+$.

Synthesis of methyl (R)-1-(4-(1-(tert-butoxycarbonyl)azetidin-3-yl)-2,6-dimethyl-benzyl)pyrrolidine-3-carboxylate

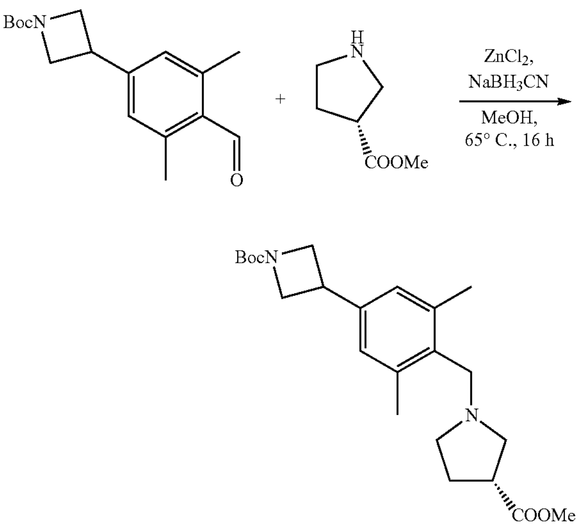

To a solution of methyl (R)-pyrrolidine-3-carboxylate HCl (161 mg, 1.244 mmol) in MeOH (15 mL) was added sodium bicarbonate (400 mg, 4.7 mmol.) and the mixture stirred for 1 h at room temperature. The mixture was filtered through celite and concentrated to yield free amine. To the free methyl (R)-pyrrolidine-3-carboxylate was added tert-butyl 3-(4-formyl-3,5-dimethylphenyl)azetidine-1-carboxylate (300 mg, 1.037 mmol) in MeOH (8 mL) and zinc chloride (141 mg, 1.037 mmol) and stirred for 1 h at 25° C. After 1 h, sodium cyanoborohydride (98 mg, 1.555 mmol) was added and the mixture was heated to 65° C. for 12 h. Upon completion of the reaction, the reaction mixture was diluted with DCM (20 mL) and washed with sat. ammonium chloride solution and water (20 mL). The organic phase was dried over $Na_2SO_4$, filtered and the solvent was evaporated under reduced pressure. The crude residue was purified by flash column chromatography on silica gel (100-200 mesh) eluting with 0-50% ethyl acetate in petroleum ether to afford methyl (R)-1-(4-(1-(tert-butoxycarbonyl)azetidin-3-yl)-2,6-dimethylbenzyl)pyrrolidine-3-carboxylate (400 mg, 96% yield) as a colorless liquid. LCMS Method 1; LCMS (ESI, m/z): 403.2 $[M+H]^+$.

Synthesis of methyl (R)-1-(4-(1-(tert-butoxycarbonyl)azetidin-3-yl)-2,6-dimethyl-benzyl)pyrrolidine-3-carboxylate

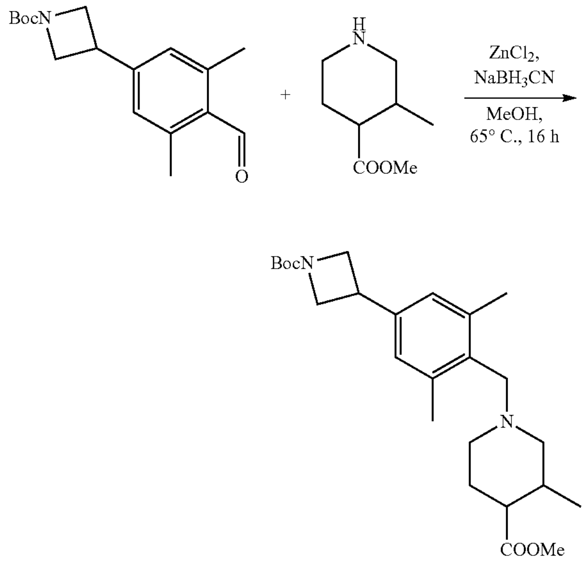

To a stirred solution of methyl 3-methylpiperidine-4-carboxylate (326 mg, 2.04 mmol) in MeOH (15 mL) was added tert-butyl 3-(4-formyl-3,5-dimethylphenyl)azetidine-1-carboxylate (600 mg, 2.04 mmol) in MeOH (8 mL). To the reaction mixture was added zinc chloride (340 mg, 2.488 mmol) and stirred for 1 h at 25° C. After 1 h, sodium cyanoborohydride (131 mg, 2.04 mmol) was added and heated to 65° C. for 12 h. Upon completion of the reaction, the reaction mixture was diluted with DCM (30 mL) and washed with sat. ammonium chloride solution and water (30 mL). The organic phase was dried over $Na_2SO_4$, filtered and the solvent was evaporated under reduced pressure. The crude was purified by flash column chromatography on silica gel (100-200 mesh) eluting with 0-50% ethyl acetate in petroleum ether to afford methyl 1-(4-(1-(tert-butoxycarbonyl)azetidin-3-yl)-2,6-dimethylbenzyl)-3-methylpiperidine-4-carboxylate (800 mg, 90% yield) as a colorless liquid. LCMS Method 1; LCMS (ESI, m/z): 431.2 $[M+H]^+$.

Synthesis of methyl 1-(4-(azetidin-3-yl)-2,6-dimethylbenzyl)azetidine-3-carboxylate, TFA salt

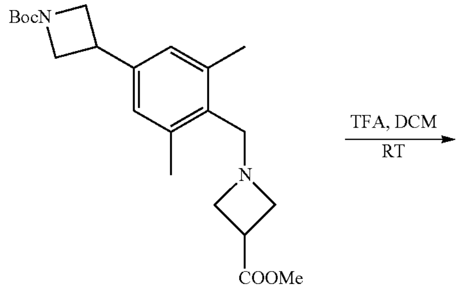

-continued

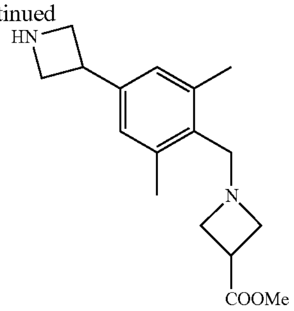

To a stirred solution of tert-butyl 3-(4-((3-(methoxycarbonyl)azetidin-1-yl)methyl)-3,5-dimethylphenyl)azetidine-1-carboxylate (300 mg, 0.772 mmol) in anhydrous DCM (20 mL) was added TFA (0.297 mL, 3.86 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(4-(azetidin-3-yl)-2,6-dimethylbenzyl)azetidine-3-carboxylate, TFA (295 mg, 94% yield) as a yellow liquid. LCMS method 1, LCMS (ESI, m/z): 289.1 $[M+H]^+$.

Synthesis of methyl (R)-1-(4-(azetidin-3-yl)-2,6-dimethylbenzyl)pyrrolidine-3-carboxylate, TFA salt

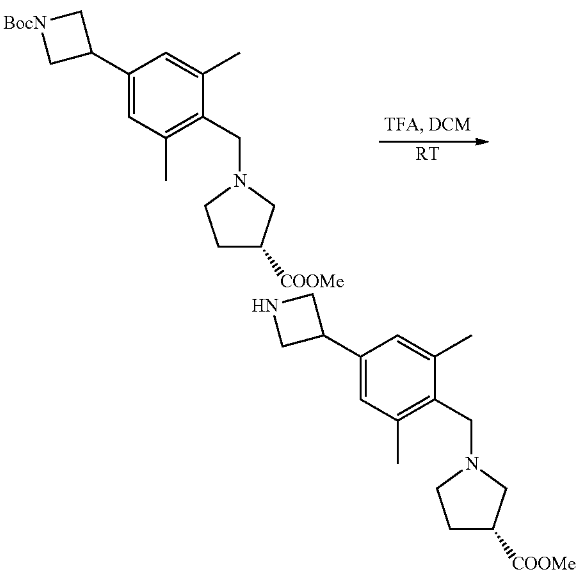

To a stirred solution of methyl (R)-1-(4-(1-(tert-butoxycarbonyl)azetidin-3-yl)-2,6-dimethylbenzyl)pyrrolidine-3-carboxylate (400 mg, 0.994 mmol) in anhydrous DCM (20 mL) was added TFA (0.383 mL, 4.97 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl (R)-1-(4-(azetidin-3-yl)-2,6-dimethylbenzyl)pyrrolidine-3-carboxylate, TFA (400 mg, 97% yield) as a yellow liquid. LCMS method 1, LCMS (ESI, m/z): 303.2 [M+H]$^+$.

Synthesis of methyl 1-(4-(azetidin-3-yl)-2,6-dimethylbenzyl)-3-methylpiperidine-4-carboxylate, TFA salt

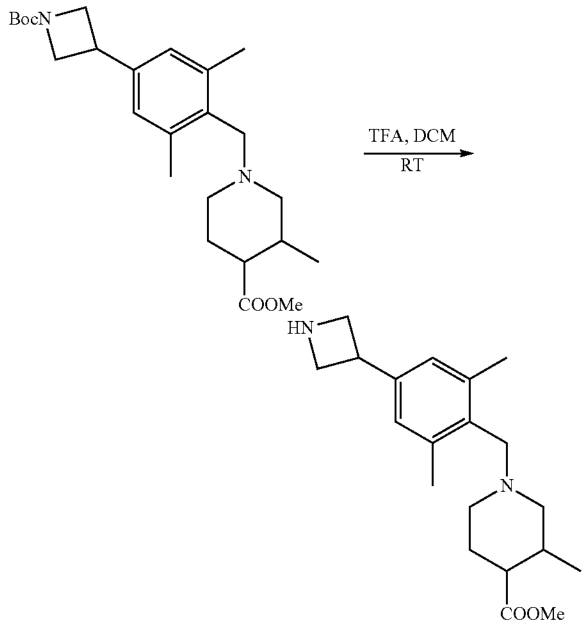

To a stirred solution of methyl 1-(4-(1-(tert-butoxycarbonyl)azetidin-3-yl)-2,6-dimethylbenzyl)-3-methylpiperidine-4-carboxylate (760 mg, 1.76 mmol) in anhydrous DCM (20 mL) was added TFA (1.1 g, 8.83 mmol) at 0° C. Then the mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(4-(azetidin-3-yl)-2,6-dimethylbenzyl)-3-methylpiperidine-4-carboxylate, TFA (610 mg, 81.2% yield) as a yellow semi-solid. LCMS method 1, LCMS (ESI, m/z): 332.6 [M+H]$^+$.

Synthesis of methyl 1-(4-(1-(2,6-dichlorophenyl)azetidin-3-yl)-2,6-dimethylbenzyl)-azetidine-3-carboxylate

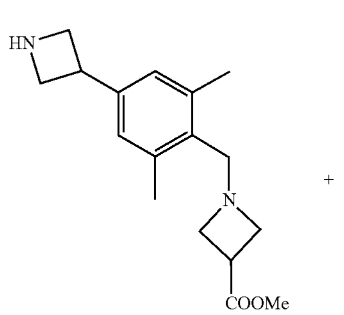

-continued

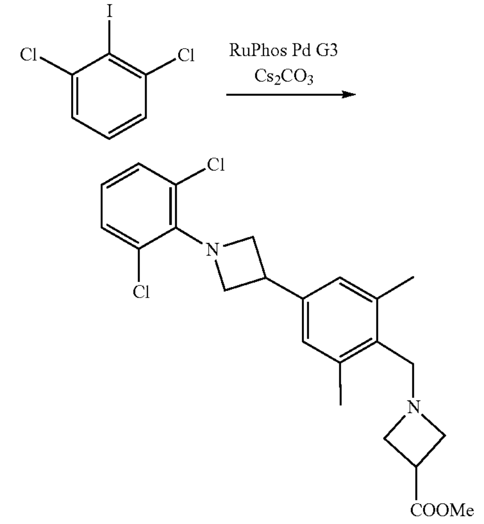

To a solution of methyl 1-(4-(azetidin-3-yl)-2,6-dimethylbenzyl)azetidine-3-carboxylate (295 mg, 1.023 mmol) and 1,3-dichloro-2-iodobenzene (335 mg, 1.228 mmol) in anhydrous 1,4 dioxane (5 mL) was added cesium carbonate (1000 mg, 3.07 mmol). The mixture was degassed with nitrogen for 10 min followed by addition of RuPhos Pd G3 (86 mg, 0.102 mmol) and heating to 100° C. After 12 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (100-200 mesh) eluting with 0-40% ethyl acetate in petroleum ether to afford methyl 1-(4-(1-(2,6-dichlorophenyl)azetidin-3-yl)-2,6-dimethylbenzyl)azetidine-3-carboxylate (300 mg, 69% yield) as a yellow liquid. LCMS method 2, LCMS (ESI, m/z): 433.1 [M+H]$^+$.

Synthesis of methyl (R)-1-(4-(1-(2,6-dichlorophenyl)azetidin-3-yl)-2,6-dimethylbenzyl) pyrrolidine-3-carboxylate

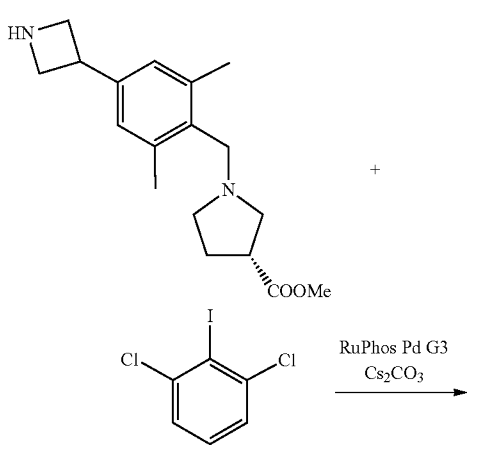

-continued

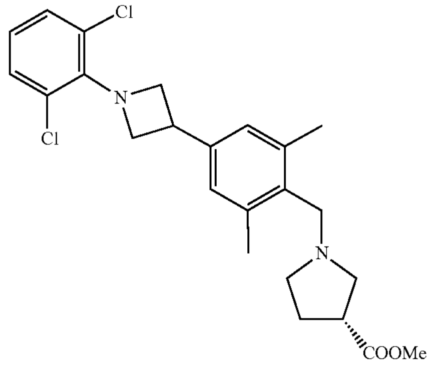

To a solution of methyl (R)-1-(4-(azetidin-3-yl)-2,6-dimethylbenzyl)pyrrolidine-3-carboxylate, TFA (529 mg, 1.323 mmol) and 1,3-dichloro-2-iodobenzene (433 mg, 1.587 mmol) in anhydrous 1,4 dioxane (5 mL) was added cesium carbonate (1.3 g, 3.97 mmol). The reaction mixture was then degassed with nitrogen for 10 min followed by addition of RuPhos Pd G3 (111 mg, 0.132 mmol) and heating to 100° C. After 12 h, TLC analysis indicated complete conversion of the starting material. The reaction mixture was cooled to room temperature and filtered through a pad of celite and which was washed with EtOAc. The filtrate was concentrated under reduced pressure and the resulting residue was purified by flash column chromatography on silica gel (100-200 mesh) eluting with 0-40% ethyl acetate in petroleum ether to afford methyl (R)-1-(4-(1-(2,6-dichlorophenyl)azetidin-3-yl)-2,6-dimethylbenzyl)pyrrolidine-3-carboxylate (300 mg, 51% yield) as a yellow liquid. LCMS method 2, LCMS (ESI, m/z): 447.1 $[M+H]^+$.

Synthesis of methyl 1-(4-(1-(2,6-dichlorophenyl)azetidin-3-yl)-2,6-dimethylbenzyl)-3-methylpiperidine-4-carboxylate

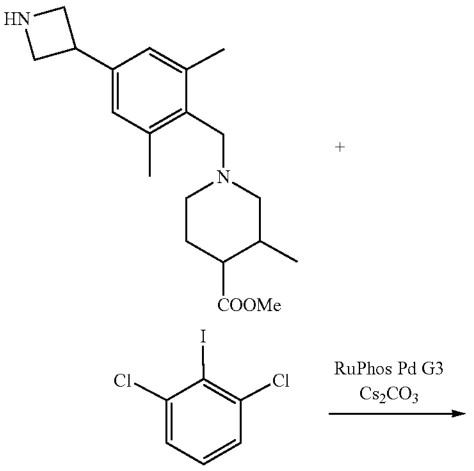

-continued

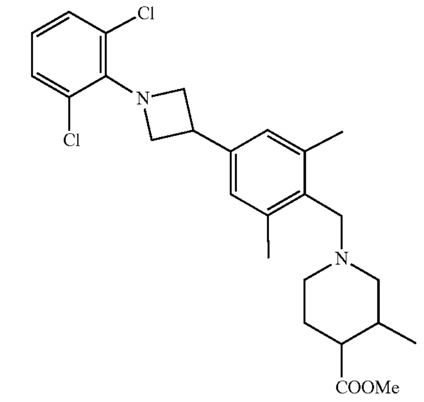

To a solution of methyl 1-(4-(azetidin-3-yl)-2,6-dimethylbenzyl)-3-methylpiperidine-4-carboxylate, TFA (502 mg, 1.173 mmol) and 1,3-dichloro-2-iodobenzene (400 mg, 1.466 mmol) in anhydrous 1,4 dioxane (5 mL) was added cesium carbonate (1433 mg, 4.40 mmol). The reaction mixture was then degassed with nitrogen for 10 min followed by addition of RuPhos Pd G3 (92 mg, 0.110 mmol) and heating to 80° C. After 12 h, TLC analysis indicated complete conversion of the starting material. The reaction mixture was cooled to room temperature and filtered through a pad of celite which was washed with EtOAc. The filtrate was concentrated under reduced pressure and the resulting residue was purified by flash column chromatography on silica gel (100-200 mesh) eluting with 0-40% ethyl acetate in petroleum ether to afford methyl 1-(4-(1-(2,6-dichlorophenyl)azetidin-3-yl)-2,6-dimethylbenzyl)-3-methylpiperidine-4-carboxylate (350 mg, 54% yield) as a yellow solid. LCMS method 1, LCMS (ESI, m/z): 475.2 $[M+H]^+$.

Example S59. 1-(4-(1-(2,6-dichlorophenyl)azetidin-3-yl)-2,6-dimethylbenzyl)azetidine-3-carboxylic acid (59)

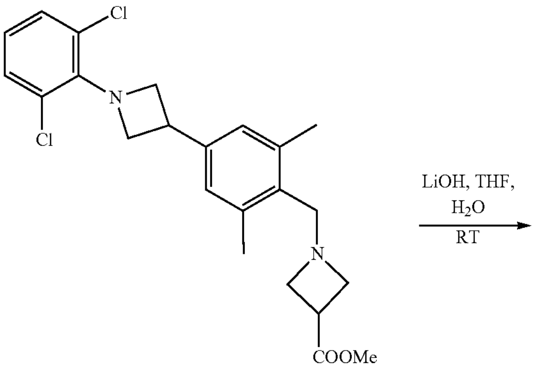

-continued

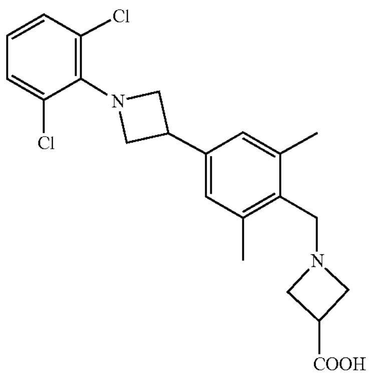

59

To a solution of methyl 1-(4-(1-(2,6-dichlorophenyl)azetidin-3-yl)-2,6-dimethylbenzyl)azetidine-3-carboxylate (300 mg, 0.692 mmol) in THF (4 mL) and water (1 mL) was added LiOH (49.7 mg, 2.077 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Xselect C18 (150×19) mm, 5 micron. Mobile phase A: 0.1% Formic acid in water Mobile phase B: Acetonitrile. The required fractions were collected and lyophilized to afford 1-(4-(1-(2,6-dichlorophenyl)azetidin-3-yl)-2,6-dimethylbenzyl)azetidine-3-carboxylic acid, formic acid salt (62.1 mg, 0.129 mmol, 18.70% yield, 97% pure) as a white solid. $^1H$ NMR: (400 MHz, MeOD): δ 7.25 (s, 2H), 7.20 (d, J=8.00 Hz, 2H), 6.73 (t, J=8.00 Hz, 1H), 4.86 (s, 1H), 4.63 (s, 1H), 4.54 (s, 2H), 4.38-4.42 (m, 2H), 4.21-4.29 (m, 4H), 3.67-3.74 (m, 1H), 3.44-3.50 (m, 1H), 2.49 (s, 6H). LCMS method 1; LCMS (ESI, m/z): 419.0 $[M+H]^+$.

Example S60. (R)-1-(4-(1-(2,6-dichlorophenyl)azetidin-3-yl)-2,6-dimethylbenzyl) pyrrolidine-3-carboxylic acid (60)

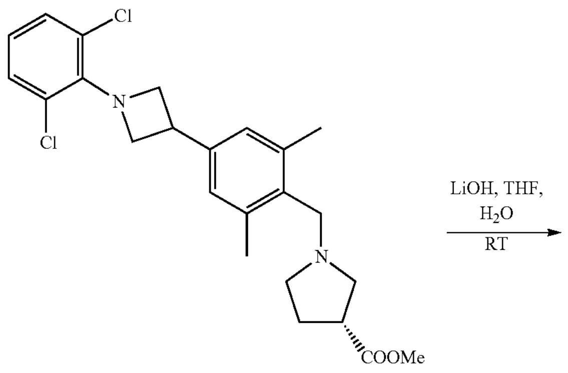

-continued

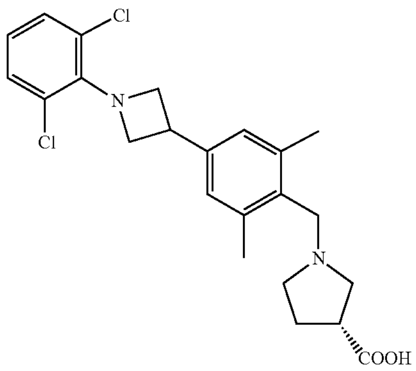

60

To a solution of methyl (R)-1-(4-(1-(2,6-dichlorophenyl)azetidin-3-yl)-2,6-dimethylbenzyl)pyrrolidine-3-carboxylate (300 mg, 0.671 mmol) in THF (4 mL) and water (1 mL) was added LiOH (48.2 mg, 2.012 mmol). The resulting mixture was stirred at ambient temperature and the progress of the reaction was monitored by TLC. After completion of the reaction, the volatiles were concentrated under reduced pressure and the residue was dissolved in water and acidified with acetic acid to a pH of 5-6. The solid thus obtained was filtered and washed with diethyl ether to yield (R)-1-(4-(1-(2,6-dichlorophenyl)azetidin-3-yl)-2,6-dimethylbenzyl)pyrrolidine-3-carboxylic acid, formic acid salt (110.3 mg, 0.225 mmol, 33.6% yield, 98% pure) as a white solid. $^1H$ NMR (400 MHz, MeOD): δ 7.26 (s, 2H), 7.20 (d, J=8.00 Hz, 2H), 6.71-6.75 (m, 1H), 4.86-4.91 (m, 2H), 4.39-4.41 (m, 2H), 3.71-3.74 (m, 2H), 3.50-3.60 (m, 2H), 3.38-3.47 (m, 3H), 3.11-3.32 (m, 1H), 2.51 (s, 6H), 2.23-2.38 (m, 2H). LCMS method 1; LCMS (ESI, m/z): 433.0 $[M+H]^+$.

Example S61. 1-(4-(1-(2,6-dichlorophenyl)azetidin-3-yl)-2,6-dimethylbenzyl)-3-methyl-piperidine-4-carboxylic acid (61)

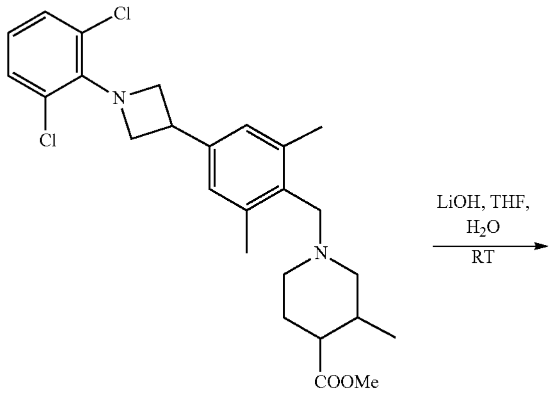

-continued

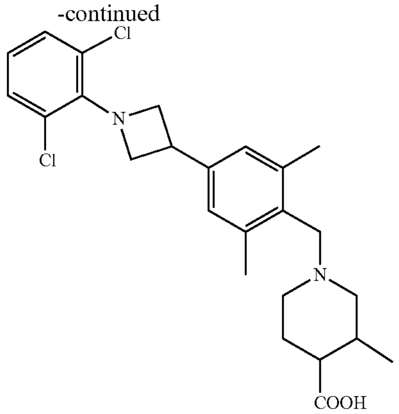

61

To a solution of methyl 1-(4-(1-(2,6-dichlorophenyl)azetidin-3-yl)-2,6-dimethylbenzyl)-3-methylpiperidine-4-carboxylate (180 mg, 0.379 mmol) in THF (4 mL) and water (1 mL) was added LiOH (79 mg, 1.893 mmol). The resulting mixture was stirred at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Xselect C18 (150×19) mm, 5 micron. Mobile phase A: 0.1% Formic acid in water. Mobile phase B: Acetonitrile. The required fractions were collected and lyophilized to afford 1-(4-(1-(2,6-dichlorophenyl)azetidin-3-yl)-2,6-dimethylbenzyl)-3-methylpiperidine-4-carboxylic acid, formic acid salt (85 mg, 0.166 mmol, 44.0% yield, 99.3% pure) as a white solid. $^1$H NMR (400 MHz, DMSO-$d_6$): δ 7.22 (t, J=14.40 Hz, 4H), 6.74 (t, J=8.00 Hz, 1H), 4.86-4.91 (m, 2H), 4.39-4.43 (m, 2H), 4.13-4.21 (m, 2H), 3.67-3.74 (m, 1H), 2.09-2.92 (m, 2H), 2.58-2.63 (m, 1H), 2.48 (d, J=6.40 Hz, 6H), 2.31 (s, 1H), 2.03 (d, J=16.40 Hz, 1H), 1.90 (s, 1H), 1.06 (d, J=6.80 Hz, 3H) (2H are merged with solvent signal). LCMS method 1; LCMS (ESI, m/z): 461.2 [M+H]$^+$.

General Route to Compounds 62-64

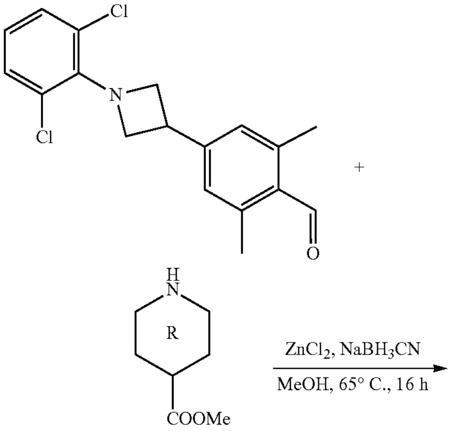

-continued

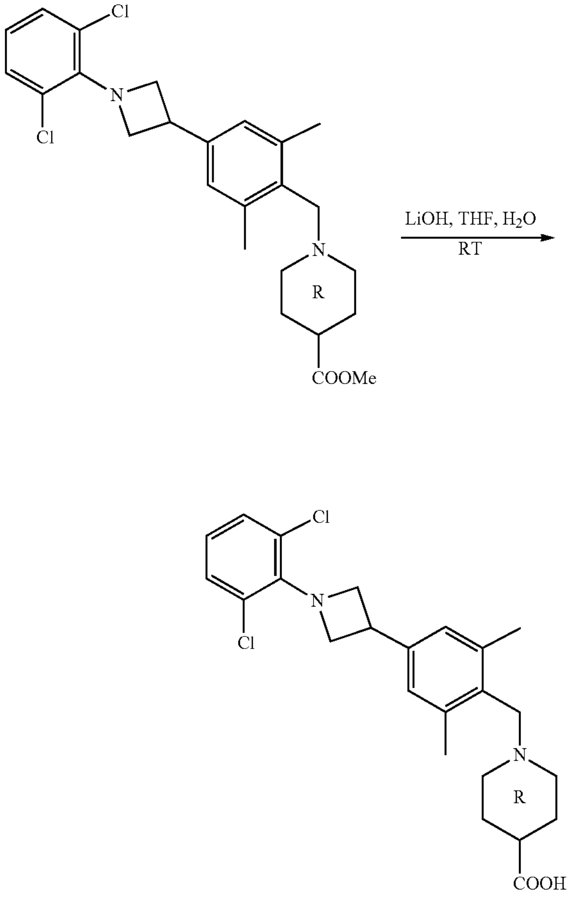

62-64

Synthesis of methyl (S)-1-(4-(1-(2,6-dichlorophenyl)azetidin-3-yl)-2,6-dimethyl-benzyl)pyrrolidine-3-carboxylate

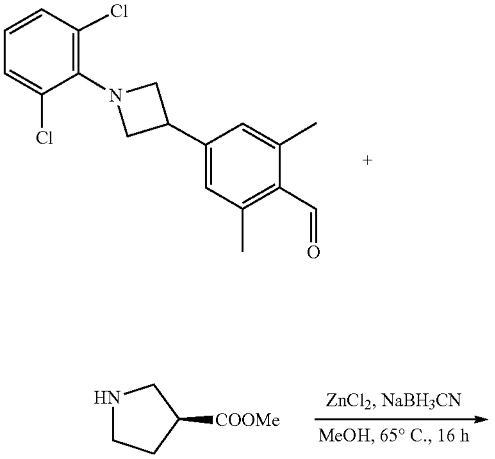

-continued

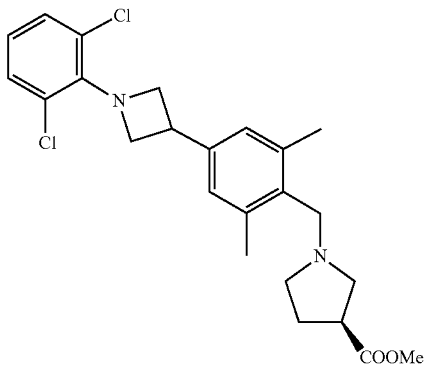

To a stirred solution of methyl (S)-pyrrolidine-3-carboxylate, HCl (155 mg, 0.935 mmol) in MeOH (15 mL) was added sodium bicarbonate (141 mg, 1.683 mmol) and then stirred for 1 h at room temperature. The mixture was filtered through celite and concentrated to yield free amine. To the free amine, 4-(1-(2,6-dichlorophenyl)azetidin-3-yl)-2,6-dimethylbenzaldehyde (250 mg, 0.748 mmol) in MeOH (8 mL) was added zinc chloride (102 mg, 0.748 mmol) and the mixture stirred for 1 h at 25° C. After 1 h, sodium cyanoborohydride (70.5 mg, 1.122 mmol) was added and heated to 65° C. for 12 h. Upon completion of the reaction, the mixture was diluted with DCM (20 mL) and washed with sat. ammonium chloride solution and water (20 mL). The organic phase was dried over $Na_2SO_4$, filtered and the solvent evaporated under reduced pressure. The crude was purified by flash column chromatography on silica gel (100-200 mesh) eluting with 0-50% ethyl acetate in petroleum ether to afford methyl (S)-1-(4-(1-(2,6-dichlorophenyl)azetidin-3-yl)-2,6-dimethylbenzyl)pyrrolidine-3-carboxylate (310 mg, 89% yield) as a light brown semi-solid. LCMS Method 1; LCMS (ESI, m/z): 447.0 $[M+H]^+$.

Synthesis of methyl 1-(4-(1-(2,6-dichlorophenyl)azetidin-3-yl)-2,6-dimethylbenzyl)-2-methylpiperidine-4-carboxylate

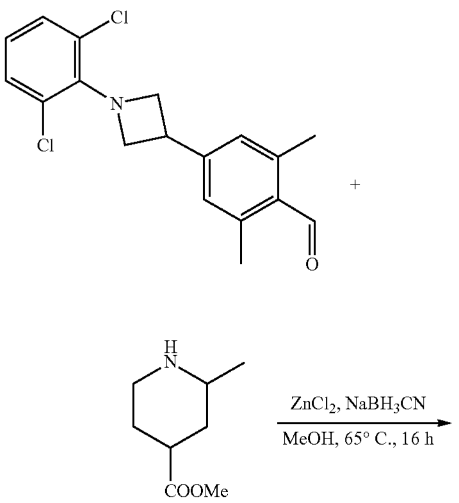

-continued

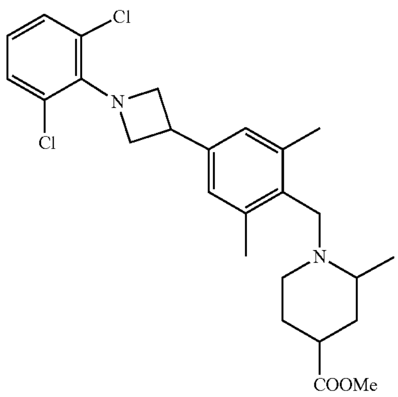

To a stirred solution of methyl 2-methylpiperidine-4-carboxylate (212 mg, 1.346 mmol) in MeOH (10 mL) was added 4-(1-(2,6-dichlorophenyl)azetidin-3-yl)-2,6-dimethylbenzaldehyde (250 mg, 0.748 mmol) and zinc chloride (147 mg, 1.077 mmol) and stirred for 1 h at 25° C. After 1 h, sodium cyanoborohydride (85 mg, 1.346 mmol) was added and the mixture was heated to 65° C. for 12 h. Upon completion of the reaction, the mixture was diluted with DCM (20 mL) and washed with sat. ammonium chloride solution and water (20 mL). The organic phase was dried over $Na_2SO_4$, filtered and the solvent evaporated under reduced pressure. The crude was purified by flash column chromatography on silica gel (100-200 mesh) eluting with 0-50% ethyl acetate in petroleum ether to afford methyl 1-(4-(1-(2,6-dichlorophenyl)azetidin-3-yl)-2,6-dimethylbenzyl)-2-methylpiperidine-4-carboxylate (268 mg, 62% yield) as an off-white solid. LCMS Method 1; LCMS (ESI, m/z): 475.4 $[M+H]^+$.

Synthesis of methyl 1-(4-(1-(2,6-dichlorophenyl)azetidin-3-yl)-2,6-dimethylbenzyl)-3-fluoropiperidine-4-carboxylate

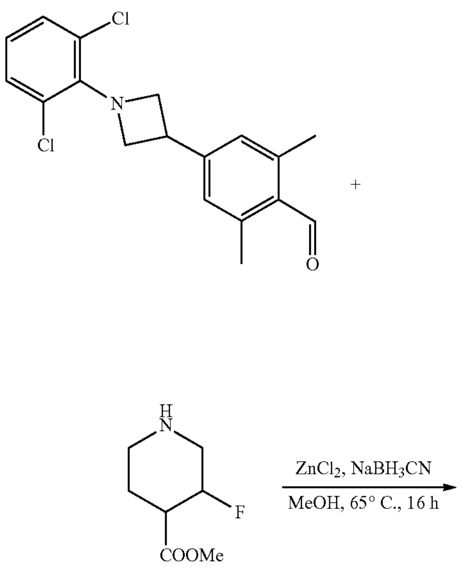

-continued

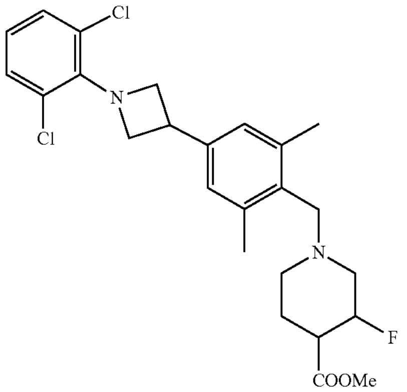

To a stirred solution of methyl 3-fluoropiperidine-4-carboxylate (181 mg, 1.122 mmol) in MeOH (10 mL) was added 4-(1-(2,6-dichlorophenyl)azetidin-3-yl)-2,6-dimethylbenzaldehyde (250 mg, 0.748 mmol) and zinc chloride (122 mg, 0.898 mmol) and the mixture was stirred for 1 h at 25° C. After 1 h, sodium cyanoborohydride (70.5 mg, 1.122 mmol) was added and heated to 65° C. for 12 h. Upon completion of the reaction, the reaction mixture was diluted with DCM (20 mL) and washed with sat. ammonium chloride solution and water (20 mL). The organic phase was dried over $Na_2SO_4$, filtered and the solvent evaporated under reduced pressure. The crude was purified by flash column chromatography on silica gel (100-200 mesh) eluting with 0-50% ethyl acetate in petroleum ether to afford methyl 1-(4-(1-(2,6-dichlorophenyl)azetidin-3-yl)-2,6-dimethylbenzyl)-3-fluoropiperidine-4-carboxylate (240 mg, 66% yield) as an off-white solid. LCMS Method 1; LCMS (ESI, m/z): 479.1 $[M+H]^+$.

Example S62. (S)-1-(4-(1-(2,6-dichlorophenyl)azetidin-3-yl)-2,6-dimethylbenzyl)-pyrrolidine-3-carboxylic acid (62)

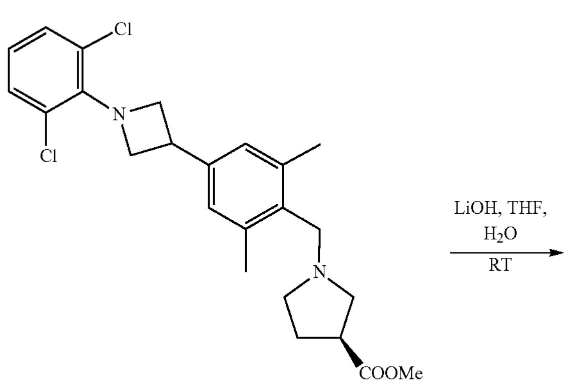

-continued

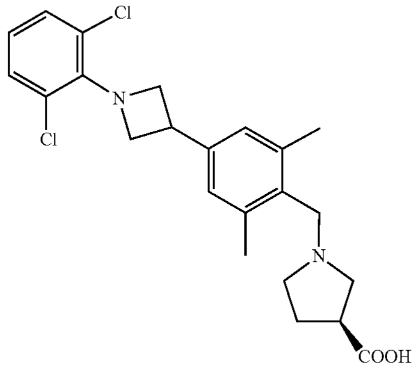

62

To a solution of methyl (S)-1-(4-(1-(2,6-dichlorophenyl)azetidin-3-yl)-2,6-dimethylbenzyl)pyrrolidine-3-carboxylate (310 mg, 0.693 mmol) in THF (4 mL) and water (1 mL) was added LiOH*H2O (83 mg, 3.46 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Symmetry C8 (300×19) mm, 7 micron. Mobile phase A: 5 mM Ammonium formate in water Mobile phase B: Acetonitrile. The required fractions were collected and lyophilized to afford (S)-1-(4-(1-(2,6-dichlorophenyl)azetidin-3-yl)-2,6-dimethylbenzyl) pyrrolidine-3-carboxylic acid, formic acid salt (40 mg, 0.083 mmol, 11.99% yield, 99.9% pure) as a light brown solid. $^1H$ NMR (400 MHz, MeOD): δ 7.26 (s, 2H), 7.19 (d, J=8.00 Hz, 2H), 6.72 (t, J=8.00 Hz, 1H), 4.53 (s, 2H), 4.39-4.42 (m, 2H), 3.60-3.73 (m, 1H), 3.57-3.59 (m, 1H), 3.38-3.47 (m, 3H), 3.08-3.12 (m, 1H), 2.51 (s, 6H), 2.36-2.40 (m, 1H), 2.23-2.26 (m, 1H). LCMS method 1; LCMS (ESI, m/z): 431.2 $[M+H]^+$.

Example S63. 1-(4-(1-(2,6-dichlorophenyl)azetidin-3-yl)-2,6-dimethylbenzyl)-2-methyl-piperidine-4-carboxylic acid (63)

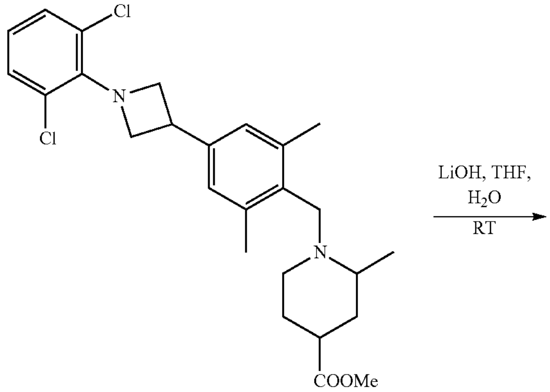

-continued

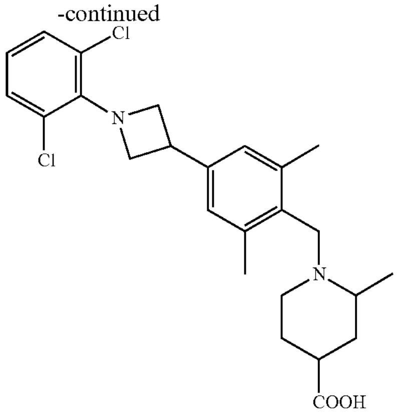

63

To a solution of methyl 1-(4-(1-(2,6-dichlorophenyl)azetidin-3-yl)-2,6-dimethylbenzyl)-2-methylpiperidine-4-carboxylate (260 mg, 0.547 mmol) in THF (4 mL) and water (1 mL) was added LiOH monohydrate (115 mg, 2.73 mmol). The resulting mixture was stirred at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column: Xselect C18 (150×19) mm, 5 micron, Mobile phase A: 0.1% Formic acid in water, Mobile phase B: Acetonitrile. The required fractions were collected and lyophilized to afford 1-(4-(1-(2,6-dichlorophenyl)azetidin-3-yl)-2,6-dimethylbenzyl)-2-methylpiperidine-4-carboxylic acid, formic acid salt (70 mg, 0.138 mmol, 25.2% yield, 99.8% pure) as a white solid. $^1H$ NMR (400 MHz, DMSO-$d_6$): δ 12.1 (s, 1H), 7.24 (d, J=8.0 Hz, 2H), 7.03 (s, 2H), 6.74 (t, J=8.0 Hz, 1H), 4.81 (t, J=8.4 Hz, 2H), 4.34 (t, J=7.6 Hz, 2H), 3.95 (d, J=12.4 Hz, 1H), 3.67 (m, 1H), 3.04 (d, J=12.4 Hz, 1H), 2.33 (s, 6H), 2.25-2.19 (m, 2H), 1.88-1.64 (m, 2H), 1.66 (d, J=12.8 Hz, 1H), 1.30-1.08 (m, 6H). LCMS method 1; LCMS (ESI, m/z): 461.2 $[M+H]^+$.

Example S64. 1-(4-(1-(2,6-dichlorophenyl)azetidin-3-yl)-2,6-dimethylbenzyl)-3-fluoro-piperidine-4-carboxylic acid (64)

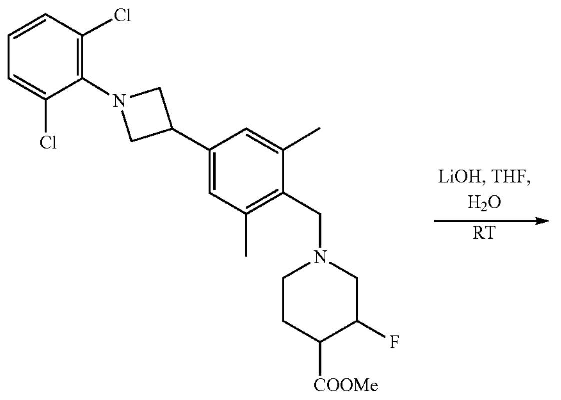

-continued

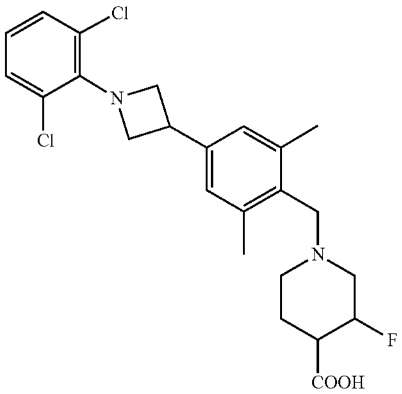

64

To a solution of methyl 1-(4-(1-(2,6-dichlorophenyl)azetidin-3-yl)-2,6-dimethylbenzyl)-3-fluoropiperidine-4-carboxylate (230 mg, 0.480 mmol) in THE (4 mL) and water (1 mL) was added LiOH monohydrate (101 mg, 2.399 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column: Xselect C18 (150×19) mm, 5 micron. Mobile phase A: 0.1% Formic acid in water, Mobile phase B: Acetonitrile. The required fractions were collected and lyophilized to afford 1-(4-(1-(2,6-dichlorophenyl)azetidin-3-yl)-2,6-dimethylbenzyl)-3-fluoropiperidine-4-carboxylic acid, formic acid salt (21 mg, 0.041 mmol, 8.47% yield, 99% pure) as a white solid. $^1H$ NMR (400 MHz, DMSO-$d_6$): δ 7.24 (d, J=8.0 Hz, 2H), 7.03 (s, 2H), 6.74 (t, J=8.0 Hz, 1H), 4.80 (t, J=8.4 Hz, 2H), 4.34 (t, J=7.2 Hz, 2H), 3.68 (m, 2H), 3.44 (s, 3H), 2.98 (t, J=10.40 Hz, 1H), 2.68 (m, 2H), 2.32 (s, 6H), 2.04 (m, 1H), 1.67-1.63 (m, 2H). LCMS method 1; LCMS (ESI, m/z): 465.0 $[M+H]^+$.

Synthetic Route to Compound 65

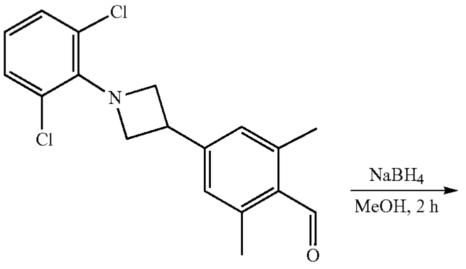

-continued

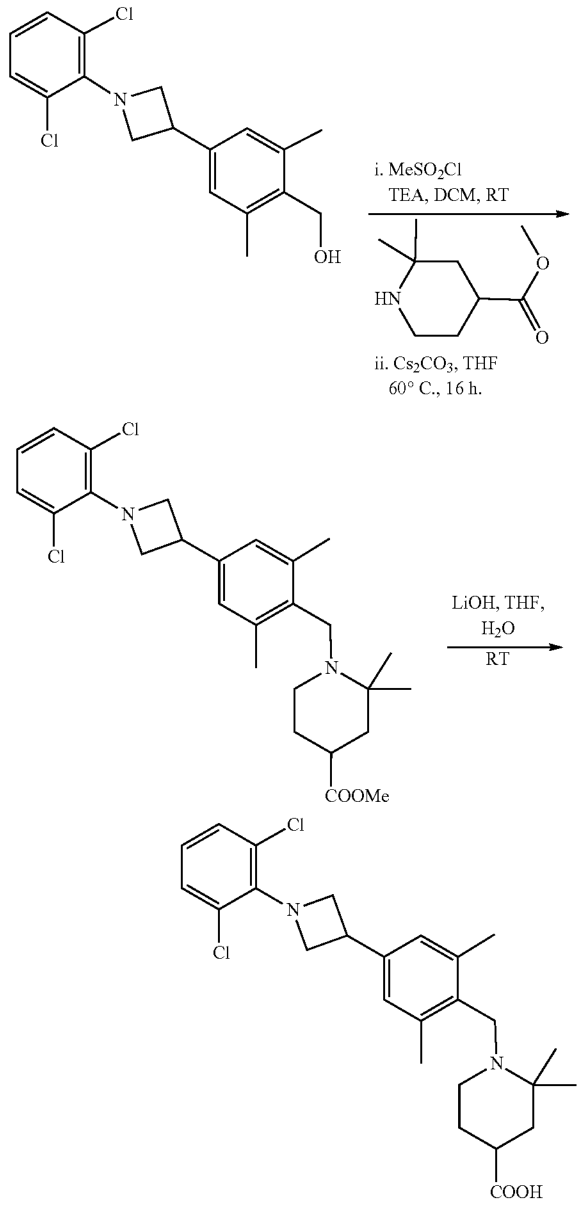

65

Synthesis of (4-(1-(2,6-dichlorophenyl)azetidin-3-yl)-2,6-dimethylphenyl)methanol

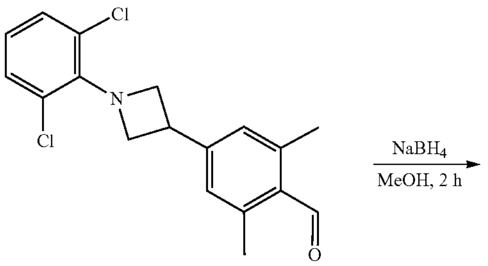

-continued

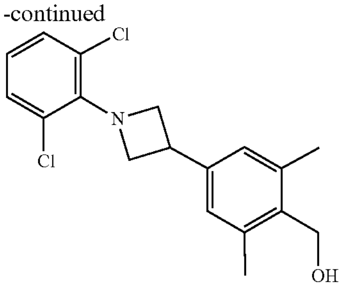

To an ice cold solution of 4-(1-(2,6-dichlorophenyl)azetidin-3-yl)-2,6-dimethylbenzaldehyde (500 mg, 1.496 mmol) in MeOH (10 mL) was added sodium borohydride (85 mg, 2.244 mmol). The reaction mixture was allowed to stir at room temperature for 2 h. After completion of the reaction, it was quenched with sat. ammonium chloride solution and extracted with EtOAc (3×10 mL). The combined organic layer was dried over sodium sulphate and concentrated under reduced pressure. The resulting residue was purified by flash column chromatography on silica gel (100-200 mesh) eluting with 0-50% ethyl acetate in petroleum ether to afford (4-(1-(2,6-dichlorophenyl)azetidin-3-yl)-2,6-dimethylphenyl)methanol (220 mg, 0.654 mmol, 43.7% yield) as a white solid. LCMS method 1, LCMS (ESI, m/z): 336.0 $[M+H]^+$.

Synthesis of methyl 1-(4-(1-(2,6-dichlorophenyl)azetidin-3-yl)-2,6-dimethylbenzyl)-2,2-dimethylpiperidine-4-carboxylate

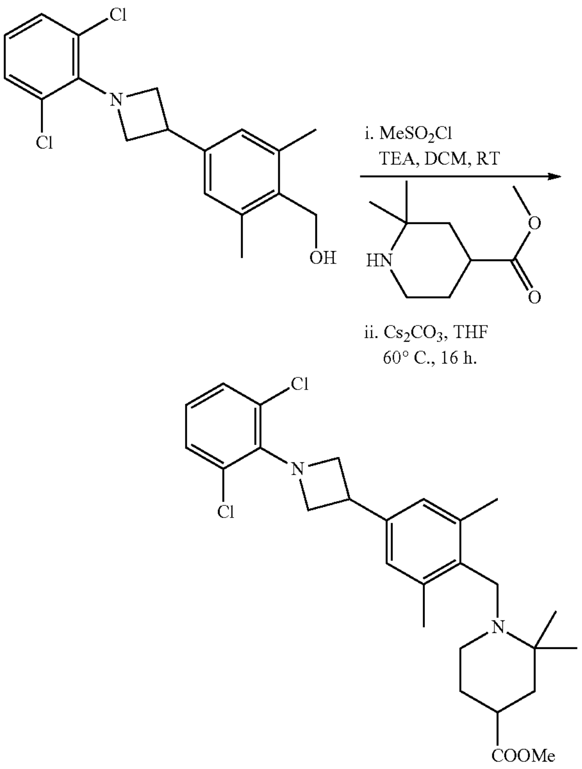

To a stirred solution of (4-(1-(2,6-dichlorophenyl)azetidin-3-yl)-2,6-dimethylphenyl)methanol (150 mg, 0.446 mmol) in DCM (5 mL) were added triethylamine (67.7 mg, 0.669 mmol) and methanesulfonyl chloride (0.104 mL, 1.338 mmol) at room temperature under nitrogen atmosphere. The reaction mixture was allowed to stir at room temperature for 1 h, followed by quenching with sat. sodium bicarbonate solution and an extraction with ethyl acetate. The combined organic layer was dried over anhydrous sodium sulphate and concentrated to yield crude 4-(1-(2,6-dichlorophenyl)azetidin-3-yl)-2,6-dimethylbenzyl methanesulfonate. To the stirred solution of crude 4-(1-(2,6-dichlorophenyl)azetidin-3-yl)-2,6-dimethylbenzyl methanesulfonate in THF (6 mL) was added cesium carbonate (204 mg, 0.628 mmol) and methyl 2,2-dimethylpiperidine-4-carboxylate (81 mg, 0.471 mmol). The reaction mixture was stirred at 60° C. for 24 h and quenched with ice cold water. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-20% ethyl acetate in petroleum ether to afford methyl 1-(4-(1-(2,6-dichlorophenyl)azetidin-3-yl)-2,6-dimethylbenzyl)-2,2-dimethylpiperidine-4-carboxylate (80 mg, 51% yield) as a colorless liquid. LCMS method 1, LCMS (ESI, m/z): 489.3 $[M+H]^+$.

Example S65. 1-(4-(1-(2,6-dichlorophenyl)azetidin-3-yl)-2,6-dimethylbenzyl)-2,2-dimethylpiperidine-4-carboxylic acid (65)

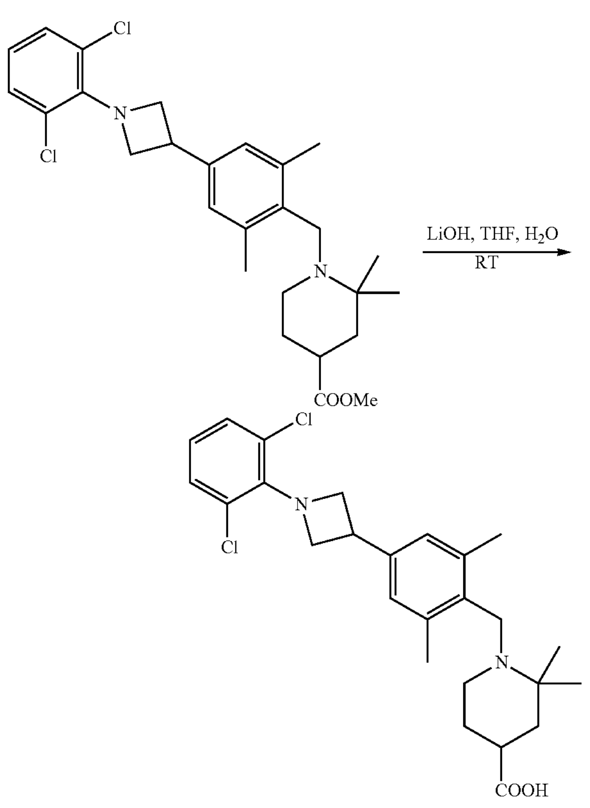

65

To a solution of methyl 1-(4-(1-(2,6-dichlorophenyl)azetidin-3-yl)-2,6-dimethylbenzyl)-2,2-dimethylpiperidine-4-carboxylate (80 mg, 0.163 mmol) in THF (4 mL) and water (1 mL) was added LiOH monohydrate (34.3 mg, 0.817 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column: Xselect C18 (150×19) mm, 5 micron. Mobile phase A: 0.1% Formic acid in water. Mobile phase B: Acetonitrile. The required fractions were collected and lyophilized to afford 1-(4-(1-(2,6-dichlorophenyl)azetidin-3-yl)-2,6-dimethylbenzyl)-2,2-dimethylpiperidine-4-carboxylic acid, formic acid salt (13 mg, 0.025 mmol, 15.16% yield, 99.4% pure) as a white solid. $^1H$ NMR (400 MHz, DMSO-$d_6$): δ 7.23 (d, J=8.00 Hz, 2H), 7.01 (s, 2H), 6.74 (t, J=8.40 Hz, 1H), 4.79 (t, J=8.40 Hz, 2H), 4.33 (t, J=7.02 Hz, 2H), 3.80 (d, J=12.0 Hz, 1H), 3.70-3.64 (m, 1H), 2.38-2.25 (m, 9H), 1.65-1.62 (m, 2H), 1.43 (t, J=13.20 Hz, 1H), 1.29 (s, 3H), 1.90-1.48 (m, 1H), 1.05 (s, 3H). LCMS method 1; LCMS (ESI, m/z): 475.0 $[M+H]^+$.

General Route to Compounds 66-75

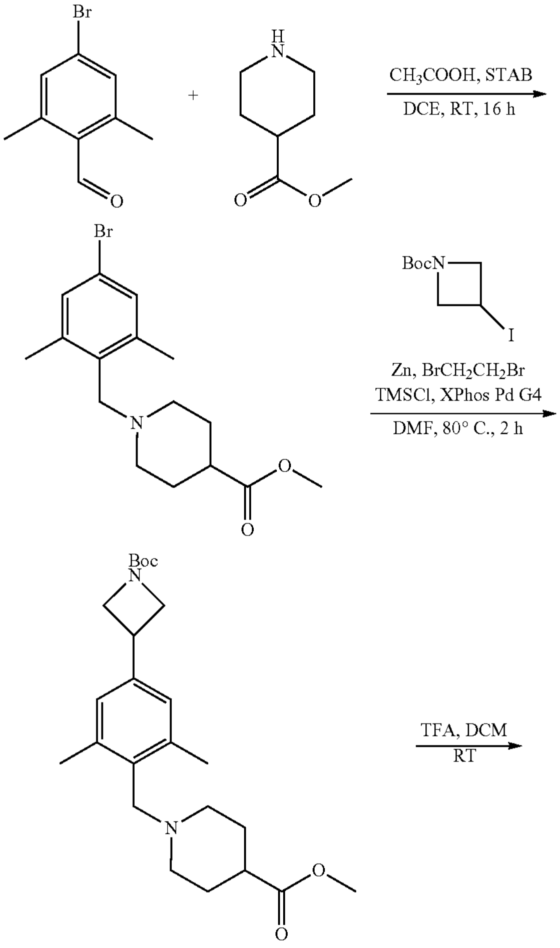

-continued

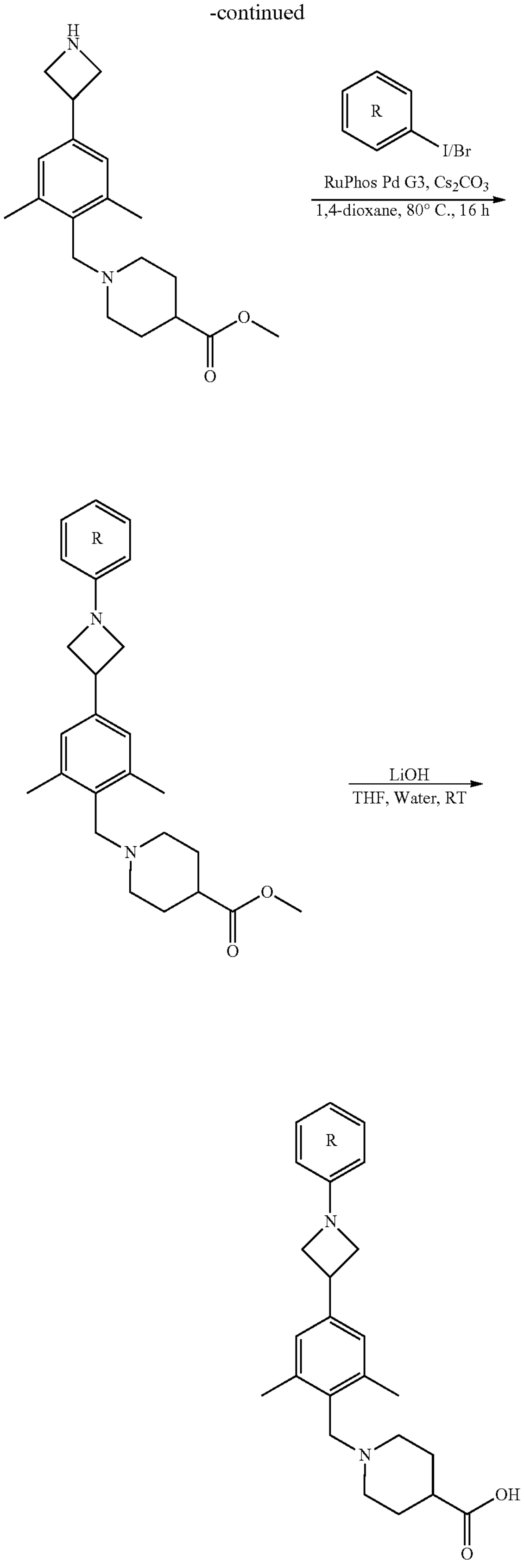

66-75

Synthesis of methyl 1-(4-(1-(2-fluoro-6-methylphenyl)azetidin-3-yl)-2,6-dimethylbenzyl)-piperidine-4-carboxylate

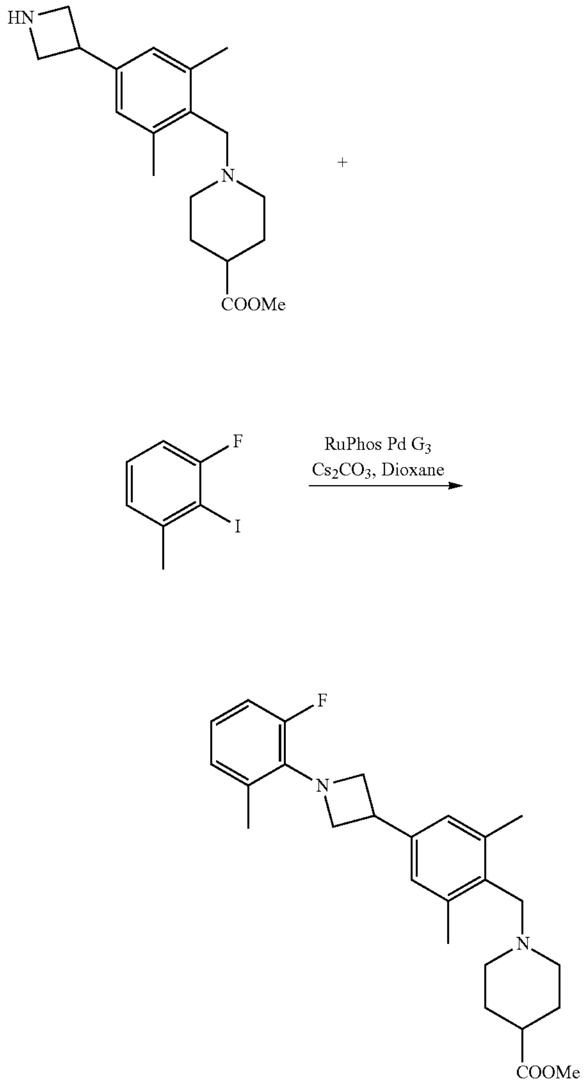

To a solution of methyl 1-(4-(azetidin-3-yl)-2,6-dimethylbenzyl)piperidine-4-carboxylate, TFA (300 mg, 0.697 mmol) and 1-fluoro-2-iodo-3-methylbenzene (206 mg, 0.871 mmol) in anhydrous 1,4 dioxane (10 mL) was added cesium carbonate (681 mg, 2.091 mmol). The reaction mixture was then degassed with nitrogen for 10 min followed by addition of RuPhos Pd G3 (58.3 mg, 0.070 mmol) and heating to 80° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2-fluoro-6-methylphenyl)azetidin-3-yl)-2,6-dimethylbenzyl) piperidine-4-carboxylate (210 mg, 71% yield) as a light brown semi-solid. LCMS method 1, LCMS (ESI, m/z): 425.2 $[M+H]^+$.

Synthesis of methyl 1-(4-(1-(2-chloro-6-methylphenyl)azetidin-3-yl)-2,6-dimethyl-benzyl)piperidine-4-carboxylate

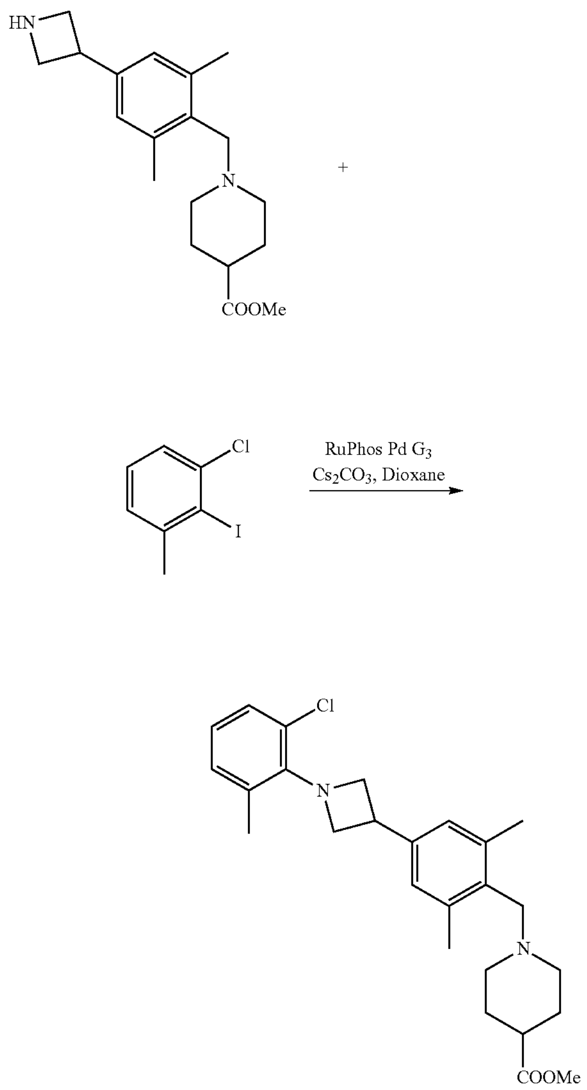

To a solution of methyl 1-(4-(azetidin-3-yl)-2,6-dimethylbenzyl)piperidine-4-carboxylate, TFA (300 mg, 0.697 mmol) and 1-chloro-2-iodo-3-methylbenzene (220 mg, 0.871 mmol) in anhydrous 1,4 dioxane (10 mL) was added cesium carbonate (681 mg, 2.091 mmol). The reaction mixture was then degassed with nitrogen for 10 min followed by addition of RuPhos Pd G3 (58.3 mg, 0.070 mmol) and heating to 80° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2-chloro-6-methylphenyl)azetidin-3-yl)-2,6-dimethylbenzyl) piperidine-4-carboxylate (210 mg, 69% yield) as a light brown semi-solid. LCMS method 1, LCMS (ESI, m/z): 441.1 $[M+H]^+$.

Synthesis of methyl 1-(4-(1-(2-ethyl-6-methylphenyl)azetidin-3-yl)-2,6-dimethylbenzyl)-piperidine-4-carboxylate

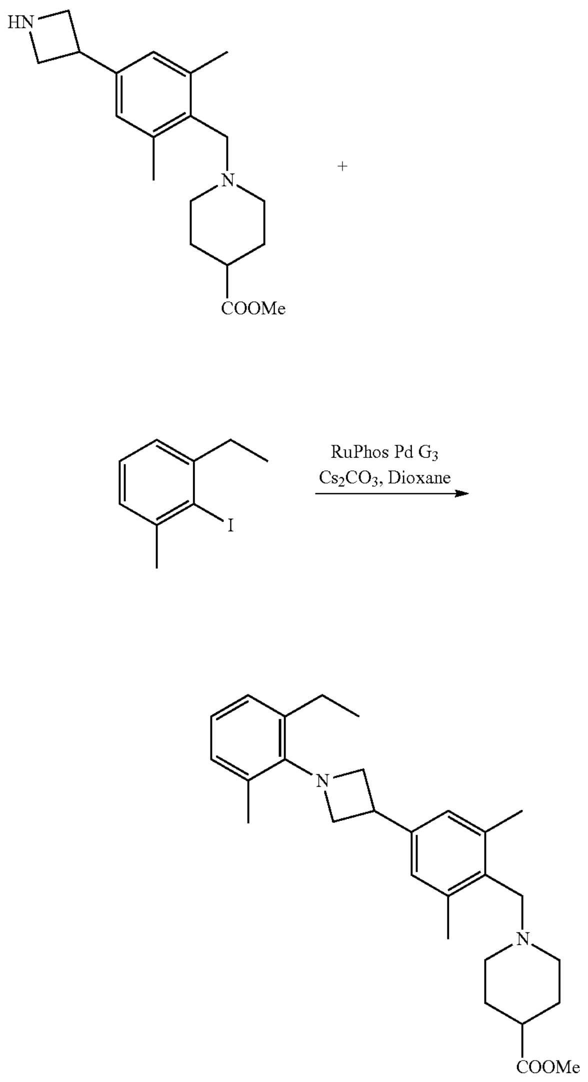

To a solution of methyl 1-(4-(azetidin-3-yl)-2,6-dimethylbenzyl)piperidine-4-carboxylate (300 mg, 0.948 mmol) and 1-ethyl-2-iodo-3-methylbenzene (467 mg, 1.896 mmol) in anhydrous 1,4 dioxane (10 mL) was added cesium carbonate (2.84 mmol). The reaction mixture was then degassed with nitrogen for 10 min followed by addition of RuPhos Pd G3 (79 mg, 0.095 mmol) and heating to 80° C. After 12 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (60-120 mesh) eluting with 0-50% ethyl acetate in petroleum ether to afford methyl 1-(4-(1-(2-ethyl-6-methylphenyl)azetidin-3-yl)-2,6-dimethylbenzyl)piperidine-4-carboxylate (170 mg, 41.0% yield) as a brown liquid. LCMS method 1, LCMS (ESI, m/z): 435.2 $[M+H]^+$.

Synthesis of methyl 1-(4-(1-(2,6-diethylphenyl) azetidin-3-yl)-2,6-dimethylbenzyl)-piperidine-4-carboxylate

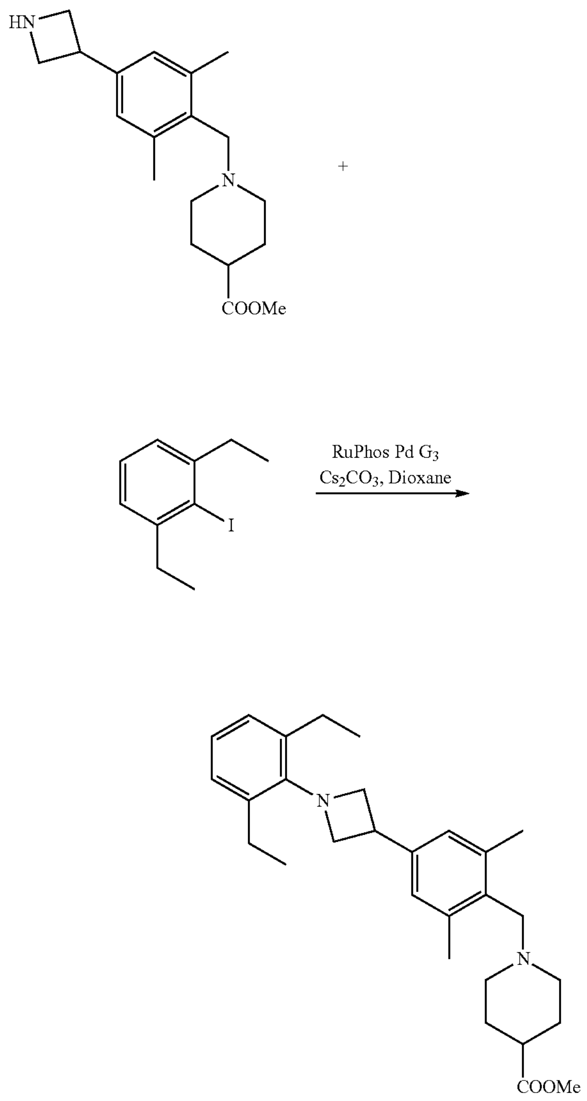

To a solution of methyl 1-(4-(azetidin-3-yl)-2,6-dimethylbenzyl)piperidine-4-carboxylate (500 mg, 1.580 mmol) and 1,3-diethyl-2-iodobenzene (493 mg, 1.896 mmol) in anhydrous 1,4 dioxane (10 mL) was added cesium carbonate (4.74 mmol). The reaction mixture was then degassed with nitrogen for 10 min followed by addition of RuPhos Pd G3 (132 mg, 0.158 mmol) and heated to 80° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (60-120 mesh) eluting with 0-50% ethyl acetate in petroleum ether to afford methyl 1-(4-(1-(2,6-diethylphenyl)azetidin-3-yl)-2,6-dimethylbenzyl)piperidine-4-carboxylate (300 mg, 42% yield) as a yellow solid. LCMS method 3, LCMS (ESI, m/z): 449.2 $[M+H]^+$.

Synthesis of methyl 1-(4-(1-(2-cyclopropylphenyl) azetidin-3-yl)-2,6-dimethylbenzyl)-piperidine-4-carboxylate

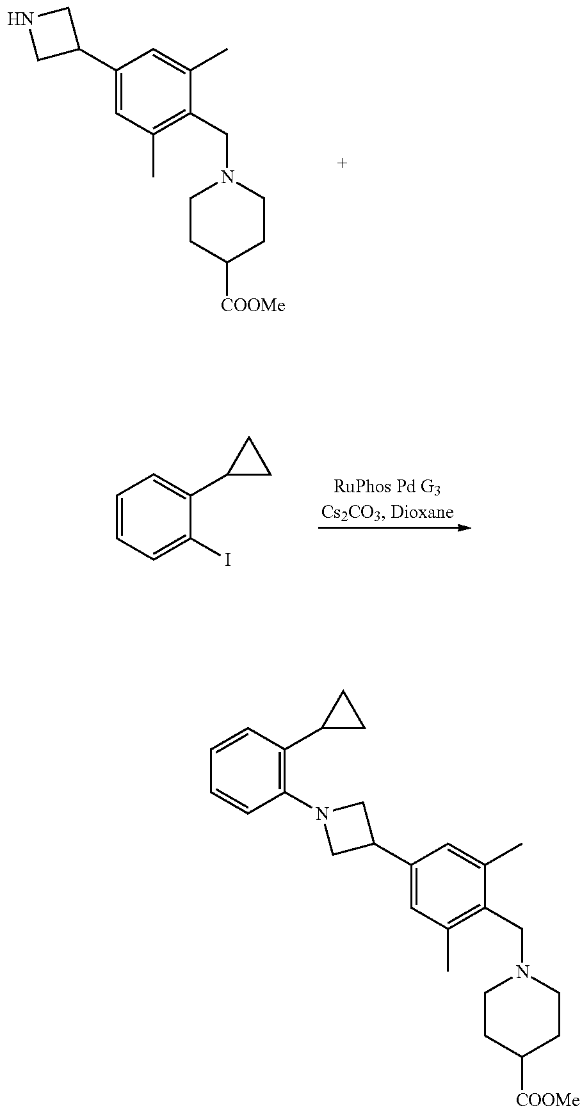

To a solution of methyl 1-(4-(azetidin-3-yl)-2,6-dimethylbenzyl)piperidine-4-carboxylate, TFA (500 mg, 1.162 mmol) and 1-cyclopropyl-2-iodobenzene (354 mg, 1.452 mmol) in anhydrous 1,4 dioxane (8 mL) was added cesium carbonate (1135 mg, 3.48 mmol). The reaction mixture was then degassed with nitrogen for 10 min followed by addition of RuPhos Pd G3 (97 mg, 0.116 mmol) and heating to 80° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (100-200 mesh) eluting with 5-30% ethyl acetate in petroleum ether to afford methyl 1-((5-(1-(2,6-dichlorophenyl)azetidin-3-yl)-3-methylpyridin-2-yl)methyl)piperidine-4-carboxylate (210 mg, 31.6% yield) as a light brown semi-solid. LCMS method 1, LCMS (ESI, m/z): 433.2 $[M+H]^+$.

Synthesis of methyl 1-(4-(1-(2-cyclopropyl-6-methylphenyl)azetidin-3-yl)-2,6-dimethylbenzyl)piperidine-4-carboxylate

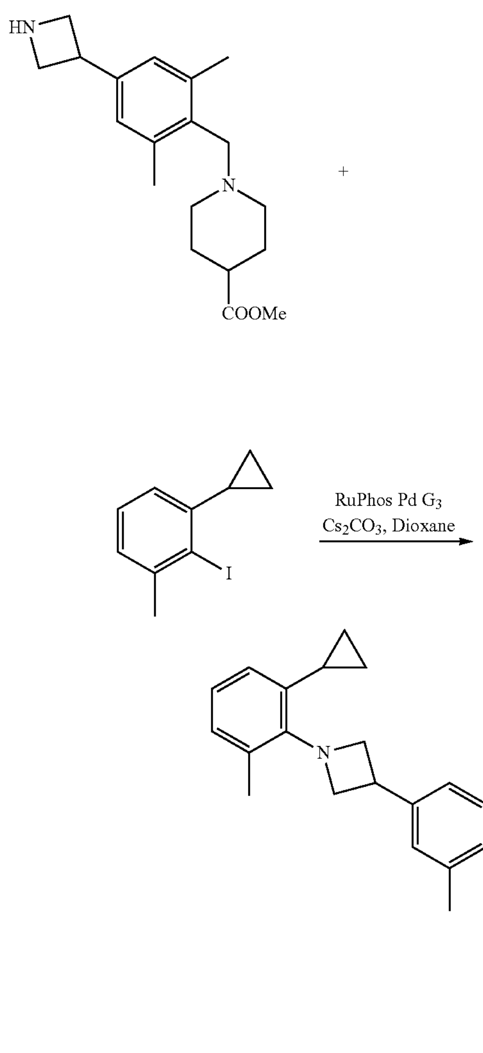

To a solution of methyl 1-(4-(azetidin-3-yl)-2,6-dimethylbenzyl)piperidine-4-carboxylate, TFA (300 mg, 0.697 mmol) and 1-cyclopropyl-2-iodo-3-methylbenzene (198 mg, 0.767 mmol) in anhydrous 1,4 dioxane (10 mL) was added cesium carbonate (681 mg, 2.091 mmol). The reaction mixture was then degassed with nitrogen for 10 min followed by addition of RuPhos Pd G3 (58.4 mg, 0.070 mmol) and heating to 100° C. After 16 h, TLC analysis indicated complete conversion of the starting material. The reaction mixture was then cooled to room temperature and filtered through a pad of celite which was washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2-cyclopropyl-6-methylphenyl)azetidin-3-yl)-2,6-dimethylbenzyl)piperidine-4-carboxylate (50 mg, 16% yield) as a colorless semi-solid. LCMS method 1, LCMS (ESI, m/z): 447.2 $[M+H]^+$.

Synthesis of methyl 1-(4-(1-(2-(difluoromethyl)-6-methylphenyl)azetidin-3-yl)-2,6-dimethylbenzyl)piperidine-4-carboxylate

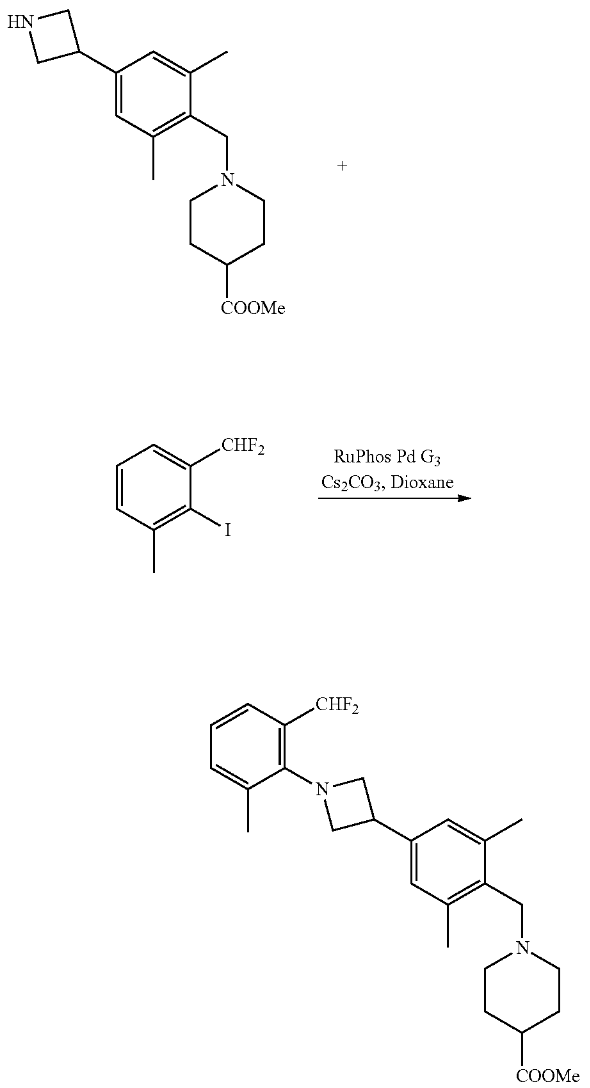

To a solution of methyl 1-(4-(azetidin-3-yl)-2,6-dimethylbenzyl)piperidine-4-carboxylate (600 mg, 1.896 mmol) and 2-bromo-1-(difluoromethyl)-3-methylbenzene (503 mg, 2.275 mmol) in anhydrous 1,4 dioxane (10 mL) was added cesium carbonate (1.8 g, 5.69 mmol). The reaction mixture was degassed with nitrogen for 10 min followed by addition of Ruphos pd G3 (159 mg, 0.190 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2-(difluoromethyl)-6-methylphenyl)azetidin-3-yl)-2,6-dimethylbenzyl)-piperidine-4-carboxylate (200 mg, 23% yield) as a brown semi-solid. LCMS method 1, LCMS (ESI, m/z): 457.3 $[M+H]^+$.

Synthesis of methyl 1-(2,6-dimethyl-4-(1-(2-methyl-6-(trifluoromethyl)phenyl)azetidin-3-yl)benzyl)piperidine-4-carboxylate

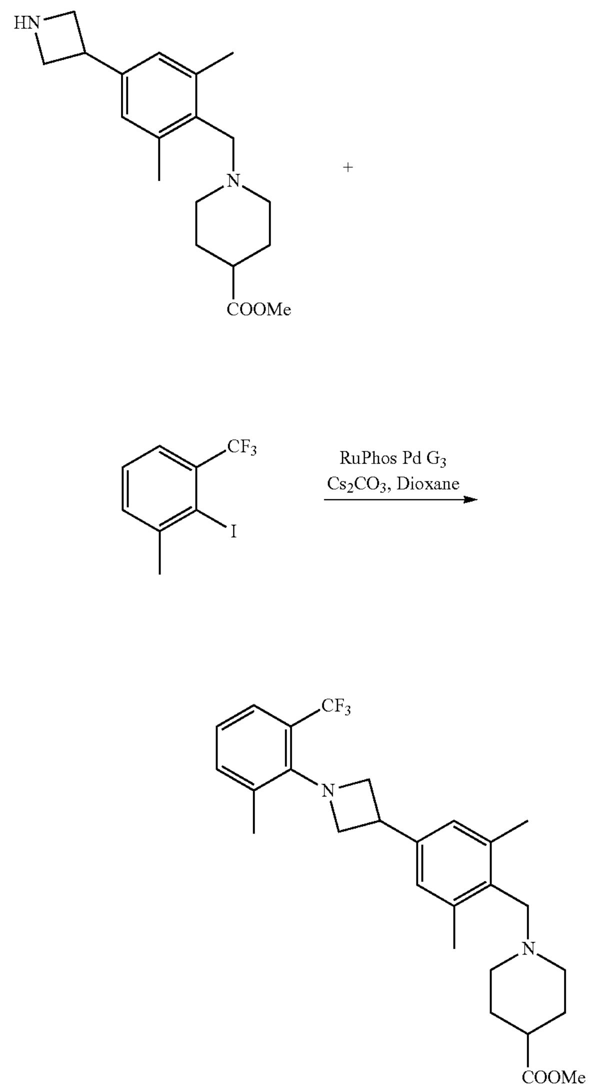

To a solution of methyl 1-(4-(azetidin-3-yl)-2,6-dimethylbenzyl)piperidine-4-carboxylate (400 mg, 1.264 mmol) and 2-iodo-1-methyl-3-(trifluoromethyl)benzene (434 mg, 1.517 mmol) in anhydrous 1,4 dioxane (10 mL) was added cesium carbonate (1234 mg, 3.79 mmol). The reaction mixture was then degassed with nitrogen for 10 min followed by addition of RuPhos Pd G3 (100 mg, 0.120 mmol) and subjected to the microwave irradiation for 2 h at 120° C. After 2 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (100-200 mesh) eluting with 0-50% ethyl acetate in petroleum ether to afford methyl 1-(2,6-dimethyl-4-(1-(2-methyl-6-(trifluoromethyl)phenyl)azetidin-3-yl)benzyl)piperidine-4-carboxylate (80 mg, 13.3% yield) as a brown semi-solid. LCMS method 1, LCMS (ESI, m/z): 475.2 $[M+H]^+$.

Synthesis of methyl 1-(4-(1-(2-cyano-6-methylphenyl)azetidin-3-yl)-2,6-dimethyl-benzyl)piperidine-4-carboxylate

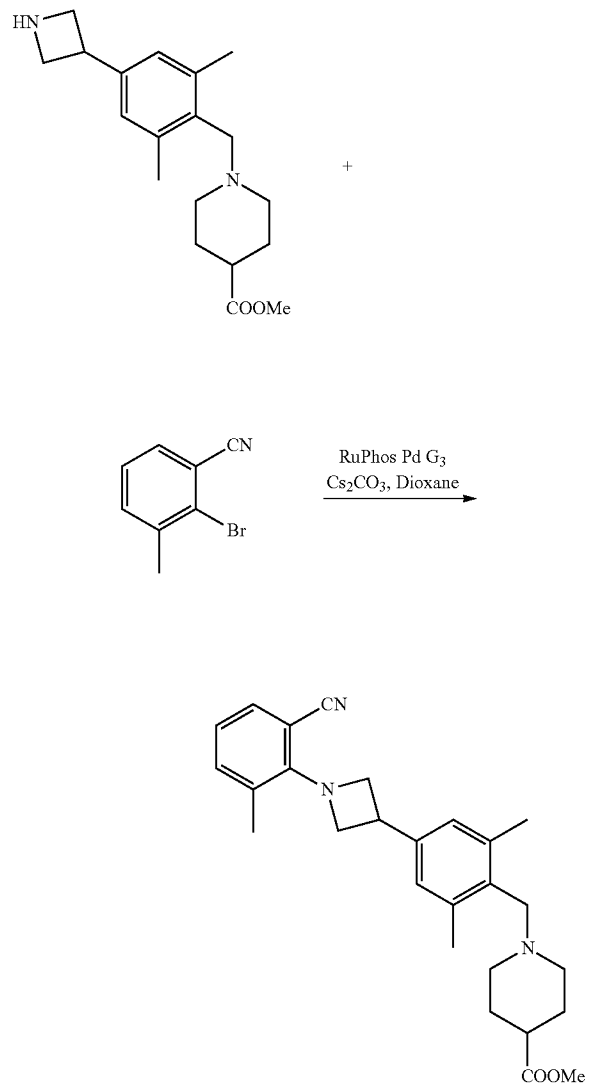

To a solution of methyl 1-(4-(azetidin-3-yl)-2,6-dimethylbenzyl)piperidine-4-carboxylate (300 mg, 0.948 mmol) and 2-bromo-3-methylbenzonitrile (223 mg, 1.138 mmol) in anhydrous 1,4 dioxane (5 mL) was added cesium carbonate (0.92 g, 2.84 mmol). The reaction mixture was then degassed with nitrogen for 10 min followed by addition of RuPhos Pd G3 (79 mg, 0.095 mmol) and heating to 80° C. After 12 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(4-(1-(2-cyano-6-methylphenyl)azetidin-3-yl)-2,6-dimethyl-benzyl)piperidine-4-carboxylate (160 mg, 39% yield) as a pale yellow liquid. LCMS method 1, LCMS (ESI, m/z): 432.2 $[M+H]^+$.

Synthesis of methyl 1-(2,6-dimethyl-4-(1-(naphthalen-1-yl)azetidin-3-yl)benzyl)-piperidine-4-carboxylate

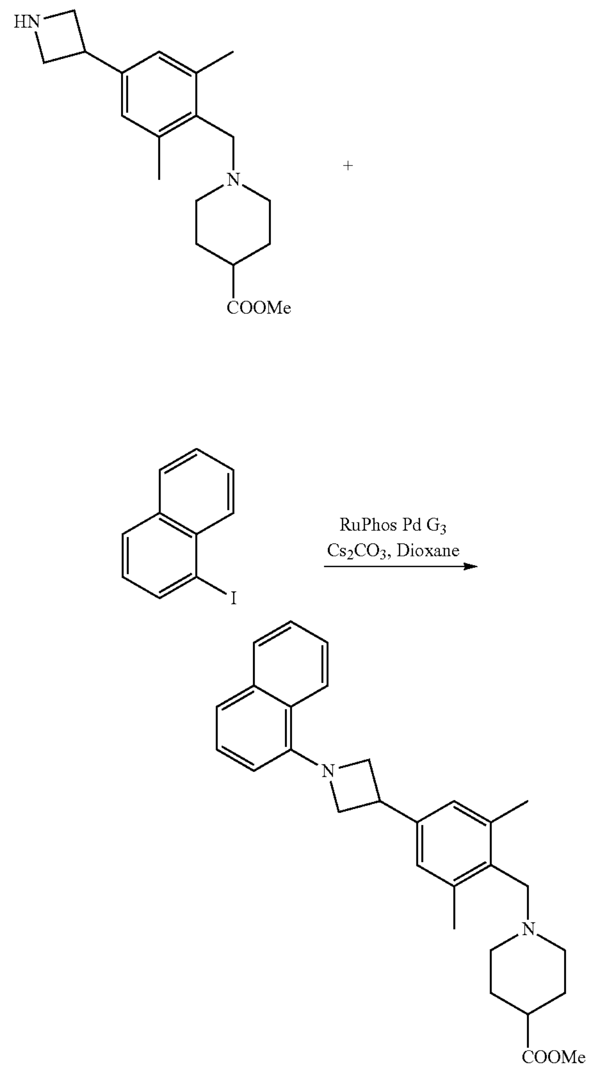

To a solution of methyl 1-(4-(azetidin-3-yl)-2,6-dimethylbenzyl)piperidine-4-carboxylate (300 mg, 0.948 mmol) and 1-iodonaphthalene (289 mg, 1.138 mmol) in anhydrous 1,4 dioxane (10 mL) was added cesium carbonate (923 mg, 2.84 mmol). The reaction mixture was then degassed with nitrogen for 10 min followed by addition of RuPhos Pd G3 (79 mg, 0.095 mmol) and heated to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (100-200 mesh) eluting with 0-50% ethyl acetate in petroleum ether to afford methyl 1-(2,6-dimethyl-4-(1-(naphthalen-1-yl)azetidin-3-yl)benzyl)piperidine-4-carboxylate (200 mg, 0.420 mmol, 47% yield) as a yellow liquid. LCMS method 1, LCMS (ESI, m/z): 443.2 [M+H]$^+$.

Example S66. 1-(4-(1-(2-fluoro-6-methylphenyl)azetidin-3-yl)-2,6-dimethylbenzyl)-piperidine-4-carboxylic acid (66)

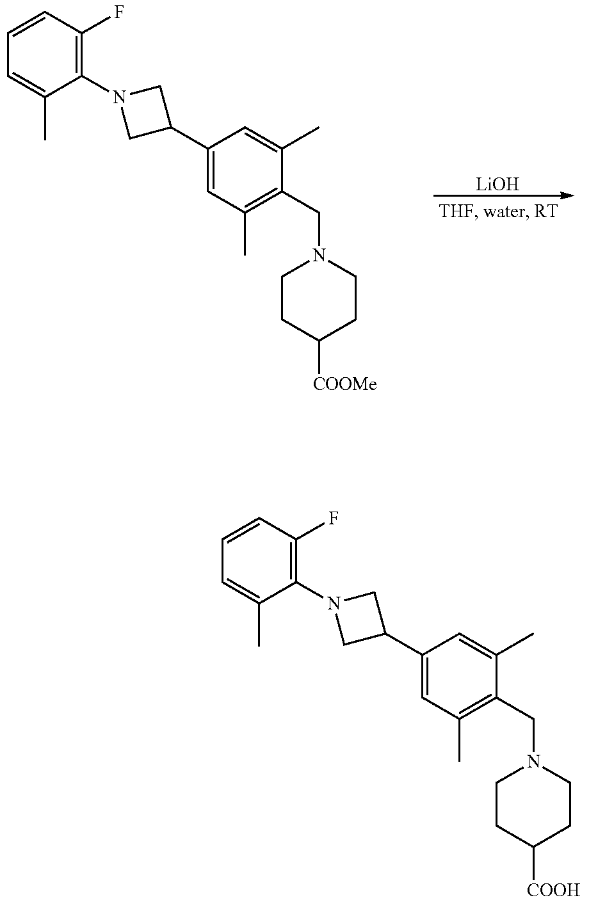

66

To a solution of methyl 1-(4-(1-(2-fluoro-6-methylphenyl)azetidin-3-yl)-2,6-dimethylbenzyl)piperidine-4-carboxylate (210 mg, 0.495 mmol) in THF (4 mL) and water (1 mL) was added LiOH (59.2 mg, 2.473 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column: Zorbax C18 (50×21.5) mm, 5 micron, Mobile phase A: 10 mM Ammonium acetate in water Mobile phase B: Acetonitrile. The required fractions were collected and lyophilized to afford 1-(4-(1-(2-fluoro-6-methylphenyl)azetidin-3-yl)-2,6-dimethylbenzyl)piperidine-4-carboxylic acid (55 mg, 0.130 mmol, 26.4% yield, 97.3% pure) as a white solid. $^1$H NMR (400 MHz, MeOD): δ 7.19 (s, 2H), 6.79-6.85 (m, 2H), 6.68-6.71 (m, 1H), 4.53-4.58 (m, 2H), 4.12-4.17 (m, 4H), 3.77-3.80 (m, 1H), 3.29 (m, 2H), 2.87-2.92 (m, 2H), 2.46 (s, 6H), 2.36-2.39 (m, 1H), 1.97-2.04 (m, 2H), 1.85-1.87 (m, 2H). LCMS method 1; LCMS (ESI, m/z): 411.2 [M+H]$^+$.

Example S67. 1-(4-(1-(2-chloro-6-methylphenyl)azetidin-3-yl)-2,6-dimethylbenzyl)-piperidine-4-carboxylic acid (67)

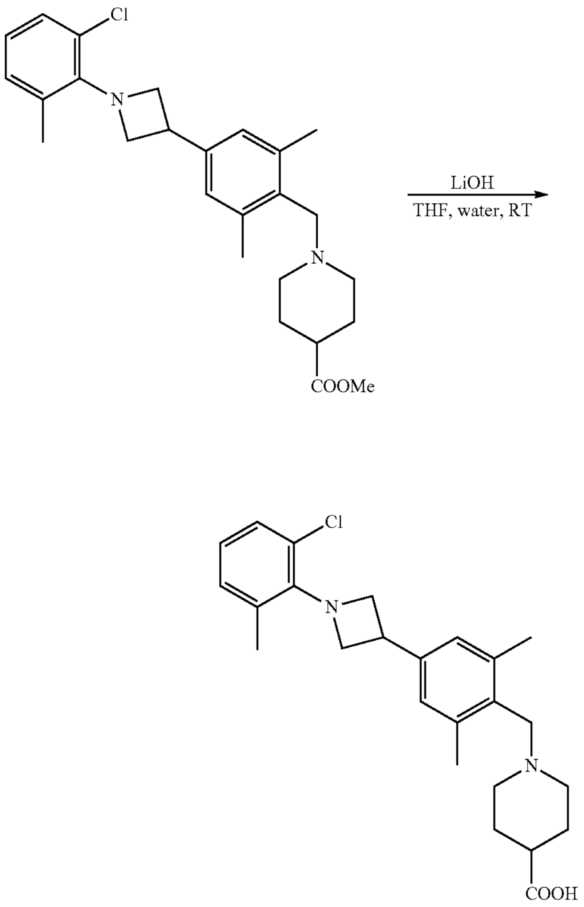

67

To a solution of methyl 1-(4-(1-(2-chloro-6-methylphenyl)azetidin-3-yl)-2,6-dimethylbenzyl)piperidine-4-carboxylate (210 mg, 0.476 mmol) in THF (4 mL) and water (1 mL) was added LiOH (57.0 mg, 2.381 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column: Zorbax C18 (50×21.5) mm, 5 micron, Mobile phase A: 10 mM Ammonium acetate in water, Mobile phase B: Acetonitrile. The required fractions were collected and lyophilized to afford 1-(4-(1-(2-chloro-6-methylphenyl)azetidin-3-yl)-2,6-dimethylbenzyl)piperidine-4-carboxylic acid (75 mg, 0.175 mmol, 36.7% yield, 99.5% pure) as an off-white solid. $^1$H NMR (400 MHz, MeOD); 7.22 (s, 2H), 7.08 (dd, J=0.80, 7.80 Hz, 1H), 6.98 (dd, J=0.80, 7.60 Hz, 1H), 6.72 (t, J=7.60 Hz, 1H), 4.68-4.72 (m, 2H), 4.22-4.25 (m, 2H), 4.12 (s, 2H), 3.69-3.76 (m, 1H), 3.29 (m, 1H), 2.87-2.92 (m, 2H), 2.36-2.42 (m, 5H), 1.96-2.04 (m, 2H), 1.81-1.90 (m, 2H). LCMS method 1; LCMS (ESI, m/z): 427.2 [M+H]$^+$.

Example S68. 1-(4-(1-(2-ethyl-6-methylphenyl)azetidin-3-yl)-2,6-dimethylbenzyl)-piperidine-4-carboxylic acid (68)

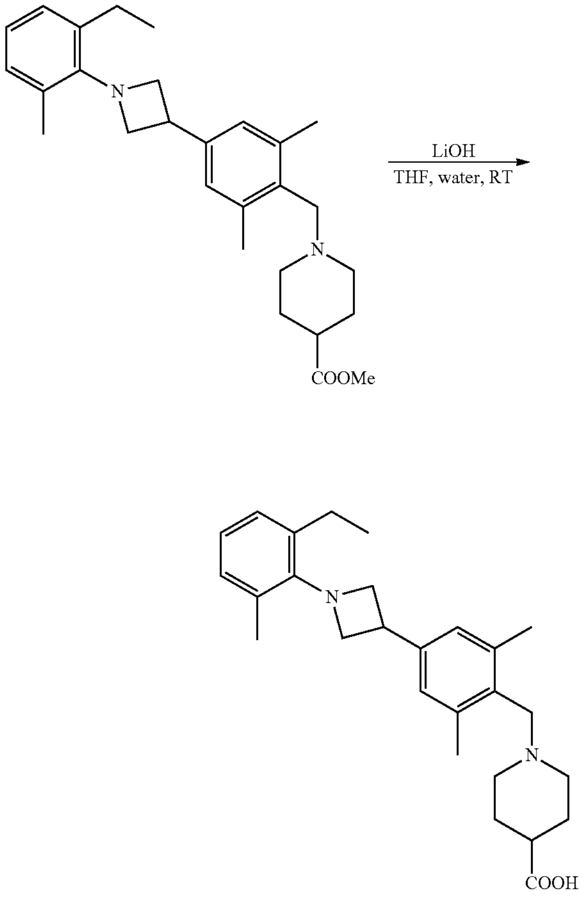

68

To a solution of methyl 1-(4-(1-(2-ethyl-6-methylphenyl)azetidin-3-yl)-2,6-dimethylbenzyl)piperidine-4-carboxylate (160 mg, 0.368 mmol) in THF (4 mL) and water (1 mL) was added LiOH (26.4 mg, 1.104 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30), Column-1: Xselect C18 (150×19) mm, 5 micron, Mobile phase A: 0.1% Formic acid in water, Mobile phase B: Acetonitrile. The required fractions were collected and lyophilized to afford 1-(4-(1-(2-ethyl-6-methylphenyl)azetidin-3-yl)-2,6-dimethylbenzyl)piperidine-4-carboxylic acid, formic acid salt (90.2 mg, 0.180 mmol, 49.0% yield, 93.3% pure) as a white solid. $^1$H NMR: (400 MHz, MeOD): δ 7.26 (m, 2H), 6.90-6.95 (m, 2H), 6.76-6.80 (m, 1H), 4.45-4.75 (m, 2H), 4.04-4.20 (m, 4H), 3.76-3.80 (m, 1H), 2.71-2.99 (m, 4H), 2.48 (m, 8H), 2.38 (m, 4H), 2.04-2.07 (m, 2H), 1.91 (s, 2H), 1.20-1.24 (m, 3H). LCMS method 1; LCMS (ESI, m/z): 421.2 [M+H]$^+$.

Example S69. 1-(4-(1-(2,6-diethylphenyl)azetidin-3-yl)-2,6-dimethylbenzyl)piperidine-4-carboxylic acid (69)

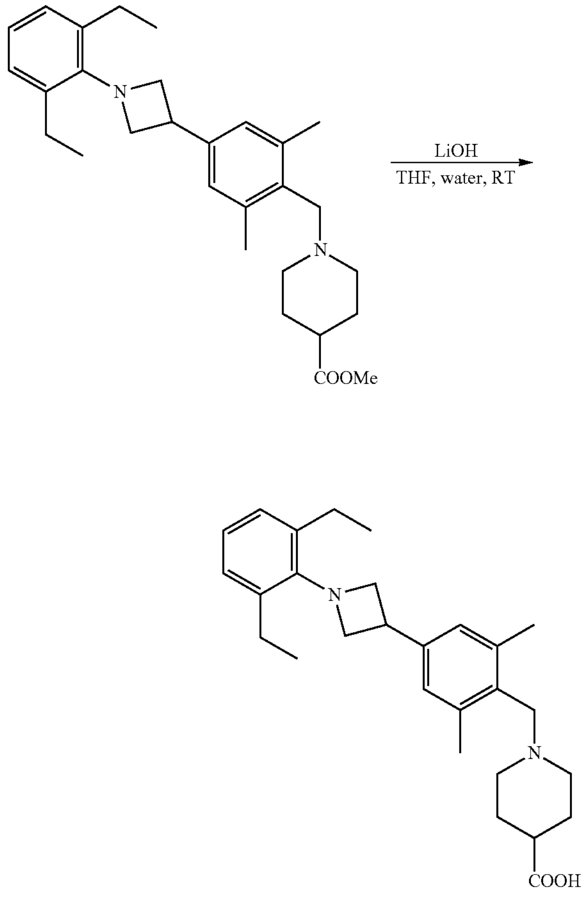

69

To a solution of methyl 1-(4-(1-(2,6-diethylphenyl)azetidin-3-yl)-2,6-dimethylbenzyl)piperidine-4-carboxylate (300 mg, 0.669 mmol) in THF (4 mL) and water (1 mL) was added LiOH (48.0 mg, 2.006 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC, prep. HPLC method: Diluent: THF:Water:ACN (50:10:40), Column-1: Xbridge C8 (150×19) mm, 5 micron, Mobile phase A: 0.1% Formic acid in water, Mobile phase B: Acetonitrile. The required fractions were collected and lyophilized to afford 1-(4-(1-(2,6-diethylphenyl)azetidin-3-yl)-2,6-dimethylbenzyl)piperidine-4-carboxylic acid, formic acid salt (106.6 mg, 0.213 mmol, 31.9% yield, 96.2% pure) as a white solid. $^1H$ NMR (400 MHz, MeOD): δ 7.30 (bs, 2H), 6.97-6.99 (m, 2H), 6.87-6.91 (m, 1H), 4.50-4.53 (m, 2H), 4.20 (s, 2H), 4.01-4.04 (m, 2H), 3.79-3.83 (m, 1H), 3.33-3.38 (m, 2H), 2.98 (bs, 2H), 2.76-2.82 (m, 4H), 2.40-2.49 (m, 8H), 2.04-2.07 (m, 2H), 1.87-2.03 (m, 2H), 1.23-1.27 (m, 6H). LCMS method 1; LCMS (ESI, m/z): 435.2 $[M+H]^+$.

Example S70. 1-(4-(1-(2-cyclopropylphenyl)azetidin-3-yl)-2,6-dimethylbenzyl)piperidine-4-carboxylic acid (70)

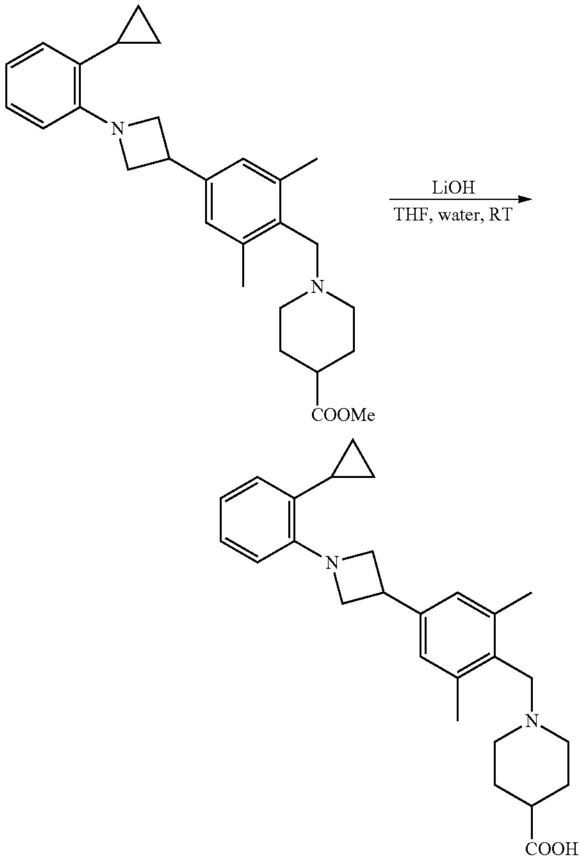

70

To a solution of methyl 1-(4-(1-(2-cyclopropylphenyl)azetidin-3-yl)-2,6-dimethylbenzyl)piperidine-4-carboxylate (160 mg, 0.370 mmol) in THF (4 mL) and water (1 mL) was added LiOH monohydrate (46.6 mg, 1.110 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-(4-(1-(2-cyclopropylphenyl)azetidin-3-yl)-2,6-dimethylbenzyl)piperidine-4-carboxylic acid, formic acid salt (62 mg, 0.133 mmol, 35.8% yield, 99.3% pure) as a white solid. $^1H$ NMR (400 MHz, MeOD): δ 7.21 (s, 2H), 7.09-7.21 (m, 1H), 6.99 (d, J=7.60 Hz, 1H), 6.77 (dt, J=1.20, 10.27 Hz, 1H), 6.59 (dd, J=0.80, 8.00 Hz, 1H), 4.41-4.45 (m, 2H), 4.13 (s, 2H), 3.95-3.99 (m, 2H), 3.84-3.86 (m, 1H), 3.29 (m, 1H), 2.90 (m, 2H), 2.46 (s, 6H), 2.04 (m, 1H), 2.00-2.04 (m, 2H). LCMS method 1; LCMS (ESI, m/z): 419.2 $[M+H]^+$.

Example S71. 1-(4-(1-(2-cyclopropyl-6-methylphenyl)azetidin-3-yl)-2,6-dimethylbenzyl)-piperidine-4-carboxylic acid (71)

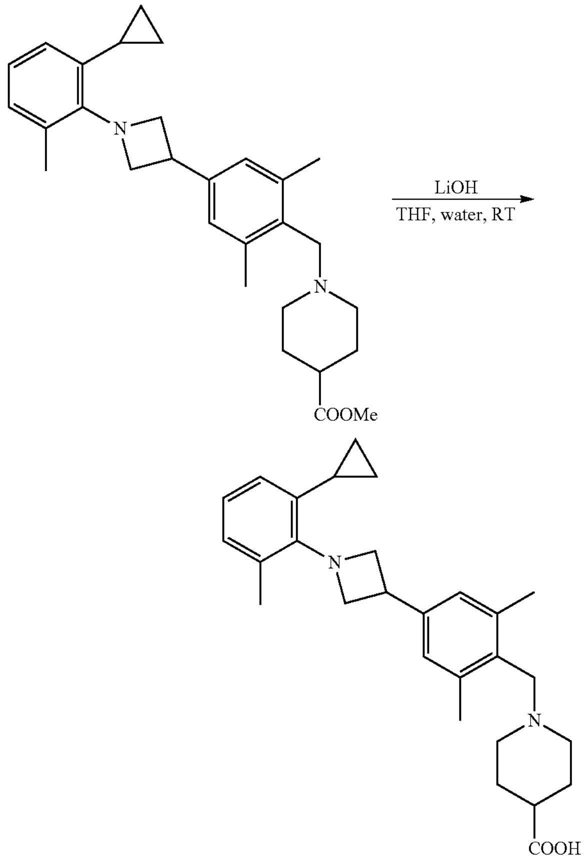

71

To a solution of methyl 1-(4-(1-(2-cyclopropyl-6-methylphenyl)azetidin-3-yl)-2,6-dimethylbenzyl)piperidine-4-carboxylate (50 mg, 0.112 mmol) in THF (2 mL) and water (0.5 mL) was added LiOH (14.09 mg, 0.336 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30) Column: Xselect C18 (150×19) mm, 5 micron, Mobile phase A: 0.1% Formic acid in water, Mobile phase B: Acetonitrile. The required fractions were collected and lyophilized to afford 1-(4-(1-(2-cyclopropyl-6-methylphenyl)azetidin-3-yl)-2,6-dimethylbenzyl)piperidine-4-carboxylic acid, formic acid salt (4.50 mg, 9.06 μmol, 8.09% yield, 96.3% pure) as an off-white solid. $^{1}H$ NMR (400 MHz, MeOD): δ 7.22 (s, 2H), δ 6.90-6.86 (m, 2H), δ 6.70-6.66 (m, 1H), δ 4.71-4.67 (m, 2H), δ 4.21-4.17 (m, 4H), δ 2.95 (bs, 2H), δ 2.46 (s, 8H), δ 2.31 (s, 3H), δ 2.09-2.01 (m, 4H), δ 1.88 (bs, 2H), δ 0.91-0.88 (m, 2H), δ 0.39-0.11 (m, 2H). LCMS method 2; LCMS (ESI, m/z): 433.2 $[M+H]^+$.

Example S72. 1-(4-(1-(2-(difluoromethyl)-6-methylphenyl)azetidin-3-yl)-2,6-dimethyl-benzyl)piperidine-4-carboxylic acid (72)

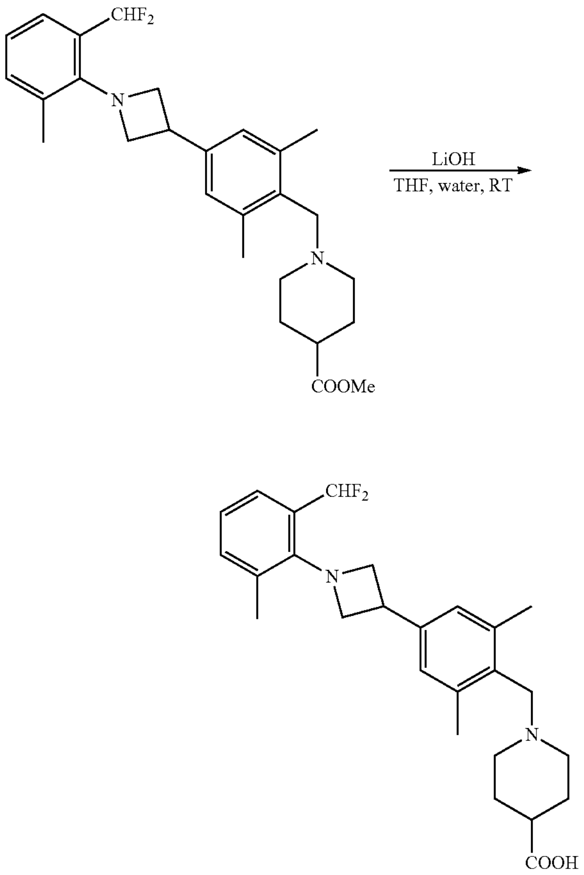

72

To a solution of methyl 1-(4-(1-(2-(difluoromethyl)-6-methylphenyl)azetidin-3-yl)-2,6-dimethylbenzyl)piperidine-4-carboxylate (200 mg, 0.438 mmol) in THF (4 mL) and water (1 mL) was added LiOH (31.5 mg, 1.314 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-(4-(1-(2-(difluoromethyl)-6-methylphenyl)azetidin-3-yl)-2,6-dimethylbenzyl)piperidine-4-carboxylic acid, formic acid salt (23.2 mg, 0.044 mmol, 10.10% yield, 93.6% pure) as a white solid. $^{1}H$ NMR (400 MHz, MeOD): δ 7.19-7.24 (m, 3H), 7.09 (s, 1H), 6.91-6.95 (m, 1H), 4.56-4.59 (m, 2H), 4.11-4.19 (m, 4H), 3.82-3.89 (m, 1H), 2.95-3.00 (m, 2H), 2.48 (s, 6H), 2.44 (m, 4H), 2.03-2.08 (m, 2H), 1.87-1.93 (m, 2H) (3H merged with solvent signals). LCMS method 1; LCMS (ESI, m/z): 443.2 $[M+H]^+$.

Example S73. 1-(2,6-dimethyl-4-(1-(2-methyl-6-(trifluoromethyl)phenyl)azetidin-3-yl)-benzyl)piperidine-4-carboxylic acid (73)

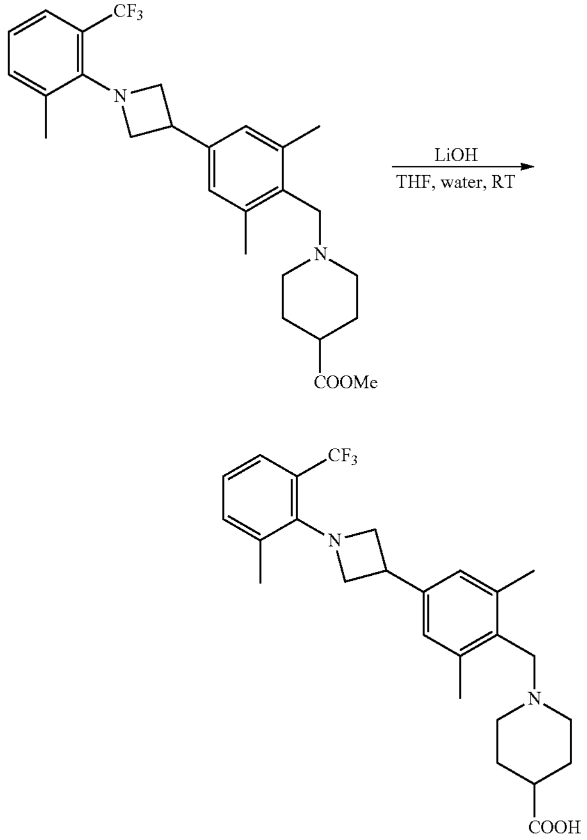

73

To a solution of methyl 1-(2,6-dimethyl-4-(1-(2-methyl-6-(trifluoromethyl)phenyl)azetidin-3-yl)benzyl)piperidine-4-carboxylate (80 mg, 0.169 mmol) in THF (4 mL) and water (1 mL) was added LiOH (12.11 mg, 0.506 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-(2,6-dimethyl-4-(1-(2-methyl-6-(trifluoromethyl)phenyl)azetidin-3-yl)benzyl)piperidine-4-carboxylic acid, formic acid salt (37.3 mg, 0.073 mmol, 43.6% yield, 99.7% pure) as a white solid. $^1$H NMR (400 MHz, MeOD): δ 7.42-7.44 (m, 1H), 7.34-7.36 (m, 1H), 7.29 (s, 2H), 7.00-7.04 (m, 1H), 4.57-4.61 (m, 2H), 4.18 (s, 2H), 4.06-4.09 (m, 2H), 3.81-3.84 (m, 1H), 3.37 (s, 1H), 2.96 (s, 2H), 2.42-2.50 (m, 10H), 2.02-2.07 (m, 2H), 1.87-1.90 (m, 2H) (2H merged with solvent peaks). LCMS method 2; LCMS (ESI, m/z): 461.0 $[M+H]^+$.

Example S74. 1-(4-(1-(2-cyano-6-methylphenyl)azetidin-3-yl)-2,6-dimethylbenzyl)-piperidine-4-carboxylic acid (74)

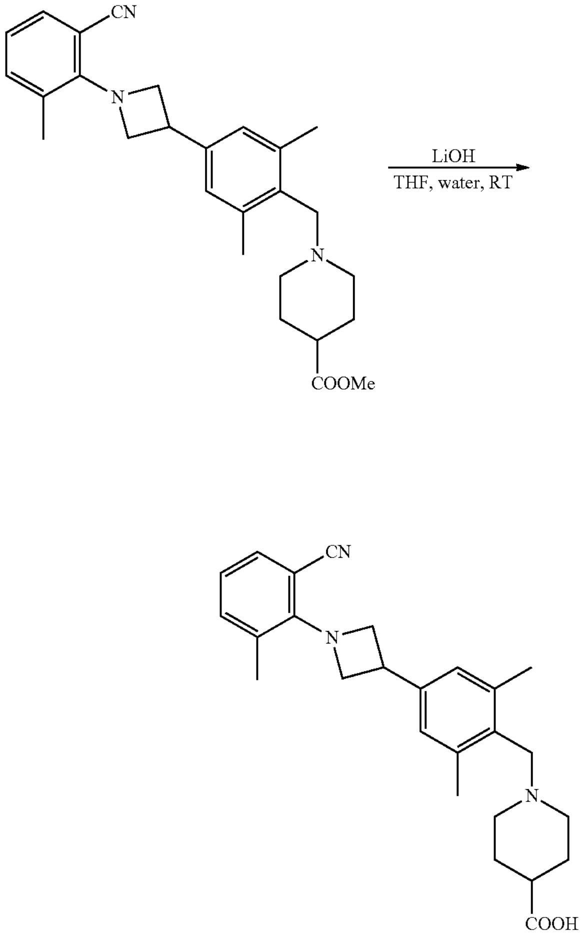

74

To a solution of methyl 1-(4-(1-(2-cyano-6-methylphenyl)azetidin-3-yl)-2,6-dimethylbenzyl)piperidine-4-carboxylate (160 mg, 0.371 mmol) in THF (4 mL) and water (1 mL) was added LiOH (26.6 mg, 1.112 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-(4-(1-(2-cyano-6-methylphenyl)azetidin-3-yl)-2,6-dimethylbenzyl)piperidine-4-carboxylic acid, formic acid salt (70.4 mg, 0.152 mmol, 40.9% yield, 99% pure) as a white solid. $^1$H NMR: (400 MHz, MeOD): δ 7.31-7.33 (m, 1H), 7.22-7.25 (m, 3H), 6.73-6.77 (m, 1H), 4.78-4.82 (m, 2H), 4.34-4.37 (m, 2H), 4.16 (s, 2H), 3.82-3.86 (m, 1H), 2.94 (s, 2H), 2.48 (s, 6H), 2.42-2.43 (m, 1H), 2.33 (s, 3H), 2.03-2.06 (m, 2H), 1.89 (s, 2H) (2H are merged with solvent signal). LCMS method 1; LCMS (ESI, m/z): 418.2 $[M+H]^+$.

Example S75. 1-(2,6-dimethyl-4-(1-(naphthalen-1-yl)azetidin-3-yl)benzyl)piperidine-4-carboxylic acid (75)

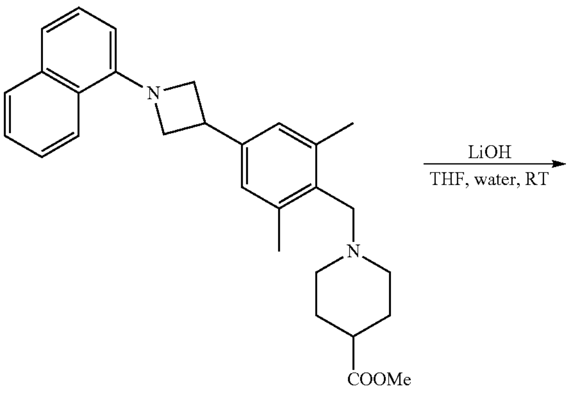

-continued

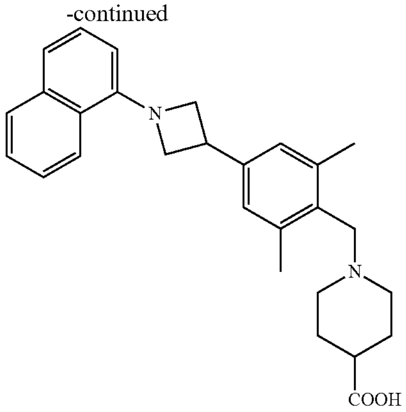

75

To a solution of methyl 1-(2,6-dimethyl-4-(1-(naphthalen-1-yl)azetidin-3-yl)benzyl)piperidine-4-carboxylate (200 mg, 0.452 mmol) in THF (4 mL) and Water (1 mL) was added LiOH (32.5 mg, 1.356 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water: CAN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-(2,6-dimethyl-4-(1-(naphthalen-1-yl)azetidin-3-yl)benzyl)piperidine-4-carboxylic acid, formic acid salt (102.8 mg, 0.216 mmol, 47.8% yield, 99.8% pure) as a white solid. $^1$H NMR (400 MHz, MeOD): δ 8.02-8.04 (m, 1H), 7.81-7.83 (m, 1H), 7.37-7.45 (m, 4H), 7.25 (m, 2H), 6.70-6.73 (m, 1H), 4.56-4.59 (m, 2H), 4.09-4.15 (m, 4H), 3.98-4.00 (m, 1H), 2.93 (s, 2H), 2.47 (s, 6H), 2.41 (s, 1H), 2.02-2.05 (m, 2H), 1.85-1.88 (m, 2H) (2H are merged with solvent signals). LCMS method 1; LCMS (ESI, m/z): 429.2 $[M+H]^+$.

General Route to Compounds 76-84

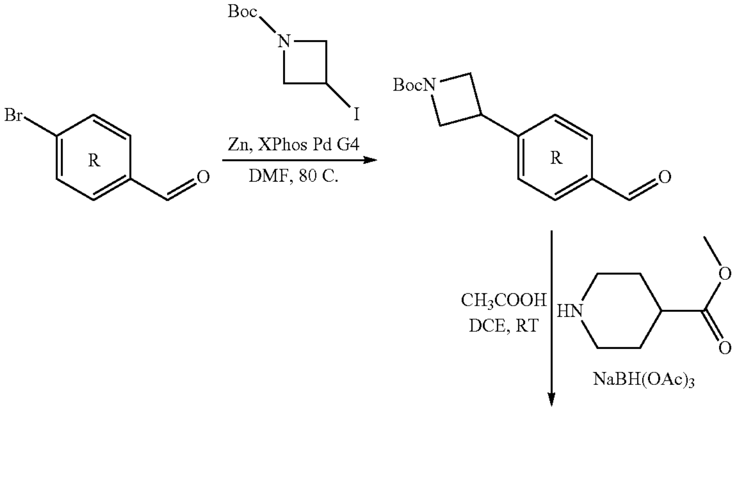

-continued
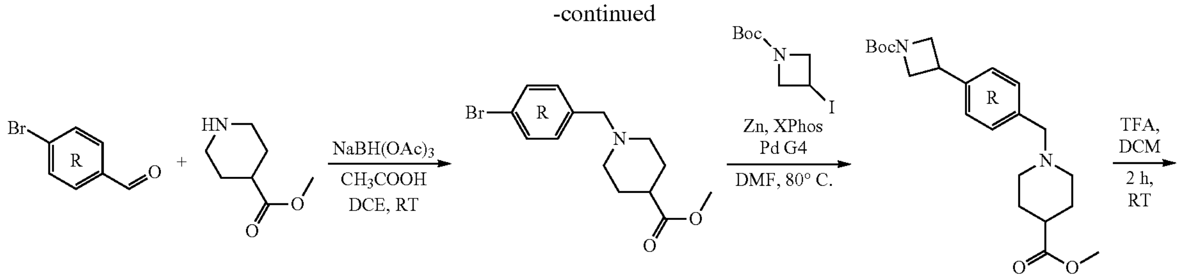
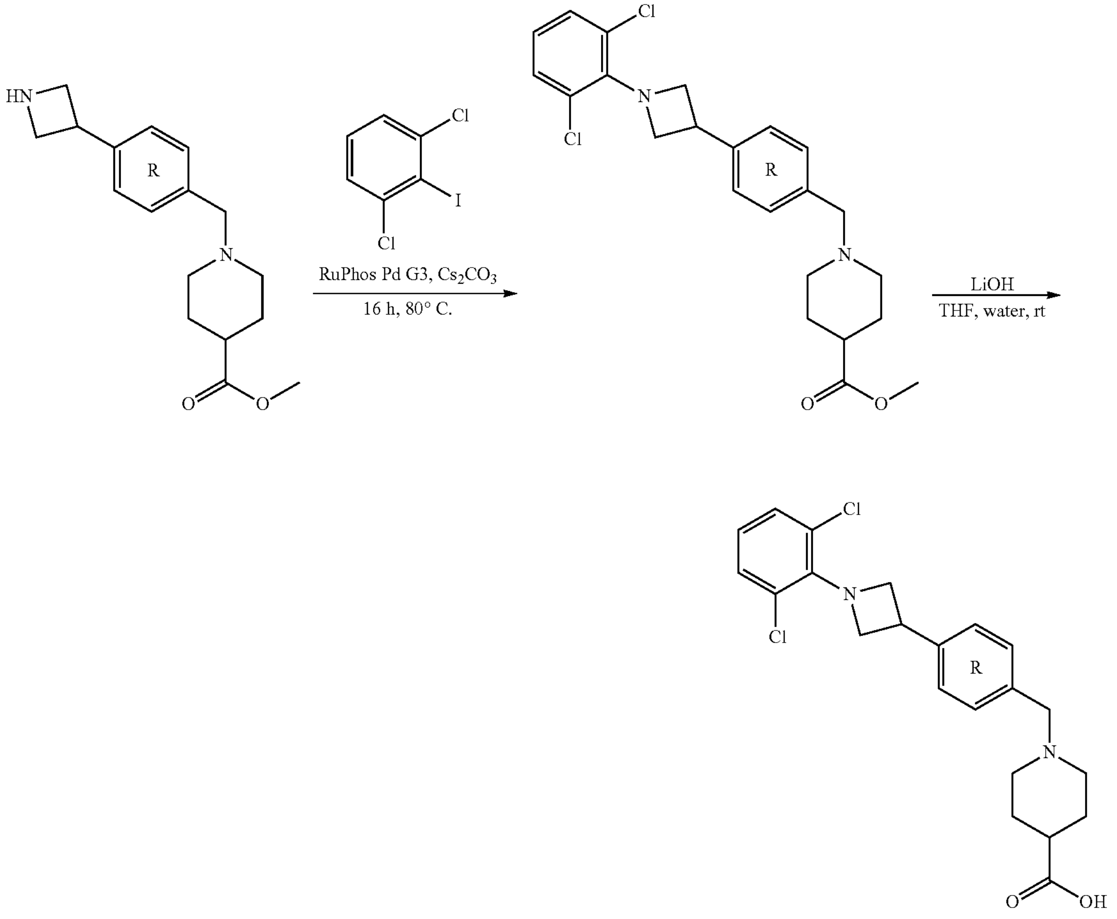
76-84
Synthesis of methyl 1-((5-bromo-3-methylpyridin-2-yl)methyl)piperidine-4-carboxylate
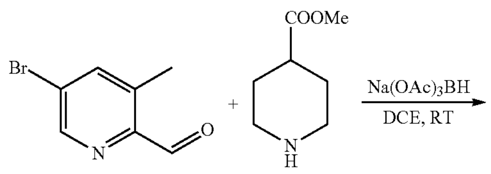
-continued
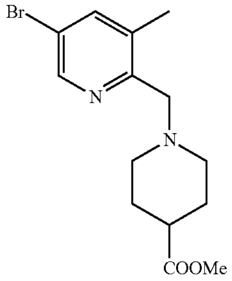

To a stirred solution of 5-bromo-3-methylpicolinaldehyde (1.0 g, 5.00 mmol) and methyl piperidine-4-carboxylate (1.074 g, 7.50 mmol) in DCE (15 mL) was added acetic acid (0.029 mL, 0.500 mmol) and the mixture stirred for 30 min at room temperature. Sodium triacetoxyborohydride (1.589 g, 7.50 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (30 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford methyl 1-((5-bromo-3-methylpyridin-2-yl)methyl) piperidine-4-carboxylate (1.52 g, 4.56 mmol, 92% yield). LCMS method 1, LCMS (ESI, m/z): 326.9 $[M+H]^+$.

Synthesis of methyl 1-((5-bromo-4-methylpyridin-2-yl)methyl)piperidine-4-carboxylate

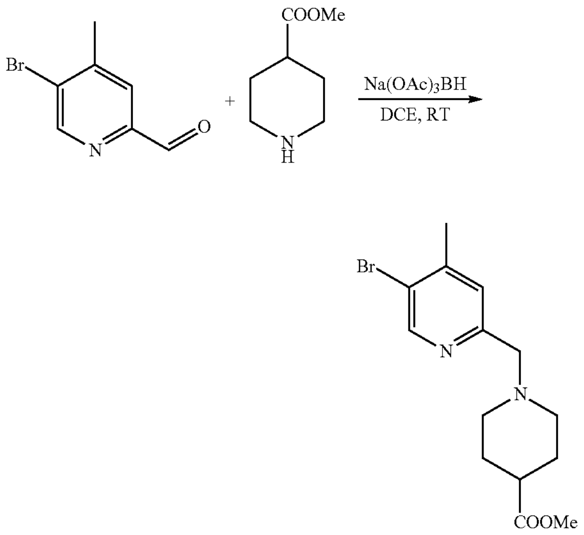

To a stirred solution of 5-bromo-4-methylpicolinaldehyde (1.0 g, 5.00 mmol) and methyl piperidine-4-carboxylate (1.074 g, 7.50 mmol) in DCE (15 mL) was added acetic acid (0.029 mL, 0.500 mmol) and the mixture was stirred for 30 min at room temperature. Sodium triacetoxyborohydride (1.589 g, 7.50 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (30 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford the methyl 1-((5-bromo-4-methylpyridin-2-yl)methyl)piperidine-4-carboxylate (1.54 g, 94% yield) as a brown liquid. LCMS method 1, LCMS (ESI, m/z): 326.9 $[M+H]^+$.

Synthesis of methyl 1-((6-bromo-4-methylpyridin-3-yl)methyl)piperidine-4-carboxylate

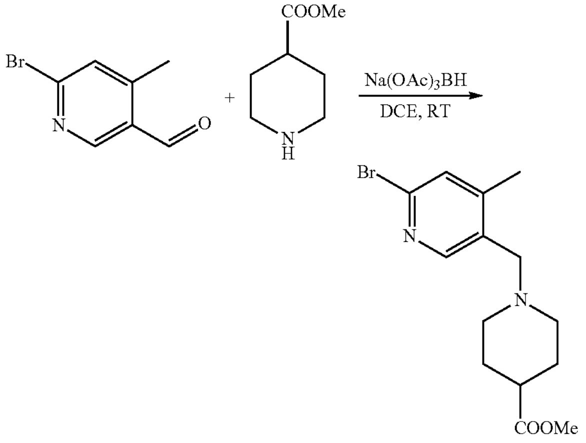

To a stirred solution of 6-bromo-4-methylnicotinaldehyde (1.0 g, 5.00 mmol) and methyl piperidine-4-carboxylate (1.074 g, 7.50 mmol) in DCE (15 mL) was added acetic acid (0.029 mL, 0.500 mmol) and the mixture was stirred for 30 min at room temperature. Sodium triacetoxyborohydride (1.589 g, 7.50 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (30 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford methyl 1-((6-bromo-4-methylpyridin-3-yl)methyl)piperidine-4-carboxylate (1.56 g, 95% yield) as a colorless liquid. LCMS method 1, LCMS (ESI, m/z): 327.0 $[M+H]^+$.

Synthesis of methyl 1-((6-bromo-5-methylpyridin-3-yl)methyl)piperidine-4-carboxylate

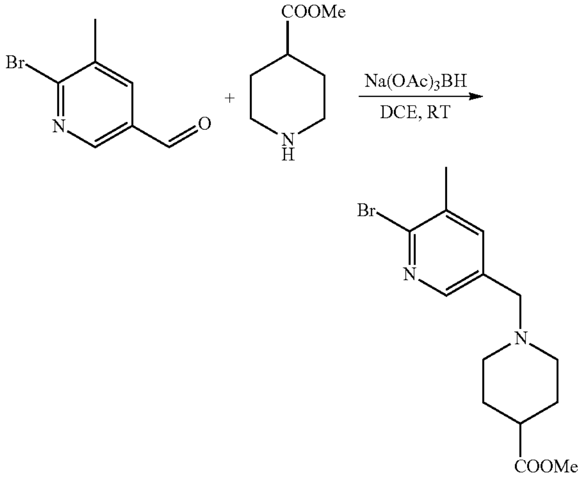

To a stirred solution of 6-bromo-5-methylnicotinaldehyde (1.0 g, 5.00 mmol) and methyl piperidine-4-carboxylate (1.074 g, 7.50 mmol) in DCE (15 mL) was added acetic acid (0.029 mL, 0.500 mmol) and the mixture stirred for 30 min at room temperature. Sodium triacetoxyborohydride (1.589 g, 7.50 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (30 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford methyl 1-((6-bromo-5-methylpyridin-3-yl)methyl) piperidine-4-carboxylate (1.46 g, 89% yield) as a brown liquid. LCMS method 1, LCMS (ESI, m/z): 329.0 $[M+2H]^+$.

Synthesis of tert-butyl 3-(6-formyl-4,5-dimethylpyridin-3-yl)azetidine-1-carboxylate

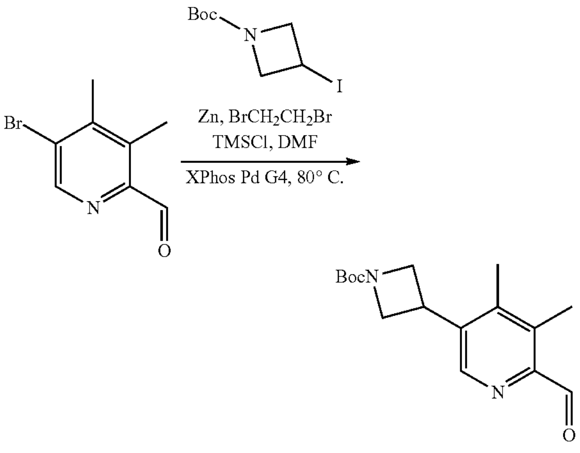

To a suspension of activated zinc (1527 mg, 23.36 mmol) in anhydrous DMF (10 mL) was added 1,2-dibromoethane (0.020 mL, 0.234 mmol) and the mixture was heated to 75° C. After 15 min, the reaction mixture was cooled to room temperature, trimethylsilyl chloride (0.030 mL, 0.234 mmol) was added and stirred at ambient temperature for additional 30 min. Then a solution of tert-butyl 3-iodoazetidine-1-carboxylate (2645 mg, 9.34 mmol) in 2 mL of anhydrous DMF was added and the mixture was stirred at room temperature for another 30 min, followed by addition of 5-bromo-3,4-dimethylpicolinaldehyde (500 mg, 2.336 mmol) and XPhos Pd G4 (201 mg, 0.234 mmol) in 2 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-50% ethyl acetate in petroleum ether to afford tert-butyl 3-(6-formyl-4,5-dimethylpyridin-3-yl)azetidine-1-carboxylate (0.25 g, 36% yield) as a colorless semi-solid. LCMS method 1, LCMS (ESI, m/z): 291.2 $[M+H]^+$.

Synthesis of methyl 1-((6-bromo-4,5-dimethylpyridin-3-yl)methyl)piperidine-4-carboxylate

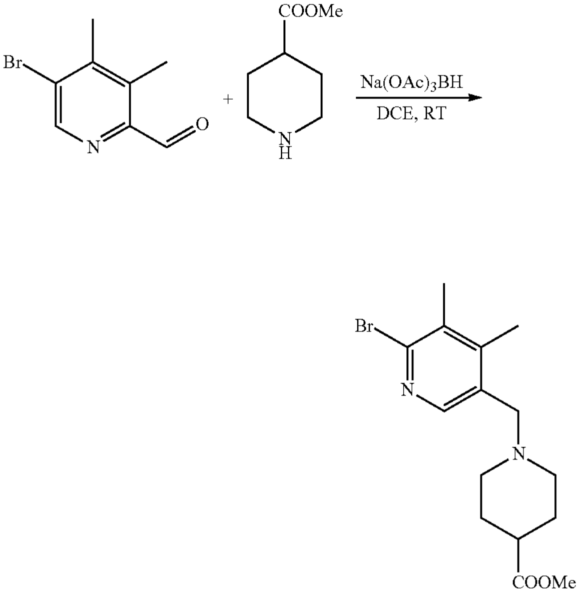

To a stirred solution of 6-bromo-4,5-dimethylnicotinaldehyde (750 mg, 3.50 mmol) and methyl piperidine-4-carboxylate (753 mg, 5.26 mmol) in DCE (20 mL) was added acetic acid (0.040 mL, 0.701 mmol) and the mixture stirred for 30 min at room temperature. Sodium triacetoxyborohydride (1114 mg, 5.26 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×10 mL), the combined organic phase was washed with water (20 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford methyl 1-((6-bromo-4,5-dimethylpyridin-3-yl)methyl)piperidine-4-carboxylate (800 mg, 67% yield) as a pale yellow semi-solid. LCMS method 3, LCMS (ESI, m/z): 343.0 $[M+2H]^+$.

Synthesis of methyl 1-((5-bromo-3,6-dimethylpyridin-2-yl)methyl)piperidine-4-carboxylate

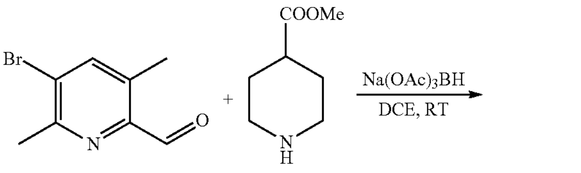

-continued

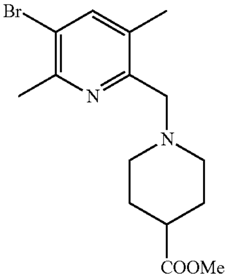

To a stirred solution of 5-bromo-3,6-dimethylpicolinaldehyde (700 mg, 3.27 mmol) and methyl piperidine-4-carboxylate (468 mg, 3.27 mmol) in DCE (20 mL) was added acetic acid (0.187 mL, 3.27 mmol) and stirred for 30 min at room temperature. Sodium triacetoxyborohydride (1040 mg, 4.91 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×10 mL), the combined organic phase was washed with water (20 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford methyl 1-((5-bromo-3,6-dimethylpyridin-2-yl)methyl)piperidine-4-carboxylate (750 mg, 66.9% yield) as a pale yellow semi-solid. LCMS method 1, LCMS (ESI, m/z): 343.0 $[M+2H]^+$.

Synthesis of methyl 1-((6-bromo-2,5-dimethylpyridin-3-yl)methyl)piperidine-4-carboxylate

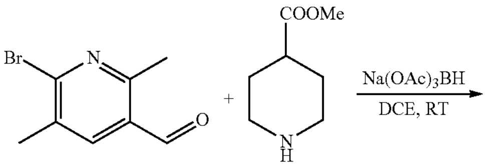

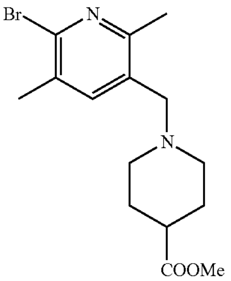

To a stirred solution of 6-bromo-2,5-dimethylnicotinaldehyde (0.800 g, 3.74 mmol) and methyl piperidine-4-carboxylate (0.642 g, 4.48 mmol) in DCE (10 mL) was added acetic acid (0.021 mL, 0.374 mmol) and the mixture was stirred for 30 min at room temperature. Sodium triacetoxyborohydride (0.792 g, 3.74 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×10 mL), the combined organic phase was washed with water (20 mL) and dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford the methyl 1-((6-bromo-2,5-dimethylpyridin-3-yl)methyl)piperidine-4-carboxylate (1.071 g, 3.14 mmol, 84% yield) as a yellow semi-solid. LCMS method 3, LCMS (ESI, m/z): 342.8 $[M+H]^+$.

Synthesis of methyl 1-((5-bromo-4,6-dimethylpyridin-2-yl)methyl)piperidine-4-carboxylate

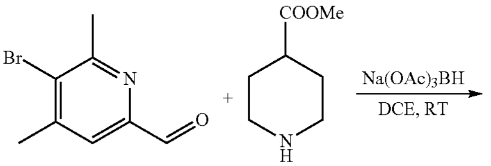

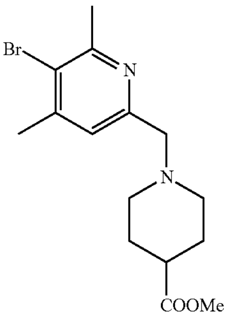

To a stirred solution of 5-bromo-4,6-dimethylpicolinaldehyde (1.1 g, 5.14 mmol) and methyl piperidine-4-carboxylate (0.736 g, 5.14 mmol) in DCE (10 mL) was added acetic acid (0.029 mL, 0.514 mmol) and the mixture was stirred for 30 min at room temperature. Sodium triacetoxyborohydride (1.634 g, 7.71 mmol) was added at ice cold temperature and the mixture was allowed to reach room temperature and stirred for 16 h. The reaction mixture was diluted with DCM (20 mL) and quenched with sat. ammonium chloride solution. The aqueous layer was extracted with DCM (2×10 mL), the combined organic phase was washed with water (20 mL), dried over $Na_2SO_4$, filtered and the solvent was evaporated under reduced pressure. The resulting residue was purified by flash column chromatography on silica gel (100-200 mesh) eluting with 30-100% ethyl acetate in petroleum ether to afford methyl 1-((5-bromo-4,6-dimethylpyridin-2-yl)methyl)piperidine-4-carboxylate (800 mg, 45% yield) as a yellow semi-solid. LCMS method 3, LCMS (ESI, m/z): 327.2 [M−15]+.

Synthesis of methyl 1-((5-(1-(tert-butoxycarbonyl)azetidin-3-yl)-3-methylpyridin-2-yl)methyl)piperidine-4-carboxylate (4a)

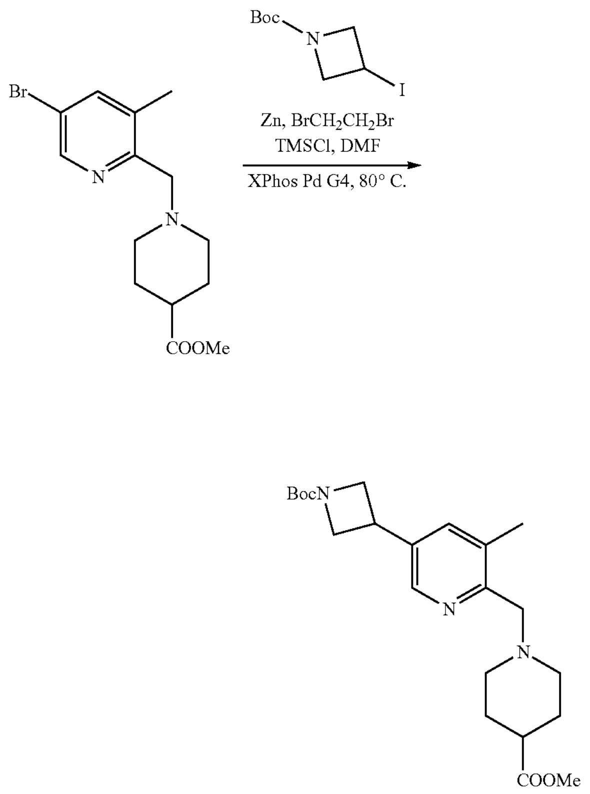

To a suspension of activated zinc dust (3.00 g, 45.8 mmol) in anhydrous DMF (30 mL) was added 1,2-dibromoethane (0.198 mL, 2.292 mmol) and the mixture was heated to 75° C. After 15 min, the reaction mixture was cooled to room temperature, trimethylsilyl chloride (0.291 mL, 2.292 mmol) was added and stirred at ambient temperature for additional 30 min. Then a solution of tert-butyl 3-iodoazetidine-1-carboxylate (3.89 g, 13.75 mmol) in 5 mL of anhydrous DMF was added and stirred at room temperature for another 30 min, followed by addition of methyl 1-((5-bromo-3-methylpyridin-2-yl)methyl)piperidine-4-carboxylate (1.5 g, 4.58 mmol) and XPhos Pd G4 (0.394 g, 0.458 mmol) in 5 mL of DMF. The reaction mixture was stirred at 80° C. for 2 h. After completion of the reaction, the reaction mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((5-(1-(tert-butoxycarbonyl)azetidin-3-yl)-3-methylpyridin-2-yl)methyl)piperidine-4-carboxylate (1.50 g, 1.692 mmol, 81% yield) as a brown semi-solid. LCMS method 1, LCMS (ESI, m/z): 404.2 $[M+H]^+$.

Synthesis of methyl 1-((5-(1-(tert-butoxycarbonyl)azetidin-3-yl)-3-methylpyridin-2-yl)methyl)piperidine-4-carboxylate

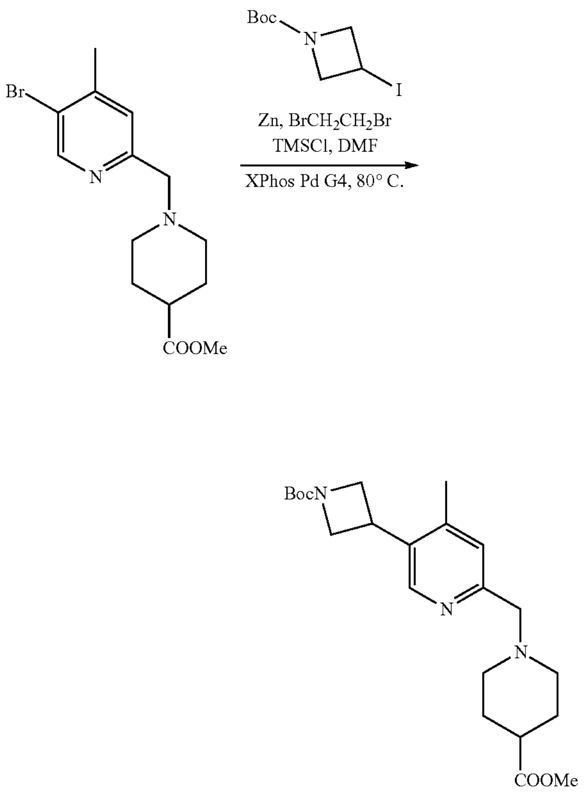

To a suspension of activated zinc dust (3.00 g, 45.8 mmol) in anhydrous DMF (30 mL) was added 1,2-dibromoethane (0.198 mL, 2.292 mmol) and the mixture was heated to 75° C. After 15 min, the reaction mixture was cooled to room temperature, trimethylsilyl chloride (0.291 mL, 2.292 mmol) was added and stirred at ambient temperature for additional 30 min. Then a solution of tert-butyl 3-iodoazetidine-1-carboxylate (3.89 g, 13.75 mmol) in 5 mL of anhydrous DMF was added to the reaction mixture and stirred at room temperature for another 30 min, followed by addition of methyl 1-((5-bromo-4-methylpyridin-2-yl)methyl)piperidine-4-carboxylate (1.5 g, 4.58 mmol) and XPhos Pd G4 (0.394 g, 0.458 mmol) in 5 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((5-(1-(tert-butoxycarbonyl)azetidin-3-yl)-4-methylpyridin-2-yl)methyl)piperidine-4-carboxylate (1.6 g, 86% yield) as a brown semi-solid. LCMS method 1, LCMS (ESI, m/z): 404.2 $[M+H]^+$.

Synthesis of methyl 1-((6-(1-(tert-butoxycarbonyl) azetidin-3-yl)-4-methylpyridin-3-yl)methyl)piperidine-4-carboxylate

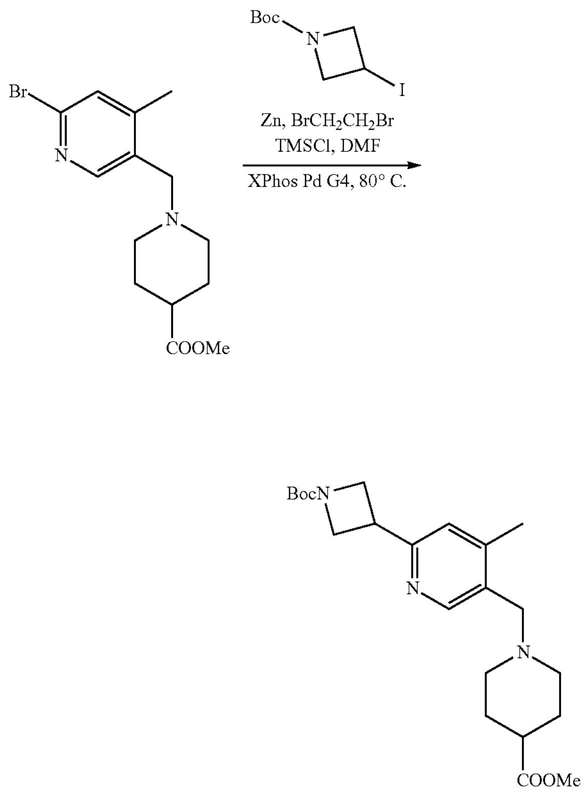

To a suspension of activated zinc dust (3.00 g, 45.8 mmol) in anhydrous DMF (20 mL) was added 1,2-dibromoethane (0.026 mL, 0.306 mmol) and the mixture was heated to 75° C. After 15 min, the reaction mixture was cooled to room temperature, trimethylsilyl chloride (0.039 mL, 0.306 mmol) was added and stirred at ambient temperature for additional 30 min. Then a solution of tert-butyl 3-iodoazetidine-1-carboxylate (2.163 g, 7.64 mmol) in 5 mL of anhydrous DMF was added to the reaction mixture and stirred at room temperature for another 30 min, followed by addition of methyl 1-((6-bromo-4-methylpyridin-3-yl) methyl)piperidine-4-carboxylate (1 g, 3.06 mmol) and XPhos Pd G4 (0.263 g, 0.306 mmol) in 5 mL of DMF. The reaction mixture was stirred at 80° C. for 2 h. After completion of the reaction, the reaction mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((6-(1-(tert-butoxycarbonyl) azetidin-3-yl)-4-methylpyridin-3-yl)methyl)piperidine-4-carboxylate (0.9 g, 72% yield) as a colorless semi-solid. LCMS method 3, LCMS (ESI, m/z): 404.2 $[M+H]^+$.

Synthesis of methyl 1-((6-(1-(tert-butoxycarbonyl) azetidin-3-yl)-5-methylpyridin-3-yl)methyl)piperidine-4-carboxylate

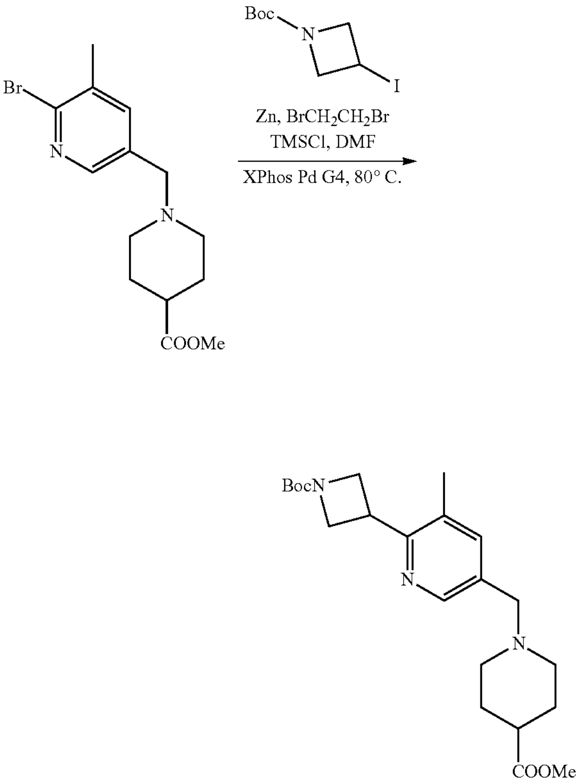

To a suspension of activated zinc dust (2.80 g, 42.8 mmol) in anhydrous DMF (20 mL) was added 1,2-dibromoethane (0.185 mL, 2.139 mmol) and the mixture was heated to 75° C. After 15 min, the reaction mixture was cooled to room temperature, trimethylsilyl chloride (0.272 mL, 2.139 mmol) was added and stirred at ambient temperature for additional 30 min. Then a solution of tert-butyl 3-iodoazetidine-1-carboxylate (3.63 g, 12.84 mmol) in 5 mL of anhydrous DMF was added and stirred at room temperature for another 30 min, followed by addition of methyl 1-((6-bromo-5-methylpyridin-3-yl)methyl)piperidine-4-carboxylate (1.4 g, 4.28 mmol) and XPhos Pd G4 (0.368 g, 0.428 mmol) in 5 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((6-(1-(tert-butoxycarbonyl)azetidin-3-yl)-5-methylpyridin-3-yl)methyl)piperidine-4-carboxylate (1.1 g, 63% yield) as a brown semi-solid. LCMS method 1, LCMS (ESI, m/z): 404.2 $[M+H]^+$.

Synthesis of methyl 1-((5-(1-(tert-butoxycarbonyl) azetidin-3-yl)-3,4-dimethylpyridin-2-yl)methyl)piperidine-4-carboxylate

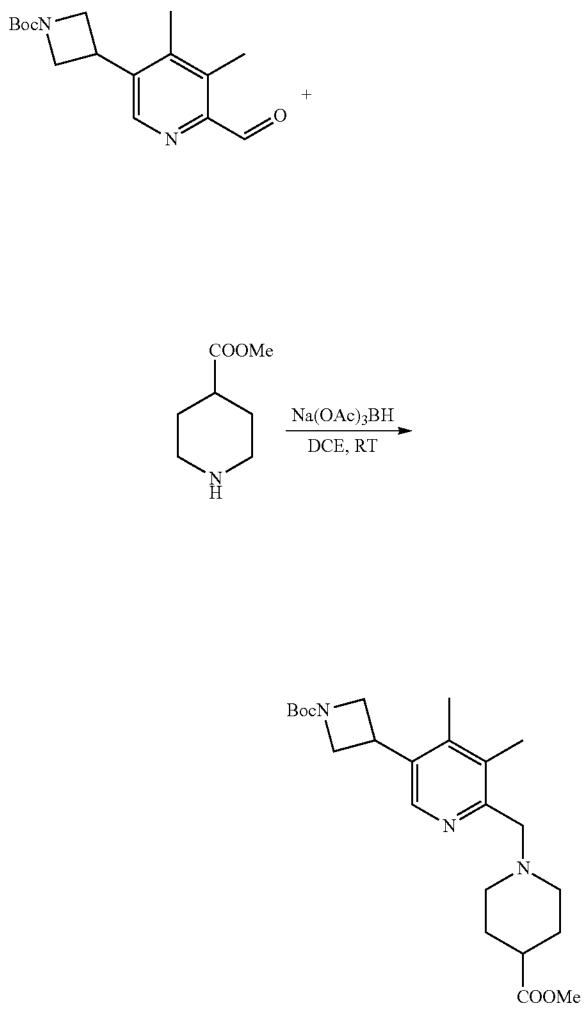

To a stirred solution of tert-butyl 3-(6-formyl-4,5-dimethylpyridin-3-yl)azetidine-1-carboxylate (250 mg, 0.861 mmol) and methyl piperidine-4-carboxylate (148 mg, 1.033 mmol) in DCE (10 mL) was added acetic acid (4.93 µl, 0.086 mmol) and stirred for 30 min at room temperature. Sodium triacetoxyborohydride (182 mg, 0.861 mmol) was added at ice cold temperature and allowed to reach room temperature and stirred for 16 h. The reaction mixture was diluted with DCM (20 mL) and quenched with sat. ammonium chloride solution. The aqueous layer was extracted with DCM (2×10 mL), the combined organic phase was washed with water (20 mL) and dried over $Na_2SO_4$, filtered and the solvents were evaporated under reduced pressure. The resulting residue was purified by flash column chromatography on silica gel (100-200 mesh) eluting with 30-100% ethyl acetate in petroleum ether to afford methyl 1-((5-(1-(tert-butoxycarbonyl)azetidin-3-yl)-3,4-dimethylpyridin-2-yl)methyl)piperidine-4-carboxylate (200 mg, 55.6% yield) as a brown semi-solid. LCMS method 3, LCMS (ESI, m/z): 418.2 [M+H].

Synthesis of methyl 1-((6-(1-(tert-butoxycarbonyl) azetidin-3-yl)-4,5-dimethylpyridin-3-yl)methyl)piperidine-4-carboxylate

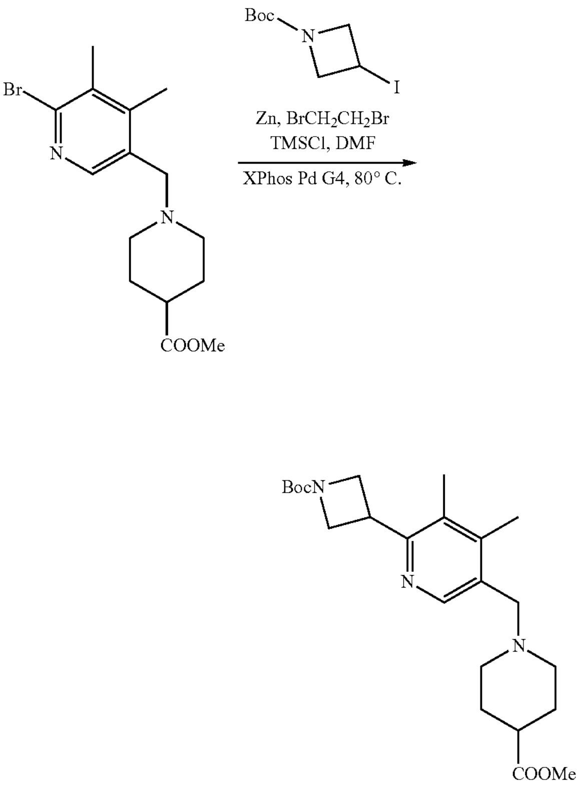

To a suspension of activated zinc (1533 mg, 23.44 mmol) in anhydrous DMF (15 mL) was added 1,2-dibromoethane (0.020 mL, 0.234 mmol) and the mixture was heated to 75° C. After 15 min, the reaction mixture was cooled to room temperature, trimethylsilyl chloride (0.030 mL, 0.234 mmol) was added and allowed to stir at ambient temperature for additional 30 min. Then a solution of tert-butyl 3-iodoazetidine-1-carboxylate (2655 mg, 9.38 mmol) in 5 mL of anhydrous DMF was added and stirred at room temperature for another 30 min, followed by addition of methyl 1-((6-bromo-4,5-dimethylpyridin-3-yl)methyl)piperidine-4-carboxylate (800 mg, 2.344 mmol) and XPhos Pd G4 (202 mg, 0.234 mmol) in 5 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((6-(1-(tert-butoxycarbonyl)azetidin-3-yl)-4,5-dimethylpyridin-3-yl)methyl)piperidine-4-carboxylate (0.85 g, 87% yield) as a colorless semi-solid. LCMS method 4, LCMS (ESI, m/z): 418.2 $[M+H]^+$.

Synthesis of methyl 1-((5-(1-(tert-butoxycarbonyl) azetidin-3-yl)-3,6-dimethylpyridin-2-yl)methyl)piperidine-4-carboxylate

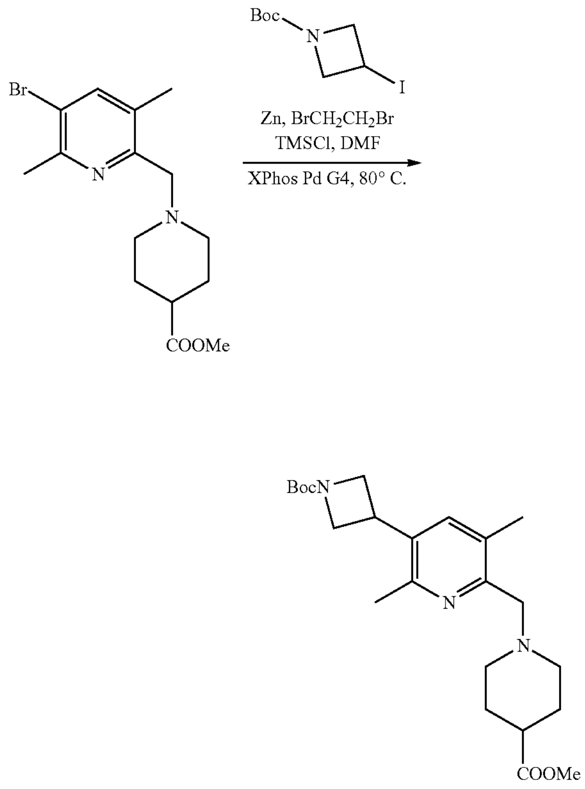

To a suspension of activated zinc (1437 mg, 21.98 mmol) in anhydrous DMF (20 mL) was added 1,2-dibromoethane (0.095 ml, 1.099 mmol) and the mixture was heated to 75° C. After 15 min, the reaction mixture was cooled to room temperature, trimethylsilyl chloride (0.285 mL, 2.229 mmol) was added and allowed to stir at ambient temperature for additional 30 min. Then a solution of tert-butyl 3-iodoazetidine-1-carboxylate (1867 mg, 6.59 mmol) in 5 mL of anhydrous DMF was added and stirred at room temperature for another 30 min, followed by addition of methyl 1-((5-bromo-3,6-dimethylpyridin-2-yl)methyl)piperidine-4-carboxylate (750 mg, 2.198 mmol) and XPhos Pd G4 (284 mg, 0.330 mmol) in 5 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((5-(1-(tert-butoxycarbonyl)azetidin-3-yl)-3,6-dimethylpyridin-2-yl)methyl)piperidine-4-carboxylate (850 mg, 92% yield) as a colorless semi-solid. LCMS method 1, LCMS (ESI, m/z): 418.5 $[M+H]^+$.

Synthesis of methyl 1-((6-(1-(tert-butoxycarbonyl) azetidin-3-yl)-2,5-dimethylpyridin-3-yl)methyl)piperidine-4-carboxylate

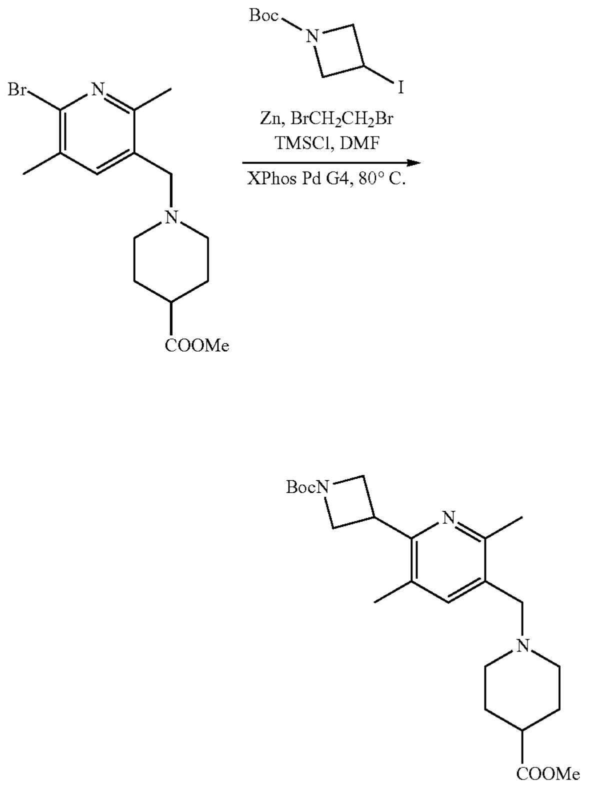

To a suspension of activated zinc (1322 mg, 20.22 mmol) in anhydrous DMF (20 mL) was added 1,2-dibromoethane (0.017 mL, 0.202 mmol) and the mixture was heated to 75° C. After 15 min, the reaction mixture was cooled to room temperature, trimethylsilyl chloride (0.026 mL, 0.202 mmol) was added and allowed to stir at ambient temperature for additional 30 min. Then a solution of tert-butyl 3-iodoazetidine-1-carboxylate (2290 mg, 8.09 mmol) in 5 mL of anhydrous DMF was added and stirred at room temperature for another 30 min, followed by addition of methyl 1-((6-bromo-2,5-dimethylpyridin-3-yl)methyl)piperidine-4-carboxylate (690 mg, 2.022 mmol) and XPhos Pd G4 (174 mg, 0.202 mmol) in 5 mL of DMF. The reaction mixture was allowed to stir at 80° C. for 2 h. After completion of the reaction, mixture was cooled to ambient temperature and quenched with sat. ammonium chloride solution. The crude was filtered through a pad of celite and washed with ethyl acetate. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-100% ethyl acetate in petroleum ether to afford methyl 1-((6-(1-(tert-butoxycarbonyl)azetidin-3-yl)-2,5-dimethylpyridin-3-yl)methyl)piperidine-4-carboxylate (420 mg, 49.7% yield) as a pale yellow semi-solid. LCMS method 3, LCMS (ESI, m/z): 418.2 $[M+H]^+$.

Synthesis of methyl 1-((5-(1-(tert-butoxycarbonyl)azetidin-3-yl)-4,6-dimethylpyridin-2-yl)methyl)piperidine-4-carboxylate

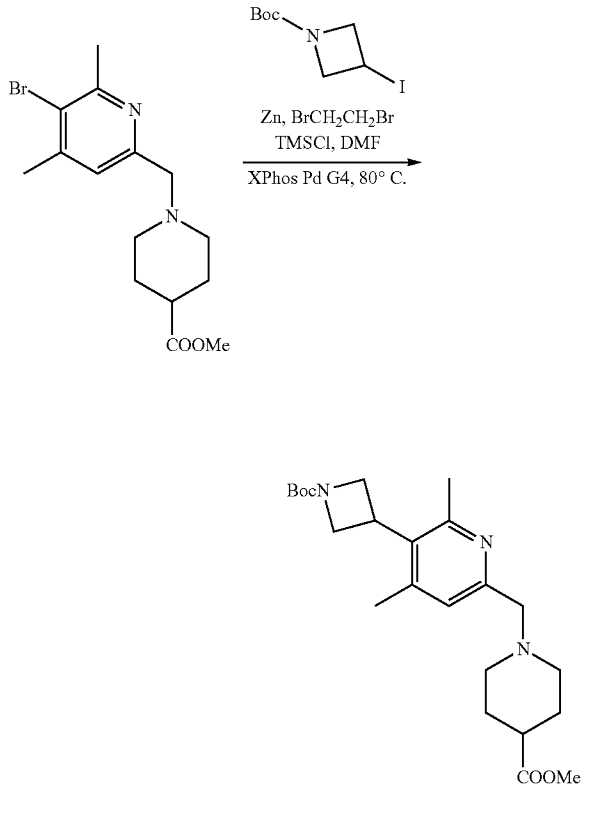

To a suspension of activated zinc (1.533 g, 23.44 mmol) in anhydrous DMF (10 mL) was added 1,2-dibromoethane (0.020 mL, 0.234 mmol) and the mixture was heated to 75° C. After 15 min, the reaction mixture was cooled to room temperature, trimethylsilyl chloride (0.030 mL, 0.234 mmol) was added and allowed to stir at ambient temperature for additional 30 min. Then a solution of tert-butyl 3-iodoazetidine-1-carboxylate (2.65 g, 9.38 mmol) in 2 mL of anhydrous DMF was added and stirred at room temperature for another 30 min, followed by addition of methyl 1-((5-bromo-4,6-dimethylpyridin-2-yl)methyl)piperidine-4-carboxylate (0.8 g, 2.344 mmol) and XPhos Pd G4 (0.202 g, 0.234 mmol) in 3 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-100% ethyl acetate in petroleum ether to afford methyl 1-((5-(1-(tert-butoxycarbonyl)azetidin-3-yl)-4,6-dimethylpyridin-2-yl)methyl)piperidine-4-carboxylate (0.7 g, 71.5% yield) as a yellow semi-solid. LCMS method 1, LCMS (ESI, m/z): 418.2 $[M+H]^+$.

Synthesis of methyl 1-((5-(azetidin-3-yl)-3-methylpyridin-2-yl)methyl)piperidine-4-carboxylate, TFA salt

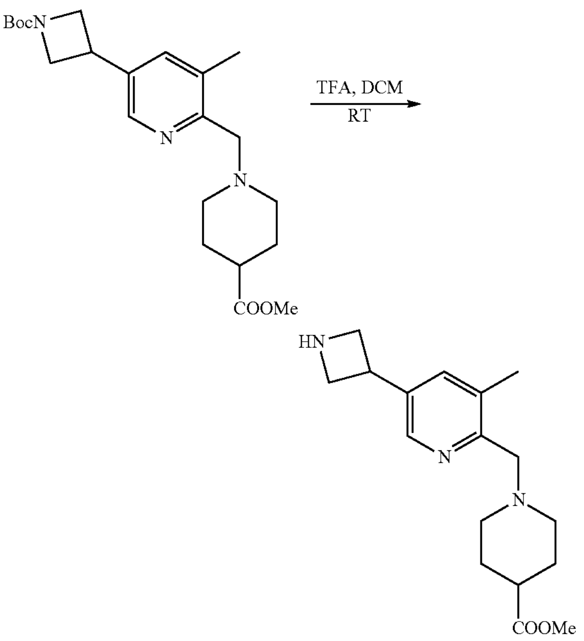

To a stirred solution of methyl 1-((5-(1-(tert-butoxycarbonyl)azetidin-3-yl)-3-methylpyridin-2-yl)methyl)piperidine-4-carboxylate (1.5 g, 3.72 mmol) in anhydrous DCM (20 mL) was added TFA (1.422 mL, 18.59 mmol) at 0° C. Then the reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-((5-(azetidin-3-yl)-3-methylpyridin-2-yl)methyl)piperidine-4-carboxylate, TFA salt (1.35 g, 2.391 mmol, 64.3% yield) as a light brown semi-solid. LCMS method 1, LCMS (ESI, m/z): 304.3 $[M+H]^+$.

Synthesis of methyl 1-((5-(azetidin-3-yl)-4-methylpyridin-2-yl)methyl)piperidine-4-carboxylate, TFA salt

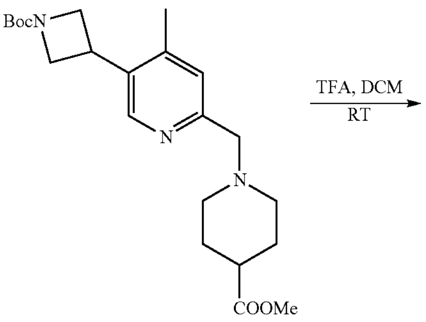

-continued

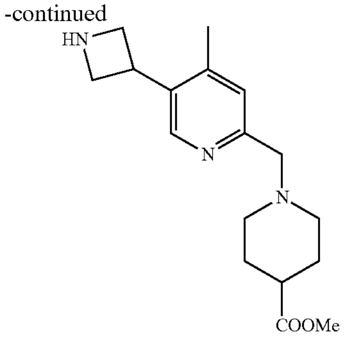

To a stirred solution of methyl 1-((5-(1-(tert-butoxycarbonyl)azetidin-3-yl)-4-methylpyridin-2-yl)methyl)piperidine-4-carboxylate (1.5 g, 3.72 mmol) in anhydrous DCM (20 mL) was added TFA (1.422 mL, 18.59 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-((5-(azetidin-3-yl)-3-methylpyridin-2-yl)methyl)piperidine-4-carboxylate, TFA salt (1.35 g, 90% yield) as a light brown semi-solid. LCMS method 1, LCMS (ESI, m/z): 304.2 [M+H]$^+$.

Synthesis of methyl 1-((6-(azetidin-3-yl)-4-methylpyridin-3-yl)methyl)piperidine-4-carboxylate, TFA salt

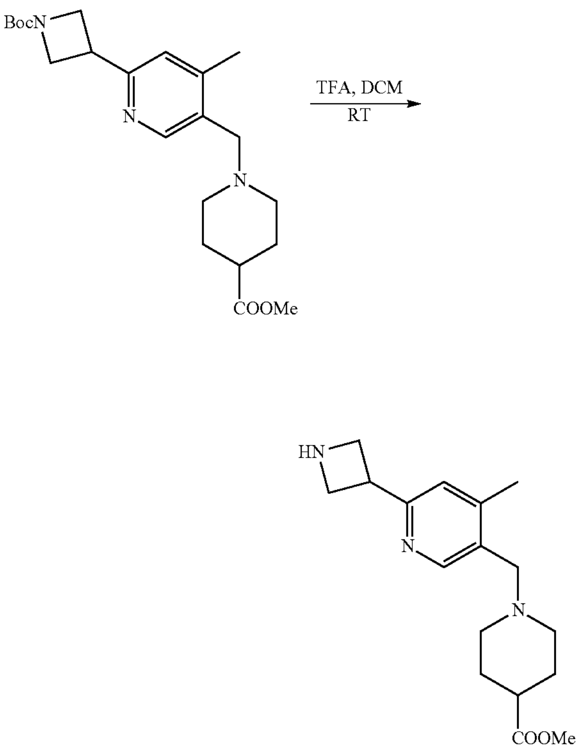

To a stirred solution of methyl 1-((6-(1-(tert-butoxycarbonyl)azetidin-3-yl)-4-methylpyridin-3-yl)methyl)piperidine-4-carboxylate (0.9 g, 2.230 mmol) in anhydrous DCM (20 mL) was added TFA (1.031 mL, 13.38 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-((6-(azetidin-3-yl)-4-methylpyridin-3-yl)methyl)piperidine-4-carboxylate, TFA salt (0.9 g, 96% yield) as a brown semi-solid. LCMS method 2, LCMS (ESI, m/z): 304.2 [M+H]$^+$.

Synthesis of methyl 1-((6-(azetidin-3-yl)-5-methylpyridin-3-yl)methyl)piperidine-4-carboxylate, TFA salt

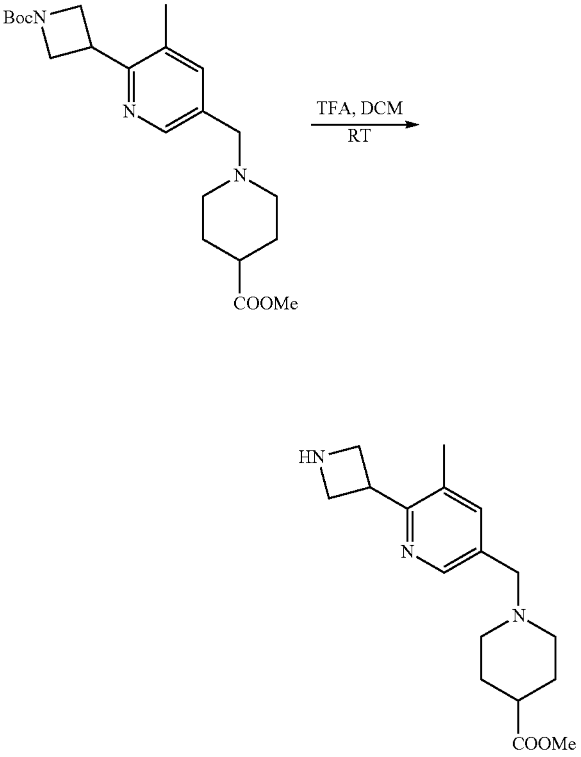

To a stirred solution of methyl 1-((6-(1-(tert-butoxycarbonyl)azetidin-3-yl)-5-methylpyridin-3-yl)methyl)piperidine-4-carboxylate (1.1 g, 2.73 mmol) in anhydrous DCM (10 mL) was added TFA (1.043 mL, 13.63 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-((6-(azetidin-3-yl)-5-methylpyridin-3-yl)methyl)piperidine-4-carboxylate, TFA salt (0.9 g, 0.755 mmol, 79% yield) as a brown semi-solid. LCMS method 2, LCMS (ESI, m/z): 304.2 [M+H]$^+$.

Synthesis of methyl 1-((5-(azetidin-3-yl)-3,4-dimethylpyridin-2-yl)methyl)piperidine-4-carboxylate, TFA salt

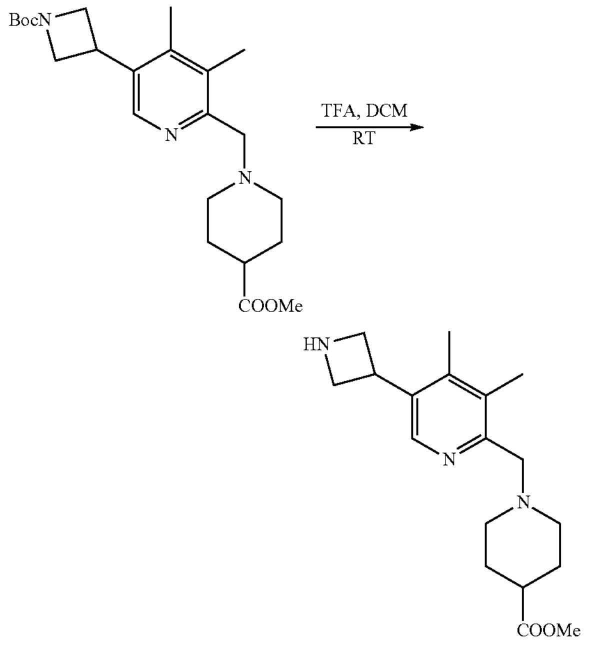

To a stirred solution of methyl 1-((5-(1-(tert-butoxycarbonyl)azetidin-3-yl)-3,4-dimethylpyridin-2-yl)methyl)piperidine-4-carboxylate (200 mg, 0.479 mmol) in anhydrous DCM (3 mL) was added TFA (0.367 mL, 4.79 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-((5-(azetidin-3-yl)-3,4-dimethylpyridin-2-yl)methyl)piperidine-4-carboxylate, TFA salt (180 mg, 87% yield) as a brown semi-solid. LCMS method 1, LCMS (ESI, m/z): 318.3 [M+H]$^+$.

Synthesis of methyl 1-((6-(azetidin-3-yl)-4,5-dimethylpyridin-3-yl)methyl)piperidine-4-carboxylate, TFA salt

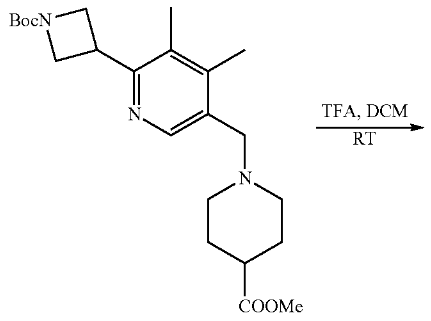

-continued

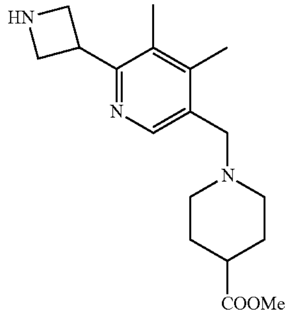

To a stirred solution of methyl 1-((6-(1-(tert-butoxycarbonyl)azetidin-3-yl)-4,5-dimethylpyridin-3-yl)methyl)piperidine-4-carboxylate (800 mg, 1.916 mmol) in anhydrous DCM (10 mL) was added TFA (0.148 mL, 1.916 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-((6-(azetidin-3-yl)-4,5-dimethylpyridin-3-yl)methyl)piperidine-4-carboxylate, TFA salt (300 mg, 36.3% yield) as a brown semi-solid. LCMS method 1, LCMS (ESI, m/z): 318.3 [M+H]$^+$.

Synthesis of methyl 1-((5-(azetidin-3-yl)-3,6-dimethylpyridin-2-yl)methyl)piperidine-4-carboxylate, TFA salt

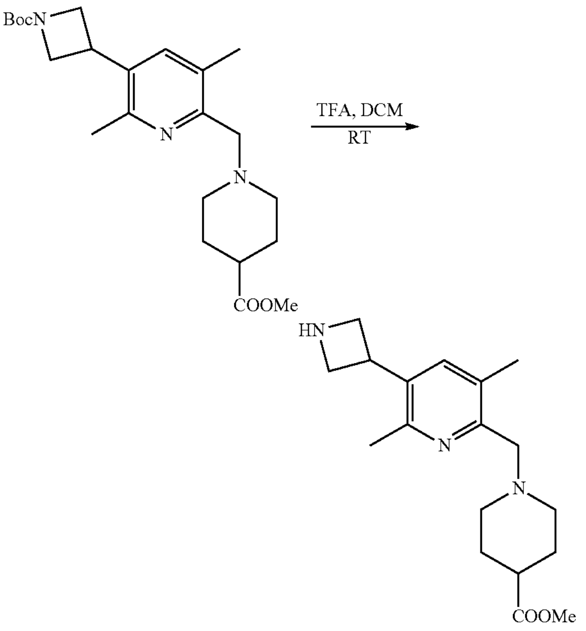

To a stirred solution of methyl 1-((5-(1-(tert-butoxycarbonyl)azetidin-3-yl)-3,6-dimethylpyridin-2-yl)methyl)piperidine-4-carboxylate (850 mg, 2.036 mmol) in anhydrous DCM (10 mL) was added TFA (2.0 mL, 26.0 mmol) at 0° C. Then reaction mixture was stirred at ambient temperature and the progress of the reaction monitored by TLC. After 3 h, TLC analysis indicated complete conversion of the starting material. The reaction mixture was concentrated under reduced pressure and the resulting residue was triturated with diethyl ether to afford methyl 1-((5-(azetidin-3-yl)-3,6-dimethylpyridin-2-yl)methyl)piperidine-4-carboxylate, TFA salt (871 g, 1.020 mmol, 99% yield) as a brown semi-solid. LCMS method 3, LCMS (ESI, m/z): 318.2 [M+2H]+.

Synthesis of methyl 1-((6-(azetidin-3-yl)-2,5-dimethylpyridin-3-yl)methyl)piperidine-4-carboxylate, TFA salt

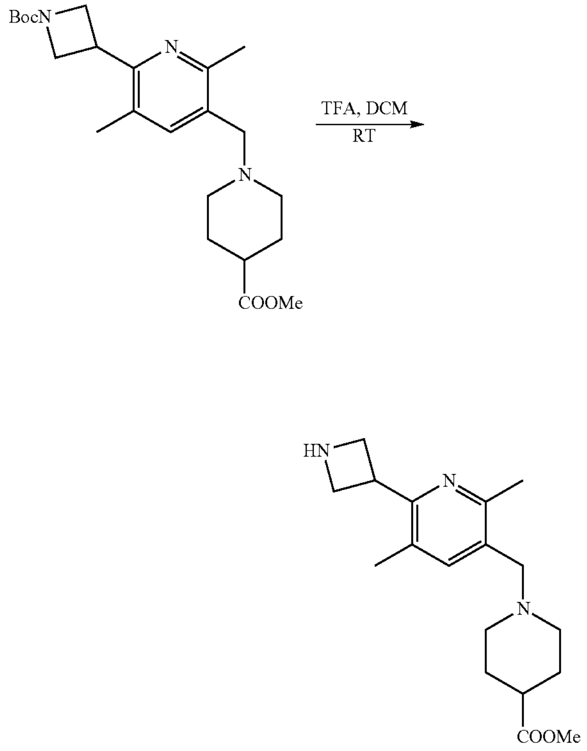

To a stirred solution of methyl 1-((6-(1-(tert-butoxycarbonyl)azetidin-3-yl)-2,5-dimethylpyridin-3-yl)methyl)piperidine-4-carboxylate (500 mg, 1.197 mmol) in anhydrous DCM (10 mL) was added TFA (2.0 mL, 26.0 mmol) at 0° C. Then reaction mixture was stirred at ambient temperature and the progress of the reaction monitored by TLC. After 3 h, TLC analysis indicated complete conversion of the starting material. The reaction mixture was concentrated under reduced pressure and the resulting residue was triturated with diethyl ether to afford methyl 1-((6-(azetidin-3-yl)-2,5-dimethylpyridin-3-yl)methyl)piperidine-4-carboxylate, TFA salt (500 mg, 96% yield) as a brown semi-solid. LCMS method 3, LCMS (ESI, m/z): 318.2 [M+2H]+.

Synthesis of methyl 1-((5-(azetidin-3-yl)-4,6-dimethylpyridin-2-yl)methyl)piperidine-4-carboxylate, TFA salt

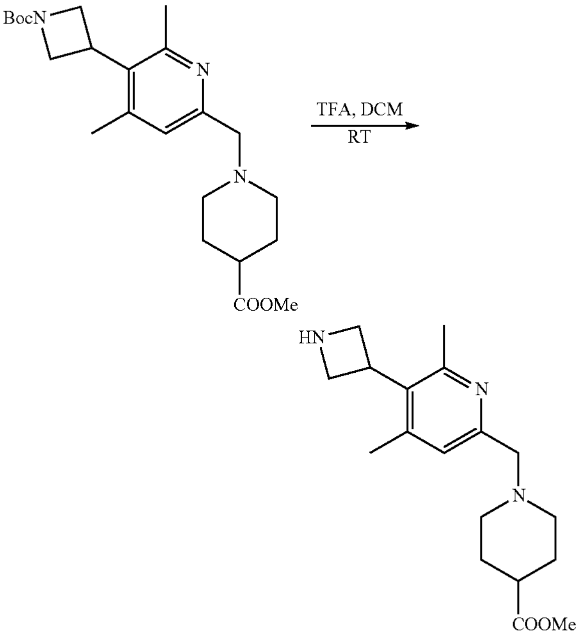

To a stirred solution of methyl 1-((5-(1-(tert-butoxycarbonyl)azetidin-3-yl)-4,6-dimethylpyridin-2-yl)methyl)piperidine-4-carboxylate (0.7 g, 1.676 mmol) in anhydrous DCM (10 mL) was added TFA (0.387 mL, 5.03 mmol) at 0° C. Then reaction mixture was stirred at ambient temperature and the progress of the reaction monitored by TLC. After 3 h, TLC analysis indicated complete conversion of the starting material. The reaction mixture was concentrated under reduced pressure and the resulting residue was triturated with diethyl ether to afford methyl 1-((5-(azetidin-3-yl)-4,6-dimethylpyridin-2-yl)methyl)piperidine-4-carboxylate, TFA salt (0.7 g, 1.622 mmol, 97% yield) as a yellow semi-solid. LCMS method 1, LCMS (ESI, m/z): 318.3 [M+2H]+.

Synthesis of methyl 1-((5-(1-(2,6-dichlorophenyl)azetidin-3-yl)-3-methylpyridin-2-yl)methyl)piperidine-4-carboxylate

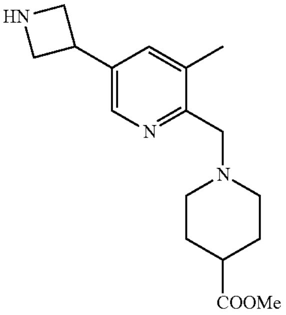

+

-continued

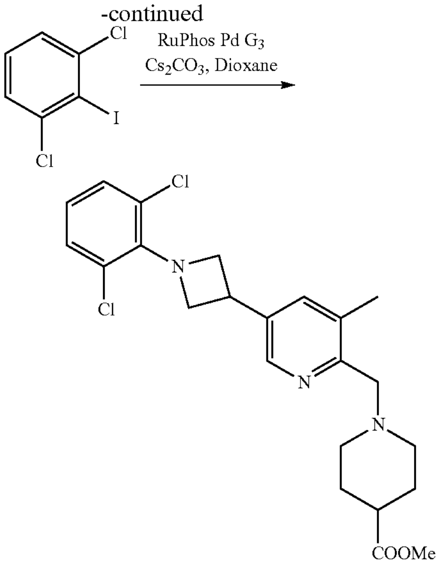

To a solution of methyl 1-((5-(azetidin-3-yl)-3-methylpyridin-2-yl)methyl)piperidine-4-carboxylate, TFA (500 mg, 1.198 mmol) and 1,3-dichloro-2-iodobenzene (490 mg, 1.797 mmol) in anhydrous 1,4 dioxane (10 mL) was added cesium carbonate (1171 mg, 3.59 mmol). The reaction mixture was then degassed with nitrogen for 10 min followed by addition of RuPhos Pd G3 (100 mg, 0.120 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-((5-(1-(2,6-dichlorophenyl)azetidin-3-yl)-3-methylpyridin-2-yl)methyl)piperidine-4-carboxylate (210 mg, 0.378 mmol, 31.6% yield) as a brown liquid. LCMS method 3, LCMS (ESI, m/z): 448.2 $[M+H]^+$.

Synthesis of methyl 1-((5-(1-(2,6-dichlorophenyl)azetidin-3-yl)-4-methylpyridin-2-yl)methyl)piperidine-4-carboxylate

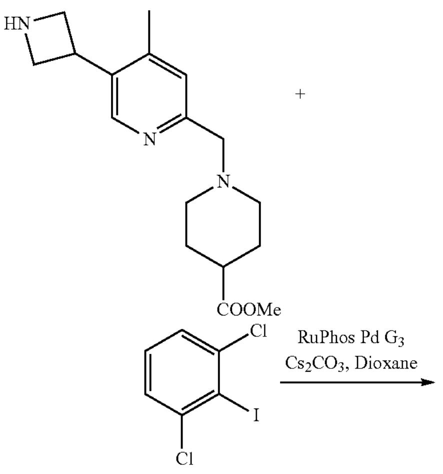

-continued

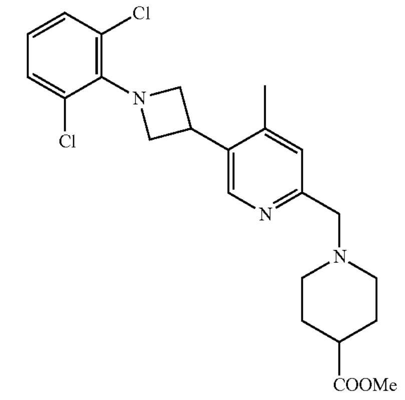

To a solution of methyl 1-((5-(azetidin-3-yl)-4-methylpyridin-2-yl)methyl)piperidine-4-carboxylate, TFA (500 mg, 1.198 mmol) and 1,3-dichloro-2-iodobenzene (490 mg, 1.797 mmol) in anhydrous 1,4 dioxane (10 mL) was added cesium carbonate (1171 mg, 3.59 mmol). The reaction mixture was then degassed with nitrogen for 10 min followed by addition of RuPhos Pd G3 (100 mg, 0.120 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-((5-(1-(2,6-dichlorophenyl)azetidin-3-yl)-4-methylpyridin-2-yl)methyl)piperidine-4-carboxylate (160 mg, 0.225 mmol, 35% yield) as a brown liquid. LCMS method 3, LCMS (ESI, m/z): 448.1 $[M+H]^+$.

Synthesis of methyl 1-((6-(1-(2,6-dichlorophenyl)azetidin-3-yl)-4-methylpyridin-3-yl)methyl)piperidine-4-carboxylate

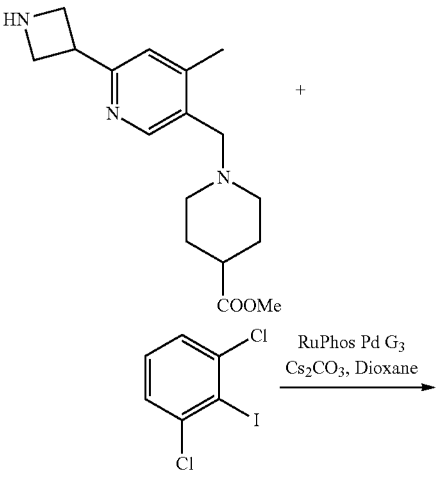

-continued

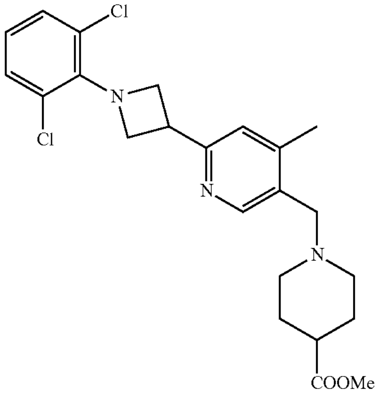

To a solution of methyl 1-((6-(azetidin-3-yl)-4-methylpyridin-3-yl)methyl)piperidine-4-carboxylate, TFA (500 mg, 1.198 mmol) and 1,3-dichloro-2-iodobenzene (392 mg, 1.437 mmol) in anhydrous 1,4 dioxane (10 mL) was added cesium carbonate (1366 mg, 4.19 mmol). The reaction mixture was then degassed with nitrogen for 10 min followed by addition of RuPhos Pd G3 (100 mg, 0.120 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-((6-(1-(2,6-dichlorophenyl)azetidin-3-yl)-4-methylpyridin-3-yl)methyl)piperidine-4-carboxylate (180 mg, 32% yield) as a yellow semi-solid. LCMS method 1, LCMS (ESI, m/z): 448.2 $[M+H]^+$.

Synthesis of methyl 1-((6-(1-(2,6-dichlorophenyl)azetidin-3-yl)-5-methylpyridin-3-yl)methyl)piperidine-4-carboxylate

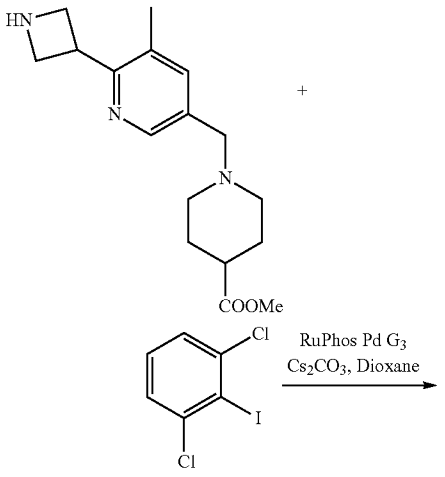

-continued

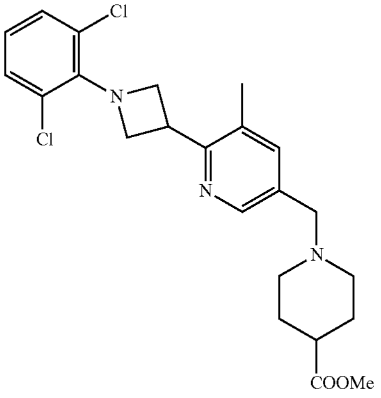

To a solution of methyl 1-((5-(azetidin-3-yl)-4-methylpyridin-2-yl)methyl)piperidine-4-carboxylate, TFA (500 mg, 1.198 mmol) and 1,3-dichloro-2-iodobenzene (490 mg, 1.797 mmol) in anhydrous 1,4 dioxane (10 mL) was added cesium carbonate (1171 mg, 3.59 mmol). The reaction mixture was then degassed with nitrogen for 10 min followed by addition of RuPhos Pd G3 (100 mg, 0.120 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-((6-(1-(2,6-dichlorophenyl)azetidin-3-yl)-5-methylpyridin-3-yl)methyl)piperidine-4-carboxylate (180 mg, 0.399 mmol, 34% yield) as a brown liquid. LCMS method 1, LCMS (ESI, m/z): 448.2 $[M+H]^+$.

Synthesis of methyl 1-((5-(1-(2,6-dichlorophenyl)azetidin-3-yl)-3,4-dimethylpyridin-2-yl)methyl)piperidine-4-carboxylate

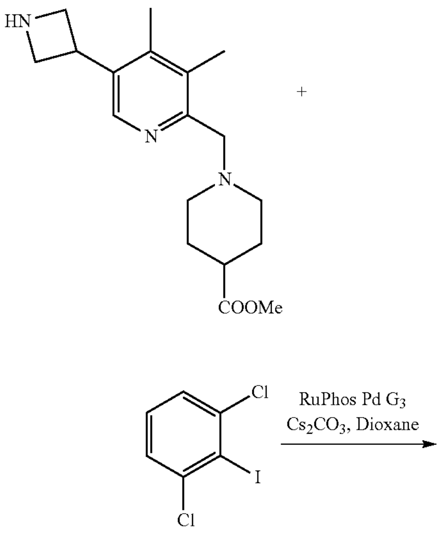

-continued

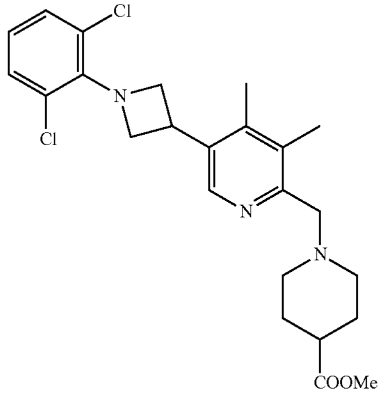

To a solution of methyl 1-((5-(azetidin-3-yl)-3,4-dimethylpyridin-2-yl)methyl)piperidine-4-carboxylate, TFA (114 mg, 0.275 mmol) and 1,3-dichloro-2-iodobenzene (83 mg, 0.302 mmol) in anhydrous 1,4 dioxane (5 mL) was added cesium carbonate (269 mg, 0.825 mmol). The reaction mixture was then degassed with nitrogen for 10 min followed by addition of RuPhos-Pd-G3 (23.00 mg, 0.027 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-100% ethyl acetate in petroleum ether to afford methyl 1-((5-(1-(2,6-dichlorophenyl)azetidin-3-yl)-3,4-dimethylpyridin-2-yl)methyl)piperidine-4-carboxylate (180 mg, 39% yield) as a brown liquid. LCMS method 3, LCMS (ESI, m/z): 462.2 $[M+H]^+$.

Synthesis of methyl 1-((6-(1-(2,6-dichlorophenyl)azetidin-3-yl)-4,5-dimethylpyridin-3-yl)methyl)piperidine-4-carboxylate

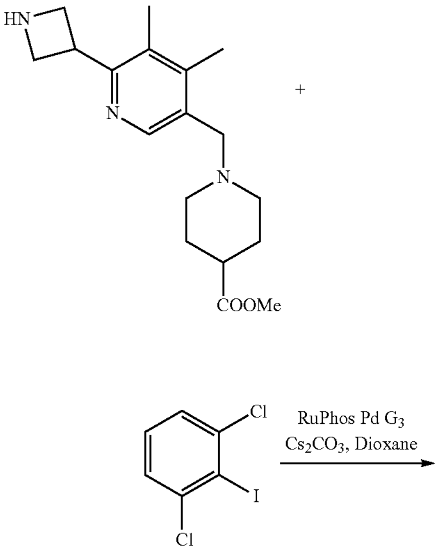

-continued

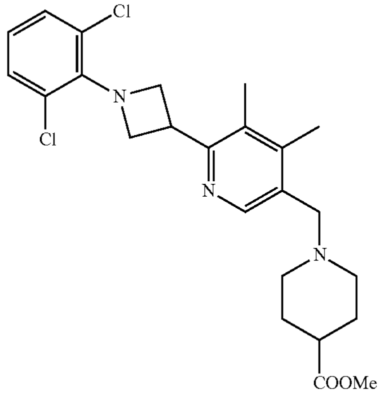

To a solution of methyl 1-((6-(azetidin-3-yl)-4,5-dimethylpyridin-3-yl)methyl)piperidine-4-carboxylate, TFA (280 mg, 0.649 mmol) and 1,3-dichloro-2-iodobenzene (177 mg, 0.649 mmol) in anhydrous 1,4 dioxane (5 mL) was added cesium carbonate (634 mg, 1.947 mmol). The reaction mixture was then degassed with nitrogen for 10 min followed by addition of XphosPdG4 (55.8 mg, 0.065 mmol) and heating to 100° C. After 16 h, TLC analysis indicated complete conversion of the starting material. The reaction mixture was then cooled to room temperature and filtered through a pad of celite and washed with EtOAc. The filtrate was concentrated under reduced pressure to yield crude methyl 1-((6-(1-(2,6-dichlorophenyl)azetidin-3-yl)-4,5-dimethylpyridin-3-yl)methyl)piperidine-4-carboxylate (220 mg, 17.5% yield, 24% pure) as a brown liquid which was used in the next step without further purification. LCMS method 4, LCMS (ESI, m/z): 463.2 $[M+2H]^+$.

Synthesis of methyl 1-((5-(1-(2,6-dichlorophenyl)azetidin-3-yl)-3,6-dimethylpyridin-2-yl)methyl)piperidine-4-carboxylate

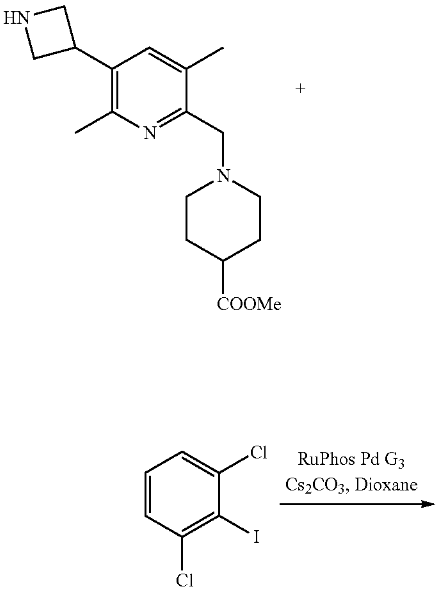

-continued

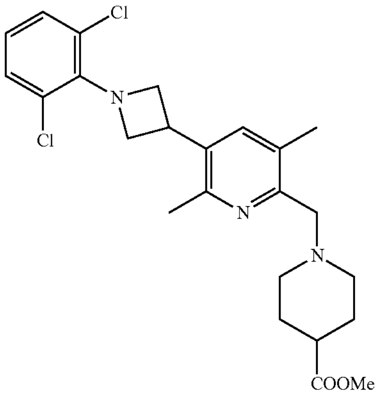

To a solution of methyl 1-((5-(azetidin-3-yl)-3,6-dimethylpyridin-2-yl)methyl)-piperidine-4-carboxylate, TFA (500 mg, 1.159 mmol) and 1,3-dichloro-2-iodobenzene (379 mg, 1.391 mmol) in anhydrous 1,4 dioxane (5 mL) was added cesium carbonate (3.48 mmol). The reaction mixture was then degassed with nitrogen for 10 min followed by addition of Ruphos pd G3 (97 mg, 0.116 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (100-200 mesh) eluting with 0-100% ethyl acetate in petroleum ether to afford methyl 1-((5-(1-(2,6-dichlorophenyl)azetidin-3-yl)-3,6-dimethylpyridin-2-yl)methyl)-piperidine-4-carboxylate (200 mg, 38% yield) as a yellow semi-solid. LCMS method 2, LCMS (ESI, m/z): 463.2 $[M+2H]^+$.

Synthesis of methyl 1-((6-(1-(2,6-dichlorophenyl)azetidin-3-yl)-2,5-dimethylpyridin-3-yl)methyl)piperidine-4-carboxylate

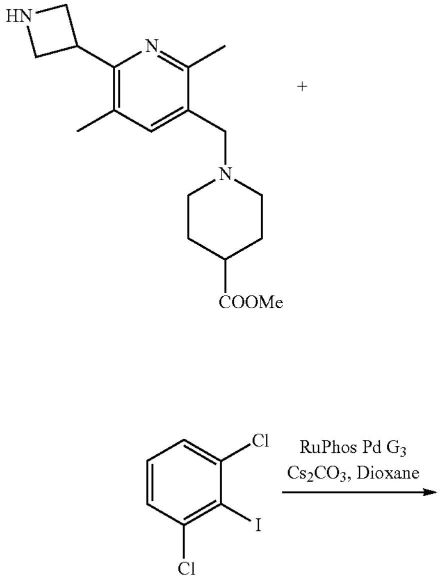

-continued

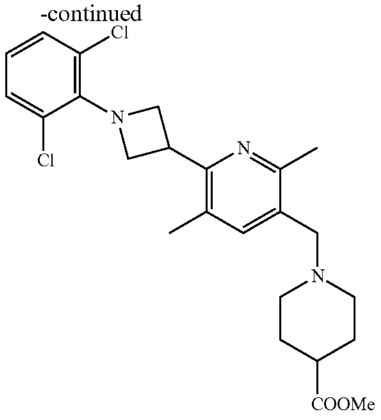

To a solution of methyl 1-((6-(azetidin-3-yl)-2,5-dimethylpyridin-3-yl)methyl)piperidine-4-carboxylate, TFA (450.0 mg, 1.043 mmol) and 1,3-dichloro-2-iodobenzene (342 mg, 1.252 mmol) in anhydrous 1,4 dioxane (5 mL) was added cesium carbonate (3.13 mmol). The reaction mixture was then degassed with nitrogen for 10 min followed by addition of Ruphos pd G3 (87 mg, 0.104 mmol) and heating to 100° C. After 12 h, TLC analysis indicated complete conversion of the starting material. The filtrate was concentrated under reduced pressure and the resulting residue was purified by flash column chromatography on silica gel (230-400 mesh) eluting with 0-100% ethyl acetate in petroleum ether to afford methyl 1-((6-(1-(2,6-dichlorophenyl)azetidin-3-yl)-2,5-dimethylpyridin-3-yl)methyl)piperidine-4-carboxylate (140 mg, 30% yield) as a yellow semi-solid. LCMS method 1, LCMS (ESI, m/z): 462.3 $[M+H]^+$.

Synthesis of methyl 1-((5-(1-(2,6-dichlorophenyl)azetidin-3-yl)-4,6-dimethylpyridin-2-yl)methyl)piperidine-4-carboxylate

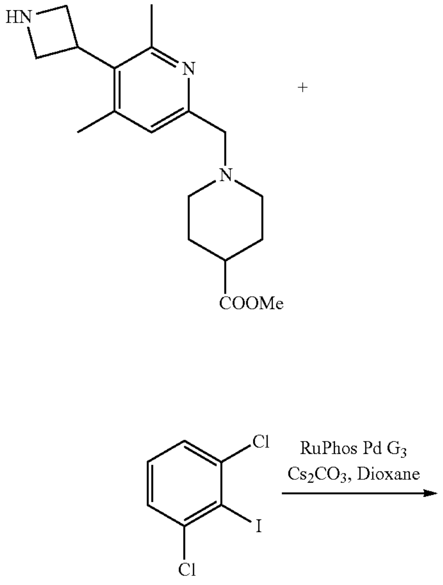

-continued

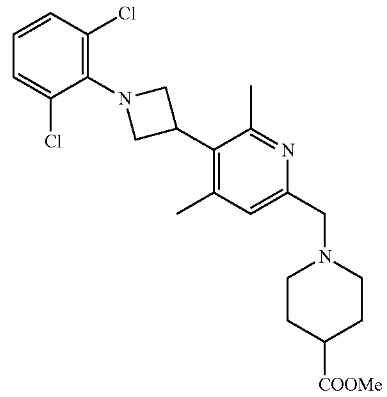

-continued

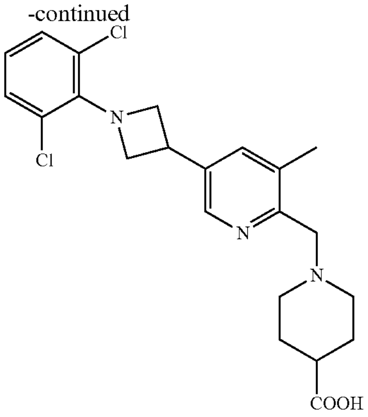

76

To a solution of methyl 1-((5-(azetidin-3-yl)-4,6-dimethylpyridin-2-yl)methyl)piperidine-4-carboxylate, TFA (360 mg, 0.834 mmol) and 1,3-dichloro-2-iodobenzene (228 mg, 0.834 mmol) in anhydrous 1,4 dioxane (5 mL) was added cesium carbonate (816 mg, 2.503 mmol). The reaction mixture was then degassed with nitrogen for 10 min followed by addition of Ruphos pd G3 (69.8 mg, 0.083 mmol) and heating to 100° C. After 12 h, TLC analysis indicated complete conversion of the starting material. The filtrate was concentrated under reduced pressure and the resulting residue was purified by flash column chromatography on silica gel (230-400 mesh) eluting with 0-100% ethyl acetate in petroleum ether to afford methyl 1-((5-(1-(2,6-dichlorophenyl)azetidin-3-yl)-4,6-dimethyl-pyridin-2-yl)methyl)piperidine-4-carboxylate (180 mg, 46% yield) as a yellow semi-solid. LCMS method 3, LCMS (ESI, m/z): 461.8 $[M+H]^+$.

Example S76. 1-((5-(1-(2,6-dichlorophenyl)azetidin-3-yl)-3-methylpyridin-2-yl)methyl)-piperidine-4-carboxylic acid (76)

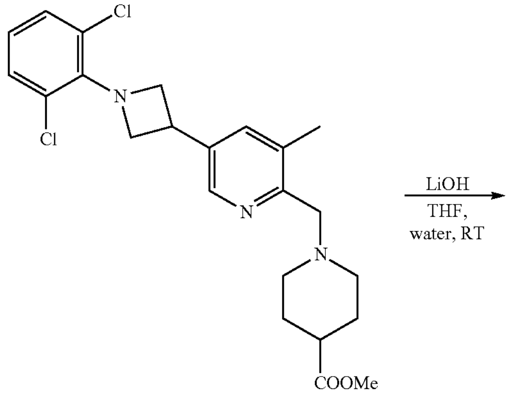

To a solution of methyl 1-((5-(1-(2,6-dichlorophenyl)azetidin-3-yl)-3-methylpyridin-2-yl)methyl)piperidine-4-carboxylate (200 mg, 0.446 mmol) in THF (4 mL) and water (1 mL) was added LiOH (56.1 mg, 1.338 mmol). The resulting mixture was allowed to stir at ambient temperature and the progress of the reaction was monitored by TLC analysis. After completion of the reaction, the mixture was concentrated under reduced pressure and the residue was dissolved in water and acidified with acetic acid. The mixture was then concentrated under reduced pressure and the resulting residue was purified by prep. HPLC, prep. HPLC method: Diluent: THF:Water:ACN (50:10:40), Column-1: Sunfire C18 (150×19) mm, 5 micron, Mobile phase A: 0.1% Formic acid in water, Mobile phase B: Acetonitrile. The required fractions were collected and lyophilized to afford 1-((5-(1-(2,6-dichlorophenyl)azetidin-3-yl)-3-methylpyridin-2-yl)methyl)piperidine-4-carboxylic acid, formic acid salt (50 mg, 0.103 mmol, 23.12% yield, 99% purity) as a white solid. $^1H$ NMR (400 MHz, DMSO-$d_6$): δ 12.17 (bs, 1H), 8.28 (d, J=2.40 Hz, 1H), 7.71 (d, J=2.00 Hz, 1H), 7.25 (d, J=7.60 Hz, 2H), 6.76 (t, J=7.60 Hz, 1H), 4.82 (t, J=8.40 Hz, 2H), 4.38 (t, J=7.02 Hz, 2H), 3.79-3.74 (m, 1H), 3.54 (s, 2H), 2.72 (d, J=11.20 Hz, 2H), 2.38 (s, 3H), 2.17-2.15 (m, 1H), 2.04 (t, J=9.60 Hz, 2H), 1.75 (d, J=13.20 Hz, 2H), 1.51-1.45 (m, 2H). LCMS method 1; LCMS (ESI, m/z): 434.2 $[M+H]^+$.

Example S77. 1-((5-(1-(2,6-dichlorophenyl)azetidin-3-yl)-4-methylpyridin-2-yl)methyl)-piperidine-4-carboxylic acid (77)

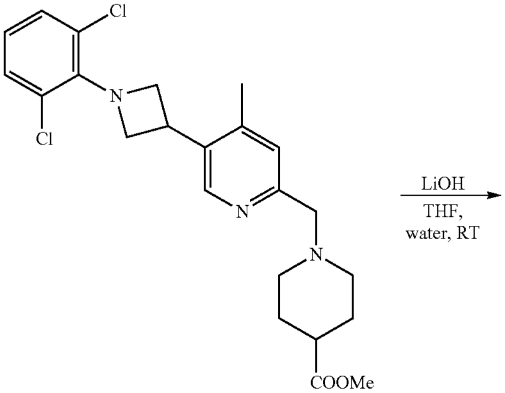

-continued

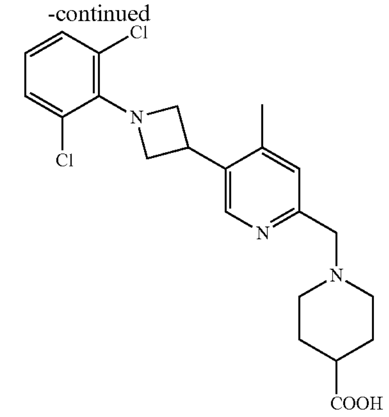

77

To a solution of methyl 1-((5-(1-(2,6-dichlorophenyl)azetidin-3-yl)-4-methylpyridin-2-yl)methyl)piperidine-4-carboxylate (160 mg, 0.357 mmol) in THF (4 mL) and water (1 mL) was added LiOH (44.9 mg, 1.071 mmol). The resulting mixture was allowed to stir at ambient temperature and the progress of the reaction was monitored by TLC analysis. After completion of the reaction, the mixture was concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column-1: Luna C18 (250×21.2) mm, 10 micron, Mobile phase A: 10 mM Ammonium acetate in water Mobile phase B: Acetonitrile. The required fractions were collected and lyophilized to afford 1-((5-(1-(2,6-dichlorophenyl)azetidin-3-yl)-4-methylpyridin-2-yl)methyl)piperidine-4-carboxylic acid, acetate salt (32 mg, 0.063 mmol, 17.70% yield, 97.3% purity) as a white solid. $^1$H NMR (400 MHz, DMSO-$d_6$): δ 8.46 (s, 1H), 7.25-7.23 (m, 3H), 6.76 (t, J=8.00 Hz, 1H), 4.87 (t, J=8.00 Hz, 2H), 4.42 (t, J=8.00 Hz, 2H), 3.98-3.94 (m, 1H), 3.49 (s, 2H), 2.72 (d, J=12.00 Hz, 2H), 2.24 (s, 3H), 2.15 (m, 1H), 2.03 (t, J=10.00 Hz, 2H), 1.77 (d, J=10.80 Hz, 2H), 1.51-1.53 (m, 2H). LCMS method 1; LCMS (ESI, m/z): 434.0 $[M+H]^+$.

Example S78. 1-((6-(1-(2,6-dichlorophenyl)azetidin-3-yl)-4-methylpyridin-3-yl)methyl)-piperidine-4-carboxylic acid (78)

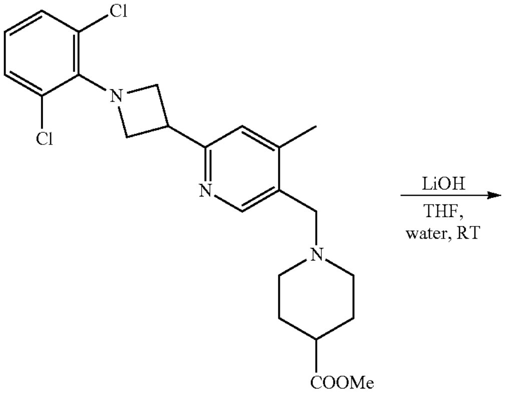

-continued

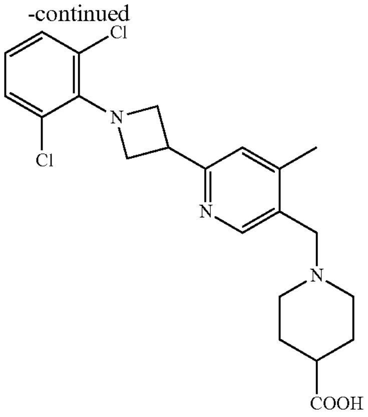

78

To a solution of methyl 1-((6-(1-(2,6-dichlorophenyl)azetidin-3-yl)-4-methylpyridin-3-yl)methyl)piperidine-4-carboxylate (180 mg, 0.401 mmol) in THF (4 mL) and water (1 mL) was added LiOH (50.5 mg, 1.204 mmol). The resulting mixture was allowed to stir at ambient temperature and the progress of the reaction was monitored by TLC analysis. After completion of the reaction, the mixture was concentrated under reduced pressure and the residue was dissolved in water and acidified with acetic acid. The mixture was then concentrated under reduced pressure and the resulting residue was purified by prep. HPLC, prep. HPLC method: Diluent: THF:Water:ACN (50:10:40), Column: Xbridge C18 (150×19) mm, 5 micron, Mobile phase A: 5 mM Ammonium formate in water, Mobile phase B: Acetonitrile. The required fractions were collected and lyophilized to afford 1-((6-(1-(2,6-dichlorophenyl)azetidin-3-yl)-4-methylpyridin-3-yl)methyl)piperidine-4-carboxylic acid, formic acid salt (40 mg, 0.083 mmol, 20.67% yield, 99.6% purity) as a white solid. $^1$H NMR (400 MHz, MeOD): δ 8.41 (s, 1H), δ 7.39 (s, 1H), δ 7.19-7.17 (d, J=8 Hz, 2H), δ 6.72-6.69 (t, J=7.6 Hz, 1H), δ 4.89-4.87 (m, 2H), δ 4.61-4.57 (m, 2H), δ 3.94-3.90 (m, 1H), δ 3.89-3.86 (m, 2H), δ 3.11-3.08 (m, 2H), δ 2.55-2.48 (m, 5H), δ 2.40-2.34 (m, 1H), δ 2.00-1.96 (m, 2H), δ 1.83-1.74 (m, 2H). LCMS method 1; LCMS (ESI, m/z): 434.2 $[M+H]^+$.

Example S79. Synthesis of 1-((6-(1-(2,6-dichlorophenyl)azetidin-3-yl)-5-methylpyridin-3-yl)methyl)piperidine-4-carboxylic acid (79)

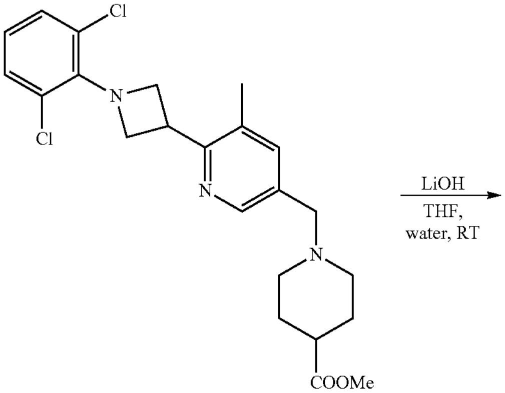

-continued

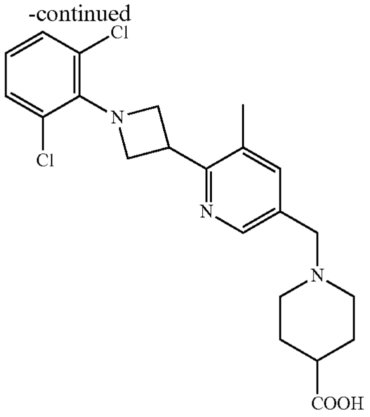

79

To a solution of methyl 1-((6-(1-(2,6-dichlorophenyl) azetidin-3-yl)-5-methylpyridin-3-yl)methyl)piperidine-4-carboxylate (180 mg, 0.401 mmol) in THF (4 mL) and water (1 mL) was added LiOH (50.5 mg, 1.204 mmol). The resulting mixture was allowed to stir at ambient temperature and the progress of the reaction was monitored by TLC analysis. After completion of the reaction, the mixture was concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:10:40), Column-1: Zorbax C18 (50×21.5) mm, 5 micron, Mobile phase A: 5 mM Ammonium formate in water, Mobile phase B: Acetonitrile. The required fractions were collected and lyophilized to afford 1-((6-(1-(2,6-dichlorophenyl)azetidin-3-yl)-5-methylpyridin-3-yl)methyl)piperidine-4-carboxylic acid, formic acid salt (107 mg, 0.222 mmol, 55.3% yield, 99.7% purity) as a white solid. $^1$H NMR (400 MHz, DMSO-$d_6$): δ 12.17 (br s, 1H), 8.28 (d, J=1.60 Hz, 1H), 7.47 (d, J=1.60 Hz, 1H), 7.22 (d, J=8.00 Hz, 2H), 6.72 (t, J=8.00 Hz, 1H), 4.81 (t, J=8.00 Hz, 2H), 4.59 (t, J=8.00 Hz, 2H), 4.13-4.07 (m, 1H), 3.41 (s, 2H), 2.73-2.67 (m, 2H), 2.24 (s, 3H), 2.19-2.15 (m, 1H), 1.97 (t, J=9.20 Hz, 2H), 1.76 (d, J=10.80 Hz, 2H), 1.57-1.51 (m, 2H). LCMS method 1; LCMS (ESI, m/z): 434.0 $[M+H]^+$.

Example S80. 1-((5-(1-(2,6-dichlorophenyl)azetidin-3-yl)-3,4-dimethylpyridin-2-yl)methyl)piperidine-4-carboxylic acid (80)

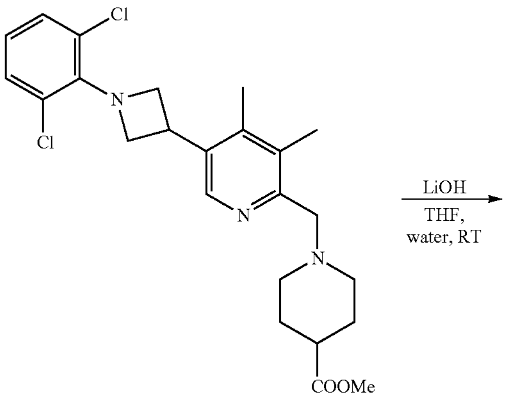

-continued

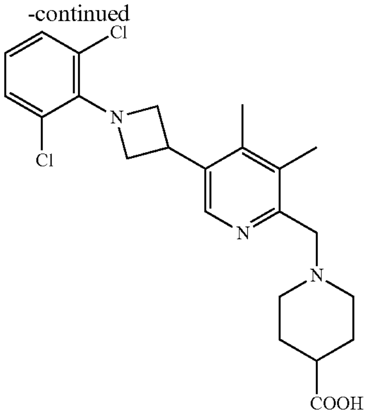

80

To a solution of methyl 1-((5-(1-(2,6-dichlorophenyl) azetidin-3-yl)-3,4-dimethylpyridin-2-yl)methyl)piperidine-4-carboxylate (180 mg, 0.389 mmol) in THF (4 mL) and water (1 mL) was added LiOH (50.5 mg, 1.204 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70), Column: YMC Triart C18 (250×20) mm, 5 micron, Mobile phase A: 0.1% Formic acid in water, Mobile phase B: Acetonitrile. The required fractions were collected and lyophilized to afford 1-((5-(1-(2,6-dichlorophenyl)azetidin-3-yl)-3,4-dimethylpyridin-2-yl)methyl)-piperidine-4-carboxylic acid, formic acid salt (14 mg, 0.028 mmol, 7.27% yield, 99.9% pure) as an off-white solid. $^1$H NMR (400 MHz, MeOD): δ 8.14 (d, J=2.00 Hz, 1H), 7.20-7.23 (m, 2H), 6.69-6.73 (m, 1H), 4.81 (t, J=8.00 Hz, 2H), 4.60 (t, J=7.60 Hz, 2H), 4.09-4.17 (m, 1H), 3.33 (s, 2H), 2.68-2.72 (m, 2H), 2.27 (s, 3H), 2.16 (s, 3H), 1.98-2.02 (m, 2H), 1.74-1.77 (m, 2H), 1.44-1.53 (m, 2H). LCMS method 1; LCMS (ESI, m/z): 448.0 $[M+H]^+$.

Example S81. Synthesis of 1-((6-(1-(2,6-dichlorophenyl)azetidin-3-yl)-4,5-dimethyl-pyridin-3-yl) methyl)piperidine-4-carboxylic acid (81)

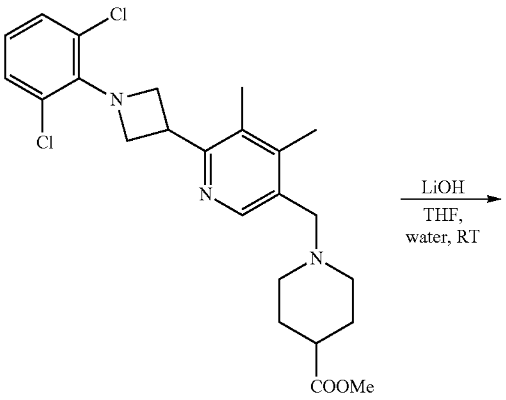

-continued

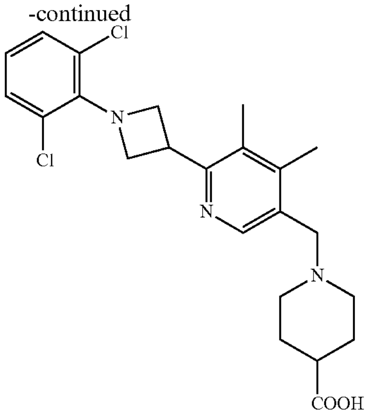

81

-continued

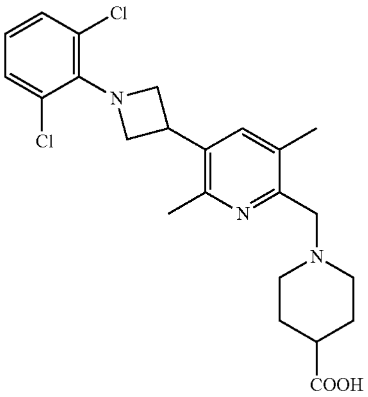

82

To a solution of methyl 1-((6-(1-(2,6-dichlorophenyl)azetidin-3-yl)-4,5-dimethylpyridin-3-yl)methyl)piperidine-4-carboxylate (190 mg (24% pure), 0.103 mmol) in THF (4 mL) and water (1 mL) was added LiOH (12.30 mg, 0.514 mmol). The resulting mixture was allowed to stir at ambient temperature and the progress of the reaction was monitored by TLC analysis. After completion of the reaction, the mixture was concentrated under reduced pressure and the residue was dissolved in water and acidified with acetic acid. The mixture was then concentrated under reduced pressure and the resulting residue was purified by prep. HPLC, prep. HPLC method: Diluent: THF:Water:ACN (50:20:30), Column: Xselect C18 (250×19) mm, 5 micron, Mobile phase A: 5 mM Ammonium formate in water, Mobile phase B: Acetonitrile. The required fractions were collected and lyophilized to afford 1-((6-(1-(2,6-dichlorophenyl)azetidin-3-yl)-4,5-dimethylpyridin-3-yl)methyl)piperidine-4-carboxylic acid (9 mg, 0.020 mmol, 19.36% yield, 99.1 pure) as a white solid. $^1$H NMR (400 MHz, DMSO-$d_6$): δ 11.73 (s, 1H), 7.24 (s, 1H), 7.22 (s, 1H), 6.74 (t, J=8.00 Hz, 1H), 6.63 (d, J=8.80 Hz, 2H), 4.75-4.79 (m, 2H), 4.28-4.32 (m, 2H), 3.58-3.61 (m, 3H), 2.79-2.82 (m, 2H), 2.14-2.33 (m, 5H), 1.82-1.84 (m, 2H), 1.52-1.58 (m, 2H) (One methyl signals merged with solvent peak). LCMS method 1; LCMS (ESI, m/z): 448.2 [M+H]$^+$.

Example S82. 1-((5-(1-(2,6-dichlorophenyl)azetidin-3-yl)-3,6-dimethylpyridin-2-yl)-methyl)piperidine-4-carboxylic acid (82)

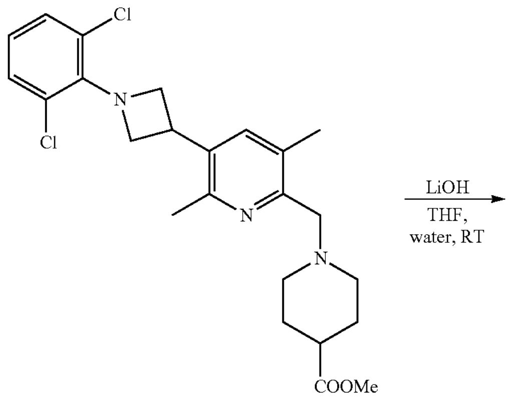

To a solution of methyl 1-((5-(1-(2,6-dichlorophenyl)azetidin-3-yl)-3,6-dimethylpyridin-2-yl)methyl)piperidine-4-carboxylate (200 mg, 0.433 mmol) in THF (4 mL) and water (1 mL) was added LiOH (104 mg, 4.33 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid to a pH of 5-6. The resulting solid was filtered and washed with diethyl ether to yield 1-((5-(1-(2,6-dichlorophenyl)azetidin-3-yl)-3,6-dimethylpyridin-2-yl)methyl)piperidine-4-carboxylic acid (89.4 mg, 0.197 mmol, 45.6% yield, 99% pure) as an off-white solid. $^1$H NMR (400 MHz, MeOD): δ 7.80 (s, 1H), 7.20 (d, J=8.00 Hz, 2H), 6.75 (t, J=8.00 Hz, 1H), 4.93-4.97 (m, 2H), 4.42-4.44 (m, 2H), 4.34-4.40 (m, 2H), 3.97-4.03 (m, 1H), 3.50-3.52 (m, 2H), 3.11-3.16 (m, 2H), 2.53 (s, 3H), 2.45 (s, 1H), 2.37 (s, 3H), 2.10-2.15 (m, 2H), 2.01-2.04 (m, 2H). LCMS method 1; LCMS (ESI, m/z): 449.0 [M+2H]$^+$.

Example S83. Synthesis of 1-((6-(1-(2,6-dichlorophenyl)azetidin-3-yl)-2,5-dimethyl-pyridin-3-yl)methyl)piperidine-4-carboxylic acid (83)

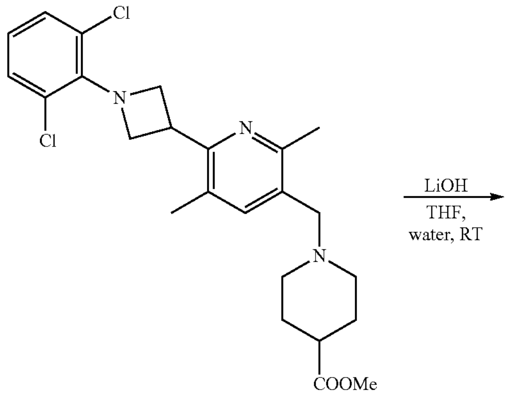

-continued

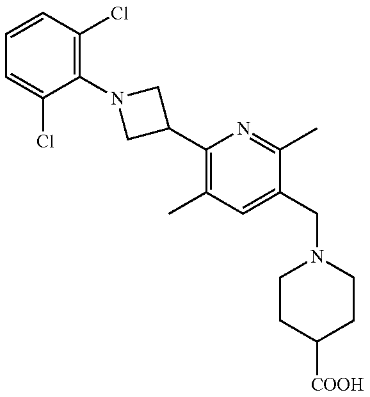

83

To a solution of methyl 1-((6-(1-(2,6-dichlorophenyl) azetidin-3-yl)-2,5-dimethylpyridin-3-yl)methyl)piperidine-4-carboxylate (140 mg, 0.303 mmol) in THF (4 mL) and water (1 mL) was added LiOH (72.5 mg, 3.03 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid to a pH of 5-6. The solid thus obtained was filtered and washed with diethyl ether to yield 1-((6-(1-(2,6-dichlorophenyl)azetidin-3-yl)-2,5-dimethylpyridin-3-yl)methyl)piperidine-4-carboxylic acid (67 mg, 0.149 mmol, 49.2% yield, 99.7% pure) as an off-white solid. $^1$H NMR (400 MHz, MeOD): δ 7.51 (s, 1H), 7.17 (d, J=8.00 Hz, 2H), 6.69 (t, J=7.60 Hz, 2H), 4.67 (t, J=7.60 Hz, 2H), 4.12-4.16 (m, 1H), 3.88 (s, 2H), 3.14-3.17 (m, 2H), 2.59 (s, 6H), 2.33-2.35 (m, 1H), 2.30 (s, 3H), 1.98-2.01 (m, 2H), 1.80-1.83 (m, 2H). LCMS method 1; LCMS (ESI, m/z): 448.2 [M+H]$^+$.

Example S84. Synthesis of 1-((5-(1-(2,6-dichlorophenyl)azetidin-3-yl)-4,6-dimethyl-pyridin-2-yl)methyl)piperidine-4-carboxylic acid (84)

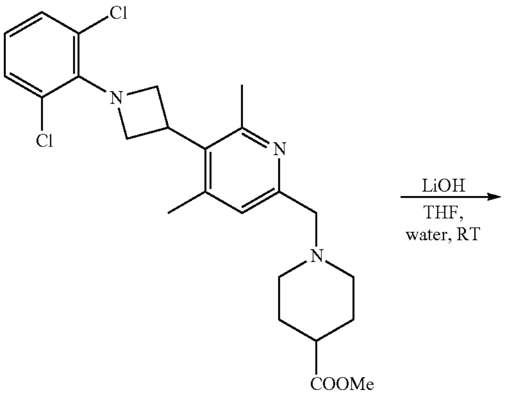

-continued

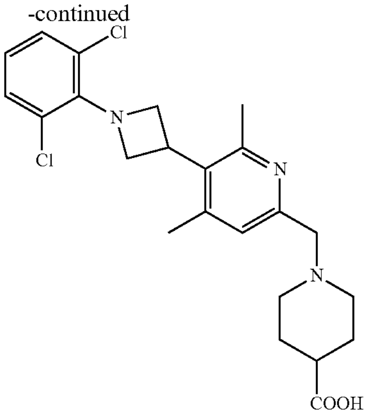

84

To a solution of methyl 1-((5-(1-(2,6-dichlorophenyl) azetidin-3-yl)-4,6-dimethylpyridin-2-yl)methyl)piperidine-4-carboxylate (180 mg, 0.389 mmol) in THF (4 mL) and water (1 mL) was added LiOH (28.0 mg, 1.168 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70), Column: YMC Triart C18 (250×20) mm, 5 micron, Mobile phase A: 0.1% Formic acid in water, Mobile phase B: Acetonitrile. The required fractions were collected and lyophilized to afford 1-((5-(1-(2,6-dichlorophenyl)azetidin-3-yl)-4,6-dimethylpyridin-2-yl)methyl)-piperidine-4-carboxylic acid, formic acid salt (24 mg, 0.045 mmol, 11.54% yield, 92.5% pure) as a yellow semi-solid. $^1$H NMR (400 MHz, MeOD): δ 7.29 (s, 1H), 7.19 (d, J=8.00 Hz, 2H), 6.72 (t, J=8.00 Hz, 1H), 4.86-4.90 (m, 2H), 4.55-4.58 (m, 2H), 3.83-3.88 (m, 3H), 3.03 (d, J=11.60 Hz, 2H), 2.64 (s, 3H), 2.47 (s, 4H), 2.35-2.40 (m, 1H), 1.94-1.99 (m, 2H), 1.78 (m, 2H). LCMS method 1; LCMS (ESI, m/z): 448.2 [M+H]$^+$.

Synthetic Route to Compound 85

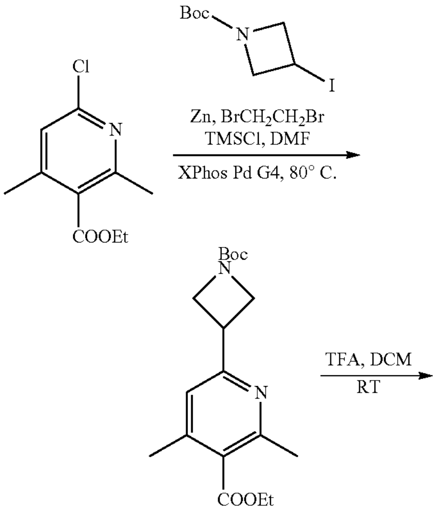

-continued

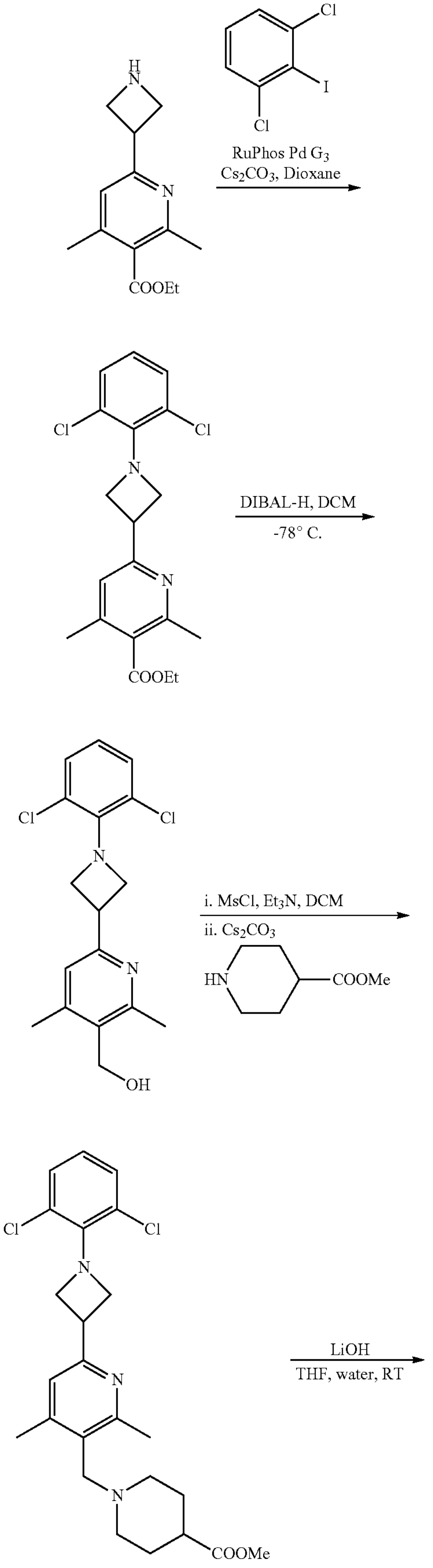

-continued

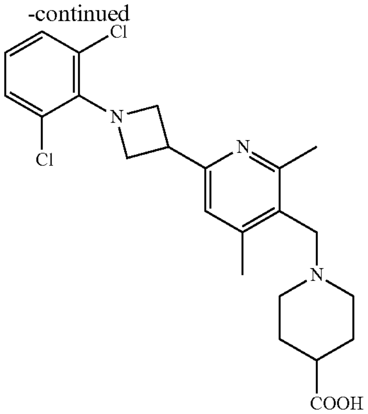

85

Synthesis of ethyl 6-(1-(tert-butoxycarbonyl)azetidin-3-yl)-2,4-dimethylnicotinate

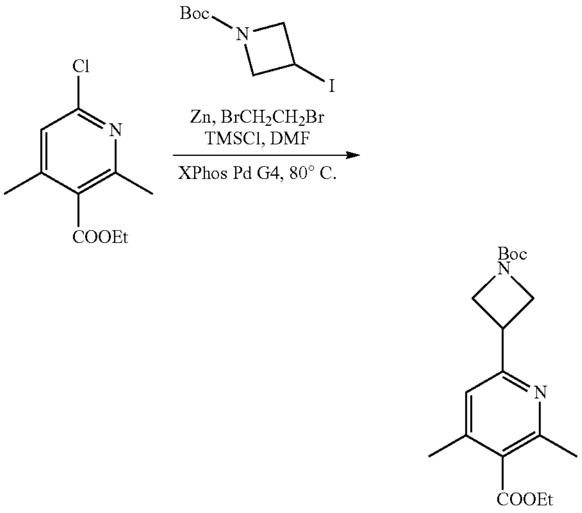

To a suspension of activated zinc (4.9 g, 74.8 mmol) in anhydrous DMF (20 mL) was added 1,2-dibromoethane (0.064 mL, 0.74 mmol) and the mixture was heated to 75° C. After 15 min, the reaction mixture was cooled to room temperature, trimethylsilyl chloride (0.096 mL, 0.74 mmol) was added and allowed to stir at ambient temperature for additional 30 min. Then a solution of tert-butyl 3-iodoazetidine-1-carboxylate (8.4 g, 18.6 mmol) in 5 mL of anhydrous DMF was added to the reaction mixture and stirred at room temperature for another 30 min, followed by addition of 5 ethyl 6-chloro-2,4-dimethylnicotinate (1.6 mg, 7.48 mmol) and XPhos Pd G4 (402 mg, 0.748 mmol) in 2 mL of DMF. The reaction mixture was stirred at 80° C. for 2 h. After completion of the reaction, the mixture was cooled to ambient temperature and quenched with sat. ammonium chloride solution. The crude was filtered through a pad of celite and washed with ethyl acetate. The filtrate was then transferred to a separating funnel and washed with cold water (40 mL), dried over anhydrous sodium sulphate and concentrated under reduced pressure. The resulting residue was purified by flash column chromatography on silica gel (100-200 mesh) eluting with 0-100% ethyl acetate in petroleum ether to afford ethyl 6-(1-(tert-butoxycarbonyl)azetidin-3-yl)-2,4-dimethylnicotinate (800 mg, 2.392 mmol, 63.9% yield) as a light brown semi-solid; LCMS method 4, LCMS (ESI, m/z): 335.2 [M+H]$^+$.

Synthesis of ethyl 6-(azetidin-3-yl)-2,4-dimethylnicotinate, TFA salt

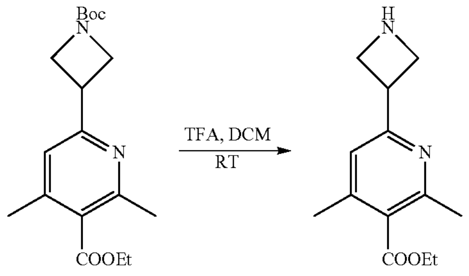

To a stirred solution of ethyl 6-(1-(tert-butoxycarbonyl)azetidin-3-yl)-2,4-dimethylnicotinate (1.6 g, 4.786 mmol) in anhydrous DCM (20 mL) was added TFA (1.1 mL, 14.3 mmol) at 0° C. Then reaction mixture was stirred at ambient temperature and the progress of the reaction monitored by TLC. After 2 h, TLC analysis indicated complete conversion of the starting material. The reaction mixture was concentrated under reduced pressure and the resulting residue was triturated with diethyl ether to afford ethyl 6-(azetidin-3-yl)-2,4-dimethylnicotinate, TFA (1.2 g, 72% yield) as a brown semi-solid. LCMS method 3, LCMS (ESI, m/z): 235.2 [M+H]$^+$.

Synthesis of ethyl 6-(1-(2,6-dichlorophenyl)azetidin-3-yl)-2,4-dimethylnicotinate

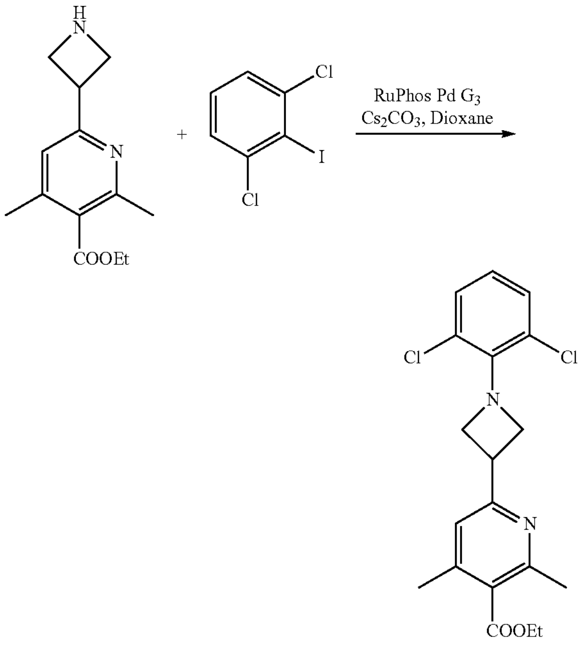

To a solution of ethyl 6-(azetidin-3-yl)-2,4-dimethylnicotinate (1.0 g, 4.27 mmol) and 1,3-dichloro-2-iodobenzene (1.514 g, 5.55 mmol) in anhydrous 1,4-dioxane (10 mL) was added cesium carbonate (4.17 g, 12.80 mmol). The reaction mixture was then degassed with nitrogen for 10 min followed by addition of RuPhos Pd G3 (0.357 g, 0.427 mmol) and heating to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (100-200 mesh) eluting with 0-100% ethyl acetate in petroleum ether to afford ethyl 6-(1-(2,6-dichlorophenyl)azetidin-3-yl)-2,4-dimethylnicotinate (500 mg, 30.9% yield) as a yellow solid. LCMS method 4, LCMS (ESI, m/z): 379.2 [M+H]$^+$.

Synthesis of (6-(1-(2,6-dichlorophenyl)azetidin-3-yl)-2,4-dimethylpyridin-3-yl)methanol

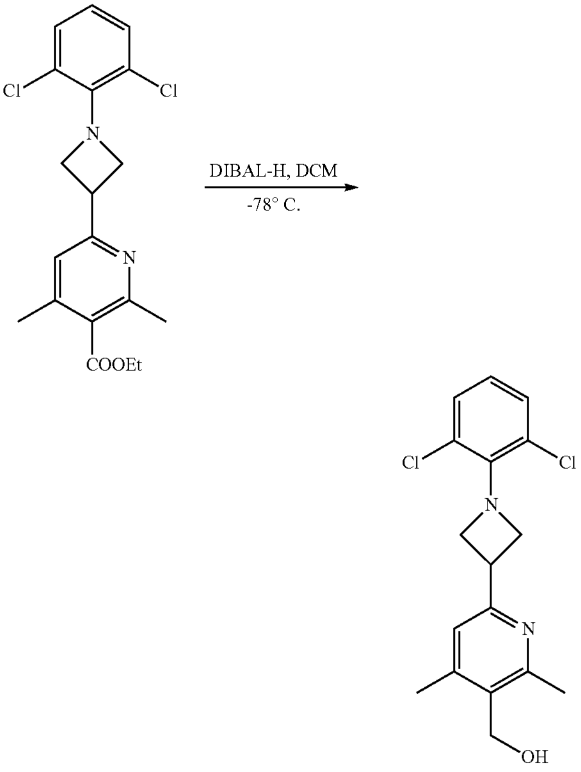 [SMILES: CCOC(=O)c1c(C)cc(C2CN(c3c(Cl)cccc3Cl)C2)nc1C ; Cc1cc(C2CN(c3c(Cl)cccc3Cl)C2)nc(C)c1CO]

To a stirred solution of ethyl 6-(1-(2,6-dichlorophenyl)azetidin-3-yl)-2,4-dimethylnicotinate (500 mg, 1.318 mmol) in DCM (10 mL) was added DIBAL-H (2.197 mL, 2.64 mmol) at −78° C. and stirred for 2 h at −78° C. The reaction mixture was quenched with saturated ammonium chloride solution (10 mL), extracted with DCM (30 mL) and washed with brine. The combined organic layer was dried over $Na_2SO_4$, filtered and the solvent was evaporated under reduced pressure. The crude was purified by silica gel column chromatography by using ethyl acetate/pet ether 0-70% to afford the title compound (6-(1-(2,6-dichlorophenyl)azetidin-3-yl)-2,4-dimethylpyridin-3-yl)methanol (0.3 g, 67% yield) as a white solid. LCMS method 2, LCMS (ESI, m/z): 337.0 [M+H]$^+$.

Synthesis of methyl 1-((6-(1-(2,6-dichlorophenyl) azetidin-3-yl)-2,4-dimethylpyridin-3-yl)methyl)piperidine-4-carboxylate

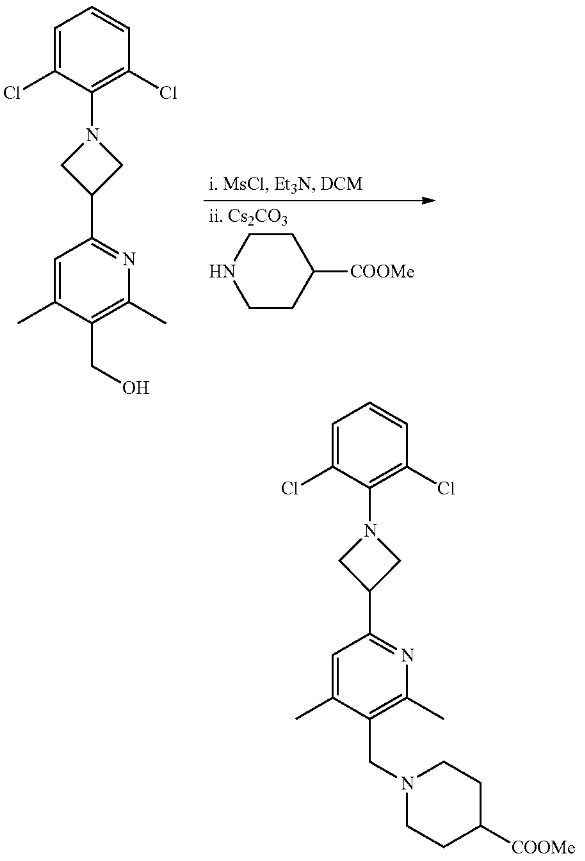 [SMILES: Cc1cc(C2CN(c3c(Cl)cccc3Cl)C2)nc(C)c1CO ; COC(=O)C1CCNCC1 ; COC(=O)C1CCN(Cc2c(C)cc(C3CN(c4c(Cl)cccc4Cl)C3)nc2C)CC1]

To a stirred solution of (6-(1-(2,6-dichlorophenyl)azetidin-3-yl)-2,4-dimethylpyridin-3-yl)methanol (300 mg, 0.890 mmol) in DCM (5 mL) were added TEA (0.248 mL, 1.779 mmol) and methane sulfonyl chloride (0.104 mL, 1.334 mmol) at room temperature under nitrogen atmosphere. The reaction mixture was allowed to stir at room temperature for 1 hour, followed by quench with sat. sodium bicarbonate solution and then extracted with ethyl acetate. The combined organic layer was dried over anhydrous sodium sulphate and concentrated to yield crude (6-(1-(2,6-dichlorophenyl)azetidin-3-yl)-2,4-dimethylpyridin-3-yl) methyl methane sulfonate. To the stirred solution of crude (6-(1-(2,6-dichlorophenyl)azetidin-3-yl)-2,4-dimethylpyridin-3-yl)methyl methane sulfonate in 1,4-dioxane (10 mL) was added cesium carbonate (235 mg, 0.722 mmol) and methyl piperidine-4-carboxylate (103 mg, 0.722 mmol). The reaction mixture was allowed to stir at 80° C. for 16 h and quenched with ice cold water. The filtrate was then transferred to a separating funnel and washed with cold water (20 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-((6-(1-(2,6-dichlorophenyl) azetidin-3-yl)-2,4-dimethylpyridin-3-yl)methyl)piperidine-4-carboxylate (0.30 g, 89% yield) as a yellow semi-solid. LCMS method 4, LCMS (ESI, m/z): 462.2 $[M+H]^+$.

Example S85. 1-((6-(1-(2,6-dichlorophenyl)azetidin-3-yl)-2,4-dimethylpyridin-3-yl)methyl)piperidine-4-carboxylic acid (85)

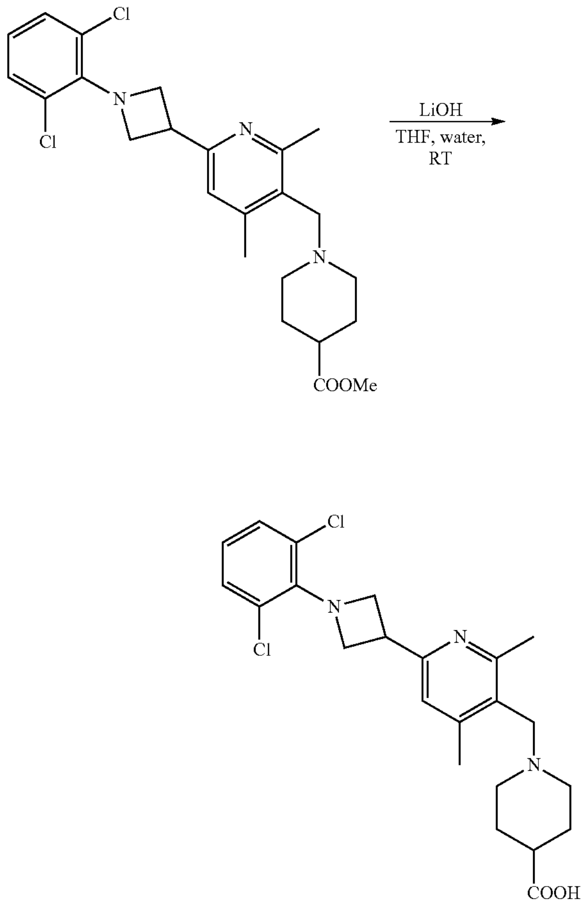

85

To a solution of methyl 1-((6-(1-(2,6-dichlorophenyl) azetidin-3-yl)-2,4-dimethylpyridin-3-yl)methyl)piperidine-4-carboxylate (300 mg, 0.649 mmol) in THF (4 mL) and water (1 mL) was added LiOH (38.8 mg, 1.622 mmol). The resulting mixture was allowed to stir at ambient temperature and the progress of the reaction was monitored by TLC analysis. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70), Column: YMC Triart C18 (250×20) mm, 5 micron, Mobile phase A: 0.1% Formic acid in water, Mobile phase B: Acetonitrile. The required fractions were collected and lyophilized to afford 1-((6-(1-(2,6-dichlorophenyl)-azetidin-3-yl)-2,4-dimethylpyridin-3-yl)methyl)piperidine-4-carboxylic acid, formic acid salt (6 mg, 10.92 μmol, 1.684% yield, 90% pure) as a white solid. $^1H$ NMR (400 MHz, MeOD): δ 8.47 (s, 1H), 7.26 (s, 1H), 7.19 (d, J=2.40 Hz, 2H), 6.71 (t, J=8.00 Hz, 1H), 4.54-4.58 (m, 2H), 3.85-3.87 (m, 1H), 3.74 (s, 2H), 2.97 (d, J=11.60 Hz, 2H), 2.60-2.62 (m, 3H), 2.47 (s, 3H), 2.41 (s, 2H), 2.33 (s, 1H), 1.90-1.95 (m, 2H), 1.70-1.73 (m, 2H). LCMS method 1; LCMS (ESI, m/z): 448.2 $[M+H]^+$.

General Route to Compounds 86-88
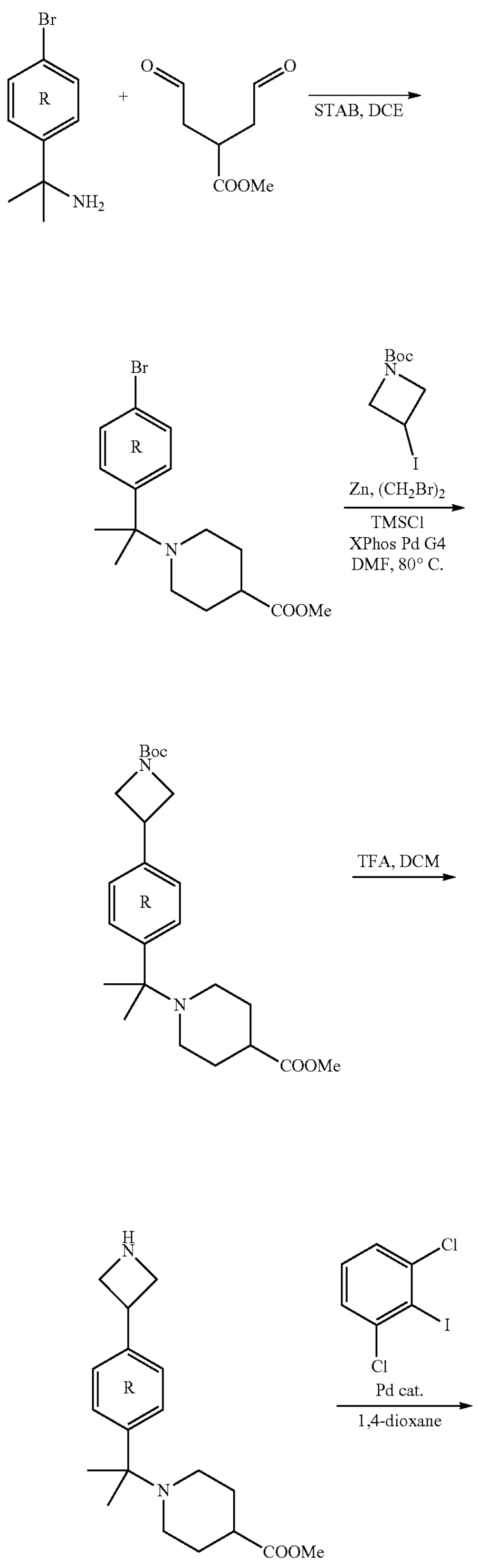
-continued
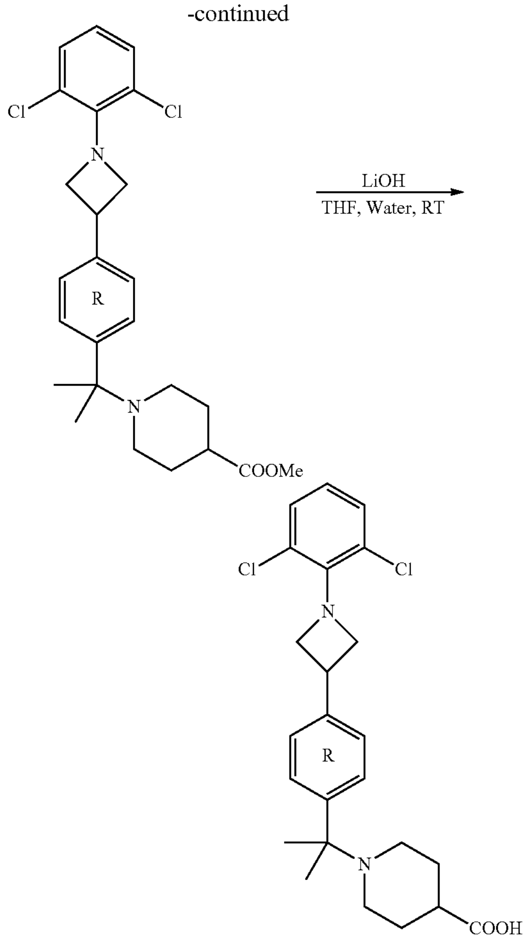
86-88
Synthesis of methyl 1-(2-(4-bromo-3,5-dimethylphenyl)propan-2-yl)piperidine-4-carboxylate
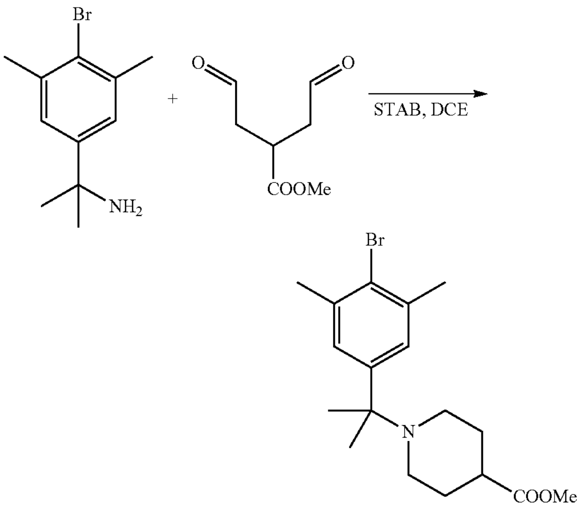
To a stirred solution of 2-(4-bromo-3,5-dimethylphenyl)propan-2-amine (4 g, 5.29 mmol) and methyl 4-oxo-2-(2-oxoethyl)butanoate (0.836 g, 5.29 mmol) in DCE (40 mL) was added sodium triacetoxyborohydride (1.680 g, 7.93 mmol) at ice cold temperature and then allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (50 mL) and dried over $Na_2SO_4$, filtered and the solvent evaporated under reduced pressure. The resulting residue was purified by flash column chromatography on silica gel (100-200 mesh) eluting with 50-100% ethyl acetate in petroleum ether to afford the methyl 1-(2-(4-bromo-3,5-dimethylphenyl)propan-2-yl)piperidine-4-carboxylate (1.9 g, 98% yield) as a brown semi-solid. LCMS method 3, LCMS (ESI, m/z): 370.0 $[M+2H]^+$.

Synthesis of methyl 1-(2-(6-bromopyridin-3-yl)propan-2-yl)piperidine-4-carboxylate

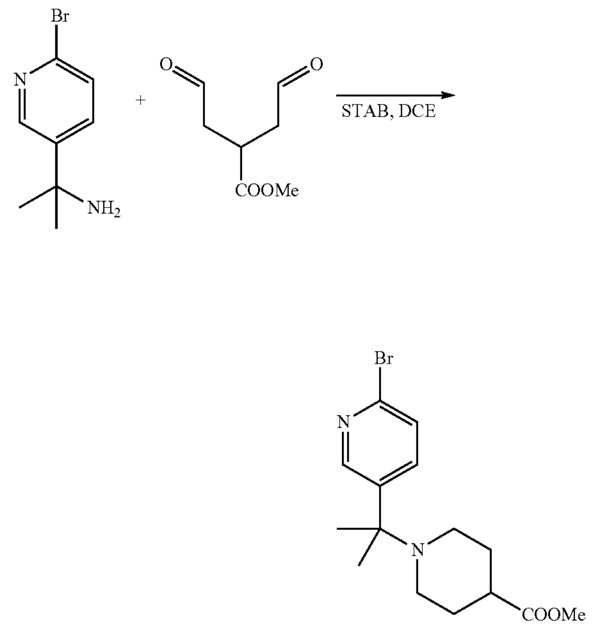

To a stirred solution of 2-(6-bromopyridin-3-yl)propan-2-amine (1.9 g, 8.83 mmol) and methyl 4-oxo-2-(2-oxoethyl)butanoate (1.397 g, 8.83 mmol) in DCE (40 mL) was added sodium triacetoxyborohydride (2.81 g, 13.25 mmol) was added at ice cold temperature and then allowed to reach room temperature and stirred for 16 h. The reaction mixture was diluted with DCM (20 mL) and quenched with sat. ammonium chloride solution. The aqueous layer was extracted with DCM (2×20 mL), the combined organic phase was washed with water (50 mL) and dried over $Na_2SO_4$, filtered and the solvent evaporated under reduced pressure. The resulting residue was purified by flash column chromatography on silica gel (100-200 mesh) eluting with 30-100% ethyl acetate in petroleum ether to afford the methyl 1-(2-(6-bromopyridin-3-yl)propan-2-yl)piperidine-4-carboxylate (2.2 g, 73.0% yield) as a light yellow liquid. LCMS method 3, LCMS (ESI, m/z): 342.8 $[M+H]^+$.

Synthesis of methyl 1-(2-(4-bromo-2-fluorophenyl)propan-2-yl)piperidine-4-carboxylate

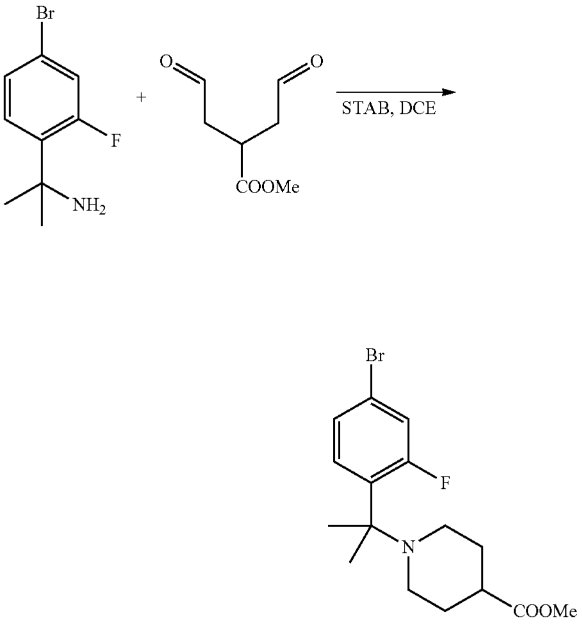

To a stirred solution of 2-(4-bromo-2-fluorophenyl)propan-2-amine, HC 980 mg, 3.65 mmol) and methyl 4-oxo-2-(2-oxoethyl)butanoate (577 mg, 3.65 mmol) in DCE (15 mL) was added sodium triacetoxyborohydride (1160 mg, 5.47 mmol) at ice cold temperature and then allowed to reach room temperature and stirred for 16 h. The reaction mixture was diluted with DCM (10 mL) and quenched with sat. ammonium chloride solution. The aqueous layer was extracted with DCM (2×10 mL), the combined organic phase was washed with water (20 mL) and dried over $Na_2SO_4$, filtered and the solvent evaporated under reduced pressure. The resulting residue was purified by flash column chromatography on silica gel (100-200 mesh) eluting with 0-100% ethyl acetate in petroleum ether to afford the methyl 1-(2-(4-bromo-2-fluorophenyl)propan-2-yl)piperidine-4-carboxylate (450 mg, 34.4% yield) as a light yellow semi-solid. LCMS method 1, LCMS (ESI, m/z): 358.4 $[M+H]^+$.

Synthesis of methyl 1-(2-(4-(1-(tert-butoxycarbonyl)azetidin-3-yl)-3,5-dimethyl-phenyl)propan-2-yl)piperidine-4-carboxylate

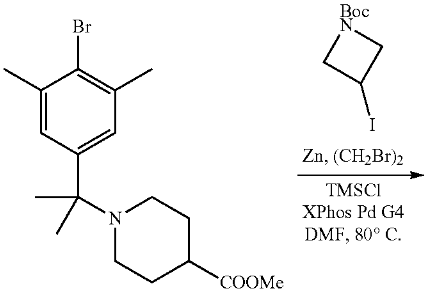

-continued

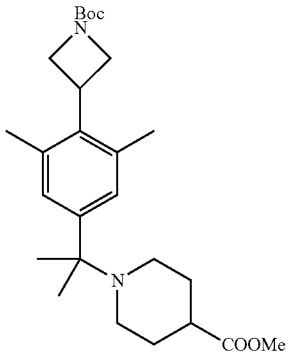

To a suspension of activated zinc (2.66 g, 40.7 mmol) in anhydrous DMF (20 mL) was added 1,2-dibromoethane (0.035 ml, 0.407 mmol) and heated to 75° C. After 15 min, the reaction mixture was cooled to room temperature, trimethylchlorosilane (0.00694 ml, 0.054 mmol) was added and allowed to stir at ambient temperature for additional 30 min. Then a solution of tert-butyl 3-iodoazetidine-1-carboxylate (4.61 g, 16.29 mmol) in 5 mL of anhydrous DMF was added and stirred at room temperature for another 30 min, followed by methyl 1-(2-(4-bromo-3,5-dimethylphenyl)propan-2-yl)piperidine-4-carboxylate (1.5 g, 4.07 mmol) and Xphos Pd G4 (0.391 g, 0.407 mmol) in 5 mL of DMF. The reaction mixture was stirred at 80° C. for 2 h. After completion of the reaction, the mixture was cooled to room temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-(2-(4-(1-(tert-butoxycarbonyl)azetidin-3-yl)-3,5-dimethylphenyl)propan-2-yl)piperidine-4-carboxylate (1.8 g, 1.984 mmol, 48.7% yield) as a yellow semi-solid. LCMS method 3, LCMS (ESI, m/z): 445.0 $[M+H]^+$.

Synthesis of methyl 1-(2-(6-(1-(tert-butoxycarbonyl)azetidin-3-yl)pyridin-3-yl)propan-2-yl)piperidine-4-carboxylate

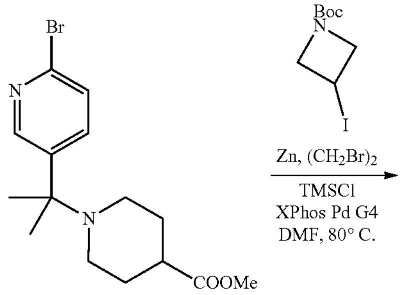

-continued

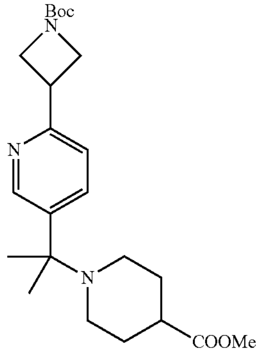

To a suspension of activated zinc (3.83 g, 58.6 mmol) in anhydrous DMF (20 mL) was added 1,2-dibromoethane (0.051 mL, 0.586 mmol) and heated to 75° C. After 15 min, the reaction mixture was cooled to room temperature, trimethylchlorosilane (0.075 mL, 0.586 mmol) was added and allowed to stir at ambient temperature for additional 30 min. Then a solution of tert-butyl 3-iodoazetidine-1-carboxylate (6.64 g, 23.44 mmol) in 5 mL of anhydrous DMF was added to the reaction mixture and stirred at room temperature for another 30 min, followed by addition of methyl 1-(2-(6-bromopyridin-3-yl)propan-2-yl)piperidine-4-carboxylate (2.0 g, 5.86 mmol) and Xphos-pd-g4 (0.563 g, 0.586 mmol) in 5 mL of DMF. The reaction mixture was stirred at 80° C. for 2 h. After completion of the reaction, the reaction mixture was cooled to ambient temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 50-100% ethyl acetate in petroleum ether to afford methyl 1-(2-(6-(1-(tert-butoxycarbonyl)azetidin-3-yl)pyridin-3-yl)propan-2-yl)piperidine-4-carboxylate (2.0 g, 4.79 mmol, 82% yield) as a brown semi-solid. LCMS method 3, LCMS (ESI, m/z): 418.0 $[M+H]^+$.

Synthesis of methyl 1-(2-(4-(1-(tert-butoxycarbonyl)azetidin-3-yl)-2-fluorophenyl)propan-2-yl)piperidine-4-carboxylate

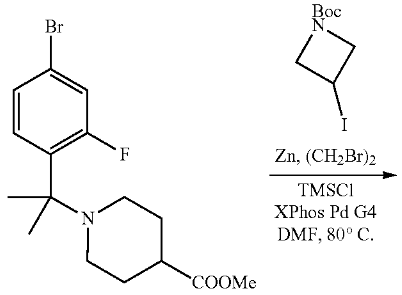

-continued

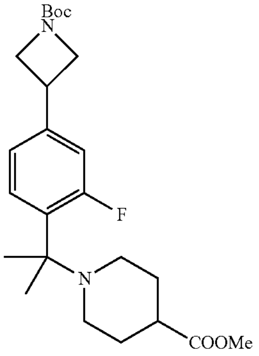

To a suspension of activated zinc (712 mg, 10.89 mmol) in anhydrous DMF (15 mL) was added 1,2-dibromoethane (0.047 mL, 0.544 mmol) and heated to 75° C. After 15 min, the reaction mixture was cooled to room temperature, trimethylchlorosilane (0.070 mL, 0.544 mmol) was added and allowed to stir at ambient temperature for 30 min. Then a solution of tert-butyl 3-iodoazetidine-1-carboxylate (925 mg, 3.27 mmol) in 2 mL of anhydrous DMF was added to the reaction mixture and stirred at room temperature for another 30 min, followed by addition of methyl 1-(2-(4-bromo-2-fluorophenyl)propan-2-yl)piperidine-4-carboxylate (390 mg, 1.089 mmol) and XPhos Pd G4 (187 mg, 0.218 mmol) in 3 mL of DMF. The reaction mixture was stirred at 80° C. for 2 h. After completion of the reaction, the reaction mixture was cooled to room temperature and quenched with sat. ammonium chloride solution. The crude was filtered through a pad of celite and washed with ethyl acetate. The filtrate was then transferred to a separating funnel and washed with cold water (50 mL), dried over anhydrous sodium sulphate and concentrated under reduced pressure. The resulting residue was purified by flash column chromatography on silica gel (100-200 mesh) eluting with 0-50% ethyl acetate in petroleum ether to afford methyl 1-(2-(4-(1-(tert-butoxycarbonyl)azetidin-3-yl)-2-fluorophenyl)propan-2-yl)piperidine-4-carboxylate (410 mg, 0.943 mmol, 87% yield) as a light brown semi-solid. LCMS method 1, LCMS (ESI, m/z): 434.0 [M+H]$^+$.

Synthesis of methyl 1-(2-(4-(azetidin-3-yl)-3,5-dimethylphenyl)propan-2-yl)piperidine-4-carboxylate

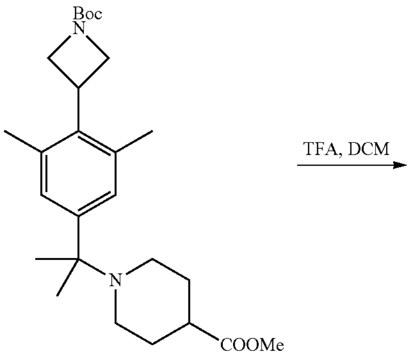

-continued

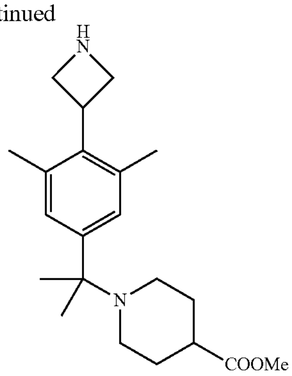

To a stirred solution of methyl 1-(2-(4-(1-(tert-butoxycarbonyl)azetidin-3-yl)-3,5-dimethylphenyl)propan-2-yl)piperidine-4-carboxylate (1.8 g, 4.05 mmol) in anhydrous DCM (20 mL) was added TFA (0.936 mL, 12.15 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(2-(4-(azetidin-3-yl)-3,5-dimethylphenyl)propan-2-yl)piperidine-4-carboxylate, TFA (1.0 g, 2.181 mmol, 53.9% yield) as a yellow semi-solid. LCMS method 3, LCMS (ESI, m/z): 345.2 [M+H]$^+$.

Synthesis of methyl 1-(2-(6-(azetidinyl-3-yl)pyridin-3-yl)propan-2-yl)piperidine-4-carboxylate

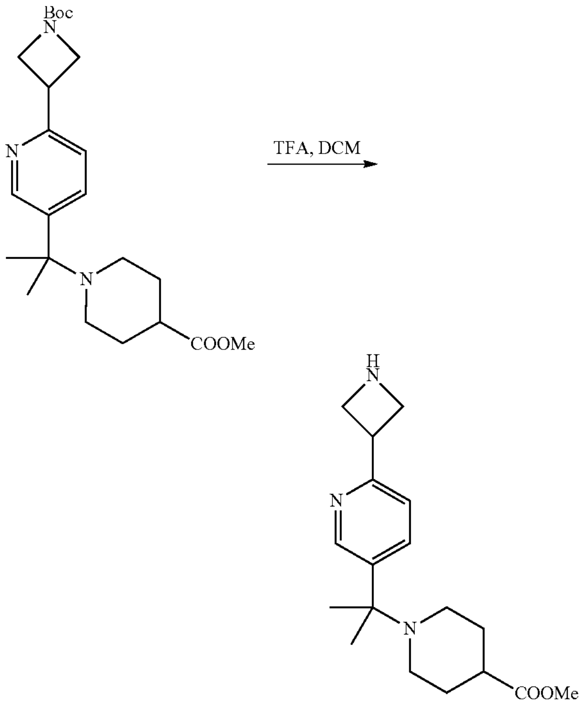

To a stirred solution of methyl 1-(2-(6-(1-(tert-butoxycarbonyl)azetidin-3-yl)pyridin-3-yl)propan-2-yl)piperidine-4-carboxylate (2 g, 4.79 mmol) in anhydrous DCM (20 mL) was added TFA (3.69 mL, 47.9 mmol) at 0° C. Then reaction mixture was stirred at ambient temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(2-(6-(azetidin-3-yl)pyridin-3-yl)propan-2-yl)piperidine-4-carboxylate, TFA (2.0 g, 99% yield) as a yellow semi-solid. LCMS method 3, LCMS (ESI, m/z): 318.2 [M+H]+.

Synthesis of methyl 1-(2-(4-(azetidin-3-yl)-2-fluoro-phenyl)propan-2-yl)piperidine-4-carboxylate

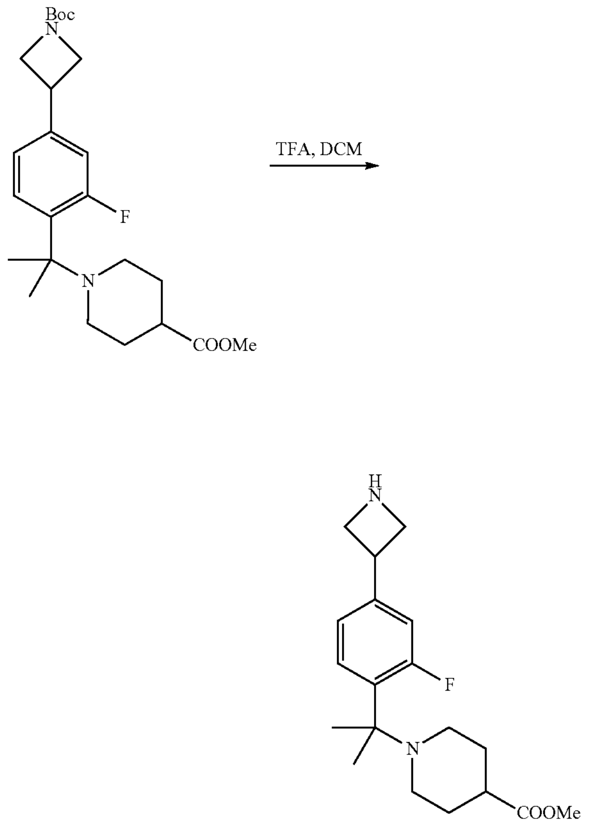

To a stirred solution of methyl 1-(2-(4-(1-(tert-butoxycarbonyl)azetidin-3-yl)-2-fluorophenyl)propan-2-yl)piperidine-4-carboxylate (400 mg, 0.920 mmol) in anhydrous DCM (10 mL) was added TFA (0.709 mL, 9.20 mmol) at 0° C. The reaction mixture was stirred at room temperature and the progress of the reaction monitored by TLC. After 1 h, TLC analysis indicated complete conversion of the starting material. The reaction mixture was concentrated under reduced pressure and the resulting residue was triturated with diethyl ether to afford methyl 1-(2-(4-(azetidin-3-yl)-2-fluorophenyl)propan-2-yl)piperidine-4-carboxylate, TFA (400 mg, 97% yield) as a light brown semi-solid. LCMS method 1, LCMS (ESI, m/z): 335.3 [M+H]+.

Synthesis of methyl 1-(2-(4-(1-(2,6-dichlorophenyl)azetidin-3-yl)-3,5-dimethylphenyl)propan-2-yl)piperidine-4-carboxylate

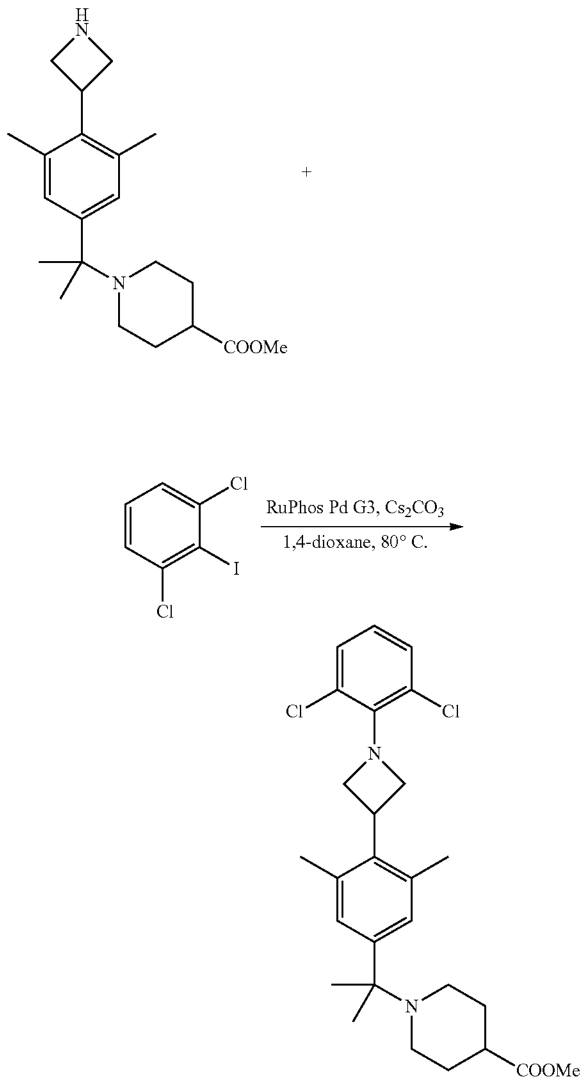

To a solution of methyl 1-(2-(4-(azetidin-3-yl)-3,5-dimethylphenyl)propan-2-yl)piperidine-4-carboxylate, TFA (0.5 g, 1.090 mmol) and 1,3-dichloro-2-iodobenzene (0.357 g, 1.309 mmol) in anhydrous 1,4 dioxane (5 mL) was added cesium carbonate (1.066 g, 3.27 mmol). The reaction mixture was then degassed with nitrogen for 10 min followed by addition of RuPhos Pd G3 (0.091 g, 0.109 mmol) and heated to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 0-50% ethyl acetate in petroleum ether to afford methyl 1-(2-(4-(1-(2,6-dichlorophenyl)azetidin-3-yl)-3, 5-dimethylphenyl)propan-2-yl)piperidine-4-carboxylate (370 mg, 0.317 mmol, 29.1% yield) as a yellow solid. LCMS method 3, LCMS (ESI, m/z): 490.8 [M+H]+.

Synthesis of methyl 1-(2-(6-(1-(2,6-dichlorophenyl)azetidin-3-yl)pyridin-3-yl)propan-2-yl)piperidine-4-carboxylate

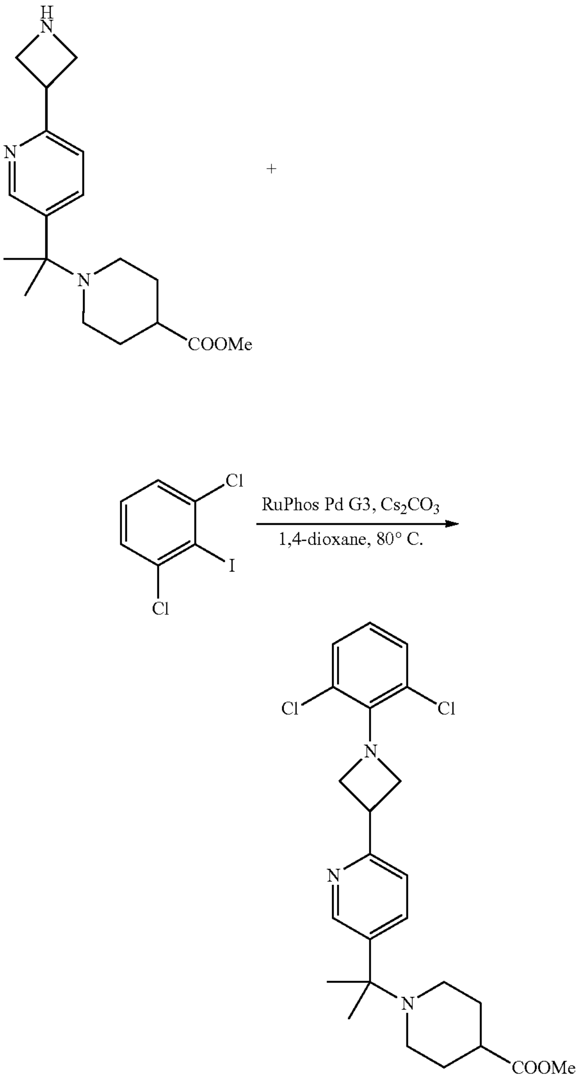

To a solution of methyl 1-(2-(6-(azetidin-3-yl)pyridin-3-yl)propan-2-yl)piperidine-4-carboxylate, TFA (0.5 g, 1.159 mmol) and 1,3-dichloro-2-iodobenzene (0.379 g, 1.391 mmol) in anhydrous 1,4-dioxane (5 mL) was added cesium carbonate (1.133 g, 3.48 mmol). The reaction mixture was degassed with nitrogen for 10 min followed by addition of RuPhos Pd G3 (0.097 g, 0.116 mmol) and heated to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 50-100% ethyl acetate in petroleum ether to afford methyl 1-(2-(6-(1-(2,6-dichlorophenyl)azetidin-3-yl)pyridin-3-yl)propan-2-yl)piperidine-4-carboxylate (0.3 g, 55% yield) as a yellow solid. LCMS method 3, LCMS (ESI, m/z): 462.2 $[M+H]^+$.

Synthesis of methyl 1-(2-(4-(1-(2,6-dichlorophenyl)azetidin-3-yl)-2-fluorophenyl)-propan-2-yl)piperidine-4-carboxylate

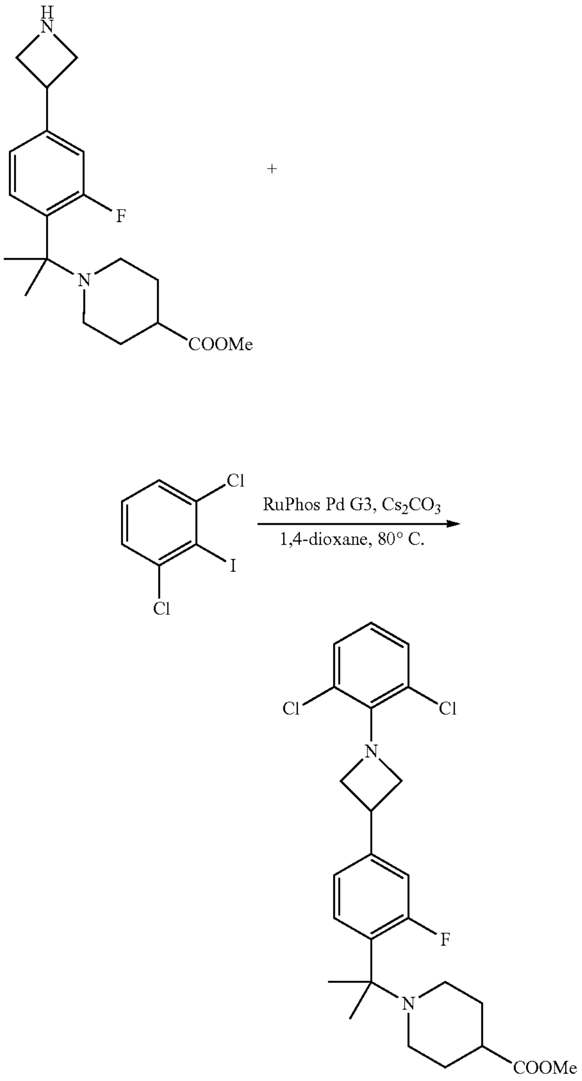

To a solution of methyl 1-(2-(4-(azetidin-3-yl)-2-fluorophenyl)propan-2-yl)piperidine-4-carboxylate, TFA (350 mg, 0.780 mmol) and 1,3-dichloro-2-iodobenzene (266 mg, 0.976 mmol) in anhydrous 1,4-dioxane (5 mL) was added cesium carbonate (763 mg, 2.341 mmol). The reaction mixture was degassed with nitrogen for 10 min followed by addition of RuPhos Pd G3 (65.3 mg, 0.078 mmol) and heated to 80° C. After 16 h, TLC analysis indicated complete conversion of the starting material. The reaction mixture was then cooled to room temperature and filtered through a pad of celite and washed with EtOAc. The filtrate was concentrated under reduced pressure and the resulting residue was purified by flash column chromatography on silica gel (230-400 mesh) eluting with 5-50% ethyl acetate in petroleum ether to afford methyl 1-(2-(4-(1-(2,6-dichlorophenyl)azetidin-3-yl)-2-fluorophenyl)propan-2-yl)piperidine-4-carboxylate (180 mg, 48.1% yield) as a yellow solid. LCMS method 4, LCMS (ESI, m/z): 478.2 $[M+H]^+$.

Example S86. 1-(2-(4-(1-(2,6-dichlorophenyl)azetidin-3-yl)-3,5-dimethylphenyl)propan-2-yl)piperidine-4-carboxylic acid (86)

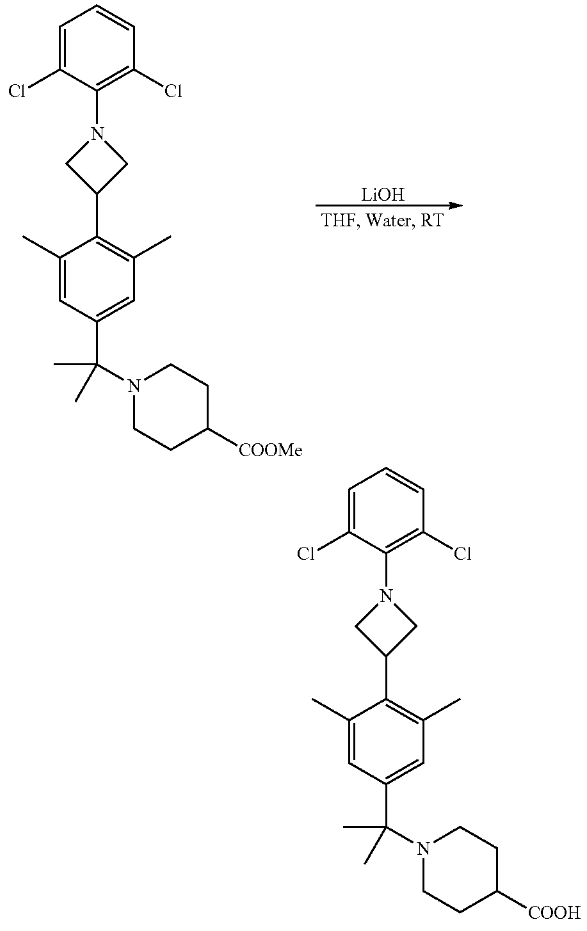

86

To a solution of methyl 1-(2-(4-(1-(2,6-dichlorophenyl)azetidin-3-yl)-3,5-dimethylphenyl)propan-2-yl)piperidine-4-carboxylate (360 mg, 0.735 mmol) in THF (6 mL) and water (2 mL) was added LiOH (52.8 mg, 2.206 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30), Column: Zorbax C18 (50×21.5) mm, 5 micron, Mobile phase A: 10 mM Ammonium bicarbonate, Mobile phase B: Acetonitrile. The required fractions were collected and lyophilized to afford 1-(2-(4-(1-(2,6-dichlorophenyl)azetidin-3-yl)-3,5-dimethylphenyl)propan-2-yl)piperidine-4-carboxylic acid (83 mg, 0.173 mmol, 23.51% yield, 99% pure) as an off-white solid. $^1$H NMR (400 MHz, DMSO-$d_6$): δ 7.23 (d, J=8.00 Hz, 2H), 7.07 (s, 2H), 6.73 (t, J=8.00 Hz, 1H), 4.96 (t, J=8.40 Hz, 2H), 4.44 (t, J=8.40 Hz, 2H), 4.14-4.19 (m, 1H), 2.68-2.69 (m, 2H), 2.27 (s, 6H), 2.07 (m, 1H), 2.02-2.04 (m, 3H), 1.73-1.76 (m, 2H), 1.48-1.50 (m, 2H), 1.22 (s, 6H). LCMS method 1; LCMS (ESI, m/z): 475.2 [M+H]$^+$.

Example S87. 1-(2-(6-(1-(2,6-dichlorophenyl)azetidin-3-yl)pyridin-3-yl)propan-2-yl)-piperidine-4-carboxylic acid (87)

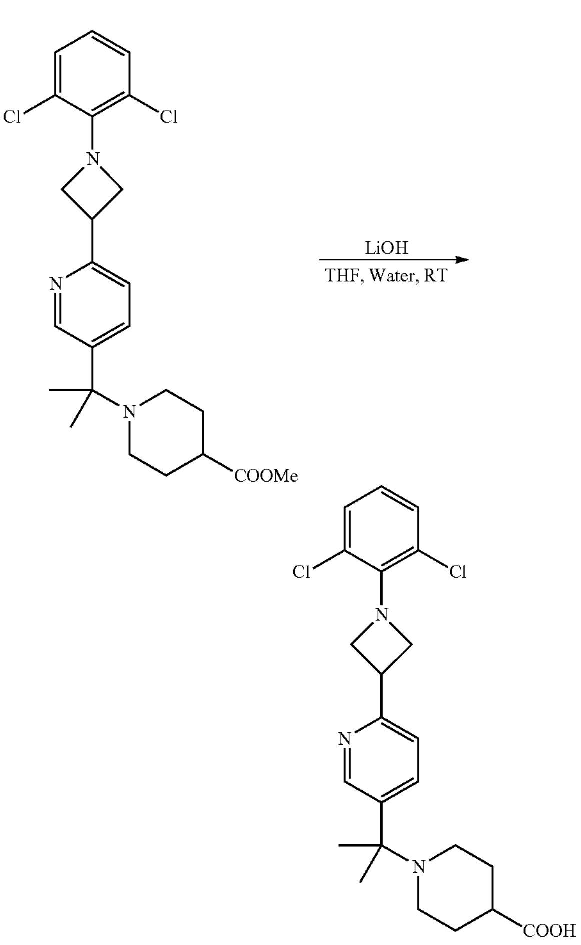

87

To a solution of methyl 1-(2-(6-(1-(2,6-dichlorophenyl)azetidin-3-yl)pyridin-3-yl)propan-2-yl)piperidine-4-carboxylate (0.3 g, 0.649 mmol) in THF (6 mL) and water (2 mL) was added LiOH (0.082 g, 1.946 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Water:ACN (50:20:30), Column: Xselect C18 (150×19) mm, 5 micron, Mobile phase A: 0.1% Formic acid in water, Mobile phase B: Acetonitrile. The required fractions were collected and lyophilized to afford 1-(2-(6-(1-(2,6-dichlorophenyl)azetidin-3-yl)pyridin-3-yl)propan-2-yl)piperidine-4-carboxylic acid, formic acid salt (58 mg, 0.114 mmol, 17.61% yield, 97.4% pure) as a white solid. $^1$H NMR (400 MHz, MeOD): δ 8.74-8.75 (m, 1H), 8.02-8.05 (m, 1H), 7.54 (d, J=8.00 Hz, 1H), 7.19 (d, J=8.00 Hz, 2H), 6.72 (t, J=8.00 Hz, 1H), 4.89-4.94 (m, 2H), 4.60-4.63 (m, 2H), 3.92-4.00 (m, 1H), 3.06 (d, J=11.20 Hz, 2H), 2.49-2.54 (m, 2H), 2.27-2.34 (m, 1H), 1.97 (d, J=10.80 Hz, 2H), 1.74-1.82 (m, 2H), 1.60 (s, 6H). LCMS method 6; LCMS (ESI, m/z): 448.2 [M+H]+.

Example S88. 1-(2-(4-(1-(2,6-dichlorophenyl)azetidin-3-yl)-2-fluorophenyl)propan-2-yl)piperidine-4-carboxylic acid (88)

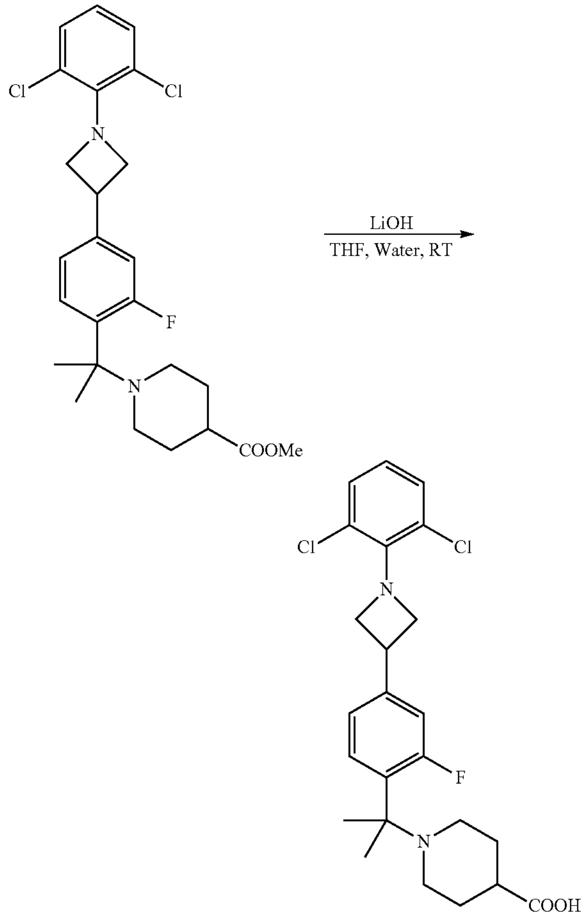

88

To a solution of methyl 1-(2-(4-(1-(2,6-dichlorophenyl)azetidin-3-yl)-2-fluorophenyl)propan-2-yl)piperidine-4-carboxylate (180 mg, 0.375 mmol) in THF (6 mL) and water (2 mL) was added LiOH (79 mg, 1.877 mmol). The resulting mixture was allowed to stir at ambient temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70), Column: YMC C18 Phenyl (250×21) mm, 5 micron, Mobile phase A: 0.1% Formic acid in water, Mobile phase B: Acetonitrile. The required fractions were collected and lyophilized to afford 1-(2-(4-(1-(2,6-dichlorophenyl)azetidin-3-yl)-2-fluorophenyl)propan-2-yl)piperidine-4-carboxylic acid, formic acid salt (95 mg, 0.184 mmol, 49.0% yield, 99% pure) as a white solid. $^1$H NMR (400 MHz, MeOD): δ 7.50 (t, J=8.40 Hz, 1H), 7.17-7.26 (m, 2H), 7.07 (d, J=8.00 Hz, 2H), 6.61 (s, 1H), 4.75 (m, 2H), 4.29-4.32 (m, 2H), 3.63-3.67 (m, 2H), 3.15 (s, 1H), 2.65-2.70 (m, 2H), 2.22-2.23 (m, 1H), 1.91-1.95 (m, 2H), 1.77-1.83 (m, 2H), 1.67 (s, 6H). LCMS method 1; LCMS (ESI, m/z): 465.0 [M+H]+.

General Route to Compounds 89 and 90

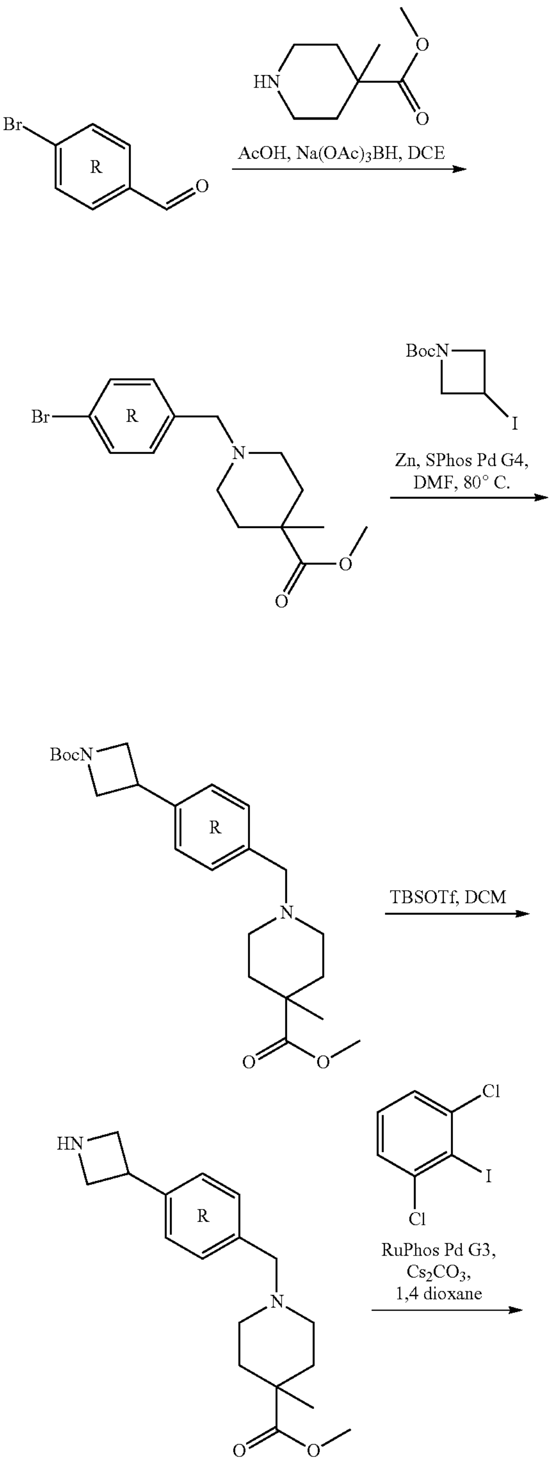

-continued

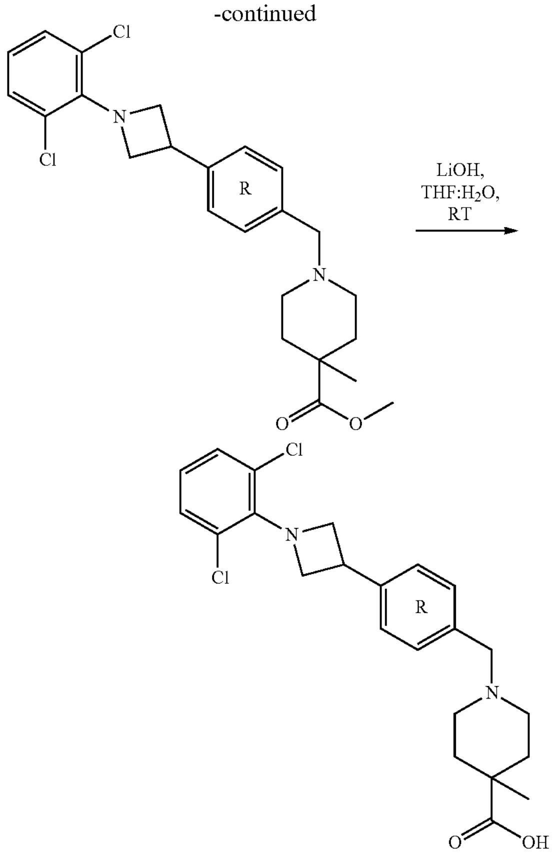

89 and 90

Synthesis of methyl 1-(4-bromobenzyl)-4-methylpiperidine-4-carboxylate

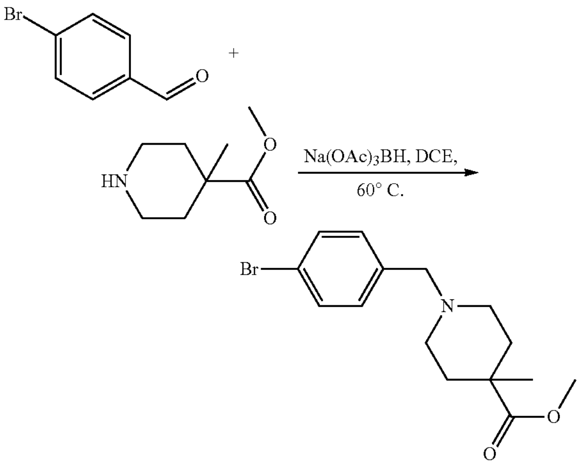

To the stirred solution of 4-bromobenzaldehyde (500 mg, 2.70 mmol) in anhydrous 1,2 dichloroethane (20 mL) was added methyl 4-methylpiperidine-4-carboxylate (425 mg, 2.70 mmol) and acetic acid (0.155 mL, 2.70 mmol) at 0° C. The reaction mixture was then allowed to stir at room temperature. After 30 min, sodium triacetoxyborohydride (859 mg, 4.05 mmol) was added and stirring at room temperature continued. The progress of the reaction was monitored by TLC. After 16 h, TLC analysis indicated complete conversion of the starting material. The reaction mixture was diluted with DCM, and washed with cold water. The organic layer was separated, dried over sodium sulphate, and concentrated under reduced pressure. The resulting residue was purified by flash column chromatography on silica gel (230-400 mesh) eluting with 0-50% ethyl acetate in petroleum ether to afford methyl 1-(4-bromobenzyl)-4-methylpiperidine-4-carboxylate (400 mg, 1.104 mmol, 40.8% yield). LCMS method 1, LCMS (ESI, m/z): 326.0, 328.0 $[M, M+2H]^+$.

Synthesis of methyl 1-(4-bromo-2,6-dimethylbenzyl)-4-methylpiperidine-4-carboxylate

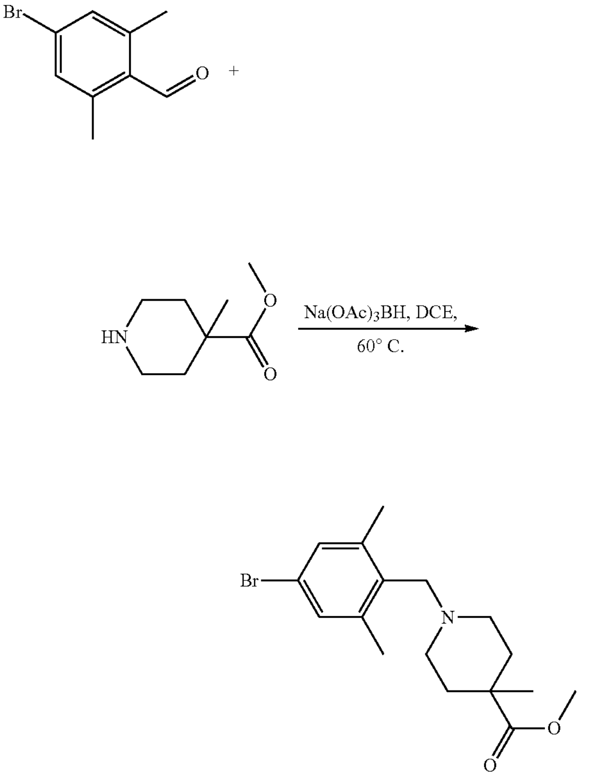

To a stirred solution of 4-bromo-2,6-dimethylbenzaldehyde (500 mg, 2.347 mmol) in anhydrous 1,2 dichloroethane (20 mL) was added methyl 4-methylpiperidine-4-carboxylate (369 mg, 2.347 mmol) and acetic acid (0.134 mL, 2.347 mmol) at 0° C. The reaction mixture was then allowed to stir at room temperature. After 30 min, sodium triacetoxyborohydride (746 mg, 3.52 mmol) was added and stirring at room temperature continued. The progress of the reaction was monitored by TLC. After 16 h, TLC analysis indicated complete conversion of the starting material. The reaction mixture was diluted with DCM and washed with cold water. The organic layer was separated, dried over sodium sulphate and concentrated under reduced pressure. The resulting residue was purified by flash column chromatography on silica gel (230-400 mesh) eluting with 0-50% ethyl acetate in petroleum ether to afford methyl 1-(4-bromo-2,6-dimethylbenzyl)-4-methylpiperidine-4-carboxylate (250 mg, 25.3% yield). LCMS (ESI, m/z): 356.2 $[M+2H]^+$.

Synthesis of methyl 1-(4-(1-(tert-butoxycarbonyl) azetidin-3-yl)benzyl)-4-methylpiperidine-4-carboxylate

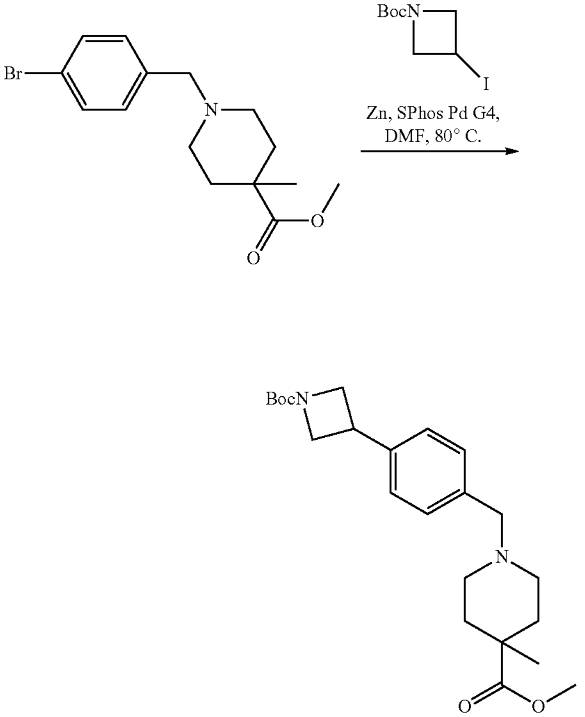

To a suspension of activated zinc (1202 mg, 18.39 mmol) in anhydrous DMF (20 mL) was added 1,2-dibromoethane (10.57 µl, 0.123 mmol) and heated to 75° C. After 15 min, the reaction mixture was cooled to room temperature, chloro trimethylsilane (0.1 mL, 0.782 mmol) was added and allowed to stir at ambient temperature for addition 30 min. Then a solution of tert-butyl 3-iodoazetidine-1-carboxylate (1736 mg, 6.13 mmol) in anhydrous DMF was added and the mixture stirred at room temperature for another 2 h. In another three neck round bottom flask, to a solution of methyl 1-(4-bromobenzyl)-4-methylpiperidine-4-carboxylate (400 mg, 1.226 mmol) in anhydrous DMF was added SPhos Pd G4 (97 mg, 0.123 mmol). Both solutions were combined under nitrogen atmosphere. The reaction mixture was then heated to 80° C. under nitrogen atmosphere and the progress of the reaction was monitored by UPLC. After 16 h, UPLC analysis indicated complete conversion of the starting material. The reaction mixture was cooled to room temperature and filtered through a pad of celite and washed with ethyl acetate. The filtrate was then transferred to a separating funnel and washed with cold water (300 mL) followed by brine (200 mL), dried over anhydrous sodium sulphate and concentrated under reduced pressure. The resulting residue was purified by flash column chromatography on silica gel (230-400 mesh) eluting with 0-50% ethyl acetate in petroleum ether to afford methyl 1-(4-(1-(tert-butoxycarbonyl)azetidin-3-yl)benzyl)-4-methylpiperidine-4-carboxylate (500 mg, 0.969 mmol, 79% yield) as a yellow oil. LCMS method 2; LCMS (ESI, m/z): 402.8 $[M+H]^+$.

Synthesis of methyl 1-(4-(1-(tert-butoxycarbonyl) azetidin-3-yl)-2,6-dimethylbenzyl)-4-methylpiperidine-4-carboxylate

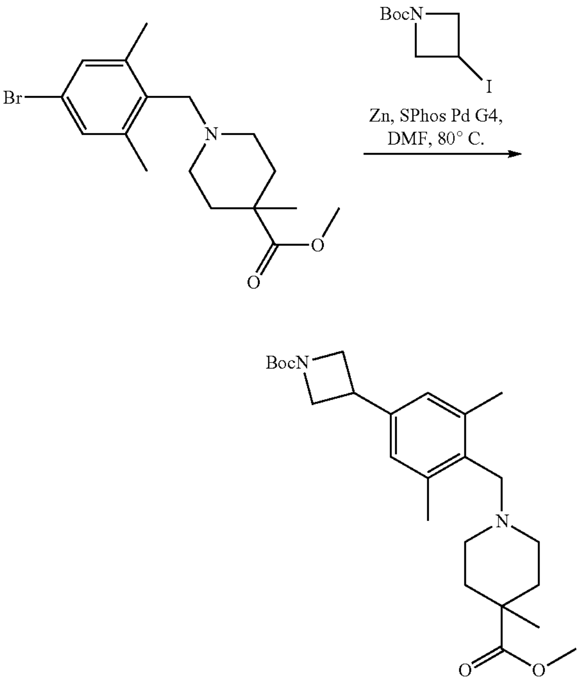

To a suspension of activated zinc (692 mg, 10.58 mmol) in anhydrous DMF (50 mL) was added 1,2-dibromoethane (6.08 µl, 0.071 mmol) and heated to 75° C. After 15 min, the reaction mixture was cooled to room temperature, chloro trimethylsilane (0.1 mL, 0.782 mmol) was added and allowed to stir at room temperature for additional 30 min. Then a solution of tert-butyl 3-iodoazetidine-1-carboxylate (999 mg, 3.53 mmol) in anhydrous DMF was added to the reaction mixture and stirred at room temperature for another 2 h to get (1-(tert-butoxycarbonyl)azetidin-3-yl)zinc(II) iodide. In another three neck round bottom flask, to a solution of methyl 1-(4-bromo-2,6-dimethylbenzyl)-4-methylpiperidine-4-carboxylate (250 mg, 0.706 mmol) in anhydrous DMF was added SPhos Pd G4 (56.0 mg, 0.071 mmol). Freshly prepared (1-(tert-butoxycarbonyl)azetidin-3-yl)zinc(II) iodide was then added to the mixture via cannula under nitrogen atmosphere. The reaction mixture was then heated to 80° C. under nitrogen atmosphere and the progress of the reaction was monitored by UPLC. After 16 h, UPLC analysis indicated complete conversion of the starting material. The reaction mixture was cooled to room temperature and filtered through a pad of celite and washed with ethyl acetate. The filtrate was then transferred to a separating funnel and washed with cold water (300 mL) followed by brine (200 mL), dried over anhydrous sodium sulphate and concentrated under reduced pressure. The resulting residue was purified by flash column chromatography on silica gel (230-400 mesh) eluting with 0-50% ethyl acetate in petroleum ether to afford methyl 1-(4-(1-(tert-butoxycarbonyl)azetidin-3-yl)-2,6-dimethylbenzyl)-4-methylpiperidine-4-carboxylate (275 mg, 77% yield) as a yellow oil. LCMS (ESI, m/z): 430.8 $[M+H]^+$.

Synthesis of methyl 1-(4-(azetidin-3-yl)benzyl)-4-methylpiperidine-4-carboxylate

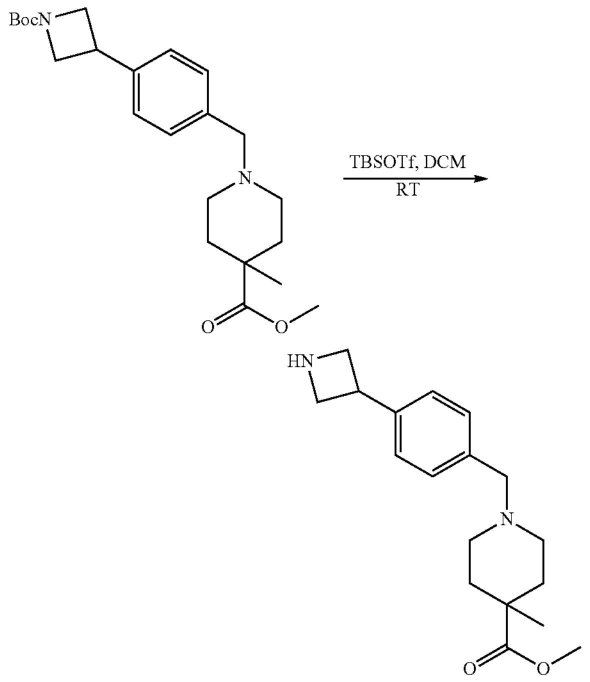

To a stirred solution of methyl 1-(4-(1-(tert-butoxycarbonyl)azetidin-3-yl)benzyl)-4-methylpiperidine-4-carboxylate (500 mg, 1.242 mmol) in anhydrous DCM (10 mL) was added tert-butyldimethylsilyl trifluoromethanesulfonate (0.857 mL, 3.73 mmol) at 0° C. The reaction mixture was allowed to stir at ambient temperature and the progress of the reaction was monitored by TLC. After 16 h, the reaction mixture was concentrated under reduced pressure to dryness and the resulting residue was purified by reverse phase preparative HPLC to afford methyl 1-(4-(azetidin-3-yl)benzyl)-4-methylpiperidine-4-carboxylate, TFA (650 mg, 1.057 mmol, 85% yield) as a white solid. LCMS method 1; LCMS (ESI, m/z): 303.2 $[M+H]^+$.

Synthesis of methyl 1-(4-(azetidin-3-yl)-2,6-dimethylbenzyl)-4-methylpiperidine-4-carboxylate

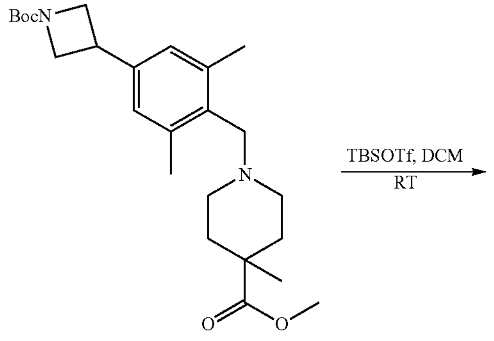

-continued

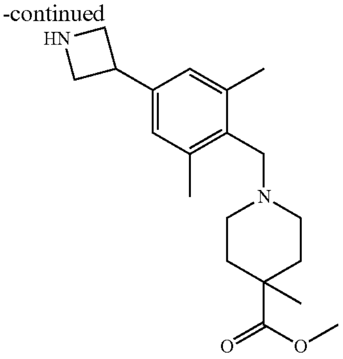

To a stirred solution of methyl 1-(4-(1-(tert-butoxycarbonyl)azetidin-3-yl)-2,6-dimethylbenzyl)-4-methylpiperidine-4-carboxylate (250 mg, 0.581 mmol) in anhydrous DCM (10 mL) was added tert-butyldimethylsilyl trifluoromethanesulfonate (0.400 mL, 1.742 mmol) at 0° C. The reaction mixture was allowed to stir at room temperature and the progress of the reaction was monitored by TLC. After 16 h, the reaction mixture was concentrated under reduced pressure to dryness and the resulting residue was purified by reverse phase preparative HPLC to afford methyl 1-(4-(azetidin-3-yl)-2,6-dimethylbenzyl)-4-methylpiperidine-4-carboxylate, TFA (250 mg, 87% yield) as a white solid. LCMS (ESI, m/z): 330.9 $[M+H]^+$.

Synthesis of methyl 1-(4-(1-(2,6-dichlorophenyl)azetidin-3-yl)benzyl)-4-methylpiperidine-4-carboxylate

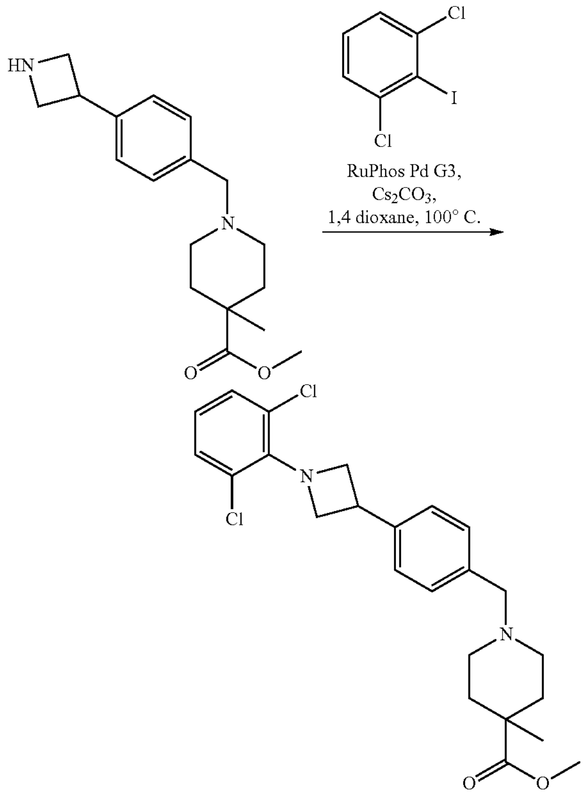

To a stirred solution of methyl 1-(4-(azetidin-3-yl)benzyl)-4-methylpiperidine-4-carboxylate (400 mg, 1.323 mmol) and 1,3-dichloro-2-iodobenzene (433 mg, 1.587 mmol) in anhydrous 1,4-dioxane (25 mL) was added cesium carbonate (1.2 g, 3.97 mmol). The reaction mixture was then degassed with nitrogen. After 15 min, RuPhos Pd G3 (111 mg, 0.132 mmol) was added and heated to 100° C. After 16 h, UPLC analysis indicated complete conversion of the starting material. The reaction mixture was then cooled to room temperature and diluted with ethyl acetate (100 mL). The organic layer was washed with ice cold water followed by brine. Then the organic layer was separated and dried over sodium sulphate and concentrated under reduced pressure. The resulting residue was purified by flash column chromatography on silica gel (230-400 mesh) eluting with 0-50% ethyl acetate in petroleum ether to afford methyl 1-(4-(1-(2,6-dichlorophenyl)azetidin-3-yl)benzyl)-4-methylpiperidine-4-carboxylate (85 mg, 0.125 mmol, 9.48% yield) as a brown liquid. LCMS method 1, LCMS (ESI, m/z): 447.0 [M+H]$^+$.

Synthesis of methyl 1-(4-(1-(2,6-dichlorophenyl)azetidin-3-yl)-2,6-dimethylbenzyl)-4-methylpiperidine-4-carboxylate

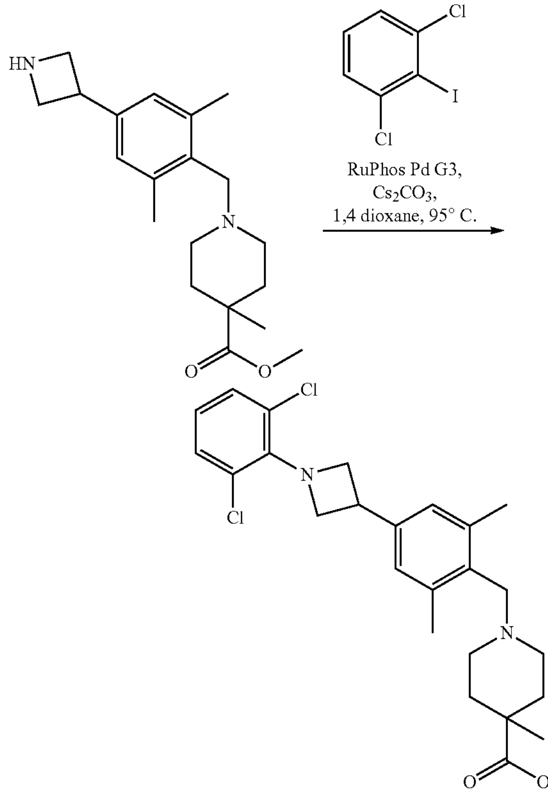

To a stirred solution of methyl 1-(4-(azetidin-3-yl)-2,6-dimethylbenzyl)-4-methylpiperidine-4-carboxylate (250 mg, 0.756 mmol) and 1,3-dichloro-2-iodobenzene (248 mg, 0.908 mmol) in anhydrous 1,4-dioxane (25 mL) was added cesium carbonate (744 mg, 2.269 mmol). The reaction mixture was then degassed with nitrogen. After 15 min, Ruphos Pd G3 (63.3 mg, 0.076 mmol) was added and heated to 95° C. After 16 h, UPLC analysis indicated complete conversion of the starting material. The reaction mixture was then cooled to room temperature and diluted with ethyl acetate (100 mL). The organic layer was washed with ice cold water followed by brine. Then the organic layer was separated and dried over sodium sulphate and concentrated under reduced pressure. The resulting residue was purified by flash column chromatography on silica gel (230-400 mesh) eluting with 0-50% ethyl acetate in petroleum ether to afford methyl 1-(4-(1-(2,6-dichlorophenyl)azetidin-3-yl)-2,6-dimethylbenzyl)-4-methylpiperidine-4-carboxylate (170 mg, 0.303 mmol, 40.0% yield) as an off-white gum. LCMS (ESI, m/z): 475.2 [M+H]$^+$.

Example S89. 1-(4-(1-(2,6-dichlorophenyl)azetidin-3-yl)benzyl)-4-methylpiperidine-4-carboxylic acid, formic acid salt (89)

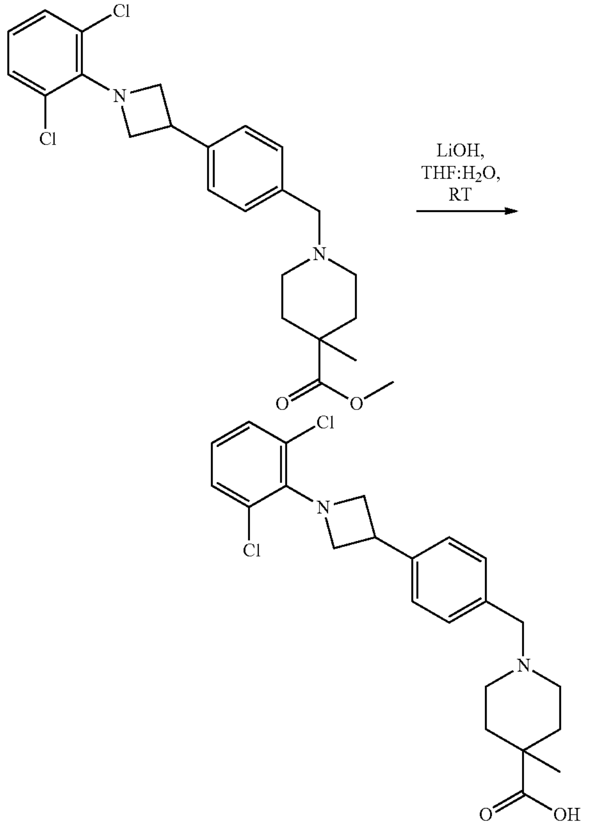

89

To a stirred solution of methyl 1-(4-(1-(2,6-dichlorophenyl)azetidin-3-yl)benzyl)-4-methylpiperidine-4-carboxylate (85 mg, 0.190 mmol) in THF (5 mL) and water (1 mL) was added LiOH (13.65 mg, 0.570 mmol). The resulting mixture was allowed to stir at room temperature and the progress of the reaction was monitored by TLC. After completion of the reaction, the volatiles were concentrated under reduced pressure and the residue was dissolved in water and acidified with acetic acid. The mixture was then concentrated under reduced pressure and the resulting residue was purified by prep. HPLC. Prep. HPLC method: Diluent: THF:Acetonitrile (30:70) Column: Xselect C18 (150×19) mm, 5 micron. Mobile phase A: 0.1% Formic acid in water. Mobile phase B: Acetonitrile. The required fractions were collected and lyophilized to afford 1-(4-(1-(2,6-dichlorophenyl)azetidin-3-yl)benzyl)-4-methylpiperidine-4-carboxylic acid, formic acid salt (8.3 mg, 0.017 mmol, 8.69% yield, 95.3% pure) as a white solid. $^1$H NMR ($CD_3OD$, 400 MHz): δ 8.51 (bs, 2H), 7.59-7.57 (m, 2H), 7.50-7.48 (m, 2H), 7.21-7.19 (m, 2H), 6.73 (t, J=8 Hz, 1H), 4.88 (m, 2H), 4.45-4.42 (m, 2H), 4.23 (s, 2H), 3.84-3.78 (m, 1H), 3.32 (m, 1H), 3.04 (m, 2H), 2.32-2.28 (m, 2H), 1.61-1.58 (m, 2H), 1.22 (s, 3H). LCMS method 1, LCMS (ESI, m/z): 435.0 $[M+H]^+$.

Example S90. 1-(4-(1-(2,6-dichlorophenyl)azetidin-3-yl)-2,6-dimethylbenzyl)-4-methyl-piperidine-4-carboxylic acid, formic acid salt (90)

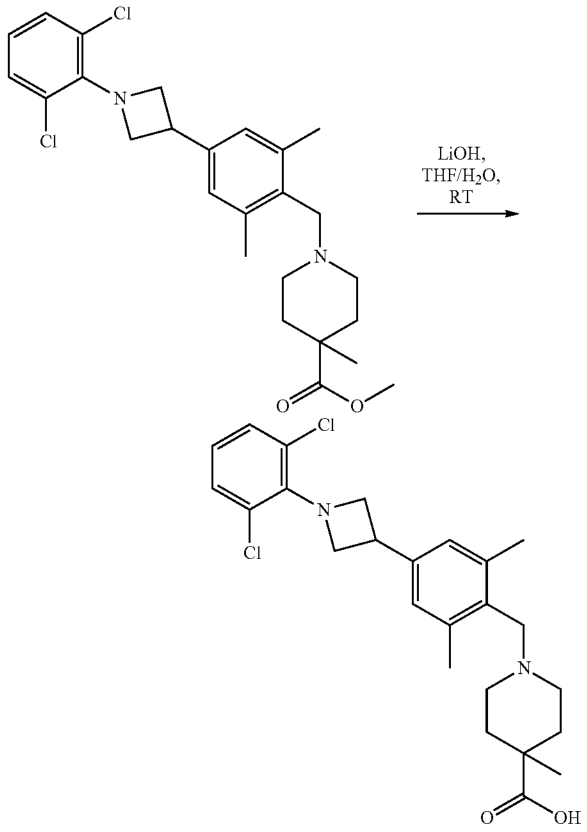

90

To a stirred solution of methyl 1-(4-(1-(2,6-dichlorophenyl)azetidin-3-yl)-2,6-dimethylbenzyl)-4-methylpiperidine-4-carboxylate (170 mg, 0.358 mmol) in THF (12 mL) and water (3 mL) was added LiOH (25.7 mg, 1.073 mmol). The reaction mixture was allowed to stir at room temperature and the progress of the reaction was monitored by TLC. After 16 h, TLC analysis indicated the presence of the starting material. LiOH (45.1 mg, 1.073 mmol) and methanol (0.5 mL) was added to the mixture and heated to 60° C. After 3 h, the reaction mixture was concentrated under reduced pressure and the resulting residue was dissolved in water and extracted with diethyl ether (20 mL). The aqueous layer was separated and acidified with acetic acid to pH 4-5 and then concentrated under reduced pressure. The resulting residue was purified by preparative HPLC. Conditions: Diluent: THF:Acetonitrile (30:70) Column: Xselect C18 (150×19) mm, 5 micron. Mobile phase A: 0.1% Formic acid in water Mobile phase B: Acetonitrile. The required fractions were collected and lyophilized to afford 1-(4-(1-(2,6-dichlorophenyl)azetidin-3-yl)-2,6-dimethylbenzyl)-4-methylpiperidine-4-carboxylic acid, formic acid salt (28 mg, 15.23% yield) as a pale yellow solid. $^1$H NMR ($CD_3OD$, 400 MHz): δ 7.23-7.18 (m, 4H), 6.72 (t, J=8 Hz, 1H), 4.88 (m, 2H), 4.22-4.38 (m, 2H), 4.24 (bs, 2H), 3.73-3.69 (m, 2H), 3.30 (m, 1H), 3.15-3.08 (m, 1H), 2.47 (s, 6H), 2.28-2.24 (m, 2H), 1.62-1.56 (m, 2H), 1.21 (s, 3H). LCMS method 1, LCMS (ESI, m/z): 461.2 $[M+H]^+$.

BIOLOGICAL EXAMPLES

Example B1. Cell Membrane Preparations

CHO cells expressing recombinant S1P5 receptors were cultured in 500 $cm^2$ culture trays and, once confluent, rinsed and detached with cell-lifting buffer (10 mM HEPES, 154 mM NaCl, 6.85 mM EDTA, pH 7.4). Cells were then pelleted by centrifugation, resuspended, and homogenized in membrane preparation buffer (10 mM HEPES and 10 mM EDTA, pH 7.4) using a Polytron PT 1200E homogenizer (Kinematica, Luzern, Switzerland). Cellular proteins were pelleted by centrifugation at 48,000×g at 4° C. for 30 minutes. The resulting supernatant was discarded, and the pellet was re-suspended again in membrane preparation buffer, homogenized for a second time, and then centrifuged again as described above. The final cellular protein pellet was suspended in ice cold resuspension buffer (10 mM HEPES and 0.1 mM EDTA, pH 7.4), divided into aliquots, and stored at −80° C. until use.

Example B2. GTPγS Binding Assay

Functional binding assays for [$^{35}$]-GTPγS were performed in 96-well non-binding surface plates with a final volume of 200 μL. The test compounds were serially diluted in DMSO and added to assay plates using a Tecan D300E digital printer with a total volume of 0.4 L. The control sphingosine-1-phosphate (SiP) was prepared separately by preparing a 400 μM stock solution from a 100 nmol pellet of SiP in 10 mM $Na_2CO_3$ with 2% O-cyclodextrin. The serial dilution of SiP was done using complete assay buffer (20 mM HEPES, 10 mM $MgCl_2$, 100 mM NaCl, 1 mM EDTA, 0.1% fatty acid free bovine serum albumin (BSA), and 30 μg/mL saponin, pH 7.4) and transferred to wells already containing 0.4 μL DMSO. All the wells were then loaded to a total volume of 40 μL of complete assay buffer, except the non-specific binding (NSB) wells. For NSB wells, 40 μL/well of 50 μM GTPγS (Sigma Aldrich, cat #G8634, St. Louis, MO) was added to wells containing 0.4 μL of DMSO. The assay was started by the addition of 120 μL/well of CHO-S1P receptor membrane solution containing 40 μg/mL of membrane protein, 16.67 μM guanosine diphosphate (GDP; Sigma Aldrich, cat #G7127, St. Louis, MO), and 2.5 mg/mL of WGA PVT SPA beads in complete buffer. Assay plates were then sealed and incubated at room temperature with gentle agitation for 30 minutes. Next, 40 μL/well of 1 nM of [$^{35}$]-GTPγS (PerkinElmer, cat #NEG030X250UC, Waltham, MA) in basic assay buffer (20 mM HEPES, 10 mM $MgCl_2$, 100 mM NaCl, and 1 mM EDTA, pH7.4) was added to the assay plates to yield a final concentration of 200 pM and the plates were further incubated for 40 minutes at room temperature with gentle agitation. The assay was terminated by centrifugation of the plates at 1000 rpm for 3 minutes using an Eppendorf 5810R centrifuge (Eppendorf, Hamburg, Germany) and G protein bound radioactivity was quantitated using a MicroBeta2 microplate scintillation counter (PerkinElmer, Waltham, MA). As G protein bound radioactivity directly correlates to receptor activation and coupling to the G protein, this assay is a measure of S1P5 agonism. Results are shown in Table 2.

TABLE 2

S1P5 GTPγS Binding of Exemplary Compounds.

| Compound No. | S1P5 GTPγS binding |
|---|---|
| 1a | ++++ |
| 1b | ++ |
| 2a | +++ |
| 2b | + |
| 3a | ++ |
| 3b | + |
| 4a | +++ |
| 4b | + |
| 5 | ++++ |
| 6 | ++++ |
| 7 | ++++ |
| 8a | + |
| 8b | ++ |
| 9a | ++++ |
| 9b | ++ |
| 10a | +++ |
| 10b | + |
| 11 | +++ |
| 12a | +++ |
| 12b | ++++ |
| 13 | ++++ |
| 14 | ++ |
| 15 | ++++ |
| 16a | +++ |
| 16b | ++++ |
| 17 | ++++ |
| 18 | ++ |
| 19 | ++++ |
| 20 | ++++ |
| 21 | +++ |
| 22 | ++++ |
| 23 | ++++ |
| 24 | +++ |
| 25 | ND |
| 26 | ND |
| 27 | ++ |
| 28 | ++++ |
| 29 | +++ |
| 30 | ++++ |
| 31 | ++++ |
| 32 | +++ |
| 33 | +++ |
| 34 | ++++ |
| 35 | + |
| 36 | +++ |
| 37 | +++ |
| 38 | ++ |
| 39 | + |
| 40 | ++ |
| 41 | + |
| 42 | ++ |
| 43 | + |
| 44 | +++ |
| 45 | ++ |
| 46 | +++ |
| 47 | ++ |
| 48 | + |
| 49 | ++ |
| 50 | ++++ |
| 51 | ++++ |
| 52 | ++++ |
| 53 | ++ |
| 54 | ++++ |
| 55 | ++++ |
| 56 | ++++ |
| 57 | ++++ |
| 58 | +++ |
| 59 | ++++ |
| 60 | ++++ |
| 61 | ++++ |
| 62 | ++++ |
| 63 | +++ |
| 64 | ++++ |
| 65 | +++ |
| 66 | ++++ |
| 67 | ++++ |
| 68 | ++++ |
| 69 | ++++ |
| 70 | +++ |
| 71 | ++++ |
| 72 | +++ |
| 73 | ++++ |
| 74 | ++++ |
| 75 | ++ |
| 76 | +++ |
| 77 | ++ |
| 78 | ++ |
| 79 | ++ |
| 80 | ND |
| 81 | ND |
| 82 | ++ |
| 83 | +++ |
| 84 | +++ |
| 85 | ND |
| 86 | ++++ |
| 87 | +++ |
| 88 | ND |
| 89 | +++ |
| 90 | ++++ |

ND = not determined
++++ indicates binding ≤10 nM
+++ indicates binding between greater than 10 nM and ≤100 nM
++ indicates binding between greater than 100 nM and ≤1,000 nM
+ indicates binding between greater than 1,000 nM and ≤10,000 nM Although the present invention has been described in some detail by way of illustration and example for purposes of clarity of understanding, the descriptions and examples should not be construed as limiting the scope of the invention. The disclosures of all patent and scientific literature cited herein are expressly incorporated herein in their entirety by reference.

The invention claimed is:

1. A compound of Formula (III):

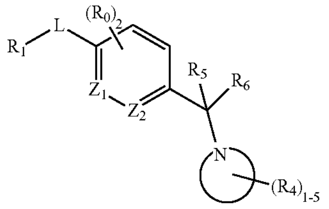

(III)

or a pharmaceutically acceptable salt thereof, wherein:

$Z_1$ and $Z_2$ are independently $CR_0$ or N;

L is azetidinyl optionally substituted with 1-5 substituents independently selected from halo and $C_1$-$C_6$ alkyl;

each $R_0$ is independently H, —CN, $C_1$-$C_6$ alkyl, $C_3$-$C_6$ cycloalkyl, halo, $C_1$-$C_6$ haloalkyl, or $C_1$-$C_6$ alkoxy, or two $R_0$ groups are taken together with the carbon atoms to which they are attached to form a fused phenylene;

$R_1$ is $C_6$-$C_{10}$ aryl or 5- to 6-membered heteroaryl, each of which is optionally substituted by 1-5 R groups, wherein the heteroaryl contains 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl, or two R' groups are taken together with the carbon atoms to which they are attached to form a fused phenylene;

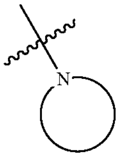

is a 4- to 6-membered heterocyclyl;

each $R_4$ is independently —$CO_2H$, halo, $C_1$-$C_6$ alkyl, $C_1$-$C_6$ haloalkyl, or $C_1$-$C_6$ alkoxy, wherein at least one $R_4$ group is-$CO_2H$; and $R_5$ and $R_6$ are independently H or $C_1$-$C_6$ alkyl.

2. The compound of claim 1, or a pharmaceutically acceptable salt thereof, wherein:

$Z_1$ and $Z_2$ are each independently $CR_0$.

3. The compound of claim 1, or a pharmaceutically acceptable salt thereof, wherein:

one of $Z_1$ and $Z_2$ is N, and the other of $Z_1$ and $Z_2$ is $CR_0$.

4. The compound of claim 1, or a pharmaceutically acceptable salt thereof, wherein:

each $R_0$ is independently H, —CN, $C_1$-$C_3$ alkyl, $C_3$-$C_5$ cycloalkyl, halo, $C_1$-$C_3$ haloalkyl, or $C_1$-$C_3$ alkoxy, or two $R_0$ groups are taken together with the carbon atoms to which they are attached to form a fused phenylene.

5. The compound of claim 1, or a pharmaceutically acceptable salt thereof, wherein:

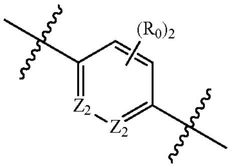

is

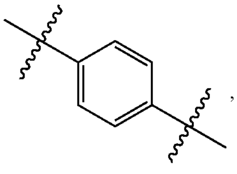,
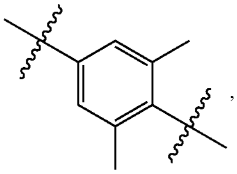,
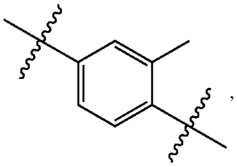,
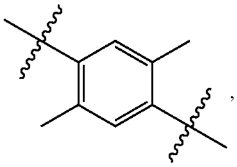,
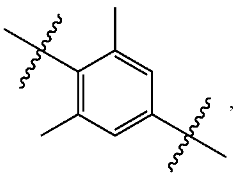,
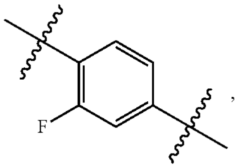,

-continued

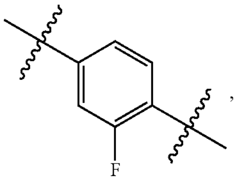,
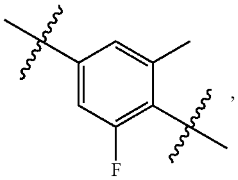,
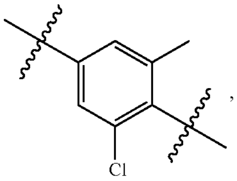,
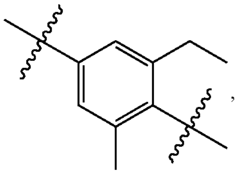,
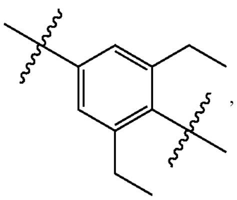,
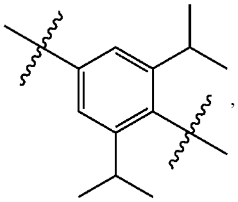,
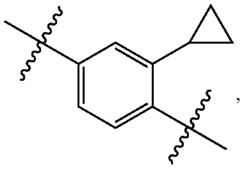,
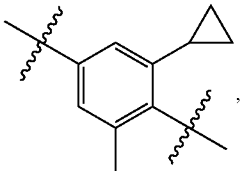,
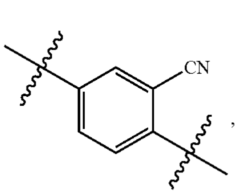,
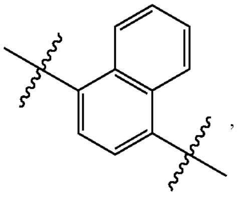,
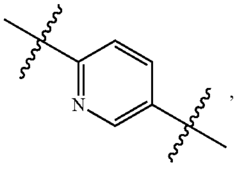,
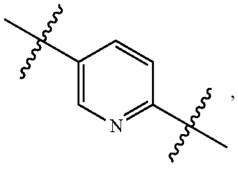,
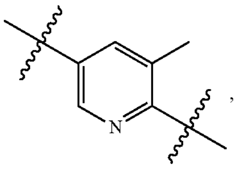,
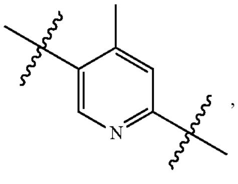,
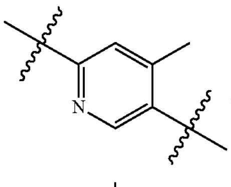,
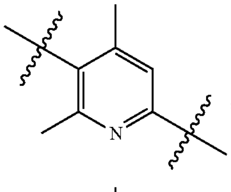,
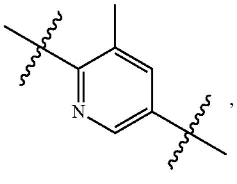,
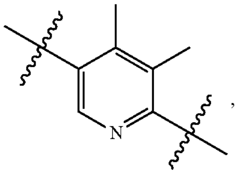, -continued

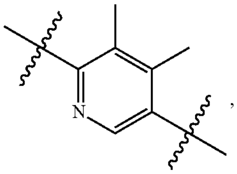, 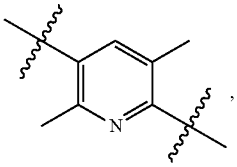, 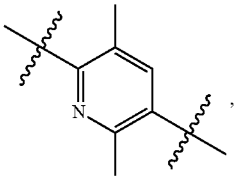, or 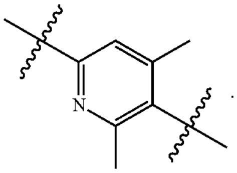.

6. The compound of claim 1, or a pharmaceutically acceptable salt thereof, wherein:

L is

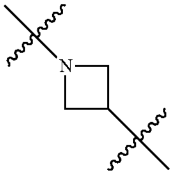 or 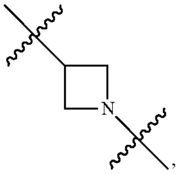, each of which is optionally substituted with 1-2 substituents independently selected from halo and $C_1$-$C_3$ alkyl.

7. The compound of claim 6, or a pharmaceutically acceptable salt thereof, wherein:

L is

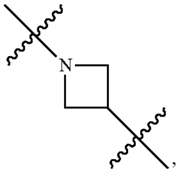, 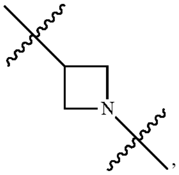, or

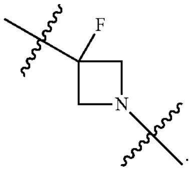.

8. The compound of claim 1, or a pharmaceutically acceptable salt thereof, wherein:

$R_1$ is phenyl optionally substituted by 1-3 R groups.

9. The compound of claim 8, or a pharmaceutically acceptable salt thereof, wherein:

each R' is independently halo, $C_1$-$C_3$ alkyl, $C_1$-$C_3$ haloalkyl, $C_1$-$C_3$ alkoxy, or $C_3$-$C_6$ cycloalkyl, or two R groups are taken together with the carbon atoms to which they are attached to form a fused phenylene.

10. The compound of claim 1, or a pharmaceutically acceptable salt thereof, wherein:

$R_1$ is

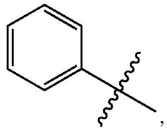, 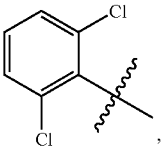,

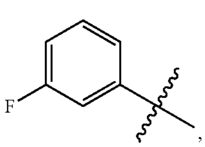, 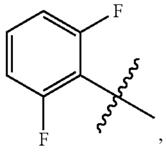,

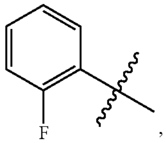, 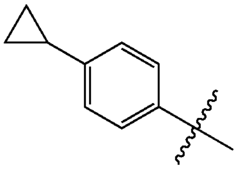,

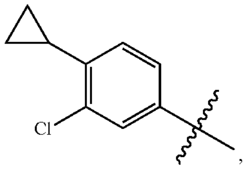, 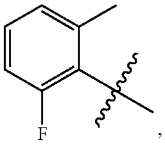,

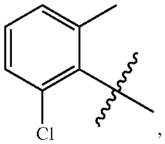, 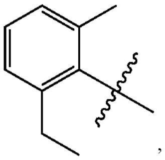, 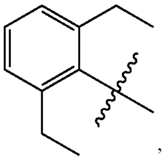,

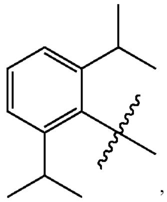, 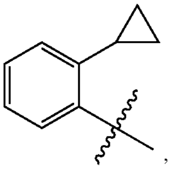,

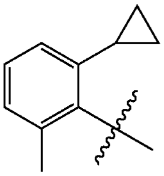, 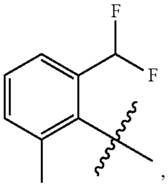, or

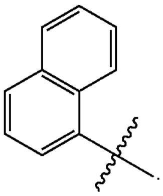.

11. The compound of claim 1, or a pharmaceutically acceptable salt thereof, wherein:

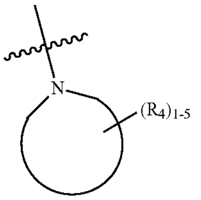

is

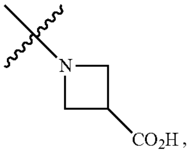 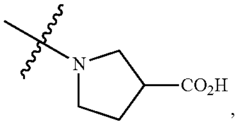 ,

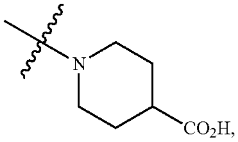 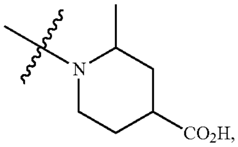

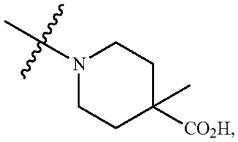 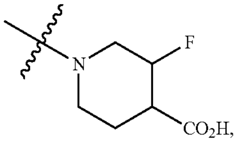

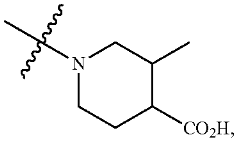 or 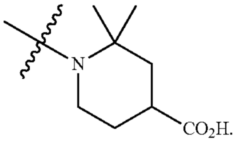

12. The compound of claim 1, or a pharmaceutically acceptable salt thereof, wherein:

$R_5$ and $R_6$ are independently H or $C_1$-$C_3$ alkyl.

13. The compound of claim 12, or a pharmaceutically acceptable salt thereof, wherein:

$R_5$ and $R_6$ are independently H or methyl.

14. A compound selected from:

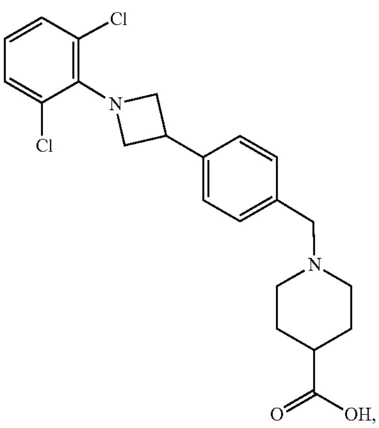

-continued

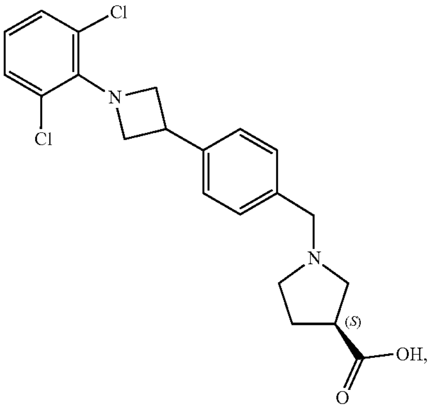

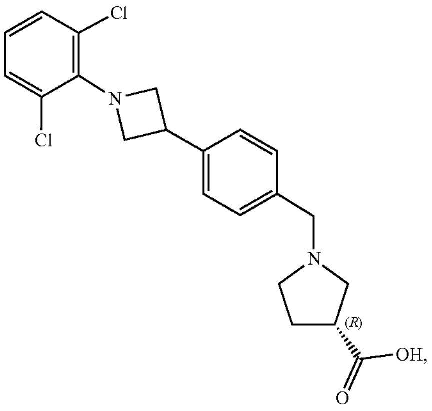

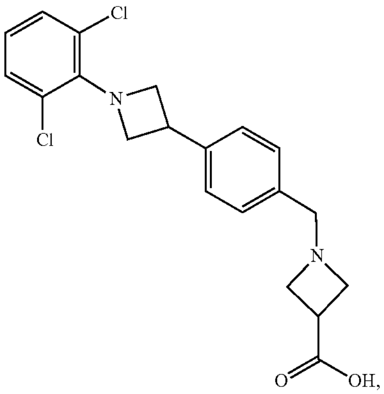

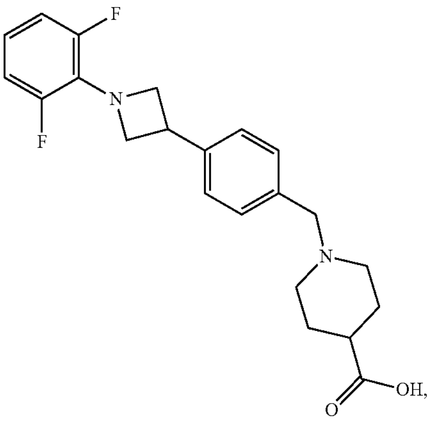

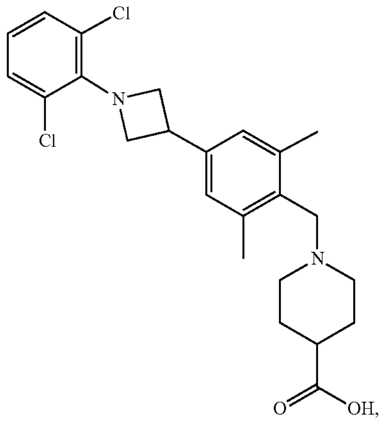
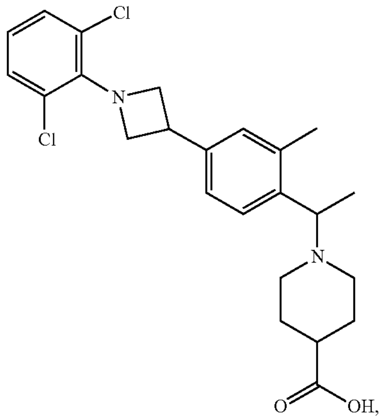
Enantiomer 1
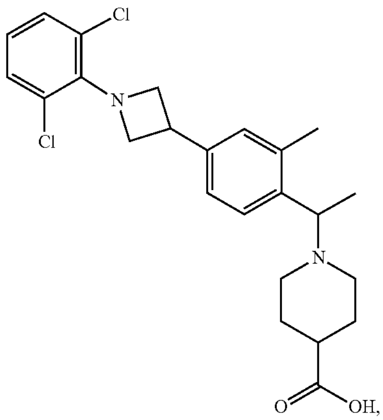
Enantiomer 2
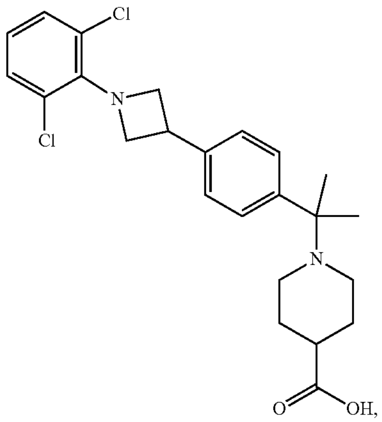
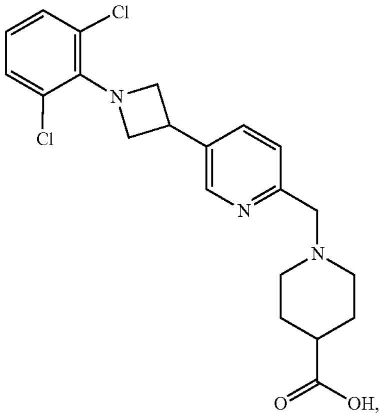
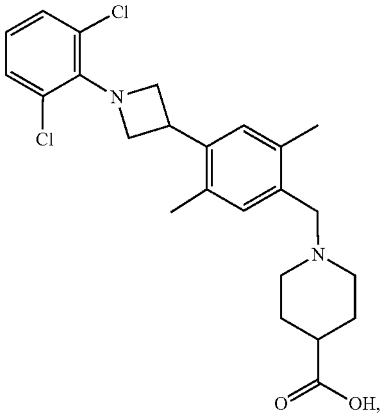
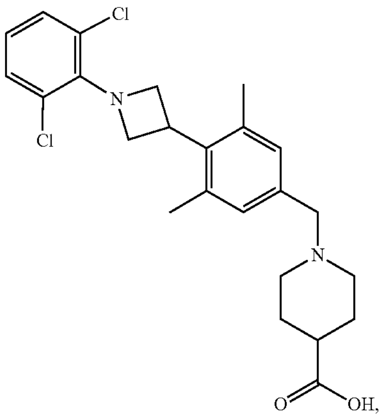

-continued
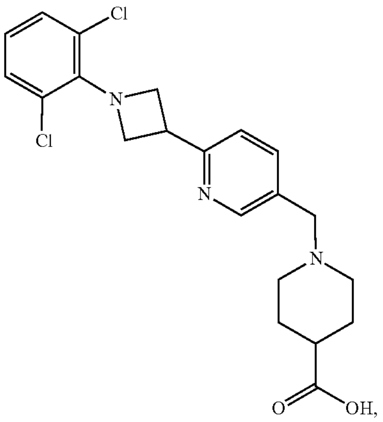
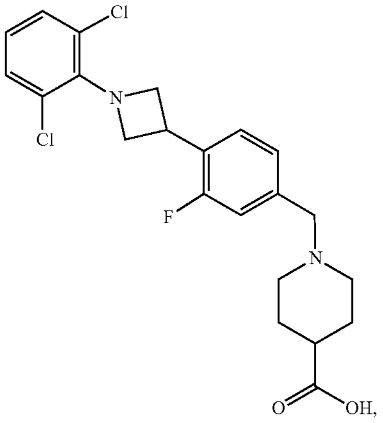
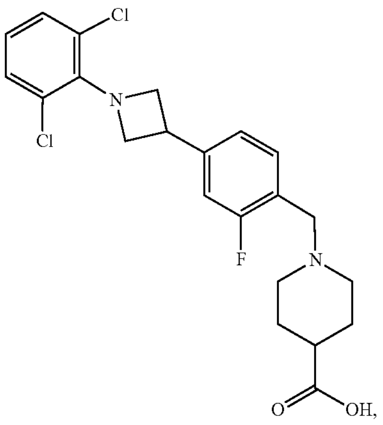
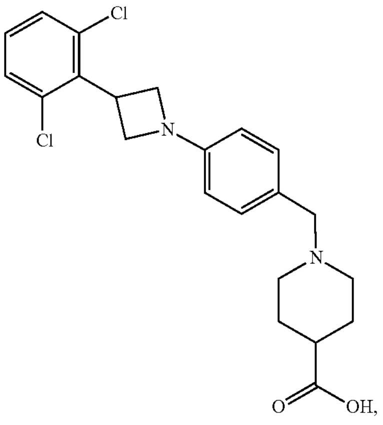
-continued
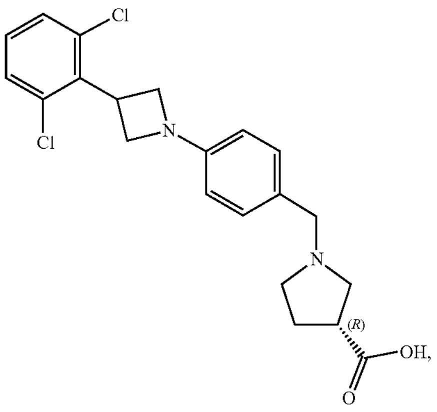
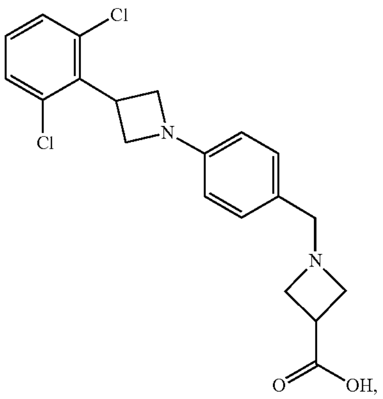
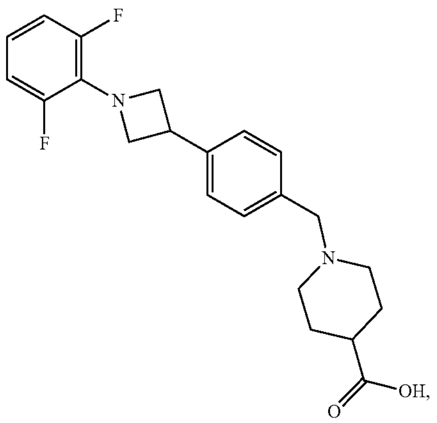
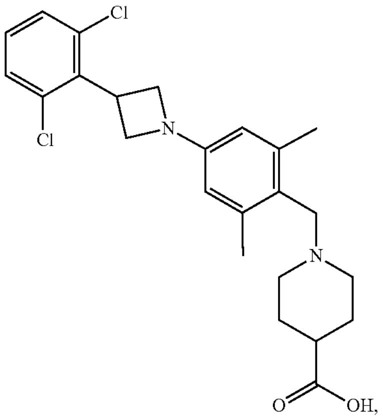

-continued
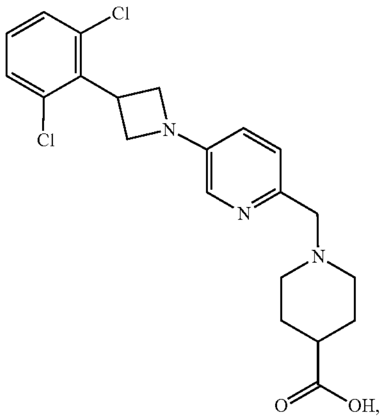
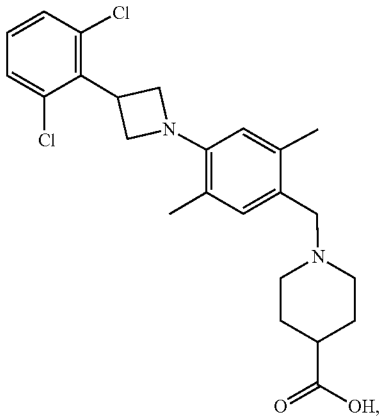
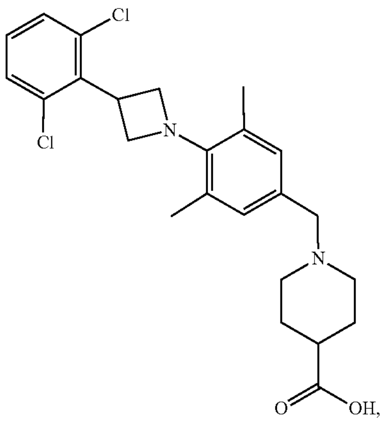
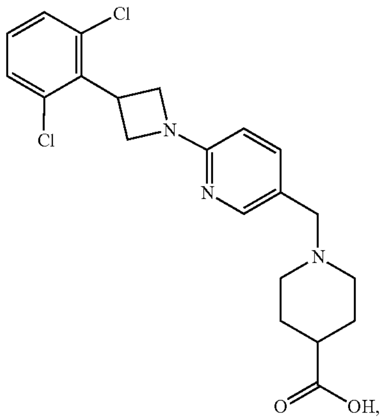
-continued
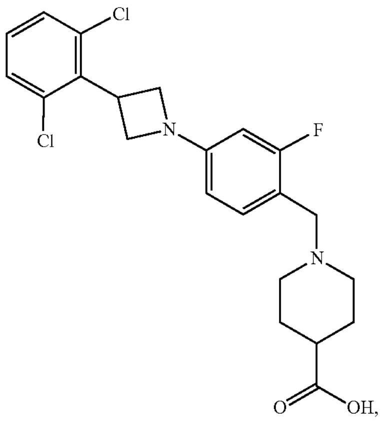
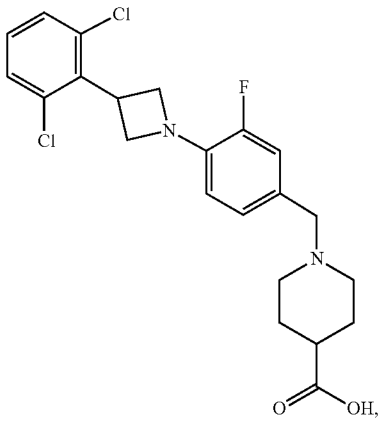
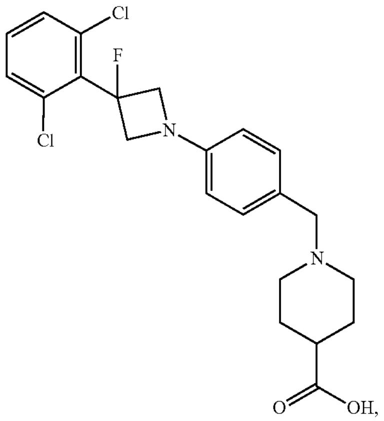
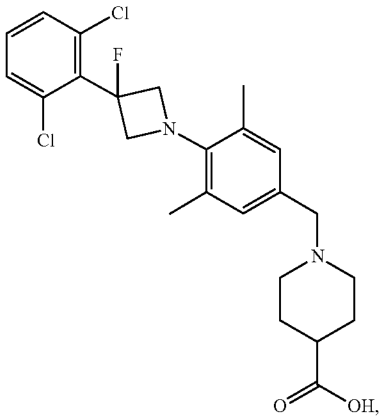

-continued
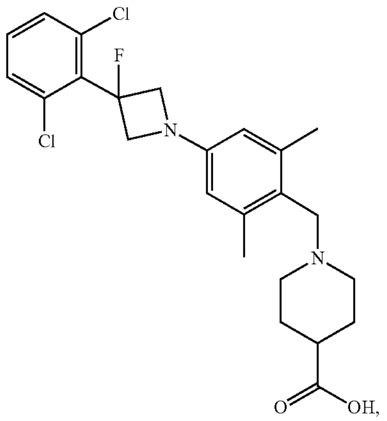
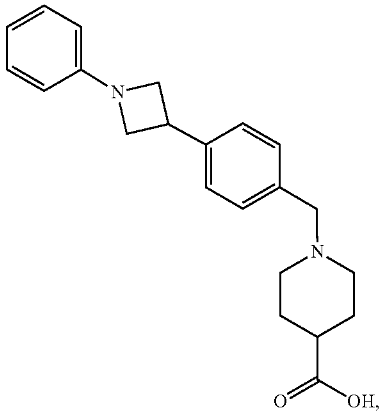
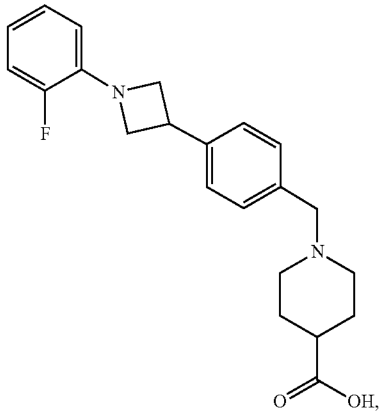
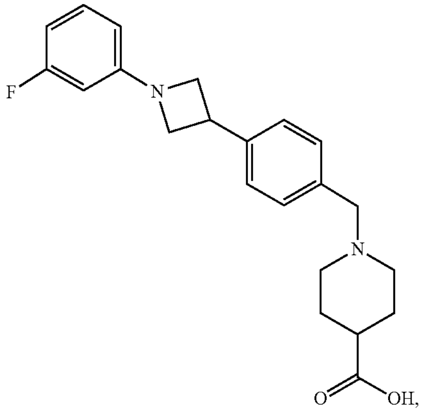
-continued
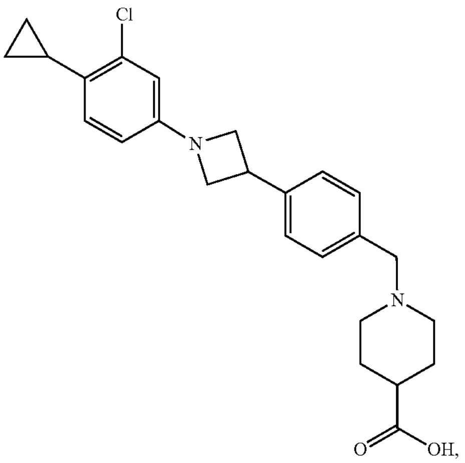
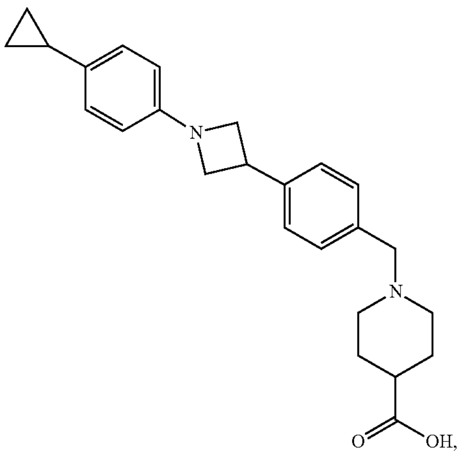
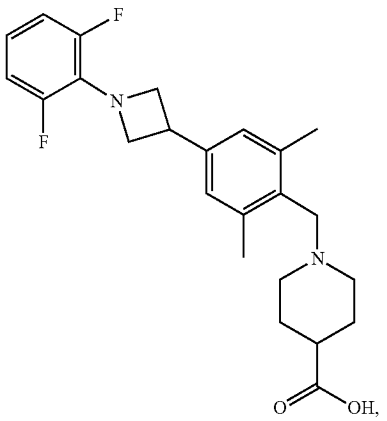

-continued
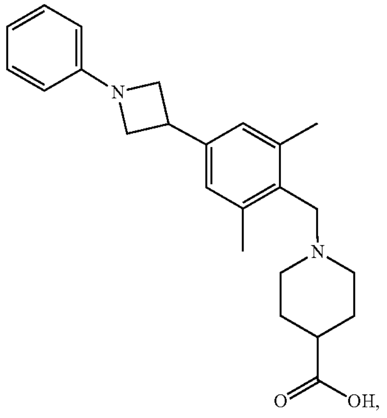
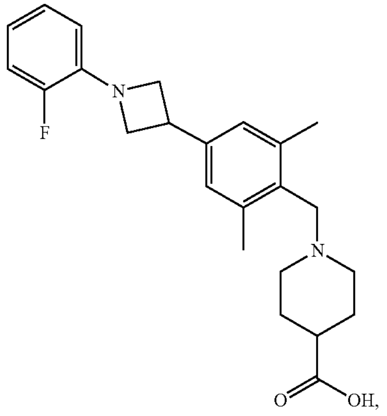
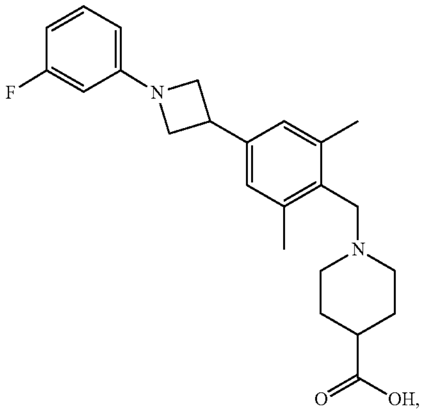
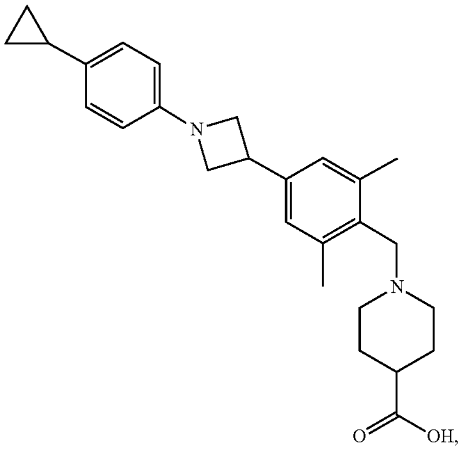
-continued
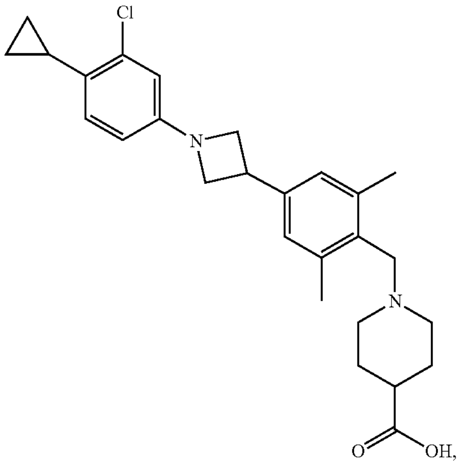
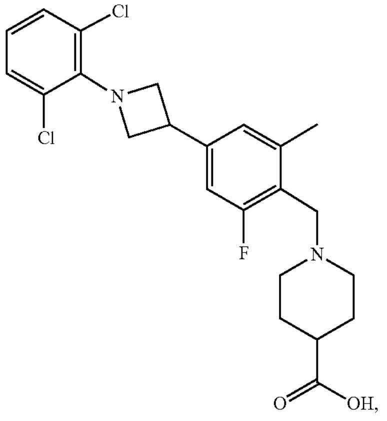
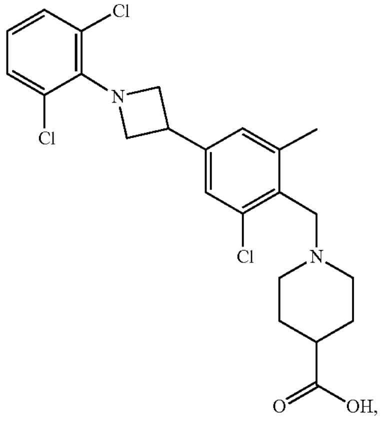
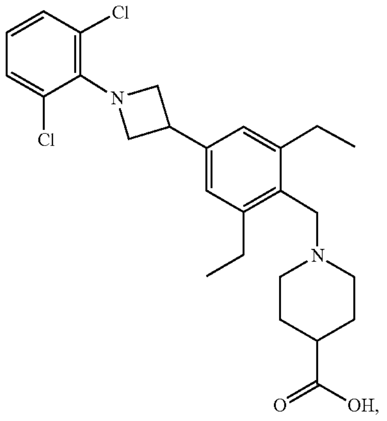

-continued
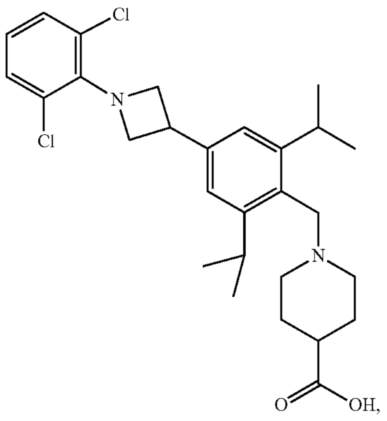
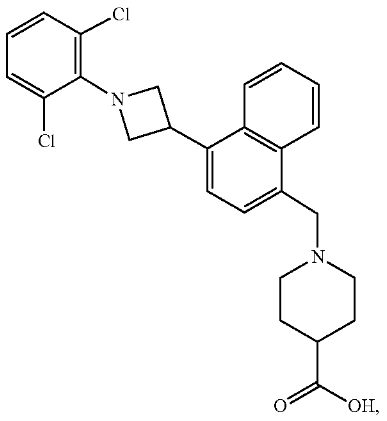
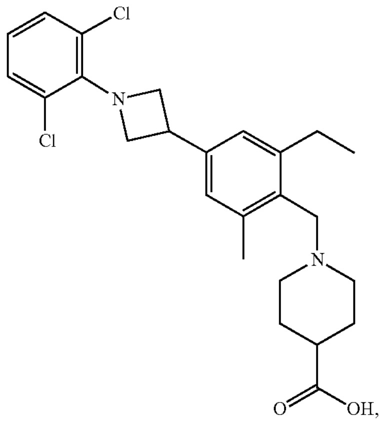
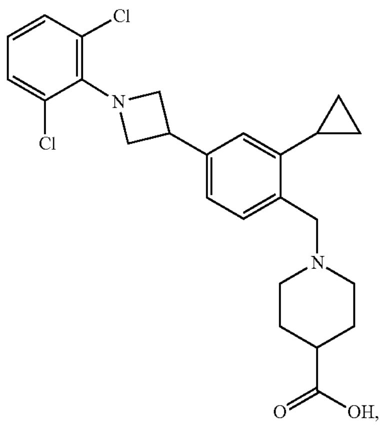
-continued
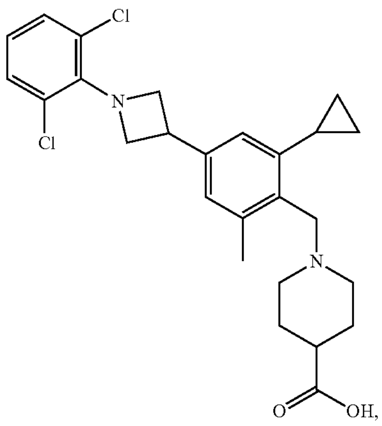
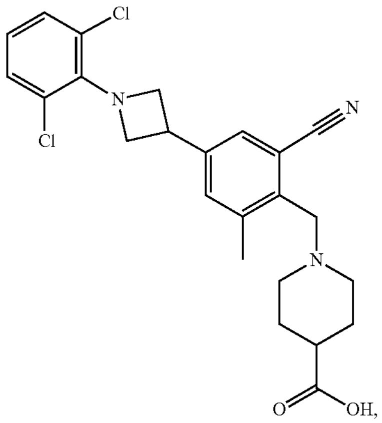
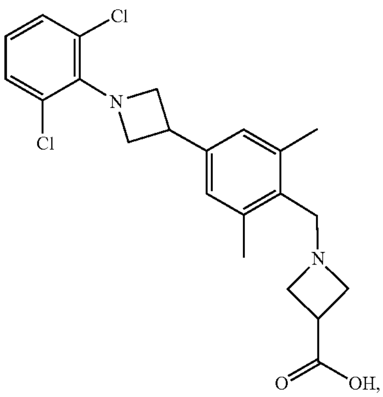
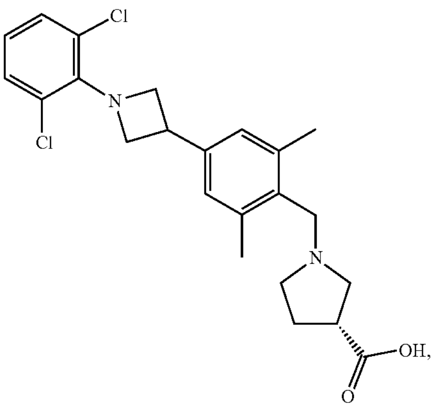

-continued
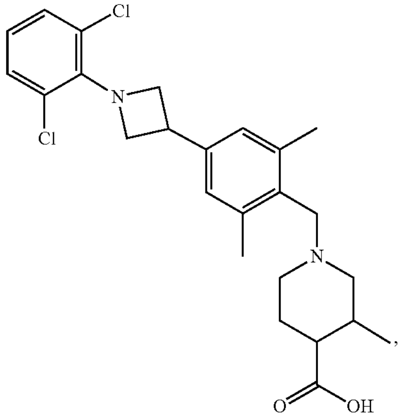
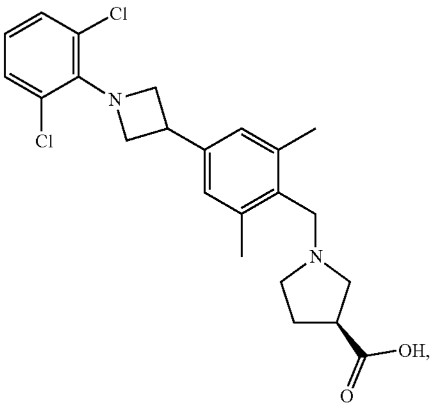
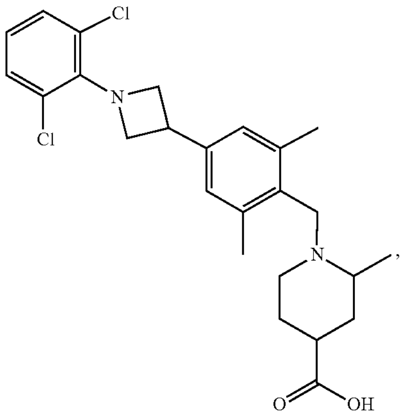
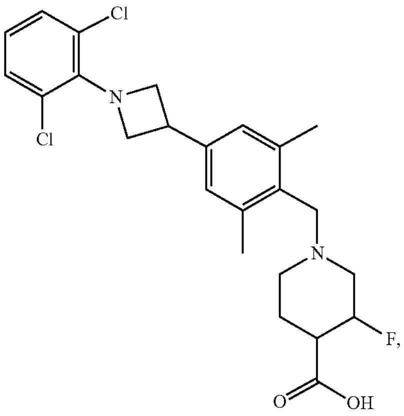
-continued
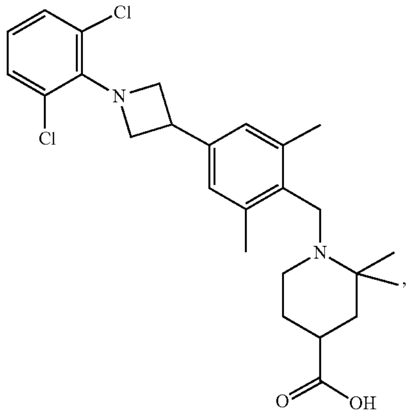
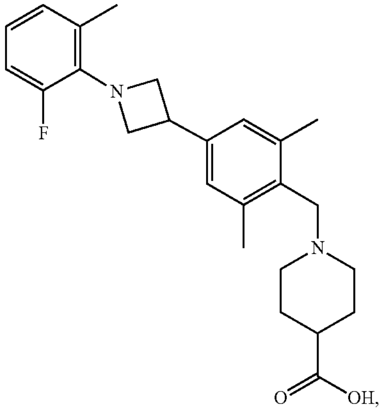
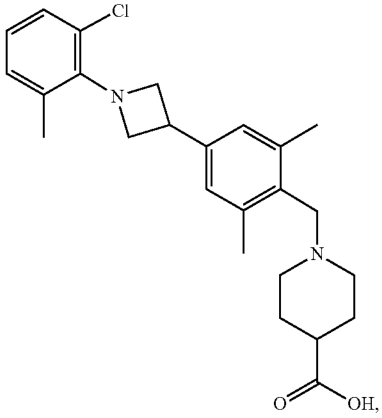
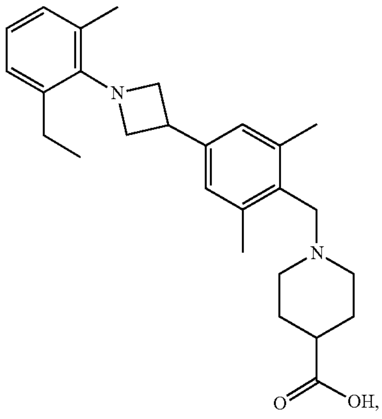

-continued
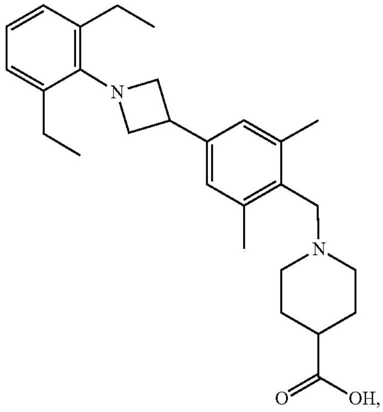
,
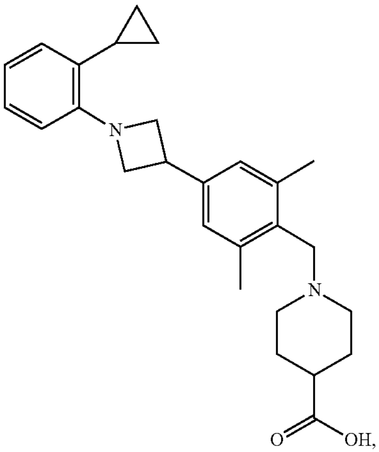
,
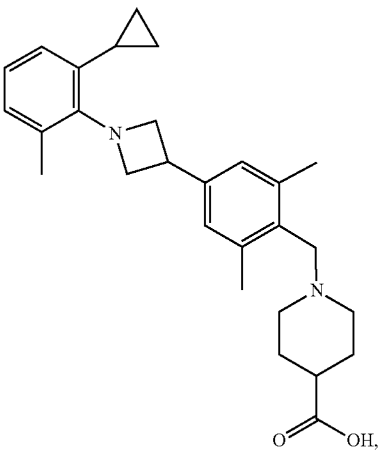
,
-continued
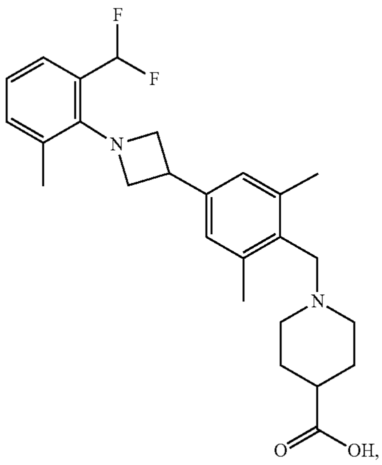
,
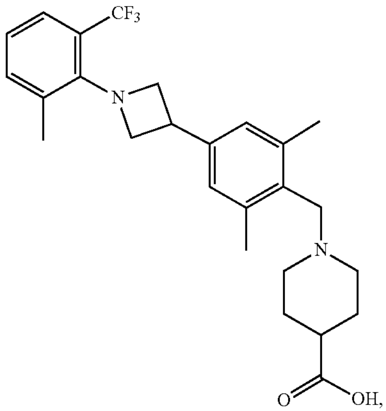
,
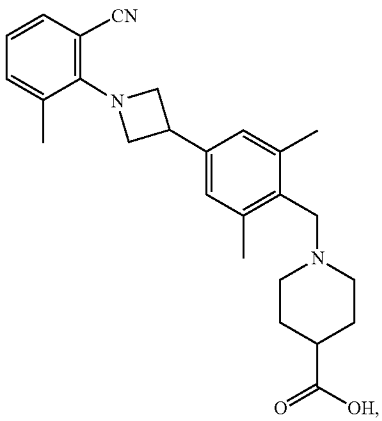
, -continued
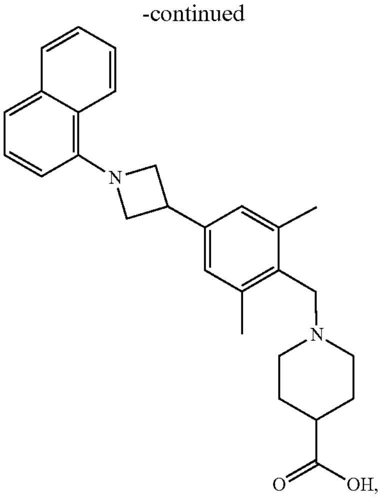
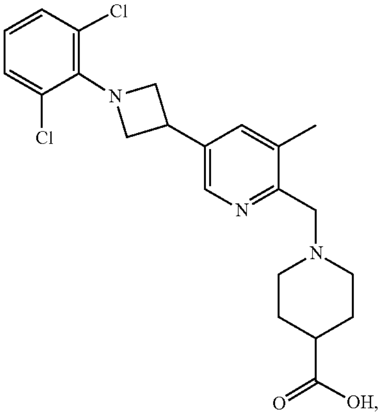
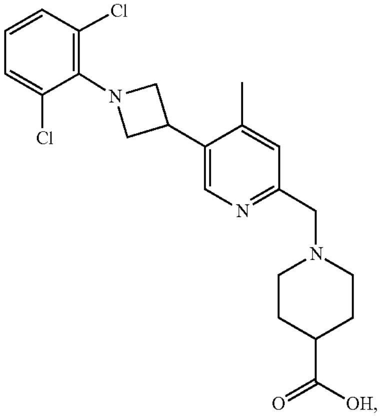
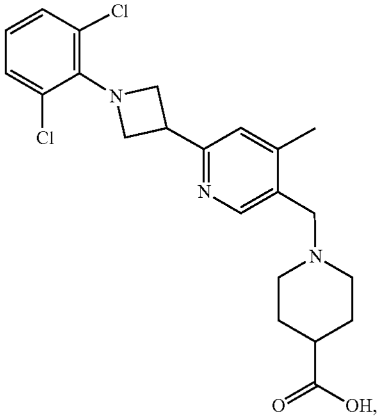
-continued
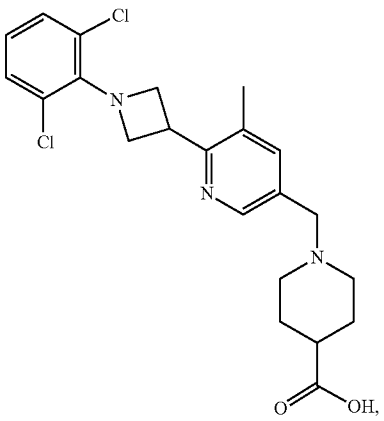
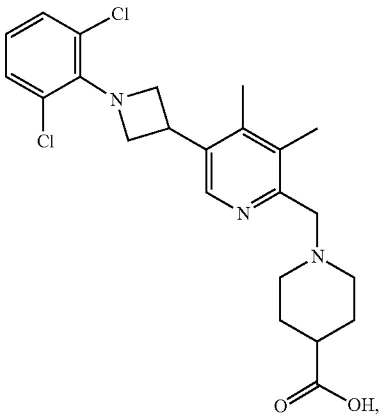
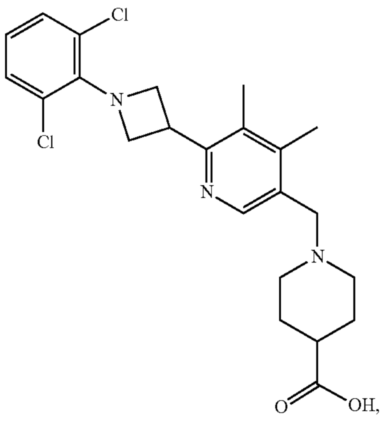
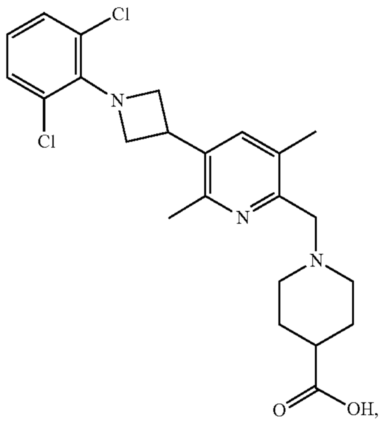

-continued
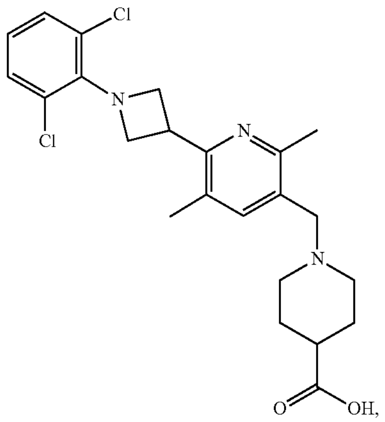
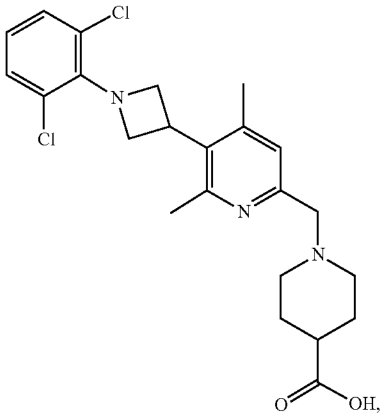
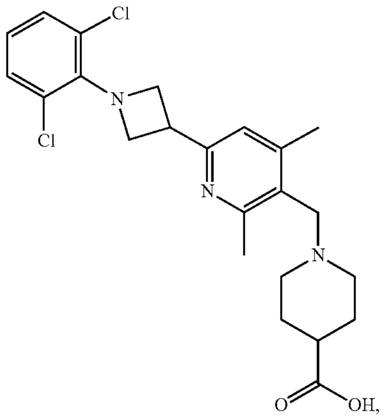
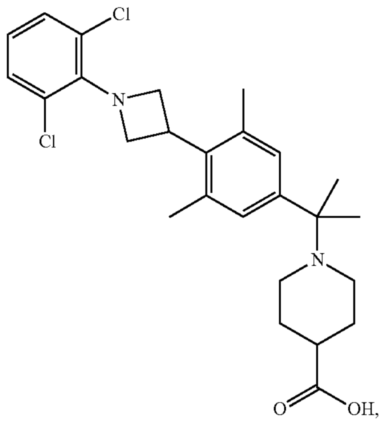
-continued
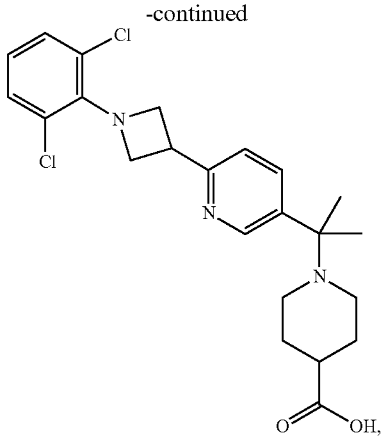
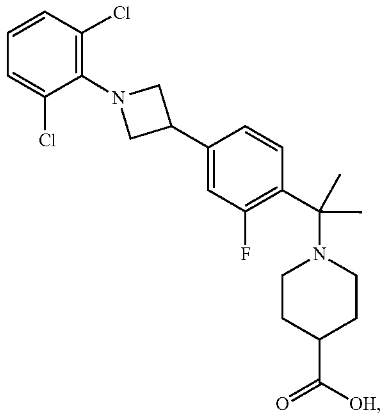
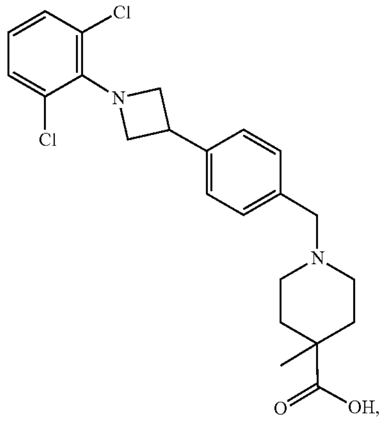
and
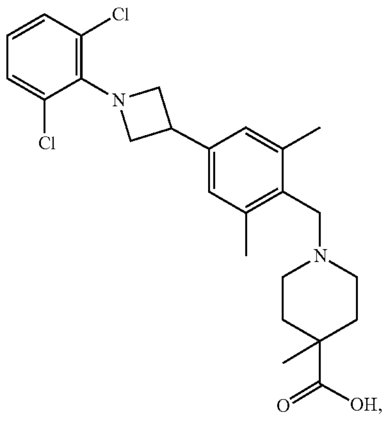
and pharmaceutically acceptable salts thereof.

15. A pharmaceutical composition comprising the compound of claim 1, or a pharmaceutically acceptable salt thereof, and a pharmaceutically acceptable excipient.

16. A method of modulating sphingosine 1-phosphate receptor 5 (S1P5) comprising contacting S1P5 with an effective amount of the compound of claim 1, or a pharmaceutically acceptable salt thereof.

17. A method of treating a neurological disease in a subject in need thereof, comprising administering to the subject an effective amount of the compound of claim 1, or a pharmaceutically acceptable salt thereof.

18. The method of claim 17, wherein the neurological disease is Alzheimer's disease or multiple sclerosis.

* * * * *